United States Patent
Huang

(10) Patent No.: US 12,161,754 B2
(45) Date of Patent: Dec. 10, 2024

(54) ABUSE DETERRENT MORPHINE SULFATE DOSAGE FORMS

(71) Applicant: Purdue Pharma L.P., Stamford, CT (US)

(72) Inventor: Haiyong Hugh Huang, Princeton Junction, NJ (US)

(73) Assignee: Purdue Pharma L.P., Stamford, CT (US)

( * ) Notice: Subject to any disclaimer, the term of this patent is extended or adjusted under 35 U.S.C. 154(b) by 321 days.

(21) Appl. No.: 16/337,743

(22) PCT Filed: Dec. 18, 2018

(86) PCT No.: PCT/US2018/066165
§ 371 (c)(1),
(2) Date: Mar. 28, 2019

(87) PCT Pub. No.: WO2019/126125
PCT Pub. Date: Jun. 27, 2019

(65) Prior Publication Data
US 2020/0337994 A1    Oct. 29, 2020

Related U.S. Application Data

(60) Provisional application No. 62/607,991, filed on Dec. 20, 2017, provisional application No. 62/687,914, filed on Jun. 21, 2018.

(51) Int. Cl.
*A61K 9/00*    (2006.01)
*A61J 3/00*    (2006.01)
(Continued)

(52) U.S. Cl.
CPC ............ *A61K 9/0056* (2013.01); *A61J 3/00* (2013.01); *A61K 9/107* (2013.01); *A61K 9/2031* (2013.01);
(Continued)

(58) Field of Classification Search
None
See application file for complete search history.

(56) References Cited

U.S. PATENT DOCUMENTS

| 5,202,128 A | 4/1993 | Morella et al. |
| 5,273,758 A | 12/1993 | Royce |

(Continued)

FOREIGN PATENT DOCUMENTS

| AU | 2017239544 A1 | 10/2017 |
| CA | 2500311 A1 | 4/2004 |

(Continued)

OTHER PUBLICATIONS

Shojaee et al. (AAPS PharmSciTech 2015;16(6):1281-1289) (Year: 2015).*

(Continued)

*Primary Examiner* — Ernst V Arnold
(74) *Attorney, Agent, or Firm* — Lowenstein Sandler LLP

(57) ABSTRACT

The present invention relates to a solid oral extended release pharmaceutical dosage form comprising a cured extended release matrix formulation, the extended release matrix formulation comprising:

a therapeutically effective amount of morphine sulfate, and polyethylene oxide.

The invention further relates to a process of preparing the dosage form as well as to a method of treating pain by administering the dosage form.

35 Claims, 81 Drawing Sheets

(51) Int. Cl.

| | |
|---|---|
| *A61K 9/107* | (2006.01) |
| *A61K 9/20* | (2006.01) |
| *A61K 31/47* | (2006.01) |
| *A61K 31/485* | (2006.01) |
| *A61K 47/02* | (2006.01) |
| *A61K 47/10* | (2017.01) |
| *A61K 47/24* | (2006.01) |
| *A61P 29/00* | (2006.01) |
| *B29C 43/00* | (2006.01) |
| *B29K 71/00* | (2006.01) |
| *B29L 31/00* | (2006.01) |

(52) U.S. Cl.
CPC .......... *A61K 9/2077* (2013.01); *A61K 31/485* (2013.01); *A61K 47/02* (2013.01); *A61K 47/10* (2013.01); *A61K 47/24* (2013.01); *B29C 43/003* (2013.01); *B29K 2071/02* (2013.01); *B29L 2031/753* (2013.01)

(56) References Cited

U.S. PATENT DOCUMENTS

| | | | |
|---|---|---|---|
| 5,593,695 A | 1/1997 | Merrill et al. | |
| 5,681,585 A | 10/1997 | Oshlack et al. | |
| 5,849,240 A | 12/1998 | Miller et al. | |
| 5,948,787 A | 9/1999 | Merrill et al. | |
| 5,958,459 A | 9/1999 | Chasin et al. | |
| 6,077,533 A | 6/2000 | Oshlack et al. | |
| 6,096,339 A | 8/2000 | Ayer et al. | |
| 6,375,957 B1 | 4/2002 | Kaiko et al. | |
| 8,834,925 B2* | 9/2014 | McKenna | B29C 35/045 424/472 |
| 2002/0114838 A1 | 8/2002 | Ayer et al. | |
| 2003/0039688 A1 | 2/2003 | Shell et al. | |
| 2003/0152622 A1 | 8/2003 | Louie-Helm et al. | |
| 2006/0240105 A1 | 10/2006 | Devane et al. | |
| 2007/0031491 A1 | 2/2007 | Levine et al. | |
| 2007/0048228 A1 | 3/2007 | Arkenau-Maric et al. | |
| 2007/0190141 A1 | 8/2007 | Dely | |
| 2007/0231268 A1 | 10/2007 | Emigh et al. | |
| 2008/0152595 A1 | 6/2008 | Emigh et al. | |
| 2008/0311162 A1 | 12/2008 | Darmuzey et al. | |
| 2009/0004281 A1 | 1/2009 | Nghiem et al. | |
| 2011/0195989 A1 | 8/2011 | Rudnic et al. | |
| 2011/0287095 A1 | 11/2011 | Park et al. | |
| 2013/0259940 A1* | 10/2013 | McKenna | A61K 47/34 424/472 |
| 2013/0261144 A1* | 10/2013 | Wright | A61K 47/10 514/282 |
| 2014/0010873 A1 | 1/2014 | Tygesen et al. | |
| 2014/0220126 A1 | 8/2014 | Tygesen et al. | |
| 2014/0271848 A1 | 9/2014 | Guido et al. | |
| 2015/0165041 A1 | 6/2015 | Thompson et al. | |
| 2016/0022590 A1 | 1/2016 | Odidi | |
| 2016/0310427 A1 | 10/2016 | Wening et al. | |
| 2017/0020820 A1 | 1/2017 | Sackler | |
| 2017/0065527 A1 | 3/2017 | McKenna et al. | |
| 2017/0071862 A1 | 3/2017 | Wening et al. | |
| 2017/0112766 A1 | 4/2017 | Wening et al. | |
| 2017/0157052 A1 | 6/2017 | Haswani et al. | |
| 2017/0312226 A1 | 11/2017 | Gumudavelli et al. | |
| 2017/0319575 A1 | 11/2017 | Rariy et al. | |
| 2019/0054024 A1* | 2/2019 | Yang | A61K 31/485 |

FOREIGN PATENT DOCUMENTS

| | | |
|---|---|---|
| CA | 2554701 A1 | 4/2007 |
| DE | 69230028 T | 4/2000 |
| DE | 19901683 A1 | 7/2000 |
| DE | 19901687 A1 | 7/2000 |
| DE | 69429710 T2 | 8/2002 |
| DE | 69619979 T2 | 11/2002 |
| EP | 0232877 A2 | 8/1987 |
| EP | 0253104 A1 | 1/1988 |
| EP | 0548448 A1 | 6/1993 |
| EP | 0630646 A1 | 12/1994 |
| EP | 0636366 A2 | 2/1995 |
| EP | 0647448 A1 | 4/1995 |
| EP | 1686966 A1 | 8/2006 |
| EP | 1827396 A2 | 9/2007 |
| EP | 1849460 A2 | 10/2007 |
| EP | 2648699 A2 | 10/2013 |
| JP | 2016222698 A | 12/2016 |
| JP | 2017190328 A | 10/2017 |
| KR | 20150059167 A | 5/2015 |
| KR | 20170118249 A | 10/2017 |
| WO | WO-86/00802 A1 | 2/1986 |
| WO | WO-94/06414 A1 | 3/1994 |
| WO | WO-94/22431 A1 | 10/1994 |
| WO | WO-95/14460 A1 | 6/1995 |
| WO | WO-95/31972 A1 | 11/1995 |
| WO | WO-96/00066 A1 | 1/1996 |
| WO | WO-96/14058 A1 | 5/1996 |
| WO | WO-97/33566 A2 | 9/1997 |
| WO | WO-97/48385 A2 | 12/1997 |
| WO | WO-98/55107 A1 | 12/1998 |
| WO | WO-98/56359 A2 | 12/1998 |
| WO | WO-99/20255 A1 | 4/1999 |
| WO | WO-99/39698 A1 | 8/1999 |
| WO | WO-99/44591 A1 | 9/1999 |
| WO | WO-00/74659 A1 | 12/2000 |
| WO | WO-01/58447 A1 | 8/2001 |
| WO | WO-03/013476 A1 | 2/2003 |
| WO | WO-03/013479 A1 | 2/2003 |
| WO | WO-03/015531 A2 | 2/2003 |
| WO | WO-03/024429 A1 | 3/2003 |
| WO | WO-03/024430 A1 | 3/2003 |
| WO | WO-03/035029 A1 | 5/2003 |
| WO | WO-03/035041 A1 | 5/2003 |
| WO | WO-03/035177 A2 | 5/2003 |
| WO | WO-03/063834 A1 | 8/2003 |
| WO | WO-03/105808 A1 | 12/2003 |
| WO | WO-2004/010983 A2 | 2/2004 |
| WO | WO-2004/010984 A2 | 2/2004 |
| WO | WO-2004/026256 A2 | 4/2004 |
| WO | WO-2004/026283 A1 | 4/2004 |
| WO | WO-2004/037230 A1 | 5/2004 |
| WO | WO-2004/037259 A1 | 5/2004 |
| WO | WO-2004/037260 A1 | 5/2004 |
| WO | WO-2004/052346 A1 | 6/2004 |
| WO | WO-2004/066910 A2 | 8/2004 |
| WO | WO-2004/084868 A1 | 10/2004 |
| WO | WO-2004/093819 A2 | 11/2004 |
| WO | WO-2005/009409 A2 | 2/2005 |
| WO | WO-2005/016313 A1 | 2/2005 |
| WO | WO-2005/016314 A1 | 2/2005 |
| WO | WO-2005/034859 A2 | 4/2005 |
| WO | WO-2005/053587 A1 | 6/2005 |
| WO | WO-2005/063206 A1 | 7/2005 |
| WO | WO-2005/063214 A1 | 7/2005 |
| WO | WO-2005/102286 A1 | 11/2005 |
| WO | WO-2005/117843 A2 | 12/2005 |
| WO | WO-2005/120507 A1 | 12/2005 |
| WO | WO-2006/002883 A1 | 1/2006 |
| WO | WO-2006/002884 A1 | 1/2006 |
| WO | WO-2006/035416 A2 | 4/2006 |
| WO | WO-2006/058249 A2 | 6/2006 |
| WO | WO-2006/079550 A2 | 8/2006 |
| WO | WO-2006/082097 A1 | 8/2006 |
| WO | WO-2006/085101 A2 | 8/2006 |
| WO | WO-2006/102446 A2 | 9/2006 |
| WO | WO-2006/103418 A1 | 10/2006 |
| WO | WO-2006/107593 A2 | 10/2006 |
| WO | WO-2006/124890 A1 | 11/2006 |
| WO | WO-2006/124898 A1 | 11/2006 |
| WO | WO-2006/127637 A2 | 11/2006 |
| WO | WO-2006/128471 A2 | 12/2006 |
| WO | WO-2006/133733 A1 | 12/2006 |
| WO | WO-2007/008752 A2 | 1/2007 |
| WO | WO-2007/014061 A1 | 2/2007 |
| WO | WO-2007/021970 A2 | 2/2007 |
| WO | WO-2007/036671 A2 | 4/2007 |

(56) References Cited

FOREIGN PATENT DOCUMENTS

| | | |
|---|---|---|
| WO | WO-2007/048233 A1 | 5/2007 |
| WO | WO-2007/054378 A1 | 5/2007 |
| WO | WO-2007/070632 A2 | 6/2007 |
| WO | WO-2007/085024 A2 | 7/2007 |
| WO | WO-2007/109104 A2 | 9/2007 |
| WO | WO-2007/112286 A2 | 10/2007 |
| WO | WO-2007/132293 A2 | 11/2007 |
| WO | WO-2007/135193 A2 | 11/2007 |
| WO | WO-2008/027350 A1 | 3/2008 |
| WO | WO-2008/027442 A2 | 3/2008 |
| WO | WO-2008/060365 A2 | 5/2008 |
| WO | WO-2008/068471 A1 | 6/2008 |
| WO | WO-2008/086804 A2 | 7/2008 |
| WO | WO-2008/107149 A2 | 9/2008 |
| WO | WO-2008/140460 A1 | 11/2008 |
| WO | WO-2008/148798 A2 | 12/2008 |
| WO | WO-2009/005613 A2 | 1/2009 |
| WO | WO-2009/023672 A2 | 2/2009 |
| WO | WO-2009/032246 A2 | 3/2009 |
| WO | WO-2009/076764 A1 | 6/2009 |
| WO | WO-2009/079518 A1 | 6/2009 |
| WO | WO-2009/089494 A2 | 7/2009 |
| WO | WO-2009/092601 A1 | 7/2009 |
| WO | WO-2009/114648 A1 | 9/2009 |
| WO | WO-2009/129282 A1 | 10/2009 |
| WO | WO-2010/032128 A1 | 3/2010 |
| WO | WO-2010/044736 A1 | 4/2010 |
| WO | WO-2010/044842 A1 | 4/2010 |
| WO | WO-2010/069050 A1 | 6/2010 |
| WO | WO-2010/080580 A2 | 7/2010 |
| WO | WO-2010/083843 A1 | 7/2010 |
| WO | WO-2010/085641 A1 | 7/2010 |
| WO | WO-2010/088911 A1 | 8/2010 |
| WO | WO-2010/105672 A1 | 9/2010 |
| WO | WO-2010/105673 A1 | 9/2010 |
| WO | WO-2010/140007 A2 | 12/2010 |
| WO | WO-2010/149169 A2 | 12/2010 |
| WO | WO-2011/009602 A1 | 1/2011 |
| WO | WO-2011/009604 A1 | 1/2011 |
| WO | WO-2011/039768 A2 | 4/2011 |
| WO | WO-2011/041414 A1 | 4/2011 |
| WO | WO-2011/068723 A1 | 6/2011 |
| WO | WO-2011/106076 A1 | 9/2011 |
| WO | WO-2011/141489 A1 | 11/2011 |
| WO | WO-2011/141490 A1 | 11/2011 |
| WO | WO-2012/028318 A1 | 3/2012 |
| WO | WO-2012/028319 A1 | 3/2012 |
| WO | WO-2012/040651 A2 | 3/2012 |
| WO | WO-2012/052955 A1 | 4/2012 |
| WO | WO-2012/056402 A2 | 5/2012 |
| WO | WO-2012/063257 A2 | 5/2012 |
| WO | WO-2012/080833 A2 | 6/2012 |
| WO | WO-2012/085656 A2 | 6/2012 |
| WO | WO-2012/085657 A2 | 6/2012 |
| WO | WO-2012/087377 A1 | 6/2012 |
| WO | WO-2012/112952 A1 | 8/2012 |
| WO | WO-2012/131463 A2 | 10/2012 |
| WO | WO-2012/159142 A1 | 11/2012 |
| WO | WO-2013/017234 A1 | 2/2013 |
| WO | WO-2013/017242 A1 | 2/2013 |
| WO | WO-2013/038267 A1 | 3/2013 |
| WO | WO-2013/038268 A1 | 3/2013 |
| WO | WO-2013/050539 A2 | 4/2013 |
| WO | WO-2013/057570 A1 | 4/2013 |
| WO | WO-2013/072395 A1 | 5/2013 |
| WO | WO-2013/077851 A1 | 5/2013 |
| WO | WO-2013/084059 A1 | 6/2013 |
| WO | WO-2013/127830 A1 | 9/2013 |
| WO | WO-2013/127831 A1 | 9/2013 |
| WO | WO-2013/153451 A2 | 10/2013 |
| WO | WO-2013/158810 A1 | 10/2013 |
| WO | WO-2013/158814 A1 | 10/2013 |
| WO | WO-2014/006004 A1 | 1/2014 |
| WO | WO-2014/011830 A1 | 1/2014 |
| WO | WO-2014/022570 A1 | 2/2014 |
| WO | WO-2014/123899 A1 | 8/2014 |
| WO | WO-2014/144027 A1 | 9/2014 |
| WO | WO-2014/191396 A1 | 12/2014 |
| WO | WO-2015/034846 A1 | 3/2015 |
| WO | WO-2015/095387 A1 | 6/2015 |
| WO | WO-2015/100197 A1 | 7/2015 |
| WO | WO-2015/120110 A2 | 8/2015 |
| WO | WO-2015/120201 A1 | 8/2015 |
| WO | WO-2015/157150 A1 | 10/2015 |
| WO | WO-2016/004170 A1 | 1/2016 |
| WO | WO-2016/038584 A1 | 3/2016 |
| WO | WO-2016/094358 A1 | 6/2016 |
| WO | WO-2016/111731 A1 | 7/2016 |
| WO | WO-2016/134454 A1 | 9/2016 |
| WO | WO-2016/169663 A1 | 10/2016 |
| WO | WO-2016/170093 A1 | 10/2016 |
| WO | WO-2016/170096 A1 | 10/2016 |
| WO | WO-2016/170097 A1 | 10/2016 |
| WO | WO-2017/002829 A1 | 1/2017 |
| WO | WO-2017/040607 A1 | 3/2017 |
| WO | WO-2017/059374 A1 | 4/2017 |
| WO | WO-2017/070462 A1 | 4/2017 |
| WO | WO-2017/070566 A1 | 4/2017 |
| WO | WO-2017/087373 A1 | 5/2017 |
| WO | WO-2017/136460 A1 | 8/2017 |
| WO | WO-2017/139106 A1 | 8/2017 |
| WO | WO-2017/172406 A1 | 10/2017 |
| WO | WO-2017/178658 A1 | 10/2017 |
| WO | WO-2017/192608 A1 | 11/2017 |
| WO | WO-2018/024709 A1 | 2/2018 |

OTHER PUBLICATIONS

Morphine sulfate ([online] retrieved on Sep. 3, 2021 from: https://www.sigmaaldrich.com/US/en/substance/morphinesulfate758836211150; 1 page). (Year: 2021).*

Swarbrick, J. (Encyclopedia of Pharmaceutical Technology 2013;6: p. 3659) 1 page (Year: 2013).*

FDA Consumer article ([online] retrieved on Feb. 22, 2022 from: https://www.fda.gov/drugs/resources-you-drugs/fda-ensures-equivalence-generic-drugs; 2002; 4 pages) (Year: 2002).*

Martin et al. (Chapter 5 Applications of Polyethyelene Oxide (POLYOX) in Hydrophilic Matrices in: Hydrophilic Matrix Tablets for Oral Controlled Release, AAPS Advances in the Pharmaceutical Sciences Series 16,2014: 123-141). (Year: 2014).*

Preechagoon et al. (AAPS PharmSciTech 2010;vol. II(3):1449-1455). (Year: 2010).*

Bartholomaeus et al., "Opioid extended-release tablets with improved tamper-resistant properties," Expert Opinion on Drug Delivery, vol. 9, No. 8 (2012).

Hodgman et al., "The Influence of Polyethylene Glycol Solution on the Dissolution Rate of Sustained Release Morphine," Journal of Medical Toxicology, vol. 12, No. 4, pp. 391-395 (Dec. 2016).

Jedinger, "The design of controlled-release formulations resistant to alcohol-induced dose dumping—A review," European Journal of Pharmaceutics and Biopharmaceutics, vol. 87, No. 2, pp. 217-226 (Jul. 2014).

Jones et al., "Drug Formulation Advances in Extended-Release Medications for Pain Control," Current Pain and Headache Reports (Jun. 2016).

Maincent et al, "Recent advances in abuse-deterrent technologies for the delivery of opioids," International Journal of Pharmaceutics, vol. 510, No. 1, pp. 57-72 (Aug. 20, 2016).

Rahman et al., "Assessing impact of formulation and process variables on in-vitro performance of directly compressed abuse deterrent formulations," International Journal of Pharmaceutics, vol. 502, No. 1-2, pp. 138-150 (Apr. 11, 2016).

Rahman et al., "Effects of excipients and curing process on the abuse deterrent properties of directly compressed tablets," International Journal of Pharmaceutics, vol. 517, No. 1-2, pp. 303-311 (Jan. 30, 2017).

Sampada et al., "Properties and Applications of Polyethylene Oxide and Ethylcellulose for Tamper Resistance and Controlled Drug Delivery," Melt Extrusion, pp. 145-158 (Oct. 11, 2013).

(56) References Cited

OTHER PUBLICATIONS

Schaeffer, "Abuse-Deterrent Formulations, an Evolving Technology Against the Abuse and Misuse of Opioid Analgesics," Journal of Medical Toxicology, vol. 8, No. 4, pp. 400-407 (Dec. 2012).

The Dow Chemical Company, "Polyox Water Soluble Resins Combining Flexibility with Consistency", Oct. 2013, pp. 1-16.

Muppalaneni, Srinath et al., "Crush resistance and insufflation potential of poly(ethylene oxide)-based abuse deterrent formulations", Expert Opinion of Drug Delivery, 13:10, 1375-1382, 2016.

* cited by examiner

Figure 78 (a)
Device: Spoons - Winco®, 18/0 stainless steel teaspoons
| Time (Mins) | Tablet | % Recovery (Total Weight) | Results | Particle Size (% Weight Retained) |
|---|---|---|---|---|
| 5 | B | 99.9% | 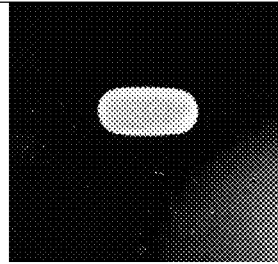 No change | NA |
| 5 | D | 99.9% | 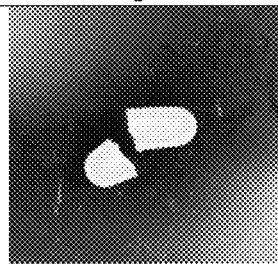 Broken into two pieces | NA |
| 5 | E | 100% | 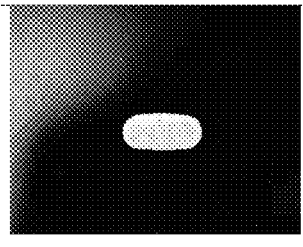 Cracked in the middle | NA |
| 5 | MS Contin 100mg | 97.9% | 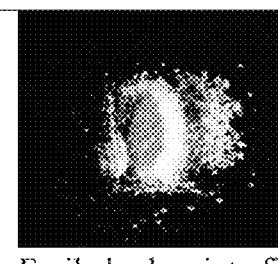 Easily broken into fine particles | (1) See Fig. 78(b) |

Figure 79 (a)
Device: Pill crusher - Life Brand
| Time (Mins) | Tablet | % Recovery (Total Weight) | Results | Particle Size (% Weight Retained) |
|---|---|---|---|---|
| 5 | B | 100% | 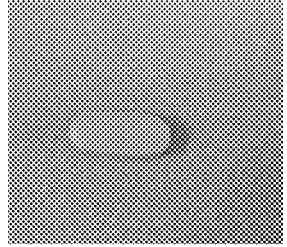 No change | NA |
| 5 | D | 100% | 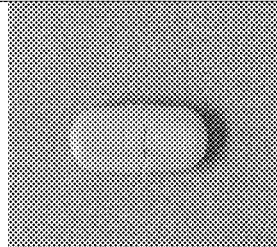 Crack in the middle | NA |
| 5 | E | 100% | 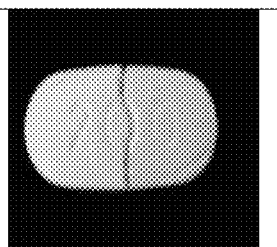 Cracked in the middle | NA |
| 5 | MS Contin 100mg | 95.0% | 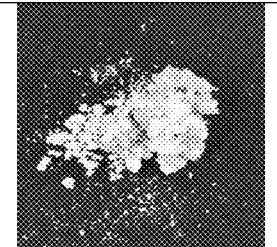 Broken into particles | (1) See Fig. 79(b) |

Figure 80 (a)

Device: Mortar/pestle - CoorsTek®, Porcelain Ceramic Mortar and Pestle # 60319

| Time (Mins) | Tablet | % Recovery (Total Weight) | Results | Particle Size (% Weight Retained) |
|---|---|---|---|---|
| 5 | B | 99.7% | 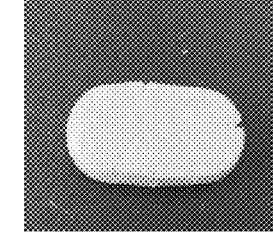 Very hard to grind. Cracks on tablet | NA |
| 5 | D | 98.6% | 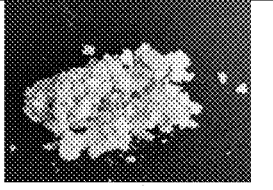 Grinded into small pieces | (1) See Fig 80(b) |
| 5 | E | 98.6% | 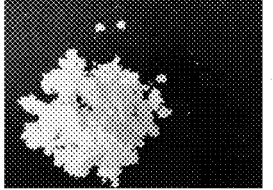 Difficult to grind, stuck together and grinded into small pieces | (2) See Fig 80(b) |
| 5 | MS Contin 100mg | 65.0% | 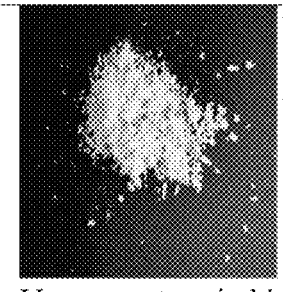 Very easy to grind into fine particles | (3) See Fig 80(b) |

Figure 81 (a)

Device: Hammer - Tekton®, 16 oz wood claw hammer

| Time (Mins) | Tablet | % Recovery (Total Weight) | Results | Particle Size (% Weight Retained) |
|---|---|---|---|---|
| 1 | B | 97.2% | 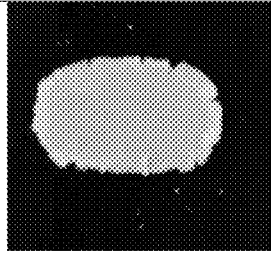 Not difficult to get a flat piece, color coating | NA |
| 1 | D | 98.5% | 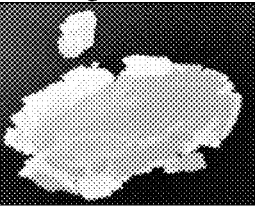 Not difficult to get a flat piece | NA |
| 1 | E | 98.9% |  Not difficult to get a flat piece with 2 small particles | (1) See Fig 81(b) |
| 1 | MS Contin 100mg | 97.7% | 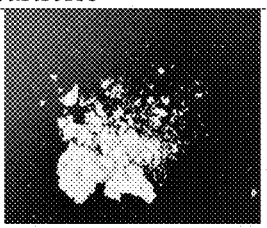 Very easy to crack the tablet into small pieces, some pieces stuck to the hammer | (2) See Fig 81(b) |

Figure 82 (a)
Device: Foot file – Ultra Pedi Tool
| Time (Mins) | Tablet | % Recovery (Total Weight) | Results | Particle Size (% Weight Retained) |
|---|---|---|---|---|
| 5 | B | 98.7% | 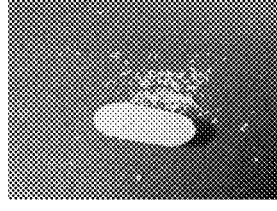 Difficult to grate | (1) See Fig. 82(b) |
| 5 | D | 95.8% |  Difficult to grate | (2) See Fig. 82(b) |
| 5 | E | 98.3% |  Difficult to grate | (3) See Fig. 82(b) |
| 5 | MS Contin 100mg | 93.7% | 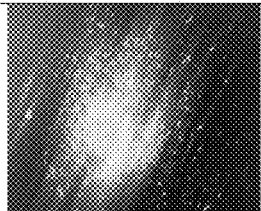 Very easy to grate | (4) See Fig. 82(b) |

Figure 83 (a)
Device: Food grater - Microplane®, 5100506, 18/8 gauge stainless steel blade
| Time (Mins) | Tablet | % Recovery (Total Weight) | Results | Particle Size (% Weight Retained) |
|---|---|---|---|---|
| 5 | B | 99.1% | 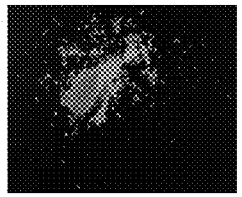 Difficult to grate and hold the tablet | (1) See Fig. 83(b) |
| 5 | D | 98.7% | 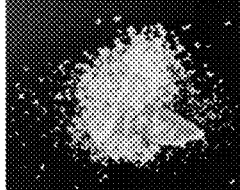 Difficult to grate | (2) See Fig. 83(b) |
| 5 | E | 99.0% | 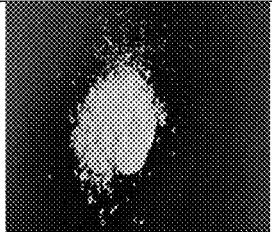 Difficult to grate | (3) See Fig. 83(b) |
| 5 | MS Contin 100mg | 98.0% |  Easily grated but difficult to hold the tablet | (4) See Fig. 83(b) |

Figure 84 (a)
Device: Razor blade –GEM® stainless steel uncoated single edge industrial
| Time (Mins) | Tablet | % Recovery (Total Weight) | Results | Particle Size (% Weight Retained) |
|---|---|---|---|---|
| 5 | B | 99.5% | 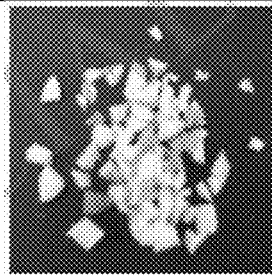 Able to cut into pieces | (1) See Fig. 84(b) |
| 5 | D | 99.4% | 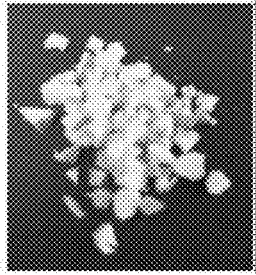 Able to cut into pieces | (2) See Fig. 84(b) |
| 5 | E | 100% | 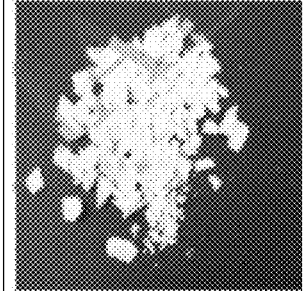 Able to cut into pieces | (3) See Fig. 84(b) |
| 5 | MS Contin 100mg | 98.2% | 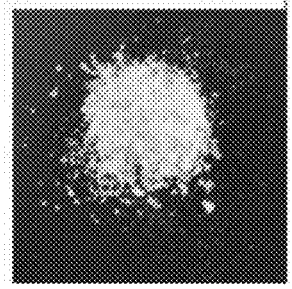 Very easy to cut into small particles | (4) See Fig. 84(b) |

Figure 85 (a)
Device: Spice grinder - Waring® Commercial, Model WSG30
| Time (Mins) | Tablet | % Recovery (Total Weight) | Results | Particle Size (% Weight Retained) |
|---|---|---|---|---|
| 1 | B | 90.7% | 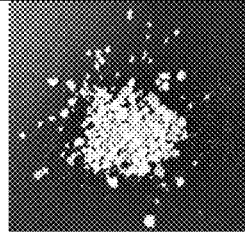<br>Easy to grind to fine particles | (1) See Fig. 85(b) |
| 1 | D | 92.4% | 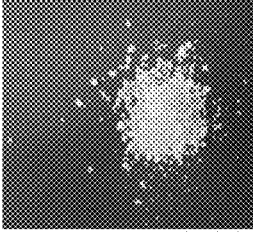<br>Easy to grind to fine particles | (2) See Fig. 85(b) |
| 1 | E | 91.4% | 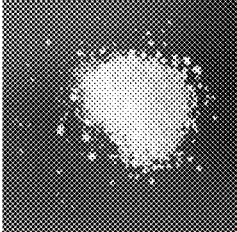<br>Easy to grind to fine particles | (3) See Fig. 85(b) |
| 1 | MS Contin 100mg | 79.2% | 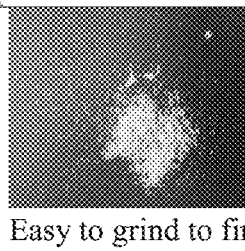<br>Easy to grind to fine particles | (4) See Fig. 85(b) |

Figure 86 (a)
Device: Coffee grinder Krups®
| Time (Mins) | Tablet | % Recovery (Total Weight) | Results | Particle Size (% Weight Retained) |
|---|---|---|---|---|
| 1 | B | 89.8% | 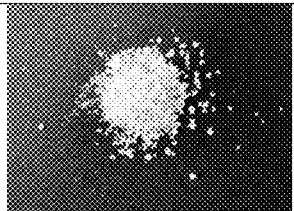<br>Easy to grind | (1) See Fig. 86(b) |
| 1 | D | 91.3% | <br>Easy to grind | (2) See Fig. 86(b) |
| 1 | E | 91.4% | 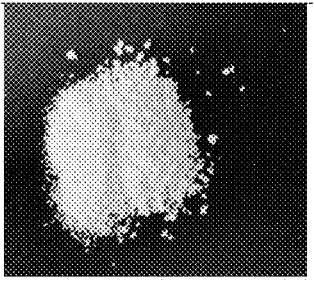<br>Easy to grind | (3) See Fig. 86(b) |
| 1 | MS Contin 100mg | 83.8% | 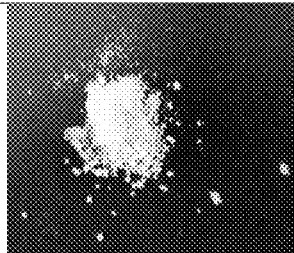<br>Very Easy to grind | (4) See Fig. 86(b) |

Figure 87 (a)
Device: Mill- IKA® A11 basic
| Time (Mins) | Tablet | % Recovery (Total Weight) | Results | Particle Size (% Weight Retained) |
|---|---|---|---|---|
| 1 | B | 90.0% | 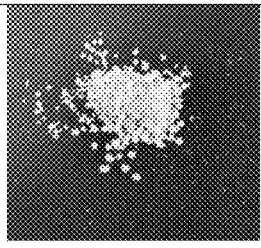 Ground into smaller particles | (1) See Fig. 87(b) |
| 1 | D | 91.8% | 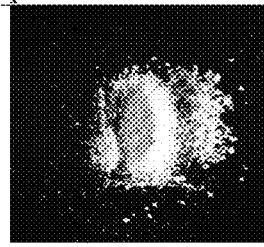 Ground into smaller particles | (2) See Fig. 87(b) |
| 1 | E | 93.2% | 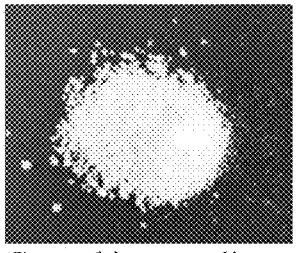 Ground into smaller particles | (3) See Fig. 87(b) |
| 1 | MS Contin 100mg | 86.4% |  Ground into smaller particles | (4) See Fig. 87(b) |

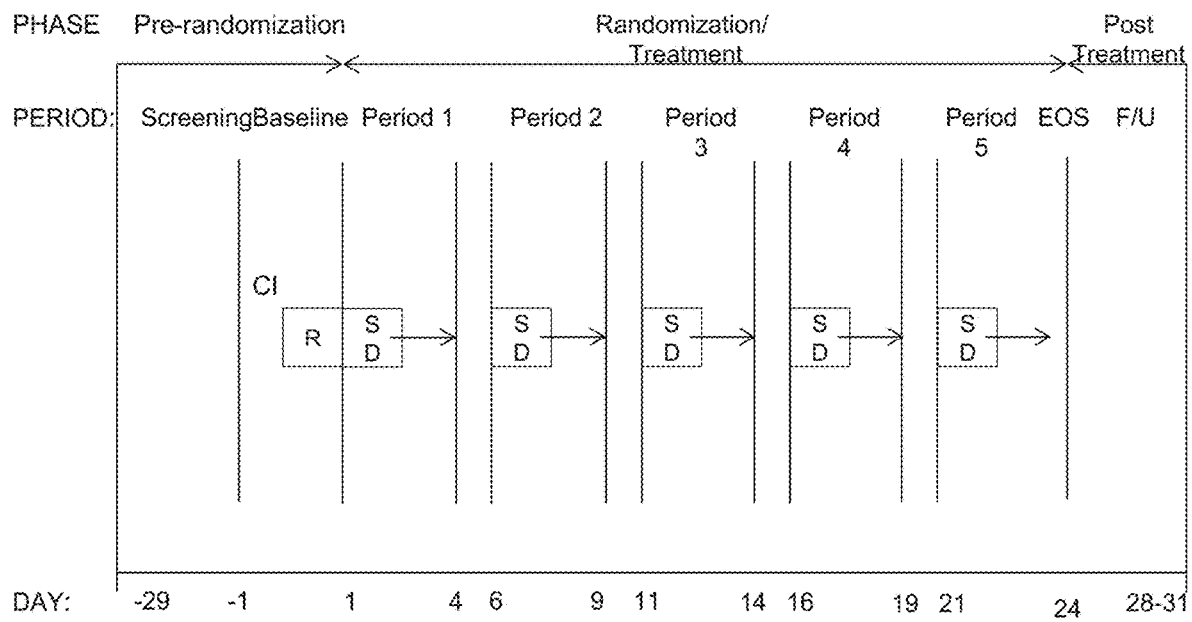

Minimum 5 day washout between study drug administrations. CI= Check-in may occur in period 1 only, however, if the subjects leave the unit in between periods (during their washout periods), they will be required to check-in at each period. R= Randomization (period 1 only). SD = Study drug administration EOS = End-of-study: This visit will take place 3 days (72 hours) after last dosing of tablets in this application or MS Contin® dosing; 1 day (24 hours) after last dosing with morphine sulfate oral solution (IR); or upon early discontinuation from the study.

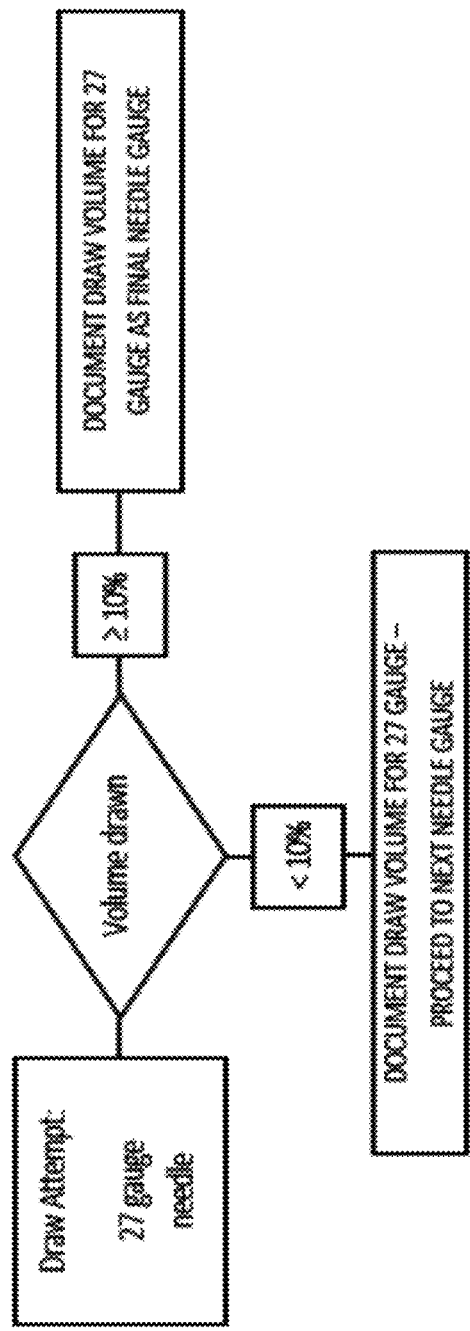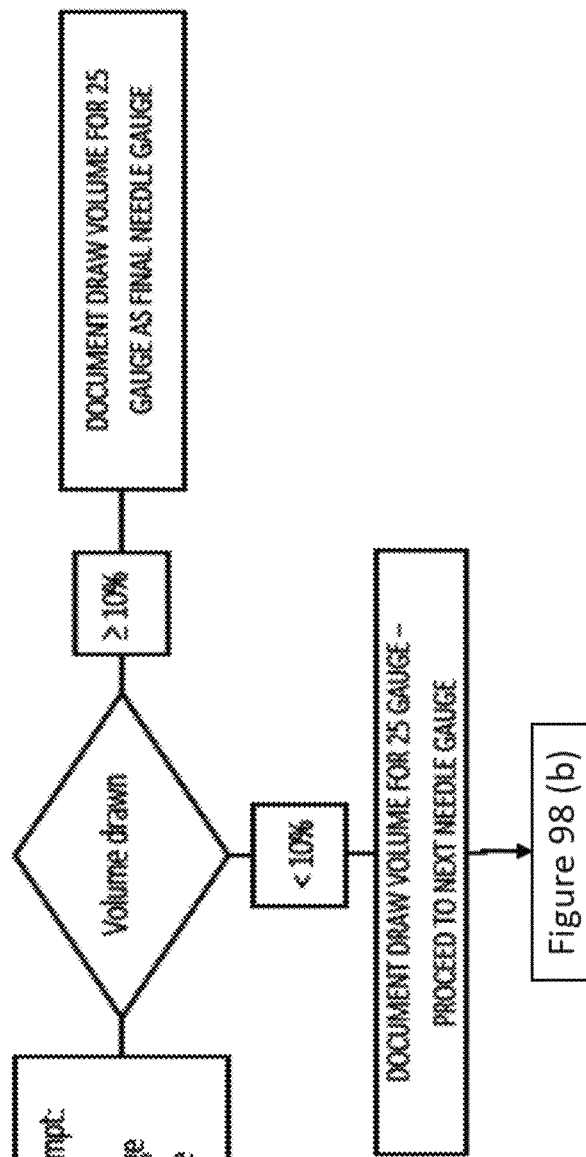
Figure 98 (a)
Figure 98 (b)

ABUSE DETERRENT MORPHINE SULFATE DOSAGE FORMS

CROSS-REFERENCE TO RELATED APPLICATIONS

This application is the U.S. national phase, pursuant to 35 U.S.C. § 371, of PCT International Application Ser. No. PCT/US2018/066165, filed on Dec. 18, 2018, designating the United States, which claims priority to U.S. Provisional Application Ser. No. 62/607,991 filed on Dec. 20, 2017, and U.S. Provisional Application Ser. No. 62/687,914, filed on Jun. 21, 2018. The contents of the afore-mentioned patent applications are incorporated herein in their entirety.

TECHNICAL FIELD OF THE INVENTION

The present invention relates to a solid oral extended release pharmaceutical dosage form of morphine sulfate. The dosage form comprises polyethylene oxide which provides for an extended release of morphine sulfate as well as for improved abuse-deterrent properties. In certain embodiments, the dosage forms of the present invention offer improved characteristics, such as a reduced potential for physical manipulation (including crushing, grinding, solvent extraction, injection, inhaling) and thus a reduced abuse potential. The present invention further relates to an extended release matrix formulation comprising morphine sulfate and polyethylene oxide, as well as to a process of preparing the solid oral extended release pharmaceutical dosage form. The present invention also relates to a method of treating pain, and to a method as well as to a use of polyethylene oxide for increasing the breaking strength and/or the cracking force and/or the crush resistance of a solid oral extended release pharmaceutical dosage form.

BACKGROUND OF THE INVENTION

Pharmaceutical dosage forms containing opioids such as morphine are potent analgesics and provide important improvements in the quality of life for patients suffering from pain. However, they may sometimes be the subject of abuse.

Extended release formulations of opioids have been developed to provide slow, continuous release of the opioid for prolonged pain relief and less frequent dosing as they can, at steady-state conditions, help maintain plasma concentration levels within the therapeutic range. This is beneficial and convenient e.g. for patients with chronic pain or elderly patients. However, extended release formulations that have been manipulated may be targets of abuse as they may contain higher amounts of the active pharmaceutical ingredient (API) than immediate release forms.

Abuse of pharmaceutical dosage forms can include physical manipulation, such as crushing, hammering, cutting/slicing, grating, grinding and milling. The resulting powders can then directly be dissolved and swallowed, taken intranasally or smoked. Additionally, the API may be extracted from intact or crushed/milled tablets in a variety of solvents (including ethanol) and subsequently injected or taken orally.

Abuse-deterrent technologies have been developed to make manipulation of opioid dosage forms more difficult and to reduce the potential rewards associated with abuse.

Published US patent application 2009/0081290 (corresponding to international application WO 2008/023261) discloses tamper resistant dosage forms including opioid analgesics. In certain embodiments these dosage forms are solid, oral extended-release pharmaceutical dosage forms comprising an extended release matrix comprising polyethylene oxide and an opioid analgesic. The tablets or multiparticulates are disclosed therein to be resistant to alcohol extraction and to dose dumping when concomitantly used with or in contact with alcohol. Additionally, the tablets or multi-particulates can be flattened without breaking, characterized by a thickness of the tablet or individual multi-particulate after the flattening which corresponds to no more than about 60% of the thickness of the tablet or individual multi particulate before flattening, and wherein said flattened dosage form provides an in-vitro dissolution rate in simulated gastric fluid (SGF) without or with ethanol as described therein that deviates only to a very low extent from the corresponding in-vitro dissolution rate of a non-flattened reference dosage form.

Morphine sulfate dosage forms are currently marketed in the United States by Purdue Pharma L.P. under the trade name MS Contin® as controlled release oral tablets in strengths of 15 mg, 30 mg, 60 mg, 100 mg and 200 mg. However, there exists a need in the art for an extended release formulation containing morphine sulfate, which has improved abuse deterrent properties.

It is therefore an object of the present invention to provide solid oral extended release pharmaceutical dosage forms of morphine sulfate for the treatment of pain that preferably have similar bioavailability as the current commercial product MS Contin® but are less prone to be able to be abused.

It is a further object of the present invention to provide solid oral extended release pharmaceutical dosage forms of morphine sulfate for the treatment of pain that preferably have similar bioavailability as the current commercial product MS Contin® but a reduced possibility of physical manipulation or tampering.

It is a further object of the present invention to provide solid oral extended release pharmaceutical dosage forms of morphine sulfate for the treatment of pain that preferably have similar bioavailability as the current commercial product MS Contin® but an increased hardness (as reflected by the breaking strength, cracking force and/or crush resistance as described herein).

It is a further object of the present invention to provide solid oral extended release pharmaceutical dosage forms of morphine sulfate for the treatment of pain that preferably have similar bioavailability as the current commercial product MS Contin® but reduced extractability in common solvents, such as water, saline, ethanol or methanol.

It is a further object of the present invention to provide solid oral extended release pharmaceutical dosage forms of morphine sulfate for the treatment of pain that preferably have similar bioavailability as the current commercial product MS Contin® but reduced syringeability.

It is a further object of the present invention to provide solid oral extended release pharmaceutical dosage forms of morphine sulfate for the treatment of pain that preferably have similar bioavailability as the current commercial product MS Contin® but lower levels of drug liking, particularly when administered intranasally.

SUMMARY OF THE INVENTION

The above objects are achieved by the embodiments of the present invention as described and claimed herein.

In its most general aspect, the present invention is directed to a solid oral extended release pharmaceutical dosage form comprising a cured extended release matrix formulation, the extended release matrix formulation comprising:
  a therapeutically effective amount of morphine sulfate, and
  polyethylene oxide.

The present invention is also generally directed to a solid oral extended release pharmaceutical dosage form comprising a cured extended release matrix formulation, wherein the cured extended release matrix formulation comprises:
  a therapeutically effective amount of morphine sulfate, and
  polyethylene oxide
and is obtainable by at least the following steps:
  (a) combining at least morphine sulfate and polyethylene oxide particles to form a composition,
  (b) shaping the composition of step (a) to form the extended release matrix formulation, and
  (c) curing the extended release matrix formulation of step (b).

In certain embodiments, the present invention is directed to a solid oral extended release pharmaceutical dosage form comprising a cured extended release matrix formulation, the extended release matrix formulation comprising:
  a therapeutically effective amount of morphine sulfate, and
  polyethylene oxide having an approximate molecular weight of from about 600,000 to about 3,000,000.

In certain embodiments, the present invention is directed to a solid oral extended release pharmaceutical dosage form comprising a cured extended release matrix formulation, wherein the cured extended release matrix formulation comprises:
  a therapeutically effective amount of morphine sulfate, and
  polyethylene oxide
and is obtainable by at least the following steps:
  (a) combining at least morphine sulfate and polyethylene oxide particles having an approximate molecular weight of from about 600,000 to about 3,000,000 to form a composition,
  (b) shaping the composition of step (a) to form the extended release matrix formulation, and
  (c) curing the extended release matrix formulation of step (b).

In certain embodiments, the present invention is directed to a solid oral extended release pharmaceutical dosage form comprising a cured extended release matrix formulation, the extended release matrix formulation comprising:
  a therapeutically effective amount of morphine sulfate and polyethylene oxide,
wherein the cured extended release matrix formulation is obtainable by at least the following steps:
  (a) combining at least morphine sulfate and polyethylene oxide particles to form a composition,
  (b) shaping the composition of step (a) to form the extended release matrix formulation, and
  (c) curing the extended release matrix formulation of step (b);
wherein the polyethylene oxide particles used in step (a) are characterized in that about 90% or more of the polyethylene oxide particles pass through a 60 mesh (0.250 mm; 250 microns) sieve; and wherein the polyethylene oxide used as the polyethylene oxide particles in step (a) has an approximate molecular weight of from about 900,000 to about 2,000,000.

In certain embodiments, the present invention is directed to a solid oral extended release pharmaceutical dosage form comprising a cured extended release matrix formulation, the extended release matrix formulation comprising:
  a therapeutically effective amount of morphine sulfate, and
  polyethylene oxide having an approximate molecular weight of from about 900,000 to about 2,000,000;
the dosage form having a breaking strength of least about 200 N.

In certain embodiments, the present invention is directed to a solid oral extended release pharmaceutical dosage form comprising a cured extended release matrix formulation, the extended release matrix formulation comprising:
  a therapeutically effective amount of morphine sulfate, and
  polyethylene oxide having an approximate molecular weight of from about 900,000 to about 2,000,000;
the dosage form having a cracking force of at least about 150 N.

In certain embodiments, the present invention is directed to a solid oral extended release pharmaceutical dosage form comprising a cured extended release matrix formulation, the extended release matrix formulation comprising:
  a therapeutically effective amount of morphine sulfate, and
  polyethylene oxide having an approximate molecular weight of from about 900,000 to about 2,000,000;
the dosage form having a crush resistance of at least about 400 N.

In certain embodiments, the present invention is directed to a solid oral extended release pharmaceutical dosage form comprising a cured extended release matrix formulation, the extended release matrix formulation comprising:
  a therapeutically effective amount of morphine sulfate, and
  polyethylene oxide;
the dosage form after administration providing a dose adjusted $C_{max}$ of morphine of from about 3 ng/mL to about 9 ng/mL per 15 mg of morphine hemi(sulfate pentahydrate) (having a molecular weight of 758.8 g/mol) or an equimolar amount of another solvate or hydrate of morphine sulfate included in the dosage form, and
the dosage form having a breaking strength of least about 200 N.

In certain embodiments, the present invention is directed to a solid oral extended release pharmaceutical dosage form comprising a cured extended release matrix formulation, the extended release matrix formulation comprising:
  a therapeutically effective amount of morphine sulfate, and
  polyethylene oxide;
the dosage form after administration providing a dose adjusted $C_{max}$ of morphine of from about 3 ng/mL to about 9 ng/mL per 15 mg of morphine hemi(sulfate pentahydrate) (having a molecular weight of 758.8 g/mol) or an equimolar amount of another solvate or hydrate of morphine sulfate included in the dosage form, and
the dosage form having a cracking force of least about 150 N.

In certain embodiments, the present invention is directed to a solid oral extended release pharmaceutical dosage form comprising a cured extended release matrix formulation, the extended release matrix formulation comprising:
  a therapeutically effective amount of morphine sulfate, and
  polyethylene oxide;
the dosage form after administration providing a dose adjusted $C_{max}$ of morphine of from about 3 ng/mL to about 9 ng/mL per 15 mg of morphine hemi(sulfate pentahydrate) (having a molecular weight of 758.8 g/mol) or an equimolar amount of another solvate or hydrate of morphine sulfate included in the dosage form, and
the dosage form having a crush resistance of at least about 400 N.

In certain embodiments, the present invention is directed to a solid oral extended release pharmaceutical dosage form comprising a cured extended release matrix formulation, the extended release matrix formulation comprising:
 a therapeutically effective amount of morphine sulfate, and
 polyethylene oxide;
the dosage form after administration providing a dose adjusted $AUC_t$ and/or a dose adjusted $AUC_{inf}$ of morphine of from about 30 ng*hr/mL to about 100 ng*hr/mL per 15 mg of morphine hemi(sulfate pentahydrate) (having a molecular weight of 758.8 g/mol) or an equimolar amount of another solvate or hydrate of morphine sulfate included in the dosage form, and the dosage form having a breaking strength of least about 200 N.

In certain embodiments, the present invention is directed to a solid oral extended release pharmaceutical dosage form comprising a cured extended release matrix formulation, the extended release matrix formulation comprising:
 a therapeutically effective amount of morphine sulfate, and
 polyethylene oxide;
the dosage form after administration providing a dose adjusted $AUC_t$ and/or a dose adjusted $AUC_{inf}$ of morphine of from about 30 ng*hr/mL to about 100 ng*hr/mL per 15 mg of morphine hemi(sulfate pentahydrate) (having a molecular weight of 758.8 g/mol) or an equimolar amount of another solvate or hydrate of morphine sulfate included in the dosage form, and the dosage form having a cracking force of least about 150 N.

In certain embodiments, the present invention is directed to a solid oral extended release pharmaceutical dosage form comprising a cured extended release matrix formulation, the extended release matrix formulation comprising:
 a therapeutically effective amount of morphine sulfate, and
 polyethylene oxide;
the dosage form after administration providing a dose adjusted $AUC_t$ and/or a dose adjusted $AUC_{inf}$ of morphine of from about 30 ng*hr/mL to about 100 ng*hr/mL per 15 mg of morphine hemi(sulfate pentahydrate) (having a molecular weight of 758.8 g/mol) or an equimolar amount of another solvate or hydrate of morphine sulfate included in the dosage form, and the dosage form having a crush resistance of at least about 400 N.

In certain embodiments, the present invention is directed to a solid oral extended release pharmaceutical dosage form of morphine sulfate, wherein the dosage form is a tablet comprising 15 mg of morphine hemi(sulfate pentahydrate) (having a molecular weight of 758.8 g/mol) or an equimolar amount of another solvate or hydrate of morphine sulfate included in an extended release matrix formulation, wherein the dosage form when tested in a comparative clinical study is bioequivalent to the commercial product MS Contin® containing an equimolar amount of morphine sulfate, and wherein the dosage form has a breaking strength of at least about 230 N and/or a cracking force of at least about 180 N and/or a crush resistance of at least about 400 N.

In certain embodiments, the present invention is directed to a solid oral extended release pharmaceutical dosage form of morphine sulfate, wherein the dosage form is a tablet comprising 15 mg of morphine hemi(sulfate pentahydrate) (having a molecular weight of 758.8 g/mol) or an equimolar amount of another solvate or hydrate of morphine sulfate included in an extended release matrix formulation, wherein the dosage form when tested in a comparative clinical study is bioequivalent to a reference tablet containing an equimolar amount of morphine sulfate in a matrix formulation, and wherein the dosage form has a breaking strength of at least about 230 N and/or a cracking force of at least about 180 N and/or a crush resistance of at least about 400 N, wherein the reference tablet contains:
 a) morphine sulfate: 15 mg/tablet
 b) lactose (spray-dried): 85 mg/tablet
 c) cetostearyl alcohol: 35 mg/tablet
 d) hydroxyethyl cellulose: 10 mg/tablet
 e) talc: 3 mg/tablet
 f) magnesium stearate: 2 mg/tablet
 g) Opadry® coating: 5 mg/tablet.

In certain embodiments, the present invention is directed to a solid oral extended release pharmaceutical dosage form of morphine sulfate, wherein the dosage form is a tablet comprising 30 mg of morphine hemi(sulfate pentahydrate) (having a molecular weight of 758.8 g/mol) or an equimolar amount of another solvate or hydrate of morphine sulfate included in an extended release matrix formulation, wherein the dosage form when tested in a comparative clinical study is bioequivalent to the commercial product MS Contin® containing an equimolar amount of morphine sulfate, and wherein the dosage form has a breaking strength of at least about 250 N and/or a cracking force of at least about 200 N and/or a crush resistance of at least about 400 N.

In certain embodiments, the present invention is directed to a solid oral extended release pharmaceutical dosage form of morphine sulfate, wherein the dosage form is a tablet comprising 30 mg of morphine hemi(sulfate pentahydrate) (having a molecular weight of 758.8 g/mol) or an equimolar amount of another solvate or hydrate of morphine sulfate included in an extended release matrix formulation, wherein the dosage form when tested in a comparative clinical study is bioequivalent to a reference tablet containing an equimolar amount of morphine sulfate in a matrix formulation, and wherein the dosage form has a breaking strength of at least about 250 N and/or a cracking force of at least about 200 N and/or a crush resistance of at least about 400 N, wherein the reference tablet contains:
 a) morphine sulfate: 30 mg/tablet
 b) lactose (spray-dried): 70 mg/tablet
 c) cetostearyl alcohol: 35 mg/tablet
 d) hydroxyethyl cellulose: 10 mg/tablet
 e) talc: 3 mg/tablet
 f) magnesium stearate: 2 mg/tablet
 g) Opadry® coating: 5 mg/tablet.

In certain embodiments, the present invention is directed to a solid oral extended release pharmaceutical dosage form of morphine sulfate, wherein the dosage form is a tablet comprising 60 mg of morphine hemi(sulfate pentahydrate) (having a molecular weight of 758.8 g/mol) or an equimolar amount of another solvate or hydrate of morphine sulfate included in an extended release matrix formulation, wherein the dosage form when tested in a comparative clinical study is bioequivalent to the commercial product MS Contin® containing an equimolar amount of morphine sulfate, and wherein the dosage form has a breaking strength of at least about 280 N and/or a cracking force of at least about 200 N and/or a crush resistance of at least about 400 N.

In certain embodiments, the present invention is directed to a solid oral extended release pharmaceutical dosage form of morphine sulfate, wherein the dosage form is a tablet comprising 60 mg of morphine hemi(sulfate pentahydrate) (having a molecular weight of 758.8 g/mol) or an equimolar amount of another solvate or hydrate of morphine sulfate included in an extended release matrix formulation, wherein the dosage form when tested in a comparative clinical study is bioequivalent to a reference tablet containing an equimolar amount of morphine sulfate in a matrix formulation, and wherein the dosage form has a breaking strength of at least about 280 N and/or a cracking force of at least about 200 N and/or a crush resistance of at least about 400 N, wherein the reference tablet contains:
  a) morphine sulfate: 60 mg/tablet
  b) lactose (spray-dried): 42.2 mg/tablet
  c) cetostearyl alcohol: 32.8 mg/tablet
  d) hydroxyethyl cellulose: 10 mg/tablet
  e) talc: 3 mg/tablet
  f) magnesium stearate: 2 mg/tablet
  g) Opadry® coating: 5 mg/tablet.

In certain embodiments, the present invention is directed to a solid oral extended release pharmaceutical dosage form of morphine sulfate, wherein the dosage form is a tablet comprising 100 mg of morphine hemi(sulfate pentahydrate) (having a molecular weight of 758.8 g/mol) or an equimolar amount of another solvate or hydrate of morphine sulfate included in an extended release matrix formulation, wherein the dosage form when tested in a comparative clinical study is bioequivalent to the commercial product MS Contin® containing an equimolar amount of morphine sulfate, and wherein the dosage form has a breaking strength of least about 200 N and/or a cracking force of at least about 170 N and/or a crush resistance of at least about 400 N.

In certain embodiments, the present invention is directed to a solid oral extended release pharmaceutical dosage form of morphine sulfate, wherein the dosage form is a tablet comprising 100 mg of morphine hemi(sulfate pentahydrate) (having a molecular weight of 758.8 g/mol) or an equimolar amount of another solvate or hydrate of morphine sulfate included in an extended release matrix formulation, wherein the dosage form when tested in a comparative clinical study is bioequivalent to a reference tablet containing an equimolar amount of morphine sulfate in a matrix formulation, and wherein the dosage form has a breaking strength of least about 200 N and/or a cracking force of at least about 170 N and/or a crush resistance of at least about 400 N, wherein the reference tablet contains:
  a) morphine sulfate: 100 mg/tablet
  b) cetostearyl alcohol: 35 mg/tablet
  c) hydroxyethyl cellulose: 10 mg/tablet
  d) talc: 3 mg/tablet
  e) magnesium stearate: 2 mg/tablet
  f) Opadry® coating: 5 mg/tablet.

In certain embodiments, the present invention is directed to a solid oral extended release pharmaceutical dosage form of morphine sulfate, wherein the dosage form is a tablet comprising 200 mg of morphine hemi(sulfate pentahydrate) (having a molecular weight of 758.8 g/mol) or an equimolar amount of another solvate or hydrate of morphine sulfate included in an extended release matrix formulation, wherein the dosage form when tested in a comparative clinical study is bioequivalent to the commercial product MS Contin® containing an equimolar amount of morphine sulfate, and wherein the dosage form has a breaking strength of least about 350 N, and/or a cracking force of at least about 180 N and/or a crush resistance of at least about 400 N.

In certain embodiments, the present invention is directed to a solid oral extended release pharmaceutical dosage form of morphine sulfate, wherein the dosage form is a tablet comprising 200 mg of morphine hemi(sulfate pentahydrate) (having a molecular weight of 758.8 g/mol) or an equimolar amount of another solvate or hydrate of morphine sulfate included in an extended release matrix formulation, wherein the dosage form when tested in a comparative clinical study is bioequivalent to a reference tablet containing an equimolar amount of morphine sulfate in a matrix formulation, and wherein the dosage form has a breaking strength of least about 350 N, and/or a cracking force of at least about 180 N and/or a crush resistance of at least about 400 N, wherein the reference tablet contains:
  a) morphine sulfate: 200 mg/tablet
  b) cetostearyl alcohol: 70 mg/tablet
  c) hydroxyethyl cellulose: 20 mg/tablet
  d) talc: 6 mg/tablet
  e) magnesium stearate: 4 mg/tablet
  f) Opadry® coating: 10 mg/tablet.

In certain embodiments, the solid oral extended release pharmaceutical dosage form of the present invention is in the form of a tablet, the dosage form comprising a cured extended release matrix formulation, wherein the extended release matrix formulation is obtainable by combining:
about 5 mg (corresponding to about 5 to 7% by weight of the extended release matrix formulation) of morphine hemi (sulfate pentahydrate) (having a molecular weight of 758.8 g/mol) or an equimolar amount of another solvate or hydrate of morphine sulfate;
about 93 to 95% by weight of the extended release matrix formulation of polyethylene oxide having an approximate molecular weight of about 2,000,000 and/or polyethylene oxide having an approximate molecular weight of about 4,000,000; and
up to about 1% by weight of the extended release matrix formulation of a lubricant, preferably magnesium stearate.

In certain embodiments, the solid oral extended release pharmaceutical dosage form of the present invention is in the form of a tablet, the dosage form comprising a cured extended release matrix formulation, wherein the extended release matrix formulation is obtainable by combining:
about 10 mg (corresponding to about 8% by weight of the extended release matrix formulation) of morphine hemi (sulfate pentahydrate) (having a molecular weight of 758.8 g/mol) or an equimolar amount of another solvate or hydrate of morphine sulfate;
about 91 to 92% by weight of the extended release matrix formulation of polyethylene oxide having an approximate molecular weight of about 2,000,000 and/or polyethylene oxide having an approximate molecular weight of about 4,000,000; and
up to about 1% by weight of the extended release matrix formulation of a lubricant, preferably magnesium stearate.

In certain embodiments, the solid oral extended release pharmaceutical dosage form of the present invention is in the form of a tablet, the dosage form comprising a cured extended release matrix formulation, wherein the extended release matrix formulation is obtainable by combining:
about 15 mg (corresponding to about 12% by weight of the extended release matrix formulation) of morphine hemi (sulfate pentahydrate) (having a molecular weight of 758.8 g/mol) or an equimolar amount of another solvate or hydrate of morphine sulfate;
about 87% by weight of the extended release matrix formulation of polyethylene oxide having an approximate molecular weight of about 2,000,000; and
about 1% by weight of the extended release matrix formulation of a lubricant, preferably magnesium stearate.

In certain other embodiments, the solid oral extended release pharmaceutical dosage form of the present invention is in the form of a tablet, the dosage form comprising a cured extended release matrix formulation, wherein the extended release matrix formulation is obtainable by combining:

about 30 mg (corresponding to about 17% by weight of the extended release matrix formulation) of morphine hemi (sulfate pentahydrate) (having a molecular weight of 758.8 g/mol) or an equimolar amount of another solvate or hydrate of morphine sulfate;

about 82% by weight of the extended release matrix formulation of polyethylene oxide having an approximate molecular weight of about 2,000,000; and about 1% by weight of the extended release matrix formulation of a lubricant, preferably magnesium stearate.

In certain other embodiments, the solid oral extended release pharmaceutical dosage form of the present invention is in the form of a tablet, the dosage form comprising a cured extended release matrix formulation, wherein the extended release matrix formulation is obtainable by combining:

about 60 mg (corresponding to about 18% by weight of the extended release matrix formulation) of morphine hemi (sulfate pentahydrate) (having a molecular weight of 758.8 g/mol) or an equimolar amount of another solvate or hydrate of morphine sulfate;

about 81% by weight of the extended release matrix formulation of polyethylene oxide having an approximate molecular weight of about 2,000,000; and about 1% by weight of the extended release matrix formulation of a lubricant, preferably magnesium stearate.

In certain other embodiments, the solid oral extended release pharmaceutical dosage form of the present invention is in the form of a tablet, the dosage form comprising a cured extended release matrix formulation, wherein the extended release matrix formulation is obtainable by combining:

about 100 mg (corresponding to about 30% by weight of the extended release matrix formulation) of morphine hemi (sulfate pentahydrate) (having a molecular weight of 758.8 g/mol) or an equimolar amount of another solvate or hydrate of morphine sulfate;

about 68% by weight of the extended release matrix formulation of polyethylene oxide having an approximate molecular weight of about 2,000,000;

about 0.5% by weight of the extended release matrix formulation of a glidant, preferably colloidal silicon dioxide, and about 1.5% by weight of the extended release matrix formulation of a lubricant, preferably magnesium stearate.

In certain embodiments, the solid oral extended release pharmaceutical dosage form of the present invention is in the form of a tablet, the dosage form comprising a cured extended release matrix formulation, wherein the extended release matrix formulation is obtainable by combining:

about 200 mg (corresponding to about 33% by weight of the extended release matrix formulation) of morphine hemi (sulfate pentahydrate) (having a molecular weight of 758.8 g/mol) or an equimolar amount of another solvate or hydrate of morphine sulfate;

about 65% by weight of the extended release matrix formulation of polyethylene oxide having an approximate molecular weight of about 1,000,000;

about 0.5% by weight of the extended release matrix formulation of a glidant, preferably colloidal silicon dioxide; and about 1.5% by weight of the extended release matrix formulation of a lubricant, preferably magnesium stearate.

In a further aspect, the present invention is directed to an extended release matrix formulation obtainable by:
(a) combining at least a therapeutically effective amount of morphine sulfate and polyethylene oxide particles to form a composition; and
(b) shaping the composition of step (a) to form the extended release matrix formulation.

In a further aspect, the present invention is directed to a method of treating pain in a subject in need thereof, the method comprising administering to the subject the solid oral extended release pharmaceutical dosage form according to the present invention.

In a further aspect, the present invention is directed to a process of preparing a solid oral extended release pharmaceutical dosage form comprising a cured extended release matrix formulation, wherein the extended release matrix formulation comprises:
  a therapeutically effective amount of morphine sulfate, and
  polyethylene oxide,
the process comprising at least the following steps:
(a) combining at least morphine sulfate and polyethylene oxide particles to form a composition,
(b) shaping the composition of step (a) to form the extended release matrix formulation, and
(c) curing the extended release matrix formulation of step (b).

In certain embodiments, the present invention is directed to a process of preparing a solid oral extended release pharmaceutical dosage form comprising a cured extended release matrix formulation, wherein the extended release matrix formulation comprises:
  a therapeutically effective amount of morphine sulfate, and
  polyethylene oxide,
the process comprising at least the following steps:
(a) combining at least morphine sulfate and polyethylene oxide particles to form a composition,
(b) shaping the composition of step (a) to form the extended release matrix formulation, and
(c) curing the extended release matrix formulation of step (b),
wherein the polyethylene oxide used as the polyethylene oxide particles in step (a) has an approximate molecular weight of from about 600,000 to about 3,000,000.

In a further aspect, the present invention is directed to a method of increasing the breaking strength and/or cracking force and/or crush resistance of a solid oral extended release pharmaceutical dosage form comprising an extended release matrix formulation, the extended release matrix formulation comprising:
  a therapeutically effective amount of morphine or a pharmaceutically acceptable salt thereof and
  polyethylene oxide,
wherein the dosage form is obtainable by at least the following steps:
(a) combining at least morphine or a pharmaceutically acceptable salt thereof and polyethylene oxide particles to form a composition, and
(b) shaping the composition of step (a) to form the extended release matrix formulation,
the method being characterized in that about 50% or more of the polyethylene oxide particles used in step (a) pass through a 25 mesh (0.707 mm; 707 microns) sieve, preferably about 90% or more of the polyethylene oxide particles used in step (a) pass through a 60 mesh (0.250 mm; 250 microns) sieve.

In a further aspect, the present invention is directed to the use of polyethylene oxide particles for increasing the breaking strength and/or cracking force and/or crush resistance of a solid oral extended release pharmaceutical dosage form comprising an extended release matrix formulation, the extended release matrix formulation comprising:
    a therapeutically effective amount of morphine or a pharmaceutically acceptable salt thereof and
    polyethylene oxide,
wherein the dosage form is obtainable by at least the following steps:
    (a) combining at least morphine or a pharmaceutically acceptable salt thereof and polyethylene oxide particles to form a composition, and
    (b) shaping the composition of step (a) to form the extended release matrix formulation,
wherein the polyethylene oxide particles used in step (a) are characterized in that about 50% or more of the polyethylene oxide particles pass through a 25 mesh (0.707 mm, 707 microns) sieve, preferably about 90% or more of the polyethylene oxide particles used in step (a) pass through a 60 mesh (0.250 mm; 250 microns) sieve.

In certain embodiments, the present invention is directed to a method for preventing or reducing recovery of morphine sulfate from a morphine sulfate containing solid oral extended release pharmaceutical dosage form by means of subjecting the dosage form to dissolution in water or saline and aspirating the resulting solution in a needle, the method comprising, in the preparation of the dosage form, the following steps:
    (a) combining at least morphine sulfate and polyethylene oxide particles to form a composition,
    (b) shaping the composition of step (a) to form an extended release matrix formulation, and
    (c) curing the extended release matrix formulation of step (b) to form the dosage form.

In certain embodiments, the present invention is directed to a solid oral extended release pharmaceutical dosage form comprising a cured extended release matrix formulation, the extended release matrix formulation comprising:
    a therapeutically effective amount of morphine sulfate, and
    polyethylene oxide,
the dosage form after administration providing a dose adjusted $C_{max}$ of morphine of from about 3 ng/mL to about 9 ng/mL per 15 mg of morphine hemi(sulfate pentahydrate) (having a molecular weight of 758.8 g/mol) or an equimolar amount of another solvate or hydrate of morphine sulfate included in the dosage form.

In certain embodiments, the present invention is directed to a solid oral extended release pharmaceutical dosage form comprising a cured extended release matrix formulation, the extended release matrix formulation comprising:
    a therapeutically effective amount of morphine sulfate, and
    polyethylene oxide,
the dosage form after administration providing a dose adjusted $AUC_t$ and/or a dose adjusted $AUC_{inf}$ of morphine of from about 30 ng*hr/mL to about 100 ng*hr/mL per 15 mg of morphine hemi(sulfate pentahydrate) (having a molecular weight of 758.8 g/mol) or an equimolar amount of another solvate or hydrate of morphine sulfate included in the dosage form.

In certain embodiments, the present invention is directed to a solid oral extended release pharmaceutical dosage form comprising a therapeutically effective amount of morphine, the dosage form after administration providing:
    a dose adjusted $C_{max}$ of morphine of from about 3 ng/mL to about 9 ng/mL and/or
    a dose adjusted $AUC_t$ of morphine of from about 30 ng*hr/mL to about 100 ng*hr/mL and/or
    a dose adjusted $AUC_{inf}$ of morphine of from about 30 ng*hr/mL to about 100 ng*hr/mL per 15 mg of morphine hemi(sulfate pentahydrate) (having a molecular weight of 758.8 g/mol) or an equimolar amount of another pharmaceutically acceptable morphine salt or solvate or hydrate thereof included in the dosage form, and
the dosage form having a breaking strength of least about 200 N.

In certain embodiments, the present invention is directed to a solid oral extended release pharmaceutical dosage form comprising a therapeutically effective amount of morphine, the dosage form after administration providing:
    a dose adjusted $C_{max}$ of morphine of from about 3 ng/mL to about 9 ng/mL and/or
    a dose adjusted $AUC_t$ of morphine of from about 30 ng*hr/mL to about 100 ng*hr/mL and/or
    a dose adjusted $AUC_{inf}$ of morphine of from about 30 ng*hr/mL to about 100 ng*hr/mL per 15 mg of morphine hemi(sulfate pentahydrate) (having a molecular weight of 758.8 g/mol) or an equimolar amount of another pharmaceutically acceptable morphine salt or solvate or hydrate thereof included in the dosage form, and
the dosage form having a cracking force of least about 150 N.

In certain embodiments, the present invention is directed to a solid oral extended release pharmaceutical dosage form comprising a therapeutically effective amount of morphine, the dosage form after administration providing:
    a dose adjusted $C_{max}$ of morphine of from about 3 ng/mL to about 9 ng/mL and/or
    a dose adjusted $AUC_t$ of morphine of from about 30 ng*hr/mL to about 100 ng*hr/mL and/or
    a dose adjusted $AUC_{inf}$ of morphine of from about 30 ng*hr/mL to about 100 ng*hr/mL per 15 mg of morphine hemi(sulfate pentahydrate) (having a molecular weight of 758.8 g/mol) or an equimolar amount of another pharmaceutically acceptable morphine salt or solvate or hydrate thereof included in the dosage form, and
the dosage form having a crush resistance of least about 500 N.

In certain embodiments, the present invention is directed to a solid oral extended release pharmaceutical dosage form comprising:
    a therapeutically effective amount of morphine sulfate, and
    polyethylene oxide,
wherein the dosage form provides an in-vitro dissolution rate of morphine sulfate, when measured in a USP Apparatus 1 (basket) at 100 rpm in 900 ml simulated gastric fluid without enzymes (SGF) at 37° C., characterized by the amount of morphine sulfate released from the dosage form, of
from about 5% to about 35% released after 0.5 hour;
from about 18% to about 50% released after 1 hour;
from about 29% to about 70% released after 2 hours;
from about 40% to about 85% released after 3 hours;
from about 49% to about 95% released after 4 hours;
greater than about 65% released after 6 hours;

greater than about 70% released after 8 hours;
greater than about 75% released after 9 hours; and/or
greater than about 85% released after 12 hours.

In certain embodiments, the present invention is directed to a solid oral extended release pharmaceutical dosage form comprising:

a therapeutically effective amount of morphine sulfate, and polyethylene oxide, the dosage form providing an in-vitro dissolution rate of morphine sulfate, when measured in a USP Apparatus 1 (basket) at 100 rpm in 900 ml simulated gastric fluid without enzymes (SGF) at 37° C., characterized by the amount of morphine sulfate released from the dosage form, of:
from about 18% to about 21% released after 0.5 hour;
from about 29% to about 33% released after 1 hour;
from about 48% to about 53% released after 2 hours;
from about 65% to about 69% released after 3 hours;
from about 77% to about 83% released after 4 hours;
from about 90% to about 97% released after 6 hours; and/or
greater than about 98% released after 9 hours.

In certain embodiments, the present invention is directed to a solid oral extended release pharmaceutical dosage form comprising:

a therapeutically effective amount of morphine sulfate, and polyethylene oxide, the dosage form providing an in-vitro dissolution rate of morphine sulfate, when measured in a USP Apparatus 1 (basket) at 100 rpm in 900 ml simulated gastric fluid without enzymes (SGF) at 37° C., characterized by the amount of morphine sulfate released from the dosage form, of:
from about 14% to about 17% released after 0.5 hour;
from about 25% to about 28% released after 1 hour;
from about 41% to about 46% released after 2 hours;
from about 56% to about 61% released after 3 hours;
from about 70% to about 75% released after 4 hours;
from about 87% to about 92% released after 6 hours; and/or
greater than about 98% released after 9 hours.

In certain embodiments, the present invention is directed to a solid oral extended release pharmaceutical dosage form comprising:

a therapeutically effective amount of morphine sulfate, and polyethylene oxide, the dosage form providing an in-vitro dissolution rate of morphine sulfate, when measured in a USP Apparatus 1 (basket) at 100 rpm in 900 ml simulated gastric fluid without enzymes (SGF) at 37° C., characterized by the amount of morphine sulfate released from the dosage form, of:
from about 13% to about 16% released after 0.5 hour;
from about 22% to about 25% released after 1 hour;
from about 36% to about 41% released after 2 hours;
from about 50% to about 55% released after 3 hours;
from about 60% to about 68% released after 4 hours;
from about 80% to about 87% released after 6 hours; and/or
greater than about 98% released after 9 hours.

In certain embodiments, the present invention is directed to a solid oral extended release pharmaceutical dosage form comprising:

a therapeutically effective amount of morphine sulfate, and polyethylene oxide, the dosage form providing an in-vitro dissolution rate of morphine sulfate, when measured in a USP Apparatus 1 (basket) at 100 rpm in 900 ml simulated gastric fluid without enzymes (SGF) at 37° C., characterized by the amount of morphine sulfate released from the dosage form, of:
from about 15% to about 19% released after 0.5 hour;
from about 25% to about 29% released after 1 hour;
from about 40% to about 46% released after 2 hours;
from about 56% to about 61% released after 3 hours;
from about 68% to about 73% released after 4 hours;
from about 87% to about 92% released after 6 hours; and/or
greater than about 98% released after 9 hours.

In certain embodiments, the present invention is directed to a solid oral extended release pharmaceutical dosage form comprising:

a therapeutically effective amount of morphine sulfate, and polyethylene oxide, the dosage form providing an in-vitro dissolution rate of morphine sulfate, when measured in a USP Apparatus 1 (basket) at 100 rpm in 900 ml simulated gastric fluid without enzymes (SGF) at 37° C. characterized by the amount of morphine sulfate released from the dosage form, of:
from about 10% to about 18% released after 0.5 hour;
from about 16% to about 25% released after 1 hour;
from about 30% to about 42% released after 2 hours;
from about 42% to about 53% released after 3 hours;
from about 52% to about 65% released after 4 hours;
from about 70% to about 85% released after 6 hours; and/or
greater than about 97% released after 9 hours.

BRIEF DESCRIPTION OF THE DRAWINGS

FIG. 96: Study Design Diagram for In Vivo Pharmacokinetic Study (Example 3)

DEFINITIONS

Figure 1:
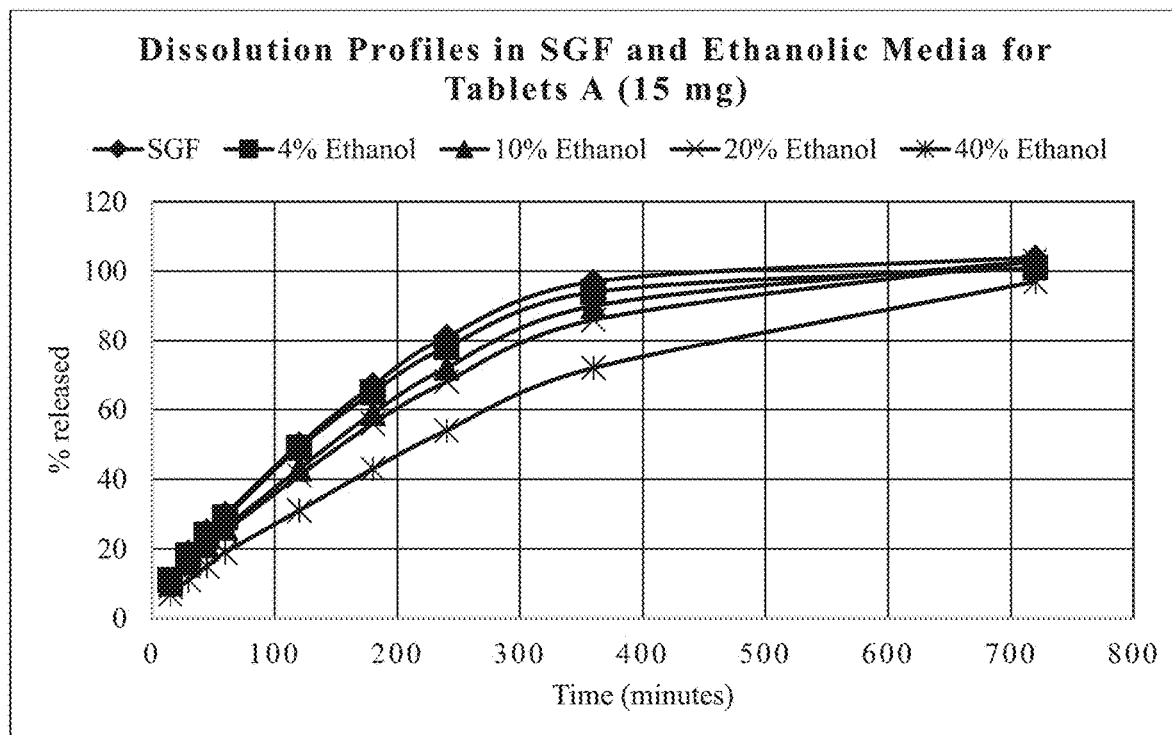
FIG. 1: Dissolution Profile for Tablets A (15 mg) in SGF and Ethanolic Media (% morphine sulfate released over time).

In describing the present invention, the following terms are to be used as defined below.

As used herein, the singular forms "a", "an", and "the" include plural references unless the context clearly indicates otherwise.

As used herein, the term "about" in connection with a measured quantity, refers to the normal variations in that measured quantity, as expected by one of ordinary skill in the art in making the measurement and exercising a level of care commensurate with the objective of measurement and the precision of the measuring equipment.

The term "at least about" in connection with a measured quantity refers to the normal variations in the measured quantity, as expected by one of ordinary skill in the art in making the measurement and exercising a level of care commensurate with the objective of measurement and precisions of the measuring equipment and any quantities higher than that.

Any recitation of ranges of values herein are intended to serve as a shorthand method of referring individually to each separate value falling within the respective range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended for purely illustrational purposes to illustrate the present invention, and does not represent any limitation of the subject matter claimed.

The term "extended release" is defined for purposes of the present invention as to refer to products which are formulated to make the drug available over an extended period after ingestion, thereby allowing a reduction in dosing frequency compared to a drug presented as a conventional dosage form (e.g., as a solution or an immediate release dosage form). The term "extended release" is intended herein to have the same meaning as, and is thus used interchangeably herein, with the term "controlled release".

The term "immediate release" is defined for purposes of the present invention as to refer to products which are formulated to allow the drug to dissolve in the gastrointestinal contents with no intention of delaying or prolonging the dissolution or absorption of the drug.

The term "solid oral extended release pharmaceutical dosage form" (also referred to herein simply as "the dosage form") refers to the form of a unit dose of morphine sulfate in extended release form such as an "extended release matrix formulation" intended for oral administration. The solid oral extended release pharmaceutical dosage form contains an extended release feature and optionally contains other adjuvants and additives conventional in the art, including one or more coating(s). Unless specifically indicated the term "solid oral extended release pharmaceutical dosage form" refers to said dosage form in intact form, i.e. prior to any tampering. The solid oral extended release pharmaceutical dosage form is preferably a tablet comprising the extended release matrix formulation, but may also be a capsule comprising the extended release matrix formulation in the form of multi particulates.

The term "extended release matrix formulation" is defined for purposes of the present invention as the shaped solid form of a composition comprising at least a therapeutically effective amount of morphine sulfate as an active agent and at least polyethylene oxide as an extended release feature. The composition can optionally comprise more than these two compounds, namely further active agents and additional retardants and/or other materials, including but not limited to pharmaceutically acceptable excipients conventional in the art. Such excipients include, but are not limited to, for example processing aids, such as lubricants or glidants (also referred to as flow enhancers).

In the extended release matrix formulation according to the present invention morphine sulfate and polyethylene oxide and optionally other adjuvants and additives may be present as an intimate mixture, such as a dispersion or as a solid solution. Morphine sulfate is released from the matrix and thus from the dosage form upon oral administration of the dosage form.

The term "oral" in the context of the present invention means that the dosage form is administered orally, i.e., by swallowing, usually of the intact dosage form.

The term "solid" in the context of the present invention means that the dosage form has a defined, tangible shape such as a tablet or capsule, and is not a free-flowing powder or a liquid.

The term "tablet" is defined for the purpose of the present invention as a solid, shaped dosage form that may be monolithic or may contain layers or a core-shell structure wherein the core is completely or partially covered by the shell. The core and/or the shell may contain active agent. The tablet may be composed of the compressed extended release matrix formulation which is covered by one or more coatings as described herein. The tablet may have any shape, for example it may be round, oval or oblong, preferably as described herein below. Preferably, the tablet according to the present invention is a monolithic tablet. It may optionally be coated with a coating e.g. as described herein below.

Figure 88:
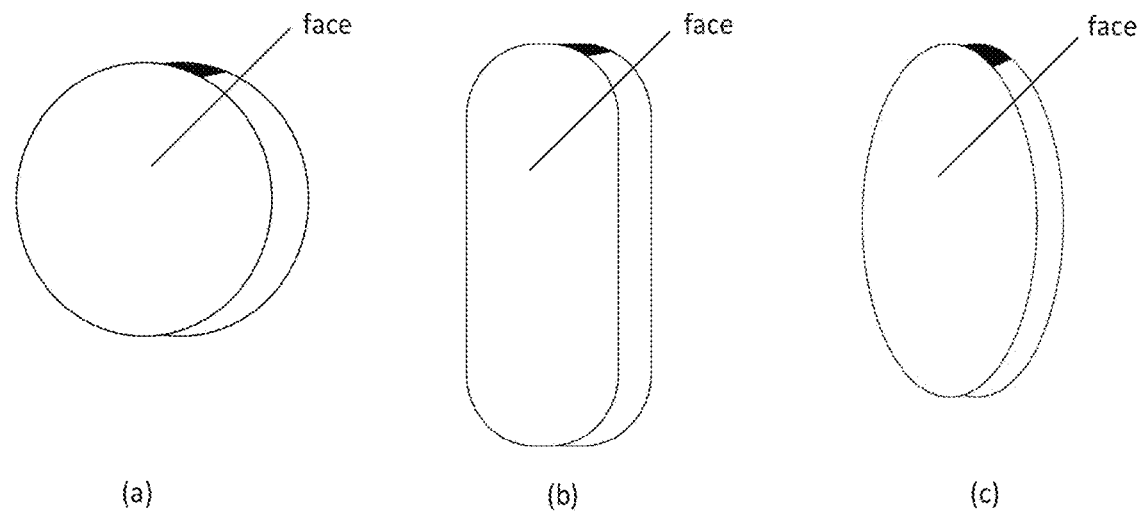
FIG. 88: Tablet Shapes
Figure 89:
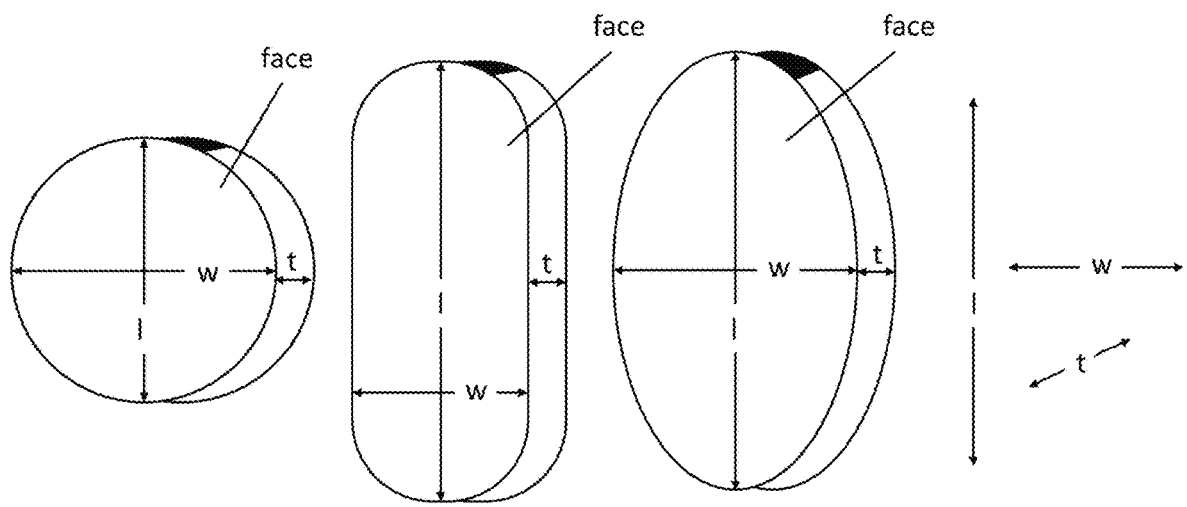
FIG. 89: Tablet Dimensions

The term "caplet" is defined for the purpose of the present invention to refer to a tablet that has an essentially oval or oblong shape (see FIGS. 88 and 89 (b) and (c)), wherein the length of the tablet (l) is greater than the width (w) of the tablet. In contrast, a "round tablet" refers to a tablet wherein the length (l) of the tablet is equal to the width (w) of the tablet (see FIG. 89(a)), and is identical to the diameter, or twice the radius, of the face of the tablet. In all tablet shapes described herein, the length (l) and the width (w) are greater than the thickness (t) (see also FIG. 89).

The term "face" of a tablet in the context of the present invention refers to the side or area of a tablet defined by the length (l) and the width (w) of the tablet (see FIGS. 88 and 89). If not specifically indicated otherwise, the entire surface of the face of the tablet, if not planar or flat, is usually slightly convex (see FIG. 91(a)). The thickness of the tablet is usually largest in the center (in case of a round tablet) or along the central axis (in the case of a caplet), see FIG. 91(a). If the dosage forms referred to herein (and specifically the dosage forms illustrated in the examples) are caplets, their entire face is preferably slightly convex.

Figure 90:
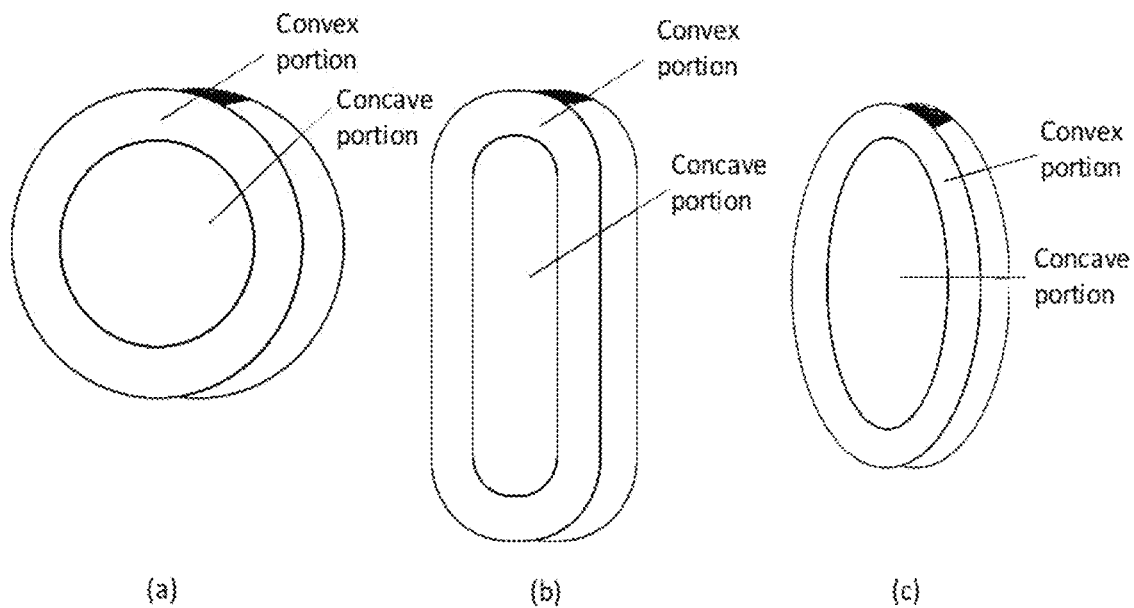
FIG. 90: 3D Tablet Representation
Figure 91:
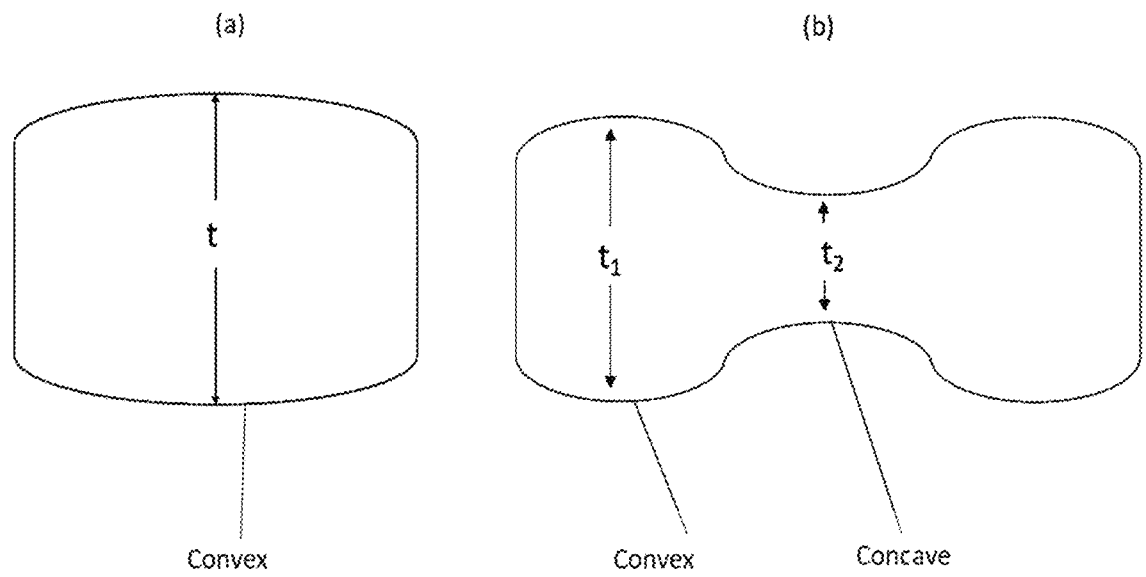
FIG. 91: Tablet Cross Section

The term "troche" in the context of a tablet or caplet is used for the purpose of the present invention to refer to a tablet as shown in FIG. 90 and FIG. 91(b). In a "troche" tablet or caplet, the thickness of the tablet in the center or along a central axis (indicated as "$t_2$" in FIG. 91(b)), is smaller than the maximum thickness of the tablet or caplet in the regions surrounding the center or central axis (indicated as "$t_1$" in FIG. 91(b)). In other words, in a "troche" tablet or caplet the surface of the face of the tablet or caplet has convex and concave portions, wherein the concave portions are located in the center or along the central axis of the tablet or caplet.

The term "simulated gastric fluid" or "SGF" used herein refers to an aqueous solution utilized in in-vitro dissolution testing to mimic the conditions of the stomach, e.g., a solution of 0.1 N HCl without enzymes. When specifically indicated herein, a certain amount, such as 4, 10, 20 or 40% by volume ethanol may be included in the SGF ("SGF with ethanol").

The term "USP Apparatus 1 (basket)" refers to the Apparatus 1 (Basket Apparatus) described in U.S. Pharmacopoeia 39 (2016) (see, in particular, Section <711> Dissolution), which is incorporated herein by reference. Furthermore, all other references in the specification are equally incorporated herein by reference. The term "in-vitro dissolution test in a USP Apparatus 1 (basket)" refers to the respective method using the Apparatus 1 (basket) as described in U.S. Pharmacopoeia 39 (2016).

For purposes of the present invention, however, the "in-vitro dissolution test in a USP Apparatus 1 (basket)" is used in a slightly modified form, by equipping the USP Apparatus 1 basket with a retaining spring placed in the upper part of the basket (above the tablet), to reduce or avoid sticking of the polyethylene oxide containing tablets to the solid underside of the top of the basket or the base of the shaft (see FIG. 92) during the dissolution test. For example, a passivized stainless steel 316 spring, 1.5-cm outside diameter and 2-cm length can be used.

The "average in vitro-dissolution rate" refers to the average of the in-vitro dissolution rates determined based on a number of (i.e. at least two) individual measurements.

The term "polyethylene oxide" ("PEO") is generally defined in the context of the present invention as having an approximate molecular weight of at least 25,000, and preferably as having an approximate molecular weight of at least 100,000, measured as is conventional in the art, and preferably measured based on rheological measurements as described further below. Compositions with lower approximate molecular weight are usually referred to as polyethylene glycols.

For the purposes of the present invention, the approximate molecular weight of a polyethylene oxide is determined based on rheological measurements. The rheological measurements are described herein below.

Polyethylene oxides are polydisperse polymers having a certain molecular weight distribution. Therefore, the approximate molecular weight of a polyethylene oxide (determined based on rheological measurements) as described herein is always an average molecular weight (i.e., an average of molecular weights).

The following polyethylene oxide grades are commercially available from Dow Chemical Company under the tradename POLYOX® Water-Soluble Resins NF and are generally suitable for use in the present invention:

TABLE PEO I:

| PEO grade | Approximate molecular weight (based on rheological measurements as specified herein) |
|---|---|
| POLYOX ® WSR N-10 NF | 100,000 |
| POLYOX ® WSR N-80 NF | 200,000 |
| POLYOX ® WSR N-750 NF | 300,000 |
| POLYOX ® WSR-205 NF | 600,000 |
| POLYOX ® WSR-1105 NF | 900,000 |
| POLYOX ® WSR N-12K NF | 1,000,000 |
| POLYOX ® WSR N-60K NF | 2,000,000 |
| POLYOX ® WSR-301 NF | 4,000,000 |
| POLYOX ® WSR Coagulant NF | 5,000,000 |
| POLYOX ® WSR-303 NF | 7,000,000 |
| POLYOX ® WSR-308 NF | 8,000,000 |

The approximate molecular weight of the polyethylene oxide particles used in the preparation of the solid oral extended release pharmaceutical dosage form of the present invention (i.e., the approximate molecular weight of the polyethylene oxide particles combined with morphine sulfate in the preparation of the extended release matrix formulation), and specifically of the POLYOX® grades listed above, is determined based on rheological measurements, as follows:

Polyethylene oxide is considered to have an approximate molecular weight of 100,000 when a 5% (by weight) aqueous solution of said polyethylene oxide using a Brookfield viscometer Model RVF, spindle No. 1, at 50 rpm, at 25° C. shows a viscosity in the range of 30 to 50 mPa s (cP);

Polyethylene oxide is considered to have an approximate molecular weight of 200,000 when a 5% (by weight) aqueous solution of said polyethylene oxide using a Brookfield viscometer Model RVF, spindle No. 1, at 50 rpm, at 25° C. shows a viscosity in the range of 55 to 90 mPa s (cP);

Polyethylene oxide is considered to have an approximate molecular weight of 300,000 when a 5% (by weight) aqueous solution of said polyethylene oxide using a Brookfield viscometer Model RVF, spindle No. 1, at 10 rpm, at 25° C. shows a viscosity in the range of 600 to 1,200 mPa s (cP);

Polyethylene oxide is considered to have an approximate molecular weight of 600,000 when a 5% (by weight) aqueous solution of said polyethylene oxide using a Brookfield viscometer Model RVF, spindle No. 2, at 2 rpm, at 25° C. shows a viscosity in the range of 4,500 to 8,800 mPa s (cP);

Polyethylene oxide is considered to have an approximate molecular weight of 900,000 when a 5% (by weight) aqueous solution of said polyethylene oxide using a Brookfield viscometer Model RVF, spindle No. 2, at 2 rpm, at 25° C. shows a viscosity in the range of 8,800 to 17,600 mPa s (cP);

Polyethylene oxide is considered to have an approximate molecular weight of 1,000,000 when a 2% (by weight) aqueous solution of said polyethylene oxide using a Brookfield viscometer Model RVF, spindle No. 1, at 10 rpm, at 25° C. shows a viscosity in the range of 400 to 800 mPa s (cP);

Polyethylene oxide is considered to have an approximate molecular weight of 2,000,000 when a 2% (by weight) aqueous solution of said polyethylene oxide using a Brookfield viscometer Model RVF, spindle No. 3, at 10 rpm, at 25° C. shows a viscosity in the range of 2,000 to 4,000 mPa s (cP);

Polyethylene oxide is considered to have an approximate molecular weight of 3,000,000 when it shows a viscosity that is above the range specified for polyethylene oxide defined to have an approximate molecular weight of 2,000,000 (see above), but below the range specified for polyethylene oxide defined to have an approximate molecular weight of 4,000,000 (see below);

Polyethylene oxide is considered to have an approximate molecular weight of 4,000,000 when a 1% (by weight) aqueous solution of said polyethylene oxide using a Brookfield viscometer Model RVF, spindle No. 2, at 2 rpm, at 25° C. shows a viscosity in the range of 1,650 to 5,500 mPa s (cP);

Polyethylene oxide is considered to have an approximate molecular weight of 5,000,000 when a 1% (by weight) aqueous solution of said polyethylene oxide using a Brookfield viscometer Model RVF, spindle No. 2, at 2 rpm, at 25° C. shows a viscosity in the range of 5,500 to 7,500 mPa s (cP);

Polyethylene oxide is considered to have an approximate molecular weight of 7,000,000 when a 1% (by weight) aqueous solution of said polyethylene oxide using a Brookfield viscometer Model RVF, spindle No. 2, at 2 rpm, at 25° C. shows a viscosity in the range of 7,500 to 10,000 mPa s (cP);

Polyethylene oxide is considered to have an approximate molecular weight of 8,000,000 when a 1% (by weight) aqueous solution of said polyethylene oxide using a Brookfield viscometer Model RVF, spindle No. 2, at 2 rpm, at 25° C. shows a viscosity in the range of 10,000 to 15,000 mPa s (cP).

For the purposes of the present invention, and in accordance with the above definitions, a polyethylene oxide having an approximate molecular weight in the range of from about 600,000 to about 3,000,000 based on rheological measurements is thus defined as showing a viscosity in the range defined at its lower end by the lowest value of the viscosity attributed herein above to polyethylene oxide having an approximate molecular weight of 600,000 and defined at its upper end by—while excluding—the lowest value of the viscosity associated above for polyethylene oxide having an approximate molecular weight of 4,000,000. The range of approximate molecular weight from about 600,000 to about 3,000,000 thus excludes polyethylene oxide having an approximate molecular weight of 4,000,000 as defined above.

In certain embodiments, the polyethylene oxide present in the solid oral extended release pharmaceutical dosage form of the present invention may result from including a single (e.g. commercially available) grade of polyethylene oxide (e.g. POLYOX® Water-Soluble Resins) and combining same with morphine sulfate in the preparation of the extended release matrix formulation according to the present invention.

In other embodiments, the polyethylene oxide present in the solid oral extended release pharmaceutical dosage form of the present invention may result from including two or more (e.g. commercially available) grades of polyethylene oxide (POLYOX® Water-Soluble Resins) and combining same with morphine sulfate in the preparation of the extended release matrix formulation according to the present invention.

The two or more polyethylene oxide grades may be used for the purposes of the present invention as a "blend" or "mixture". These terms, when used in connection with polyethylene oxide herein, are interchangeable and refer to a combination of two or more polyethylene oxide materials or grades.

A polyethylene oxide "grade" is one kind or class of polyethylene oxide material or product that may be commercially available and to which an approximate molecular weight or approximate molecular weight range is assigned. Non-limiting examples of (commercially available) polyethylene oxide grades are provided above in Table PEO I.

The approximate molecular weight may characterize the polyethylene oxide present in the solid oral extended release pharmaceutical dosage form of the present invention, and/or may characterize the polyethylene oxide (particles) used for preparing the solid oral extended release pharmaceutical dosage form of the present invention by combining the polyethylene oxide (particles) with morphine sulfate.

In certain embodiments, the polyethylene oxide present in the solid oral extended release pharmaceutical dosage form of the invention (whether originating from a single grade or a combination of two or more grades) has an approximate molecular weight of from about 600,000 to about 4,000,000; preferably from about 600,000 to about 3,000,000; more preferably from about 900,000 to about 2,000,000; more preferably from about 1,000,000 to about 2,000,000, and most preferably of about 1,000,000 or about 2,000,000. In this case, the overall approximate molecular weight of the polyethylene oxide present in the dosage form is within these ranges, regardless of whether the polyethylene oxide present in the dosage form results from one or more individual (grades of) polyethylene oxide used during the preparation of the dosage form.

In certain embodiments, in the preparation of the solid oral extended release pharmaceutical dosage form, specifically in the preparation of the extended release matrix formulation (according to step (a) of the process for preparing the solid oral extended release pharmaceutical dosage form of the present invention), polyethylene oxide may be combined with morphine sulfate, wherein the polyethylene oxide used has an approximate molecular weight overall of from about 600,000 to about 4,000,000; preferably from about 600,000 to about 3,000,000; more preferably from about 900,000 to about 2,000,000; more preferably from about 1,000,000 to about 2,000,000, and most preferably of about 1,000,000 or about 2,000,000.

Specifically, in the preparation of the solid oral extended release pharmaceutical dosage form, specifically in the preparation of the extended release matrix formulation (according to step (a) of the process for preparing the solid oral extended release pharmaceutical dosage form of the present invention) preferably one or any combination of two or more of the following polyethylene oxide grades may be used: polyethylene oxide having an approximate molecular weight of about 900,000, polyethylene oxide having an approximate molecular weight of about 1,000,000, and polyethylene oxide having an approximate molecular weight of about 2,000,000 (all determined based on rheological measurements as defined herein).

In certain embodiments, preferably one or more of the following materials are used as polyethylene oxide particles in the preparation of the extended release matrix formulation (including mixtures of two or all of these grades, or mixtures of any of these grades with other polyethylene oxides not specifically listed here):

polyethylene oxide showing a viscosity in the range of 8,800 to 17,600 mPa s (cP) when the viscosity of a 5% (by weight) aqueous solution of said polyethylene oxide is determined using a Brookfield viscometer Model RVF, spindle No. 2, at 2 rpm, at 25° C. (corresponding to an approximate molecular weight of 900,000);

polyethylene oxide showing a viscosity in the range of 400 to 800 mPa s (cP) when the viscosity of a 2% (by weight) aqueous solution of said polyethylene oxide is determined using a Brookfield viscometer Model RVF, spindle No. 1, at 10 rpm, at 25° C. (corresponding to an approximate molecular weight of 1,000,000); and polyethylene oxide showing a viscosity in the range of 2,000 to 4,000 mPa s (cP) when the viscosity of a 2% (by weight) aqueous solution of said polyethylene oxide is determined using a Brookfield viscometer Model RVF, spindle No. 3, at 10 rpm, at 25° C. (corresponding to an approximate molecular weight of 2,000,000).

Specifically, in certain embodiments, one of the following three grades may be used solely as the polyethylene oxide (particles) in the preparation of the extended release matrix formulation and thus the preparation of the solid oral extended release dosage forms of the present invention; or mixtures or blends of any two or of all of the following three grades with each other, or with other polyethylene oxide grades not contained in the following table may be used:

TABLE PEO II:

| PEO grade | Approximate molecular weight (based on rheological measurements as indicated above) |
| --- | --- |
| POLYOX ® WSR-1105 NF | 900,000 |
| POLYOX ® WSR N-12K NF | 1,000,000 |
| POLYOX ® WSR N-60K NF | 2,000,000 |

All above-listed POLYOX® Water-Soluble Resins available from Dow Chemical Company are illustrative of polyethylene oxide grades that are suitable for use in the present invention, but the present invention is not limited to these grades. Other commercially available polyethylene oxide grades, including but not limited to PEO Water-Soluble Thermoplastic Resins from Sumitomo Seika Chemicals Co., Ltd., may equally be used for the purposes of the present invention, provided they meet the definitions of approximate molecular weight (or approximate molecular weight range), determined based on rheological measurements as explained herein above. Equally, the same definitions and explanations as provided above with respect to POLYOX® Water-Soluble Resins apply mutatis mutandis to such other (e.g. commercially available) polyethylene oxide grades.

The situation may arise that the viscosity measured for a polyethylene oxide (single grade or combination of grades) using the above-described rheological test conditions, falls within an herein "undefined" viscosity range, which is herein not assigned to a specific approximate molecular weight. For example, a polyethylene oxide might show a viscosity, which exceeds the viscosity range herein assigned to an approximate molecular weight of 1,000,000 (under the respective test conditions as specified above), and which, on the other hand, lies below the viscosity range herein assigned to an approximate molecular weight of 2,000,000 (under the respective test conditions as specified above). For purposes of the present invention, such a polyethylene oxide is herein defined to have an approximate molecular weight which is associated with the viscosity range closest to the measured viscosity. For the avoidance of doubt, this does not apply to polyethylene oxide having an approximate molecular weight of 3,000,000, as such polyethylene oxide is specifically defined herein above.

In certain embodiments, the polyethylene oxide used for the purposes of the present invention for preparing the solid oral extended release pharmaceutical dosage forms (specifically, in step (a) for preparing the extended release matrix formulation) has a certain, defined particle size distribution. Thus, the polyethylene oxide used in accordance with the present invention for preparing the extended release matrix formulation in step (a) as described herein is referred to herein as the "polyethylene oxide particles". For the purposes of the present invention, the particle size of the polyethylene oxide particles used in the present invention is determined by sieving. In a preferred embodiment, the polyethylene oxide used for the purposes of the present invention is characterized in that about 50% or more, preferably about 70% or more, more preferably about 90% or more, most preferably about 96% or more of the polyethylene oxide particles pass through a 25 mesh (0.707 mm; 707 microns) sieve. In a more preferred embodiment, about 50% or more, preferably about 70% or more, more preferably about 90% or more, most preferably about 96% or more of the polyethylene oxide particles pass through a 35 mesh (0.500 mm; 500 microns) sieve. In a yet more preferred embodiment, about 50% or more, preferably about 70% or more, more preferably about 90% or more, most preferably about 96% or more of the polyethylene oxide particles pass through a 60 mesh (0.250 mm; 250 microns) sieve. In the context of the present invention, the terms "sieve" or "screen" when used in relation to the determination of particle size are used interchangeably. All percentages recited herein for the purpose of determining particle size (distribution) refers to weight-% (% by weight). Thus, preferably, about 50% by weight or more, preferably about 70% by weight or more, more preferably about 90% by weight or more, most preferably about 96% by weight or more of the polyethylene oxide particles pass through a 60 mesh (0.250 mm; 250 microns) sieve.

Dow Chemical Company's POLYOX® Water Soluble Resin grades available for pharmaceutical use are designated by the NF (National Formulary) classification. Dow Chemical Company provides the NF grades in two particle sizes, available as regular grades and as fine particle (FP) grades. In particular the following grades are available as FP grades (as also used in certain examples of the present invention):

TABLE PEO III:

| PEO grade | Approximate molecular weight (based on rheological measurements as indicated above) |
| --- | --- |
| POLYOX ® WSR N-12K FP, NF | 1,000,000 |
| POLYOX ® WSR N-60K FP, NF | 2,000,000 |

According to specification, 96 to 100% of the polyethylene oxide particles of these FP grades pass through a 60 mesh (0.250 mm: 250 microns) sieve. For the purposes of the present invention, preferably the FP grades (or combinations of FP grades) of the respective polyethylene oxide grades as identified above are used. In certain embodiments, also a combination of one or more FP grade(s) and one or more regular NF grade(s) may be used. Preferably, the entire combined polyethylene oxide material fulfills the requirements regarding particle size as defined herein.

As is evident from the above, the term "particle(s)" as used herein is not intended to limit the present invention regarding the type of "particles" of any substance used, preferably of polyethylene oxide. Specifically, the term "particles" is not intended to mean that the particles have been shaped by any particular method, and/or that they have a specific (defined) shape. Rather, the term "particle" in its most general meaning as used herein refers to any (small) portion of matter, usually in the solid state, e.g. in the form of a dust or powder, in the form of pellets, granules or grains or in any other solid form. Generally, a "particle" can have any size, although in the present invention as described herein for certain substances, particularly for polyethylene oxide, specific particle sizes may be used or are preferred, as also disclosed herein. Thus, specifically in the context of polyethylene oxide, the term "particles" is used simply in order to be able to refer to a particular size (or size distribution) of the particles used in the preparation of the dosage form, as defined above. In other words, the polyethylene oxide material used in the present invention is or may be used as commercially available grades (i.e., as commercially available without further shaping of the "particles" and—in case the commercially available grade already has the desired particle size distribution—also without further sieving etc.). Thus, the polyethylene oxide particles used in the present invention for preparing the extended release matrix formulation and thus the solid oral extended release pharmaceutical dosage form of the present invention preferably do not contain any other substances in addition to the polyethylene oxide itself (apart from low amounts of anti-oxidants, stabilizers, etc. that have been added already by the manufacturer and thus are already present in the commercial polyethylene oxide grades used). Preferably, the polyethylene oxide used in the present invention is used as a FP (fine particle) grade as described above.

It is thus evident from the above that the present invention is not primarily directed to so-called multiparticulate dosage forms in which specifically shaped particles e.g. containing active agent in addition to certain excipients are embedded in a matrix of e.g. controlled release excipient (although such multiparticulate dosage forms are also not generally excluded from the present disclosure). Rather, in the solid oral extended release pharmaceutical dosage forms according to the present invention the morphine sulfate is preferably (substantially) homogeneously dispersed in polyethylene oxide (and optional further pharmaceutically acceptable excipients as explained herein below), such (substantially) homogeneous mixture forming the extended release matrix formulation, which is shaped (e.g. compressed into tablets) and cured to form the solid oral extended release pharmaceutical dosage form according to the present invention.

For purposes of the present invention, the term "morphine sulfate" refers to either the solvent-free form, such as the anhydrous form, or a solvated form, such as the hydrated form, of morphine sulfate, as well as to mixtures of the foregoing. Preferably, morphine sulfate is used in the present invention in the hydrated form, most preferably in the form of morphine hemi(sulfate pentahydrate) (sometimes also referred to as "morphine sulfate (salt) pentahydrate") having a molecular weight of 758.8 g/mol and a chemical formula of $C_{34}H_{50}N_2O_{15}S$ (or $C_{34}H_{40}N_2O_{10}S \times 5\ H_2O$; CAS registry no. 6211-15-0) as shown below:

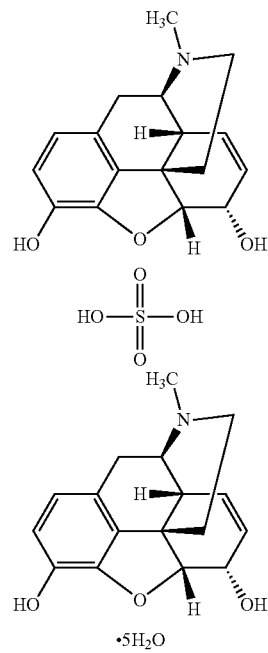

In certain embodiments, in the present invention other pharmaceutically acceptable solvates or hydrates of morphine sulfate may also be used. However, unless specified otherwise, whenever morphine sulfate or morphine hemi (sulfate pentahydrate) is referred to in the present invention in the context of a specific amount, ratio or (e.g. weight)

percentage, this amount, ratio or percentage is calculated based on the amount of morphine hemi(sulfate pentahydrate) (having a molecular weight of 758.8 g/mol) included into the solid oral extended release pharmaceutical dosage form of the invention during its preparation, i.e., when combining morphine hemi(sulfate pentahydrate) with polyethylene oxide to prepare the extended release matrix formulation. In certain embodiments of the present invention instead of the respective amount, ratio or percentage of morphine hemi(sulfate pentahydrate) an equimolar (herein used interchangeably with "equivalent") amount of another pharmaceutically acceptable solvate or hydrate of morphine sulfate other than morphine hemi(sulfate pentahydrate) may be used.

To illustrate the above, if in a certain dosage form according to the present invention e.g. 10 mg morphine hemi(sulfate pentahydrate) is included, this amount corresponds to approximately 7.5 mg morphine (free base). Accordingly, if 5, 15, 30, 60, 100 or 200 mg morphine hemi(sulfate pentahydrate) are included in a certain dosage form according to the present invention, this corresponds to approximately 3.7, 11, 22.5, 45, 75, and 150 mg, respectively, of morphine free base.

The term "abuse" is defined for purposes of the present invention as the intentional, non-therapeutic use of a drug product or substance, even once, to achieve a desirable psychological or physiological effect.

The terms "abuse-deterrent properties" or "tamper-resistant properties" are defined for the purposes of the present invention as those properties shown to meaningfully deter abuse, even if they do not fully prevent abuse. In connection with pharmaceutical dosage forms these terms mean that such dosage forms provide at least some physical and/or chemical barriers such as deterrence or resistance to, for example, crushing, chewing, cutting, grating or grinding of the dosage form, extraction of the opioid from the dosage form using common solvents (e.g., water, simulated biological media, alcohol or organic solvents), smoking, aspirating into a syringe and injecting, or any combination thereof. The dosage forms may include agonist/antagonist combinations to interfere with, reduce or defeat the euphoria associated with abuse.

As used herein, the term "therapeutically effective" refers to the amount of drug or active agent needed to produce a desired therapeutic result after administration.

As used herein, the term "analgesically effective amount" refers to an amount of a drug or active agent sufficient to provide analgesia.

The term "pain" means moderate to severe, acute, and/or chronic pain of malignant and non-malignant origin, in particular severe to most severe, acute and chronic pain of malignant and non-malignant origin, including but not limited to nociceptive pain, neuropathic pain, and visceral pain. Examples include, but are not limited to, severe pain resulting from diseases such as cancer, rheumatism and arthritis. Further examples are post-operative pain, cluster headaches, dental pain, surgical pain, pain resulting from severe burns, pain from third degree burns, back pain, lower back pain, herpes neuralgia, phantom limb pain, central pain, bone injury pain, and pain during labor and delivery.

The term "patient" means a subject, such as a mammal, particularly a human, who has presented a clinical manifestation of a particular symptom or symptoms suggesting the need for treatment, who is treated preventatively or prophylactically for a condition, or who has been diagnosed with a condition to be treated. The term "subject" is inclusive of the definition of the term "patient" and does not exclude individuals who are entirely normal in all respects or with respect to a particular condition.

The terms "population of patients," "population of subjects," and "population of healthy subjects" refer to the mean pharmacokinetic parameters of at least two patients, subjects, or healthy subjects; preferably at least six patients, subjects or healthy subjects; more preferably at least twelve patients, subjects or healthy subjects.

The term "bioavailability" means the relevant extent to which a drug is absorbed from a dosage form. Bioavailability is also reflected by the AUC (i.e., area under the plasma concentration/time curve).

The terms "bioequivalent/bioequivalence" are defined for the purposes of the present invention to refer to a dosage form that provides geometric mean values of $C_{max}$, $AUC_t$, and $AUC_{inf}$ for morphine, wherein the 90% confidence intervals (90% CI) estimated for the ratio (test/reference) fall within the range of 80.00% to 125.00%, preferably 90.00% to 110.00%.

The reference product for determining bioequivalence is the commercial product MS Contin®, which is available in strengths of 15 mg, 30 mg, 60 mg, 100 mg and 200 mg of morphine sulfate. The MS Contin® 15 mg, 30 mg, 60 mg and 100 mg dosage forms are available in the form of round tablets, and the MS Contin® 200 mg dosage form is available in the form of a caplet. The MS Contin® dosage forms have the compositions as indicated in Table VIII in the examples (formulations as commercially available in the United States in the year 2017). Similar products are marketed under a different tradename in other countries (including, e.g. MS Continus® in the UK).

For the purposes of certain embodiments of the present invention, the terms "lower" and "upper" in the context of $C_{max}$ values refer to the 90% confidence interval ranges for the $C_{max}$ ratio values.

The term "$C_{max}$" denotes the maximum plasma concentration of morphine observed during the dosing interval. The unit of $C_{max}$ is ng/mL, unless indicated otherwise.

The term "$C_{max}$ ratio" denotes the ratio of the $C_{max}$ value determined for a certain test dosage form according to the present invention to the $C_{max}$ value determined (in the same in vivo pharmacokinetic study) for a corresponding reference dosage form. For example, a $C_{max}$ ratio may be formed from the $C_{max}$ value determined for a 100 mg morphine sulfate tablet according to the present invention divided by the $C_{max}$ value determined in the same in vivo pharmacokinetic study for the 100 mg morphine sulfate MS Contin® reference tablet. The C ratio is a measure of the bioequivalence as explained above.

The term "$T_{max}$" denotes the time to maximum plasma concentration ($C_{max}$). The unit of $T_{max}$ is hours (also referred to herein as h or hr), unless indicated otherwise. The $C_{max}/T_{max}$ ratio corresponds to the average rate of increase in plasma concentration between administration and $T_{max}$.

The "$AUC_t$" (Area Under the Curve) value corresponds to the area of the plasma drug concentration versus time curve. The AUC value is proportional to the amount of active agent absorbed into a subject's blood circulation in total and hence, is a measure for the bioavailability. The unit of AUC ($AUC_t$ and $AUC_{inf}$) is ng*h/mL (sometimes also referred to as "ng*hr/mL"), unless indicated otherwise.

The $AUC_t$ value corresponds to the area under the plasma drug concentration versus time curve from the time of administration to the last measurable plasma drug concentration and is calculated by the linear up/log down trapezoidal rule.

AUC$_{inf}$ is the area under the plasma drug concentration versus time curve extrapolated to infinity and is calculated using the formula:

$$AUC_{inf} = AUC_t + C_t\lambda_z$$

where C$_t$ is the last measurable plasma concentration and $\lambda_z$ is the apparent terminal phase rate constant.

The term "AUC$_t$ ratio" or "AUC$_{inf}$ ratio" denotes the ratio of the AUC$_t$ or AUC$_{inf}$ value determined for a certain test dosage form according to the present invention to the AUC$_t$ or AUC$_{inf}$ value, respectively, determined (in the same in vivo pharmacokinetic study) for a corresponding reference dosage form in the same way as defined above for the C$_{max}$ ratio. The AUC$_t$ ratio and the AUC$_{inf}$ ratio are also a measure of the bioequivalence as explained above.

t$_{1/2z}$ (also referred to herein as t$_{1/2}$) is the apparent plasma terminal phase half-life and is commonly determined as t$_{1/2z}$=(ln 2)/$\lambda_z$. The unit of t$_{1/2z}$ is hours (also referred to herein as h or hr), unless indicated otherwise.

The lag time t$_{lag}$ (in hours) is estimated as the point in time immediately prior to the first measurable plasma concentration value.

Any pharmacokinetic values of C$_{max}$, AUC$_t$, AUC$_{inf}$ and T$_{max}$ recited herein are mean values obtained after a first administration to a population of human subjects, even when this is not specifically mentioned herein.

For purposes of the present disclosure, certain formulations disclosed herein may be "dose proportional". In dose proportional formulations, the pharmacokinetic parameters (e.g., AUC$_t$, AUC$_{inf}$ and/or C$_{max}$ values or range of values) increase linearly from one dosage strength to another and are thus proportional to the amount (in mg) of active agent contained in the dosage form as described herein.

The term "steady state administration," in the context of administration of a drug to a subject, refers to where the overall intake of a drug is in dynamic equilibrium with its elimination.

The term "E$_{max}$" denotes the maximum effect or peak score of ("at this moment") Drug Liking Visual Analog Scale (VAS), or of Overall Drug Liking (ODL) VAS, or of Take Drug Again (TDA) VAS.

If the term "Drug Liking VAS" is used herein like this, i.e., without any more detailed denomination, it always refers to the "at the moment" Drug Liking VAS, as defined in Example 17.

The term "E$_{min}$" denotes the minimum effect of Drug Liking Visual Analog Scale (VAS), or of Overall Drug Liking (ODL) VAS, or of Take Drug Again (TDA) VAS.

The term "IQR" denotes the inter-quartile range or the median difference between a particular pharmacodynamic parameter (e.g., mean E$_{max}$) for a drug as compared to a control and/or a placebo.

The term "direct compression" is defined for purposes of the present invention as referring to a tableting process, wherein a tablet or any other compressed shaped solid form (such as, e.g., the core and/or the shell of a core-shell structure as described herein) is made by a process comprising the steps of dry blending the compounds to form a composition, e.g., by using a diffusion blend and/or convection mixing process (e.g., Guidance for Industry, SUPAC-IR/MR: Immediate Release and Modified Release Solid Oral Dosage Forms, Manufacturing Equipment Addendum), and by compressing the composition to obtain the shaped solid form. For example, according to the present invention, at least morphine sulfate and polyethylene oxide particles as defined above may be combined and dry blended to form a composition, which composition is then shaped e.g. by direct compression, to form the extended release matrix formulation.

The term "curing" refers to applying an elevated temperature (i.e., heating) to a shaped extended release matrix formulation, or a tablet, for a certain period of time during or after preparation of the dosage form.

The period of time during which the shaped extended release matrix formulation is subjected to an elevated temperature is hereinafter referred to as the curing time. The temperature or temperature range to which the shaped extended release matrix formulation is subjected is hereinafter referred to as the curing temperature. Preferably, the curing temperature is a target temperature or target temperature range. For the measurement of the curing time, a starting point and an end point of the curing step are defined. For the purposes of the present invention, the starting point of the curing step is defined to be the point in time when the curing temperature is reached.

In certain embodiments, the temperature profile during the curing step shows a plateau-like form between the starting point and the end point of the curing. In such embodiments, the end point of the curing step is defined to be the point in time when the heating is stopped or at least reduced, e.g. by terminating or reducing the heating and/or by starting a subsequent cooling step, and the temperature subsequently drops below the curing temperature by more than about 10° C. and/or below the lower limit of the softening temperature range of polyethylene oxide (e.g. below 62° C.).

When the curing temperature is reached and the curing step is thus started, deviations from the curing temperature in the course of the curing step can occur. Such deviations are tolerated as long as they do not exceed a value of about +10° C., preferably about 6° C., and more preferably about 3° C. For example, if a curing temperature of at least about 75° C. is to be maintained, the measured temperature may temporarily increase to a value of about 85° C., about 81° C., or about 78° C., and the measured temperature may also temporarily drop down to a value of about 65° C., about 69° C. or about 72° C. In the cases of a larger decrease of the temperature and/or in the case that the temperature drops below the lower limit of the softening temperature range of polyethylene oxide, for example below about 62° C., the curing step is discontinued, i.e. an end point is reached. Curing can be restarted by again reaching the curing temperature.

In other embodiments, the temperature profile during the curing step shows a parabolic or triangular form between the starting point and the end point of the curing. This means that after the starting point, i.e., the point in time when the curing temperature is reached, the temperature further increases to reach a maximum, and then decreases. In such embodiments, the end point of the curing step is defined to be the point in time when the temperature drops below the curing temperature.

Depending on the apparatus used for the curing (i.e., curing device), different temperatures within the curing device can be measured to characterize the curing temperature.

In certain embodiments, the curing step may take place in an oven. In such embodiments, the temperature inside the oven is measured. When the curing step takes place in an oven, the curing temperature is defined to be the target inside temperature of the oven, and the starting point of the curing step is defined to be the point in time when the inside temperature of the oven reaches the curing temperature. The end point of the curing step is defined to be (1) the point in time when the heating is stopped or at least reduced and the temperature inside the oven subsequently drops below the curing temperature by more than about 10° C. and/or below the lower limit of the softening temperature range of polyethylene oxide, for example below about 62° C., in a plateau-like temperature profile or (2) the point in time when the temperature inside the oven drops below the curing temperature in a parabolic or triangular temperature profile.

In certain other embodiments, the curing takes place in curing devices that are heated by an air flow and comprise a heated air supply (inlet) and an exhaust, e.g., a coating pan or fluidized bed. Such curing devices will hereinafter be called convection curing devices. In such curing devices, it is possible to measure the temperature of the inlet air, i.e., the temperature of the heated air entering the convection curing device and/or the temperature of the exhaust air, i.e., the temperature of the air leaving the convection curing device. It is also possible to determine or at least estimate the temperature of the formulations inside the convection curing device during the curing step, e.g., by using infrared temperature measurement instruments (such as an IR gun) or by measuring the temperature using a temperature probe that was placed inside the curing device near the formulations. When the curing step takes place in a convection curing device, the curing temperature can be defined and the curing time can be measured as follows.

In one embodiment (method 1), the curing temperature is defined to be the target inlet air temperature and the starting point of the curing step is defined to be the point in time when the inlet air temperature reaches the curing temperature. The end point of the curing step is defined to be (1) the point in time when the heating is stopped or at least reduced and the inlet air temperature subsequently drops below the curing temperature by more than about 10° C. and/or below the lower limit of the softening temperature range of polyethylene oxide, for example below about 62° C., in a plateau-like temperature profile, or (2) the point in time when the inlet air temperature drops below the curing temperature in a parabolic or triangular temperature profile.

In another embodiment (method 2), the curing temperature is defined to be the target exhaust air temperature, and the starting point of the curing step is defined to be the point in time when the exhaust air temperature reaches the curing temperature. The end point of the curing step is defined to be (1) the point in time when the heating is stopped or at least reduced and the exhaust air temperature subsequently drops below the curing temperature by more than about 10° C. and/or below the lower limit of the softening temperature range of polyethylene oxide, for example below about 62° C., in a plateau-like temperature profile, or (2) the point in time when the exhaust air temperature drops below the curing temperature in a parabolic or triangular temperature profile.

In a further embodiment (method 3), the curing temperature is defined to be the target temperature of the formulations and the starting point of the curing step is defined to be the point in time when the temperature of the formulations, which can be measured for example by an IR gun, reaches the curing temperature. The end point of the curing step is defined to be (1) the point in time when the heating is stopped or at least reduced and the temperature of the formulations subsequently drops below the curing temperature by more than about 10° C. and/or below the lower limit of the softening temperature range of polyethylene oxide, for example below about 62° C., in a plateau-like temperature profile or (2) the point in time when the temperature of the formulations drops below the curing temperature in a parabolic or triangular temperature profile.

In still another embodiment (method 4), the curing temperature is defined to be the target temperature measured using a temperature probe, such as a wire thermocouple, that is placed inside the curing device near the formulations, and the starting point of the curing step is defined to be the point in time when the temperature measured using the temperature probe reaches the curing temperature. The end point of the curing step is defined to be (1) the point in time when the heating is stopped or at least reduced and the temperature measured using the temperature probe subsequently drops below the curing temperature by more than about 10° C. and/or below the lower limit of the softening temperature range of polyethylene oxide, for example below about 62° C., in a plateau-like temperature profile, or (2) the point in time when the temperature measured using the temperature probe drops below the curing temperature in a parabolic or triangular temperature profile.

If curing takes place in a convection curing device, the curing time can be measured by any of the methods described above. Preferably, the curing time herein is determined by method 2 described above, wherein the curing temperature is defined to be the target exhaust air temperature.

In certain embodiments, the curing temperature is defined as a target temperature range, for example, the curing temperature is defined as a target inlet air temperature range or preferably a target exhaust air temperature range. In such embodiments, the starting point of the curing step is defined to be the point in time when the lower limit of the target temperature range is reached, and the end point of the curing step is defined to be the point in time when the heating is stopped or at least reduced, and the temperature subsequently drops below the lower limit of the target temperature range by more than about 10° C. and/or below the lower limit of the softening temperature range of polyethylene oxide, for example, below about 62° C.

The term "flattening" and related terms as used in the context of flattening tablets or other dosage forms in accordance with the present invention means that a tablet is subjected to force applied from a direction substantially perpendicular to the diameter and substantially in line with the thickness of e.g. a tablet. The force may be applied with a Carver style bench press (unless expressly mentioned otherwise) to the extent necessary to achieve the target flatness/reduced thickness. According to certain embodiments of the invention the flattening does not result in breaking the tablet in pieces, however, edge spits and cracks may occur. The flatness is described in terms of the thickness of the flattened tablet compared to the thickness of the non-flattened tablet expressed in % thickness, based on the thickness of the non-flattened tablet. Apart from tablets, the flattening can be applied to any shape of a dosage form, wherein the force is applied from a direction substantially in line with the smallest diameter (i.e. the thickness) of the shape when the shape is other than spherical and from any direction when the shape is spherical. The flatness is then described in terms of the thickness/smallest diameter of the flattened shape compared to the thickness/smallest diameter of the non-flattened shape expressed in % thickness, based on the thickness/smallest diameter of the non-flattened shape, when the initial shape is non-spherical, or the % thickness, based on the non-flattened diameter when the initial shape is spherical. The thickness is measured using a thickness gauge (e.g., digital thickness gauge or digital caliper).

When conducting the breaking strength test of the dosage forms (which is sometimes also referred to as the "hardness test" as it provides information on the hardness of the tested dosage forms) as described in Remington's Pharmaceutical Sciences, 18th edition, 1990, Chapter 89 "Oral Solid Dosage Forms", pages 1633-1665, which is incorporated herein by reference, using a Schleuniger Apparatus the tablet/dosage form is put between a pair of flat plates arranged in parallel, and pressed by means of the flat plates, such that the force is applied substantially perpendicular to the thickness and substantially in line with the diameter of the tablet, thereby reducing the diameter in that direction. The force pre-set for the breaking strength measurements performed in the context of the present invention is 438 N (44.7 Kp). The reduced diameter may be described in terms of % diameter, based on the diameter of the tablet/dosage form before conducting the breaking strength test. The breaking strength value indicated by the apparatus is the recorded force at the end-point of the measurement. The end point may be the point when the tablet/dosage form breaks, or when the measurement stops due to another event, such as another physical change (bending, deformation etc.) of the tablet/dosage form. If the maximum force of the measurement of 438 N (44.7 Kp) is reached without interruption or stop, this means that the tablet is resistant to breaking at that force. Tablets which are only deformed, but did not break at that force are considered to be break-resistant at that force.

For the purposes of the present invention, the term "breaking strength" as used herein thus refers to the hardness of the tablets/dosage forms as measured using a Schleuniger apparatus as described herein.

A further test to quantify the strength of tablets/dosage forms is the indentation test using a Texture Analyzer, such as the TA-XT2 Texture Analyzer (Texture Technologies Corp., 18 Fairview Road, Scarsdale, NY 10583). In this method, the tablets/dosage forms are placed on top of a stainless steel stand with slightly concaved surface and subsequently penetrated by the descending probe of the Texture Analyzer, such as a TA-8A ⅛ inch diameter stainless steel ball probe. Before starting the measurement, the tablets are aligned directly under the probe, such that the descending probe will penetrate the tablet pivotally, i.e. in the center of the tablet, and such that the force of the descending probe is applied substantially perpendicular to the diameter and substantially in line with the thickness of the tablet. First, the probe of the Texture Analyzer starts to move towards the tablet sample at the pre-test speed. When the probe contacts the tablet surface and the trigger force set is reached, the probe continues its movement with the test speed and penetrates the tablet. For each penetration depth of the probe, which will hereinafter be referred to as "distance" in the context of this measurement, the corresponding force is measured, and the data are collected. When the probe has reached the desired maximum penetration depth, it changes direction and moves back at the post-test speed, while further data can be collected. The "cracking force" is defined herein to be the force of the first local maximum that is reached in the corresponding force/distance diagram and is calculated using for example the Texture Analyzer software "Texture Expert Exceed, Version 2.64 English". Without wanting to be bound by any theory, it is believed that at this point, some (internal) structural damage to the tablet/dosage form may occur in form of cracking. However, the thus cracked tablets/dosage forms according to certain embodiments of the present invention may remain cohesive, as evidenced by the continued resistance to the descending probe. The corresponding distance at the first local maximum is herein referred to as the "penetration depth to crack" distance.

For the purposes of the present invention, the term "cracking force" as used herein thus refers to the strength of the tablets/dosage forms as measured in the indentation test using a Texture Analyzer as described herein.

The resistance to crushing of the tablets/dosage forms is determined by means of an Instron instrument in accordance with the European Pharmacopoeia (EP, 2.9.8 Resistance to Crushing of Tablets). The results obtained from this test are hereinafter referred to as the "crush resistance". The test is performed as follows: The tablet is placed on the lower compression platen such that the load is perpendicular to the thickness and in line with the diameter of the tablet/dosage form. In the case of caplets, tweezers are used in order to hold the caplet upright on the lower platen. The upper platen is lowered so that it is just above the tablet/dosage form end; the upper platen should not be touching the tablet/dosage form end. Thus, the height of the upper platen position has to be adjusted to the length of the tested tablet/dosage form. A pretest speed is set to 5 mm/min and a maximum force of 1N. The crosshead (upper platen) test speed to lower the upper platen is then set at 60 mm/min, and the upper force limit to 500N (51 Kp). (In case of a caplet, once the caplet is held in place between the two platens, the tweezers can be removed). At the end of the test (after the upper platen has raised again), the tablet/dosage form is removed.

For the purposes of the present invention, the term "crush resistance" as used herein thus refers to the resistance to crushing of the tablets/dosage forms as measured in the by an Instron instrument as described herein.

For the purposes of certain embodiments of the present invention, the term "% RSD" refers to the percentage relative standard deviation. The term "LS" stands for "least squares".

"Milliliter" is abbreviated herein as "ml" or "mL".

DETAILED DESCRIPTION

In its most general aspect, the present invention is directed to a solid oral extended release pharmaceutical dosage form comprising a cured extended release matrix formulation, the extended release matrix formulation comprising:
a therapeutically effective amount of morphine sulfate, and
polyethylene oxide.

Specifically, the present invention is directed to a solid oral extended release pharmaceutical dosage form comprising a cured extended release matrix formulation, the extended release matrix formulation comprising:
a therapeutically effective amount of morphine sulfate, and
polyethylene oxide having an approximate molecular weight of from about 600,000 to about 3,000,000.

The present invention is also generally directed to a solid oral extended release pharmaceutical dosage form comprising a cured extended release matrix formulation, wherein the extended release matrix formulation comprises:
a therapeutically effective amount of morphine sulfate, and
polyethylene oxide
and is obtainable by at least the following steps:
(a) combining at least morphine sulfate and polyethylene oxide particles to form a composition,
(b) shaping the composition of step (a) to form the extended release matrix formulation, and (c) curing the extended release matrix formulation of step (b).

The present invention is specifically directed to a solid oral extended release pharmaceutical dosage form comprising a cured extended release matrix formulation, wherein the cured extended release matrix formulation comprises:
  a therapeutically effective amount of morphine sulfate, and
  polyethylene oxide
and is obtainable by at least the following steps:
  (a) combining at least morphine sulfate and polyethylene oxide particles having an approximate molecular weight of from about 600,000 to about 3,000,000 to form a composition,
  (b) shaping the composition of step (a) to form the extended release matrix formulation, and
  (c) curing the extended release matrix formulation of step (b).

In another aspect, the present invention is directed to an extended release matrix formulation obtainable by:
  (a) combining at least a therapeutically effective amount of morphine sulfate and polyethylene oxide particles to form a composition, and
  (b) shaping the composition of step (a) to form the extended release matrix formulation.

The present invention is specifically directed to an extended release matrix formulation obtainable by:
  (a) combining at least a therapeutically effective amount of morphine sulfate and polyethylene oxide particles to form a composition, and
  (b) shaping the composition of step (a) to form the extended release matrix formulation, wherein the polyethylene oxide used as the polyethylene oxide particles in step (a) has an approximate molecular weight of from about 600,000 to about 3,000,000.

Active Agent (Morphine Sulfate)

The solid oral extended release pharmaceutical dosage form of the present invention contains morphine in the form of morphine sulfate. According to the present invention, morphine sulfate is combined with polyethylene oxide (particles) to form a composition, which is then shaped to form the extended release matrix formulation. The extended release matrix formulation is subsequently cured and optionally coated to form the solid oral extended release pharmaceutical dosage form.

In certain embodiments, the morphine sulfate is included into the extended release matrix formulation in the form of morphine hemi(sulfate pentahydrate) (having a molecular weight of 758.8 g/mol) as defined in the section "Definitions" herein above.

In certain embodiments, the morphine sulfate is included in the extended release matrix formulation in the form of morphine hemi(sulfate pentahydrate) (having a molecular weight of 758.8 g/mol) in an amount of about 2.5 to about 40% by weight, 5 to about 40% by weight, preferably in an amount of about 8 to about 35% by weight, more preferably in an amount of about 10 to about 20% by weight, or in an amount of about 25 to about 35% by weight, or in an amount of about 12 to about 33% by weight of the extended release matrix formulation. Instead of morphine hemi(sulfate pentahydrate) (having a molecular weight of 758.8 g/mol) also an equimolar amount of another solvate or hydrate of morphine sulfate can be incorporated into the extended release matrix formulation.

In certain embodiments, the morphine sulfate is included in the extended release matrix formulation in the form of morphine hemi(sulfate pentahydrate) (having a molecular weight of 758.8 g/mol) in an amount of from about 2.5 mg to about 300 mg, preferably in an amount of from about 5 mg to about 250 mg, more preferably from about 10 mg to about 250 mg, more preferably in an amount of from about 15 mg to about 200 mg, particularly in an amount of about 5 mg, about 10 mg, about 15 mg, about 30 mg, about 60 mg, about 100 mg or about 200 mg, or in an equimolar amount of another solvate or hydrate of morphine sulfate.

In certain embodiments, the morphine or pharmaceutically acceptably salt thereof, specifically the morphine sulfate as used herein, may have a D90 particle size of from about 50 μm to about 70 μm, preferably from about 55 μm to about 65 μm, or from about 20 μm to about 40 μm, preferably from about 25 μm to about 35 μm, or from about 8 μm to about 20 μm, preferably from about 10 μm to about 18 μm as measured by the Malvern method (light scattering).

In certain embodiments the dosage form of the present invention may include other active agents in combination with morphine sulfate.

In certain embodiments, the dosage form of the present invention may include, in addition to morphine sulfate, one or more other pharmaceutically acceptable salt(s) of morphine including, but not limited to, inorganic acid salts such as hydrochloride, hydrobromide, phosphate and the like; organic acid salts such as formate, acetate, trifluoroacetate, maleate, tartrate and the like; sulfonates such as methanesulfonate, benzenesulfonate, p-toluenesulfonate, and the like; amino acid salts such as arginate, asparaginate, glutamate and the like, and metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like, including any hydrates or other solvates of the foregoing. It is believed that the principles of the present invention are equally applicable mutatis mutandis to any of these other pharmaceutically acceptable salts of morphine.

In certain embodiments, the dosage form of the present invention may include, in addition to morphine sulfate, one or more other opioid agonist(s). Opioid agonists useful in the dosage forms in the present invention in combination with morphine sulfate include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, dihydroetorphine, fentanyl and derivatives, hydrocodone, hydromorphone, hydroxypethidine, isomethadone, ketobemidone, levorphanol, levophenacylmorphan, lofentanil, meperidine, meptazinol, metazocine, methadone, metopon, myrophine, narceine, nicomorphine, norlevorphanol, normethadone, nalorphine, nalbuphene, normorphine, norpipanone, opium, oxycodone, oxymorphone, papavereturn, pentazocine, phenadoxone, phenomorphan, phenazocine, phenoperidine, piminodine, piritramide, propheptazine, promedol, properidine, propoxyphene, sufentanil, tilidine, tramadol, as well as their pharmaceutically acceptable salts, hydrates and solvates thereof, mixtures of any of the foregoing, and the like.

In certain embodiments, the dosage form of the present invention may include, in addition to morphine sulfate, one or more opioid antagonist(s). Opioid antagonists useful in combination with morphine sulfate or the other opioid agonists described above include, but are not limited to, naloxone, naltrexone and nalmephene, as well as their pharmaceutically acceptable salts and their hydrates and solvates, and mixtures of any of the foregoing, and the like.

In certain embodiments, the dosage form of the present invention may include, in addition to morphine sulfate, one or more other active agent(s) including, but not limited to, antihistamines (e.g., dimenhydrinate, diphenhydramine, chlorpheniramine and dexchlorpheniramine maleate), non-steroidal anti-inflammatory agents (e.g., naproxen, diclofenac, indomethacin, ibuprofen, sulindac, Cox-2 inhibitors) and acetaminophen, anti-emetics (e.g., metoclopramide, methylnaltrexone), anti-epileptics (e.g., phenyloin, meprobamate and nitrazepam), vasodilators (e.g., nifedipine, papaverine, diltiazem and nicardipine), anti-tussive agents and expectorants (e.g. codeine phosphate), anti-asthmatics (e.g. theophylline), antacids, anti-spasmodics (e.g. atropine, scopolamine), antidiabetics (e.g., insulin), diuretics (e.g., ethacrynic acid, bendrofluthiazide), anti-hypotensives (e.g., propranolol, clonidine), antihypertensives (e.g., clonidine, methyldopa), bronchodilators (e.g., albuterol), steroids (e.g., hydrocortisone, triamcinolone, prednisone), antibiotics (e.g., tetracycline), antihemorrhoidals, hypnotics, psychotropics, antidiarrheals, mucolytics, sedatives, decongestants (e.g. pseudoephedrine), laxatives, vitamins, stimulants (including appetite suppressants such as phenylpropanolamine), barbiturates, CNS-depressants (e.g. benzodiazepines) and cannabinoids, as well as their pharmaceutically acceptable salts and their hydrates and solvates.

Polyethylene Oxide

The solid oral extended release pharmaceutical dosage form of the present invention comprises polyethylene oxide. Polyethylene oxide is included in the dosage form as polyethylene oxide particles, which are combined with morphine sulfate to form a composition, which composition is then shaped to form the extended release matrix formulation. The extended release matrix formulation is subsequently cured and optionally coated to form the solid oral extended release pharmaceutical dosage form of the present invention.

Both the polyethylene oxide present in the final dosage form, as well as the polyethylene oxide particles included into the extended release matrix formulation (i.e., the polyethylene oxide particles combined with morphine sulfate during the preparation of the dosage form) may be characterized by a certain approximate molecular weight, or may fall within a certain approximate molecular weight range. Said approximate molecular weight is determined and defined based on rheological measurements as defined herein (in the section "Definitions").

In certain embodiments, the polyethylene oxide present in the dosage form has an approximate molecular weight of from about 600,000 to about 4,000,000, preferably from about 600,000 to about 3,000,000, more preferably from about 900,000 to about 2,000,000, more preferably from about 1,000,000 to about 2,000,000, and most preferably of about 1,000,000 or about 2,000,000. The polyethylene oxide present in the dosage form may originate from a single (e.g. commercially available) grade of polyethylene oxide or from a combination of two or more (e.g. commercially available) grades. If originating from two or more (e.g. commercially available) polyethylene oxide grades, the approximate molecular weight of the polyethylene oxide overall present in the dosage form is from about 600,000 to about 4,000,000, preferably from about 600,000 to about 3,000,000, more preferably from about 900,000 to about 2,000,000, more preferably from about 1,000,000 to about 2,000,000, and most preferably of about 1,000,000 or about 2,000,000.

In certain embodiments, the polyethylene oxide included into the extended release matrix formulation (i.e., the polyethylene oxide particles combined with morphine sulfate during the preparation of the dosage form) has an approximate molecular weight of from about 600,000 to about 4,000,000, preferably from about 600,000 to about 3,000,000, more preferably from about 900,000 to about 2,000,000, more preferably from about 1,000,000 to about 2,000,000, and most preferably of about 1,000,000 or about 2,000,000. The polyethylene oxide included into the extended release matrix formulation may constitute a single (e.g. commercially available) grade of polyethylene oxide or a combination (e.g. a blend or mixture) of two or more (e.g. commercially available) grades. If two or more (e.g. commercially available) polyethylene oxide grades are included into the extended release matrix formulation, the approximate molecular weight of the included polyethylene oxide overall is preferably from about 600,000 to about 4,000,000, preferably from about 600,000 to about 3,000,000, more preferably from about 900,000 to about 2,000,000, more preferably from about 1,000,000 to about 2,000,000, and most preferably of about 1,000,000 or about 2,000,000.

In certain embodiments, one or more of the following polyethylene oxide grades are used as the polyethylene oxide particles in step (a) when preparing the solid oral extended release pharmaceutical dosage form of the invention (i.e. the polyethylene oxide particles combined with morphine sulfate when preparing the extended release matrix formulation):

polyethylene oxide having an approximate molecular weight of about 900,000 and/or showing a viscosity in the range of 8,800 to 17,600 mPa s (cP) when the viscosity of a 5% (by weight) aqueous solution of said polyethylene oxide is determined using a Brookfield viscometer Model RVF, spindle No. 2, at 2 rpm, at 25° C.; e.g. the grade POLYOX® WSR-1105 NF commercially available from the Dow Chemical Company;

polyethylene oxide having an approximate molecular weight of about 1,000,000 and/or showing a viscosity in the range of 400 to 800 mPa s (cP) when the viscosity of a 2% (by weight) aqueous solution of said polyethylene oxide is determined using a Brookfield viscometer Model RVF, spindle No. 1, at 10 rpm, at 25° C., e.g. the grade POLYOX® WSR-N-12K NF commercially available from the Dow Chemical Company; and polyethylene oxide having an approximate molecular weight of about 2,000,000 and/or showing a viscosity in the range of 2,000 to 4,000 mPa s (cP) when the viscosity of a 2% (by weight) aqueous solution of said polyethylene oxide is determined using a Brookfield viscometer Model RVF, spindle No. 3, at 10 rpm, at 25° C., e.g. the grade POLYOX® WSR-N-60K NF commercially available from the Dow Chemical Company.

Without wishing to be bound by any theory, it is believed that the approximate molecular weight of the polyethylene oxide determines, in combination with other factors, including but not limited to the amount of polyethylene oxide (or the ratio of morphine sulfate to polyethylene oxide) incorporated into the dosage forms, the in-vitro as well as the in-vivo release characteristics of the dosage forms. In particular, it is believed that incorporating polyethylene oxide with a relatively lower approximate molecular weight (such as in the range from about 600,000 to about 3,000,000) into the dosage forms may provide for a relatively faster release of morphine sulfate, both in vitro and in vivo, than incorporating polyethylene oxide with a relatively higher approximate molecular weight (such as about 4,000,000 and above).

In certain embodiments, the dosage forms according to the present invention prepared by combining polyethylene oxide with an approximate molecular weight within the ranges as defined herein, specifically with an approximate molecular weight of about 1,000,000 or about 2,000,000 with morphine sulfate are bioequivalent as defined herein to commercially available reference tablets MS Contin® of the same strength as also defined herein (see e.g. Table VIII and the "Definitions" section).

In certain embodiments, the solid oral extended release pharmaceutical dosage form of the present invention is characterized in that the polyethylene oxide present in the dosage form is included in the extended release matrix formulation in an amount of about 55 to about 95% by weight thereof, preferably in an amount of about 60 to about 90% by weight thereof, more preferably in an amount of about 78 to about 90% by weight thereof or in an amount of about 60 to about 70% by weight thereof, or in an amount of about 64 to about 87% by weight thereof. In a particularly preferred embodiment, about 55 to about 90% by weight of polyethylene oxide and about 5 to about 40% by weight of morphine sulfate is included into the extended release matrix formulation. In an even more preferred embodiment, about 64 to about 87% by weight of polyethylene oxide and about 12 to about 33% by weight of morphine sulfate is included in the extended release matrix formulation.

In a certain embodiment, about 4 to about 8% by weight of morphine sulfate and about 92 to about 96% by weight of polyethylene oxide is included in the extended release matrix formulation. In this embodiment, the extended release matrix formulation preferably contains about 5 mg of morphine sulfate.

In another embodiment, about 6 to about 10% by weight of morphine sulfate and about 88 to about 93% by weight of polyethylene oxide is included in the extended release matrix formulation. In this embodiment, the extended release matrix formulation preferably contains about 10 mg of morphine sulfate.

In another embodiment, about 10 to about 15% by weight of morphine sulfate and about 84 to about 91% by weight of polyethylene oxide is included in the extended release matrix formulation. In this embodiment, the extended release matrix formulation preferably contains about 15 mg of morphine sulfate.

In another embodiment, about 15 to about 20% by weight of morphine sulfate and about 78 to about 86% by weight of polyethylene oxide is included in the extended release matrix formulation. In this embodiment, the extended release matrix formulation preferably contains about 30 or about 60 mg of morphine sulfate.

In another embodiment, about 27 to about 36% by weight of morphine sulfate and about 60 to about 70% by weight of polyethylene oxide is included in the extended release matrix formulation. In this embodiment, the extended release matrix formulation preferably contains about 100 or about 200 mg of morphine sulfate.

In the above embodiments, and throughout the entire disclosure of the present invention, the morphine sulfate is included in the extended release matrix formulation in the form of morphine hemi(sulfate pentahydrate) (having a molecular weight of 758.8 g/mol) in the respective amounts indicated, or in a respective equimolar amount of another solvate or hydrate of morphine sulfate.

In certain embodiments the morphine sulfate and the polyethylene oxide are included in the extended release matrix formulation in a weight ratio of from about 1:100 to about 1:1, or from about 1:25 to about 1:1, or from about 1:20 to about 1:1.25, or from about 1:10 to about 1.17, calculated on the basis of the amount of morphine hemi (sulfate pentahydrate)(having a molecular weight of 758.8 g/mol) and the amount of polyethylene oxide included into the extended release formulation.

In certain embodiments, the polyethylene oxide particles used and included in the preparation of the extended release matrix formulation (i.e., in step (a)) have a certain particle size distribution as defined herein (in the section "Definitions"). Preferably, fine particle (FP) grades or any combination of fine particle and regular grades of polyethylene oxide particles may be used. Most preferably, the polyethylene oxide particles used (whether solely fine particle grade(s) or combination(s) of regular and fine particle grade(s)) exhibit a particle size distribution as specified in the following:

In certain embodiments, the polyethylene oxide particles are characterized in that substantially all particles, or at least a portion of the particles pass through at least a 25 mesh, preferably at least a 35 mesh, more preferably at least a 45 mesh, more preferably at least a 50 mesh, most preferably at least a 60 mesh sieve as defined in the "Definitions" section, above.

In certain embodiments, the polyethylene oxide particles are characterized in that about 50/o or more, preferably about 70% or more, more preferably about 90% or more of the polyethylene oxide particles pass through a 25 mesh (0.707 mm; 707 microns) sieve.

In certain embodiments the polyethylene oxide particles are characterized in that about 50% or more, preferably about 70% or more, more preferably about 90% or more of the polyethylene oxide particles pass through a 35 mesh (0.500 mm; 500 microns) sieve.

In certain specific embodiments the polyethylene oxide particles are characterized in that about 50% or more, preferably about 70% or more, more preferably about 90% or more, most preferably about 96% or more of the polyethylene oxide particles pass through a 60 mesh (0.250 mm; 250 microns) sieve.

All percentages recited herein above with respect to the particle size distribution refer to % by weight. Thus, in certain embodiments, most preferably about 96% by weight of the polyethylene oxide particles included in the extended release matrix formulation pass through a 60 mesh (0.250 mm; 250 microns) sieve.

In certain embodiments, polyethylene oxide particles suitable for the preparation of the extended release matrix formulation are Dow Chemical Company's POLYOX® Water Soluble Resin grades, which may be used as regular and as fine particle (FP) grades, preferably as fine particle grades. In specific embodiments, POLYOX® WSR N-12K FP, NF (having an approximate molecular weight of 1,000,000 as defined herein) and POLYOX® WSR N-60K FP, NF (having an approximate molecular weight of 2,000,000 as defined herein) are used. According to specification, about 96 to about 100% of the polyethylene oxide particles of these FP grades pass through a 60 mesh (0.250 mm; 250 microns) sieve.

In certain embodiments, a combination of one or more fine particle grade(s) and one or more regular particle size grade(s) of polyethylene oxide may be used to prepare the extended release matrix formulation and thus the solid oral extended release pharmaceutical dosage form of the present invention. Preferably, the particle size of the entire combined polyethylene oxide material used in the present invention lies within the ranges of particle size as recited above with reference to the various mesh sieves. Most preferably, 90% or more, most preferably about 96% or more of all the polyethylene oxide particles used for the preparation of the extended release matrix formulation pass through a 60 mesh (0.250 mm; 250 microns) sieve.

It is believed, without wishing to be bound by any theory, that by using polyethylene oxide fine particles as defined above in the preparation of the extended release matrix formulation of the present invention, the resulting dosage form comprising the cured extended release matrix formulation has improved hardness as expressed e.g. through improved breaking strength, improved cracking force and/or improved crush resistance as further described herein below and as illustrated in the examples when compared to similar dosage forms that comprise an extended release matrix composition made using corresponding polyethylene oxide regular size particles of similar approximate molecular weight. The dosage forms of the present invention also have an improved hardness as expressed e.g. by an increased breaking strength as compared to reference dosage forms (of the same strength) of the commercial product MS Contin® as defined herein (see Example 7).

It is further believed, again without wishing to be bound by any theory, that the relatively lower molecular weight polyethylene oxide as used for the preparation of the extended release matrix formulation and thus for the dosage form of the present invention (such as polyethylene oxide having an approximate molecular weight in the range of from about 600,000 to about 3,000,000 or in the preferred ranges identified above (see e.g. tablets A to E according to the present invention identified in Table I below)—as opposed to polyethylene oxide having a relatively higher approximate molecular weight of about 4,000,000 and above (see e.g. reference tablets F, G and J identified in Table II below or reference tablets O, P and Q identified in Table III below)) may in certain circumstances lower the hardness or physical strength of a dosage form containing such relatively low molecular weight polyethylene oxide in combination with morphine sulfate. It has been found that this hardness-lowering effect can be countered by using polyethylene oxide(s) of said approximate molecular weight (range) that has/have a particle size distribution as defined herein, i.e., by using fine particle grade(s) of the respective polyethylene oxide(s). By using polyethylene oxide grades having a particle size distribution as defined herein, the hardness of the final dosage form can be improved even if the approximate molecular weight of the polyethylene oxide is relatively low, i.e., within the ranges as specified above.

Due to their improved hardness (as manifested e.g. by improved breaking strength, improved cracking force and/or improved crush resistance as defined herein) as compared to the commercially available reference product MS Contin® the dosage forms, and particularly the tablets of the present invention show a reduced potential for physical manipulation (such as by crushing between spoons or by using mortar and pestle or other tools as illustrated in the examples, see in particular Example 12) when compared to MS Contin® tablets of the same strength, which contributes to preventing or reducing the likelihood of abuse of the dosage forms according to the present invention.

In addition to polyethylene oxide, the solid oral extended release pharmaceutical dosage form of the present invention may contain other materials which may also provide for controlled release, including, but not limited to, alkylcellulose, cellulose ethers, acrylic polymers, other polyalkylene oxides, polycarbonates, aliphatic alcohols, polyethylene glycol, starch, gums or any mixtures of these.

Other Excipients

The solid oral extended release pharmaceutical dosage form of the present invention may contain one or more pharmaceutically acceptable additives or excipients known to those of ordinary skill in the art. Suitable additives or excipients include, but are not limited to, lubricants, glidants (also referred to in the art as flow enhancers), binders, disintegrants, buffering agents, plasticizers, colorants, flavors, sweeteners, anti-oxidants (such as butylated hydroxytoluene, BHT), surfactants, diluents, stabilizers, preservatives, and aversive agents (such as emetics, antagonists, irritants, e.g., nasal irritants, bittering agents and others).

In certain embodiments, the solid oral extended release pharmaceutical dosage form of the present invention may contain a lubricant, which may be included in an amount of from about 0.1 to about 5% by weight of the extended release matrix formulation, preferably in an amount of from about 0.5 to about 3% by weight, more preferably in an amount of from about 0.75 to about 2% by weight of the extended release matrix formulation. In certain embodiments, the lubricant may be or may comprise magnesium stearate. The presence of the lubricant (sometimes also referred to in the art as "anti-adherent") may avoid or reduce the propensity of solid, compressed dosage forms to film and to stick to the molds or punches during manufacturing.

Other suitable lubricants include, but are not limited to, glyceryl behenate (Compritol™ 888), other metallic stearates (e.g., calcium and sodium stearates), stearic acid, hydrogenated vegetable oils (e.g., Sterotex™), talc, waxes such as beeswax and carnauba wax, silica, fumed silica, colloidal silica, calcium stearate, long chain fatty alcohols, boric acid, sodium benzoate and sodium acetate, sodium chloride, DL-Leucine, polyethylene glycols (e.g., Carbowax™ 4000 and Carbowax™ 6000), sodium oleate, sodium benzoate, sodium acetate, sodium lauryl sulfate, sodium stearyl fumarate (Pruv™), magnesium lauryl sulfate, stearic acid, stearyl alcohol, mineral oil, paraffin, microcrystalline cellulose, glycerin, propylene glycol and combinations thereof.

In certain embodiments, the solid oral extended release pharmaceutical dosage form of the present invention may contain a glidant (also referred to as "flow enhancer"). Glidants are used to improve the flow characteristics of a formulation in the form of a powder during manufacturing. The glidant may be included in an amount of from about 0.1 to about 2.5% by weight of the extended release matrix formulation, preferably in an amount of from about 0.4 to about 0.6% by weight of the extended release matrix formulation of the present invention. In certain embodiments, the glidant may be or may comprise silicon dioxide, preferably colloidal silicon dioxide. An exemplary glidant is colloidal silicon dioxide (CARB-O-SIL®)).

Preferably, if any additives or excipients (in other words, any ingredients other than morphine sulfate and polyethylene oxide) are used in the preparation of the solid oral extended release pharmaceutical dosage form according to the present invention, each of such additives or excipients alone, or all of such additives or excipients together, are preferably used and are preferably present in the final dosage form in less than 5% by weight, preferably in less than 3% by weight, most preferably in less than 2% by weight.

Particularly, if any plasticizer(s), e.g. one or more poloxamer(s) or other plasticizer(s) known in the art, are used at all in the preparation of the dosage form, they are preferably used and present in the final dosage form in less than 5% by weight, preferably less than 3% by weight, more preferably less than 2% by weight. Most preferably the solid oral extended release pharmaceutical dosage form according to the present invention is free or substantially free of plasticizers.

Furthermore, if any surfactant(s) of any kind, such as anionic, cationic or non-ionic surfactant(s), specifically non-ionic surfactant(s) comprising or made of synthetic copolymers of ethylene oxide and propylene oxide, is/are used at all in the preparation of the dosage form, such surfactant(s) are preferably used and present in the final dosage form in less than 5% by weight, preferably less than 3% by weight, more preferably less than 2% and even more preferably less than 1% by weight. Most preferably the solid oral extended release pharmaceutical dosage form according to the present invention is free or substantially free of any surfactant.

Anti-oxidants may be present in the solid oral extended release pharmaceutical dosage form according to the present invention in low amounts if needed. One exemplary suitable anti-oxidant is butylated hydroxytoluene (BHT). Commercial grades of polyethylene oxide may already contain a certain amount of anti-oxidant such as BHT. Additional anti-oxidant may be added during the preparation of the dosage form, and may be present in the final dosage form, in amounts of not more than 2% by weight, preferably not more than 1% by weight, more preferably not more than 0.5% by weight of the final dosage form. Most preferably the solid oral extended release pharmaceutical dosage form according to the present invention is substantially free of any additional anti-oxidant. In case any binders are used (i.e., in addition to polyethylene oxide as described above) to prepare the solid oral extended release pharmaceutical dosage form according to the present invention, such as poly(vinylpyrrolidone) or other binders known in the art, such binders are preferably used or present in the final dosage form in less than 7% by weight, preferably less than 5% by weight, more preferably less than 2.5% by weight, and even more preferably less than 1% by weight. Most preferably the solid oral extended release pharmaceutical dosage form according to the present invention is free or substantially free of such binders (other than polyethylene oxide).

Process of Preparation

The present invention is in another aspect also directed to a process of preparing a solid oral extended release pharmaceutical dosage form comprising a cured extended release matrix formulation, wherein the extended release matrix formulation comprises:
 a therapeutically effective amount of morphine sulfate, and
 polyethylene oxide,
the process comprising at least the following steps:
 (a) combining at least morphine sulfate and polyethylene oxide particles to form a composition,
 (b) shaping the composition of step (a) to form the extended release matrix formulation, and
 (c) curing the extended release formulation of step (b).

The present invention is specifically directed to a process of preparing a solid oral extended release pharmaceutical dosage form comprising a cured extended release matrix formulation, wherein the extended release matrix formulation comprises:
 a therapeutically effective amount of morphine sulfate, and
 polyethylene oxide,
the process comprising at least the following steps:
 (a) combining at least morphine sulfate and polyethylene oxide particles to form a composition,
 (b) shaping the composition of step (a) to form the extended release matrix formulation, and
 (c) curing the extended release matrix formulation of step (b),
wherein the polyethylene oxide used as the polyethylene oxide particles in step (a) has an approximate molecular weight of from about 600,000 to about 3,000,000.
Preparing and Shaping the Composition:

In step (a), morphine sulfate (specifically, morphine hemi (sulfate pentahydrate) or another hydrate or solvate form of morphine sulfate as defined herein) is combined with polyethylene oxide. Polyethylene oxide is used in the form of particles, preferably having a certain particle size distribution as defined herein. In certain embodiments, morphine sulfate and polyethylene oxide are dry-mixed or dry-blended, e.g. in a V-blender with or without an I-bar, which is preferably equipped with a sifter, such as a centrifugal sifter having a 7-mesh, 8-mesh, 10-mesh, 12 mesh, or 20 mesh screen through which the components are passed while being charged into the blender. All components may be charged into the blender at the same time (in such case the components may optionally have been pre-mixed), or may be charged one after the other. In certain embodiments, in order to obtain optimal mixing, first a certain portion of the polyethylene oxide may be charged into the blender, then a certain portion or all of the morphine sulfate, followed by another portion of polyethylene oxide, and so on (if necessary). The components are blended for a certain period of time, such as from about 5 to about 60 min, until a satisfactory degree of mixing is achieved.

In certain embodiments a glidant as defined above (e.g. colloidal silicon dioxide) may be added during or after the mixing of morphine sulfate and polyethylene oxide (and optionally lubricant). The glidant may be added at the same time as (the first portion of) the morphine sulfate.

Likewise, in certain embodiments, a lubricant (e.g., magnesium stearate) as defined above may be added during or after the mixing of morphine sulfate and polyethylene oxide (and optionally glidant) in order to avoid clumping and sticking of the components.

The resulting composition of morphine sulfate, polyethylene oxide, optionally lubricant and optionally glidant is then blended for a certain period of time, such as from about 30 seconds to about 10 minutes, until a satisfactory degree of mixing is achieved. Furthermore, in certain embodiments, other ingredients or excipients as listed above may be added in the same manner.

In step (b), the final composition of step (a) of morphine sulfate, polyethylene oxide, the lubricant, the glidant and optionally further components is shaped to form the extended release matrix formulation. Preferably, for shaping a direct (i.e., dry) compression step is used. However, any other process for manufacturing tablets as known in the art may equally be used, including but not limited to wet granulation and subsequent compression, or 3D-printing. In certain embodiments, the extended release matrix formulation is a tablet, which tablet preferably has a certain target weight. In certain embodiments, the target weight of the shaped (uncured and uncoated) extended release matrix formulation of the present invention is from about 50 mg to about 700 mg, preferably from about 100 mg to about 650 mg, more preferably from about 125 mg to about 630 mg; most preferably about 125 mg, about 175 mg, about 330 mg, or about 600 mg. The tablet may have different shapes, as further described below.

Dry compression may be accomplished on a tablet press (e.g., a rotary tablet press, a Carver press, etc.), applying a certain compression force. The compression force may preferably be from about 1 kN to about 26 kN, more preferably from about 2 kN to about 14 kN. In certain specific embodiments, the target compression force may be about 2 kN, about 4 kN to about 5 kN, about 7 kN to about 8 kN, about 9 kN, about 10 kN to about 11 kN, about 12 kN, or about 14 kN. The applicable compression force depends inter alia on the total weight and on the size of the tablet.

In alternative embodiments, the composition comprising morphine sulfate, polyethylene oxide and excipients as listed above may be in the form of multiparticulates. For example, the morphine sulfate may be coated with polyethylene oxide to form particles or multiparticulates. In further implementations, the morphine sulfate as active agent may be coated over an inert particle or bead core to form an active agent layer, and the polyethylene oxide may be coated over the active agent layer to form an extended release layer to form multiparticulates. In certain implementations, instead of an inert particle or bead core, the core of the dosage form may be formed from a(nother) controlled release material, an aversive agent, another active agent, any other excipient or any combination thereof. Morphine sulfate may be present in any one or more of the layers of the multiparticulates.

In further alternative embodiments, the extended release matrix composition and thus the solid oral extended release pharmaceutical dosage form of the present invention may be in the form of an extrudate.

Curing:

The curing of the shaped extended release formulation (of step (b) of the process of the invention), which curing is comprised in step (c) of the process of the present invention, provides increased hardness to the solid oral extended release pharmaceutical dosage form. Hardness may be expressed e.g. by means of breaking strength, cracking force and/or crush resistance as described herein. The curing time and temperature are chosen to achieve the resistance to physical manipulation (and thus the abuse-deterrent potential) as disclosed herein. The skilled person is aware that the size/the dimension and the weight of the extended release matrix formulation may determine the curing time and temperature required to achieve the said resistance to physical manipulation. Without wanting to be bound by any theory, it is believed that in the case of a large extended release matrix formulation, such as a large tablet, a longer curing time is necessary to conduct the heat into the interior of the formulation than in the case of a corresponding extended release matrix formulation with smaller size (i.e., a smaller tablet). Higher temperature increases the thermal conductivity rate and thereby decreases the curing time required to achieve the desired hardness/resistance to physical manipulation. Other factors which influence the curing time and temperature required to achieve a certain desired resistance to physical manipulation are the amount of morphine sulfate contained in the dosage form (a larger amount of morphine sulfate is also believed to require a longer curing time and/or a higher temperature), and the particle size of the polyethylene oxide.

In those embodiments where the curing of the extended release matrix formulation in step (c) comprises at least a curing step wherein the extended release matrix formulation is subjected to a certain elevated temperature (or elevated temperature range) for a certain period of time, this period of time is hereinafter referred to as the curing time, and this elevated temperature (or elevated temperature range) is hereinafter referred to as the curing temperature. For the measurement of the curing time, the starting point and the end point of the curing step is determined as defined herein (in the section "Definitions").

In certain embodiments, the curing of the extended release matrix formulation in step (c) comprises at least a curing step wherein the polyethylene oxide in the extended release matrix formulation at least partially melts. For example, at least about 20%, at least about 30%, at least about 40%, at least about 50%, at least about 60%, at least about 75% or at least about 90% of the polyethylene oxide in the extended release matrix formulation melts. In a preferred embodiment, about 100% of the polyethylene oxide melts.

In certain embodiments, the curing temperature is at least as high as the softening temperature of the polyethylene oxide present in the extended release matrix formulation. Preferably, the curing temperature is at least as high as the lower limit of the softening temperature range of the polyethylene oxide or at least about 62° C., preferably at least about 68° C. More preferably, the curing temperature is within or above the softening temperature range of the polyethylene oxide or at least about 70° C. Even more preferably, the curing temperature is at least as high as the upper limit of the softening temperature range of the polyethylene oxide or at least about 72° C. In an alternative embodiment, the curing temperature is higher than the upper limit of the softening temperature range of the polyethylene oxide, for example the curing temperature is at least about 75° C. or at least about 80° C. Without wanting to be bound to any theory it is believed that the curing at a temperature that is at least as high as the softening temperature of the polyethylene oxide causes the polyethylene oxide particles to at least adhere to each other or even to fuse.

In certain embodiments the curing temperature is at least about 60° C., preferably at least about 65° C., more preferably at least about 70° C., most preferably at least about 72° C., or at least about 75° C. In certain embodiments, the curing temperature is less than about 90° C., preferably less than about 85° C., more preferably less than about 80° C., most preferably less than about 78° C. Specifically, in certain embodiments the curing temperature may be from about 65° C. to about 85° C., preferably from about 70° C. to about 80° C., more preferably from about 72° C. to about 78° C., most preferably about 72° C. or about 75° C.

In certain embodiments, the curing time period is at least about 15 minutes, preferably at least about 20 minutes, more preferably at least about 25 minutes, most preferably at least about 30 minutes. In certain embodiments, the curing time period is less than about 2 hours, preferably less than about 1.5 hours, more preferably less than about 1 hour and most preferably less than about 50 minutes. Specifically, in certain embodiments, the curing time period is from about 15 minutes to about 2 hours, preferably from about 20 minutes to about 75 minutes, more preferably from about 30 minutes to about 1 hour, most preferably from about 30 minutes to about 45 minutes. Specifically, the curing period in certain embodiments may be about 30 minutes or about 45 minutes.

In certain specific embodiments, the shaped extended release matrix formulation is subjected in step (c) to a curing temperature of from about 65° C. to about 85° C. for a period of from about 15 minutes to about 2 hours, preferably to a curing temperature from about 70° C. to about 80° C. for a period of from about 20 minutes to about 1 hour, more preferably to a curing temperature from about 72° C. to about 78° C. for a period of from about 20 minutes to about 60 minutes, or from about 74° C. to about 78° C. for at least 40 minutes.

Curing of the shaped extended release matrix formulation may be performed in any vessel or container suitable for heating the extended release matrix formulation to the desired curing temperature for the desired period of time. In certain embodiments, curing may be performed in a coating pan in a rotating tablet bed in order to ensure even heating of the uncured tablets. Specifically, in such embodiments, the rotating tablet bed is heated until the target exhaust temperature as defined herein (in the section "Definitions") is achieved, and curing is continued at the target exhaust temperature for the desired curing time period. At the end of the curing, the tablets are cooled, optionally coated and then packaged.

Without wishing to be bound by any theory, it is believed that the curing of the shaped extended release matrix formulation at the specified curing temperature (range) and for the specified curing time period contributes to achieving a desired hardness of the final solid oral extended release pharmaceutical dosage form, as expressed by certain values of breaking strength, cracking force and/or crush resistance, as well as by a certain desired resistance to physical manipulation as described herein below and in the examples.

Coating

In certain embodiments the solid oral extended release pharmaceutical dosage is further obtainable by coating the cured extended release matrix formulation with one or more coatings. In other words, the solid oral extended release pharmaceutical dosage forms of the present invention may contain one or more coatings, such one or more film coating(s). In certain embodiments, the coatings may be applied to the dosage form after the extended release matrix formulation has been cured. The coating may also be applied to the extended release matrix formulation prior to curing. In certain embodiments, a certain amount of coating (referred to as a "sub-coat", "pre-coat" or "initial coat") may be applied to the extended release matrix formulation prior to curing, in order to avoid or reduce the propensity of the compressed extended release matrix formulation tablets to stick or adhere to each other during the curing process. Such initial coat may result in a weight gain of the compressed extended release matrix formulation of about 0.5% to 1.5%. After curing has been completed, the remaining amount of the coating may be applied.

In certain embodiments the coating of the solid oral extended release pharmaceutical dosage form comprises about 5% by weight or less, preferably from about 1% to about 4.5% by weight, more preferably from about 2% to about 4% by weight of the entire solid oral extended release pharmaceutical dosage form.

In certain embodiments the coating comprises hydroxypropylmethylcellulose, polyethylene glycol, polyvinyl alcohol, talc, pigments, or any mixture of two of more thereof. A suitable coating for the purposes is a cosmetic film coating such as an Opadry® coating.

The coating may serve to color-code the dosage forms, and/or to increase the storage stability (increase the shelf-life) of the dosage forms. Also, the coating may serve to make the dosage forms easier to swallow.

Shape of the Dosage Form

In certain embodiments, the solid oral extended release pharmaceutical dosage form of the present invention is in the form of a tablet. Preferably, the length of the tablet is greater than the width and the thickness of the tablet, and the thickness of the tablet is less than or equal to the width of the tablet. Such tablets are also referred to herein as "caplets". Preferably, the length is at least about 1.5 times the width and/or thickness of the tablet, and the width is at least twice the thickness of the tablet. More preferably, the length of the tablets is at least about twice, more preferably at least about three times the width and about four times the thickness of the tablet. The dimensions length (l), width (w) and thickness (t) of the tablets are illustrated for various tablet shapes in FIGS. 89(a), (b) and (c).

In certain embodiments, the solid oral extended release pharmaceutical dosage form is in the form of a round, oblong or oval tablet as exemplarily shown (without limitation) in FIG. 88. Tablets of any of these shapes are defined to have a so-called "face" of the tablet, which face is defined by the length and the width of the tablet, as also illustrated in FIGS. 88 and 89.

In certain embodiments, the surface of one or both of the faces of the tablet is convex or has convex portions; or the surface of one or both of the faces of the tablet has convex and concave portions.

In certain embodiments, the solid oral extended release pharmaceutical dosage form is in the form of a tablet with convex and concave portions, wherein in the case of a caplet the concave portion extends along the central axis of the tablet defined by half the width of the tablet. In the case of a round tablet, the concave portion is in the center of the tablet. The concave portions in the round tablets and caplets are surrounded by convex portions. For illustration purposes, see FIGS. 90(a), (b), and (c). Caplets as just described and having a concave portion that extends along the central axis of the tablet defined by half the width of the tablet are herein also referred to as "troche" or "troche caplets". In such troche tablet or caplet, as shown in FIG. 91(b), the minimal thickness of the tablet in the concave portions ($t_2$) is less than the thickness of the tablet in the convex portions ($t_1$). Preferably, however, the thickness in the concave portions ($t_2$) is not less than 0.25 times the maximum thickness of the tablet, i.e., the maximum thickness ($t_1$) in the convex portions.

Without wishing to be bound by any theory, it is believed that the shape of the dosage form contributes to defining the in vitro as well as the in vivo release profile, i.e., the in vitro dissolution profile as well as the bioavailability as defined herein. Again, without wishing to be bound by any theory, it is believed that due to the larger overall surface of a tablet in "troche caplet" shape, this tablet provides for a faster release of morphine sulfate than a tablet of regular caplet shape (i.e., one without any concave portion on the surface of its face). A regular caplet as just mentioned in turn provides for a faster release of morphine sulfate than a regular round tablet (again, without any concave portion on its surface). See Example 2, Table 2.8.

In certain embodiments of the present invention, the preferred shape of the solid oral extended release dosage form is a caplet. In other embodiments of the present invention, the preferred shape of the solid oral extended release dosage form is a troche caplet. In comparison, the commercially available reference product, MS Contin® is a round tablet in case of the 15 mg, 30 mg, 60 mg and 100 mg strengths, and a caplet in case of the 200 mg strength.

Preferred Dosage Forms

A preferred solid oral extended release pharmaceutical dosage form according to the present invention comprises a cured extended release matrix formulation, the extended release matrix formulation comprising:
  a therapeutically effective amount of morphine sulfate and polyethylene oxide,
wherein the extended release matrix formulation is obtainable by at least the following steps:
  (a) combining at least morphine sulfate and polyethylene oxide particles to form a composition,
  (b) shaping the composition of step (a) to form the extended release matrix formulation, and
  (c) curing the extended release matrix formulation of step (b);
wherein the polyethylene oxide used as the polyethylene oxide particles in step (a) has an approximate molecular weight of from about 900,000 to about 2,000,000.

A further preferred solid oral extended release pharmaceutical dosage form according to the present invention comprises a cured extended release matrix formulation, the extended release matrix formulation comprising:
  a therapeutically effective amount of morphine sulfate and polyethylene oxide,
wherein the extended release matrix formulation is obtainable by at least the following steps:
  (a) combining at least morphine sulfate and polyethylene oxide particles to form a composition,
  (b) shaping the composition of step (a) to form the extended release matrix formulation, and
  (c) curing the extended release matrix formulation of step (b);
wherein the polyethylene oxide particles used in step (a) are characterized in that about 90% or more of the polyethylene oxide particles pass through a 60 mesh (0.250 mm; 250 microns) sieve; and wherein the polyethylene oxide used as the polyethylene oxide particles in step (a) has an approximate molecular weight of from about 900,000 to about 2,000,000.

A particularly preferred solid oral extended release pharmaceutical dosage form according to the present invention is a solid oral extended release pharmaceutical dosage form in the form of a tablet, the dosage form comprising a cured extended release matrix formulation, wherein the extended release matrix formulation is obtainable by combining:
about 12% by weight of the extended release matrix formulation of morphine hemi(sulfate pentahydrate) (having a molecular weight of 758.8 g/mol) or an equimolar amount of another solvate or hydrate of morphine sulfate;
about 87% by weight of the extended release matrix formulation of polyethylene oxide having an approximate molecular weight of about 2,000,000; and
about 1% by weight of the extended release matrix formulation of a lubricant, preferably magnesium stearate.

In this preferred dosage form, the extended release matrix formulation is preferably obtainable by combining:
about 15 mg of morphine hemi(sulfate pentahydrate) (having a molecular weight of 758.8 g/mol) or an equimolar amount of another solvate or hydrate of morphine sulfate;
about 109 mg of polyethylene oxide having an approximate molecular weight of about 2,000,000; and
about 1 mg of a lubricant, preferably magnesium stearate.

Specifically, in this preferred dosage form the extended release matrix formulation is obtainable by:
  (a) combining the morphine hemi(sulfate pentahydrate) or another solvate of morphine sulfate and the polyethylene oxide particles to form a composition,
  (b) shaping the composition of step (a) to form the extended release matrix formulation, and
  (c) curing the extended release matrix formulation of step (b), preferably by subjecting it to a temperature from about 70° C. to about 78° C. for a period of from about 20 minutes to about 60 minutes,
wherein the polyethylene oxide particles used in step (a) are characterized in that about 90% or more of the polyethylene oxide particles pass through a 60 mesh sieve (0.250 mm; 250 microns).

This preferred solid oral extended release pharmaceutical dosage form preferably has a total weight of about 130 mg (including coating; a weight of about 125 mg without the coating), has a breaking strength of at least about 230 N and/or a cracking force of at least about 180 N and/or a crush resistance of at least about 500 N, and is in the form of an oval or oblong tablet, wherein the face of the tablet has a convex surface. Further, this preferred dosage form may preferably comprise a film coating on the extended release matrix formulation, wherein the film coating comprises about 4% by weight of the entire dosage form.

This preferred 15 mg morphine sulfate dosage form according to the present invention is illustrated by tablet A in Table I of the Examples.

Another particularly preferred solid oral extended release pharmaceutical dosage form according to the present invention is a solid oral extended release pharmaceutical dosage form in the form of a tablet, the dosage form comprising a cured extended release matrix formulation, wherein the extended release matrix formulation is obtainable by combining:
about 17% by weight of the extended release matrix formulation of morphine hemi(sulfate pentahydrate) (having a molecular weight of 758.8 g/mol) or an equimolar amount of another solvate or hydrate of morphine sulfate;
about 82% by weight of the extended release matrix formulation of polyethylene oxide having an approximate molecular weight of about 2,000,000; and
about 1% by weight of the extended release matrix formulation of a lubricant, preferably magnesium stearate.

In this preferred dosage form, the extended release matrix formulation is preferably obtainable by combining:
about 30 mg of morphine hemi(sulfate pentahydrate) (having a molecular weight of 758.8 g/mol) or an equimolar amount of another solvate or hydrate of morphine sulfate;
about 143 mg of polyethylene oxide having an approximate molecular weight of about 2,000,000; and
about 2 mg of a lubricant, preferably magnesium stearate.

Specifically, in this preferred dosage form the extended release matrix formulation is obtainable by:
  (a) combining the morphine hemi(sulfate pentahydrate) or another solvate of morphine sulfate and the polyethylene oxide particles to form a composition,
  (b) shaping the composition of step (a) to form the extended release matrix formulation, and
  (c) curing the extended release matrix formulation of step (b), preferably by subjecting it to a temperature from about 70° C. to about 78° C. for a period of from about 20 minutes to about 60 minutes, wherein the polyethylene oxide particles used in step (a) are characterized in that about 90% or more of the polyethylene oxide particles pass through a 60 mesh sieve (0.250 mm; 250 microns).

This preferred solid oral extended release pharmaceutical dosage form preferably has a total weight of about 182 mg (including coating; a weight of about 175 mg without the coating), has a breaking strength of at least about 250 N and/or a cracking force of at least about 200 N and/or a crush resistance of at least about 500 N, and is in the form of an oval or oblong tablet, wherein the face of the tablet has a convex surface. Further, this preferred dosage form may preferably comprise a film coating on the extended release matrix formulation, wherein the film coating comprises about 4% by weight of the entire dosage form.

This preferred 30 mg morphine sulfate dosage form according to the present invention is illustrated by tablet B in Table I of the Examples.

Another particularly preferred solid oral extended release pharmaceutical dosage form according to the present invention is a solid oral extended release pharmaceutical dosage form in the form of a tablet, the dosage form comprising a cured extended release matrix formulation, wherein the extended release matrix formulation is obtainable by combining:
about 18% by weight of the extended release matrix formulation of morphine hemi(sulfate pentahydrate) (having a molecular weight of 758.8 g/mol) or an equimolar amount of another solvate or hydrate of morphine sulfate;
about 81% by weight of the extended release matrix formulation of polyethylene oxide having an approximate molecular weight of about 2,000,000; and
about 1% by weight of the extended release matrix formulation of a lubricant, preferably magnesium stearate.

In this preferred dosage form, the extended release matrix formulation is preferably obtainable by combining:
about 60 mg of morphine hemi(sulfate pentahydrate) (having a molecular weight of 758.8 g/mol) or an equimolar amount of another solvate or hydrate of morphine sulfate;
about 267 mg of polyethylene oxide having an approximate molecular weight of about 2,000,000; and
about 3 mg of a lubricant, preferably magnesium stearate.

Specifically, in this preferred dosage form the extended release matrix formulation is obtainable by:
  (a) combining the morphine hemi(sulfate pentahydrate) or another solvate of morphine sulfate and the polyethylene oxide particles to form a composition,
  (b) shaping the composition of step (a) to form the extended release matrix formulation, and
  (c) curing the extended release matrix formulation of step (b), preferably by subjecting it to a temperature from about 70° C. to about 78° C. for a period of from about 20 minutes to about 60 minutes,
wherein the polyethylene oxide particles used in step (a) are characterized in that about 90% or more of the polyethylene oxide particles pass through a 60 mesh sieve (0.250 mm; 250 microns).

This preferred solid oral extended release pharmaceutical dosage form preferably has a total weight of about 343 mg (including coating; a weight of about 330 mg without the coating), has a breaking strength of at least about 280 N and/or a cracking force of at least about 200 N and/or a crush resistance of at least about 500 N, and is in the form of an oval or oblong tablet, wherein the face of the tablet has convex and concave portions, wherein the concave portions extend along the central axis of the tablet defined by half the width of the tablet. Further, this preferred dosage form may preferably comprise a film coating on the extended release matrix formulation, wherein the film coating comprises about 4% by weight of the entire dosage form.

This preferred 60 mg morphine sulfate dosage form according to the present invention is illustrated by tablet C in Table I of the Examples.

Another particularly preferred solid oral extended release pharmaceutical dosage form according to the present invention is a solid oral extended release pharmaceutical dosage form in the form of a tablet, the dosage form comprising a cured extended release matrix formulation, wherein the extended release matrix formulation is obtainable by combining:
about 30% by weight of the extended release matrix formulation of morphine hemi(sulfate pentahydrate) (having a molecular weight of 758.8 g/mol) or an equimolar amount of another solvate or hydrate of morphine sulfate;
about 68% by weight of the extended release matrix formulation of polyethylene oxide having an approximate molecular weight of about 2,000,000;
about 0.5% by weight of the extended release matrix formulation of a glidant, preferably colloidal silicon dioxide, and
about 1.5% by weight of the extended matrix formulation of a lubricant, preferably magnesium stearate.

In this preferred dosage form, the extended release matrix formulation is preferably obtainable by combining:
about 100 mg of morphine hemi(sulfate pentahydrate)(having a molecular weight of 758.8 g/mol) or an equimolar amount of another solvate or hydrate of morphine sulfate;
about 224 mg of polyethylene oxide having an approximate molecular weight of about 2,000,000;
about 1.5 mg of a glidant, preferably colloidal silicon dioxide, and about 4 mg of a lubricant, preferably magnesium stearate.

Specifically, in this preferred dosage form the extended release matrix formulation is obtainable by:
  (a) combining the morphine hemi(sulfate pentahydrate) or another solvate of morphine sulfate and the polyethylene oxide particles to form a composition,
  (b) shaping the composition of step (a) to form the extended release matrix formulation, and
  (c) curing the extended release matrix formulation of step (b), preferably by subjecting it to a temperature from about 74° C. to about 78° C. for a period of at least about 40 minutes,
wherein the polyethylene oxide particles used in step (a) are characterized in that about 90% or more of the polyethylene oxide particles pass through a 60 mesh sieve (0.250 mm; 250 microns).

This preferred solid oral extended release pharmaceutical dosage form preferably has a total weight of about 343 mg (including coating; a weight of about 330 mg without the coating), has a breaking strength of at least about 200 N and/or a cracking force of at least about 170 N and/or a crush resistance of at least about 500 N, and is in the form of an oval or oblong tablet, wherein the face of the tablet has convex and concave portions, wherein the concave portions extend along the central axis of the tablet defined by half the width of the tablet. Further, this preferred dosage form may preferably comprise a film coating on the extended release matrix formulation, wherein the film coating comprises about 4% by weight of the entire dosage form.

This preferred 100 mg morphine sulfate dosage form according to the present invention is illustrated by tablet D in Table I of the Examples.

Another particularly preferred solid oral extended release pharmaceutical dosage form according to the present invention is a solid oral extended release pharmaceutical dosage form in the form of a tablet, the dosage form comprising a cured extended release matrix formulation, wherein the extended release matrix formulation is obtainable by combining:

about 33% by weight of the extended release matrix formulation of morphine hemi(sulfate pentahydrate) (having a molecular weight of 758.8 g/mol) or an equimolar amount of another solvate or hydrate of morphine sulfate;

about 65% by weight of the extended release matrix formulation of polyethylene oxide having an approximate molecular weight of about 1,000,000;

about 0.5% by weight of the extended release matrix formulation of a glidant, preferably colloidal silicon dioxide, and about 1.5% by weight of the extended release matrix formulation of a lubricant, preferably magnesium stearate.

In this preferred dosage form, the extended release matrix formulation is preferably obtainable by combining:
about 200 mg of morphine hemi(sulfate pentahydrate)(having a molecular weight of 758.8 g/mol) or an equimolar amount of another solvate or hydrate of morphine sulfate;
about 388 mg of polyethylene oxide having an approximate molecular weight of about 1,000,000;
about 3 mg of a glidant, preferably colloidal silicon dioxide, and
about 9 mg of a lubricant, preferably magnesium stearate.

Specifically, in this preferred dosage form the extended release matrix formulation is obtainable by:
(a) combining the morphine hemi(sulfate pentahydrate) or another solvate of morphine sulfate and the polyethylene oxide particles to form a composition,
(b) shaping the composition of step (a) to form the extended release matrix formulation, and
(c) curing the extended release matrix formulation of step (b), preferably by subjecting it to a temperature from about 74° C. to about 78° C. for a period of at least about 40 minutes,
wherein the polyethylene oxide particles used in step (a) are characterized in that about 90% or more of the polyethylene oxide particles pass through a 60 mesh sieve (0.250 mm; 250 microns).

This preferred solid oral extended release pharmaceutical dosage form preferably has a total weight of about 624 mg (including coating; a weight of about 600 mg without the coating), has a breaking strength of at least about 350 N and/or a cracking force of at least about 180 N and/or a crush resistance of at least about 500 N, and is in the form of an oval or oblong tablet, wherein the face of the tablet has a convex surface. Further, this preferred dosage form may preferably comprise a film coating on the extended release matrix formulation, wherein the film coating comprises about 4% by weight of the entire dosage form.

This preferred 200 mg morphine sulfate dosage form according to the present invention is illustrated by tablet E in Table I of the Examples.

Another particularly preferred solid oral extended release pharmaceutical dosage form according to the present invention is a solid oral extended release pharmaceutical dosage form in the form of a tablet, the dosage form comprising a cured extended release matrix formulation, wherein the extended release matrix formulation is obtainable by combining:
about 5 to 7% by weight of the extended release matrix formulation of morphine hemi(sulfate pentahydrate) (having a molecular weight of 758.8 g/mol) or an equimolar amount of another solvate or hydrate of morphine sulfate;
about 93 to 95% by weight of the extended release matrix formulation of polyethylene oxide having an approximate molecular weight of about 2,000,000 and/or polyethylene oxide having an approximate molecular weight of about 4,000,000; and up to about 1% by weight of the extended release matrix formulation of a lubricant, preferably magnesium stearate.

In this preferred dosage form, the extended release matrix formulation may preferably be obtainable by combining:
about 5 mg of morphine hemi(sulfate pentahydrate) (having a molecular weight of 758.8 g/mol) or an equimolar amount of another solvate or hydrate of morphine sulfate;
about 118 to 119 mg of polyethylene oxide having an approximate molecular weight of about 2,000,000 and/or polyethylene oxide having an approximate molecular weight of about 4,000,000; and
about 1 to 2 mg of a lubricant, preferably magnesium stearate.

This preferred 5 mg morphine sulfate solid oral extended release pharmaceutical dosage form preferably has a total weight of about 130 mg (including coating; a weight of about 125 mg without the coating) and is in the form of a round, oval or oblong tablet, wherein the face of the tablet has a convex surface. This preferred 5 mg morphine sulfate dosage form according to the present invention is illustrated by tablet AK in Table IX of the Examples.

In the preparation of another preferred dosage form, the extended release matrix formulation may preferably be obtainable by combining:
about 5 mg of morphine hemi(sulfate pentahydrate) (having a molecular weight of 758.8 g/mol) or an equimolar amount of another solvate or hydrate of morphine sulfate;
about 94 to 95 mg of polyethylene oxide having an approximate molecular weight of about 2,000,000 and/or polyethylene oxide having an approximate molecular weight of about 4,000,000; and up to 1 mg of a lubricant, preferably magnesium stearate.

This preferred 5 mg morphine sulfate solid oral extended release pharmaceutical dosage form preferably has a total weight of about 105 mg (including coating; a weight of about 100 mg without the coating) and is in the form of a round, oval or oblong tablet, wherein the face of the tablet has a convex surface. This preferred 5 mg morphine sulfate dosage form according to the present invention is illustrated by tablet AL in Table IX of the Examples.

Another particularly preferred solid oral extended release pharmaceutical dosage form according to the present invention is a solid oral extended release pharmaceutical dosage form in the form of a tablet, the dosage form comprising a cured extended release matrix formulation, wherein the extended release matrix formulation is obtainable by combining:
about 8% by weight of the extended release matrix formulation of morphine hemi(sulfate pentahydrate) (having a molecular weight of 758.8 g/mol) or an equimolar amount of another solvate or hydrate of morphine sulfate;
about 91 to about 92% by weight of the extended release matrix formulation of polyethylene oxide having an approximate molecular weight of about 2,000,000 and/or polyethylene oxide having an approximate molecular weight of about 4,000,000; and
up to about 1% by weight of the extended release matrix formulation of a lubricant, preferably magnesium stearate.

In this preferred dosage form, the extended release matrix formulation may preferably be obtainable by combining:

about 10 mg of morphine hemi(sulfate pentahydrate) (having a molecular weight of 758.8 g/mol) or an equimolar amount of another solvate or hydrate of morphine sulfate;
about 113 to 114 mg of polyethylene oxide having an approximate molecular weight of about 2,000,000 and/or polyethylene oxide having an approximate molecular weight of about 4,000,000; and
up to about 1 mg of a lubricant, preferably magnesium stearate.

Such preferred 10 mg morphine sulfate solid oral extended release pharmaceutical dosage form preferably has a total weight of about 130 mg (including coating; a weight of about 125 mg without the coating) and is in the form of a round, oval or oblong tablet, wherein the face of the tablet has a convex surface. Preferred 10 mg morphine sulfate dosage forms according to the present invention are illustrated by tablets AM and AN in Table IX of the Examples.

Specifically, in the preferred 5 and 10 mg morphine sulfate dosage forms described above the extended release matrix formulation is obtainable by:
(a) combining the morphine hemi(sulfate pentahydrate) or another solvate of morphine sulfate and the polyethylene oxide particles in the amounts specified above to form a composition,
(b) shaping the composition of step (a) to form the extended release matrix formulation, and
(c) curing the extended release matrix formulation of step (b), preferably by subjecting it to a temperature from about 70° C. to about 78° C. for a period of from about 20 minutes to about 60 minutes,
wherein preferably the polyethylene oxide particles used in step (a) are characterized in that about 90% or more of the polyethylene oxide particles pass through a 60 mesh sieve (0.250 mm, 250 microns).

Preferably, any of the above-disclosed preferred dosage forms of the present invention is, when tested in a comparative clinical study, bioequivalent to the respective commercial product MS Contin® marketed in the United States (or a similar product marketed under a different tradename in another country) containing an equimolar amount of morphine sulfate.

In-Vitro Dissolution

The solid oral extended release pharmaceutical dosage forms of the present invention exhibit a certain in vitro-dissolution profile when subjected to an in-vitro dissolution test in a USP Apparatus 1 (basket) at 100 rpm in 900 ml simulated gastric fluid without enzymes (SGF) at 37.0 (±0.5)° C., see Example 2.

In certain embodiments, the solid oral extended release pharmaceutical dosage form of the present invention, when subjected to an in-vitro dissolution test in a USP Apparatus 1 (basket) at 100 rpm in 900 ml simulated gastric fluid without enzymes (SGF) at 37.0 (0.5)° C., provides a dissolution rate characterized by the amount of morphine sulfate released from the dosage form, of
from about 5% to about 35% released after 0.5 hour;
from about 18% to about 50% released after 1 hour;
from about 29% to about 70% released after 2 hours;
from about 40% to about 85% released after 3 hours;
from about 49% to about 95% released after 4 hours;
greater than about 65% released after 6 hours;
greater than about 70% released after 8 hours;
greater than about 75% released after 9 hours; and/or
greater than about 85% released after 12 hours.

In certain preferred embodiments, the solid oral extended release pharmaceutical dosage form as described herein, when subjected to an in-vitro dissolution test in a USP Apparatus 1 (basket) at 100 rpm in 900 ml simulated gastric fluid without enzymes (SGF) at 37.0 (0.5)° C., provides a dissolution rate characterized by the amount of morphine sulfate released from the dosage form, of:
from about 11% to about 31% released after 0.5 hour;
from about 18% to about 46% released after 1 hour;
from about 31% to about 65% released after 2 hours;
from about 43% to about 69% released after 3 hours;
from about 54% to about 87% released after 4 hours;
from about 70% to about 99% released after 6 hours;
greater than about 80% released after 8 hours;
greater than about 85% released after 9 hours; and/or
greater than about 90% released after 12 hours.

In certain more preferred embodiments, the solid oral extended release pharmaceutical dosage form as described herein, when subjected to an in-vitro dissolution test in a USP Apparatus 1 (basket) at 100 rpm in 900 ml simulated gastric fluid without enzymes (SGF) at 37.0 (±0.5)° C., provides a dissolution rate characterized by the amount of morphine sulfate released from the dosage form, of:
from about 13% to about 21% released after 0.5 hour;
from about 21% to about 34% released after 1 hour;
from about 34% to about 53% released after 2 hours;
from about 46% to about 67% released after 3 hours;
from about 57% to about 81% released after 4 hours;
from about 74% to about 98% released after 6 hours;
greater than about 89% released after 8 hours;
greater than about 89% released after 9 hours; and/or
greater than about 94% released after 12 hours. In preferred embodiments, any of the solid oral extended release pharmaceutical dosage forms of the present invention as described herein exhibits the above-defined in-vitro dissolution rates (of this and any of the other above paragraphs) in the period from 1 to 6 hours, preferably from 1 to 4 hours, most preferably after 4 hours.

In a specific embodiment, the present invention is directed to a solid oral extended release pharmaceutical dosage form comprising:
a therapeutically effective amount of morphine sulfate, and
polyethylene oxide,
the dosage form providing an in-vitro dissolution rate of morphine sulfate, when measured in a USP Apparatus 1 (basket) at 100 rpm in 900 ml simulated gastric fluid without enzymes (SGF) at 37° C., characterized by the amount of morphine sulfate released from the dosage form, of:
from about 18% to about 21% released after 0.5 hour;
from about 29% to about 33% released after 1 hour;
from about 48% to about 53% released after 2 hours;
from about 65% to about 69% released after 3 hours;
from about 77% to about 83% released after 4 hours;
from about 90% to about 97% released after 6 hours; and/or
greater than about 98% released after 9 hours.

In this embodiment the dosage form preferably provides an in-vitro dissolution rate of morphine sulfate, when measured in a USP Apparatus 1 (basket) at 100 rpm in 900 ml simulated gastric fluid without enzymes (SGF) at 37° C., characterized by the amount of morphine sulfate released from the dosage form, of:
from about 19% to about 20% released after 0.5 hour;
from about 30% to about 32% released after 1 hour;
from about 49% to about 52% released after 2 hours;
from about 66% to about 68% released after 3 hours;

from about 78% to about 82% released after 4 hours; and/or from about 91% to about 95% released after 6 hours.

Most preferably, in this embodiment the dosage form contains about 15 mg of morphine hemi(sulfate pentahydrate) (having a molecular weight of 758.8 g/mol) or an equimolar amount of another solvate or hydrate of morphine sulfate included into the dosage form.

In another specific embodiment, the present invention is directed to a solid oral extended release pharmaceutical dosage form comprising:

a therapeutically effective amount of morphine sulfate, and polyethylene oxide, the dosage form providing an in-vitro dissolution rate of morphine sulfate, when measured in a USP Apparatus 1 (basket) at 100 rpm in 900 ml simulated gastric fluid without enzymes (SGF) at 37° C., characterized by the amount of morphine sulfate released from the dosage form, of:

from about 14% to about 17% released after 0.5 hour;
from about 25% to about 28% released after 1 hour;
from about 41% to about 46% released after 2 hours;
from about 56% to about 61% released after 3 hours;
from about 70% to about 75% released after 4 hours;
from about 87% to about 92% released after 6 hours; and/or greater than about 98% released after 9 hours.

In this embodiment the dosage form preferably provides an in-vitro dissolution rate of morphine sulfate, when measured in a USP Apparatus 1 (basket) at 100 rpm in 900 ml simulated gastric fluid without enzymes (SGF) at 37° C., characterized by the amount of morphine sulfate released from the dosage form, of:

from about 15% to about 16% released after 0.5 hour;
from about 26% to about 27% released after 1 hour;
from about 42% to about 45% released after 2 hours;
from about 57% to about 60% released after 3 hours;
from about 71% to about 74% released after 4 hours; and/or from about 89% to about 91% released after 6 hours Most preferably, in this embodiment the dosage form contains 30 mg of morphine hemi(sulfate pentahydrate) (having a molecular weight of 758.8 g/mol) or an equimolar amount of another solvate or hydrate of morphine sulfate included into the dosage form.

In another specific embodiment, the present invention is directed to a solid oral extended release pharmaceutical dosage form comprising:

a therapeutically effective amount of morphine sulfate, and polyethylene oxide, the dosage form providing an in-vitro dissolution rate of morphine sulfate, when measured in a USP Apparatus 1 (basket) at 100 rpm in 900 ml simulated gastric fluid without enzymes (SGF) at 37° C., characterized by the amount of morphine sulfate released from the dosage form, of:

from about 13% to about 16% released after 0.5 hour;
from about 22% to about 25% released after 1 hour;
from about 36% to about 41% released after 2 hours;
from about 50% to about 55% released after 3 hours;
from about 60% to about 68% released after 4 hours;
from about 80% to about 87% released after 6 hours; and/or greater than about 98% released after 9 hours.

In this embodiment the dosage form preferably provides an in-vitro dissolution rate of morphine sulfate, when measured in a USP Apparatus 1 (basket) at 100 rpm in 900 ml simulated gastric fluid without enzymes (SGF) at 37° C., characterized by the amount of morphine sulfate released from the dosage form, of:

from about 14% to about 15% released after 0.5 hour;
from about 23% to about 24% released after 1 hour;
from about 37% to about 39% released after 2 hours;
from about 52% to about 54% released after 3 hours;
from about 64% to about 66% released after 4 hours; and/or from about 82% to about 86% released after 6 hours.

Most preferably, in this embodiment the dosage form contains 60 mg of morphine hemi(sulfate pentahydrate) (having a molecular weight of 758.8 g/mol) or an equimolar amount of another solvate or hydrate of morphine sulfate included into the dosage form.

In another specific embodiment, the present invention is directed to a solid oral extended release pharmaceutical dosage form comprising:

a therapeutically effective amount of morphine sulfate, and polyethylene oxide, the dosage form providing an in-vitro dissolution rate of morphine sulfate, when measured in a USP Apparatus 1 (basket) at 100 rpm in 900 ml simulated gastric fluid without enzymes (SGF) at 37° C., characterized by the amount of morphine sulfate released from the dosage form, of:

from about 15% to about 19% released after 0.5 hour;
from about 25% to about 29%/o released after 1 hour;
from about 40% to about 46% released after 2 hours;
from about 56% to about 61% released after 3 hours;
from about 68% to about 73% released after 4 hours;
from about 87% to about 92% released after 6 hours; and/or greater than about 98% released after 9 hours.

In this embodiment the dosage form preferably provides an in-vitro dissolution rate of morphine sulfate, when measured in a USP Apparatus 1 (basket) at 100 rpm in 900 ml simulated gastric fluid without enzymes (SGF) at 37° C., characterized by the amount of morphine sulfate released from the dosage form, of:

from about 16% to about 18% released after 0.5 hour;
from about 26% to about 28% released after 1 hour;
from about 41% to about 45% released after 2 hours;
from about 57% to about 60% released after 3 hours;
from about 69% to about 72% released after 4 hours; and/or from about 88% to about 91% released after 6 hours.

Most preferably, in this embodiment the dosage form contains 100 mg of morphine hemi(sulfate pentahydrate) (having a molecular weight of 758.8 g/mol) or an equimolar amount of another solvate or hydrate of morphine sulfate included into the dosage form.

In another specific embodiment, the present invention is directed to a solid oral extended release pharmaceutical dosage form comprising:

a therapeutically effective amount of morphine sulfate, and polyethylene oxide, the dosage form providing an in-vitro dissolution rate of morphine sulfate, when measured in a USP Apparatus 1 (basket) at 100 rpm in 900 ml simulated gastric fluid without enzymes (SGF) at 37° C., characterized by the amount of morphine sulfate released from the dosage form, of:

from about 10% to about 18% released after 0.5 hour;
from about 16% to about 25% released after 1 hour;
from about 30% to about 42% released after 2 hours;
from about 42% to about 53% released after 3 hours;

from about 52% to about 65% released after 4 hours;
from about 70% to about 85% released after 6 hours; and/or
greater than about 97% released after 9 hours.

In this embodiment the dosage form preferably provides an in-vitro dissolution rate of morphine sulfate, when measured in a USP Apparatus 1 (basket) at 100 rpm in 900 ml simulated gastric fluid without enzymes (SGF) at 37° C., characterized by the amount of morphine sulfate released from the dosage form, of:
from about 11% to about 16% released after 0.5 hour;
from about 18% to about 25% released after 1 hour;
from about 31% to about 40% released after 2 hours;
from about 43% to about 50% released after 3 hours;
from about 54% to about 60% released after 4 hours; and/or
from about 72% to about 80% released after 6 hours.

Most preferably, in this embodiment the dosage form contains 200 mg of morphine hemi(sulfate pentahydrate) (having a molecular weight of 758.8 g/mol) or an equimolar amount of another solvate or hydrate of morphine sulfate included into the dosage form.

It has been observed that the solid oral extended release pharmaceutical dosage forms of the present invention are storage stable when stored at room temperature or at elevated temperature (such as 40° C.) at 60% or 75% relative humidity, both in the presence and in the absence of an oxygen absorber packet included in the packaging of the dosage forms (e.g. a plastic bottle or container). In particular, the dosage forms of the present invention show no significant increase in degradant formation when stored in the absence of an oxygen absorber. Thus, the dosage forms of the present invention may or may not be packaged together with oxygen absorber.

In certain embodiments the solid oral extended release pharmaceutical dosage form as described herein displays a decrease of less than about 5%, preferably less than about 2% in the average in-vitro dissolution rate of morphine sulfate after storage for 6 months at 25° C. and 60% relative humidity at one or more time points selected from 1 hour, 2 hours, 6 hours and 12 hours, or selected from 1 hour, 3 hours, 9 hours and 12 hours, when measured in a USP Apparatus 1 (basket) at 100 rpm in 900 ml simulated gastric fluid without enzymes (SGF) at 37° C. with or without added oxygen absorber.

In certain embodiments the solid oral extended release pharmaceutical dosage form as described herein displays a decrease of less than about 5%, preferably less than about 2% in the average in-vitro dissolution rate of morphine sulfate after storage for 6 months at 40° C. and 75% relative humidity at one or more time points selected from 1 hour, 2 hours, 6 hours and 12 hours, or selected from 1 hour, 3 hours, 9 hours and 12 hours, when measured in a USP Apparatus 1 (basket) at 100 rpm in 900 ml simulated gastric fluid without enzymes (SGF) at 37° C. with or without added oxygen absorber.

In certain embodiments the solid oral extended release pharmaceutical dosage form as described herein displays an increase in the average in-vitro dissolution rate of morphine sulfate of less than about 5%, preferably less than about 2% after 6 months storage at 25° C. and 60% relative humidity at one or more time points selected from 1 hour, 2 hours, 6 hours and 12 hours, or selected from 1 hour, 3 hours, 9 hours and 12 hours, when measured in a USP Apparatus 1 (basket) at 100 rpm in 900 ml simulated gastric fluid without enzymes (SGF) at 37° C. with or without added oxygen absorber.

In certain embodiments the solid oral extended release pharmaceutical dosage form as described herein displays an increase in the average in-vitro dissolution rate of morphine sulfate of less than about 10%, preferably less than about 5% after 6 months storage at 40° C. and 75% relative humidity at one or more time points selected from 1 hour, 2 hours, 6 hours and 12 hours, or selected from 1 hour, 3 hours, 9 hours and 12 hours, when measured in a USP Apparatus 1 (basket) at 100 rpm in 900 ml simulated gastric fluid without enzymes (SGF) at 37° C. with or without added oxygen absorber.

It has been observed that the release rate of morphine sulfate decreased in ethanolic media, i.e. in SGF with 4%, 10%, 20% and 40% ethanol, as compared to SGF without ethanol. The rate of release is related to the amount of ethanol added in the SGF. SGF containing various amounts of ethanol mimics to a certain extent the conditions and potential alcohol concentration in the stomach after alcoholic beverages such as beer, wine, mixed drinks or liquor were co-administered with morphine sulfate containing tablets. According to the in-vitro dissolution data (see Example 1 herein), there is no alcohol-induced dose dumping of morphine sulfate in the presence of various concentrations of ethanol. It has further been observed that the amount of morphine sulfate released initially (i.e., after 0.5 and/or after 1 hour) in SGF with alcohol does not deviate to a large extent from the corresponding in-vitro dissolution rate of morphine sulfate in SGF without alcohol.

Specifically, in certain embodiments, the solid oral extended release pharmaceutical dosage form of the present invention provides an in-vitro dissolution rate of morphine sulfate, when measured in a USP Apparatus 1 (basket) at 100 rpm in 900 ml simulated gastric fluid without enzymes (SGF) comprising 4%, 10%, 20% or 40% ethanol at 37° C., characterized in that the amount of morphine sulfate released from the dosage form after 0.5 hours deviates no more than 20%-points, preferably no more than 10%-points from the amount of morphine sulfate released from the dosage form after 0.5 hours when measured in a USP Apparatus 1 (basket) at 100 rpm in 900 ml simulated gastric fluid without enzymes (SGF) without ethanol at 37° C.

More specifically, in certain embodiments, the solid controlled release oral dosage form of the present invention provides a dissolution rate of morphine sulfate, when measured in a USP Apparatus 1 (basket) at 100 rpm in 900 ml simulated gastric fluid without enzymes (SGF) comprising 4%, 10%, 20% or 40% ethanol at 37° C., characterized in that the amount of morphine sulfate released form the dosage form after 0.5 hours and after 1 hour deviates no more than 20%-points, preferably no more than 10%-points from the amount of morphine sulfate released from the dosage form after 0.5 hours and after 1 hour when measured in a USP Apparatus 1 (basket) at 100 rpm in 900 ml simulated gastric fluid without enzymes (SGF) without ethanol at 37° C.

It has been observed that after thermal treatment the in-vitro dissolution rate of morphine sulfate from the (intact) dosage forms of the present invention may increase to a certain extent. Thermal treatment may be conducted e.g. in an oven, at elevated temperatures (i.e., at temperatures distinct from and considerably higher than the curing temperatures specified above) of at least about 90° C. (for various periods of exposure, such as for about 30 to about 480 minutes) and up to temperatures as high as about 190° C., about 210° C. or even about 230° C. (for shorter periods of exposure, such as about 10 or about 30 minutes). However, the controlled release properties of the dosage forms of the present invention are not significantly affected through thermal treatment. Any changes observed in the release rate is believed to be an indication of the change in the physical properties of the polyethylene oxide included in the dosage forms of the present invention. Finally, it has been observed that microwave treatment does not significantly alter the in-vitro dissolution rate of the dosage forms of the present invention.

In Vivo Pharmacokinetics

In certain embodiments, the bioavailability of the solid oral extended release pharmaceutical dosage forms of the present invention is dose-proportional to the amount of active agent (morphine sulfate) incorporated into the dosage forms. Specifically, in certain embodiments the solid oral extended release pharmaceutical dosage forms of the present invention display $C_{max}$, $AUC_{inf}$ and $AUC_{inf}$ values that are proportional to the amount of morphine sulfate (in the form of morphine hemi(sulfate pentahydrate) having a molecular weight of 758.8 g/mol as defined herein) included in the dosage form as further specified below.

Specifically, in certain embodiments, the solid oral extended release pharmaceutical dosage form of the present invention after administration provides a dose adjusted $C_{max}$ of morphine of from about 3 ng/mL to about 9 ng/mL per 15 mg, preferably from about 4 ng/mL to about 7 ng/mL, more preferably from about 5 ng/mL to about 7 ng/mL per 15 mg of morphine hemi(sulfate pentahydrate) (having a molecular weight of 758.8 g/mol) or an equimolar amount of another solvate or hydrate of morphine sulfate included in the dosage form.

Specifically, in certain embodiments, the solid oral extended release pharmaceutical dosage form of the present invention after administration provides a dose adjusted $AUC_t$ of morphine of from about 30 ng*hr/mL to about 100 ng*hr/mL per 15 mg, preferably from about 40 ng*hr/mL to about 80 ng*hr/mL per 15 mg of morphine hemi(sulfate pentahydrate) (having a molecular weight of 758.8 g/mol) or an equimolar amount of another solvate or hydrate of morphine sulfate included in the dosage form.

Specifically, in certain embodiments, the solid oral extended release pharmaceutical dosage form of the present invention after administration provides a dose adjusted $AUC_{inf}$ of morphine of from about 30 ng*hr/mL to about 100 ng*hr/mL mg per 15 mg, preferably from about 40 ng*hr/m L to about 80 ng*hr/mL per 15 mg of morphine hemi(sulfate pentahydrate) (having a molecular weight of 758.8 g/mol) or an equimolar amount of another solvate or hydrate of morphine sulfate included in the dosage form.

In a preferred embodiment, a solid oral extended release pharmaceutical dosage form of the present invention, in which morphine sulfate is included in the extended release matrix formulation in the form of morphine hemi(sulfate pentahydrate) (having a molecular weight of 758.8 g/mol) in an amount of about 15 mg or an equimolar amount of another solvate or hydrate of morphine sulfate, provides after administration a $C_{max}$ of morphine of from about 3 ng/mL to about 9 ng/mL, preferably of from about 4 ng/mL to about 7 ng/mL, an $AUC_t$ of morphine of from about 30 ng*hr/mL to about 70 ng*hr/mL, preferably of from about 40 ng*hr/mL to about 60 ng*hr/mL, an $AUC_{inf}$ of morphine of from about 35 ng*hr/mL to about 70 ng*hr/mL, preferably of from about 40 ng*hr/mL to about 65 ng*hr/mL, and/or a T. of from about 1 to about 4.5 hours, preferably from about 1.5 to about 4 hours, more preferably from about 2 to about 3.5 hours after administration in the fasted state or a T. of from about 2 to about 6 hours, preferably from about 3 to about 5 hours after administration in the fed state.

In another preferred embodiment, a solid oral extended release pharmaceutical dosage form of the present invention, in which morphine sulfate is included in the extended release matrix formulation in the form of morphine hemi(sulfate pentahydrate) (having a molecular weight of 758.8 g/mol) in an amount of about 30 mg or an equimolar amount of another solvate or hydrate of morphine sulfate, provides after administration a Cm. of morphine of from about 8 ng/mL to about 18 ng/mL, preferably of from about 9 ng/mL to about 17 ng/mL, an $AUC_t$ of morphine of from about 90 ng*hr/mL to about 180 ng*hr/mL, preferably of from about 105 ng*hr/mL to about 165 ng*hr/mL, an $AUC_{inf}$ of morphine of from about 110 ng*hr/mL to about 230 ng*hr/mL, preferably of from about 120 ng*hr/mL to about 210 ng*hr/mL, and/or a $T_{max}$ of from about 1 to about 6 hours, preferably of from about 1.5 to about 4.5 hours after administration, more preferably of from about 2 to about 4 hours after administration in the fasted state.

In another preferred embodiment, a solid oral extended release pharmaceutical dosage form of the present invention, in which morphine sulfate is included in the extended release matrix formulation in the form of morphine hemi(sulfate pentahydrate) (having a molecular weight of 758.8 g/mol) in an amount of about 60 mg or an equimolar amount of another solvate or hydrate of morphine sulfate, provides after administration a $C_{max}$ of morphine of from about 14 ng/mL to about 36 ng/mL, preferably of from about 17 ng/mL to about 30 ng/mL, an $AUC_t$ of morphine of from about 175 ng*hr/mL to about 325 ng*hr/mL, preferably of from about 195 ng*hr/mL to about 305 ng*hr/mL, an $AUC_{inf}$ of morphine of from about 190 ng*hr/mL to about 340 ng*hr/mL, preferably of from about 210 ng*hr/mL to about 320 ng*hr/mL, and/or a $T_{max}$ of from about 1 to about 6 hours after administration, preferably a T. of from about 2 to about 5 hours after administration in the fasted state.

In another preferred embodiment, a solid oral extended release pharmaceutical dosage form of the present invention, in which morphine sulfate is included in the extended release matrix formulation in the form of morphine hemi(sulfate pentahydrate) (having a molecular weight of 758.8 g/mol) in an amount of about 100 mg or an equimolar amount of another solvate or hydrate of morphine sulfate, provides after administration a $C_{max}$ of morphine of from about 26 ng/mL to about 60 ng/mL, preferably from about 30 ng/mL to about 50 ng/mL, an $AUC_t$ of morphine of from about 360 ng*hr/mL to about 640 ng*hr/mL, preferably of from about 390 ng*hr/mL to about 610 ng*hr/mL, an AUC; of morphine of from about 370 ng*hr/mL to about 650 ng*hr/mL, preferably of from about 395 ng*hr/mL to about 620 ng*hr/mL, in the fasted or in the fed state, preferably in the fasted state. In these embodiments, the $T_{max}$ is from about 0.5 to about 5 hours, preferably from about 3 to about 5 hours, more preferably from about 2 to about 4.5 hours after administration in the fasted state and/or from about 2 to about 8 hours, preferably from about 4 to about 7 hours, more preferably from about 3 to about 6 hours after administration in the fed state.

In another preferred embodiment, a solid oral extended release pharmaceutical dosage form of the present invention, in which morphine sulfate is included in the extended release matrix formulation in the form of morphine hemi(sulfate pentahydrate) (having a molecular weight of 758.8 g/mol) in an amount of about 200 mg or an equimolar amount of another solvate or hydrate of morphine sulfate, provides after administration a $C_{max}$ of morphine of from about 52 ng/mL to about 120 ng/mL, preferably of from about 60 ng/mL to about 105 ng/mL, an $AUC_t$ of morphine of from about 700 ng*hr/mL to about 1350 ng*hr/mL, preferably of from about 800 ng*hr/mL to about 1250 ng*hr/mL, an $AUC_{inf}$ of morphine of from about 750 ng*hr/mL to about 1400 ng*hr/mL, preferably of from about 850 ng*hr/mL to about 1300 ng*hr/mL in the fasted or in the fed state, preferably in the fasted state. In these embodiments, the $T_{max}$ is from about 1 to about 6 hours, preferably from about 2 to about 5 hours after administration in the fasted state and from about 5 to about 10 hours, preferably from about 6 to about 8 hours after administration in the fed state.

The values or ranges of $C_{max}$, $AUC_{inf}$ and/or $AUC_{inf}$ of morphine referred to above and elsewhere herein are mean values determined after a single-dose administration of the dosage form to a population of healthy human subjects in the fasted or in the fed state, preferably in the fasted state. In-vivo studies are further illustrated in Examples 3 and 4 herein below.

In certain embodiments, a solid oral extended release pharmaceutical dosage form comprising a certain amount (e.g. 5 mg, 10 mg, 15 mg, 30 mg, 60 mg, 100 mg or 200 mg) of morphine sulfate in the form of morphine hemi(sulfate pentahydrate) (having a molecular weight of 758.8 g/mol) or an equimolar amount of another solvate or hydrate of morphine sulfate included in an extended release matrix formulation, is bioequivalent to the commercial reference product MS Contin® as defined herein (see Table VIII below and the section "Definitions") containing an equimolar amount of morphine sulfate when tested in a comparative clinical study.

Hardness

Hardness of the Dosage Form:

The solid oral extended release pharmaceutical dosage forms according to the present invention exhibit sufficient hardness to avoid or reduce physical manipulation such as crushing, breaking, milling or grinding etc. The hardness of the dosage forms can be expressed by various parameters, including the breaking strength as determined by the Schleuniger test as defined herein, the cracking force as determined by the indentation test using a texture analyzer as defined herein, and the crush resistance determined by an Instron instrument as defined herein (see the section "Definitions" herein above).

The dosage forms of the present invention exhibit improved hardness (i.e., improved breaking strength, cracking force and/or crush resistance) as exemplified in Examples 5 to 9 herein. This is all the more surprising, as compared to other (e.g. commercial) tamper-resistant solid oral extended release pharmaceutical dosage forms comprising polyethylene oxide, in the dosage forms of the present invention polyethylene oxide of a relatively lower approximate molecular weight (in the ranges as specified herein above, such as from about 600,000 to about 3,000,000, and specifically of from about 1,000,000 to about 2,000,000) is included. A person of ordinary skill in the art would expect that the use of polyethylene oxide of such relatively lower approximate molecular weight reduces the hardness of the resulting dosage forms. However, unexpectedly, the dosage forms of the present invention exhibit an improved hardness, as expressed by the breaking strength, the cracking force and/or the crush resistance as reported herein.

As explained above, the hardness may be improved by using polyethylene oxide particles of a particular particle size distribution, preferably by using fine particle grade polyethylene oxide as defined above, for preparing the dosage forms of the present invention.

Furthermore, also curing the shaped extended release matrix formulation for a certain period of time at a certain curing temperature (or within a certain curing temperature range) as also defined above further contributes to an improved hardness of the final dosage form.

In certain embodiments, the solid oral extended release pharmaceutical dosage form of the present invention has a breaking strength (as measured by a Schleuniger apparatus as described herein) of at least about 200 N, preferably at least about 250 N, more preferably at least about 300 N, more preferably at least about 350 N, most preferably at least about 400 N.

In certain embodiments, the solid oral extended release pharmaceutical dosage form of the present invention has a cracking force (as determined by an indentation test using a texture analyser as described herein) of at least about 150 N, preferably at least about 170 N, more preferably at least about 200 N, most preferably at least about 230 N.

In certain embodiments, the solid oral extended release pharmaceutical dosage form of the present invention has a penetration depth to crack (as also determined by an indentation test using a texture analyser as described herein) of at least about 1.25 mm, preferably at least about 1.5 mm, more preferably at least about 1.75 mm, most preferably at least about 2 mm.

In certain embodiments, the solid oral extended release pharmaceutical dosage form of the present invention has a crush resistance (as determined by means of an Instron instrument as described herein) of at least about 400 N, preferably at least about 500 N.

In certain embodiments, the present invention is also directed to a solid oral extended release pharmaceutical dosage form comprising a cured extended release matrix formulation, the extended release matrix formulation comprising:
   a therapeutically effective amount of morphine sulfate, and
   polyethylene oxide having an approximate molecular weight of from about 900,000 to about 2,000,000;
the dosage form having a breaking strength of least about 200 N, or at least about 300 N, or at least about 400 N.

In certain embodiments, the present invention is also directed to a solid oral extended release pharmaceutical dosage form comprising a cured extended release matrix formulation, the extended release matrix formulation comprising:
   a therapeutically effective amount of morphine sulfate, and
   polyethylene oxide having an approximate molecular weight of from about 900,000 to about 2,000,000;
the dosage form having a cracking force of least about 150 N, or at least about 200 N, or at least about 230 N.

In certain embodiments, the present invention is also directed to a solid oral extended release pharmaceutical dosage form comprising a cured extended release matrix formulation, the extended release matrix formulation comprising:
   a therapeutically effective amount of morphine sulfate, and
   polyethylene oxide having an approximate molecular weight of from about 900,000 to about 2,000,000;
the dosage form having a crush resistance of at least about 400 N, or at least about 500 N.

In a specific embodiment, the present invention is directed to a solid oral extended release pharmaceutical dosage form comprising a cured extended release matrix formulation, the extended release matrix formulation comprising:
a therapeutically effective amount of morphine sulfate, and
polyethylene oxide;
the dosage form after administration providing a dose adjusted $C_{max}$ of morphine of from about 3 ng/mL to about 9 ng/mL per 15 mg, preferably of from about 4 ng/mL to about 7 ng/mL, more preferably from about 5 ng/mL to about 7 ng/mL per 15 mg of morphine hemi(sulfate pentahydrate) (having a molecular weight of 758.8 g/mol) or an equimolar amount of another solvate or hydrate of morphine sulfate included in the dosage form, and the dosage form having a breaking strength of least about 200 N, preferably at least about 300 N, most preferably at least about 400 N.

In another specific embodiment, the present invention is directed to a solid oral extended release pharmaceutical dosage form comprising a cured extended release matrix formulation, the extended release matrix formulation comprising:
a therapeutically effective amount of morphine sulfate, and
polyethylene oxide;
the dosage form after administration providing a dose adjusted $C_{max}$, of morphine of from about 3 ng/mL to about 9 ng/mL per 15 mg, preferably of from about 4 ng/mL to about 7 ng/mL, more preferably from about 5 ng/mL to about 7 ng/mL per 15 mg of morphine hemi(sulfate pentahydrate) (having a molecular weight of 758.8 g/mol) or an equimolar amount of another solvate or hydrate of morphine sulfate included in the dosage form,
and the dosage form having a cracking force of least about 150 N, preferably at least about 200 N, most preferably at least about 230 N.

In another specific embodiment, the present invention is directed to a solid oral extended release pharmaceutical dosage form comprising a cured extended release matrix formulation, the extended release matrix formulation comprising:
a therapeutically effective amount of morphine sulfate, and
polyethylene oxide;
the dosage form after administration providing a dose adjusted $C_{max}$ of morphine of from about 3 ng/mL to about 9 ng/mL per 15 mg, preferably of from about 4 ng/mL to about 7 ng/mL, more preferably from about 5 ng/mL to about 7 ng/mL per 15 mg of morphine hemi(sulfate pentahydrate) (having a molecular weight of 758.8 g/mol) or an equimolar amount of another solvate or hydrate of morphine sulfate included in the dosage form,
and the dosage form having a crush resistance of at least about 400 N, preferably at least about 500 N.

In another specific embodiment, the present invention is directed to a solid oral extended release pharmaceutical dosage form comprising a cured extended release matrix formulation, the extended release matrix formulation comprising:
a therapeutically effective amount of morphine sulfate, and
polyethylene oxide:
the dosage form after administration providing a dose adjusted $AUC_t$ and/or a dose adjusted $AUC_{inf}$ of morphine of from about 30 ng/mL to about 100 ng/mL per 15 mg, preferably of from about 40 ng/mL to about 80 ng/mL per 15 mg of morphine hemi(sulfate pentahydrate) (having a molecular weight of 758.8 g/mol) or an equimolar amount of another solvate or hydrate of morphine sulfate included in the dosage form, and the dosage form having a breaking strength of at least about 200 N, preferably at least about 300 N, more preferably at least about 400 N.

In another specific embodiment, the present invention is directed to a solid oral extended release pharmaceutical dosage form comprising a cured extended release matrix formulation, the extended release matrix formulation comprising:
a therapeutically effective amount of morphine sulfate, and
polyethylene oxide;
the dosage form after administration providing a dose adjusted $AUC_t$ and/or a dose adjusted $AUC_{inf}$ of morphine of from about 30 ng/mL to about 100 ng/mL per 15 mg, preferably of from about 40 ng/mL to about 80 ng/mL per 15 mg of morphine hemi(sulfate pentahydrate) (having a molecular weight of 758.8 g/mol) or an equimolar amount of another solvate or hydrate of morphine sulfate included in the dosage form, and the dosage form having a cracking force of at least about 150 N, preferably at least about 200 N, more preferably at least about 230 N.

In another specific embodiment, the present invention is directed to a solid oral extended release pharmaceutical dosage form comprising a cured extended release matrix formulation, the extended release matrix formulation comprising:
a therapeutically effective amount of morphine sulfate, and
polyethylene oxide:
the dosage form after administration providing a dose adjusted $AUC_t$ and/or a dose adjusted $AUC_{inf}$ of morphine of from about 30 ng/mL to about 100 ng/mL per 15 mg, preferably of from about 40 ng/mL to about 80 ng/mL per 15 mg of morphine hemi(sulfate pentahydrate) (having a molecular weight of 758.8 g/mol) or an equimolar amount of another solvate or hydrate of morphine sulfate included in the dosage form, and the dosage form having a crush resistance of at least about 400 N, preferably at least about 500 N.

In a further embodiment, the present invention is directed to a solid oral extended release pharmaceutical dosage form comprising a therapeutically effective amount of morphine,
the dosage form after administration providing:
a dose adjusted $C_{max}$ of morphine of from about 3 ng/mL to about 9 ng/mL and/or
a dose adjusted $AUC_t$ of morphine of from about 30 ng*hr/mL to about 100 ng*hr/mL and/or
a dose adjusted $AUC_{inf}$ of morphine of from about 30 ng*hr/mL to about 100 ng*hr/mL per 15 mg of morphine hemi(sulfate pentahydrate) (having a molecular weight of 758.8 g/mol) or an equimolar amount of another pharmaceutically acceptable morphine salt or solvate or hydrate thereof included in the dosage form, and
the dosage form having a breaking strength of least about 200 N, preferably at least about 300 N, most preferably at least about 400 N.

In a yet further embodiment, the present invention is directed to a solid oral extended release pharmaceutical dosage form comprising a therapeutically effective amount of morphine,
the dosage form after administration providing:
a dose adjusted $C_{max}$ of morphine of from about 3 ng/mL to about 9 ng/mL and/or
a dose adjusted $AUC_t$ of morphine of from about 30 ng*hr/mL to about 100 ng*hr/mL and/or a dose adjusted $AUC_{inf}$ of morphine of from about 30 ng*hr/mL to about 100 ng*hr/mL per 15 mg of morphine hemi(sulfate pentahydrate) (having a molecular weight of 758.8 g/mol) or an equimolar amount of another pharmaceutically acceptable morphine salt or solvate or hydrate thereof included in the dosage form, and the dosage form having a cracking force of least about 150 N, preferably at least about 200 N, most preferably at least about 230 N.

In a yet further embodiment, the present invention is directed to a solid oral extended release pharmaceutical dosage form comprising a therapeutically effective amount of morphine, the dosage form after administration providing:
a dose adjusted $C_{max}$ of morphine of from about 3 ng/mL to about 9 ng/mL and/or
a dose adjusted $AUC_t$ of morphine of from about 30 ng*hr/mL to about 100 ng*hr/mL and/or
a dose adjusted $AUC_{inf}$ of morphine of from about 30 ng*hr/mL to about 100 ng*hr/mL per 15 mg of morphine hemi(sulfate pentahydrate) (having a molecular weight of 758.8 g/mol) or an equimolar amount of another pharmaceutically acceptable morphine salt or solvate or hydrate thereof included in the dosage form, and the dosage form having a crush resistance of at least about 500 N.

In any of the three preceding embodiments, the dosage form after administration preferably provides:
a dose adjusted $C_{max}$ of morphine of from about 4 ng/mL to about 7 ng/mL and/or
a dose adjusted $AUC_t$ of morphine of from about 40 ng*hr/mL to about 80 ng*hr/mL and/or
a dose adjusted $AUC_{inf}$ of morphine of from about 40 ng*hr/mL to about 80 ng*hr/mL per 15 mg of morphine hemi(sulfate pentahydrate) (having a molecular weight of 758.8 g/mol) or an equimolar amount of another pharmaceutically acceptable morphine salt or solvate or hydrate thereof included in the dosage form.

In certain embodiments, the solid oral extended release pharmaceutical dosage forms of the present invention containing a certain amount of morphine sulfate (preferably in the form of morphine hemi(sulfate pentahydrate) having a molecular weight of 758.8 g/mol as defined herein) are bioequivalent to the commercial product MS Contin® of the same strength, but exhibit an improved hardness in terms of breaking strength, cracking force and/or crush resistance as compared to the commercial product MS Contin® of the same strength. Thus, advantageously, the present invention provides for a dosage form that has improved abuse deterrent properties and therefore making it more difficult to physically manipulate than the current commercial product MS Contin®, but preferably has the same bioavailability as MS Contin®. The present invention therefore provides an improvement both in terms of the individual patient's health as well as the public health aspect as compared to existing solid oral pharmaceutical dosage forms comprising morphine sulfate for the treatment of pain. The composition of the various strengths of commercial MS Contin® is indicated in Table VIII, below.

Therefore, in certain embodiments, the present invention is directed to a solid oral extended release pharmaceutical dosage form of morphine sulfate, wherein the dosage form is a tablet comprising 15 mg of morphine hemi(sulfate pentahydrate) (having a molecular weight of 758.8 g/mol) or an equimolar amount of another solvate or hydrate of morphine sulfate included in an extended release matrix formulation, wherein the dosage form when tested in a comparative clinical study may be or is bioequivalent to the commercial product MS Contin® containing an equimolar amount of morphine sulfate in a matrix formulation, and wherein the dosage form has a breaking strength of at least about 230 N and/or a cracking force of at least about 180 N and/or a crush resistance of at least about 400 N, preferably a breaking strength of at least about 250 N and/or a cracking force of at least about 200 N and/or a crush resistance of at least about 500 N.

In certain embodiments, the present invention is thus directed to a solid oral extended release pharmaceutical dosage form of morphine sulfate, wherein the dosage form is a tablet comprising 15 mg of morphine hemi(sulfate pentahydrate) (having a molecular weight of 758.8 g/mol) or an equimolar amount of another solvate or hydrate of morphine sulfate included in an extended release matrix formulation, wherein the dosage form when tested in a comparative clinical study is bioequivalent to a reference tablet containing an equimolar amount of morphine sulfate in a matrix formulation, and wherein the dosage form has a breaking strength of at least about 230 N and/or a cracking force of at least about 180 N and/or a crush resistance of at least about 400 N, preferably a breaking strength of at least about 250 N and/or a cracking force of at least about 200 N and/or a crush resistance of at least about 500 N, wherein the reference tablet contains: morphine sulfate: 15 mg/tablet, lactose (spray-dried): 85 mg/tablet, cetostearyl alcohol: 35 mg/tablet, hydroxyethyl cellulose: 10 mg/tablet, talc: 3 mg/tablet, magnesium stearate: 2 mg/tablet, Opadry® coating: 5 mg/tablet.

In certain embodiments, the present invention is directed to a solid oral extended release pharmaceutical dosage form of morphine sulfate, wherein the dosage form is a tablet comprising 30 mg of morphine hemi(sulfate pentahydrate) (having a molecular weight of 758.8 g/mol) or an equimolar amount of another solvate or hydrate of morphine sulfate included in an extended release matrix formulation, wherein the dosage form when tested in a comparative clinical study is bioequivalent to the commercial product MS Contin® containing an equimolar amount of morphine sulfate in a matrix formulation, and wherein the dosage form has a breaking strength of at least about 250 N and/or a cracking force of at least about 200 N and/or a crush resistance of at least about 400 N, preferably a breaking strength of at least about 300 N and/or a cracking force of at least about 230 N and/or a crush resistance of at least about 500 N.

In certain embodiments, the present invention is directed to a solid oral extended release pharmaceutical dosage form of morphine sulfate, wherein the dosage form is a tablet comprising 30 mg of morphine hemi(sulfate pentahydrate) (having a molecular weight of 758.8 g/mol) or an equimolar amount of another solvate or hydrate of morphine sulfate included in an extended release matrix formulation, wherein the dosage form when tested in a comparative clinical study is bioequivalent to a reference tablet containing an equimolar amount of morphine sulfate in a matrix formulation, and wherein the dosage form has a breaking strength of at least about 250 N and/or a cracking force of at least about 200 N and/or a crush resistance of at least about 400 N, preferably a breaking strength of at least about 300 N and/or a cracking force of at least about 230 N and/or a crush resistance of at least about 500 N, wherein the reference tablet contains: morphine sulfate: 30 mg/tablet, lactose (spray-dried): 70 mg/tablet, cetostearyl alcohol: 35 mg/tablet, hydroxyethyl cellulose: 10 mg/tablet, talc: 3 mg/tablet, magnesium stearate: 2 mg/tablet, Opadry® coating: 5 mg/tablet.

In certain embodiments, the present invention is directed to a solid oral extended release pharmaceutical dosage form of morphine sulfate, wherein the dosage form is a tablet comprising 60 mg of morphine hemi(sulfate pentahydrate) (having a molecular weight of 758.8 g/mol) or an equimolar amount of another solvate or hydrate of morphine sulfate included in an extended release matrix formulation, wherein the dosage form when tested in a comparative clinical study is bioequivalent to the commercial product MS Contin® containing an equimolar amount of morphine sulfate in a matrix formulation, and wherein the dosage form has a breaking strength of at least about 280 N and/or a cracking force of at least about 200 N and/or a crush resistance of at least about 400 N, preferably a breaking strength of at least about 320 N and/or a cracking force of at least about 230 N and/or a crush resistance of at least about 500 N.

In certain embodiments, the present invention is directed to a solid oral extended release pharmaceutical dosage form of morphine sulfate, wherein the dosage form is a tablet comprising 60 mg of morphine hemi(sulfate pentahydrate) (having a molecular weight of 758.8 g/mol) or an equimolar amount of another solvate or hydrate of morphine sulfate included in an extended release matrix formulation, wherein the dosage form when tested in a comparative clinical study is bioequivalent to a reference tablet containing an equimolar amount of morphine sulfate in a matrix formulation, and wherein the dosage form has a breaking strength of at least about 280 N and/or a cracking force of at least about 200 N and/or a crush resistance of at least about 400 N, preferably a breaking strength of at least about 320 N and/or a cracking force of at least about 230 N and/or a crush resistance of at least about 500 N,
wherein the reference tablet contains: morphine sulfate: 60 mg/tablet, lactose (spray-dried): 42.2 mg/tablet, cetostearyl alcohol: 32.8 mg/tablet, hydroxyethyl cellulose: 10 mg/tablet, talc: 3 mg/tablet, magnesium stearate: 2 mg/tablet, Opadry® coating: 5 mg/tablet.

In certain embodiments, the present invention is directed to a solid oral extended release pharmaceutical dosage form of morphine sulfate, wherein the dosage form is a tablet comprising 100 mg of morphine hemi(sulfate pentahydrate) (having a molecular weight of 758.8 g/mol) or an equimolar amount of another solvate or hydrate of morphine sulfate included in an extended release matrix formulation, wherein the dosage form when tested in a comparative clinical study is bioequivalent to the commercial product MS Contin® containing an equimolar amount of morphine sulfate in a matrix formulation, and wherein the dosage form has a breaking strength of least about 200 N and/or a cracking force of at least about 170 N and/or a crush resistance of at least about 400 N, preferably a breaking strength of at least about 250 N and/or a cracking force of at least about 190 N and/or a crush resistance of at least about 500 N.

In certain embodiments, the present invention is directed to a solid oral extended release pharmaceutical dosage form of morphine sulfate, wherein the dosage form is a tablet comprising 100 mg of morphine hemi(sulfate pentahydrate) (having a molecular weight of 758.8 g/mol) or an equimolar amount of another solvate or hydrate of morphine sulfate included in an extended release matrix formulation, wherein the dosage form when tested in a comparative clinical study is bioequivalent to a reference tablet containing an equimolar amount of morphine sulfate in a matrix formulation, and wherein the dosage form has a breaking strength of least about 200 N and/or a cracking force of at least about 170 N and/or a crush resistance of at least about 400 N, preferably a breaking strength of at least about 250 N and/or a cracking force of at least about 190 N and/or a crush resistance of at least about 500 N,
wherein the reference tablet contains: morphine sulfate: 100 mg/tablet, cetostearyl alcohol: 35 mg/tablet, hydroxyethyl cellulose: 10 mg/tablet, talc: 3 mg/tablet, magnesium stearate: 2 mg/tablet, Opadry® coating: 5 mg/tablet.

In certain embodiments, the present invention is directed to a solid oral extended release pharmaceutical dosage form of morphine sulfate, wherein the dosage form is a tablet comprising 200 mg of morphine hemi(sulfate pentahydrate) (having a molecular weight of 758.8 g/mol) or an equimolar amount of another solvate or hydrate of morphine sulfate included in an extended release matrix formulation, wherein the dosage form when tested in a comparative clinical study is bioequivalent to the commercial product MS Contin® containing an equimolar amount of morphine sulfate in a matrix formulation, and wherein the dosage form has a breaking strength of least about 350 N, and/or a cracking force of at least about 180 N and/or a crush resistance of at least about 400 N, preferably a breaking strength of at least about 400 N and/or a cracking force of at least about 210 N and/or a crush resistance of at least about 500 N.

In certain embodiments, the present invention is directed to a solid oral extended release pharmaceutical dosage form of morphine sulfate, wherein the dosage form is a tablet comprising 200 mg of morphine hemi(sulfate pentahydrate) (having a molecular weight of 758.8 g/mol) or an equimolar amount of another solvate or hydrate of morphine sulfate included in an extended release matrix formulation, wherein the dosage form when tested in a comparative clinical study is bioequivalent to a reference tablet containing an equimolar amount of morphine sulfate in a matrix formulation, and wherein the dosage form has a breaking strength of least about 350 N, and/or a cracking force of at least about 180 N and/or a crush resistance of at least about 400 N, preferably a breaking strength of at least about 400 N and/or a cracking force of at least about 210 N and/or a crush resistance of at least about 500 N,
wherein the reference tablet contains: morphine sulfate: 200 mg/tablet, cetostearyl alcohol: 70 mg/tablet, hydroxyethyl cellulose: 20 mg/tablet, talc: 6 mg/tablet, magnesium stearate: 4 mg/tablet, Opadry® coating: 10 mg/tablet.

Preferably, in all preceding embodiments herein, preferred ranges for the approximate molecular weight, the particle size distribution and the amount of polyethylene oxide included into the solid oral extended release pharmaceutical dosage form apply as specified herein above in the section "Polyethylene Oxide".

Hardness of the Extended Release Matrix Formulation:

Also the (uncured) shaped extended release matrix formulation of the present invention (which may be regarded as an "intermediate" in the preparation of the solid oral extended release pharmaceutical dosage form of the present invention) has improved hardness as expressed by the breaking strength, the cracking force and/or the crush resistance.

Specifically, in certain embodiments the present invention provides an extended release matrix formulation comprising morphine sulfate in the form of morphine hemi(sulfate pentahydrate) (having a molecular weight of 758.8 g/mol) in an amount of about 15 mg included into the extended release matrix formulation or an equimolar amount of another solvate or hydrate of morphine sulfate, which extended release matrix formulation has a breaking strength of at least about 70 N and/or a cracking force of at least about 140 N and/or a penetration depth to crack of at least about 1.1 mm, preferably a breaking strength of at least about 90 N and/or a cracking force of at least about 150 N and/or a penetration depth to crack of at least about 1.2 mm, more preferably a breaking strength of at least about 100 N and/or a cracking force of at least about 160 N and/or a penetration depth to crack of at least about 1.3 mm.

Specifically, in certain embodiments the present invention provides an extended release matrix formulation comprising morphine sulfate in the form of morphine hemi(sulfate pentahydrate) (having a molecular weight of 758.8 g/mol) in an amount of about 30 mg included into the extended release matrix formulation or an equimolar amount of another solvate or hydrate of morphine sulfate, which has a breaking strength of at least about 80 N and/or a cracking force of at least about 110 N and/or a penetration depth to crack of at least about 1.1 mm, preferably a breaking strength of at least about 100 N and/or a cracking force of at least about 120 N and/or a penetration depth to crack of at least about 1.2 mm, more preferably a breaking strength of at least about 120 N and/or a cracking force of at least about 130 N and/or a penetration depth to crack of at least about 1.3 mm.

Specifically, in certain embodiments the present invention provides an extended release matrix formulation, comprising morphine sulfate in the form of morphine hemi(sulfate pentahydrate) (having a molecular weight of 758.8 g/mol) in an amount of about 60 mg included into the extended release matrix formulation or an equimolar amount of another solvate or hydrate of morphine sulfate, which has a breaking strength of at least about 100 N and/or a cracking force of at least about 130 N and/or a penetration depth to crack of at least about 1.0 mm, preferably a breaking strength of at least about 120 N and/or a cracking force of at least about 140 N and/or a penetration depth to crack of at least about 1.05 mm, more preferably a breaking strength of at least about 135 N and/or a cracking force of at least about 150 N and/or a penetration depth to crack of at least about 1.1 mm.

Specifically, in certain embodiments the present invention provides an extended release matrix formulation, comprising morphine sulfate in the form of morphine hemi(sulfate pentahydrate) (having a molecular weight of 758.8 g/mol) in an amount of about 100 mg included into the extended release matrix formulation or an equimolar amount of another solvate or hydrate of morphine sulfate, which has a breaking strength of at least about 80 N and/or a cracking force of at least about 100 N and/or a penetration depth to crack of at least about 0.7 mm, preferably a breaking strength of at least about 100 N and/or a cracking force of at least about 105 N and/or a penetration depth to crack of at least about 0.75 mm, more preferably a breaking strength of at least about 120 N and/or a cracking force of at least about 110 N and/or a penetration depth to crack of at least about 0.8 mm.

Specifically, in certain embodiments the present invention provides an extended release matrix formulation, comprising morphine sulfate in the form of morphine hemi(sulfate pentahydrate) (having a molecular weight of 758.8 g/mol) in an amount of about 200 mg included into the extended release matrix formulation or an equimolar amount of another solvate or hydrate of morphine sulfate, which has a breaking strength of at least about 110 N and/or a cracking force of at least about 100 N and/or a penetration depth to crack of at least about 0.9 mm, preferably a breaking strength of at least about 125 N and/or a cracking force of at least about 115 N and/or a penetration depth to crack of at least about 1.0 mm, more preferably a breaking strength of at least about 140 N and/or a cracking force of at least about 130 N and/or a penetration depth to crack of at least about 1.1 mm.

Method of Increasing the Hardness

The present invention is furthermore directed to a method of increasing the breaking strength and/or cracking force and/or crush resistance of a solid oral extended release pharmaceutical dosage form comprising an extended release matrix formulation, the extended release matrix formulation comprising:
  a therapeutically effective amount of morphine or a pharmaceutically acceptable salt thereof, preferably morphine sulfate, and
  polyethylene oxide,
wherein the dosage form is obtainable by at least the following steps:
  (a) combining at least morphine or a pharmaceutically acceptable salt thereof and polyethylene oxide particles to form a composition,
  (b) shaping the composition of step (a) to form the extended release matrix formulation,
  (c) and optionally curing the extended release formulation of step (b);
the method being characterized in that about 50% or more of the polyethylene oxide particles used in step (a) pass through a 25 mesh (0.707 mm; 707 microns) sieve.

The present invention is further directed to the use of polyethylene oxide particles for increasing the breaking strength and/or cracking force and/or crush resistance of a solid oral extended release pharmaceutical dosage form comprising an extended release matrix formulation, the extended release matrix formulation comprising:
  a therapeutically effective amount of morphine or a pharmaceutically acceptable salt thereof, preferably morphine sulfate, and
  polyethylene oxide,
wherein the dosage form is obtainable by at least the following steps:
  (a) combining at least morphine or a pharmaceutically acceptable salt thereof and polyethylene oxide particles to form a composition, and
  (b) shaping the composition of step (a) to form the extended release matrix formulation, wherein the polyethylene oxide particles used in step (a) are characterized in that about 50% or more of the polyethylene oxide particles pass through a 25 mesh (0.707 mm; 707 microns) sieve; and optionally
  (c) curing the extended release formulation of step (b).

In preferred embodiments of the above method and use the same preferred values or ranges specified herein above for the particle size distribution and/or the approximate molecular weight of the polyethylene oxide apply. Furthermore, preferably, in step (c) of the above method and use the extended release matrix formulation is subjected to a temperature of from about 65° C. to about 85° C. for a period of from about 15 minutes to about 2 hours, more preferably a temperature of from about 70° C. to about 80° C. for a period of from about 20 minutes to about 1 hours, most preferably a temperature of from about 72° C. to about 78° C. for a period of from about 30 minutes to about 45 minutes.

In certain embodiments, by the above method and use the breaking strength is increased to at least about 200 N and/or the cracking force is increased to at least about 150 N and/or the crush resistance is increased to at least about 400 N.

Preferably, the breaking strength is increased to at least about 250 N and/or the cracking force is increased to at least about 170 N and/or the crush resistance is increased to at least about 500 N. More preferably, the breaking strength is increased to at least about 300 N and/or the cracking force is increased to at least about 200 N. Even more preferably, the breaking strength is increased to at least about 350 N and/or the cracking force is increased to at least about 215 N. Most preferably, the breaking strength is increased to at least about 400 N and/or the cracking force is increased to at least about 230 N. It is believed that this method of increasing the hardness (as expressed by the breaking strength and/or the cracking force and/or the crush resistance) as well as the corresponding use of the present invention can equally be used in principle also in connection with other active agents, specifically other opioids and other salts of opioids, including other salts of morphine.

Physical Manipulation

Physical manipulation of opioid containing tablets e.g. to obtain a powder is often the first step of preparing tablets for abuse, such as for inhaling or dissolving and injecting which could allow immediate access to the active component by increasing the surface area. Common tools to manipulate tablets are household tools, such as spoons, knives, cutters, graters, slicers and mills.

It is observed that, due to their improved hardness as explained above and as illustrated in the Examples, the solid oral extended release pharmaceutical dosage forms of the present invention are less likely to be physically manipulated, as they are more difficult to crush, break, grate, grind or mill with common and easily available (e.g., household) tools. The dosage forms of the present invention are more difficult to manipulate as compared to commercially available reference products (e.g. MS Contin®), and therefore more time and effort would be required e.g. to prepare a fine powder. Also, when preparing a powder from the dosage forms of the invention e.g. by grinding or milling, usually the resulting particles are still coarser (i.e., the particle size overall is larger) than for the corresponding reference product MS Contin®. See Example 12 herein below.

In certain embodiments, the present invention is directed to a solid oral extended release pharmaceutical dosage form as described herein, wherein crushing the dosage form between two spoons or by means of a mortar and pestle results in less than about 10%, preferably less than about 5%, more preferably less than about 2.5% of the resulting particles having a particle size of less than 1000 µm. In these embodiments, the crushing may be performed for up to about 5 min. Prior to the crushing the dosage form may have been thermally treated, e.g. by heating in an oven or by microwave treatment. The thermal treatment may have been performed at a temperature of at least about 50° C., at least about 90° C., at least about 200° C., or at least about 230° C. Thermal treatment may have lasted for at least about 2 hours, at least about 3 hours, or at least about 4 hours.

In certain embodiments, after thermal pre-treatment (e.g. at 90° C. or 230° C. as indicated above for extended periods of time in an oven) the dosage forms according to the invention may become harder so that only a few cracks occur when such pre-treated dosage forms are manipulated e.g. with a mortar and pestle for 5 minutes. Additionally, neither freezing nor microwave pre-treatment conditions alter or facilitate the manipulation of the dosage forms of the present invention.

In certain embodiments, due to their improved hardness, the dosage forms of the present invention can be flattened to a certain degree (i.e., to a certain thickness of the flattened dosage form as compared (expressed in % thickness as measured e.g. by a thickness gauge) to their original thickness before flattening) without breaking. The force may be applied with a Carver style bench press or another instrument, such as a hammer. In case of a hammer, hammer strikes may be applied manually from a direction substantially perpendicular to the diameter (or width) of the dosage form. In certain instances, the flattening may not result in breaking the dosage form (e.g., tablet) into pieces; however, edge splits and cracks may occur.

In certain embodiments the present invention is directed to a solid oral extended release pharmaceutical dosage form as described herein, which can at least be flattened without breaking, characterized by a thickness of the tablet after the flattening which corresponds to no more than about 60%, preferably to no more than about 40%, more preferably to no more than about 20% of the thickness of the tablet before flattening.

In certain specific embodiments, the amount of morphine sulfate released after 0.5 hours from the solid oral extended release pharmaceutical dosage form of the present invention flattened to no more than about 60% of the thickness of the dosage form before flattening deviates no more than about 20%-points, preferably no more than about 10%-points from the amount of morphine sulfate released from a corresponding non-flattened dosage form as measured by an in-vitro dissolution in a USP Apparatus 1 (basket) at 100 rpm in 900 ml simulated gastric fluid without enzymes (SGF) at 37° C. after 0.5 hours.

Preferably, the amount of morphine sulfate released after 0.5 hours and after 1 hour from such flattened dosage form deviates no more than about 20%-points, preferably no more than about 10%-points from a non-flattened dosage form as measured by an in-vitro dissolution in a USP Apparatus 1 (basket) at 100 rpm in 900 ml simulated gastric fluid without enzymes (SGF) at 37° C. after 0.5 hours and after 1 hour.

It has been observed that the in-vitro release rate of morphine sulfate is directly related to the particle size. When the dosage forms of the invention are physically manipulated, i.e., cut into various size pieces (such as halved or quartered) or sliced, this reduction in particle size increases the surface area of the dosage forms, and therefore, the dissolution rate increases. It has also been observed that in the case of milling, even though the milled particles are smaller than the cut or sliced particles the rate of dissolution is nevertheless slower for the milled particles. Without wishing to be bound by any theory it is believed that this is related to the hydrogelling properties of the polyethylene oxide included in the dosage forms of the present invention. As the particle size is reduced further, the effect of the gelling becomes more pronounced, thus reducing the rate of dissolution. See Example 10 herein below. Importantly, however, any increase in dissolution rate due to a reduced particle size after physical manipulation does not significantly affect the extended/controlled release properties. Even after manipulation, some degree of controlled release is still maintained for the dosage forms of the present invention.

In-Vitro Dissolution Rates in Common Solvents

It has been observed that the rate of dissolution of morphine sulfate from the dosage forms of the present invention in water or SGF is related to temperature and to the degree of physical manipulation (and the size of the particles resulting from physically manipulating the dosage forms such as by slicing, grinding or milling etc.). This also applies in other (common) solvents, such as household solvents, various organic solvents or buffered solutions. The corresponding in vitro dissolution study is represented in Example 11 herein below. Extraction of morphine sulfate from certain dosage forms according to the present invention was studied with intact and milled dosage forms and compared to the intact and grinded reference product, commercially available MS Contin®, in a variety of solvents and at room temperature as well as elevated temperature (90° C.) as described in Example 11.

Gelling/Syringeability

Intact, sliced and milled dosage forms of the present invention were subjected to a comprehensive series of in vitro tests to evaluate their resistance to abuse via injection. This testing included three volumes (2 mL, 5 mL, 10 mL), altogether four injectable solvents (water, saline solution, 40% ethanol and 95% ethanol), at room temperature (i.e., 25° C.) and elevated temperature (60° C. or 90° C.), with and without agitation at 200 RPM, for intact, sliced, and milled tablets. In some tests, the dosage forms were pretreated by heating in an oven or by microwave prior to the syringeability tests. At some conditions, the dosage forms of the present invention were compared to a commercially available reference dosage form MS Contin® in intact, sliced and ground form. Syringe-ability testing was generally performed using an iterative process (illustrated by the syringeability decision tree, see FIGS. 98(a) and (b)) whereby attempts were first made to draw the extraction media into a small needle gauge (27-gauge). If ≤10% of the initial extraction media could be drawn into the syringe, then larger needles (25-gauge, 22-gauge, and 18-gauge) were subsequently attempted. When ≥10% was syringeable, the volume was recorded and syringeable liquid was analyzed for morphine sulfate content via analytical testing. However, in the syringeability tests with thermal or microwave pre-treatment only an 18-gauge needle was used. In the syringeability tests using 40% or 95% ethanol as extraction medium a 27- and 18-gauge needle was used. Details of the method are presented in Example 13 herein below, along with the results.

It was observed that the reference product MS Contin® (intact, as well as sliced and ground) could easily and quickly be extracted in small volumes of solvent and could easily be drawn into a small 27 gauge needle. Heating the samples to 90° C. increased the release of morphine sulfate even further as compared to room temperature. By contrast, the tested dosage forms of the present invention containing polyethylene oxide were difficult to prepare for injection under laboratory conditions. In most cases, the experiments did not result in enough syringeable material to be analyzed for viscosity, even if a relatively large volume (10 mL) of solvent was used. Increasing the temperature to 90° C. increased the release of morphine sulfate also for the dosage forms according to the present invention, but the amount of morphine recovered was still considerably lower than with the comparator MS Contin®. Tablets according to the invention that were manipulated by slicing or milling in these tests formed a gelatinous material that often required larger needle gauges, but nevertheless resulted in low recoveries of syringeable liquid.

Figure 101:
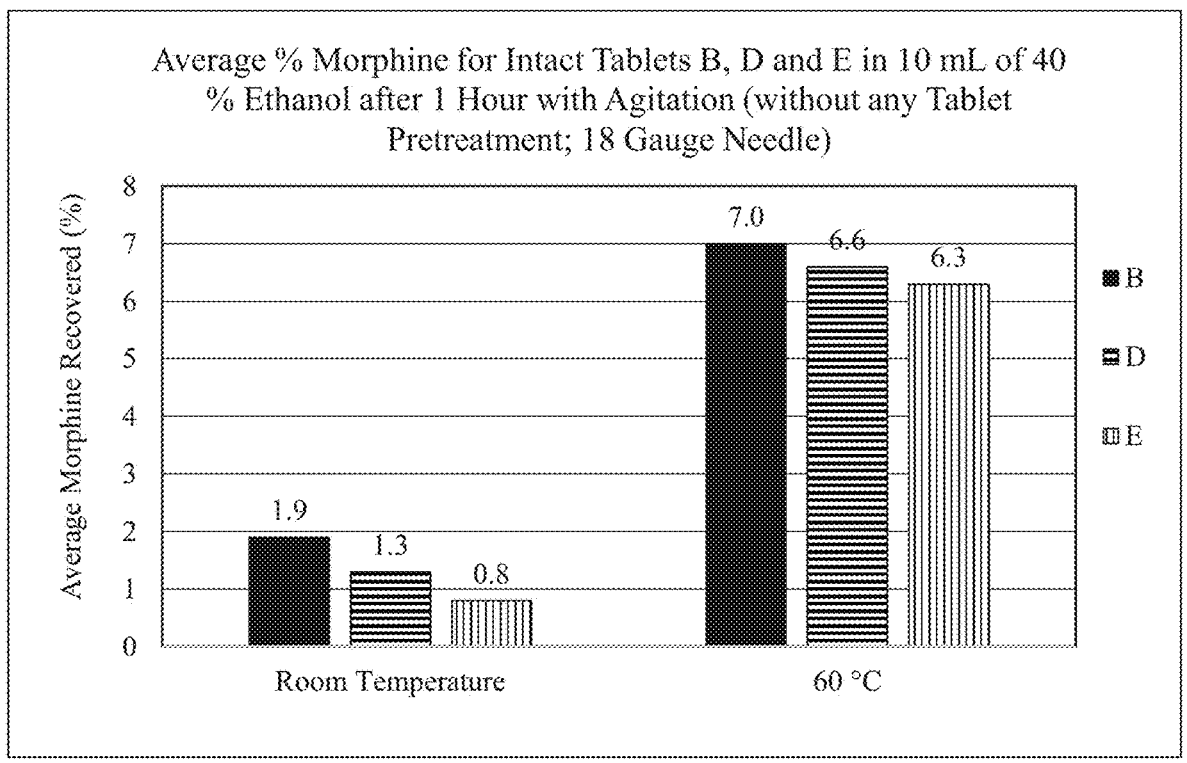
FIG. 101: The Average Percentage of Morphine Recovered for Intact Tablets in 10 mL of 40% Ethanol after 1 Hour with Agitation
Figure 102:
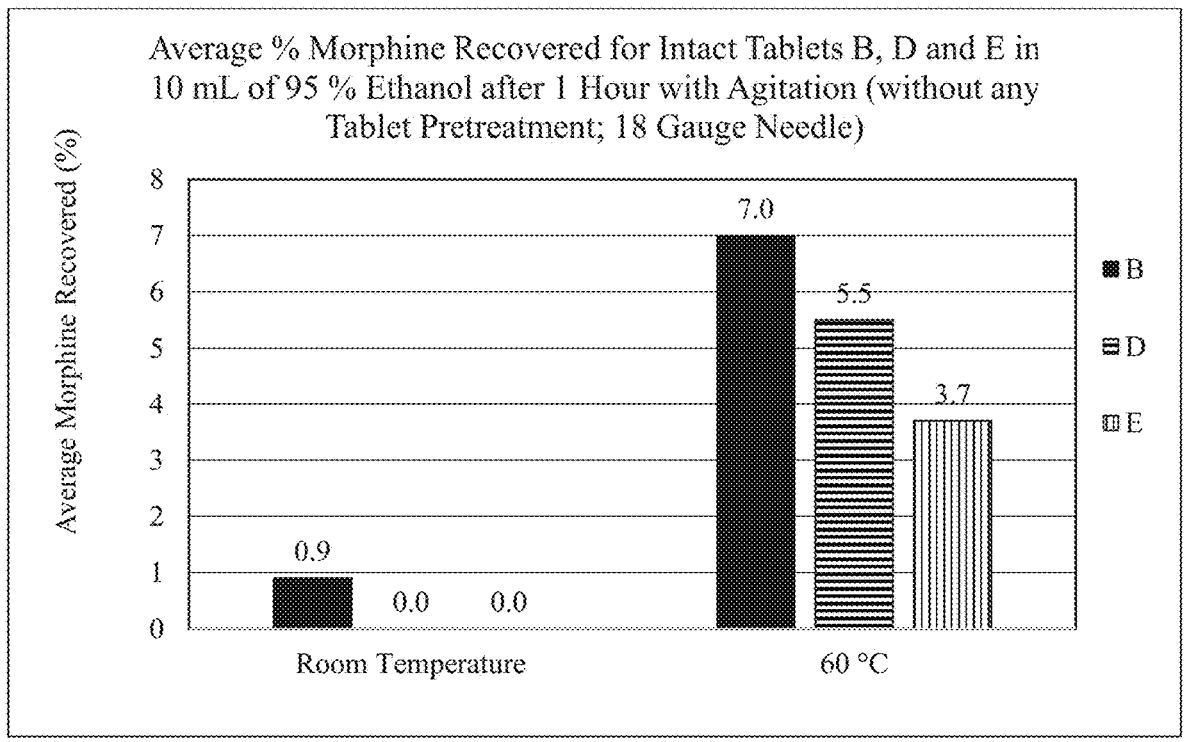
FIG. 102: The Average Percentage of Morphine Recovered for Intact Tablets in 10 mL of 95% Ethanol after 1 Hour with Agitation

Extraction attempts with the intact dosage forms according to the present invention in 10 mL of 40% or 95% ethanol for one hour resulted in very low amounts of morphine recovered, specifically not more than 2% recovery of morphine when extracted at room temperature, and even when extracted at 60° C. not more than 7% of morphine could be recovered (see FIGS. 101 and 102). From extraction attempts with milled dosage forms according to the invention in 10 mL of 40% ethanol after 30 min at room temperature or at 60° C. (see FIG. 103), no morphine could be recovered at all. Only very low amounts of morphine could be recovered from 10 mL of 95% ethanol after 30 minutes at 60° C. due to increased viscosity of the solution at this temperature. Extraction from 10 mL of 95% ethanol after 30 minutes at room temperature was higher (see FIG. 104). However, injection of ethanol, let alone in large volumes such as 10 mL, is usually not practiced by potential abusers.

Figure 105:
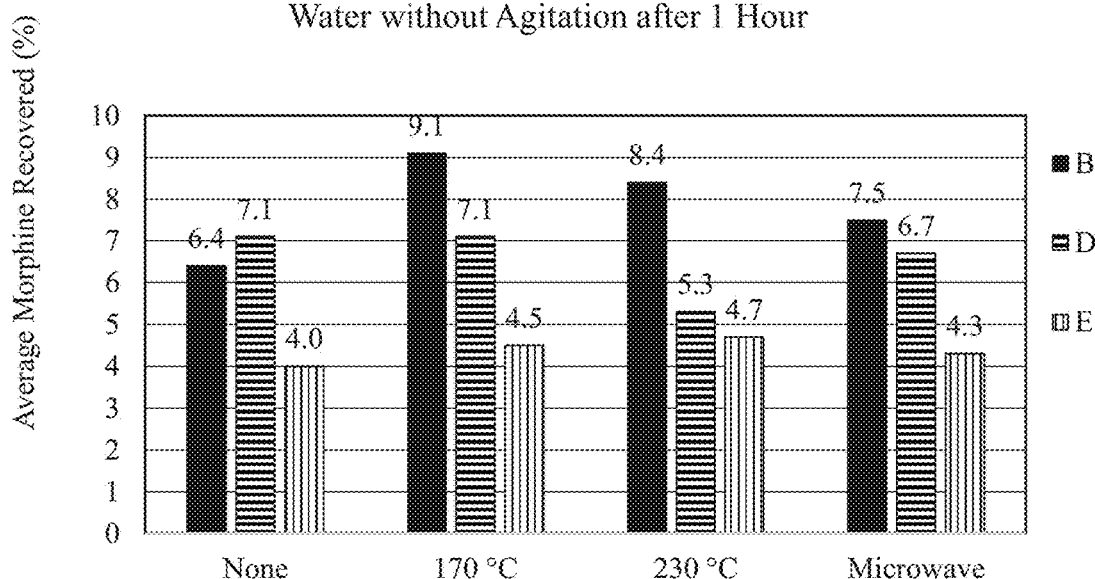
FIG. 105: The Average Percentage of Morphine Recovered in the Expelled Fraction for Intact Tablets in 10 mL of Room Temperature Tap Water without Agitation after 1 Hour
Figure 106:
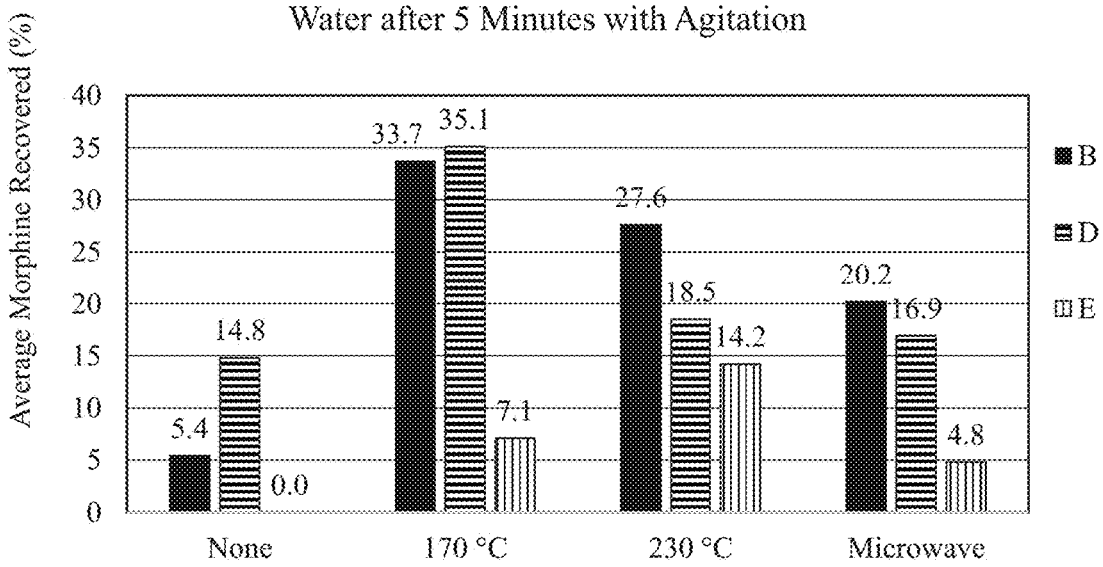
FIG. 106: The Average Percentage of Morphine Recovered in the Expelled Fraction for Milled Tablets in 10 mL of Room Temperature Tap Water after 5 Minutes with Agitation.
Figure 107:
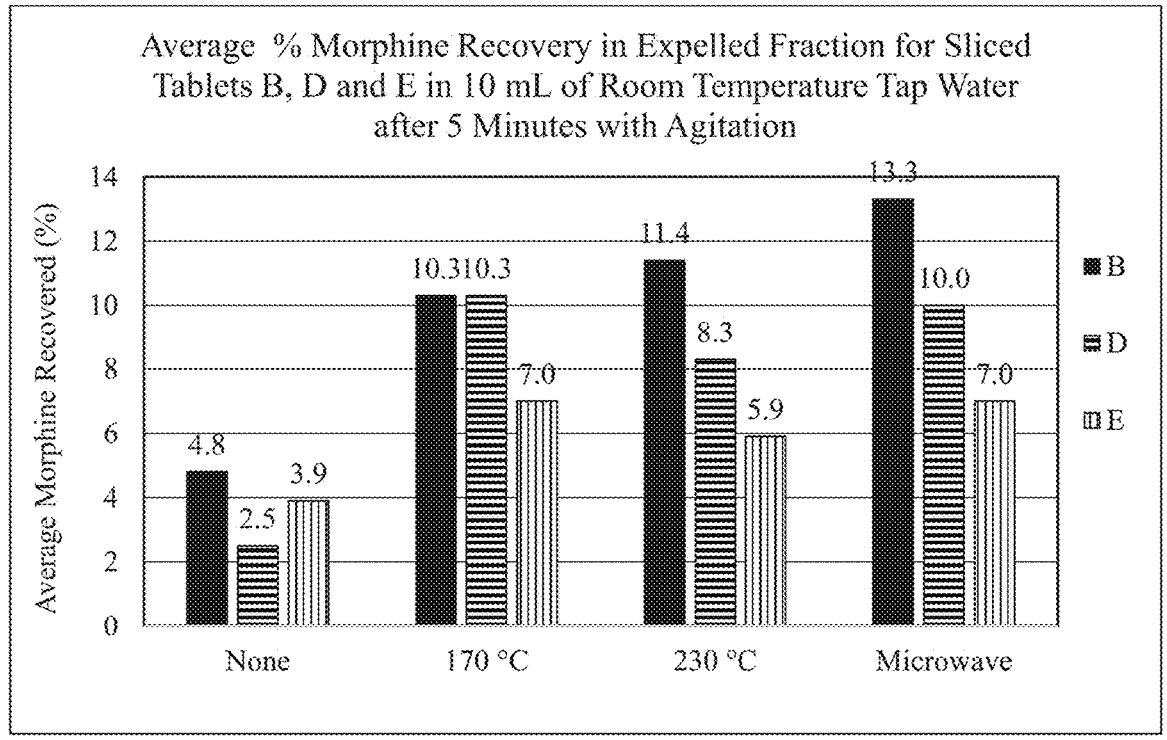
FIG. 107: The Average Percentage of Morphine Recovered in the Expelled Fraction for Sliced Tablets in 10 mL of Room Temperature Tap Water after 5 Minutes with Agitation.
Figure 108:
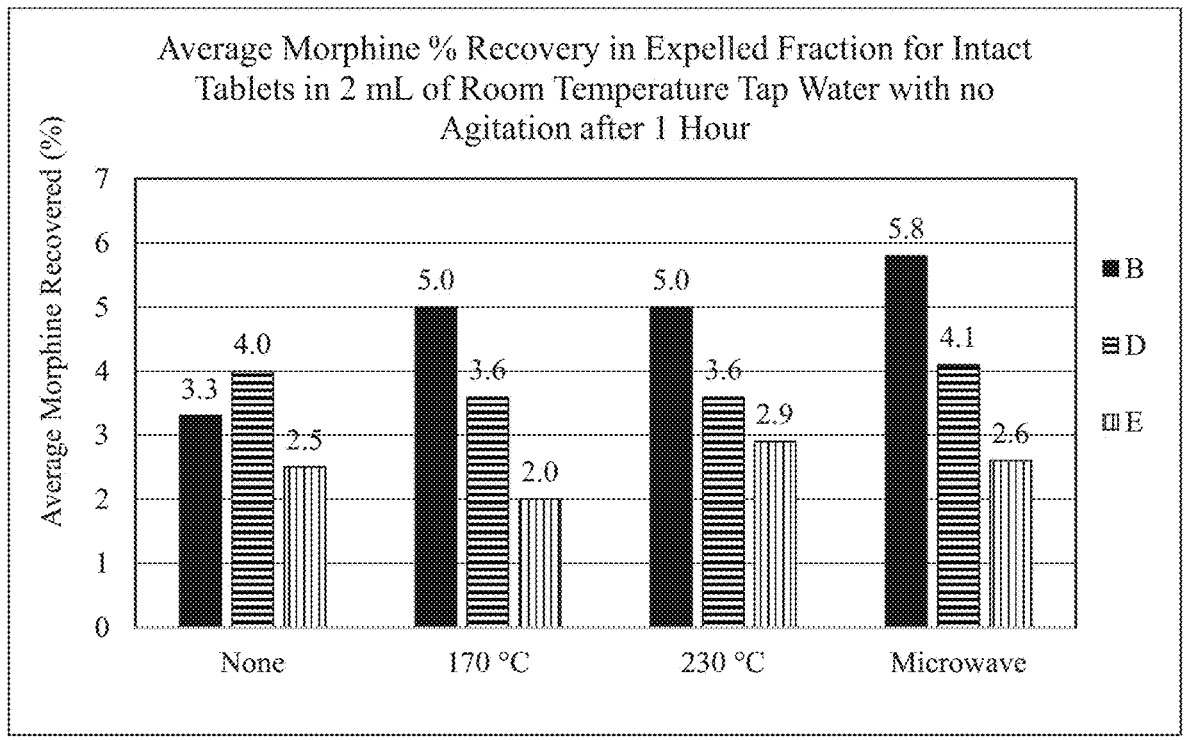
FIG. 108: The Average Percentage of Morphine Recovered in the Expelled Fraction for Intact Tablets in 2 mL of Room Temperature Tap Water without Agitation after 1 Hour
Figure 109:
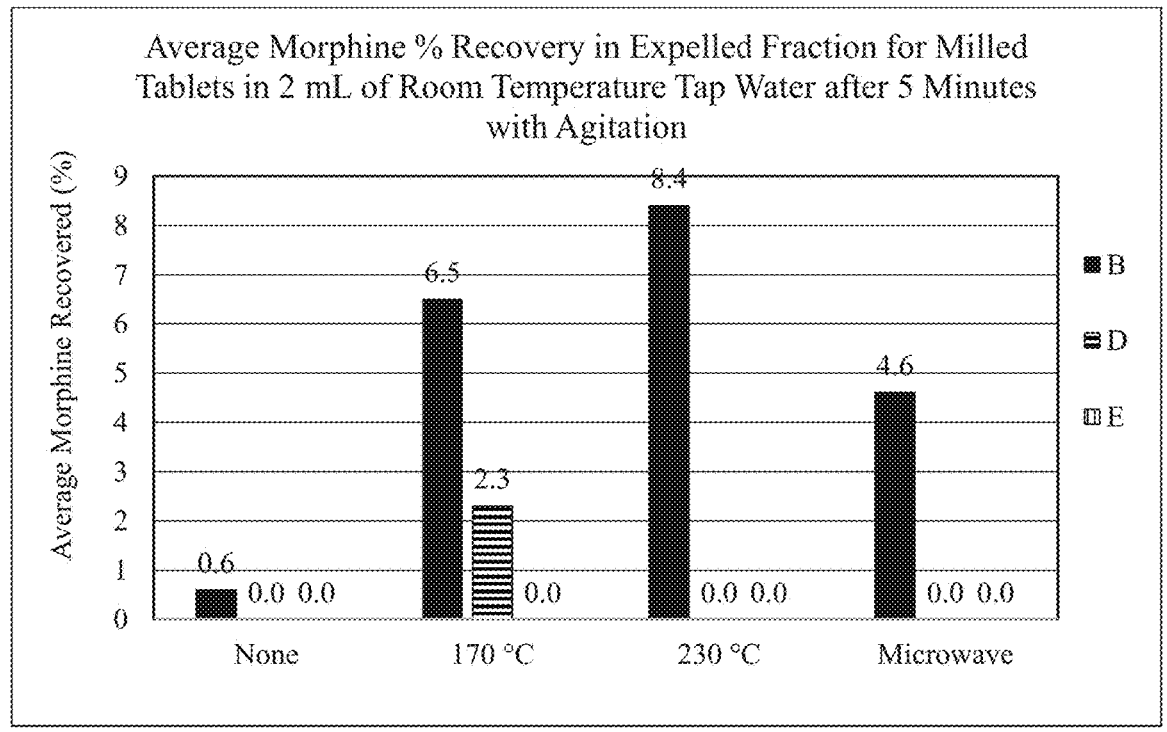
FIG. 109: The Average Percentage of Morphine Recovered in the Expelled Fraction for Milled Tablets in 2 mL of Room Temperature Tap Water after 5 Minutes with Agitation
Figure 110:
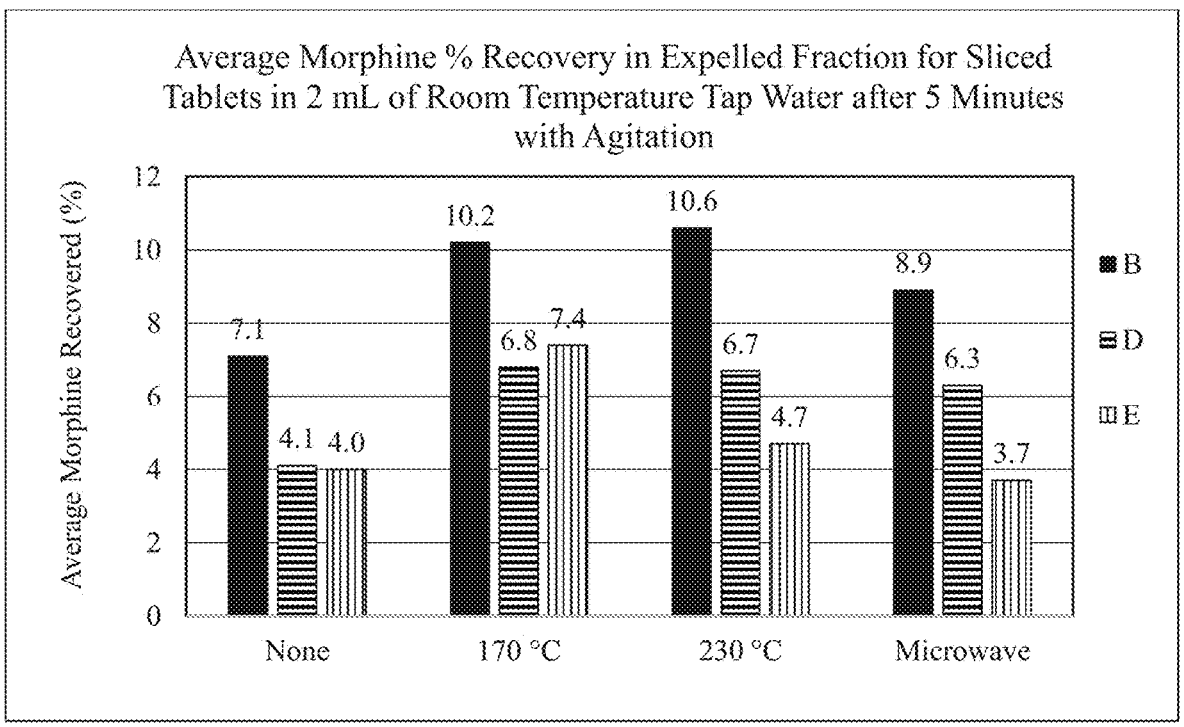
FIG. 110: The Average Percentage of Morphine Recovered in the Expelled Fraction for Sliced Tablets in 2 mL of Room Temperature Tap Water after 5 Minutes with Agitation

Thermal pretreatment of the dosage forms according to the present invention, such as heating in an oven for several minutes at temperatures of e.g. 170° C. or at 230° C. or treating in a microwave only had a minor effect on the amount of morphine recovered from the intact tablets, and only slightly increased the recovered amounts of morphine in the case of sliced tablets, when extracted in room temperature tap water for one hour (see FIGS. 105, 107). For milled dosage forms (see FIGS. 106,109), an increase of recovered amounts after such thermal pretreatment could be observed, but overall the recovered amounts were still low even if a large 18-gauge needle was used. This applies to small (2 mL) as well as large (10 mL) extraction volumes of room temperature water. The same trend regarding the effect of thermal or microwave pretreatment on extractability can also be observed when water near boiling temperature (90° C.) is used for extraction.

Without wishing to be bound by any theory, it is believed that the amount of recovered morphine available for intravenous injection from the dosage forms according to the present invention depends on the one hand on the gelling properties of the dosage forms containing polyethylene oxide as matrix material (influencing the volume that can be drawn up into the needle) and on the other hand on the solubility of the morphine sulfate itself in the respective solvents chosen for extraction (determining the amount of morphine recovered). These factors are further influenced by the conditions (temperature, incubation time, agitation) applied during the extraction.

Overall, compared to MS Contin®, tablets B, D and E according to the invention were highly resistant to preparation for extraction and generally required the use of large bore needles (e.g., 18 gauge) for aspirating the solution. Percent recovery of morphine sulfate from all three dosage strengths of dosage forms according to the invention subjected to the syringeability tests presented here was consistently lower compared to MS Contin® over a broad range of test conditions.

Thermal pre-treatment at 170° C. and 230° C. or microwave pre-treatment generally increased the amount of morphine sulfate able to be syringed relative to the non-pretreated samples. However, significant resistance to extraction for intravenous abuse was retained, and at the low extraction volumes typically favored by abusers (i.e., 2 mL), the amount of morphine sulfate available was relatively low (not more than 10-30% of the dose contained in the respective tablet).

Overall, these data show that the dosage forms according to the present invention are difficult to prepare for abuse via injection. Firstly, they are more difficult to manipulate (reduce to small particles) due to their increased hardness with respect to the reference, MS Contin®. Additionally, when manipulated and dissolved in small volumes of injectable solvent, the dosage forms according to the present invention containing polyethylene oxide form a viscous, gelatinous material making passage through a needle difficult (thus requiring larger needles) or even impossible in many circumstances. Furthermore, when syringeable liquid was analyzed for morphine sulfate content, it was observed that the dosage forms of the present invention released only low amounts of morphine sulfate. Furthermore, even when these small volume extractions were heated to near boiling temperatures for extended periods of time the dosage forms according to the present invention showed substantial resistance to extraction for injection.

It is thus believed that the presence of polyethylene oxide in the dosage form of the present invention in the amounts specified herein provides for an increased gelling of the dosage form upon attempts to dissolve the dosage form in liquids, such as water, saline or other household solvents. Compared to the commercially available reference products that do not contain any polyethylene oxide, this gelling effect results in a generally lower extractability of morphine (sulfate) from the dosage forms of the present invention in such solvents, and a reduced syringeability as described herein. This effect further contributes to preventing or reducing the likelihood of abuse of the dosage forms according to the present invention.

The present invention is thus also directed to a solid oral extended release pharmaceutical dosage form as described herein, wherein recovery of the morphine sulfate is less than about 20%, preferably less than about 10%, more preferably less than about 5%, based on a syringeability test whereby one intact dosage form is subjected to dissolution in 2, 5, or 10 ml of water or saline without or with agitation at room temperature for 1 hour or 24 hours and the resultant solution is aspirated by an iterative process starting with a 27 gauge needle and subsequently using 25, 22 and 18 gauge needles in case less than 10% of the extraction volume could be loaded in the respective larger gauge (smaller diameter) needle.

The present invention is also directed to a solid oral extended release pharmaceutical dosage form as described herein, wherein recovery of the morphine sulfate is less than about 65%, preferably less than about 40%, more preferably less than about 30%, more preferably less than about 25%, most preferably less than about 20%, based on a syringeability test whereby one intact dosage form is subjected to extraction in 2, 5, or 10 ml of water without or with agitation at 90° C. for 1 hour or 24 hours and the resultant solution is aspirated by an iterative process starting with a 27 gauge needle and subsequently using 25, 22 and 18 gauge needles in case less than 10% of the extraction volume could be loaded in the respective larger gauge (smaller diameter) needle.

The present invention is also directed to a solid oral extended release pharmaceutical dosage form as described herein, wherein recovery of the morphine sulfate is less than about 30%, preferably less than about 20%, more preferably less than about 15%, based on a syringeability test whereby one intact dosage form is subjected to extraction in 2, 5, or 10 ml of saline without or with agitation at 90° C. for 24 hours and the resultant solution is aspirated by an iterative process starting with a 27 gauge needle and subsequently using 25, 22 and 18 gauge needles in case less than 10% of the extraction volume could be loaded in the respective larger gauge (smaller diameter) needle.

The present invention is also directed to a solid oral extended release pharmaceutical dosage form as described herein, wherein recovery of the morphine sulfate is less than about 15%, preferably less than about 10%, more preferably less than about 5%, based on a syringeability test whereby one sliced dosage form is subjected to extraction in 2, 5, or 10 ml of water or saline without or with agitation at room temperature for 30 minutes and the resultant solution is aspirated by an iterative process starting with a 27 gauge needle and subsequently using 25, 22 and 18 gauge needles in case less than 10% of the extraction volume could be loaded in the respective larger gauge (smaller diameter) needle.

The present invention is also directed to a solid oral extended release pharmaceutical dosage form as described herein, wherein recovery of the morphine sulfate is less than about 50%, preferably less than about 35%, more preferably less than about 20%, based on a syringeability test whereby one sliced dosage form is subjected to extraction in 2, 5, or 10 ml of water or saline without or with agitation at 90° C. for 30 minutes and the resultant solution is aspirated by an iterative process starting with a 27 gauge needle and subsequently using 25, 22 and 18 gauge needles in case less than 10% of the extraction volume could be loaded in the respective larger gauge (smaller diameter) needle.

The present invention is also directed to a solid oral extended release pharmaceutical dosage form as described herein, wherein recovery of the morphine sulfate is less than about 20%, preferably less than about 10%, more preferably less than about 5%, based on a syringeability test whereby one milled dosage form is subjected to extraction in 2, 5, or 10 ml of water or saline without or with agitation at room temperature for 30 minutes and the resultant solution is aspirated by an iterative process starting with a 27 gauge needle and subsequently using 25, 22 and 18 gauge needles in case less than 10% of the extraction volume could be loaded in the respective larger gauge (smaller diameter) needle.

The present invention is also directed to a solid oral extended release pharmaceutical dosage form as described herein, wherein recovery of the morphine sulfate is less than about 30%, preferably less than about 20%, more preferably less than about 10%, based on a syringeability test whereby one milled dosage form is subjected to extraction in 2, 5, or 10 ml of water or saline without or with agitation at 90° C. for 30 minutes and the resultant solution is aspirated by an iterative process starting with a 27 gauge needle and subsequently using 25, 22 and 18 gauge needles in case less than 10% of the extraction volume could be loaded in the respective larger gauge (smaller diameter) needle.

The present invention is also directed to a solid oral extended release pharmaceutical dosage form as described herein, wherein recovery of the morphine sulfate is less than about 5%, preferably less than about 3%, more preferably about 2% or less, based on a syringeability test whereby one intact dosage form is subjected to dissolution in 10 mL of 40% or 95% ethanol with agitation at room temperature for 1 hour and the resultant solution is aspirated with an 18-gauge needle.

The present invention is also directed to a solid oral extended release pharmaceutical dosage form as described herein, wherein recovery of the morphine sulfate is less than about 15%, preferably less than about 10%, more preferably about 7% or less, based on a syringeability test whereby one intact dosage form is subjected to dissolution in 10 mL of 40% or 95% ethanol with agitation at 60° C. for 1 hour and the resultant solution is aspirated with an 18-gauge needle.

The present invention is also directed to a solid oral extended release pharmaceutical dosage form as described herein, wherein recovery of the morphine sulfate is less than about 3%, preferably less than about 2%, more preferably about 1% or less, based on a syringeability test whereby one milled dosage form is subjected to dissolution in 10 mL of 40% ethanol with agitation at room temperature or 60° C. for 30 minutes and the resultant solution is aspirated with a 27-gauge needle or an 18-gauge needle.

The present invention is also directed to a solid oral extended release pharmaceutical dosage form as described herein, wherein recovery of the morphine sulfate is less than about 35%, preferably less than about 25%, more preferably less than about 10%, even more preferably less than about 7%, based on a syringeability test whereby one milled dosage form is subjected to dissolution in 10 mL of 95% ethanol with agitation at room temperature for 30 minutes and the resultant solution is aspirated with a 27-gauge needle or an 18-gauge needle.

The present invention is also directed to a solid oral extended release pharmaceutical dosage form as described herein, wherein recovery of the morphine sulfate is less than about 7.5%, preferably less than about 5%, more preferably about 3% or less, based on a syringeability test whereby one milled dosage form is subjected to dissolution in 10 mL of 95% ethanol with agitation at 60° C. for 30 minutes and the resultant solution is aspirated with a 27-gauge needle or an 18-gauge needle.

The present invention is also directed to a solid oral extended release pharmaceutical dosage form as described herein, wherein recovery of the morphine sulfate is less than about 10%, preferably about 8% or less, more preferably about 6% or less, based on a syringeability test whereby one intact dosage form is subjected to dissolution in 10 mL water without agitation at room temperature for 1 hour and the resultant solution is aspirated with an 18-gauge needle, wherein the intact dosage form has optionally been subjected to thermal treatment at about 17° C. or about 230° C. or to microwave treatment prior to subjecting it to dissolution.

The present invention is also directed to a solid oral extended release pharmaceutical dosage form as described herein, wherein recovery of the morphine sulfate is less than about 6%, preferably about 4% or less, more preferably about 3% or less, based on a syringeability test whereby one intact dosage form is subjected to dissolution in 2 mL water without agitation at room temperature for 1 hour and the resultant solution is aspirated with an 18-gauge needle, wherein the intact dosage form has optionally been subjected to thermal treatment at about 170° C. or about 230° C. or to microwave treatment prior to subjecting it to dissolution.

The present invention is also directed to a solid oral extended release pharmaceutical dosage form as described herein, wherein recovery of the morphine sulfate is less than about 40%, preferably less than about 30%, more preferably about 20% or less, based on a syringeability test whereby one milled dosage form is subjected to dissolution in 10 mL water with agitation at room temperature for 5 minutes and the resultant solution is aspirated with an 18-gauge needle, wherein the milled dosage form has optionally been subjected to thermal treatment at about 170° C. or about 230° C. or to microwave treatment prior to subjecting it to dissolution.

The present invention is also directed to a solid oral extended release pharmaceutical dosage form as described herein, wherein recovery of the morphine sulfate is less than about 10%, preferably less than about 7%, more preferably less than about 5%, based on a syringeability test whereby one milled dosage form is subjected to dissolution in 2 mL water with agitation at room temperature for 5 minutes and the resultant solution is aspirated with an 18-gauge needle, wherein the milled dosage form has optionally been subjected to thermal treatment at about 170° C. or about 230° C. or to microwave treatment prior to subjecting it to dissolution.

The present invention is also directed to a solid oral extended release pharmaceutical dosage form as described herein, wherein recovery of the morphine sulfate is less than about 15%, preferably about 10% or less, more preferably about 7% or less, based on a syringeability test whereby one sliced dosage form is subjected to dissolution in 10 mL water with agitation at room temperature for 5 minutes and the resultant solution is aspirated with an 18-gauge needle, wherein the sliced dosage form has optionally been subjected to thermal treatment at about 170° C. or about 230° C. or to microwave treatment prior to subjecting it to dissolution.

The present invention is also directed to a solid oral extended release pharmaceutical dosage form as described herein, wherein recovery of the morphine sulfate is less than about 11%, preferably about 7% or less, more preferably about 5% or less, based on a syringeability test whereby one sliced dosage form is subjected to dissolution in 2 mL water with agitation at room temperature for 5 minutes and the resultant solution is aspirated with an 18-gauge needle, wherein the sliced dosage form has optionally been subjected to thermal treatment at about 170° C. or about 230° C. or to microwave treatment prior to subjecting it to dissolution.

In all embodiments described hereinabove relating to recovery of morphine sulfate based on a syringeability test, in case thermal treatment is applied prior to subjecting the dosage form to dissolution, such thermal treatment may be conducted at about 230° C. for a time period of up to about 10 minutes, preferably from about 3 to about 10 minutes, more preferably from about 4 to about 8 minutes. Most preferably, the treatment at about 230° C. is conducted for a time period of from about 4 or about 5 minutes in the case of sliced or milled dosage forms, and for a time period of from about 5 to about 8 minutes in the case of intact dosage forms. At about 170° C. the thermal pre-treatment may be conducted for a time period of up to one hour, preferably from about 20 to about 50 minutes, most preferably for a time period of from about 30 to about 40 minutes for intact, sliced and milled dosage forms. The microwave treatment may generally be conducted (e.g. in 30 second increments) until the dosage form has turned golden-brown.

The present invention is further directed to a method for preventing or reducing recovery of the morphine sulfate from a morphine sulfate containing solid oral extended release pharmaceutical dosage form by means of subjecting the dosage form to dissolution in water or saline and aspirating the resulting solution in a needle, the method comprising, in the preparation of the dosage form, the following steps:
  (a) combining at least morphine sulfate and polyethylene oxide particles to form a composition,
  (b) shaping the composition of step (a) to form an extended release matrix formulation, and
  (c) curing the extended release matrix formulation of step (b) to form the dosage form.

Figure 98:
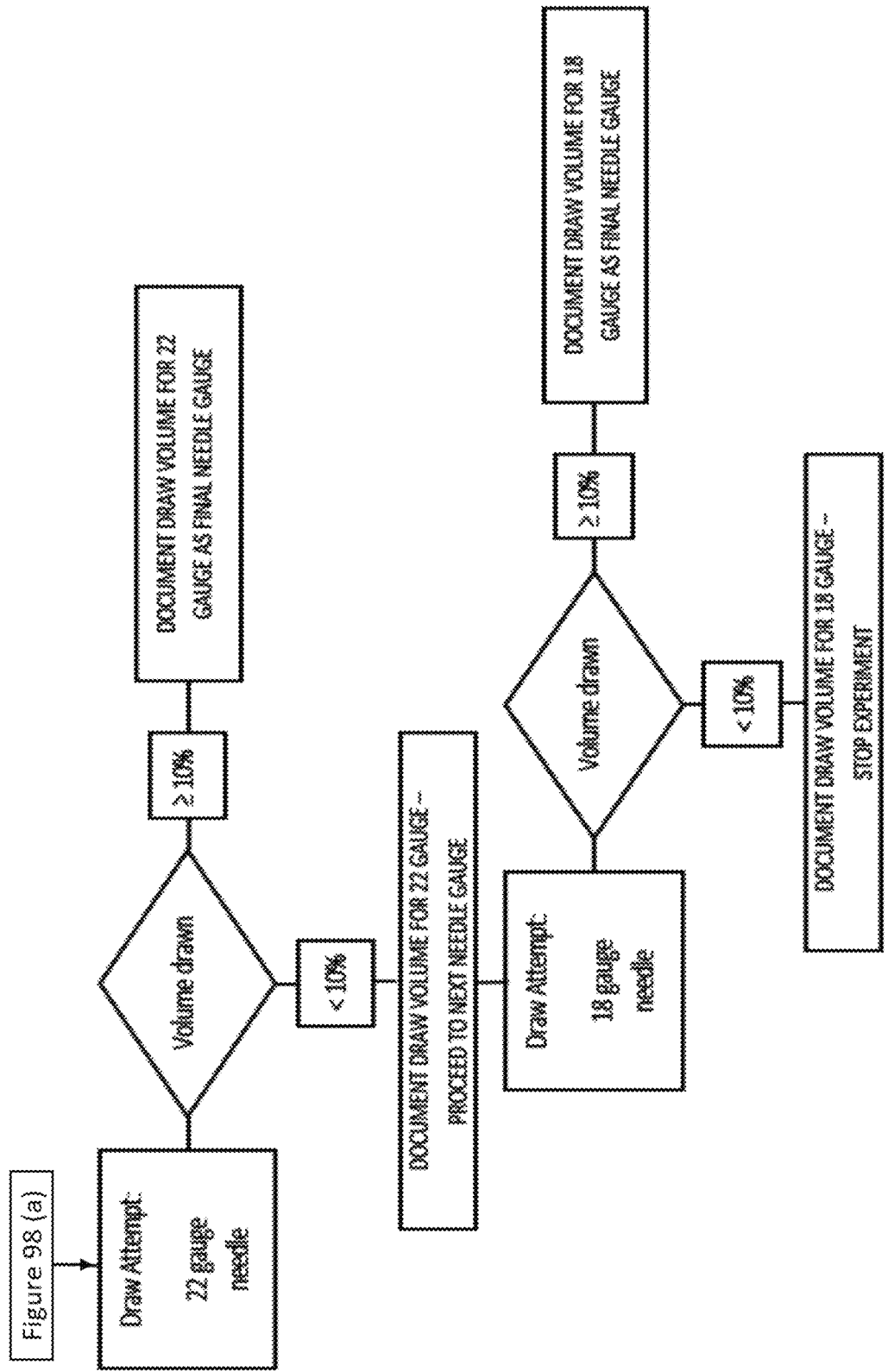

Also, in this method the needle is preferably a 27 or smaller gauge (larger diameter) needle, more preferably a 27, 25, 22 or 18 gauge needle, see e.g. the syringeability decision tree in FIG. 98. The syringeability test is described in detail in Example 13.

Drug Liking

It was observed in the course of an in vivo study (see Example 17 herein below) that in certain embodiments the physicochemical properties of the dosage forms of the present invention provide effective barriers against abuse, in particular that they provide for a low intranasal abuse potential.

It was observed in this study that intranasal administration of a manipulated (ground to a powder by means of mortar and pestle) dosage form according to the present invention (particularly, a tablet containing 60 mg of morphine sulfate; tablet C herein, see Table 1) produced temporary aversive nasal effects and statistically significant reductions in peak positive subjective measures of drug liking (e.g., primary measures such as Drug Liking VAS $E_{max}$, ODL $E_{max}$, and TDA $E_{max}$) compared with intranasal administration of the manipulated reference product MS Contin® also containing 60 mg of morphine sulfate. The rate and extent of morphine exposure ($C_{max}$, $AUC_{last}$, and $AUC_{inf}$) were lowest after intranasal administration of manipulated tablet C. Taken together, the results of the study indicate that the physicochemical properties of the tablets provide barriers that lower the intranasal abuse potential of the dosage forms of the present invention compared to the reference product MS Contin®. Further details on this study are presented in Example 17.

The solid oral extended release pharmaceutical dosage forms of the present invention comprising morphine sulfate and polyethylene oxide thus deter, or at least reduce, the potential for intranasal abuse. This is due to reductions in drug liking as well as to temporary aversive effects when nasally insufflated (such as nasal congestion, need to blow nose, nasal irritation).

In certain embodiments, the present invention is thus directed to a solid oral extended release pharmaceutical dosage form as described herein, the dosage form comprising 60 mg of morphine hemi(sulfate pentahydrate) (having a molecular weight of 758.8 g/mol) or an equimolar amount of another solvate or hydrate of morphine sulfate, wherein intranasal administration of the dosage form as finely crushed powder has a mean "at this moment" drug liking ($E_{max}$) of about 45 to about 75, preferably of about 57 to about 63.

In certain embodiments, the present invention is directed to a solid oral extended release pharmaceutical dosage form as described herein, the dosage form comprising 60 mg of morphine hemi(sulfate pentahydrate) (having a molecular weight of 758.8 g/mol) or an equimolar amount of another solvate or hydrate of morphine sulfate, wherein oral administration of the dosage form intact as compared to intranasal administration of a placebo powder has a median difference (IQR) in "at this moment" drug liking ($E_{max}$) of about 1 to about 20, preferably of about 12 to about 16.

In certain embodiments, the present invention is directed to a solid oral extended release pharmaceutical dosage form as described herein, the dosage form comprising 60 mg of morphine hemi(sulfate pentahydrate) (having a molecular weight of 758.8 g/mol) or an equimolar amount of another solvate or hydrate of morphine sulfate, wherein intranasal administration of the dosage form as finely crushed powder as compared to intranasal administration of a placebo powder has a median difference (IQR) in "at this moment" drug liking ($E_{max}$) of about 0 to about 9, preferably of about 0 to about 3.

In certain embodiments, the present invention is directed to a solid oral extended release pharmaceutical dosage form as described herein, the dosage form comprising 60 mg of morphine hemi(sulfate pentahydrate) (having a molecular weight of 758.8 g/mol) or an equimolar amount of another solvate or hydrate of morphine sulfate, wherein intranasal administration of the dosage form as finely crushed powder as compared to oral administration of the dosage form intact has a median difference (IQR) in "at this moment" drug liking ($E_{max}$) of about −17 to about 0, preferably of about −10 to about −5.

In certain embodiments, the present invention is directed to a solid oral extended release pharmaceutical dosage form as described herein, the dosage form comprising 60 mg of morphine hemi(sulfate pentahydrate) (having a molecular weight of 758.8 g/mol) or an equimolar amount of another solvate or hydrate of morphine sulfate, wherein oral administration of the dosage form intact as compared to intranasal administration of the commercial product MS Contin® containing an equimolar amount of morphine sulfate as finely crushed powder has a median difference (IQR) in "at this moment" drug liking ($E_{max}$) of about −33 to about −8, preferably of about −25 to about −15.

In certain embodiments, the present invention is directed to a solid oral extended release pharmaceutical dosage form as described herein, the dosage form comprising 60 mg of morphine hemi(sulfate pentahydrate) (having a molecular weight of 758.8 g/mol) or an equimolar amount of another solvate or hydrate of morphine sulfate, wherein intranasal administration of the dosage form as finely crushed powder as compared to intranasal administration of the commercial product MS Contin® containing an equimolar amount of morphine sulfate as finely crushed powder has a median difference (IQR) in "at this moment" drug liking ($E_{max}$) of about −49 to about −12, preferably of about −30 to about −20.

In certain embodiments, the present invention is directed to a solid oral extended release pharmaceutical dosage form as described herein, the dosage form comprising 60 mg of morphine hemi(sulfate pentahydrate) (having a molecular weight of 758.8 g/mol) or an equimolar amount of another solvate or hydrate of morphine sulfate, wherein intranasal administration of the dosage form as finely crushed powder has a mean ODL (overall drug liking) ($E_{max}$) of about 0 to about 100, preferably of about 40 to about 60.

In certain embodiments, the present invention is directed to a solid oral extended release pharmaceutical dosage form as described herein, the dosage form comprising 60 mg of morphine hemi(sulfate pentahydrate) (having a molecular weight of 758.8 g/mol) or an equimolar amount of another solvate or hydrate of morphine sulfate, wherein oral administration of the dosage form intact as compared to intranasal administration of a placebo powder has a median difference (IQR) in ODL (overall drug liking) ($E_{max}$) of about 0 to about 26, preferably of about 10 to about 18.

In certain embodiments, the present invention is directed to a solid oral extended release pharmaceutical dosage form as described herein, the dosage form comprising 60 mg of morphine hemi(sulfate pentahydrate) (having a molecular weight of 758.8 g/mol) or an equimolar amount of another solvate or hydrate of morphine sulfate, wherein intranasal administration of the dosage form as finely crushed powder as compared to intranasal administration of a placebo powder has a median difference (IQR) in ODL (overall drug liking) ($E_{max}$) of about −4 to about 10, preferably of about 0 to about 5.

In certain embodiments, the present invention is directed to a solid oral extended release pharmaceutical dosage form as described herein, the dosage form comprising 60 mg of morphine hemi(sulfate pentahydrate) (having a molecular weight of 758.8 g/mol) or an equimolar amount of another solvate or hydrate of morphine sulfate, wherein intranasal administration of the dosage form as finely crushed powder as compared to oral administration of the dosage form intact has a median difference (IQR) in ODL (overall drug liking) ($E_{max}$) of about −26 to about 0, preferably of about −15 to about −8.

In certain embodiments, the present invention is directed to a solid oral extended release pharmaceutical dosage form as described herein, the dosage form comprising 60 mg of morphine hemi(sulfate pentahydrate) (having a molecular weight of 758.8 g/mol) or an equimolar amount of another solvate or hydrate of morphine sulfate, wherein oral administration of the dosage form intact as compared to intranasal administration of the commercial product MS Contin® containing an equimolar amount of morphine sulfate as finely crushed powder has a median difference (IQR) in ODL (overall drug liking) ($E_{max}$) of about −32 to about −1, preferably of about −18 to about −10.

In certain embodiments, the present invention is directed to a solid oral extended release pharmaceutical dosage form as described herein, the dosage form comprising 60 mg of morphine hemi(sulfate pentahydrate) (having a molecular weight of 758.8 g/mol) or an equimolar amount of another solvate or hydrate of morphine sulfate, wherein intranasal administration of the dosage form as finely crushed powder as compared to intranasal administration of the commercial product MS Contin® containing an equimolar amount of morphine sulfate as finely crushed powder has a median difference (IQR) in ODL (overall drug liking) ($E_{max}$) of about −50 to about −7, preferably of about −35 to about −20.

In certain embodiments, the present invention is directed to a solid oral extended release pharmaceutical dosage form as described herein, the dosage form comprising 60 mg of morphine hemi(sulfate pentahydrate) (having a molecular weight of 758.8 g/mol) or an equimolar amount of another solvate or hydrate of morphine sulfate, wherein intranasal administration of the dosage form as finely crushed powder has a mean TDA (take drug again) effect ($E_{max}$) of about 10 to about 75, preferably of about 35 to about 55.

In certain embodiments, the present invention is directed to a solid oral extended release pharmaceutical dosage form as described herein, the dosage form comprising 60 mg of morphine hemi(sulfate pentahydrate) (having a molecular weight of 758.8 g/mol) or an equimolar amount of another solvate or hydrate of morphine sulfate, wherein oral administration of the dosage form intact as compared to intranasal administration of a placebo powder has a median difference (IQR) in TDA (take drug again) effect ($E_{max}$) of about 1 to about 25, preferably of about 12 to about 16.

In certain embodiments, the present invention is directed to a solid oral extended release pharmaceutical dosage form as described herein, the dosage form comprising 60 mg of morphine hemi(sulfate pentahydrate) (having a molecular weight of 758.8 g/mol) or an equimolar amount of another solvate or hydrate of morphine sulfate, wherein intranasal administration of the dosage form as finely crushed powder as compared to intranasal administration of a placebo powder has a median difference (IQR) in TDA (take drug again) effect ($E_{max}$) of about −40 to about 11, preferably of about −5 to about 5.

In certain embodiments, the present invention is directed to a solid oral extended release pharmaceutical dosage form as described herein, the dosage form comprising 60 mg of morphine hemi(sulfate pentahydrate) (having a molecular weight of 758.8 g/mol) or an equimolar amount of another solvate or hydrate of morphine sulfate, wherein intranasal administration of the dosage form as finely crushed powder as compared to oral administration of the dosage form intact has a median difference (IQR) in TDA (take drug again) effect ($E_{max}$) of about −47 to about 0, preferably of about −25 to about −15.

In certain embodiments, the present invention is directed to a solid oral extended release pharmaceutical dosage form as described herein, the dosage form comprising 60 mg of morphine hemi(sulfate pentahydrate) (having a molecular weight of 758.8 g/mol) or an equimolar amount of another solvate or hydrate of morphine sulfate, wherein oral administration of the dosage form intact as compared to intranasal administration of the commercial product MS Contin® containing an equimolar amount of morphine sulfate as finely crushed powder has a median difference (IQR) in TDA (take drug again) effect ($E_{max}$) of about −33 to about 0, preferably of about −27 to about −20.

In certain embodiments, the present invention is directed to a solid oral extended release pharmaceutical dosage form as described herein, the dosage form comprising 60 mg of morphine hemi(sulfate pentahydrate) (having a molecular weight of 758.8 g/mol) or an equimolar amount of another solvate or hydrate of morphine sulfate, wherein intranasal administration of the dosage form as finely crushed powder as compared to intranasal administration of the commercial product MS Contin® containing an equimolar amount of morphine sulfate as finely crushed powder has a median difference (IQR) in TDA (take drug again) effect ($E_{max}$) of about −50 to about −22, preferably of about −40 to about −30.

Method of Treatment

The present invention is also directed to a method of treating pain in a subject in need thereof, the method comprising administering to the subject the solid oral extended release pharmaceutical dosage form according to the present invention as defined herein. Likewise, the present invention is also directed to the use of a solid oral extended release pharmaceutical dosage form according to the present invention as defined herein for (the manufacture of a medicament for) the treatment of pain in a subject.

Preferably, the subject is a patient, more preferably a mammal, most preferably a human patient.

The solid oral extended release pharmaceutical dosage form of the present invention can be used to treat or prevent acute or chronic pain. For example, the dosage forms can be used to treat or prevent pain, including, but not limited to, cancer pain, central pain, labor pain, myocardial infarction pain, pancreatic pain, colic pain, post-operative pain, headache pain, muscle pain, and pain associated with intensive care. The solid oral extended release pharmaceutical dosage form of the present invention can also be used for treating or preventing pain associated with inflammation or with an inflammatory disease in a subject. The inflammation or inflammatory disease can arise where there is an inflammation of the body tissue, and which can be a local inflammatory response and/or a systemic inflammation.

In certain embodiments, the method comprises administering the solid oral extended release dosage form to the subject twice a day or every 12 hours. In this embodiment, the analgesic effect preferably lasts for at least about 12 hours.

The solid oral extended release dosage form of the present invention may also be administered to the subject three times a day or every 8 hours in cases where the analgesic effect preferably lasts for at least about 8 hours.

In certain embodiments, particularly in the treatment of chronic pain or e.g. cancer pain, the dosage forms of the present invention may be administered in combination with an immediate release dosage form comprising the same or another analgesic (such as another opioid) as a rescue medication for treating breakthrough pain.

FURTHER EMBODIMENTS

In view of the above, certain embodiments of the present invention relate to the following items:

1. A solid oral extended release pharmaceutical dosage form comprising a cured extended release matrix formulation, the extended release matrix formulation comprising:
   a therapeutically effective amount of morphine sulfate, and
   polyethylene oxide.

2. A solid oral extended release pharmaceutical dosage form comprising a cured extended release matrix formulation, wherein the cured extended release matrix formulation comprises:
   a therapeutically effective amount of morphine sulfate, and
   polyethylene oxide
   and is obtainable by at least the following steps:
   (a) combining at least morphine sulfate and polyethylene oxide particles to form a composition,
   (b) shaping the composition of step (a) to form the extended release matrix formulation, and
   (c) curing the extended release matrix formulation of step (b).

3. The solid oral extended release pharmaceutical dosage form of embodiment 2, wherein the polyethylene oxide particles used in step (a) are characterized in that about 50% or more of the polyethylene oxide particles pass through a 25 mesh (0.707 mm; 707 microns) sieve.

4. The solid oral extended release pharmaceutical dosage form of embodiment 3, wherein about 70% or more of the polyethylene oxide particles pass through a 25 mesh (0.707 mm; 707 microns) sieve.

5. The solid oral extended release pharmaceutical dosage form of embodiment 4, wherein about 90% or more of the polyethylene oxide particles pass through a 25 mesh (0.707 mm; 707 microns) sieve.

6. The solid oral extended release pharmaceutical dosage form of any of embodiments 2 to 5, wherein the polyethylene oxide particles used in step (a) are characterized in that about 50% or more of the polyethylene oxide particles pass through a 35 mesh (0.500 mm; 500 microns) sieve.

7. The solid oral extended release pharmaceutical dosage form of embodiment 6, wherein about 70% or more of the polyethylene oxide particles pass through a 35 mesh (0.500 mm; 500 microns) sieve.

8. The solid oral extended release pharmaceutical dosage form of embodiment 7, wherein about 90% or more of the polyethylene oxide particles pass through a 35 mesh (0.500 mm; 500 microns) sieve.

9. The solid oral extended release pharmaceutical dosage form of any of embodiments 2 to 8, wherein the polyethylene oxide particles used in step (a) are characterized in that about 50% or more of the polyethylene oxide particles pass through a 60 mesh (0.250 mm; 250 microns) sieve.

10. The solid oral extended release pharmaceutical dosage form of embodiment 9, wherein about 70% or more of the polyethylene oxide particles pass through a 60 mesh (0.250 mm; 250 microns) sieve.

11. The solid oral extended release pharmaceutical dosage form of embodiment 10, wherein about 90% or more of the polyethylene oxide particles pass through a 60 mesh (0.250 mm; 250 microns) sieve.

12. The solid oral extended release pharmaceutical dosage form of embodiment 11, wherein about 96% or more of the polyethylene oxide particles pass through a 60 mesh (0.250 mm; 250 microns) sieve.

13. The solid oral extended release pharmaceutical dosage form of any of the preceding embodiments, wherein the polyethylene oxide present in the dosage form has an approximate molecular weight of from about 600,000 to about 3,000,000.

14. The solid oral extended release pharmaceutical dosage form of embodiment 13, wherein the polyethylene oxide present in the dosage form has an approximate molecular weight of from about 900,000 to about 2,000,000.

15. The solid oral extended release pharmaceutical dosage form of embodiment 14, wherein the polyethylene oxide present in the dosage form has an approximate molecular weight of from about 1,000,000 to about 2,000,000.

16. The solid oral extended release pharmaceutical dosage form of any of the preceding embodiments, wherein the polyethylene oxide present in the dosage form has an approximate molecular weight of about 1,000,000 or about 2,000,000.

17. The solid oral extended release pharmaceutical dosage form of any of embodiments 2 to 16, wherein the polyethylene oxide used as polyethylene oxide particles in step (a) has an approximate molecular weight of from about 600,000 to about 3,000,000.

18. The solid oral extended release pharmaceutical dosage form of embodiment 17, wherein the polyethylene oxide used as polyethylene oxide particles in step (a) has an approximate molecular weight of from about 900,000 to about 2,000,000.

19. The solid oral extended release pharmaceutical dosage form of embodiment 18, wherein the polyethylene oxide used as polyethylene oxide particles in step (a) has an approximate molecular weight of from about 1,000,000 to about 2,000,000, or of about 1,000,000 or of about 2,000,000.

20. The solid oral extended release pharmaceutical dosage form of any of embodiments 2 to 19, wherein the polyethylene oxide particles used in step (a) originate from a single grade of polyethylene oxide or from a combination of two or more grades of polyethylene oxide.

21. The solid oral extended release pharmaceutical dosage form of embodiment 20, wherein one or more of the following polyethylene oxide grades are used as the polyethylene oxide particles in step (a):
polyethylene oxide having an approximate molecular weight of about 900,000 and/or showing a viscosity in the range of 8,800 to 17,600 mPa s (cP) when the viscosity of a 5% (by weight) aqueous solution of said polyethylene oxide is determined using a Brookfield viscometer Model RVF, spindle No. 2, at 2 rpm, at 25° C.;

polyethylene oxide having an approximate molecular weight of about 1,000,000 and/or showing a viscosity in the range of 400 to 800 mPa s (cP) when the viscosity of a 2% (by weight) aqueous solution of said polyethylene oxide is determined using a Brookfield viscometer Model RVF, spindle No. 1, at 10 rpm, at 25° C.; and polyethylene oxide having an approximate molecular weight of about 2,000,000 and/or showing a viscosity in the range of 2,000 to 4,000 mPa s (cP) when the viscosity of a 2% (by weight) aqueous solution of said polyethylene oxide is determined using a Brookfield viscometer Model RVF, spindle No. 3, at 10 rpm, at 25° C.

22. A solid oral extended release pharmaceutical dosage form comprising a cured extended release matrix formulation, the extended release matrix formulation comprising:
 a therapeutically effective amount of morphine sulfate and polyethylene oxide,
wherein the cured extended release matrix formulation is obtainable by at least the following steps:
 (a) combining at least morphine sulfate and polyethylene oxide particles to form a composition,
 (b) shaping the composition of step (a) to form the extended release matrix formulation, and
 (c) curing the extended release matrix formulation of step (b);
wherein the polyethylene oxide particles used in step (a) are characterized in that about 90% or more of the polyethylene oxide particles pass through a 60 mesh (0.250 mm; 250 microns) sieve; and wherein the polyethylene oxide used as the polyethylene oxide particles in step (a) has an approximate molecular weight of from about 900,000 to about 2,000,000.

23. The solid oral extended release pharmaceutical dosage form of any of embodiments 2 to 22, wherein step (b) comprises dry compression of the composition.

24. The solid oral extended release pharmaceutical dosage form of any of the preceding embodiments, wherein curing of the extended release matrix formulation is performed at a temperature of at least the softening point of the polyethylene oxide.

25. The solid oral extended release pharmaceutical dosage form of any of the preceding embodiments, wherein curing of the extended release matrix formulation is performed at a temperature of from about 65° C. to about 85° C.

26. The solid oral extended release pharmaceutical dosage form of embodiment 25, wherein curing of the extended release matrix formulation is performed at a temperature of from about 72° C. to about 78° C.

27. The solid oral extended release pharmaceutical dosage form of embodiment 26, wherein curing of the extended release matrix formulation is performed at a temperature of about 72° C., about 75° C. or about 78° C.

28. The solid oral extended release pharmaceutical dosage form of any of the preceding embodiments, wherein curing of the extended release matrix formulation is performed for a time period of at least 20 min.

29. The solid oral extended release pharmaceutical dosage form of embodiment 28, wherein curing of the extended release matrix formulation is performed for a time period of at least 30 min.

30. The solid oral extended release pharmaceutical dosage form of embodiment 28, wherein curing of the extended release matrix formulation is performed for a time period of from about 20 to about 75 min.

31. The solid oral extended release pharmaceutical dosage form of embodiment 29, wherein curing of the extended release matrix formulation is performed for a time period of from about 30 to about 60 min.

32. The solid oral extended release pharmaceutical dosage form of embodiment 31, wherein curing of the extended release matrix formulation is performed for a time period of about 30 min or about 45 min.

33. The solid oral extended release pharmaceutical dosage form of any of the preceding embodiments, in which the extended release matrix formulation is coated with a film coating.

34. The solid oral extended release pharmaceutical dosage form of any of the preceding embodiments, wherein the polyethylene oxide is included in the extended release matrix formulation in an amount of about 55 to about 95% by weight thereof.

35. The solid oral extended release pharmaceutical dosage form of embodiment 34, wherein the polyethylene oxide is included in the extended release matrix formulation in an amount of about 60 to about 90% by weight thereof.

36. The solid oral extended release pharmaceutical dosage form of embodiment 35, wherein the polyethylene oxide is included in the extended release matrix formulation in an amount of about 78 to about 90% by weight thereof.

37. The solid oral extended release pharmaceutical dosage form of embodiment 35, wherein the polyethylene oxide is included in the extended release matrix formulation in an amount of about 60 to about 70% by weight thereof.

38. The solid oral extended release pharmaceutical dosage form of any of the preceding embodiments, wherein the morphine sulfate present in the dosage form is included in the extended release matrix formulation in the form of morphine hemi(sulfate pentahydrate) (having a molecular weight of 758.8 g/mol) in an amount of about 5 to about 40% by weight of the extended release matrix formulation or in an equimolar amount of another solvate or hydrate of morphine sulfate.

39. The solid oral extended release pharmaceutical dosage form of embodiment 38, wherein the morphine sulfate present in the dosage form is included in the extended release matrix formulation in the form of morphine hemi (sulfate pentahydrate) (having a molecular weight of 758.8 g/mol) in an amount of about 8 to about 35% by weight of the extended release matrix formulation or in an equimolar amount of another solvate or hydrate of morphine sulfate.

40. The solid oral extended release pharmaceutical dosage form of embodiment 39, wherein the morphine sulfate present in the dosage form is included in the extended release matrix formulation in the form of morphine hemi (sulfate pentahydrate) (having a molecular weight of 758.8 g/mol) in an amount of about 10 to about 20% by weight of the extended release matrix formulation or in an equimolar amount of another solvate or hydrate of morphine sulfate.

41. The solid oral extended release pharmaceutical dosage form of embodiment 39, wherein the morphine sulfate present in the dosage form is included in the extended release matrix formulation in the form of morphine hemi (sulfate pentahydrate) (having a molecular weight of 758.8 g/mol) in an amount of about 25 to about 35% by weight of the extended release matrix formulation or in an equimolar amount of another solvate or hydrate of morphine sulfate.

42. The solid oral extended release pharmaceutical dosage form of any of the preceding embodiments, wherein the morphine sulfate and the polyethylene oxide are included in the extended release matrix formulation in a weight ratio of from about 1:100 to about 1:1, calculated on the basis of the amount of morphine hemi(sulfate pentahydrate) (having a molecular weight of 758.8 g/mol) and the amount of polyethylene oxide included in the extended release matrix formulation.

43. The solid oral extended release pharmaceutical dosage form of embodiment 42, wherein the morphine sulfate and the polyethylene oxide are included in the extended release matrix formulation in a weight ratio of from about 1:20 to about 1:1.25.

44. The solid oral extended release pharmaceutical dosage form of embodiment 43, wherein the morphine sulfate and the polyethylene oxide are included in the extended release matrix formulation in a weight ratio of from about 1:10 to about 1:1.7.

45. The solid oral extended release pharmaceutical dosage form of any of the preceding embodiments, in which the morphine sulfate is included in the extended release matrix formulation in the form of morphine hemi(sulfate pentahydrate) (having a molecular weight of 758.8 g/mol) in an amount of from about 10 to about 250 mg or in an equimolar amount of another solvate or hydrate of morphine sulfate.

46. The solid oral extended release pharmaceutical dosage form of embodiment 45, in which the morphine sulfate is included in the extended release matrix formulation in the form of morphine hemi(sulfate pentahydrate) (having a molecular weight of 758.8 g/mol) in an amount of from about 15 to about 200 mg or in an equimolar amount of another solvate or hydrate of morphine sulfate.

47. The solid oral extended release pharmaceutical dosage form of embodiment 46, in which the morphine sulfate is included in the extended release matrix formulation in the form of morphine hemi(sulfate pentahydrate) (having a molecular weight of 758.8 g/mol) in an amount of about 15, about 30, about 60, about 100 or about 200 mg or in an equimolar amount of another solvate or hydrate of morphine sulfate.

48. The solid oral extended release pharmaceutical dosage form of any of embodiments 2 to 47, wherein the dosage form is further obtainable by:
   (d) coating the cured extended release matrix formulation of step (c) with one or more coating(s).

49. The solid oral extended release pharmaceutical dosage form of embodiment 1 or embodiment 48, wherein the dosage form contains at least one coating(s), which is a film coat.

50. The solid oral extended release pharmaceutical dosage form of embodiment 48 or 49, wherein the one or more coating(s) comprise(s) about 5% by weight or less of the entire solid oral extended release pharmaceutical dosage form.

51. The solid oral extended release pharmaceutical dosage form of embodiment 49 or 50, wherein the film coat comprises hydroxypropylmethylcellulose, polyethylene glycol, polyvinyl alcohol, talc, pigments, or any mixture of two or more thereof.

52. The solid oral extended release pharmaceutical dosage form of any of the preceding embodiments in the form of a tablet.

53. The solid oral extended release pharmaceutical dosage form of embodiment 52 in the form of a tablet, wherein the length of the tablet is greater than the width and the thickness of the tablet, and the thickness of the tablet is less than or equal to the width of the tablet.

54. The solid oral extended release pharmaceutical dosage form of embodiment 53, wherein the length of the tablet is at least about 1.5 times the width and/or the thickness of the tablet, and the width is at least twice the thickness of the tablet.

55. The solid oral extended release pharmaceutical dosage form of embodiment 54, wherein the length of the tablet is at least about twice the width and about four times the thickness of the tablet.

56. The solid oral extended release pharmaceutical dosage form of embodiment 55, wherein the width of the tablet is at least about three times the thickness of the tablet.

57. The solid oral extended release pharmaceutical dosage form of any of embodiments 53 to 56, wherein the tablet is an oval or oblong tablet.

58. The solid oral extended release pharmaceutical dosage form of any of embodiments 53 to 57, wherein the surface of one or both of the faces of the tablet is convex or has convex portions.

59. The solid oral extended release pharmaceutical dosage form of any of embodiments 53 to 57, wherein the surface of one or both of the faces of the tablet has convex and concave portions.

60. The solid oral extended release pharmaceutical dosage form of embodiment 59, wherein the concave portions extend along the central axis of the tablet defined by half the width of the tablet.

61. The solid oral extended release pharmaceutical dosage form of embodiment 59 or 60, wherein the minimal thickness of the tablet in the concave portions is not less than 0.25 times the maximum thickness of the tablet.

62. The solid oral extended release pharmaceutical dosage form of any of the preceding embodiments, the dosage form having a breaking strength of at least about 200 N.

63. The solid oral extended release pharmaceutical dosage form of embodiment 62, the dosage form having a breaking strength of at least about 250 N.

64. The solid oral extended release pharmaceutical dosage form of embodiment 63, the dosage form having a breaking strength of at least about 300 N.

65. The solid oral extended release pharmaceutical dosage form of embodiment 64, the dosage form having a breaking strength of at least about 350 N.

66. The solid oral extended release pharmaceutical dosage form of embodiment 65, the dosage form having a breaking strength of at least about 400 N.

67. The solid oral extended release pharmaceutical dosage form of any of the preceding embodiments, the dosage form having a cracking force of at least about 150 N.

68. The solid oral extended release pharmaceutical dosage form of embodiment 67, the dosage form having a cracking force of at least about 170 N.

69. The solid oral extended release pharmaceutical dosage form of embodiment 68, the dosage form having a cracking force of at least about 200 N.

70. The solid oral extended release pharmaceutical dosage form of embodiment 69, the dosage form having a cracking force of at least about 230 N.

71. The solid oral extended release pharmaceutical dosage form of any of the preceding embodiments, the dosage form having a penetration depth to crack of at least about 1.25 mm.

72. The solid oral extended release pharmaceutical dosage form of embodiment 71, the dosage form having a penetration depth to crack of at least about 1.5 mm.

73. The solid oral extended release pharmaceutical dosage form of embodiment 72, the dosage form having a penetration depth to crack of at least about 1.75 mm.

74. The solid oral extended release pharmaceutical dosage form of embodiment 73, the dosage form having a penetration depth to crack of at least about 2 mm.

75. The solid oral extended release pharmaceutical dosage form of any of the preceding embodiments, the dosage form having a crush resistance of at least about 400 N.

76. The solid oral extended release pharmaceutical dosage form of embodiment 75, the dosage form having a crush resistance of at least about 500 N.

77. The solid oral extended release pharmaceutical dosage form of any of the preceding embodiments wherein the extended release matrix formulation contains one or more pharmaceutically acceptable excipients.

78. The solid oral extended release pharmaceutical dosage form of embodiment 77, wherein the extended release matrix formulation contains a lubricant.

79. The solid oral extended release pharmaceutical dosage form of embodiment 78, wherein the lubricant is included in an amount of about 0.1 to about 5% by weight of the extended release matrix formulation.

80. The solid oral extended release pharmaceutical dosage form of embodiment 79, wherein the lubricant is included in an amount of about 0.75 to about 2% by weight of the extended release matrix formulation.

81. The solid oral extended release pharmaceutical dosage form of any of embodiments 78 to 80, wherein the lubricant is or comprises magnesium stearate.

82. The solid oral extended release pharmaceutical dosage form of any of embodiments 77 to 81, wherein the extended release matrix formulation contains a glidant.

83. The solid oral extended release pharmaceutical dosage form of embodiment 82, wherein the glidant is included in an amount of about 0.1 to about 2.5% by weight of the extended release matrix formulation.

84. The solid oral extended release pharmaceutical dosage form of embodiment 83, wherein the glidant is included in about 0.4 to about 0.6% by weight of the extended release matrix formulation.

85. The solid oral extended release pharmaceutical dosage form of any of embodiments 82 to 84, wherein the glidant is or comprises colloidal silicon dioxide.

86. The solid oral extended release pharmaceutical dosage form of any of the preceding embodiments, the dosage form after administration providing a dose adjusted $C_{max}$ of morphine of from about 3 ng/mL to about 9 ng/mL per 15 mg of morphine hemi(sulfate pentahydrate) (having a molecular weight of 758.8 g/mol) or an equimolar amount of another solvate or hydrate of morphine sulfate included in the dosage form.

87. The solid oral extended release pharmaceutical dosage form of embodiment 86, the dosage form after administration providing a dose adjusted $C_{max}$ of morphine of from about 5 ng/mL to about 7 ng/mL per 15 mg of morphine hemi(sulfate pentahydrate) (having a molecular weight of 758.8 g/mol) or an equimolar amount of another solvate or hydrate of morphine sulfate included in the dosage form.

88. The solid oral extended release pharmaceutical dosage form of any of the preceding embodiments, the dosage form after administration providing a dose adjusted $AUC_t$ of morphine of from about 30 ng*hr/mL to about 100 ng*hr/mL per 15 mg of morphine hemi(sulfate pentahydrate) (having a molecular weight of 758.8 g/mol) or an equimolar amount of another solvate or hydrate of morphine sulfate included in the dosage form.

89. The solid oral extended release pharmaceutical dosage form of embodiment 88, the dosage form after administration providing a dose adjusted $AUC_t$ of morphine after administration of from about 40 ng*hr/mL to about 80 ng*hr/mL per 15 mg of morphine hemi(sulfate pentahydrate) (having a molecular weight of 758.8 g/mol) or an equimolar amount of another solvate or hydrate of morphine sulfate included in the dosage form.

90. The solid oral extended release pharmaceutical dosage form of any of the preceding embodiments, the dosage form after administration providing a dose adjusted $AUC_{inf}$ of morphine after administration of from about 30 ng*hr/mL to about 100 ng*hr/mL per 15 mg of morphine hemi(sulfate pentahydrate) (having a molecular weight of 758.8 g/mol) or an equimolar amount of another solvate or hydrate of morphine sulfate included in the dosage form.

91. The solid oral extended release pharmaceutical dosage form of embodiment 90 the dosage form after administration providing a dose adjusted $AUC_{inf}$ of morphine of from about 40 ng*hr/mL to about 80 ng*hr/mL per 15 mg of morphine hemi(sulfate pentahydrate) (having a molecular weight of 758.8 g/mol) or an equimolar amount of another solvate or hydrate of morphine sulfate included in the dosage form.

92. The solid oral extended release pharmaceutical dosage form of any of the preceding embodiments, wherein the morphine sulfate is included in the extended release matrix formulation in the form of morphine hemi(sulfate pentahydrate) (having a molecular weight of 758.8 g/mol) in an amount of about 15 mg or an equimolar amount of another solvate or hydrate of morphine sulfate, the dosage form after administration providing a $C_{max}$ of morphine of from about 3 ng/mL to about 9 ng/mL.

93. The solid oral extended release pharmaceutical dosage form of embodiment 92, the dosage form after administration providing a $C_{max}$ of morphine after administration of from about 4 ng/mL to about 7 ng/mL.

94. The solid oral extended release pharmaceutical dosage form of embodiment 92 or 93, the dosage form after administration providing an $AUC_t$ of morphine of from about 30 ng*hr/mL to about 70 ng*hr/mL.

95. The solid oral extended release pharmaceutical dosage form of embodiment 94, the dosage form after administration providing an $AUC_t$ of morphine of from about 40 ng*hr/mL to about 60 ng*hr/mL.

96. The solid oral extended release pharmaceutical dosage form of any of embodiments 92 to 95, the dosage form after administration providing an $AUC_{inf}$ of morphine of from about 35 ng*hr/mL to about 70 ng*hr/mL.

97. The solid oral extended release pharmaceutical dosage form of embodiment 96, the dosage form after administration providing an $AUC_{inf}$ of morphine of from about 40 ng*hr/mL to about 65 ng*hr/mL.

98. The solid oral extended release pharmaceutical dosage form of any of embodiments 92 to 97, the dosage form providing a T. of from about 1 to about 4.5 hours or from about 2 to about 3.5 hours after administration in the fasted state.

99. The solid oral extended release pharmaceutical dosage form of embodiment 98, the dosage form providing a T, of from about 2 to about 6 hours or from about 3 to about 5 hours after administration in the fed state.

100. The solid oral extended release pharmaceutical dosage form of any of embodiments 1 to 91, wherein the morphine sulfate is included in the extended release matrix formulation in the form of morphine hemi(sulfate pentahydrate) (having a molecular weight of 758.8 g/mol) in an amount of about 30 mg or an equimolar amount of another solvate or hydrate of morphine sulfate, the dosage form after administration providing a $C_{max}$ of morphine of from about 8 ng/mL to about 18 ng/mL.

101. The solid oral extended release pharmaceutical dosage form of embodiment 100, the dosage form after administration providing a $C_{max}$ of morphine of from about 9 ng/mL to about 17 ng/mL.

102. The solid oral extended release pharmaceutical dosage form of embodiment 100 or 101, the dosage form after administration providing an $AUC_t$ of morphine of from about 90 ng*hr/mL to about 180 ng*hr/mL.

103. The solid oral extended release pharmaceutical dosage form of embodiment 102, the dosage form after administration providing an $AUC_t$ of morphine of from about from about 105 ng*hr/mL to about 165 ng*hr/mL.

104. The solid oral extended release pharmaceutical dosage form of any of embodiments 100 to 103, the dosage form after administration providing an $AUC_{inf}$ of morphine of from about 110 ng*hr/mL to about 230 ng*hr/mL.

105. The solid oral extended release pharmaceutical dosage form of embodiment 104, the dosage form after administration providing an $AUC_{inf}$ of morphine of from about 120 ng*hr/mL to about 210 ng*hr/mL.

106. The solid oral extended release pharmaceutical dosage form of any of embodiments 100 to 105, the dosage form providing a T. of from about 1 to about 6 hours after administration in the fasted state.

107. The solid oral extended release pharmaceutical dosage form of embodiment 106, the dosage form providing a T. of from about 2 to about 4 hours after administration in the fasted 30 state.

108. The solid oral extended release pharmaceutical dosage form of any of embodiments 1 to 91, wherein the morphine sulfate is included in the extended release matrix formulation in the form of morphine hemi(sulfate pentahydrate) (having a molecular weight of 758.8 g/mol) in an amount of about 60 mg or an equimolar amount of another solvate or hydrate of morphine sulfate, the dosage form after administration providing a $C_{max}$ of morphine of from about 14 ng/mL to about 36 ng/mL.

109. The solid oral extended release pharmaceutical dosage form of embodiment 108, the dosage form after administration providing a $C_{max}$ of morphine of from about 17 ng/mL to about 30 ng/mL.

110. The solid oral extended release pharmaceutical dosage form of embodiment 108 or 109, the dosage form after administration providing an $AUC_t$ of morphine of from about 175 ng*hr/mL to about 325 ng*hr/mL.

111. The solid oral extended release pharmaceutical dosage form of embodiment 110, the dosage form after administration providing an $AUC_t$ of morphine of from about 195 ng*hr/mL to about 305 ng*hr/mL.

112. The solid oral extended release pharmaceutical dosage form of embodiment 108, the dosage form after administration providing an $AUC_{inf}$ of morphine of from about 190 ng*hr/mL to about 340 ng*hr/mL.

113. The solid oral extended release pharmaceutical dosage form of embodiment 112, the dosage form after administration providing an $AUC_{inf}$ of morphine of from about 210 ng*hr/mL to about 320 ng*hr/mL.

114. The solid oral extended release pharmaceutical dosage form of any of embodiments 108 to 113, the dosage form providing a T. of from about 1 to about 6 hours after administration in the fasted state.

115. The solid oral extended release pharmaceutical dosage form of embodiment 114, the dosage form providing a T. of from about 2 to about 5 hours in the fasted state.

116. The solid oral extended release pharmaceutical dosage form of any of embodiments 1 to 91, wherein the morphine sulfate is included in the extended release matrix formulation in the form of morphine hemi(sulfate pentahydrate) (having a molecular weight of 758.8 g/mol) in an amount of about 100 mg or an equimolar amount of another solvate or hydrate of morphine sulfate, the dosage form after administration providing a $C_{max}$ of morphine of from about 26 ng/mL to about 60 ng/mL.

117. The solid oral extended release pharmaceutical dosage form of embodiment 116, the dosage form after administration providing a $C_{max}$ of morphine of from about 30 ng/mL to about 50 ng/mL.

118. The solid oral extended release pharmaceutical dosage form of embodiment 116 or 117, the dosage form after administration providing an $AUC_t$ of morphine of from about 360 ng*hr/mL to about 640 ng*hr/mL.

119. The solid oral extended release pharmaceutical dosage form of embodiment 118, the dosage form after administration providing an $AUC_t$ of morphine of from about 390 ng*hr/mL to about 610 ng*hr/mL.

120. The solid oral extended release pharmaceutical dosage form of any of embodiments 116 to 119, the dosage form after administration providing an $AUC_{inf}$ of morphine of from about 370 ng*hr/mL to about 650 ng*hr/mL.

121. The solid oral extended release pharmaceutical dosage form of embodiment 120, the dosage form after administration providing an $AUC_{inf}$ of morphine of from about 395 ng*hr/mL to about 620 ng*hr/mL.

122. The solid oral extended release pharmaceutical dosage form of any of embodiments 116 to 121, the dosage form providing a T. of from about 0.5 to about 5 hours of from about 2 to about 4.5 hours after administration in the fasted state.

123. The solid oral extended release pharmaceutical dosage form of any of embodiments 116 to 121, the dosage form providing a T. of from about 2 to about 8 hours or from about 4 to about 7 hours after administration in the fed state.

124. The solid oral extended release pharmaceutical dosage form of any of embodiments 1 to 91, wherein the morphine sulfate is included in the extended release matrix formulation in the form of morphine hemi(sulfate pentahydrate) (having a molecular weight of 758.8 g/mol) in an amount of about 200 mg or an equimolar amount of another solvate or hydrate of morphine sulfate, the dosage form after administration providing a $C_{max}$ of morphine of from about 52 ng/mL to about 120 ng/mL.

125. The solid oral extended release pharmaceutical dosage form of embodiment 124, the dosage form after administration providing a $C_{max}$ of morphine of from about 60 ng/mL to about 105 ng/mL.

126. The solid oral extended release pharmaceutical dosage form of embodiment 124 or 125, the dosage form after administration providing an $AUC_t$ of morphine of from about 700 ng*hr/mL to about 1350 ng*hr/mL.

127. The solid oral extended release pharmaceutical dosage form of embodiment 126, the dosage form after administration providing an $AUC_t$ of morphine of from about 800 ng*hr/mL to about 1250 ng*hr/mL.

128. The solid oral extended release pharmaceutical dosage form of any of embodiments 124 to 127, the dosage form after administration providing an $AUC_1$ of morphine of from about 750 ng*hr/mL to about 1400 ng*hr/mL.

129. The solid oral extended release pharmaceutical dosage form of embodiment 128, the dosage form after administration providing an $AUC_{inf}$ of morphine of from about 850 ng*hr/mL to about 1300 ng*hr/mL.

130. The solid oral extended release pharmaceutical dosage form of any of embodiments 124 to 129, the dosage form providing a $T_c$ of from about 1 to about 6 hours or from about 2 to about 5 hours after administration in the fasted state.

131. The solid oral extended release pharmaceutical dosage form of any of embodiments 124 to 129, the dosage form providing a $T_c$ of from about 5 to about 10 hours or from about 6 to about 8 hours after administration in the fed state.

132. The solid oral extended release pharmaceutical dosage form of any of embodiments 86 to 121 and 124 to 129, wherein the $C_{max}$, $AUC_t$, and/or $AUC_{inf}$ of morphine is/are determined after a single-dose administration of the dosage form to a healthy human subject in the fasted or in the fed state.

133. The solid oral extended release pharmaceutical dosage form of any of embodiments 86 to 121 and 124 to 129, wherein the $C_{max}$, $AUC_t$, and/or $AUC_{inf}$ of morphine is/are (a) mean value(s) determined after a single-dose administration of the dosage form to a population of healthy human subjects in the fasted or in the fed state.

134. A solid oral extended release pharmaceutical dosage form comprising a cured extended release matrix formulation, the extended release matrix formulation comprising:
a therapeutically effective amount of morphine sulfate, and
polyethylene oxide having an approximate molecular weight of from about 900,000 to about 2,000,000;
the dosage form having a breaking strength of least about 200 N.

135. The solid oral extended release pharmaceutical dosage form of embodiment 134, the dosage form having a breaking strength of least about 300 N.

136. The solid oral extended release pharmaceutical dosage form of embodiment 135, the dosage form having a breaking strength of least about 400 N.

137. A solid oral extended release pharmaceutical dosage form comprising a cured extended release matrix formulation, the extended release matrix formulation comprising:
a therapeutically effective amount of morphine sulfate, and
polyethylene oxide having an approximate molecular weight of from about 900,000 to about 2,000,000;
the dosage form having a cracking force of at least about 150 N.

138. The solid oral extended release pharmaceutical dosage form of embodiment 137, the dosage form having a cracking force of at least about 200 N.

139. The solid oral extended release pharmaceutical dosage form of embodiment 138, the dosage form having a cracking force of at least about 230 N.

140. A solid oral extended release pharmaceutical dosage form comprising a cured extended release matrix formulation, the extended release matrix formulation comprising:
a therapeutically effective amount of morphine sulfate, and
polyethylene oxide having an approximate molecular weight of from about 900,000 to about 2,000,000;
the dosage form having a crush resistance of at least about 400 N.

141. The solid oral extended release pharmaceutical dosage form of embodiment 140, the dosage form having a crush resistance of at least about 500 N.

142. The solid oral extended release pharmaceutical dosage form of any of embodiments 134 to 141, wherein the polyethylene oxide has an approximate molecular weight of from about 1,000,000 to about 2,000,000.

143. The solid oral extended release pharmaceutical dosage form of embodiment 142, wherein the polyethylene oxide has an approximate molecular weight of about 1,000,000 or about 2,000,000.

144. The solid oral extended release pharmaceutical dosage form of any of embodiments 134 to 143, wherein the polyethylene oxide used for preparing the dosage form is characterized in that about 90% or more of the polyethylene oxide particles pass through a 60 mesh (0.250 mm; 250 microns) sieve.

145. A solid oral extended release pharmaceutical dosage form comprising a cured extended release matrix formulation, the extended release matrix formulation comprising:
a therapeutically effective amount of morphine sulfate, and
polyethylene oxide;
the dosage form after administration providing a dose adjusted $C_{max}$ of morphine of from about 3 ng/mL to about 9 ng/mL per 15 mg of morphine hemi(sulfate pentahydrate) (having a molecular weight of 758.8 g/mol) or an equimolar amount of another solvate or hydrate of morphine sulfate included in the dosage form, and
the dosage form having a breaking strength of least about 200 N.

146. The solid oral extended release pharmaceutical dosage form of embodiment 145, the dosage form after administration providing a dose adjusted $C_{max}$ of morphine of from about 5 ng/mL to about 7 ng/mL per 15 mg of morphine hemi(sulfate pentahydrate) (having a molecular weight of 758.8 g/mol) or an equimolar amount of another solvate or hydrate of morphine sulfate included in the dosage form, and
the dosage form having a breaking strength of least about 300 N.

147. The solid oral extended release pharmaceutical dosage form of embodiment 146, the dosage form having a breaking strength of least about 400 N.

148. A solid oral extended release pharmaceutical dosage form comprising a cured extended release matrix formulation, the extended release matrix formulation comprising:
a therapeutically effective amount of morphine sulfate, and
polyethylene oxide;
the dosage form after administration providing a dose adjusted $C_{max}$ of morphine of from about 3 ng/mL to about 9 ng/mL per 15 mg of morphine hemi(sulfate pentahydrate) (having a molecular weight of 758.8 g/mol) or an equimolar amount of another solvate or hydrate of morphine sulfate included in the dosage form, and
the dosage form having a cracking force of least about 150 N.

149. The solid oral extended release pharmaceutical dosage form of embodiment 148, the dosage form after administration providing a dose adjusted $C_{max}$ of morphine of from about 5 ng/mL to about 7 ng/mL per 15 mg of morphine hemi(sulfate pentahydrate) (having a molecular weight of 758.8 g/mol) or an equimolar amount of another solvate or hydrate of morphine sulfate included in the dosage form, and
the dosage form having a cracking force of least about 200 N.

150. The solid oral extended release pharmaceutical dosage form of embodiment 149, the dosage form having a cracking force of least about 230 N.

151. A solid oral extended release pharmaceutical dosage form comprising a cured extended release matrix formulation, the extended release matrix formulation comprising:

a therapeutically effective amount of morphine sulfate, and
polyethylene oxide;
the dosage form after administration providing a dose adjusted $C_{max}$ of morphine of from about 3 ng/mL to about 9 ng/mL per 15 mg of morphine hemi(sulfate pentahydrate) (having a molecular weight of 758.8 g/mol) or an equimolar amount of another solvate or hydrate of morphine sulfate included in the dosage form, and
the dosage form having a crush resistance of at least about 400 N.

152. The solid oral extended release pharmaceutical dosage form of embodiment 151, the dosage form after administration providing a dose adjusted $C_{max}$ of morphine of from about 5 ng/mL to about 7 ng/mL per 15 mg of morphine hemi(sulfate pentahydrate) (having a molecular weight of 758.8 g/mol) or an equimolar amount of another solvate or hydrate of morphine sulfate included in the dosage form, and the dosage form having a crush resistance of at least about 500 N.

153. A solid oral extended release pharmaceutical dosage form comprising a cured extended release matrix formulation, the extended release matrix formulation comprising:
a therapeutically effective amount of morphine sulfate, and
polyethylene oxide;
the dosage form after administration providing a dose adjusted $AUC_t$ and/or a dose adjusted $AUC_{inf}$ of morphine of from about 30 ng*hr/mL to about 100 ng*hr/mL per 15 mg of morphine hemi(sulfate pentahydrate) (having a molecular weight of 758.8 g/mol) or an equimolar amount of another solvate or hydrate of morphine sulfate included in the dosage form, and the dosage form having a breaking strength of least about 200 N.

154. The solid oral extended release pharmaceutical dosage form of embodiment 153, the dosage form after administration providing a dose adjusted $AUC_t$ and/or a dose adjusted $AUC_{inf}$ of morphine of from about 40 ng*hr/mL to about 80 ng*hr/mL per 15 mg of morphine hemi(sulfate pentahydrate) (having a molecular weight of 758.8 g/mol) or an equimolar amount of another solvate or hydrate of morphine sulfate included in the dosage form, and the dosage form having a breaking strength of least about 300 N.

155. The solid oral extended release pharmaceutical dosage form of embodiment 154, the dosage form having a breaking strength of least about 400 N.

156. A solid oral extended release pharmaceutical dosage form comprising a cured extended release matrix formulation, the extended release matrix formulation comprising:
a therapeutically effective amount of morphine sulfate, and
polyethylene oxide;
the dosage form after administration providing a dose adjusted $AUC_t$ and/or a dose adjusted $AUC_{inf}$ of morphine of from about 30 ng*hr/mL to about 100 ng*hr/mL per 15 mg of morphine hemi(sulfate pentahydrate) (having a molecular weight of 758.8 g/mol) or an equimolar amount of another solvate or hydrate of morphine sulfate included in the dosage form, and
the dosage form having a cracking force of least about 150 N.

157. The solid oral extended release pharmaceutical dosage form of embodiment 156, the dosage form after administration providing a dose adjusted $AUC_t$ and/or a dose adjusted $AUC_{inf}$ of morphine of from about 40 ng*hr/mL to about 80 ng*hr/mL per 15 mg of morphine hemi(sulfate pentahydrate) (having a molecular weight of 758.8 g/mol) or an equimolar amount of another solvate or hydrate of morphine sulfate included in the dosage form, and the dosage form having a cracking force of least about 200 N.

158. The solid oral extended release pharmaceutical dosage form of embodiment 157, the dosage form having a cracking force of least about 230 N.

159. A solid oral extended release pharmaceutical dosage form comprising a cured extended release matrix formulation, the extended release matrix formulation comprising:
a therapeutically effective amount of morphine sulfate, and
polyethylene oxide;
the dosage form after administration providing a dose adjusted $AUC_t$ and/or a dose adjusted $AUC_{inf}$ of morphine of from about 30 ng*hr/mL to about 100 ng*hr/mL per 15 mg of morphine hemi(sulfate pentahydrate) (having a molecular weight of 758.8 g/mol) or an equimolar amount of another solvate or hydrate of morphine sulfate included in the dosage form, and the dosage form having a crush resistance of at least about 400 N.

160. The solid oral extended release pharmaceutical dosage form of embodiment 159, the dosage form after administration providing a dose adjusted $AUC_t$ and/or a dose adjusted $AUC_{inf}$ of morphine of from about 40 ng*hr/mL to about 80 ng*hr/mL per 15 mg of morphine hemi(sulfate pentahydrate) (having a molecular weight of 758.8 g/mol) or an equimolar amount of another solvate or hydrate of morphine sulfate included in the dosage form, and the dosage form having a crush resistance of at least about 500 N.

161. The solid oral extended release pharmaceutical dosage form of embodiment 160, wherein the dosage form has been prepared using polyethylene oxide particles characterized in that about 90% or more of the polyethylene oxide particles pass through a 60 mesh (0.250 mm, 250 microns) sieve.

162. The solid oral extended release pharmaceutical dosage form of any of embodiments 134 to 161, wherein the polyethylene oxide present in the dosage form has an approximate molecular weight of from about 900,000 to about 2,000,000.

163. The solid oral extended release pharmaceutical dosage form of embodiment 162, wherein the polyethylene oxide present in the dosage form has an approximate molecular weight of from about 1,000,000 to about 2,000,000.

164. The solid oral extended release pharmaceutical dosage form of embodiment 163, wherein the polyethylene oxide has an approximate molecular weight of about 1,000,000 or about 2,000,000.

165. The solid oral extended release pharmaceutical dosage form of any of embodiments 134 to 164, wherein the polyethylene oxide is included in the extended release matrix formulation in an amount of about 55 to about 95% by weight thereof.

166. The solid oral extended release pharmaceutical dosage form of embodiment 165, wherein the polyethylene oxide is included in the extended release matrix formulation in an amount of about 64 to about 87% by weight thereof.

167. The solid oral extended release pharmaceutical dosage form of any of embodiments 134 to 166, wherein the morphine sulfate is included in the extended release matrix formulation in the form of morphine hemi(sulfate pentahydrate) (having a molecular weight of 758.8 g/mol) in an amount of about 5 to about 40% by weight of the extended release matrix formulation or in an equimolar amount of another solvate or hydrate of morphine sulfate.

168. The solid oral extended release pharmaceutical dosage form of embodiment 166, wherein the morphine sulfate is included in the extended release matrix formulation in the form of morphine hemi(sulfate pentahydrate) (having a molecular weight of 758.8 g/mol) in an amount of about 12 to about 33% by weight of the extended release matrix formulation or in an equimolar amount of another solvate or hydrate of morphine sulfate.

169. A solid oral extended release pharmaceutical dosage form of morphine sulfate, wherein the dosage form is a tablet comprising 15 mg of morphine hemi(sulfate pentahydrate)(having a molecular weight of 758.8 g/mol) or an equimolar amount of another solvate or hydrate of morphine sulfate included in an extended release matrix formulation, wherein the dosage form when tested in a comparative clinical study is bioequivalent to the commercial product MS Contin® containing an equimolar amount of morphine sulfate, and wherein the dosage form has a breaking strength of at least about 230 N and/or a cracking force of at least about 180 N and/or a crush resistance of at least about 400 N.

170. A solid oral extended release pharmaceutical dosage form of morphine sulfate, wherein the dosage form is a tablet comprising 15 mg of morphine hemi(sulfate pentahydrate)(having a molecular weight of 758.8 g/mol) or an equimolar amount of another solvate or hydrate of morphine sulfate included in an extended release matrix formulation, wherein the dosage form when tested in a comparative clinical study is bioequivalent to a reference tablet containing an equimolar amount of morphine sulfate in a matrix formulation, and wherein the dosage form has a breaking strength of at least about 230 N and/or a cracking force of at least about 180 N and/or a crush resistance of at least about 400 N,
wherein the reference tablet contains:
 a) morphine sulfate: 15 mg/tablet
 b) lactose (spray-dried): 85 mg/tablet
 c) cetostearyl alcohol: 35 mg/tablet
 d) hydroxyethyl cellulose: 10 mg/tablet
 e) talc: 3 mg/tablet
 f) magnesium stearate: 2 mg/tablet
 g) Opadry® coating: 5 mg/tablet.

171. The solid oral extended release pharmaceutical dosage form of morphine sulfate of embodiment 169 or embodiment 170, the dosage form having a breaking strength of at least about 250 N and/or a cracking force of at least about 200 N and/or a crush resistance of at least about 500 N.

172. A solid oral extended release pharmaceutical dosage form of morphine sulfate, wherein the dosage form is a tablet comprising 30 mg of morphine hemi(sulfate pentahydrate) (having a molecular weight of 758.8 g/mol) or an equimolar amount of another solvate or hydrate of morphine sulfate included in an extended release matrix formulation, wherein the dosage form when tested in a comparative clinical study is bioequivalent to the commercial product MS Contin® containing an equimolar amount of morphine sulfate, and wherein the dosage form has a breaking strength of at least about 250 N and/or a cracking force of at least about 200 N and/or a crush resistance of at least about 400 N.

173. A solid oral extended release pharmaceutical dosage form of morphine sulfate, wherein the dosage form is a tablet comprising 30 mg of morphine hemi(sulfate pentahydrate) (having a molecular weight of 758.8 g/mol) or an equimolar amount of another solvate or hydrate of morphine sulfate included in an extended release matrix formulation, wherein the dosage form when tested in a comparative clinical study is bioequivalent to a reference tablet containing an equimolar amount of morphine sulfate in a matrix formulation, and wherein the dosage form has a breaking strength of at least about 250 N and/or a cracking force of at least about 200 N and/or a crush resistance of at least about 400 N, wherein the reference tablet contains:
 a) morphine sulfate: 30 mg/tablet
 b) lactose (spray-dried): 70 mg/tablet
 c) cetostearyl alcohol: 35 mg/tablet
 d) hydroxyethyl cellulose: 10 mg/tablet
 e) talc: 3 mg/tablet
 f) magnesium stearate: 2 mg/tablet
 g) Opadry® coating: 5 mg/tablet.

174. The solid oral extended release pharmaceutical dosage form of morphine sulfate of embodiment 172 or embodiment 173, the dosage form having a breaking strength of at least about 300 N and/or a cracking force of at least about 230 N and/or a crush resistance of at least about 500 N.

175. A solid oral extended release pharmaceutical dosage form of morphine sulfate, wherein the dosage form is a tablet comprising 60 mg of morphine hemi(sulfate pentahydrate) (having a molecular weight of 758.8 g/mol) or an equimolar amount of another solvate or hydrate of morphine sulfate included in an extended release matrix formulation, wherein the dosage form when tested in a comparative clinical study is bioequivalent to the commercial product MS Contin® containing an equimolar amount of morphine sulfate, and wherein the dosage form has a breaking strength of at least about 280 N and/or a cracking force of at least about 200 N and/or a crush resistance of at least about 400 N.

176. A solid oral extended release pharmaceutical dosage form of morphine sulfate, wherein the dosage form is a tablet comprising 60 mg of morphine hemi(sulfate pentahydrate) (having a molecular weight of 758.8 g/mol) or an equimolar amount of another solvate or hydrate of morphine sulfate included in an extended release matrix formulation, wherein the dosage form when tested in a comparative clinical study is bioequivalent to a reference tablet containing an equimolar amount of morphine sulfate in a matrix formulation, and wherein the dosage form has a breaking strength of at least about 280 N and/or a cracking force of at least about 200 N and/or a crush resistance of at least about 400 N,
wherein the reference tablet contains:
 a) morphine sulfate: 60 mg/tablet
 b) lactose (spray-dried): 42.2 mg/tablet
 c) cetostearyl alcohol: 32.8 mg/tablet
 d) hydroxyethyl cellulose: 10 mg/tablet
 e) talc: 3 mg/tablet
 f) magnesium stearate: 2 mg/tablet
 g) Opadry® coating: 5 mg/tablet.

177. The solid oral extended release pharmaceutical dosage form of morphine sulfate of embodiment 175 or embodiment 176, the dosage form having a breaking strength of at least about 320 N and/or a cracking force of at least about 230 N and/or a crush resistance of at least about 500 N.

178. A solid oral extended release pharmaceutical dosage form of morphine sulfate, wherein the dosage form is a tablet comprising 100 mg of morphine hemi(sulfate pentahydrate) (having a molecular weight of 758.8 g/mol) or an equimolar amount of another solvate or hydrate of morphine sulfate included in an extended release matrix formulation, wherein the dosage form when tested in a comparative clinical study is bioequivalent to the commercial product MS Contin® containing an equimolar amount of morphine sulfate, and wherein the dosage form has a breaking strength of least about 200 N and/or a cracking force of at least about 170 N and/or a crush resistance of at least about 400 N.

179. A solid oral extended release pharmaceutical dosage form of morphine sulfate, wherein the dosage form is a tablet comprising 100 mg of morphine hemi(sulfate pentahydrate) (having a molecular weight of 758.8 g/mol) or an equimolar amount of another solvate or hydrate of morphine sulfate included in an extended release matrix formulation, wherein the dosage form when tested in a comparative clinical study is bioequivalent to a reference tablet containing an equimolar amount of morphine sulfate in a matrix formulation, and wherein the dosage form has a breaking strength of least about 200 N and/or a cracking force of at least about 170 N and/or a crush resistance of at least about 400 N, wherein the reference tablet contains:
   a) morphine sulfate: 100 mg/tablet
   b) cetostearyl alcohol: 35 mg/tablet
   c) hydroxyethyl cellulose: 10 mg/tablet
   d) talc: 3 mg/tablet
   e) magnesium stearate: 2 mg/tablet
   f) Opadry® coating: 5 mg/tablet.

180. The solid oral extended release pharmaceutical dosage form of morphine sulfate of embodiment 178 or embodiment 179, the dosage form having a breaking strength of at least about 250 N and/or a cracking force of at least about 190 N and/or a crush resistance of at least about 500 N.

181. A solid oral extended release pharmaceutical dosage form of morphine sulfate, wherein the dosage form is a tablet comprising 200 mg of morphine hemi(sulfate pentahydrate) (having a molecular weight of 758.8 g/mol) or an equimolar amount of another solvate or hydrate of morphine sulfate included in an extended release matrix formulation, wherein the dosage form when tested in a comparative clinical study is bioequivalent to the commercial product MS Contin® containing an equimolar amount of morphine sulfate, and wherein the dosage form has a breaking strength of least about 350 N, and/or a cracking force of at least about 180 N and/or a crush resistance of at least about 400 N.

182. A solid oral extended release pharmaceutical dosage form of morphine sulfate, wherein the dosage form is a tablet comprising 200 mg of morphine hemi(sulfate pentahydrate) (having a molecular weight of 758.8 g/mol) or an equimolar amount of another solvate or hydrate of morphine sulfate included in an extended release matrix formulation, wherein the dosage form when tested in a comparative clinical study is bioequivalent to a reference tablet containing an equimolar amount of morphine sulfate in a matrix formulation, and wherein the dosage form has a breaking strength of least about 350 N, and/or a cracking force of at least about 180 N and/or a crush resistance of at least about 400 N, wherein the reference tablet contains:
   a) morphine sulfate: 200 mg/tablet
   b) cetostearyl alcohol: 70 mg/tablet
   c) hydroxyethyl cellulose: 20 mg/tablet
   d) talc: 6 mg/tablet
   e) magnesium stearate: 4 mg/tablet
   f) Opadry® coating: 10 mg/tablet.

183. The solid oral extended release pharmaceutical dosage form of morphine sulfate of embodiment 181 or embodiment 182, the dosage form having a breaking strength of at least about 400 N and/or a cracking force of at least about 210 N and/or a crush resistance of at least about 500 N.

184. A solid oral extended release pharmaceutical dosage form in the form of a tablet, the dosage form comprising a cured extended release matrix formulation, wherein the extended release matrix formulation is obtainable by combining:

about 12% by weight of the extended release matrix formulation of morphine hemi(sulfate pentahydrate) (having a molecular weight of 758.8 g/mol) or an equimolar amount of another solvate or hydrate of morphine sulfate;

about 87% by weight of the extended release matrix formulation of polyethylene oxide having an approximate molecular weight of about 2,000,000; and about 1% by weight of the extended release matrix formulation of a lubricant, preferably magnesium stearate.

185. The solid oral extended release pharmaceutical dosage form of embodiment 184, wherein the extended release matrix formulation is obtainable by combining:

about 15 mg of morphine hemi(sulfate pentahydrate) (having a molecular weight of 758.8 g/mol) or an equimolar amount of another solvate or hydrate of morphine sulfate;

about 109 mg of polyethylene oxide having an approximate molecular weight of about 2,000,000; and about 1 mg of a lubricant, preferably magnesium stearate.

186. The solid oral extended release pharmaceutical dosage form of embodiment 185, wherein the cured extended release matrix formulation is obtainable by:
   (a) combining the morphine hemi(sulfate pentahydrate) or another solvate of morphine sulfate and the polyethylene oxide particles to form a composition,
   (b) shaping the composition of step (a) to form the extended release matrix formulation, and
   (c) curing the extended release matrix formulation of step (b), wherein the polyethylene particles used in step (a) are characterized in that about 90% or more of the polyethylene particles pass through a 60 mesh sieve (0.250 mm; 250 microns).

187. The solid oral extended release pharmaceutical dosage form of embodiment 186, wherein in step (c) the extended release matrix formulation is subjected to a temperature from about 70° C. to about 78° C. for a period of from about 20 minutes to about 60 minutes.

188. The solid oral extended release pharmaceutical dosage form of embodiment 187, wherein the dosage form has a total weight of about 130 mg.

189. The solid oral extended release pharmaceutical dosage form of embodiment 188, wherein the dosage form has a breaking strength of at least about 230 N and/or a cracking force of at least about 180 N and/or a crush resistance of at least about 500 N.

190. The solid oral extended release pharmaceutical dosage form of embodiment 189 in the form of an oval or oblong tablet, wherein the face of the tablet has a convex surface.

191. The solid oral extended release pharmaceutical dosage form of embodiment 190, comprising a film coating on the extended release matrix formulation, wherein the film coating comprises about 4% by weight of the entire dosage form.

192. A solid oral extended release pharmaceutical dosage form in the form of a tablet, the dosage form comprising a cured extended release matrix formulation, wherein the extended release matrix formulation is obtainable by combining:

about 17% by weight of the extended release matrix formulation of morphine hemi(sulfate pentahydrate) (having a molecular weight of 758.8 g/mol) or an equimolar amount of another solvate or hydrate of morphine sulfate;

about 82% by weight of the extended release matrix formulation of polyethylene oxide having an approximate molecular weight of about 2,000,000; and about 1% by weight of the extended release matrix formulation of a lubricant, preferably magnesium stearate.

193. The solid oral extended release pharmaceutical dosage form of embodiment 192, wherein the extended release matrix formulation is obtainable by combining:
about 30 mg of morphine hemi(sulfate pentahydrate) (having a molecular weight of 758.8 g/mol) or an equimolar amount of another solvate or hydrate of morphine sulfate;
about 143 mg of polyethylene oxide having an approximate molecular weight of about 2,000,000;
and about 2 mg of a lubricant, preferably magnesium stearate.

194. The solid oral extended release pharmaceutical dosage form of embodiment 193, wherein the cured extended release matrix formulation is obtainable by:
(a) combining the morphine hemi(sulfate pentahydrate) or another solvate of morphine sulfate and the polyethylene oxide particles to form a composition,
(b) shaping the composition of step (a) to form the extended release matrix formulation, and
(c) curing the extended release matrix formulation of step (b),
wherein the polyethylene particles used in step (a) are characterized in that about 90% or more of the polyethylene particles pass through a 60 mesh sieve (0.250 mm; 250 microns).

195. The solid oral extended release pharmaceutical dosage form of embodiment 194, wherein in step (c) the extended release matrix formulation is subjected to a temperature from about 70° C. to about 78° C. for a period of from about 20 minutes to about 60 minutes.

196. The solid oral extended release pharmaceutical dosage form of embodiment 195, wherein the dosage form has a total weight of about 182 mg.

197. The solid oral extended release pharmaceutical dosage form of embodiment 196, wherein the dosage form has a breaking strength of at least about 250 N and/or a cracking force of at least about 200 N and/or a crush resistance of at least about 500 N.

198. The solid oral extended release pharmaceutical dosage form of embodiment 197 in the form of an oval or oblong tablet, wherein the face of the tablet has a convex surface.

199. The solid oral extended release pharmaceutical dosage form of embodiment 198, comprising a film coating on the extended release matrix formulation, wherein the film coating comprises about 4% by weight of the entire dosage form.

200. A solid oral extended release pharmaceutical dosage form in the form of a tablet, the dosage form comprising a cured extended release matrix formulation, wherein the extended release matrix formulation is obtainable by combining:
about 18% by weight of the extended release matrix formulation of morphine hemi(sulfate pentahydrate) (having a molecular weight of 758.8 g/mol) or an equimolar amount of another solvate or hydrate of morphine sulfate;
about 81% by weight of the extended release matrix formulation of polyethylene oxide having an approximate molecular weight of about 2,000,000; and
about 1% by weight of the extended release matrix formulation of a lubricant, preferably magnesium stearate.

201. The solid oral extended release pharmaceutical dosage form of embodiment 200, wherein the extended release matrix formulation is obtainable by combining:
about 60 mg of morphine hemi(sulfate pentahydrate) (having a molecular weight of 758.8 g/mol) or an equimolar amount of another solvate or hydrate of morphine sulfate;
about 267 mg of polyethylene oxide having an approximate molecular weight of about 2,000,000; and
about 3 mg of a lubricant, preferably magnesium stearate.

202. The solid oral extended release pharmaceutical dosage form of embodiment 201, wherein the cured extended release matrix formulation is obtainable by:
(a) combining the morphine hemi(sulfate pentahydrate) or another solvate of morphine sulfate and the polyethylene oxide particles to form a composition,
(b) shaping the composition of step (a) to form the extended release matrix formulation, and
(c) curing the extended release matrix formulation of step (b),
wherein the polyethylene particles used in step (a) are characterized in that about 90% or more of the polyethylene particles pass through a 60 mesh sieve (0.250 mm; 250 microns).

203. The solid oral extended release pharmaceutical dosage form of embodiment 202, wherein in step (c) the extended release matrix formulation is subjected to a temperature from about 70° C. to about 78° C. for a period of from about 20 minutes to about 60 minutes.

204. The solid oral extended release pharmaceutical dosage form of embodiment 203, wherein the dosage form has a total weight of about 343 mg.

205. The solid oral extended release pharmaceutical dosage form of embodiment 204, wherein the dosage form has a breaking strength of at least about 280 N and/or a cracking force of at least about 200 N and/or a crush resistance of at least about 500 N.

206. The solid oral extended release pharmaceutical dosage form of embodiment 205 in the form of an oval or oblong tablet, wherein the face of the tablet has convex and concave portions, wherein the concave portions extend along the central axis of the tablet defined by half the width of the tablet.

207. The solid oral extended release pharmaceutical dosage form of embodiment 206, comprising a film coating on the extended release matrix formulation, wherein the film coating comprises about 4% by weight of the entire dosage form.

208. A solid oral extended release pharmaceutical dosage form in the form of a tablet, the dosage form comprising a cured extended release matrix formulation, wherein the extended release matrix formulation is obtainable by combining:
about 30% by weight of the extended release matrix formulation of morphine hemi(sulfate pentahydrate) (having a molecular weight of 758.8 g/mol) or an equimolar amount of another solvate or hydrate of morphine sulfate;
about 68% by weight of the extended release matrix formulation of polyethylene oxide having an approximate molecular weight of about 2,000,000;
about 0.5% by weight of the extended release matrix formulation of a glidant, preferably colloidal silicon dioxide, and
about 1.5% by weight of the extended release matrix formulation of a lubricant, preferably magnesium stearate.

209. The solid oral extended release pharmaceutical dosage form of embodiment 208, wherein the extended release matrix formulation is obtainable by combining:
about 100 mg of morphine hemi(sulfate pentahydrate)(having a molecular weight of 758.8 g/mol) or an equimolar amount of another solvate or hydrate of morphine sulfate;
about 224 mg of polyethylene oxide having an approximate molecular weight of about 2,000,000;
about 1.5 mg of a glidant, preferably colloidal silicon dioxide, and
about 4 mg of a lubricant, preferably magnesium stearate.

210. The solid oral extended release pharmaceutical dosage form of embodiment 209, wherein the cured extended release matrix formulation is obtainable by:
(a) combining the morphine hemi(sulfate pentahydrate) or another solvate of morphine sulfate and the polyethylene oxide particles to form a composition,
(b) shaping the composition of step (a) to form the extended release matrix formulation, and
(c) curing the extended release matrix formulation of step (b),
wherein the polyethylene particles used in step (a) are characterized in that about 90% or more of the polyethylene particles pass through a 60 mesh sieve (0.250 mm; 250 microns).

211. The solid oral extended release pharmaceutical dosage form of embodiment 210, wherein in step (c) the extended release matrix formulation is subjected to a temperature from about 74° C. to about 78° C. for at least about 40 minutes.

212. The solid oral extended release pharmaceutical dosage form of embodiment 211, wherein the dosage form has a total weight of about 343 mg.

213. The solid oral extended release pharmaceutical dosage form of embodiment 212, wherein the dosage form has a breaking strength of at least about 200 N and/or a cracking force of at least about 170 N and/or a crush resistance of at least about 500 N.

214. The solid oral extended release pharmaceutical dosage form of embodiment 213 in the form of an oval or oblong tablet, wherein the face of the tablet has convex and concave portions, wherein the concave portions extend along the central axis of the tablet defined by half the width of the tablet.

215. The solid oral extended release pharmaceutical dosage form of embodiment 214, comprising a film coating on the extended release matrix formulation, wherein the film coating comprises about 4% by weight of the entire dosage form.

216. A solid oral extended release pharmaceutical dosage form in the form of a tablet, the dosage form comprising a cured extended release matrix formulation, wherein the extended release matrix formulation is obtainable by combining:
about 33% by weight of the extended release matrix formulation of morphine hemi(sulfate pentahydrate) (having a molecular weight of 758.8 g/mol) or an equimolar amount of another solvate or hydrate of morphine sulfate;
about 65% by weight of the extended release matrix formulation of polyethylene oxide having an approximate molecular weight of about 1,000,000;
about 0.5% by weight of the extended release matrix formulation of a glidant, preferably colloidal silicon dioxide; and
about 1.5% by weight of the extended release matrix formulation of a lubricant, preferably magnesium stearate.

217. The solid oral extended release pharmaceutical dosage form of embodiment 216, wherein the extended release matrix formulation is obtainable by combining:
about 200 mg of morphine hemi(sulfate pentahydrate)(having a molecular weight of 758.8 g/mol) or an equimolar amount of another solvate or hydrate of morphine sulfate;
about 388 mg of polyethylene oxide having an approximate molecular weight of about 1,000,000;
about 3 mg of a glidant, preferably colloidal silicon dioxide; and
about 9 mg of a lubricant, preferably magnesium stearate.

218. The solid oral extended release pharmaceutical dosage form of embodiment 217, wherein the cured extended release matrix formulation is obtainable by:
(a) combining the morphine hemi(sulfate pentahydrate) or another solvate of morphine sulfate and the polyethylene oxide particles to form a composition,
(b) shaping the composition of step (a) to form the extended release matrix formulation, and
(c) curing the extended release matrix formulation of step (b),
wherein the polyethylene particles used in step (a) are characterized in that 90% or more of the polyethylene particles pass through a 60 mesh sieve (0.250 mm; 250 microns).

219. The solid oral extended release pharmaceutical dosage form of embodiment 218, wherein in step (c) the extended release matrix formulation is subjected to a temperature from about 74° C. to about 78° C. for at least about 40 minutes.

220. The solid oral extended release pharmaceutical dosage form of embodiment 219, wherein the dosage form has a total weight of about 624 mg.

221. The solid oral extended release pharmaceutical dosage form of embodiment 220, wherein the dosage form has a breaking strength of at least about 350 N and/or a cracking force of at least about 180 N and/or a crush resistance of at least about 500 N.

222. The solid oral extended release pharmaceutical dosage form of embodiment 221 in the form of an oval or oblong tablet, wherein the face of the tablet has a convex surface.

223. The solid oral extended release pharmaceutical dosage form of embodiment 222, comprising a film coating on the extended release matrix formulation, wherein the film coating comprises about 4% by weight of the entire dosage form.

224. The solid oral extended release pharmaceutical dosage form of any of the preceding embodiments, wherein the dosage form provides an in-vitro dissolution rate of morphine sulfate, when measured in a USP Apparatus 1 (basket) at 100 rpm in 900 ml simulated gastric fluid without enzymes (SGF) at 37° C., characterized by the amount of morphine sulfate released from the dosage form, of
from about 5% to about 35% released after 0.5 hour;
from about 18% to about 50% released after 1 hour;
from about 29% to about 70% released after 2 hours;
from about 40% to about 85% released after 3 hours;
from about 49% to about 95% released after 4 hours;
greater than about 65% released after 6 hours;
greater than about 70% released after 8 hours;
greater than about 75% released after 9 hours; and/or
greater than about 85% released after 12 hours.

225. The solid oral extended release pharmaceutical dosage form of embodiment 224, wherein the dosage form provides an in-vitro dissolution rate of morphine sulfate, when measured in a USP Apparatus 1 (basket) at 100 rpm in 900 ml simulated gastric fluid without enzymes (SGF) at 37° C., characterized by the amount of morphine sulfate released from the dosage form, of
from about 11% to about 31% released after 0.5 hour;
from about 18% to about 46% released after 1 hour;
from about 31% to about 65% released after 2 hours;
from about 43% to about 69% released after 3 hours;
from about 54% to about 87% released after 4 hours;
from about 70% to about 99% released after 6 hours;
greater than about 80% released after 8 hours;
greater than about 85% released after 9 hours; and/or
greater than about 90% released after 12 hours.

226. The solid oral extended release pharmaceutical dosage form of embodiment 225, wherein the dosage form provides an in-vitro dissolution rate of morphine sulfate, when measured in a USP Apparatus 1 (basket) at 100 rpm in 900 ml simulated gastric fluid without enzymes (SGF) at 37° C., characterized by the amount of morphine sulfate released from the dosage form, of
from about 13% to about 21% released after 0.5 hour;
from about 21% to about 34% released after 1 hour;
from about 34 to about 53% released after 2 hours;
from about 46% to about 67% released after 3 hours;
from about 57% to about 81% released after 4 hours;
from about 74% to about 98% released after 6 hours;
greater than about 89% released after 8 hours;
greater than about 89% released after 9 hours; and/or
greater than about 94% released after 12 hours.

227. The solid oral extended release pharmaceutical dosage form of any of the preceding embodiments, wherein the average in-vitro dissolution rate of morphine sulfate decreases by less than about 5% after 6 months storage at 25° C. and 60% relative humidity at one or more time points selected from 1 hour, 2 hours, 6 hours and 12 hours, or selected from 1 hour, 3 hours, 9 hours and 12 hours, when measured in a USP Apparatus 1 (basket) at 100 rpm in 900 ml simulated gastric fluid without enzymes (SGF) at 37° C. with or without added oxygen absorber.

228. The solid oral extended release pharmaceutical dosage form of embodiment 227, wherein the average in-vitro dissolution rate of morphine sulfate decreases by less than about 2% after 6 months storage at 25° C. and 60% relative humidity at one or more time points selected from 1 hour, 2 hours, 6 hours and 12 hours, or selected from 1 hour, 3 hours, 9 hours and 12 hours, when measured in a USP Apparatus 1 (basket) at 100 rpm in 900 ml simulated gastric fluid without enzymes (SGF) at 37° C. with or without added oxygen absorber.

229. The solid oral extended release pharmaceutical dosage form of any of the preceding embodiments, wherein the average in-vitro dissolution rate of morphine sulfate decreases by less than about 5% after 6 months storage at 40° C. at 75% relative humidity at one or more time points selected from 1 hour, 2 hours, 6 hours and 12 hours, or selected from 1 hour, 3 hours, 9 hours and 12 hours, when measured in a USP Apparatus 1 (basket) at 100 rpm in 900 ml simulated gastric fluid without enzymes (SGF) at 37° C. with or without added oxygen absorber.

230. The solid oral extended release pharmaceutical dosage form of embodiment 229, wherein the average in-vitro dissolution rate of morphine sulfate decreases by less than about 2% after 6 months storage at 40° C. at 75% relative humidity at one or more time points selected from 1 hour, 2 hours, 6 hours and 12 hours, or selected from 1 hour, 3 hours, 9 hours and 12 hours, when measured in a USP Apparatus 1 (basket) at 100 rpm in 900 ml simulated gastric fluid without enzymes (SGF) at 37° C. with or without added oxygen absorber.

231. The solid oral extended release pharmaceutical dosage form of any of the preceding embodiments, wherein the average in-vitro dissolution rate of morphine sulfate increases by less than about 5% after 6 months storage at 25° C. and 60% relative humidity at one or more time points selected from 1 hour, 2 hours, 6 hours and 12 hours, or selected from 1 hour, 3 hours, 9 hours and 12 hours, when measured in a USP Apparatus 1 (basket) at 100 rpm in 900 ml simulated gastric fluid without enzymes (SGF) at 37° C. with or without added oxygen absorber.

232. The solid oral extended release pharmaceutical dosage form of embodiment 231, wherein the average in-vitro dissolution rate of morphine sulfate increases by less than about 2% after 6 months storage at 25° C. and 60% relative humidity at one or more time points selected from 1 hour, 2 hours, 6 hours and 12 hours, or selected from 1 hour, 3 hours, 9 hours and 12 hours, when measured in a USP Apparatus 1 (basket) at 100 rpm in 900 ml simulated gastric fluid without enzymes (SGF) at 37° C. with or without added oxygen absorber.

233. The solid oral extended release pharmaceutical dosage form of any of the preceding embodiments, wherein the average in-vitro dissolution rate of morphine sulfate increases by less than about 10% after 6 months storage at 40° C. and 75% relative humidity at one or more time points selected from 1 hour, 2 hours, 6 hours and 12 hours, or selected from 1 hour, 3 hours, 9 hours and 12 hours, when measured in a USP Apparatus 1 (basket) at 100 rpm in 900 ml simulated gastric fluid without enzymes (SGF) at 37° C. with or without added oxygen absorber.

234. The solid oral extended release pharmaceutical dosage form of embodiment 233, wherein the average in-vitro dissolution rate of morphine sulfate increases by less than about 5% after 6 months storage at 40° C. and 75% relative humidity at one or more time points selected from 1 hour, 2 hours, 6 hours and 12 hours, or selected from 1 hour, 3 hours, 9 hours and 12 hours, when measured in a USP Apparatus 1 (basket) at 100 rpm in 900 ml simulated gastric fluid without enzymes (SGF) at 37° C. with or without added oxygen absorber.

235. The solid oral extended release pharmaceutical dosage form of any of the preceding embodiments, wherein the dosage form can be flattened without breaking, wherein the thickness of the dosage form after flattening corresponds to no more than about 60% of the thickness of the dosage form before flattening.

236. The solid oral extended release pharmaceutical dosage form of embodiment 235, wherein the dosage form can be flattened without breaking, wherein the thickness of the dosage form after flattening corresponds to no more than about 40% of the thickness of the dosage form before flattening.

237. The solid oral extended release pharmaceutical dosage form of embodiment 236, wherein the dosage form can be flattened without breaking, wherein the thickness of the dosage form after flattening corresponds to no more than about 20% of the thickness of the dosage form before flattening.

238. The solid oral extended release pharmaceutical dosage form of any of the preceding embodiments, wherein the amount of morphine sulfate released after 0.5 hours from a dosage form flattened to no more than about 60% of the thickness of the dosage form before flattening deviates no more than about 20%-points from the amount of morphine sulfate released from a corresponding non-flattened dosage form as measured by an in-vitro dissolution in a USP Apparatus 1 (basket) at 100 rpm in 900 ml simulated gastric fluid without enzymes (SGF) at 37° C. after 0.5 hours.

239. The solid oral extended release pharmaceutical dosage form of embodiment 238, wherein the amount of morphine sulfate released from the dosage form after 0.5 hours deviates no more than about 10%-points from the amount of morphine sulfate released from a corresponding non-flattened dosage form as measured by an in-vitro dissolution in a USP Apparatus 1 (basket) at 100 rpm in 900 ml simulated gastric fluid without enzymes (SGF) at 37° C. after 0.5 hours.

240. The solid oral extended release pharmaceutical dosage form of embodiment 239, wherein the amount of morphine sulfate released from the dosage form after 0.5 hours and after 1 hour deviates no more than about 20%-points from a non-flattened dosage form as measured by an in-vitro dissolution in a USP Apparatus 1 (basket) at 100 rpm in 900 ml simulated gastric fluid without enzymes (SGF) at 37° C. after 0.5 hours and after 1 hour.

241. The solid oral extended release pharmaceutical dosage form of embodiment 240, wherein the amount of morphine sulfate released from the dosage form after 0.5 hours and after 1 hour deviates no more than about 10%-points from the amount of morphine sulfate released from a corresponding non-flattened dosage form as measured by an in-vitro dissolution in a USP Apparatus 1 (basket) at 100 rpm in 900 ml simulated gastric fluid without enzymes (SGF) at 37° C. after 0.5 hours and after 1 hour.

242. The solid oral extended release pharmaceutical dosage form of any of the preceding embodiments, wherein the dosage form provides an in-vitro dissolution rate of morphine sulfate, when measured in a USP Apparatus 1 (basket) at 100 rpm in 900 ml simulated gastric fluid without enzymes (SGF) comprising 4%, 10%, 20% or 40% ethanol at 37° C., characterized in that the amount of morphine sulfate released from the dosage form after 0.5 hours deviates no more than 20%-points from the amount of morphine sulfate released from the dosage form after 0.5 hours when measured in a USP Apparatus 1 (basket) at 100 rpm in 900 ml simulated gastric fluid without enzymes (SGF) without ethanol at 37° C.

243. The solid oral extended release pharmaceutical dosage form of embodiment 242, wherein the amount of morphine sulfate released form the dosage form after 0.5 hours deviates no more than 10%-points from the amount of morphine sulfate released from the dosage form after 0.5 hours when measured in a USP Apparatus 1 (basket) at 100 rpm in 900 ml simulated gastric fluid without enzymes (SGF) without ethanol at 37° C.

244. The solid oral extended release pharmaceutical dosage form of embodiment 242, wherein the amount of morphine sulfate released form the dosage form after 0.5 hours and after 1 hour deviates no more than 20%-points from the amount of morphine sulfate released from the dosage form after 0.5 hours and after 1 hour when measured in a USP Apparatus 1 (basket) at 100 rpm in 900 ml simulated gastric fluid without enzymes (SGF) without ethanol at 37° C.

245. The solid oral extended release pharmaceutical dosage form of embodiment 244, wherein the amount of morphine sulfate released from the dosage form at 0.5 hours and at 1 hour deviates no more than 10%-points from the amount of morphine sulfate released from the dosage form after 0.5 hours and after 1 hour when measured in a USP Apparatus 1 (basket) at 100 rpm in 900 ml simulated gastric fluid without enzymes (SGF) without ethanol at 37° C.

246. The solid oral extended release pharmaceutical dosage form of any of the preceding embodiments, wherein crushing the dosage form between two spoons or by means of a mortar and pestle results in less than about 10% of the resulting particles having a particle size of less than 1000 μm.

247. The solid oral extended release pharmaceutical dosage form of embodiment 246, wherein crushing the dosage form between two spoons or by means of a mortar and pestle results in less than about 5% of the resulting particles having a particle size of less than 1000 μm.

248. The solid oral extended release pharmaceutical dosage form of embodiment 247, wherein crushing the dosage form between two spoons or by means of a mortar and pestle results in less than about 2.5% of the resulting particles having a particle size of less than 1000 μm.

249. The solid oral extended release pharmaceutical dosage form of any of embodiments 246 to 248, wherein the crushing is performed for up to about 5 min.

250. The solid oral extended release pharmaceutical dosage form of any of embodiments 246 to 249, wherein prior to the crushing the dosage form has been thermally treated by heating or freezing.

251. The solid oral extended release pharmaceutical dosage form of embodiment 250, wherein thermal treatment comprises heating in an oven or microwave treatment.

252. The solid oral extended release pharmaceutical dosage form of embodiment 251, wherein the dosage form has been thermally treated at least at about 50° C.

253. The solid oral extended release pharmaceutical dosage form of embodiment 252, wherein the dosage form has been thermally treated at least at about 90° C.

254. The solid oral extended release pharmaceutical dosage form of embodiment 253, wherein the dosage form has been thermally treated at least at about 200° C.

255. The solid oral extended release pharmaceutical dosage form of embodiment 254, wherein the dosage form has been thermally treated at least at about 230° C.

256. The solid oral extended release pharmaceutical dosage form of any of embodiments 250 to 255, wherein the dosage form has been thermally treated for a period of at least about 2 hours.

257. The solid oral extended release pharmaceutical dosage form of any embodiment 256, wherein the dosage form has been thermally treated for a period of at least about 3 hours.

258. The solid oral extended release pharmaceutical dosage form of embodiment 257, wherein the dosage form has been thermally treated for a period of at least about 4 hours.

259. The solid oral extended release pharmaceutical dosage form of any of the preceding embodiments, wherein recovery of the morphine sulfate is less than about 20% based on a syringeability test whereby one intact dosage form is subjected to dissolution in 2, 5, or 10 ml of water or saline without or with agitation at room temperature for 1 hour or for 24 hours and the resultant solution is aspirated by an iterative process starting with a 27 gauge needle and subsequently using 25, 22 and 18 gauge needles in case less than 10% of the extraction volume could be loaded in the respective larger gauge (smaller diameter) needle.

260. The solid oral extended release pharmaceutical dosage form of embodiment 258, wherein recovery of the morphine sulfate is less than about 10%.

261. The solid oral extended release pharmaceutical dosage form of embodiment 260, wherein recovery of the morphine sulfate is less than about 5%.

262. The solid oral extended release pharmaceutical dosage form of any of the preceding embodiments, wherein recovery of the morphine sulfate is less than about 65%, based on a syringeability test whereby one intact dosage form is subjected to extraction in 2, 5, or 10 ml of water without or with agitation at 90° C. for 1 hour or for 24 hours and the resultant solution is aspirated by an iterative process starting with a 27 gauge needle and subsequently using 25, 22 and 18 gauge needles in case less than 10% of the extraction volume could be loaded in the respective larger gauge (smaller diameter) needle.

263. The solid oral extended release pharmaceutical dosage form of embodiment 262, wherein recovery of the morphine sulfate is less than about 40%.

264. The solid oral extended release pharmaceutical dosage form of embodiment 263, wherein recovery of the morphine sulfate is less than about 25%.
265. The solid oral extended release pharmaceutical dosage form of any of the preceding embodiments, wherein recovery of the morphine sulfate is less than about 30% based on a syringeability test whereby one intact dosage form is subjected to extraction in 2, 5, or 10 ml of saline without or with agitation at 90° C. for 24 hours and the resultant solution is aspirated by an iterative process starting with a 27 gauge needle and subsequently using 25, 22 and 18 gauge needles in case less than 10% of the extraction volume could be loaded in the respective larger gauge (smaller diameter) needle.
266. The solid oral extended release pharmaceutical dosage form of embodiment 265, wherein recovery of the morphine sulfate is less than about 20%.
267. The solid oral extended release pharmaceutical dosage form of embodiment 266, wherein recovery of the morphine sulfate is less than about 15%.
268. The solid oral extended release pharmaceutical dosage form of any of the preceding embodiments, wherein recovery of the morphine sulfate is less than about 15% based on a syringeability test whereby one sliced dosage form is subjected to extraction in 2, 5, or 10 ml of water or saline without or with agitation at room temperature for 30 minutes and the resultant solution is aspirated by an iterative process starting with a 27 gauge needle and subsequently using 25, 22 and 18 gauge needles in case less than 10% of the extraction volume could be loaded in the respective larger gauge (smaller diameter) needle.
269. The solid oral extended release pharmaceutical dosage form of embodiment 268, wherein recovery of the morphine sulfate is less than about 10%.
270. The solid oral extended release pharmaceutical dosage form of embodiment 269, wherein recovery of the morphine sulfate is less than about 5%.
271. The solid oral extended release pharmaceutical dosage form of any of the preceding embodiments, wherein recovery of the morphine sulfate is less than about 50%, based on a syringeability test whereby one sliced dosage form is subjected to extraction in 2, 5, or 10 ml of water or saline without or with agitation at 90° C. for 30 minutes and the resultant solution is aspirated by an iterative process starting with a 27 gauge needle and subsequently using 25, 22 and 18 gauge needles in case less than 10% of the extraction volume could be loaded in the respective larger gauge (smaller diameter) needle.
272. The solid oral extended release pharmaceutical dosage form of embodiment 271, wherein recovery of the morphine sulfate is less than about 35%.
273. The solid oral extended release pharmaceutical dosage form of embodiment 272, wherein recovery of the morphine sulfate is less than about 20%.
274. The solid oral extended release pharmaceutical dosage form of any of the preceding embodiments, wherein recovery of the morphine sulfate is less than about 20% based on a syringeability test whereby one milled dosage form is subjected to extraction in 2, 5, or 10 ml of water or saline without or with agitation at room temperature for 30 minutes and the resultant solution is aspirated by an iterative process starting with a 27 gauge needle and subsequently using 25, 22 and 18 gauge needles in case less than 10% of the extraction volume could be loaded in the respective larger gauge (smaller diameter) needle.
275. The solid oral extended release pharmaceutical dosage form of embodiment 274, wherein recovery of the morphine sulfate is less than about 10%.
276. The solid oral extended release pharmaceutical dosage form of embodiment 275, wherein recovery of the morphine sulfate is less than about 5%.
277. The solid oral extended release pharmaceutical dosage form of any of the preceding embodiments, wherein recovery of the morphine sulfate is less than about 30% based on a syringeability test whereby one milled dosage form is subjected to extraction in 2, 5, or 10 ml of water or saline without or with agitation at 90° C. for 30 minutes and the resultant solution is aspirated by an iterative process starting with a 27 gauge needle and subsequently using 25, 22 and 18 gauge needles in case less than 10% of the extraction volume could be loaded in the respective larger gauge (smaller diameter) needle.
278. The solid oral extended release pharmaceutical dosage form of embodiment 277, wherein recovery of the morphine sulfate is less than about 20%.
279. The solid oral extended release pharmaceutical dosage form of embodiment 278, wherein recovery of the morphine sulfate is less than about 10%.
280. The solid oral extended release pharmaceutical dosage form of any of the preceding embodiments, the dosage form comprising 60 mg of morphine hemi(sulfate pentahydrate) (having a molecular weight of 758.8 g/mol) or an equimolar amount of another solvate or hydrate of morphine sulfate, wherein intranasal administration of the dosage form as finely crushed powder has a mean "at this moment" drug liking ($E_{max}$ of about 45 to about 75.
281. The solid oral extended release pharmaceutical dosage form of embodiment 280, wherein intranasal administration of the dosage form as finely crushed powder has a mean "at this moment" drug liking ($E_{max}$) of about 57 to about 63.
282. The solid oral extended release pharmaceutical dosage form of any of the preceding embodiments, the dosage form comprising 60 mg of morphine hemi(sulfate pentahydrate) (having a molecular weight of 758.8 g/mol) or an equimolar amount of another solvate or hydrate of morphine sulfate, wherein oral administration of the dosage form intact as compared to intranasal administration of a placebo powder has a median difference (IQR) in "at this moment" drug liking ($E_{max}$) of about 1 to about 20.
283. The solid oral extended release pharmaceutical dosage form of embodiment 282, wherein oral administration of the dosage form intact as compared to intranasal administration of a placebo powder has a median difference (IQR) in "at this moment" drug liking ($E_{max}$) of about 12 to about 16.
284. The solid oral extended release pharmaceutical dosage form of any of the preceding embodiments, the dosage form comprising 60 mg of morphine hemi(sulfate pentahydrate) (having a molecular weight of 758.8 g/mol) or an equimolar amount of another solvate or hydrate of morphine sulfate, wherein intranasal administration of the dosage form as finely crushed powder as compared to intranasal administration of a placebo powder has a median difference (IQR) in "at this moment" drug liking ($E_{max}$) of about 0 to about 9.
285. The solid oral extended release pharmaceutical dosage form of embodiment 284, wherein intranasal administration of the dosage form as finely crushed powder as compared to oral administration of the dosage form intact has a median difference (IQR) in "at this moment" drug liking ($E_{max}$) of about 0 to about 3.
286. The solid oral extended release pharmaceutical dosage form of any of the preceding embodiments, the dosage form comprising 60 mg of morphine hemi(sulfate pentahydrate) (having a molecular weight of 758.8 g/mol) or an equimolar amount of another solvate or hydrate of morphine sulfate, wherein intranasal administration of the dosage form as finely crushed powder as compared to oral administration of the dosage form intact has a median difference (IQR) in "at this moment" drug liking ($E_{max}$) of about −17 to about 0.

287. The solid oral extended release pharmaceutical dosage form of embodiment 286, wherein intranasal administration of the dosage form as finely crushed powder as compared to oral administration of the dosage form intact has a median difference (IQR) in "at this moment" drug liking ($E_{max}$) of about −10 to about −5.

288. The solid oral extended release pharmaceutical dosage form of any of the preceding embodiments, the dosage form comprising 60 mg of morphine hemi(sulfate pentahydrate) (having a molecular weight of 758.8 g/mol) or an equimolar amount of another solvate or hydrate of morphine sulfate, wherein oral administration of the dosage form intact as compared to intranasal administration of the commercial product MS Contin® containing an equimolar amount of morphine sulfate as finely crushed powder has a median difference (IQR) in "at this moment" drug liking ($E_{max}$) of about −33 to about −8.

289. The solid oral extended release pharmaceutical dosage form of embodiment 288, wherein oral administration of the dosage form intact as compared to intranasal administration of the commercial product MS Contin® containing an equimolar amount of morphine sulfate as finely crushed powder has a median difference (IQR) in "at this moment" drug liking ($E_{max}$) of about −25 to about −15.

290. The solid oral extended release pharmaceutical dosage form of any of the preceding embodiments, the dosage form comprising 60 mg of morphine hemi(sulfate pentahydrate) (having a molecular weight of 758.8 g/mol) or an equimolar amount of another solvate or hydrate of morphine sulfate, wherein intranasal administration of the dosage form as finely crushed powder as compared to intranasal administration of the commercial product MS Contin® containing an equimolar amount of morphine sulfate as finely crushed powder has a median difference (IQR) in "at this moment" drug liking ($E_{max}$) of about −49 to about −12.

291. The solid oral extended release pharmaceutical dosage form of embodiment 290, wherein intranasal administration of the dosage form as finely crushed powder as compared to intranasal administration of the commercial product MS Contin® containing an equimolar amount of morphine sulfate as finely crushed powder has a median difference (IQR) in "at this moment" drug liking ($E_{max}$) of about −30 to about −20.

292. The solid oral extended release pharmaceutical dosage form of any of the preceding embodiments, the dosage form comprising 60 mg of morphine hemi(sulfate pentahydrate) (having a molecular weight of 758.8 g/mol) or an equimolar amount of another solvate or hydrate of morphine sulfate, wherein intranasal administration of the dosage form as finely crushed powder has a mean ODL (overall drug liking) ($E_{max}$) of about 0 to about 100.

293. The solid oral extended release pharmaceutical dosage form of embodiment 292, wherein intranasal administration of the dosage form as finely crushed powder has a mean ODL (overall drug liking) ($E_{max}$) of about 40 to about 60.

294. The solid oral extended release pharmaceutical dosage form of any of the preceding embodiments, the dosage form comprising 60 mg of morphine hemi(sulfate pentahydrate) (having a molecular weight of 758.8 g/mol) or an equimolar amount of another solvate or hydrate of morphine sulfate, wherein oral administration of the dosage form intact as compared to intranasal administration of a placebo powder has a median difference (IQR) in ODL (overall drug liking) ($E_{max}$) of about 0 to about 26.

295. The solid oral extended release pharmaceutical dosage form of embodiment 294, wherein oral administration of the dosage form intact as compared to intranasal administration of a placebo powder has a median difference (IQR) in ODL (overall drug liking) ($E_{max}$) of about 10 to about 18.

296. The solid oral extended release pharmaceutical dosage form of any of the preceding embodiments, the dosage form comprising 60 mg of morphine hemi(sulfate pentahydrate) (having a molecular weight of 758.8 g/mol) or an equimolar amount of another solvate or hydrate of morphine sulfate, wherein intranasal administration of the dosage form as finely crushed powder as compared to intranasal administration of a placebo powder has a median difference (IQR) in ODL (overall drug liking) ($E_{max}$) of about −4 to about 10.

297. The solid oral extended release pharmaceutical dosage form of embodiment 296, wherein intranasal administration of the dosage form as finely crushed powder as compared to oral administration of the dosage form intact has a median difference (IQR) in ODL (overall drug liking) ($E_{max}$) of about 0 to about 5.

298. The solid oral extended release pharmaceutical dosage form of any of the preceding embodiments, the dosage form comprising 60 mg of morphine hemi(sulfate pentahydrate) (having a molecular weight of 758.8 g/mol) or an equimolar amount of another solvate or hydrate of morphine sulfate, wherein intranasal administration of the dosage form as finely crushed powder as compared to oral administration of the dosage form intact has a median difference (IQR) in ODL (overall drug liking) ($E_{max}$) of about −26 to about 0.

299. The solid oral extended release pharmaceutical dosage form of embodiment 298, wherein intranasal administration of the dosage form as finely crushed powder as compared to oral administration of the dosage form intact has a median difference (IQR) in ODL (overall drug liking) ($E_{max}$) of about −15 to about −8.

300. The solid oral extended release pharmaceutical dosage form of any of the preceding embodiments, the dosage form comprising 60 mg of morphine hemi(sulfate pentahydrate) (having a molecular weight of 758.8 g/mol) or an equimolar amount of another solvate or hydrate of morphine sulfate, wherein oral administration of the dosage form intact as compared to intranasal administration of the commercial product MS Contin® containing an equimolar amount of morphine sulfate as finely crushed powder has a median difference (IQR) in ODL (overall drug liking) ($E_{max}$) of about −32 to about −1.

301. The solid oral extended release pharmaceutical dosage form of embodiment 300, wherein oral administration of the dosage form intact as compared to intranasal administration of the commercial product MS Contin® containing an equimolar amount of morphine sulfate as finely crushed powder has a median difference (IQR) in ODL (overall drug liking) ($E_{max}$) of about −18 to about −10.

302. The solid oral extended release pharmaceutical dosage form of any of the preceding embodiments, the dosage form comprising 60 mg of morphine hemi(sulfate pentahydrate) (having a molecular weight of 758.8 g/mol) or an equimolar amount of another solvate or hydrate of morphine sulfate, wherein intranasal administration of the dosage form as finely crushed powder as compared to intranasal administration of the commercial product MS Contin® containing an equimolar amount of morphine sulfate as finely crushed powder has a median difference (IQR) in ODL (overall drug liking) ($E_{max}$) of about −50 to about −7.

303. The solid oral extended release pharmaceutical dosage form of embodiment 302, wherein intranasal administration of the dosage form as finely crushed powder as compared to intranasal administration of the commercial product MS Contin® containing an equimolar amount of morphine sulfate as finely crushed powder has a median difference (IQR) in ODL (overall drug liking) ($E_{max}$) of about −35 to about −20.

304. The solid oral extended release pharmaceutical dosage form of any of the preceding embodiments, the dosage form comprising 60 mg of morphine hemi(sulfate pentahydrate) (having a molecular weight of 758.8 g/mol) or an equimolar amount of another solvate or hydrate of morphine sulfate, wherein intranasal administration of the dosage form as finely crushed powder has a mean TDA (take drug again) effect ($E_{max}$) of about 10 to about 75.

305. The solid oral extended release pharmaceutical dosage form of embodiment 304, wherein intranasal administration of the dosage form as finely crushed powder has a mean TDA (take drug again) effect ($E_{max}$) of about 35 to about 55.

306. The solid oral extended release pharmaceutical dosage form of any of the preceding embodiments, the dosage form comprising 60 mg of morphine hemi(sulfate pentahydrate) (having a molecular weight of 758.8 g/mol) or an equimolar amount of another solvate or hydrate of morphine sulfate, wherein oral administration of the dosage form intact as compared to intranasal administration of a placebo powder has a median difference (IQR) in TDA (take drug again) effect ($E_{max}$) of about 1 to about 25.

307. The solid oral extended release pharmaceutical dosage form of embodiment 306, wherein oral administration of the dosage form intact as compared to intranasal administration of a placebo powder has a median difference (IQR) in TDA (take drug again) effect ($E_{max}$) of about 12 to about 16.

308. The solid oral extended release pharmaceutical dosage form of any of the preceding embodiments, the dosage form comprising 60 mg of morphine hemi(sulfate pentahydrate) (having a molecular weight of 758.8 g/mol) or an equimolar amount of another solvate or hydrate of morphine sulfate, wherein intranasal administration of the dosage form as finely crushed powder as compared to intranasal administration of a placebo powder has a median difference (IQR) in TDA (take drug again) effect ($E_{max}$) of about −40 to about 11.

309. The solid oral extended release pharmaceutical dosage form of embodiment 308, wherein intranasal administration of the dosage form as finely crushed powder as compared to intranasal administration of a placebo powder intact has a median difference (IQR) in TDA (take drug again) effect ($E_{max}$) of about −5 to about 5.

310. The solid oral extended release pharmaceutical dosage form of any of the preceding embodiments, the dosage form comprising 60 mg of morphine hemi(sulfate pentahydrate) (having a molecular weight of 758.8 g/mol) or an equimolar amount of another solvate or hydrate of morphine sulfate, wherein intranasal administration of the dosage form as finely crushed powder as compared to oral administration of the dosage form intact has a median difference (IQR) in TDA (take drug again) effect ($E_{max}$) of about −47 to about 0.

311. The solid oral extended release pharmaceutical dosage form of embodiment 310, wherein intranasal administration of the dosage form as finely crushed powder as compared to oral administration of the dosage form intact has a median difference (IQR) in TDA (take drug again) effect ($E_{max}$) of about −25 to about −15.

312. The solid oral extended release pharmaceutical dosage form of any of the preceding embodiments, the dosage form comprising 60 mg of morphine hemi(sulfate pentahydrate) (having a molecular weight of 758.8 g/mol) or an equimolar amount of another solvate or hydrate of morphine sulfate, wherein oral administration of the dosage form intact as compared to intranasal administration of the commercial product MS Contin® containing an equimolar amount of morphine sulfate as finely crushed powder has a median difference (IQR) in TDA (take drug again) effect ($E_{max}$) of about −33 to about 0.

313. The solid oral extended release pharmaceutical dosage form of embodiment 312, wherein oral administration of the dosage form intact as compared to intranasal administration of the commercial product MS Contin® containing an equimolar amount of morphine sulfate as finely crushed powder has a median difference (IQR) in TDA (take drug again) effect ($E_{max}$) of about −27 to about −20.

314. The solid oral extended release pharmaceutical dosage form of any of the preceding embodiments, the dosage form comprising 60 mg of morphine hemi(sulfate pentahydrate) (having a molecular weight of 758.8 g/mol) or an equimolar amount of another solvate or hydrate of morphine sulfate, wherein intranasal administration of the dosage form as finely crushed powder as compared to intranasal administration of the commercial product MS Contin® containing an equimolar amount of morphine sulfate as finely crushed powder has a median difference (IQR) in TDA (take drug again) effect ($E_{max}$) of about −50 to about −22.

315. The solid oral extended release pharmaceutical dosage form of embodiment 314, wherein intranasal administration of the dosage form as finely crushed powder as compared to intranasal administration of the commercial product MS Contin® containing an equimolar amount of morphine sulfate as finely crushed powder has a median difference (IQR) in TDA (take drug again) effect ($E_{max}$) of about −40 to about −30.

316. An extended release matrix formulation obtainable by:
(a) combining at least a therapeutically effective amount of morphine sulfate and polyethylene oxide particles to form a composition, and
(b) shaping the composition of step (a) to form the extended release matrix formulation.

317. The extended release matrix formulation of embodiment 316 for use in the preparation of a solid oral extended release pharmaceutical dosage form by means of curing the shaped extended release matrix formulation of step (b).

318. The extended release matrix formulation of embodiment 316 or 317, wherein about 50% or more of the polyethylene oxide particles used in step (a) pass through a 60 mesh (0.250 mm; 250 microns) sieve.

319. The extended release matrix formulation of embodiment 319, wherein about 70% or more of the polyethylene oxide particles used in step (a) pass through a 60 mesh (0.250 mm; 250 microns) sieve.

320. The extended release matrix formulation of embodiment 319, wherein about 90% or more of the polyethylene oxide particles used in step (a) pass through a 60 mesh (0.250 mm; 250 microns) sieve.

321. The extended release matrix formulation of any of embodiments 316 to 320, wherein the polyethylene oxide used as the polyethylene oxide particles in step (a) has an approximate molecular weight of from about 600,000 to about 3,000,000.

322. The extended release matrix formulation of embodiment 321, wherein the polyethylene oxide used as the polyethylene oxide particles in step (a) has an approximate molecular weight of from about 900,000 to about 2,000,000.

323. The extended release matrix formulation of embodiment 322, wherein the polyethylene oxide used as the polyethylene oxide particles in step (a) has an approximate molecular weight of from about 1,000,000 to about 2,000,000.

324. The extended release matrix formulation of any of embodiments 316 to 323, wherein one or more of the following polyethylene oxide grades are used as the polyethylene oxide particles in step (a):

polyethylene oxide having an approximate molecular weight of about 900,000 and/or showing a viscosity in the range of 8,800 to 17,600 mPa s (cP) when the viscosity of a 5% (by weight) aqueous solution of said polyethylene oxide is determined using a Brookfield viscometer Model RVF, spindle No. 2, at 2 rpm, at 25° C.;

polyethylene oxide having an approximate molecular weight of about 1,000,000 and/or showing a viscosity in the range of 400 to 800 mPa s (cP) when the viscosity of a 2% (by weight) aqueous solution of said polyethylene oxide is determined using a Brookfield viscometer Model RVF, spindle No. 1, at 10 rpm, at 25° C.; and polyethylene oxide having an approximate molecular weight of about 2,000,000 and/or showing a viscosity in the range of 2,000 to 4,000 mPa s (cP) when the viscosity of a 2% (by weight) aqueous solution of said polyethylene oxide is determined using a Brookfield viscometer Model RVF, spindle No. 3, at 10 rpm, at 25° C.

325. The extended release matrix formulation of any of embodiments 316 to 324, wherein the polyethylene oxide particles used in step (a) originate from a single grade of polyethylene oxide.

326. The extended release matrix formulation of any of embodiments 316 to 324, wherein the polyethylene oxide particles used in step (a) originate from a combination of two or more grades of polyethylene oxide.

327. The extended release matrix formulation of any of embodiments 316 to 326, wherein step (b) comprises dry compression of the composition.

328. The extended release matrix formulation of embodiment 327, wherein the compression force applied is from about 2 to about 14 kN.

329. The extended release matrix formulation of any of embodiments 316 to 328, comprising morphine sulfate in the form of morphine hemi(sulfate pentahydrate) (having a molecular weight of 758.8 g/mol) in an amount of about 15 mg included into the extended release matrix formulation or an equimolar amount of another solvate or hydrate of morphine sulfate, and having a breaking strength of at least about 70 N and/or a cracking force of at least about 140 N and/or a penetration depth to crack of at least about 1.1 mm.

330. The extended release matrix formulation of embodiment 329, having a breaking strength of at least about 90 N and/or a cracking force of at least about 150 N and/or a penetration depth to crack of at least about 1.2 mm.

331. The extended release matrix formulation of embodiment 330, having a breaking strength of at least about 100 N and/or a cracking force of at least about 160 N and/or a penetration depth to crack of at least about 1.3 mm.

332. The extended release matrix formulation of any of embodiments 316 to 328, comprising morphine sulfate in the form of morphine hemi(sulfate pentahydrate) (having a molecular weight of 758.8 g/mol) in an amount of about 30 mg included into the extended release matrix formulation or an equimolar amount of another solvate or hydrate of morphine sulfate, and having a breaking strength of at least about 80 N and/or a cracking force of at least about 110 N and/or a penetration depth to crack of at least about 1.1 mm.

333. The extended release matrix formulation of embodiment 332, having a breaking strength of at least about 100 N and/or a cracking force of at least about 120 N and/or a penetration depth to crack of at least about 1.2 mm.

334. The extended release matrix formulation of embodiment 333, having a breaking strength of at least about 120 N and/or a cracking force of at least about 130 N and/or a penetration depth to crack of at least about 1.3 mm.

335. The extended release matrix formulation of embodiments 316 to 328, comprising morphine sulfate in the form of morphine hemi(sulfate pentahydrate) (having a molecular weight of 758.8 g/mol) in an amount of about 60 mg included into the extended release matrix formulation or an equimolar amount of another solvate or hydrate of morphine sulfate, and having a breaking strength of at least about 100 N and/or a cracking force of at least about 130 N and/or a penetration depth to crack of at least about 1.0 mm.

336. The extended release matrix formulation of embodiment 335, having a breaking strength of at least about 120 N and/or a cracking force of at least about 140 N and/or a penetration depth to crack of at least about 1.05 mm.

337. The extended release matrix formulation of embodiment 336, having a breaking strength of at least about 135 N and/or a cracking force of at least about 150 N and/or a penetration depth to crack of at least about 1.1 mm.

338. The extended release matrix formulation of any of embodiments 316 to 328, comprising morphine sulfate in the form of morphine hemi(sulfate pentahydrate) (having a molecular weight of 758.8 g/mol) in an amount of about 100 mg included into the extended release matrix formulation or an equimolar amount of another solvate or hydrate of morphine sulfate, and having a breaking strength of at least about 80 N and/or a cracking force of at least about 100 N and/or a penetration depth to crack of at least about 0.7 mm.

339. The extended release matrix formulation of embodiment 338, having a breaking strength of at least about 100 N and/or a cracking force of at least about 105 N and/or a penetration depth to crack of at least about 0.75 mm.

340. The extended release matrix formulation of embodiment 339, having a breaking strength of at least about 120 N and/or a cracking force of at least about 110 N and/or a penetration depth to crack of at least about 0.8 mm.

341. The extended release matrix formulation of any of embodiments 316 to 328, comprising morphine sulfate in the form of morphine hemi(sulfate pentahydrate) (having a molecular weight of 758.8 g/mol) in an amount of about 200 mg included into the extended release matrix formulation or an equimolar amount of another solvate or hydrate of morphine sulfate, and having a breaking strength of at least about 110 N and/or a cracking force of at least about 100 N and/or a penetration depth to crack of at least about 0.9 mm.

342. The extended release matrix formulation of embodiment 341, having a breaking strength of at least about 125 N and/or a cracking force of at least about 115 N and/or a penetration depth to crack of at least about 1.0 mm.

343. The extended release matrix formulation of embodiment 342, having a breaking strength of at least about 140 N and/or a cracking force of at least about 130 N and/or a penetration depth to crack of at least about 1.1 mm.

344. A method of treating pain in a subject in need thereof, the method comprising administering to the subject the solid oral extended release pharmaceutical dosage form according to any of embodiments 1 to 315.

345. The method of treating pain of embodiment 344, the method comprising administering the solid oral extended release dosage form to the subject twice a day or every 12 hours.

346. The method of treating pain of embodiment 345, the method comprising administering the solid oral extended release dosage form to the subject three times a day or every 8 hours.

347. The method of treating pain of any of embodiments 344 to 346, wherein the analgesic effect lasts for at least about 8 hours.

348. The method of treating pain of any of embodiments 344, 345 and 347, wherein the analgesic effect lasts for at least about 12 hours.

349. A process of preparing a solid oral extended release pharmaceutical dosage form comprising a cured extended release matrix formulation, wherein the extended release matrix formulation comprises:
   a therapeutically effective amount of morphine sulfate, and
   polyethylene oxide,
the process comprising at least the following steps:
   (a) combining at least morphine sulfate and polyethylene oxide particles to form a composition,
   (b) shaping the composition of step (a) to form the extended release matrix formulation, and
   (c) curing the extended release matrix formulation of step (b).

350. The process of embodiment 349, wherein about 50% or more of the polyethylene oxide particles used in step (a) pass through a 25 mesh (0.707 mm; 707 microns) sieve.

351. The process of embodiment 350, wherein about 70% or more of the polyethylene oxide particles used in step (a) pass through a 25 mesh (0.707 mm: 707 microns) sieve.

352. The process of embodiment 351, wherein about 90% or more of the polyethylene oxide particles used in step (a) pass through a 25 mesh (0.707 mm; 707 microns) sieve.

353. The process of any of embodiments 349 to 352, wherein about 50% or more of the polyethylene oxide particles used in step (a) pass through a 35 mesh (0.500 mm; 500 microns) sieve.

354. The process of embodiment 353, wherein about 70% or more of the polyethylene oxide particles used in step (a) pass through a 35 mesh (0.500 mm; 500 microns) sieve.

355. The process of embodiment 354, wherein about 90% or more of the polyethylene oxide particles used in step (a) pass through a 35 mesh (0.500 mm; 500 microns) sieve.

356. The process of any of embodiments 349 to 355, wherein about 50% or more of the polyethylene oxide particles used in step (a) pass through a 60 mesh (0.250 mm; 250 microns) sieve.

357. The process of embodiment 356, wherein about 70% or more of the polyethylene oxide particles used in step (a) pass through a 60 mesh (0.250 mm; 250 microns) sieve.

358. The process of embodiment 357, wherein about 90% or more of the polyethylene oxide particles used in step (a) pass through a 60 mesh (0.250 mm; 250 microns) sieve.

359. The process of embodiment 358, wherein about 96% or more of the polyethylene oxide particles used in step (a) pass through a 60 mesh (0.250 mm; 250 microns) sieve.

360. The process of any of embodiments 349 to 359, wherein the polyethylene oxide used as the polyethylene oxide particles in step (a) has an approximate molecular weight of from about 600,000 to about 3,000,000.

361. The process of embodiment 360, wherein the polyethylene oxide used as the polyethylene oxide particles in step (a) has an approximate molecular weight of from about 900,000 to about 2,000,000.

362. The process of embodiment 361, wherein the polyethylene oxide used as the polyethylene oxide particles in step (a) has an approximate molecular weight of from about 1,000,000 to about 2,000,000.

363. The process of any of embodiments 349 to 362, wherein the polyethylene oxide particles used in step (a) originate from a single grade of polyethylene oxide or from a combination of two or more grades of polyethylene oxide.

364. The process of embodiment 363, wherein one or more of the following polyethylene oxide grades are used as the polyethylene oxide particles in step (a):
polyethylene oxide having an approximate molecular weight of about 900,000 and/or showing a viscosity in the range of 8,800 to 17,600 mPa s (cP) when the viscosity of a 5% (by weight) aqueous solution of said polyethylene oxide is determined using a Brookfield viscometer Model RVF, spindle No. 2, at 2 rpm, at 25° C.:
polyethylene oxide having an approximate molecular weight of about 1,000,000 and/or showing a viscosity in the range of 400 to 800 mPa s (cP) when the viscosity of a 2% (by weight) aqueous solution of said polyethylene oxide is determined using a Brookfield viscometer Model RVF, spindle No. 1, at 10 rpm, at 25° C.; and
polyethylene oxide having an approximate molecular weight of about 2,000,000 and/or showing a viscosity in the range of 2,000 to 4,000 mPa s (cP) when the viscosity of a 2% (by weight) aqueous solution of said polyethylene oxide is determined using a Brookfield viscometer Model RVF, spindle No. 3, at 10 rpm, at 25° C.

365. The process of any of embodiments 349 to 364, wherein step (c) comprises subjecting the extended release matrix formulation to a temperature which is at least the softening temperature of the polyethylene oxide.

366. The process of any of embodiments 349 to 365, wherein in step (c) the extended release matrix formulation is subjected to a temperature of from about 65° C. to about 85° C. for a period of from about 15 minutes to about 2 hours.

367. The process of embodiment 366, wherein in step (c) the extended release matrix formulation is subjected to a temperature of from about 70° C. to about 80° C. for a period of from about 20 minutes to about 1 hour.

368. The process of embodiment 367, wherein in step (c) the extended release matrix formulation is subjected to a temperature of from about 72° C. to about 78° C. for a period of from about 25 minutes to about 60 minutes.

369. The process of any of embodiments 365 to 368, wherein in step (c) at least about 20% of the polyethylene oxide melts.

370. The process of embodiment 369, wherein least about 40% of the polyethylene oxide melts.

371. The process of embodiment 370, wherein least about 75% of the polyethylene oxide melts.

372. The process of embodiment 371, wherein about 100% of the polyethylene oxide melts.

373. The process of any of embodiments 349 to 372, wherein in step (b) the composition is shaped by means of dry compression.

374. The process of embodiment 373, wherein in step (b) the composition is shaped to form an extended release matrix formulation in the form of a tablet.

375. The process of embodiment 374, wherein the length of the tablet is greater than the width and the thickness of the tablet, and the thickness of the tablet is less than or equal to the width of the tablet.

376. The process of embodiment 375, wherein the length of the tablet is at least about twice the width and about four times the thickness of the tablet.

377. The process of embodiment 376, wherein the width of the tablet is at least about three times the thickness of the tablet.

378. The process of any of embodiments 374 to 377, wherein the tablet is an oval or oblong tablet.

379. The process of any of embodiments 374 to 378 wherein the surface of one or both of the faces of the tablet is convex or has convex portions.

380. The process of embodiment 378 or 379, wherein the surface of one or both of the faces of the tablet has convex and concave portions.

381. The process of embodiment 380, wherein the concave portions extend along the central axis of the tablet defined by half the width of the tablet.

382. The process of embodiment 380 or 381, wherein the minimal thickness of the tablet in the concave portions is not less than 0.25 times the maximum thickness of the tablet.

383. The process of any of embodiments 349 to 382, comprising a further step (d) of coating the cured extended release matrix formulation of step (c) with one or more coatings.

384. The process of any of embodiments 349 to 383, wherein the polyethylene oxide is included in the extended release matrix formulation in an amount of about 55 to about 95% by weight thereof.

385. The process of embodiment 384, wherein the polyethylene oxide is included in the extended release matrix formulation in an amount of about 60 to about 90% by weight thereof.

386. The process of embodiment 385, wherein the polyethylene oxide is included in the extended release matrix formulation in an amount of about 78 to about 90% by weight thereof.

387. The process of embodiment 385, wherein the polyethylene oxide is included in the extended release matrix formulation in an amount of about 60 to about 70% by weight thereof.

388. The process of any of embodiments 349 to 387, wherein the morphine sulfate is included in the extended release matrix formulation in the form of morphine hemi(sulfate pentahydrate) (having a molecular weight of 758.8 g/mol) in an amount of about 5 to about 40% by weight of the extended release matrix formulation or in an equimolar amount of another solvate or hydrate of morphine sulfate.

389. The process of embodiment 388, wherein the morphine sulfate is included in the extended release matrix formulation in the form of morphine hemi(sulfate pentahydrate) (having a molecular weight of 758.8 g/mol) in an amount of about 8 to about 35% by weight of the extended release matrix formulation or in an equimolar amount of another solvate or hydrate of morphine sulfate.

390. The process of embodiment 389, wherein the morphine sulfate is included in the extended release matrix formulation in the form of morphine hemi(sulfate pentahydrate) (having a molecular weight of 758.8 g/mol) in an amount of about 10 to about 20% by weight of the extended release matrix formulation or in an equimolar amount of another solvate or hydrate of morphine sulfate.

391. The process of embodiment 389, wherein the morphine sulfate is included in the extended release matrix formulation in the form of morphine hemi(sulfate pentahydrate) (having a molecular weight of 758.8 g/mol) in an amount of about 25 to about 35% by weight of the extended release matrix formulation or in an equimolar amount of another solvate or hydrate of morphine sulfate.

392. The process of any of embodiments 349 to 391, wherein the morphine sulfate and the polyethylene oxide are included in the extended release matrix formulation in a weight ratio of from about 1:100 to about 1:1, calculated on the basis of the amount of morphine hemi(sulfate pentahydrate) (having a molecular weight of 758.8 g/mol) and the amount of polyethylene oxide included into the extended release matrix formulation.

393. The process of embodiment 392, wherein the morphine sulfate and the polyethylene oxide are included in the extended release matrix formulation in a weight ratio of from about 1:20 to about 1:1.25.

394. The process of embodiment 393, wherein the morphine sulfate and the polyethylene oxide are included in the extended release matrix formulation in a weight ratio of from about 1:10 to about 1:1.7.

395. The process of embodiment 383, wherein the or at least one of the coating(s) in step (d) is a film coat.

396. The process of embodiment 383 or 395, wherein the one or more coating(s) in step (d) represent(s) about 5% by weight or less of the entire solid oral extended release pharmaceutical dosage form.

397. The process of embodiment 395 or 396, wherein the film coat comprises hydroxypropylmethylcellulose, polyethylene glycol, polyvinyl alcohol, talc, pigments, or any mixture of two of more thereof.

398. The process of any of embodiments 349 to 397, wherein in step (a) one or more pharmaceutically acceptable excipients is/are combined with morphine sulfate and polyethylene oxide.

399. The process of embodiment 398, wherein in step (a) a lubricant is added.

400. The process of embodiment 399, wherein the lubricant is included the extended release matrix formulation in an amount of about 0.1 to about 5% by weight thereof.

401. The process of embodiment 400, wherein the lubricant is included the extended release matrix formulation in an amount of about 0.5 to about 3% by weight thereof.

402. The process of embodiment 401 wherein the lubricant is included the extended release matrix formulation in an amount of about 0.75 to about 2% by weight thereof.

403. The process of any of embodiments 399 to 402, wherein the lubricant is or comprises magnesium stearate.

404. The process of any of embodiments 398 to 403, wherein in step (a) a glidant is added.

405. The process of embodiment 404, wherein the glidant is included the extended release matrix formulation in an amount of about 0.1 to about 2.5% by weight thereof.

406. The process of embodiment 405, wherein the glidant is included the extended release matrix formulation in an amount of about 0.25 to about 1% by weight thereof.

407. The process of embodiment 406, wherein the glidant is included the extended release matrix formulation in an amount of about 0.4 to about 0.6% by weight thereof.

408. The process of any of embodiments 404 to 407, wherein the glidant is or comprises colloidal silicon dioxide.

409. A method of increasing the breaking strength and/or cracking force and/or crush resistance of a solid oral extended release pharmaceutical dosage form comprising an extended release matrix formulation, the extended release matrix formulation comprising:

a therapeutically effective amount of morphine or a pharmaceutically acceptable salt thereof and
polyethylene oxide,
wherein the dosage form is obtainable by at least the following steps:
(a) combining at least morphine or a pharmaceutically acceptable salt thereof and polyethylene oxide particles to form a composition, and
(b) shaping the composition of step (a) to form the extended release matrix formulation, the method being characterized in that about 50% or more of the polyethylene oxide particles used in step (a) pass through a 25 mesh (0.707 mm; 707 microns) sieve.

410. Use of polyethylene oxide particles for increasing the breaking strength and/or cracking force and/or crush resistance of a solid oral extended release pharmaceutical dosage form comprising an extended release matrix formulation, the extended release matrix formulation comprising:
a therapeutically effective amount of morphine or a pharmaceutically acceptable salt thereof and
polyethylene oxide,
wherein the dosage form is obtainable by at least the following steps:
(a) combining at least morphine or a pharmaceutically acceptable salt thereof and polyethylene oxide particles to form a composition, and
(b) shaping the composition of step (a) to form the extended release matrix formulation, wherein the polyethylene oxide particles used in step (a) are characterized in that about 50% or more of the polyethylene oxide particles pass through a 25 mesh (0.707 mm; 707 microns) sieve.

411. The method of embodiment 409 or the use of embodiment 410, wherein about 50% or more of the polyethylene oxide particles used in step (a) pass through a 35 mesh (0.500 mm; 500 microns) sieve.

412. The method of embodiment 409 or the use of embodiment 410, wherein about 50% or more of the polyethylene oxide particles used in step (a) pass through a 60 mesh (0.250 mm; 250 microns) sieve.

413. The method or use of embodiment 412, wherein about 70% or more of the polyethylene oxide particles used in step (a) pass through a 60 mesh (0.250 mm; 250 microns) sieve.

414. The method or use of embodiment 413, wherein about 90% or more of the polyethylene oxide particles used in step (a) pass through a 60 mesh (0.250 mm; 250 microns) sieve.

415. The method or use of embodiment 414, wherein about 96% or more of the polyethylene oxide particles used in step (a) pass through a 60 mesh (0.250 mm; 250 microns) sieve.

416. The method of any of embodiments 409 and 411 to 415 or the use of any of embodiments 410 to 415, wherein the breaking strength is increased to at least about 200 N and/or the cracking force is increased to at least about 150 N and/or the crush resistance is increased to at least about 400 N.

417. The method or use of embodiment 416, wherein the breaking strength is increased to at least about 250 N and/or the cracking force is increased to at least about 170 N and/or the crush resistance is increased to at least about 500 N.

418. The method or use of embodiment 417, wherein the breaking strength is increased to at least about 300 N and/or the cracking force is increased to at least about 200 N.

419. The method or use of embodiment 418, wherein the breaking strength is increased to at least about 350 N and/or the cracking force is increased to at least about 215 N.

420. The method or use of embodiment 419, wherein the breaking strength is increased to at least about 400 N and/or the cracking force is increased to at least about 230 N.

421. The method of any of embodiments 409 and 411 to 420 or the use of any of embodiments 410 to 420, wherein the extended release matrix formulation comprises morphine sulfate.

422. The method or use of embodiment 421, wherein the morphine sulfate is included in the extended release matrix formulation in the form of morphine hemi(sulfate pentahydrate) (having a molecular weight of 758.8 g/mol) or another solvate or hydrate of morphine sulfate.

423. The method of any of embodiments 409 and 411 to 422 or the use of any of embodiments 410 to 422, wherein the polyethylene oxide used as the polyethylene oxide particles in step (a) has an approximate molecular weight of from about 600,000 to about 3,000,000.

424. The method or use of embodiment 423, wherein the polyethylene oxide used as the polyethylene oxide particles in step (a) has an approximate molecular weight of from about 900,000 to about 2,000,000.

425. The method or use of embodiment 424, wherein the polyethylene oxide used as the polyethylene oxide particles in step (a) has an approximate molecular weight of about 1,000,000 or about 2,000,000.

426. The method of any of embodiments 409 and 411 to 425 or the use of any of embodiments 410 to 425, wherein the dosage form is obtainable by additionally: (c) curing the extended release matrix formulation.

427. The method or use of embodiment 426, wherein in step (c) the extended release matrix formulation is subjected to a temperature of from about 65° C. to about 85° C. for a period of from about 15 minutes to about 2 hours.

428. The method or use of embodiment 427, wherein in step (c) the extended release matrix formulation is subjected to a temperature of from about 70° C. to about 80° C. for a period of from about 25 minutes to about 1 hour.

429. The method or use of embodiment 428, wherein in step (c) the extended release matrix formulation is subjected to a temperature of from about 72° C. to about 78° C. for a period of from about 30 minutes to about 45 minutes.

430. A method for preventing or reducing recovery of morphine sulfate from a morphine sulfate containing solid oral extended release pharmaceutical dosage form by means of subjecting the dosage form to dissolution in water or saline and aspirating the resulting solution in a needle, the method comprising, in the preparation of the dosage form, the following steps:
(a) combining at least morphine sulfate and polyethylene oxide particles to form a composition,
(b) shaping the composition of step (a) to form an extended release matrix formulation, and
(c) curing the extended release matrix formulation of step (b) to form the dosage form.

431. The method of embodiment 430, wherein the needle is a 27 or smaller gauge (larger diameter) needle.

432. The method of embodiment 431, wherein the needle is a 27, 25, 22 or 18 gauge needle.

433. The method of any of embodiments 430 to 432, wherein the polyethylene oxide particles used in step (a) are characterized in that about 50% or more of the polyethylene oxide particles pass through a 60 mesh (0.250 mm; 250 microns) sieve.

434. The method of embodiment 433, wherein the polyethylene oxide particles used in step (a) are characterized in that about 70% or more of the polyethylene oxide particles pass through a 60 mesh (0.250 mm; 250 microns) sieve.

435. The method of embodiment 434, wherein the polyethylene oxide particles used in step (a) are characterized in that about 90% or more of the polyethylene oxide particles pass through a 60 mesh (0.250 mm; 250 microns) sieve.

436. The method of embodiment 435, wherein the polyethylene oxide particles used in step (a) are characterized in that about 96% or more of the polyethylene oxide particles pass through a 60 mesh (0.250 mm; 250 microns) sieve.

437. A solid oral extended release pharmaceutical dosage form comprising a cured extended release matrix formulation, the extended release matrix formulation comprising:
  a therapeutically effective amount of morphine sulfate, and
  polyethylene oxide,
the dosage form after administration providing a dose adjusted $C_{max}$ of morphine of from about 3 ng/mL to about 9 ng/mL per 15 mg of morphine hemi(sulfate pentahydrate) (having a molecular weight of 758.8 g/mol) or an equimolar amount of another solvate or hydrate of morphine sulfate included in the dosage form.

438. The solid oral extended release pharmaceutical dosage form of embodiment 437, the dosage form after administration providing a dose adjusted $C_{max}$ of morphine of from about 5 ng/mL to about 7 ng/mL per 15 mg of morphine hemi(sulfate pentahydrate) (having a molecular weight of 758.8 g/mol) or an equimolar amount of another solvate or hydrate of morphine sulfate included in the dosage form.

439. A solid oral extended release pharmaceutical dosage form comprising a cured extended release matrix formulation, the extended release matrix formulation comprising:
  a therapeutically effective amount of morphine sulfate, and
  polyethylene oxide,
the dosage form after administration providing a dose adjusted $AUC_t$ and/or a dose adjusted $AUC_{inf}$ of morphine of from about 30 ng*hr/mL to about 100 ng*hr/mL per 15 mg of morphine hemi(sulfate pentahydrate) (having a molecular weight of 758.8 g/mol) or an equimolar amount of another solvate or hydrate of morphine sulfate included in the dosage form.

440. The solid oral extended release pharmaceutical dosage form of embodiment 439, the dosage form after administration providing a dose adjusted $AUC_t$ and/or a dose adjusted $AUC_{inf}$ of morphine of from about 40 ng*hr/mL to about 80 ng*hr/mL per 15 mg of morphine hemi(sulfate pentahydrate) (having a molecular weight of 758.8 g/mol) or an equimolar amount of another solvate or hydrate of morphine sulfate included in the dosage form.

441. A solid oral extended release pharmaceutical dosage form comprising a therapeutically effective amount of morphine,
the dosage form after administration providing:
  a dose adjusted $C_{max}$ of morphine of from about 3 ng/mL to about 9 ng/mL and/or
  a dose adjusted $AUC_t$ of morphine of from about 30 ng*hr/mL to about 100 ng*hr/mL and/or
  a dose adjusted $AUC_{inf}$ of morphine of from about 30 ng*hr/mL to about 100 ng*hr/mL
  per 15 mg of morphine hemi(sulfate pentahydrate) (having a molecular weight of 758.8 g/mol) or an equimolar amount of another pharmaceutically acceptable morphine salt or solvate or hydrate thereof included in the dosage form, and
the dosage form having a breaking strength of least about 200 N.

442. The solid oral extended release pharmaceutical dosage form of embodiment 441, having a breaking strength of at least about 300 N.

443. The solid oral extended release pharmaceutical dosage form of embodiment 442, having a breaking strength of at least about 400 N.

444. A solid oral extended release pharmaceutical dosage form comprising a therapeutically effective amount of morphine,
the dosage form after administration providing:
  a dose adjusted $C_{max}$ of morphine of from about 3 ng/mL to about 9 ng/mL and/or
  a dose adjusted $AUC_t$ of morphine of from about 30 ng*hr/mL to about 100 ng*hr/mL and/or
  a dose adjusted $AUC_{inf}$ of morphine of from about 30 ng*hr/mL to about 100 ng*hr/mL
  per 15 mg of morphine hemi(sulfate pentahydrate) (having a molecular weight of 758.8 g/mol) or an equimolar amount of another pharmaceutically acceptable morphine salt or solvate or hydrate thereof included in the dosage form, and
the dosage form having a cracking force of least about 150 N.

445. The solid oral extended release pharmaceutical dosage form of embodiment 444, having a cracking force of least about 200 N.

446. The solid oral extended release pharmaceutical dosage form of embodiment 445, having a cracking force of least about 230 N.

447. A solid oral extended release pharmaceutical dosage form comprising a therapeutically effective amount of morphine,
the dosage form after administration providing:
  a dose adjusted $C_{max}$ of morphine of from about 3 ng/mL to about 9 ng/mL and/or
  a dose adjusted $AUC_t$ of morphine of from about 30 ng*hr/mL to about 100 ng*hr/mL and/or
  a dose adjusted $AUC_{inf}$ of morphine of from about 30 ng*hr/mL to about 100 ng*hr/mL
  per 15 mg of morphine hemi(sulfate pentahydrate) (having a molecular weight of 758.8 g/mol) or an equimolar amount of another pharmaceutically acceptable morphine salt or solvate or hydrate thereof included in the dosage form, and
the dosage form having a crush resistance of least about 500 N.

448. The solid oral extended release pharmaceutical dosage form of any of embodiments 441 to 447, the dosage form after administration providing:
  a dose adjusted $C_{max}$ of morphine of from about 5 ng/mL to about 7 ng/mL and/or
  a dose adjusted $AUC_t$ of morphine of from about 40 ng*hr/mL to about 80 ng*hr/mL and/or
  a dose adjusted $AUC_{inf}$ of morphine of from about 40 ng*hr/m L to about 80 ng*hr/mL per 15 mg of morphine hemi(sulfate pentahydrate) (having a molecular weight of 758.8 g/mol) or an equimolar amount of another pharmaceutically acceptable morphine salt or solvate or hydrate thereof included in the dosage form.

449. A solid oral extended release pharmaceutical dosage form comprising:
  a therapeutically effective amount of morphine sulfate, and
  polyethylene oxide,
wherein the dosage form provides an in-vitro dissolution rate of morphine sulfate, when measured in a USP Apparatus 1 (basket) at 100 rpm in 900 ml simulated gastric fluid without enzymes (SGF) at 37° C., characterized by the amount of morphine sulfate released from the dosage form, of from about 5% to about 35% released after 0.5 hour;
from about 18% to about 50% released after 1 hour;
from about 29% to about 70% released after 2 hours;
from about 40% to about 85% released after 3 hours;
from about 49% to about 95% released after 4 hours;
greater than about 65% released after 6 hours;
greater than about 70% released after 8 hours;
greater than about 75% released after 9 hours; and/or
greater than about 85% released after 12 hours.

450. A solid oral extended release pharmaceutical dosage form comprising:
a therapeutically effective amount of morphine sulfate, and
polyethylene oxide,
the dosage form providing an in-vitro dissolution rate of morphine sulfate, when measured in a USP Apparatus 1 (basket) at 100 rpm in 900 ml simulated gastric fluid without enzymes (SGF) at 37° C., characterized by the amount of morphine sulfate released from the dosage form, of:
from about 18% to about 21% released after 0.5 hour;
from about 29% to about 33% released after 1 hour;
from about 48% to about 53% released after 2 hours;
from about 65% to about 69% released after 3 hours;
from about 77% to about 83% released after 4 hours;
from about 90% to about 97% released after 6 hours; and/or
greater than about 98% released after 9 hours.

451. The solid oral extended release pharmaceutical dosage form of any of embodiments 1 to 315 or embodiment 449, the dosage form providing an in-vitro dissolution rate of morphine sulfate, when measured in a USP Apparatus 1 (basket) at 100 rpm in 900 ml simulated gastric fluid without enzymes (SGF) at 37° C., characterized by the amount of morphine sulfate released from the dosage form, of:
from about 18% to about 21% released after 0.5 hour;
from about 29% to about 33% released after 1 hour;
from about 48% to about 53% released after 2 hours;
from about 65% to about 69% released after 3 hours;
from about 77% to about 83% released after 4 hours;
from about 90% to about 97% released after 6 hours; and/or
greater than about 98% released after 9 hours.

452. The solid oral extended release pharmaceutical dosage form of embodiment 450 or 451, the dosage form providing an in-vitro dissolution rate of morphine sulfate, when measured in a USP Apparatus 1 (basket) at 100 rpm in 900 ml simulated gastric fluid without enzymes (SGF) at 37° C., characterized by the amount of morphine sulfate released from the dosage form, of:
from about 19% to about 20% released after 0.5 hour;
from about 30% to about 32% released after 1 hour;
from about 49% to about 52% released after 2 hours;
from about 66% to about 68% released after 3 hours;
from about 78% to about 82% released after 4 hours; and/or
from about 91% to about 95% released after 6 hours.

453. The solid oral extended release pharmaceutical dosage form of any of embodiments 450 to 452, comprising 15 mg of morphine hemi(sulfate pentahydrate) (having a molecular weight of 758.8 g/mol) or an equimolar amount of another solvate or hydrate of morphine sulfate included into the dosage form.

454. A solid oral extended release pharmaceutical dosage form comprising:
a therapeutically effective amount of morphine sulfate, and
polyethylene oxide,
the dosage form providing an in-vitro dissolution rate of morphine sulfate, when measured in a USP Apparatus 1 (basket) at 100 rpm in 900 ml simulated gastric fluid without enzymes (SGF) at 37° C. characterized by the amount of morphine sulfate released from the dosage form, of:
from about 14% to about 17% released after 0.5 hour;
from about 25% to about 28% released after 1 hour;
from about 41% to about 46% released after 2 hours;
from about 56% to about 61% released after 3 hours;
from about 70% to about 75% released after 4 hours;
from about 87% to about 92% released after 6 hours; and/or
greater than about 98% released after 9 hours.

455. The solid oral extended release pharmaceutical dosage form of any of embodiments 1 to 315 or embodiment 449, the dosage form providing an in-vitro dissolution rate of morphine sulfate, when measured in a USP Apparatus 1 (basket) at 100 rpm in 900 ml simulated gastric fluid without enzymes (SGF) at 37° C., characterized by the amount of morphine sulfate released from the dosage form, of:
from about 14% to about 17% released after 0.5 hour;
from about 25% to about 28% released after 1 hour;
from about 41% to about 46% released after 2 hours;
from about 56% to about 61% released after 3 hours;
from about 70% to about 75% released after 4 hours;
from about 87% to about 92% released after 6 hours; and/or
greater than about 98% released after 9 hours.

456. The solid oral extended release pharmaceutical dosage form of embodiment 454 or 455, the dosage form providing an in-vitro dissolution rate of morphine sulfate, when measured in a USP Apparatus 1 (basket) at 100 rpm in 900 ml simulated gastric fluid without enzymes (SGF) at 37° C., characterized by the amount of morphine sulfate released from the dosage form, of:
from about 15% to about 16% released after 0.5 hour;
from about 26% to about 27% released after 1 hour;
from about 42% to about 45% released after 2 hours;
from about 57% to about 60% released after 3 hours;
from about 71% to about 74% released after 4 hours; and/or
from about 89% to about 91% released after 6 hours.

457. The solid oral extended release pharmaceutical dosage form of any of embodiments 454 to 456, comprising 30 mg of morphine hemi(sulfate pentahydrate) (having a molecular weight of 758.8 g/mol) or an equimolar amount of another solvate or hydrate of morphine sulfate included into the dosage form.

458. A solid oral extended release pharmaceutical dosage form comprising:
a therapeutically effective amount of morphine sulfate, and
polyethylene oxide,
the dosage form providing an in-vitro dissolution rate of morphine sulfate, when measured in a USP Apparatus 1 (basket) at 100 rpm in 900 ml simulated gastric fluid without enzymes (SGF) at 37° C., characterized by the amount of morphine sulfate released from the dosage form, of:
from about 13% to about 16% released after 0.5 hour;
from about 22% to about 25% released after 1 hour;
from about 36% to about 41% released after 2 hours;
from about 50% to about 55% released after 3 hours;
from about 60% to about 68% released after 4 hours;
from about 80% to about 87% released after 6 hours; and/or
greater than about 98% released after 9 hours.

459. The solid oral extended release pharmaceutical dosage form of any of embodiments 1 to 315 or embodiment 449, the dosage form providing an in-vitro dissolution rate of morphine sulfate, when measured in a USP Apparatus 1 (basket) at 100 rpm in 900 ml simulated gastric fluid without enzymes (SGF) at 37° C., characterized by the amount of morphine sulfate released from the dosage form, of:

from about 13% to about 16% released after 0.5 hour;
from about 22% to about 25% released after 1 hour;
from about 36% to about 41% released after 2 hours;
from about 50% to about 55% released after 3 hours;
from about 60% to about 68% released after 4 hours;
from about 80% to about 87% released after 6 hours; and/or
greater than about 98% released after 9 hours.

460. The solid oral extended release pharmaceutical dosage form of embodiment 458 or 459, the dosage form providing an in-vitro dissolution rate of morphine sulfate, when measured in a USP Apparatus 1 (basket) at 100 rpm in 900 ml simulated gastric fluid without enzymes (SGF) at 37° C., characterized by the amount of morphine sulfate released from the dosage form, of:
from about 14% to about 15% released after 0.5 hour;
from about 23% to about 24% released after 1 hour;
from about 37% to about 39% released after 2 hours;
from about 52% to about 54% released after 3 hours;
from about 64% to about 66% released after 4 hours; and/or
from about 82% to about 86% released after 6 hours.

461. The solid oral extended release pharmaceutical dosage form of any of embodiments 458 to 460, comprising 60 mg of morphine hemi(sulfate pentahydrate) (having a molecular weight of 758.8 g/mol) or an equimolar amount of another solvate or hydrate of morphine sulfate included into the dosage form.

462. A solid oral extended release pharmaceutical dosage form comprising:
  a therapeutically effective amount of morphine sulfate, and
  polyethylene oxide,
the dosage form providing an in-vitro dissolution rate of morphine sulfate, when measured in a USP Apparatus 1 (basket) at 100 rpm in 900 ml simulated gastric fluid without enzymes (SGF) at 37° C., characterized by the amount of morphine sulfate released from the dosage form, of:
from about 15% to about 19% released after 0.5 hour;
from about 25% to about 29% released after 1 hour;
from about 40% to about 46% released after 2 hours;
from about 56% to about 61% released after 3 hours;
from about 68% to about 73% released after 4 hours;
from about 87% to about 92% released after 6 hours; and/or
greater than about 98% released after 9 hours.

463. The solid oral extended release pharmaceutical dosage form of any of embodiments 1 to 315 or embodiment 449, the dosage form providing an in-vitro dissolution rate of morphine sulfate, when measured in a USP Apparatus 1 (basket) at 100 rpm in 900 ml simulated gastric fluid without enzymes (SGF) at 37° C., characterized by the amount of morphine sulfate released from the dosage form, of:
from about 15% to about 19% released after 0.5 hour;
from about 25% to about 29% released after 1 hour;
from about 40% to about 46% released after 2 hours;
from about 56% to about 61% released after 3 hours;
from about 68% to about 73% released after 4 hours;
from about 87% to about 92% released after 6 hours; and/or
greater than about 98% released after 9 hours.

464. The solid oral extended release pharmaceutical dosage form of embodiment 462 or 463, the dosage form providing an in-vitro dissolution rate of morphine sulfate, when measured in a USP Apparatus 1 (basket) at 100 rpm in 900 ml simulated gastric fluid without enzymes (SGF) at 37° C., characterized by the amount of morphine sulfate released from the dosage form, of:
from about 16% to about 18% released after 0.5 hour;
from about 26% to about 28% released after 1 hour;
from about 41% to about 45% released after 2 hours;
from about 57% to about 60% released after 3 hours;
from about 69% to about 72% released after 4 hours; and/or
from about 88% to about 91% released after 6 hours.

465. The solid oral extended release pharmaceutical dosage form of any of embodiments 462 to 464, comprising 100 mg of morphine hemi(sulfate pentahydrate) (having a molecular weight of 758.8 g/mol) or an equimolar amount of another solvate or hydrate of morphine sulfate included into the dosage form.

466. A solid oral extended release pharmaceutical dosage form comprising:
  a therapeutically effective amount of morphine sulfate, and
  polyethylene oxide,
the dosage form providing an in-vitro dissolution rate of morphine sulfate, when measured in a USP Apparatus 1 (basket) at 100 rpm in 900 ml simulated gastric fluid without enzymes (SGF) at 37° C., characterized by the amount of morphine sulfate released from the dosage form, of:
from about 10% to about 18% released after 0.5 hour;
from about 16% to about 25% released after 1 hour;
from about 30% to about 42% released after 2 hours;
from about 42% to about 53% released after 3 hours;
from about 52% to about 65% released after 4 hours;
from about 70% to about 85% released after 6 hours; and/or
greater than about 97% released after 9 hours.

467. The solid oral extended release pharmaceutical dosage form of any of embodiments 1 to 315 or embodiment 449, the dosage form providing an in-vitro dissolution rate of morphine sulfate, when measured in a USP Apparatus 1 (basket) at 100 rpm in 900 ml simulated gastric fluid without enzymes (SGF) at 37° C., characterized by the amount of morphine sulfate released from the dosage form, of:
from about 10% to about 18% released after 0.5 hour;
from about 16% to about 25% released after 1 hour;
from about 30% to about 42% released after 2 hours;
from about 42% to about 53% released after 3 hours;
from about 52% to about 65% released after 4 hours;
from about 70% to about 85% released after 6 hours; and/or
greater than about 97% released after 9 hours.

468. The solid oral extended release pharmaceutical dosage form of embodiment 466 or 467, the dosage form providing an in-vitro dissolution rate of morphine sulfate, when measured in a USP Apparatus 1 (basket) at 100 rpm in 900 ml simulated gastric fluid without enzymes (SGF) at 37° C., characterized by the amount of morphine sulfate released from the dosage form, of:
from about 11% to about 16% released after 0.5 hour;
from about 18% to about 25% released after 1 hour;
from about 31% to about 40% released after 2 hours;
from about 43% to about 50% released after 3 hours;
from about 54% to about 60% released after 4 hours; and/or
from about 72% to about 80% released after 6 hours.

469. The solid oral extended release pharmaceutical dosage form of any of embodiments 466 to 468, comprising 200 mg of morphine hemi(sulfate pentahydrate) (having a molecular weight of 758.8 g/mol) or an equimolar amount of another solvate or hydrate of morphine sulfate included into the dosage form.

470. The solid oral extended release pharmaceutical dosage form of any of embodiments 1 to 315 or 437 to 469, wherein recovery of the morphine sulfate is less than about 5% based on a syringeability test whereby one intact dosage form is subjected to dissolution in 10 mL of 40% or 95% ethanol with agitation at room temperature for 1 hour and the resultant solution is aspirated with an 18-gauge needle.

471. The solid oral extended release pharmaceutical dosage form of embodiment 470, wherein recovery of the morphine sulfate is less than about 3%.
472. The solid oral extended release pharmaceutical dosage form of embodiment 471, wherein recovery of the morphine sulfate is about 2% or less.
473. The solid oral extended release pharmaceutical dosage form of any of embodiments 1 to 315 or 437 to 472, wherein recovery of the morphine sulfate is less than about 15% based on a syringeability test whereby one intact dosage form is subjected to dissolution in 10 mL of 40% or 95% ethanol with agitation at 60° C. for 1 hour and the resultant solution is aspirated with an 18-gauge needle.
474. The solid oral extended release pharmaceutical dosage form of embodiment 473, wherein recovery of the morphine sulfate is less than about 10%.
475. The solid oral extended release pharmaceutical dosage form of embodiment 474, wherein recovery of the morphine sulfate is about 7% or less.
476. The solid oral extended release pharmaceutical dosage form of any of embodiments 1 to 315 or 437 to 475, wherein recovery of the morphine sulfate is less than about 3% based on a syringeability test whereby one milled dosage form is subjected to dissolution in 10 mL of 40% ethanol with agitation at room temperature or 60° C. for 30 minutes and the resultant solution is aspirated with a 27-gauge needle or an 18-gauge needle.
477. The solid oral extended release pharmaceutical dosage form of embodiment 476, wherein recovery of the morphine sulfate is less than about 2%.
478. The solid oral extended release pharmaceutical dosage form of embodiment 477, wherein recovery of the morphine sulfate is about 1% or less.
479. The solid oral extended release pharmaceutical dosage form of any of embodiments 1 to 315 or 437 to 478, wherein recovery of the morphine sulfate is less than about 35% based on a syringeability test whereby one milled dosage form is subjected to dissolution in 10 mL of 95% ethanol with agitation at room temperature for 30 minutes and the resultant solution is aspirated with a 27-gauge needle or an 18-gauge needle.
480. The solid oral extended release pharmaceutical dosage form of embodiment 479, wherein recovery of the morphine sulfate is less than about 25%.
481. The solid oral extended release pharmaceutical dosage form of embodiment 480, wherein recovery of the morphine sulfate is less than about 10%.
482. The solid oral extended release pharmaceutical dosage form of embodiment 481, wherein recovery of the morphine sulfate is less than about 7%.
483. The solid oral extended release pharmaceutical dosage form of any of embodiments 1 to 315 or 437 to 482, wherein recovery of the morphine sulfate is less than about 7.5% based on a syringeability test whereby one milled dosage form is subjected to dissolution in 10 mL of 95% ethanol with agitation at 60° C. for 30 minutes and the resultant solution is aspirated with a 27-gauge needle or an 18-gauge needle.
484. The solid oral extended release pharmaceutical dosage form of embodiment 483, wherein recovery of the morphine sulfate is less than about 5%.
485. The solid oral extended release pharmaceutical dosage form of embodiment 484, wherein recovery of the morphine sulfate is about 3% or less.
486. The solid oral extended release pharmaceutical dosage form of any of embodiments 1 to 315 or 437 to 485, wherein recovery of the morphine sulfate is less than about 10% based on a syringeability test whereby one intact dosage form is subjected to dissolution in 10 mL water without agitation at room temperature for 1 hour and the resultant solution is aspirated with an 18-gauge needle, wherein the intact dosage form has optionally been subjected to thermal treatment at about 170° C. or about 230° C. or to microwave treatment prior to subjecting it to dissolution.
487. The solid oral extended release pharmaceutical dosage form of embodiment 486, wherein recovery of the morphine sulfate is about 8% or less.
488. The solid oral extended release pharmaceutical dosage form of embodiment 487, wherein recovery of the morphine sulfate is about 6% or less.
489. The solid oral extended release pharmaceutical dosage form of any of embodiments 1 to 315 or 437 to 488, wherein recovery of the morphine sulfate is less than about 6% based on a syringeability test whereby one intact dosage form is subjected to dissolution in 2 mL water without agitation at room temperature for 1 hour and the resultant solution is aspirated with an 18-gauge needle, wherein the intact dosage form has optionally been subjected to thermal treatment at about 170° C. or about 230° C. or to microwave treatment prior to subjecting it to dissolution.
490. The solid oral extended release pharmaceutical dosage form of embodiment 489, wherein recovery of the morphine sulfate is about 4% or less.
491. The solid oral extended release pharmaceutical dosage form of embodiment 490, wherein recovery of the morphine sulfate is about 3% or less.
492. The solid oral extended release pharmaceutical dosage form of any of embodiments 1 to 315 or 437 to 491, wherein recovery of the morphine sulfate is less than about 40% based on a syringeability test whereby one milled dosage form is subjected to dissolution in 10 mL water with agitation at room temperature for 5 minutes and the resultant solution is aspirated with an 18-gauge needle, wherein the milled dosage form has optionally been subjected to thermal treatment at about 170° C. or about 230° C. or to microwave treatment prior to subjecting it to dissolution.
493. The solid oral extended release pharmaceutical dosage form of embodiment 492, wherein recovery of the morphine sulfate is less than about 30%.
494. The solid oral extended release pharmaceutical dosage form of embodiment 493, wherein recovery of the morphine sulfate is about 20% or less.
495. The solid oral extended release pharmaceutical dosage form of any of embodiments 1 to 315 or 437 to 494, wherein recovery of the morphine sulfate is less than about 10% based on a syringeability test whereby one milled dosage form is subjected to dissolution in 2 mL water with agitation at room temperature for 5 minutes and the resultant solution is aspirated with an 18-gauge needle, wherein the milled dosage form has optionally been subjected to thermal treatment at about 170° C. or about 230° C. or to microwave treatment prior to subjecting it to dissolution.
496. The solid oral extended release pharmaceutical dosage form of embodiment 495, wherein recovery of the morphine sulfate is less than about 7%.
497. The solid oral extended release pharmaceutical dosage form of embodiment 496, wherein recovery of the morphine sulfate is less than about 5%.
498. The solid oral extended release pharmaceutical dosage form of any of embodiments 1 to 315 or 437 to 497, wherein recovery of the morphine sulfate is less than about 15% based on a syringeability test whereby one sliced dosage form is subjected to dissolution in 10 mL water with agitation at room temperature for 5 minutes and the resultant solution is aspirated with an 18-gauge needle, wherein the sliced dosage form has optionally been subjected to thermal treatment at about 170° C. or about 230° C. or to microwave treatment prior to subjecting it to dissolution.

499. The solid oral extended release pharmaceutical dosage form of embodiment 498, wherein recovery of the morphine sulfate is about 10% or less.

500. The solid oral extended release pharmaceutical dosage form of embodiment 499, wherein recovery of the morphine sulfate is about 7% or less.

501. The solid oral extended release pharmaceutical dosage form of any of embodiments 1 to 315 or 437 to 500, wherein recovery of the morphine sulfate is less than about 11% based on a syringeability test whereby one sliced dosage form is subjected to dissolution in 2 mL water with agitation at room temperature for 5 minutes and the resultant solution is aspirated with an 18-gauge needle, wherein the sliced dosage form has optionally been subjected to thermal treatment at about 170° C. or about 230° C. or to microwave treatment prior to subjecting it to dissolution.

502. The solid oral extended release pharmaceutical dosage form of embodiment 501, wherein recovery of the morphine sulfate is about 7% or less.

503. The solid oral extended release pharmaceutical dosage form of embodiment 502, wherein recovery of the morphine sulfate is about 5% or less.

504. The solid oral extended release pharmaceutical dosage form of any of embodiments 486 to 503, wherein the thermal treatment is conducted for a time period of from about 3 to about 10 minutes at about 230° C., or for a time period of from about 20 to about 50 minutes at about 170° C.

505. The solid oral extended release pharmaceutical dosage form of embodiment 504, wherein the thermal treatment is conducted for a time period of from about 4 to about 8 minutes at about 230° C., or for a time period of from about 30 to about 40 minutes at about 170° C.

506. The solid oral extended release pharmaceutical dosage form of any of embodiments 486 to 503, wherein the microwave treatment is conducted until the dosage form has turned golden-brown.

507. A method of treating pain in a subject in need thereof, the method comprising administering to the subject the solid oral extended release pharmaceutical dosage form according to any of embodiments 437 to 506.

508. The solid oral extended release pharmaceutical dosage form of embodiment 284, wherein intranasal administration of the dosage form as finely crushed powder as compared to intranasal administration of a placebo powder has a median difference (IQR) in "at this moment" drug liking ($E_{max}$) of about 0 to about 3.

509. The solid oral extended release pharmaceutical dosage form of embodiment 296, wherein intranasal administration of the dosage form as finely crushed powder as compared to intranasal administration of a placebo powder has a median difference (IQR) in ODL (overall drug liking) ($E_{max}$) of about 0 to about 5.

EXAMPLES

The following examples are included to demonstrate certain aspects and embodiments of the invention as described in the claims. It should be appreciated by those of skill in the art, however, that these examples are illustrative only and should not be taken in any way as a restriction of the invention.

Materials and Formulations

A summary of the compositions used in the Examples for in vivo and in vitro testing is presented in the following tables.

TABLE I 15, 30, 60, 100 and 200 mg Morphine Sulfate Formulations Used e.g. For Clinical and Tamper-Resistance Testing

| | A | | B | | C | | D | | E | |
|---|---|---|---|---|---|---|---|---|---|---|
| | | | | | Tablet Strength | | | | | |
| | 15 mg | | 30 mg | | 60 mg | | 100 mg | | 200 mg | |
| | mg/unit | %/unit | mg/unit | %/unit | mg/unit | %/unit | mg/unit | %/unit | mg/unit | %/unit |
| Morphine Sulfate(mg) | 15 | 12.0% | 30 | 17.1% | 60 | 18.2% | 100 | 30.3% | 200 | 33.3% |
| POLYOX N60K FP (Fine Particle) Mw 2,000,000 | 108.7 | 87.0% | 143.2 | 81.8% | 266.7 | 80.8% | 224.3 | 68.0% | 0 | 0.00% |
| POLYOX N12K FP (Fine Particle) Mw 1,000,000 | 0 | | 0 | | 0 | | 0 | | 388 | 64.7% |
| Colloidal Silicon Dioxide | 0 | 0% | 0 | 0% | 0 | 0.0% | 1.5 | 0.5% | 3 | 0.5% |
| Magnesium Stearate | 1.3 | 1.0% | 1.8 | 1.0% | 3.3 | 1.0% | 4.2 | 1.3% | 9 | 1.5% |
| Core tablet weight (=unit) | 125 | 100% | 175 | 100% | 330 | 100% | 330 | 100% | 600 | 100% |
| Opadry II Blue 85F90631 | 5.0 | 4.0% | 0.0 | | 0.0 | | 0.0 | | 0.0 | |
| Opadry II Purple 85F100018 | 0.0 | | 7.0 | 4.0% | 0.0 | | 0.0 | | 0.0 | |
| Opadry II Orange 85F93439 | 0.0 | | 0.0 | | 13.0 | 3.9% | 0.0 | | 0.0 | |
| Opadry II Gray 85F17670 | 0.0 | | 0.0 | | 0 | | 13.0 | 3.9% | 0.0 | |
| Opadry II White 85F18422 | 0.0 | | 0.0 | | 0 | | 0 | | 24.0 | 4.0% |
| Film-coated tablet weight (=unit) | 130 | | 182 | | 343 | | 343 | | 624 | |
| Shape of tablet | Caplet, (10.20 × 4.20 mm) | | Caplet, (11.33 × 5.36 mm) | | Troche caplet, (16.13 × 6.35 mm) | | Troche caplet, (16.13 × 6.35 mm) | | Caplet, (17.27 × 8.13 mm) | |
| Curing Time (min) | 30 | | 30 | | 30 | | 45 | | 45 | |
| Curing Temperature (° C.) | 72 | | 72 | | 72 | | 75 | | 75 | |

TABLE II

Formulations Containing 15, 30 and 60 mg of Morphine Sulfate e.g. for In vitro Dissolution Testing and In vivo PK Studies

| Ingredient (mg/unit) | F 15 mg | G 15 mg | H 15 mg | I 15 mg | J 15 mg | K 15 mg | L 30 mg | M 30 mg | N 60 mg |
|---|---|---|---|---|---|---|---|---|---|
| Morphine Sulfate (mg) | 15 | 15 | 15 | 15 | 15 | 15 | 30 | 30 | 60 |
| POLYOX 301 (MW 4,000,000) | 58.875 | 83.5 | 157.375 | | | | | | |
| POLYOX 1105 (MW 900,000) | | | | | | | | | |
| POLYOX N12K (MW 1,000,000) | | | | | | | | | |
| POLYOX N60K (MW 2,000,000) | | | | 108.7 | 148.4 | 108.7 | 93.7 | 143.3 | 266.7 |
| Colloidal Silicon Dioxide | 0.375 | 0.5 | 0.875 | | | | | | |
| Magnesium Stearate | 0.75 | 1 | 1.75 | 1.3 | 1.6 | 1.3 | 1.3 | 1.7 | 3.3 |
| Total (uncoated) (mg) | 75[2] | 100[2] | 175[2] | 125 | 165 | 125 | 125 | 175 | 330 |
| Tablet shape | Round ¼ (6.35 mm) | Round 9/32 (7.14 mm) | Round 9/32 (7.14 mm) | Caplet (10.21 × 4.19 mm) | Caplet (11.33 × 5.36 mm) | Caplet (10.21 × 4.19 mm) | Caplet (10.21 × 4.19 mm) | Caplet (11.33 × 5.36 mm) | Troche (16.13 × 6.35 mm) |
| Curing Time (mins) | 15 | 15 | 15 | 15 | 15 | 30 | 30 | 30 | 30 |
| Curing Temperature (° C.) | 72 | 72 | 72 | 72 | 72 | 72 | 72 | 72 | 72 |
| Compression force (kN) | n/a | n/a | n/a | 4.8930 | 4.8930 | 4.8930 | 4.8930 (3)[1] | 4.8930 (4)[1] | 4.8930 (7)[1] |

[1]The values indicated are representative of unit dose tablets made and used for the in-vitro dissolution studies. The values in parentheses are representatives of tablets made and used for in-vivo testing.
[2]Final tablets were film-coated.

TABLE III

Formulations Containing 100 mg Morphine Sulfate e.g. for In vitro Dissolution Testing and In vivo PK Studies

| Ingredient (mg/unit) | O 100 mg | P 100 mg | Q 100 mg | R 100 mg | S 100 mg | T 100 mg | U 100 mg | V 100 mg | W 100 mg | X 100 mg | Y 100 mg |
|---|---|---|---|---|---|---|---|---|---|---|---|
| Morphine Sulfate | 100 | 100 | 100 | 100 | 100 | 100 | 100 | 100 | 100 | 100 | 100 |
| POLYOX 301 (MW 4,000,000) | 187.292 | 220.125 | 244.75 | | | | | | | | |
| POLYOX 1105 (MW 900,000) | | | | 197 | | | | | | | |
| POLYOX N12K (MW 1,000,000) | | | | | 197 | | | | | | |
| POLYOX N60K (MW 2,000,000) | | | | | | 197 | 207 | 217 | 226.7 | 236.7 | 246.7 |
| Colloidal Silicon Dioxide | 1.458 | 1.625 | 1.75 | | | | | | | | |
| Magnesium Stearate | 2.916 | 3.25 | 3.5 | 3 | 3 | 3 | 3 | 3 | 3.3 | 3.3 | 3.3 |
| Total (uncoated) (mg) | 291.666[1] | 325[1] | 350[1] | 300 | 300 | 300 | 310 | 320 | 330 | 340 | 350 |
| Tablet shape | Troche (16.13 × 6.35 mm) | Troche (16.13 × 6.35 mm) | Troche (16.13 × 6.35 mm) | Troche (16.13 × 6.35 mm) | Troche (16.13 × 6.35 mm) | Troche (16.13 × 6.35 mm) | Troche (16.13 × 6.35 mm) | Troche (16.13 × 6.35 mm) | Troche (16.13 × 6.35 mm) | Troche (16.13 × 6.35 mm) | Troche (16.13 × 6.35 mm) |
| Curing temperature (° C.) | 72 | 72 | 72 | | | (72)[2] | 72 | 72 | 72 | 72 | 72 |
| Curing time (min) | 30 | 30 | 30 | | | (30)[2] | 30 | 30 | 30 | 30 | 30 |

[1]Final tablets were film-coated.
[2]Oven-cured at 72° C. for 30 min for in-vitro dissolution tests.

TABLE IV

Formulations Containing 200 mg Morphine Sulfate and Formulations with Various Tablet Shapes

| Ingredient (mg/unit) | Z 200 mg | AA 200 mg | AB 200 mg | AC 200 mg | AD 200 mg | AE 200 mg |
|---|---|---|---|---|---|---|
| Morphine Sulfate | 200 | 200 | 200 | 200 | 200 | 200 |
| POLYOX 205 (MW 600,000) | 394 | | | | | |
| POLYOX N12K (MW 1,000,000) | | | 394 | 391 | 394 | 394 |
| POLYOX N60K (MW 2,000,000) | | 394 | | | | |
| Magnesium Stearate | 6 | 6 | 6 | 9 | 6 | 6 |
| Total (uncoated) (mg) | 600 | 600 | 600 | 600 | 600 | 600 |
| Tablet shape | Troche (19 × 7.62 mm) | Troche (19 × 7.62 mm) | Troche (19 × 7.62 mm) | Caplet (17.27 × 8.13 mm) | Round (11.5 mm) | Troche) (19.81 × 7.62 mm) |
| Curing Time (mins) | 30 | 45 | 45 | 45 | n/a | n/a |
| Curing Temperature (° C.) | 72 | 75 | 75 | 75 | n/a | n/a |
| Compression force (kN) | 4.8930 | 8.8964 | 8.8964 | n/a | n/a | n/a |

TABLE V

Bilayer Tablet Formulation

| Ingredient (mg/unit) | AF |
|---|---|
| Morphine Sulfate | 167 |
| POLYOX N750 (MW 900,000) | 328 |
| Magnesium Stearate | 5 |
| Subtotal (mg) | 500 |
| Morphine Sulfate | 33 |
| POLYOX N60K (MW 2,000,000) | 66 |
| Magnesium Stearate | 1 |
| Subtotal (mg) | 100 |
| Total (uncoated) (mg) | 600 |
| Tablet shape | Troche (0.780 × 0.300 in) |
| Curing Time (mins) | 30 |
| Curing Temperature (° C.) | 72 |
| Compression force (kN) | 4.8930 |

TABLE VI

Formulations used to demonstrate the effect of particle size

| Ingredient | AG mg/unit | AH mg/unit |
|---|---|---|
| Morphine Sulfate | 100 | 100 |
| POLYOX N60K (regular grade) (MW 2,000,000) | 224.3 | |
| POLYOX N60K FP (=fine particle grade) (MW 2,000,000) | | 224.3 |
| Colloidal Silicon Dioxide | 1.5 | 1.5 |
| Magnesium Stearate | 4.2 | 4.2 |
| Total (uncoated core) (mg) | 330 | 330 |

TABLE VII

Formulations used to investigate experimental stability

| | Tablet | |
|---|---|---|
| | AI | AJ |
| Ingredient (mg/unit) | Strength | |
| | 15 mg | 100 mg |
| Morphine Sulfate | 15 | 100 |
| POLYOX 301 FP (MW 4,000,000) | 163.2 | 185.65 |
| Colloidal Silicon Dioxide | 0.9 | 1.45 |
| Magnesium Stearate | 0.9 | 2.9 |
| Total (uncoated) (mg) | 180 | 290 |

TABLE VIII

Commercial MS Contin ® formulations (reference)

| Ingredient (mg/unit): | Strength | | | | |
|---|---|---|---|---|---|
| | 15 mg | 30 mg | 60 mg | 100 mg | 200 mg |
| Morphine Sulfate | 15 | 30 | 60 | 100 | 200 |
| Lactose, spray-dried | 85 | 70 | 42.2 | | |
| Cetostearyl Alcohol | 35 | 35 | 32.8 | 35 | 70 |
| Hydroxyethyl Cellulose | 10 | 10 | 10 | 10 | 20 |
| Talc | 3 | 3 | 3 | 3 | 6 |
| Magnesium Stearate | 2 | 2 | 2 | 2 | 4 |
| Opadry Coating | 5 | 5 | 5 | 5 | 10 |
| Total (mg) | 155 | 155 | 155 | 155 | 310 |
| Shape | Round | round | round | round | caplet |

TABLE IX

Prophetic formulations with 5 and 10 mg morphine sulfate

| | \multicolumn{8}{c|}{Prophetic Tablet} |
| Ingredient | \multicolumn{2}{c|}{AK} | \multicolumn{2}{c|}{AL} | \multicolumn{2}{c|}{AM} | \multicolumn{2}{c|}{AN} |

| | AK | | AL | | AM | | AN | |
|---|---|---|---|---|---|---|---|---|
| | \multicolumn{8}{c}{Strength} |
| | 5 mg | | 5 mg | | 10 mg | | 10 mg | |
| Ingredient | mg/unit | %/unit | mg/unit | %/unit | mg/unit | %/unit | mg/unit | %/unit |
| Morphine Sulfate | 5 | 6.4 | 5 | 5 | 10 | 8 | 10 | 8 |
| POLYOX N60K FP (MW 2,000,000) | 118.7 | 95 | 94.5 | 94.5 | 113.7 | 91 | 114 | 91.2 |
| Magnesium Stearate | 1.3 | 1 | 0.5 | 0.5 | 1.3 | 1 | 1 | 0.8 |
| Total (uncoated) | 125 | 100 | 100 | 100 | 125 | 100 | 125 | 100 |

In the formulations and tablets described herein and used in the Examples whenever it is referred to "morphine sulfate" as an ingredient in a formulation or tablet, morphine sulfate was always used in the form of morphine hemi (sulfate pentahydrate) (having a molecular weight of 758.8 g/mol as defined in the "Definitions", above), even if not specifically indicated so.

Generalized Process of Manufacture

The processing steps in the manufacture of the tablets were as follows: Morphine sulfate, polyethylene oxide, colloidal silicon dioxide (if present) and magnesium stearate were dry mixed in a V-blender and then compressed to a target weight on a rotary tablet press. The tablets were cured and film coated in a perforated coating pan. Prior to initiating the curing process, the tablets were film coated with Opadry II (mixed with purified water) to a weight gain of 0.5-1.5% to eliminate tablet sticking during the curing process. After this initial film coat was achieved, the curing process was initiated. The rotating tablet bed was heated until the target exhaust temperature (see method 2 described in the "Definitions", above) was achieved, and curing continued at the target exhaust temperature for the time specified in the batch record. At the end of the curing process the tablet bed was cooled and film coating was continued until the target weight gain was achieved.

In Vitro Dissolution Tests

Example 1

Figure 92:
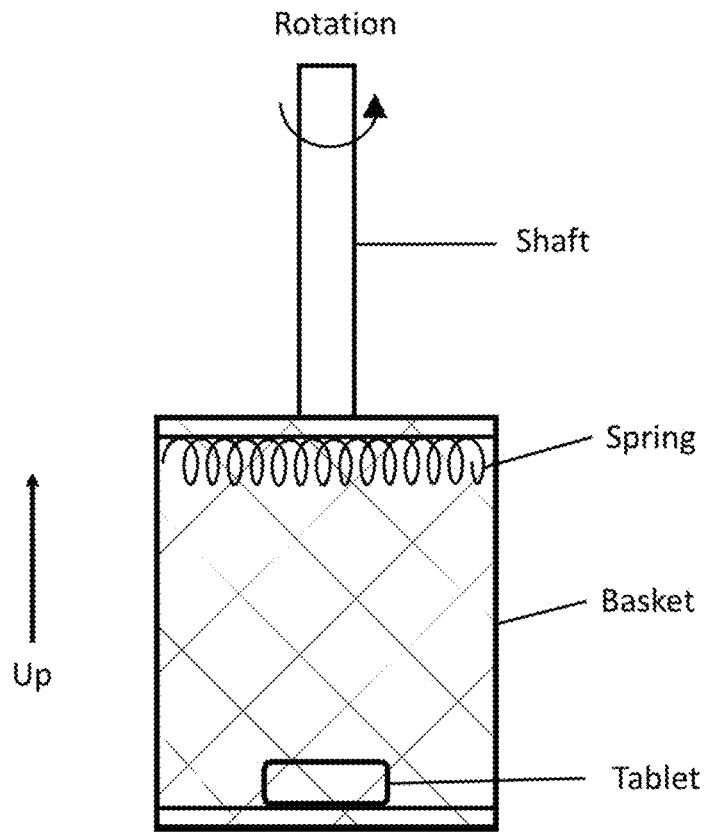
FIG. 92: Diagram of a USP Basket 1 with a Spring

In example 1 in vitro dissolution tests were carried out with intact tablets A to E and 100 mg MS Contin® as reference tablet using a USP Apparatus 1 (basket) with a stainless steel spring inserted into the top of the basket as shown in FIG. 92 at 100 rpm in 900 mL dissolution media at 37±0.5° C. The dissolution media tested was Simulated Gastric Fluid without enzymes (SGF), SGF containing 4% ethanol, SGF containing 10% ethanol, SGF containing 20% ethanol, and SGF containing 40% ethanol. The dissolution vessels were covered to prevent evaporation of solvent.

The dissolution samples were analyzed by reverse-phase high performance liquid chromatography (HPLC) using the following protocol:

| Equipment | Conditions |
|---|---|
| Mobile phase | Ammonium acetate/Hexanesulfonic acid Buffer pH 4.36/Acetonitrile - 90:10 (v/v) |
| Flow rate | 1.0 mL/min |
| Column | Waters XBridge Shield RP18, 4.6 × 100 mm, 3.5 μm |
| Column temperature | 45° C. |
| Injection volume | 10 μL (5 μL for SGF with 40% EtOH) |
| Detector | UV set at 240 nm |
| Run time | Approximately 5 min |

The results of the above in vitro dissolution test in the USP Apparatus 1 for tablets A (15 mg morphine sulfate) are given in Table 1.1 (the dissolution rate is % morphine sulfate released; average of 12 units). These results are displayed graphically in FIG.

TABLE 1.1

| Minutes | SGF | 4% Ethanol | 10% Ethanol | 20% Ethanol | 40% Ethanol |
|---|---|---|---|---|---|
| 15 | 11 | 11 | 10 | 9 | 7 |
| 30 | 19 | 18 | 16 | 15 | 11 |
| 45 | 25 | 24 | 21 | 20 | 15 |
| 60 | 30 | 29 | 26 | 25 | 19 |
| 120 | 50 | 49 | 43 | 41 | 31 |
| 180 | 67 | 65 | 59 | 56 | 43 |
| 240 | 81 | 78 | 72 | 68 | 54 |
| 360 | 97 | 94 | 90 | 86 | 77 |
| 720 | 104 | 101 | 103 | 103 | 97 |

Figure 2:
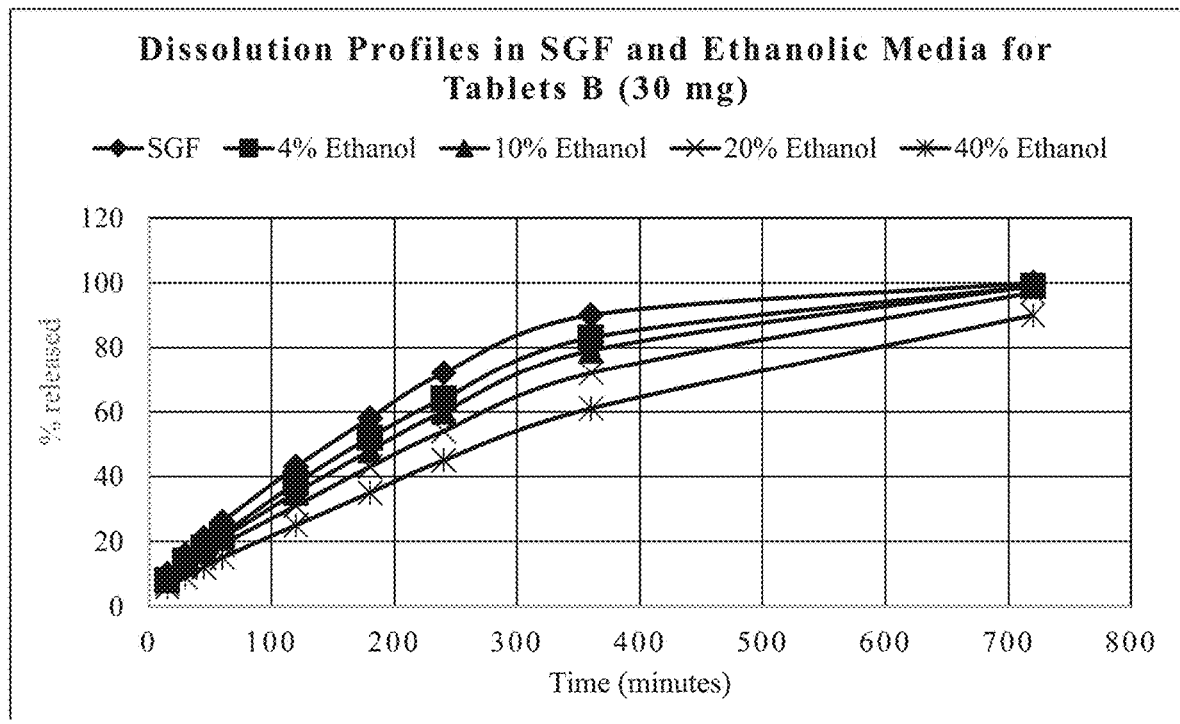
FIG. 2: Dissolution Profile for Tablets B (30 mg) in SGF and Ethanolic Media (% morphine sulfate released over time).

The results of the above in vitro dissolution test in the USP Apparatus 1 for tablets B (30 mg morphine sulfate) are given in Table 1.2 (the dissolution rate is % morphine sulfate released; average of 12 units). These results are displayed graphically in FIG. 2.

TABLE 1.2

| Minutes | SGF | 4% Ethanol | 10% Ethanol | 20% Ethanol | 40% Ethanol |
|---|---|---|---|---|---|
| 15 | 10 | 8 | 8 | 7 | 6 |
| 30 | 16 | 14 | 13 | 12 | 9 |
| 45 | 21 | 18 | 17 | 15 | 12 |
| 60 | 26 | 22 | 21 | 19 | 15 |
| 120 | 43 | 38 | 35 | 31 | 25 |
| 180 | 58 | 52 | 48 | 43 | 35 |
| 240 | 72 | 64 | 60 | 54 | 45 |
| 360 | 90 | 83 | 79 | 72 | 61 |
| 720 | 100 | 99 | 99 | 97 | 90 |

Figure 3:
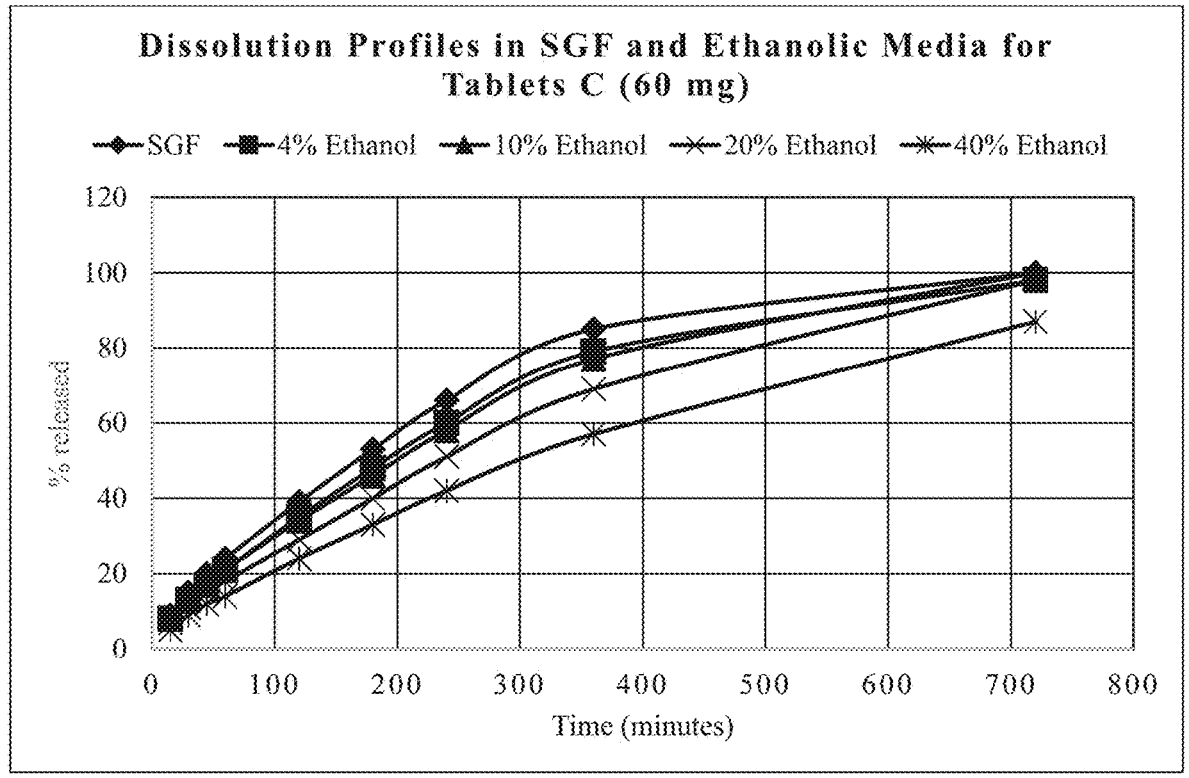
FIG. 3: Dissolution Profile for Tablets C (60 mg) in SGF and Ethanolic Media (% morphine sulfate released over time).

The results of an in vitro dissolution test in the USP Apparatus 1 for tablets C (60 mg morphine sulfate) are given in Table 1.3 (the dissolution rate is % morphine sulfate released; average of 12 units). These results are displayed graphically in FIG. 3.

TABLE 1.3

| Minutes | SGF | 4% Ethanol | 10% Ethanol | 20% Ethanol | 40% Ethanol |
|---|---|---|---|---|---|
| 15 | 9 | 8 | 8 | 7 | 5 |
| 30 | 15 | 13 | 13 | 11 | 9 |
| 45 | 20 | 17 | 17 | 15 | 12 |
| 60 | 24 | 21 | 21 | 18 | 14 |
| 120 | 39 | 35 | 34 | 29 | 24 |
| 180 | 53 | 48 | 46 | 40 | 33 |
| 240 | 66 | 60 | 58 | 51 | 42 |
| 360 | 85 | 79 | 77 | 69 | 57 |
| 720 | 100 | 98 | 100 | 98 | 87 |

Figure 4:
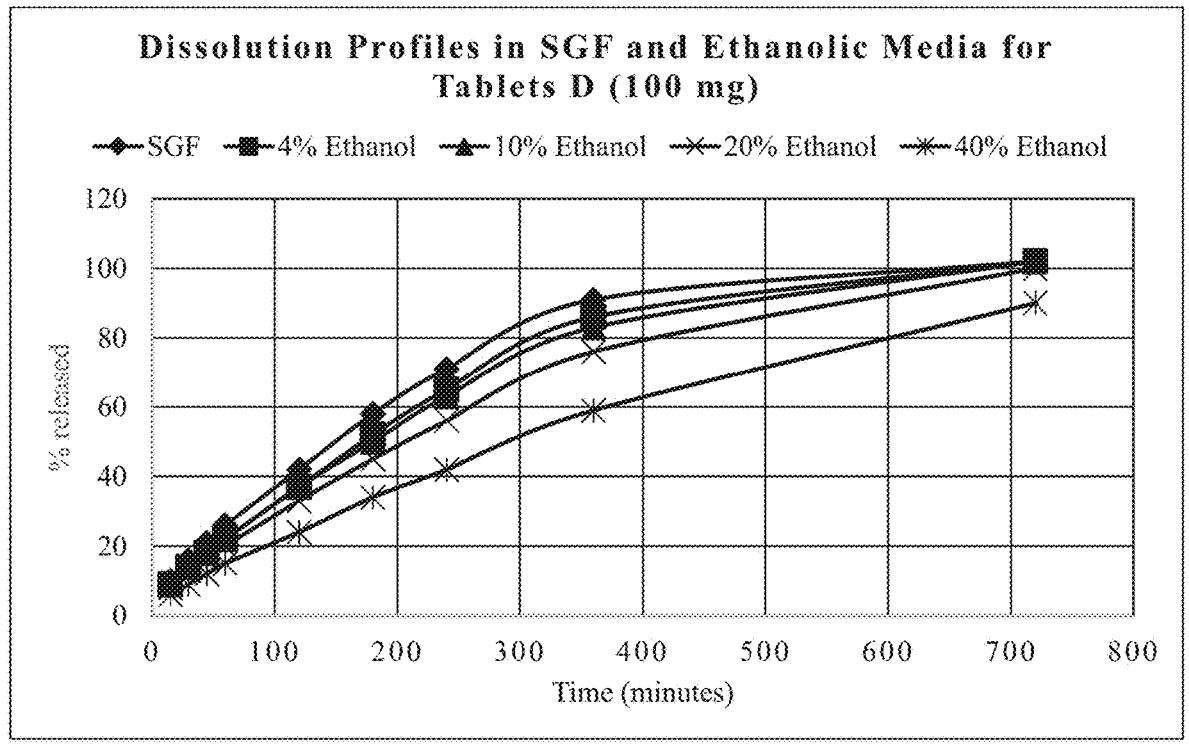
FIG. 4: Dissolution Profile for Tablets D (100 mg) in SGF and Ethanolic Media (% morphine sulfate released over time).

The results of an in vitro dissolution test in the USP Apparatus 1 for tablets D (100 mg morphine sulfate) are given in Table 1.4 (the dissolution rate is % morphine sulfate released; average of 12 units). These results are displayed graphically in FIG. 4.

TABLE 1.4

| Minutes | SGF | 4% Ethanol | 10% Ethanol | 20% Ethanol | 40% Ethanol |
|---|---|---|---|---|---|
| 15 | 10 | 9 | 9 | 8 | 6 |
| 30 | 16 | 14 | 14 | 13 | 9 |
| 45 | 21 | 18 | 18 | 16 | 12 |
| 60 | 26 | 22 | 22 | 20 | 15 |
| 120 | 42 | 37 | 37 | 33 | 24 |
| 180 | 58 | 52 | 50 | 45 | 34 |
| 240 | 71 | 65 | 63 | 56 | 42 |
| 360 | 91 | 86 | 83 | 76 | 59 |
| 720 | 102 | 102 | 102 | 100 | 90 |

Figure 5:
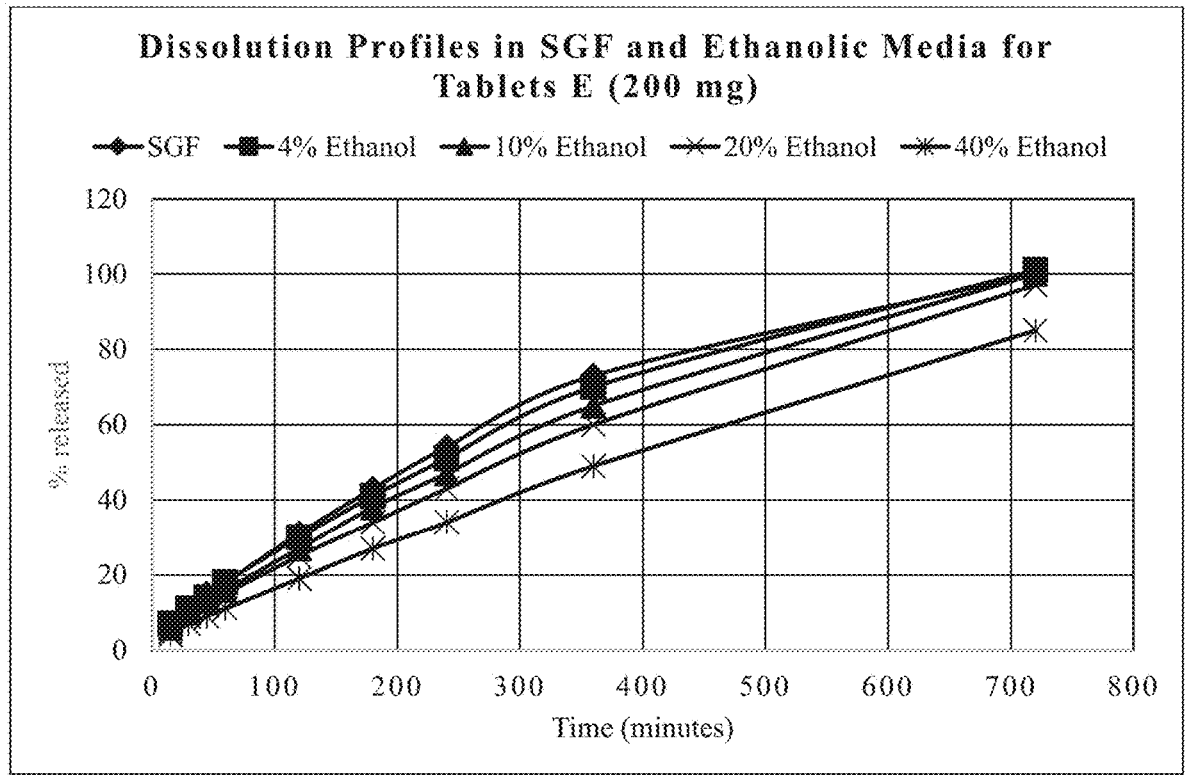
FIG. 5: Dissolution Profile for Tablets E (200 mg) in SGF and Ethanolic Media (% morphine sulfate released over time).

The results of an in vitro dissolution test in the USP Apparatus 1 for tablets E (200 mg morphine sulfate) are given in Table 1.5 (the dissolution rate is % morphine sulfate released; average of 12 units). These results are displayed graphically in FIG. 5.

TABLE 1.5

| Minutes | SGF | 4% Ethanol | 10% Ethanol | 20% Ethanol | 40% Ethanol |
|---|---|---|---|---|---|
| 15 | 7 | 7 | 6 | 5 | 4 |
| 30 | 11 | 11 | 10 | 9 | 7 |
| 45 | 15 | 14 | 13 | 12 | 9 |
| 60 | 18 | 18 | 16 | 15 | 11 |
| 120 | 31 | 30 | 27 | 25 | 19 |
| 180 | 43 | 41 | 38 | 34 | 27 |
| 240 | 54 | 51 | 47 | 43 | 34 |
| 360 | 73 | 70 | 65 | 60 | 49 |
| 720 | 100 | 101 | 100 | 97 | 85 |

Figure 6:
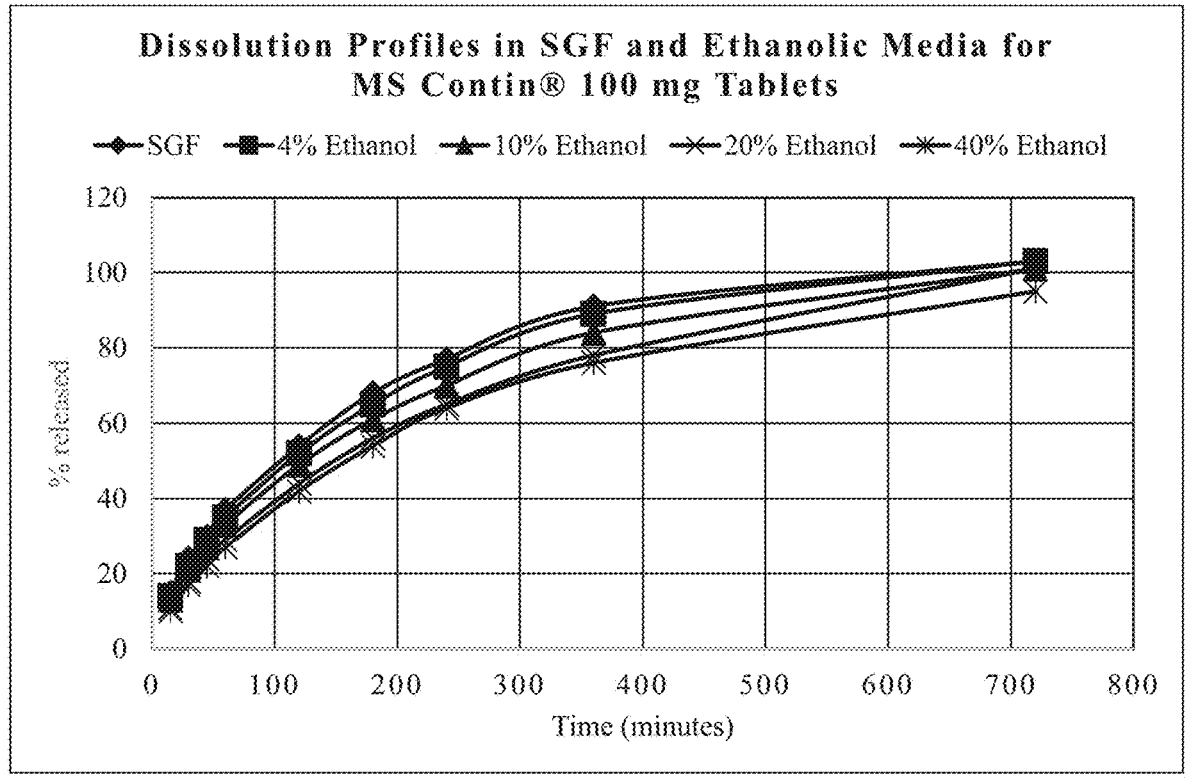
FIG. 6: Dissolution Profile for MS Contin® 00 mg Tablets in SGF and Ethanolic Media (% morphine sulfate released over time).

As a reference example the results of an in vitro dissolution study for commercially available 100 mg MS Contin® tablets are given in Table 1.6 (the dissolution rate is % morphine sulfate released; average of 12 units). These results are displayed graphically in FIG. 6.

TABLE 1.6

| Minutes | SGF | 4% Ethanol | 10% Ethanol | 20% Ethanol | 40% Ethanol |
|---|---|---|---|---|---|
| 15 | 15 | 14 | 13 | 11 | 10 |
| 30 | 24 | 22 | 21 | 18 | 17 |
| 45 | 30 | 29 | 27 | 24 | 22 |
| 60 | 37 | 35 | 33 | 29 | 27 |
| 120 | 54 | 52 | 49 | 44 | 42 |
| 180 | 68 | 65 | 61 | 56 | 54 |
| 240 | 77 | 75 | 70 | 65 | 64 |
| 360 | 91 | 89 | 84 | 78 | 76 |
| 720 | 103 | 103 | 101 | 101 | 95 |

The results obtained demonstrated that there is no rapid drug dissolution or unexpected high release of the drug in the presence of various amounts of ethanol compared to SGF. The in vitro data thus indicate that dose dumping of morphine sulfate did not occur in the presence of various concentrations of ethanol. All five of the different strength tablets A to E and the reference MS Contin® tablet show a similar trend and profile. Increasing concentrations of ethanol in the dissolution medium resulted in a decrease in the rate of release of morphine sulfate from tablets A to E as compared to control (i.e., SGF without ethanol). The dissolution rate decreased in the order of $4^{\%}$, 10%, 20% and 40% ethanol contained in SGF.

Example 2

In Example 2 additional in vitro dissolution tests were carried out with intact tablets in a USP Apparatus (Basket 1 with a spring, see FIG. 92) at 100 rpm at 37° C. in 900 mL SGF (without alcohol). Dissolution vessels were covered at all times to minimize any evaporation effects. HPLC analysis of the dissolution samples was generally performed as described in Example 1 or by an equivalent HPLC method.

Figure 7:
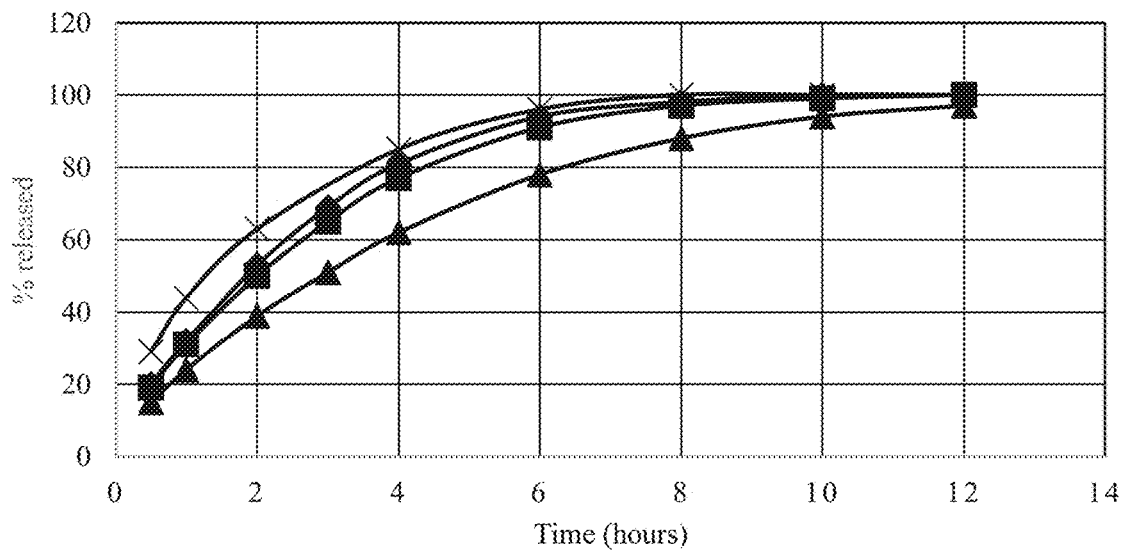
FIG. 7: Dissolution Profile of Tablets F, G, H and Reference Tablet MS Contin® 15 mg (Table 2.1) (% morphine sulfate released over time).

For each test, 12 units (tablets) were tested. Table 2.1 shows a reference example in which tablets F, G and H containing POLYOX 301 (MW 4,000,000) and 15 mg morphine sulfate were tested (the dissolution rate is % morphine sulfate released). These results are displayed graphically in FIG. 7.

TABLE 2.1

| | Reference Example | | | |
|---|---|---|---|---|
| | 2.1 | 2.2 | 2.3 | 2.4 |
| | Tablet | | | |
| Time (hours) | F | G | H | MS Contin® 15 mg |
| 0.5 | 20 | 19 | 15 | 29 |
| 1 | 32 | 31 | 24 | 44 |
| 2 | 53 | 50 | 39 | 63 |
| 3 | 69 | 65 | 51 | — |
| 4 | 81 | 77 | 62 | 85 |
| 6 | 94 | 91 | 78 | 96 |
| 8 | 98 | 97 | 88 | 100 |
| 10 | 100 | 99 | 94 | 100 |
| 12 | 100 | 100 | 97 | 100 |

Figure 8:
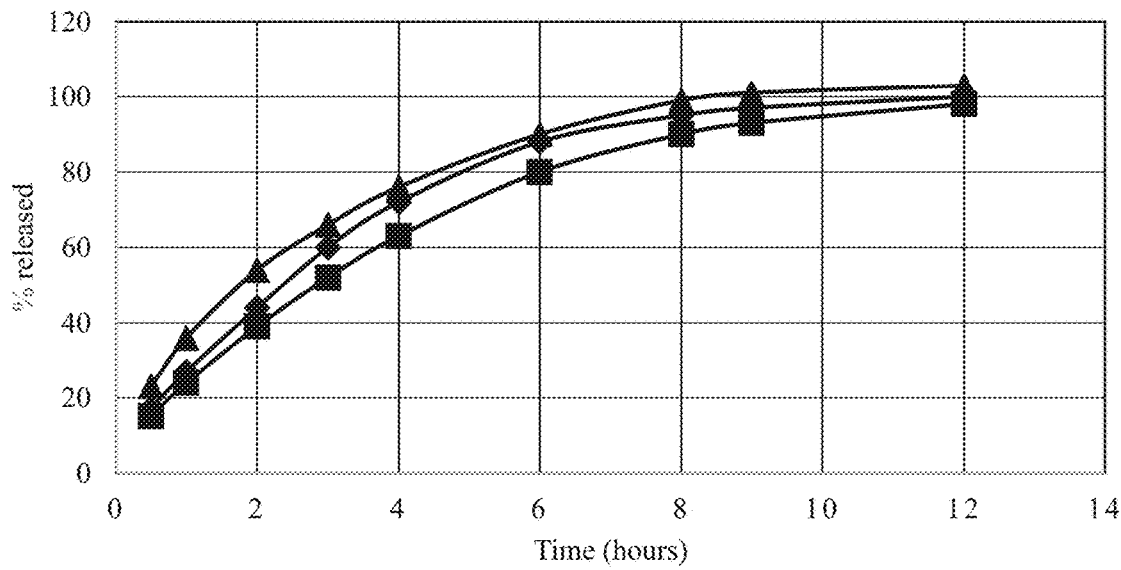
FIG. 8: Dissolution Profile of Tablets O, P and Reference Tablet MS Contin® 100 mg (Table 2.2) (% morphine sulfate released over time).

The results of the in vitro dissolution tests carried out on tablets O and P (also containing POLYOX 301; MW 4,000,000) which each contain 100 mg of morphine sulfate are shown in Table 2.2. A commercially available 100 mg MS Contin® tablet was used as reference (dissolution rate is % morphine sulfate released). These results are displayed graphically in FIG. 8.

TABLE 2.2

| | Reference Example | | |
|---|---|---|---|
| | 2.5 | 2.6 | 2.10 |
| | | Tablet | |
| Time (hours) | O | P | MS Contin® 100 mg |
| 0.5 | 17 | 15 | 23 |
| 1 | 27 | 24 | 36 |
| 2 | 44 | 39 | 54 |
| 3 | 60 | 52 | 66 |
| 4 | 72 | 63 | 76 |
| 6 | 88 | 80 | 90 |
| 8 | 95 | 90 | 99 |
| 9 | 97 | 93 | 101 |
| 12 | 100 | 98 | 103 |

Figure 9:
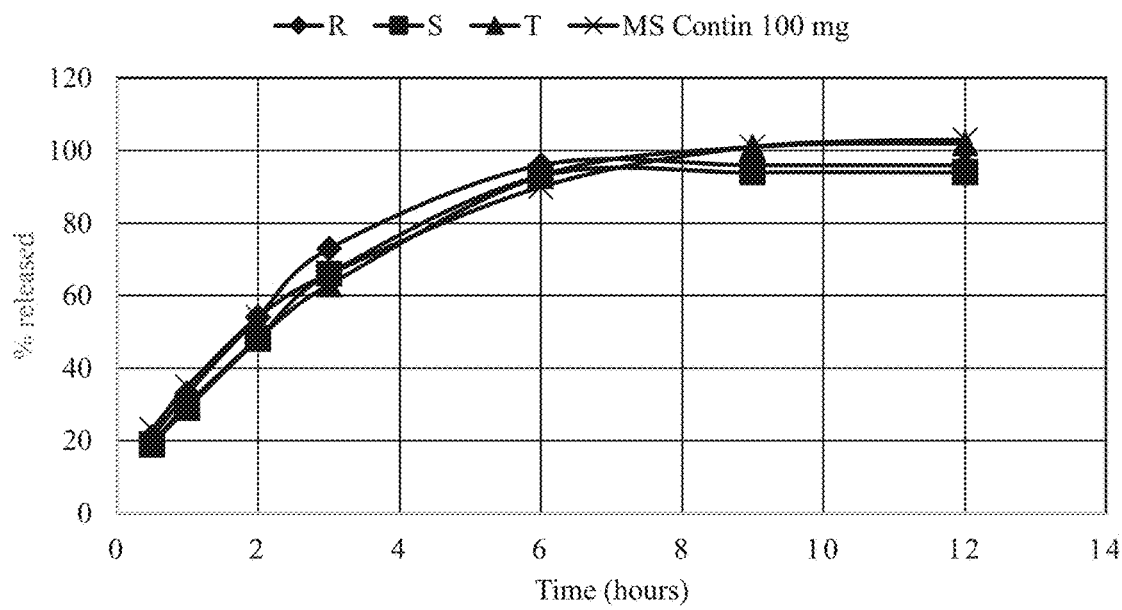
FIG. 9: Dissolution Profile of Tablets R, S, T and Reference Tablet MS Contin® 100 mg (Table 2.3) (% morphine sulfate released over time).

In vitro dissolution tests were also carried out on experimental individual unit dose tablets R, S and T (that were compounded at the clinical site for an in vivo PK study, see Example 3 below and in particular Table 3.3) which each contain 100 mg of morphine sulfate in order to demonstrate the effect of the molecular weight of polyethylene oxide in the formulations of the present invention. However, for tablet R, the formulation used for making the experimental unit dose tablets used for the present in vitro dissolution study was slightly different from that indicated in Table II, above: Namely, the formulation for the individual experimental unit dose tablets R contained 195.5 mg of polyethylene oxide (Polyox 1105) instead of 197 mg, resulting in a total tablet weight of 298.5 mg (instead of 300 mg). A commercially available 100 mg MS Contin® tablet was used as the reference example. The final results of these dissolution tests with the experimental unit dose tablets are displayed in Table 2.3 (dissolution rate is % morphine sulfate released; average of 6 units for tablets R to T, average of 12 units for MS Contin®). The results obtained with these formulations are displayed graphically in FIG. 9.

TABLE 2.3

| | Example | | | Reference example 2.10 |
|---|---|---|---|---|
| | 2.7 | 2.8 | 2.9 | |
| | | | Tablet | |
| Time (hours) | R | S | T | MS Contin® 100 mg |
| 0.5 | 21 | 19 | 19 | 23 |
| 1 | 33 | 29 | 30 | 35 |
| 2 | 54 | 48 | 48 | 54 |
| 3 | 73 | 66 | 63 | 66 |
| 6 | 96 | 93 | 93 | 90 |
| 9 | 96 | 94 | 101 | 101 |
| 12 | 96 | 94 | 102 | 103 |

Figure 10:
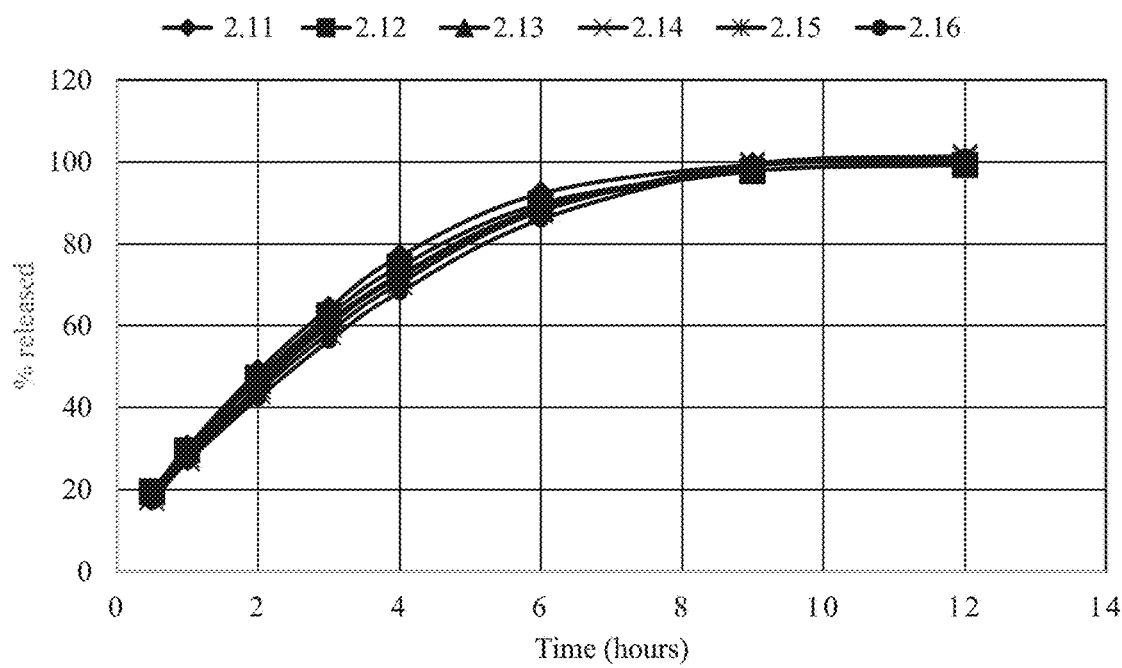
FIG. 10: Dissolution Profile of Tablets T to Y (Table 2.4) (% morphine sulfate released over time).

Additionally, several 100 mg morphine sulfate formulations were prepared individually using a single station Carver press with various content of polyethylene oxide (i.e., various weight ratios of morphine sulfate to polyethylene oxide) in order to study and demonstrate the effect of the polyethylene content (or weight ratio of morphine sulfate to polyethylene oxide) on drug release. Tablets T, U, V, W, X, and Y thus all contained 100 mg of morphine sulfate, but increasing amounts of polyethylene oxide (PEO N60K; MW 2,000,000), see Table III above. The data for the in vitro dissolution tests carried out with these particular formulations are given in Table 2.4. These results are displayed graphically in FIG. 10.

TABLE 2.4

| | Example | | | | | |
|---|---|---|---|---|---|---|
| | 2.11 | 2.12 | 2.13 | 2.14 | 2.15 | 2.16 |
| | | | Tablet | | | |
| Time (h) | T | U | V | W | X | Y |
| 0.5 | 19.5 | 19.5 | 19.3 | 18 | 17.8 | 17 |
| 1 | 30.3 | 29.5 | 29.7 | 28.3 | 27.5 | 26.8 |
| 2 | 48.8 | 47.3 | 46.5 | 45 | 43.8 | 42.3 |
| 3 | 64.3 | 62.5 | 61 | 60 | 58.3 | 56.3 |
| 4 | 77 | 74.5 | 72.5 | 72 | 70.5 | 68.3 |
| 6 | 92.3 | 89.8 | 88.7 | 88.5 | 88 | 86 |
| 9 | 99.3 | 97.8 | 97.8 | 99 | 99.5 | 99 |
| 12 | 100.2 | 99.3 | 99.5 | 100.8 | 101.5 | 101.3 |

Figure 11:
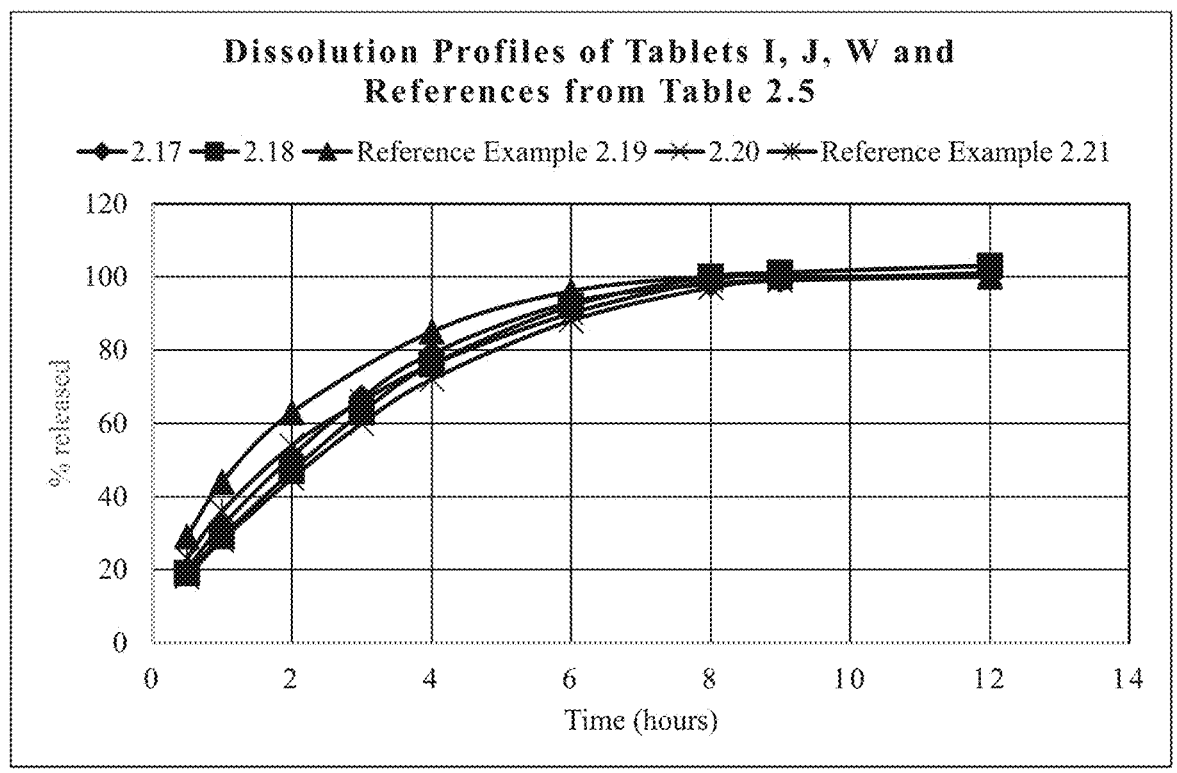
FIG. 11: Dissolution Profile of Tables I, J, W and Reference Tablets MS Contin® 15 mg and MS Contin® 100 mg (Table 2.5) (% morphine sulfate released over time).

In vitro dissolution tests were also carried out with a 100 mg morphine sulfate table (W) and a 100 mg MS Contin® reference tablet, as well as with two 15 mg tablet formulations (I, J) and 15 mg MS Contin® reference tablet. All tablet formulations contained POLYOX N60K (MW 2,000,000). The results of these tests are given in Table 2.5. These results are displayed graphically in FIG. 11.

TABLE 2.5

| | Example | | | | |
|---|---|---|---|---|---|
| | 2.17 | 2.18 | Reference Example 2.19 | 2.20 | Reference Example 2.21 |
| | | | Mass morphine sulfate (mg) | | |
| | 15 | 15 | 15 | 100 | 100 |
| | | | Tablet | | |
| Time (hours) | I | J | MS Contin® 15 mg | W | MS Contin® 100 mg |
| 0.5 | 20 | 19 | 29 | 18 | 23 |
| 1 | 32 | 29 | 44 | 28 | 36 |
| 2 | 51 | 47 | 63 | 45 | 54 |
| 3 | 67 | 63 | — | 60 | 66 |
| 4 | 79 | 76 | 85 | 72 | 76 |
| 6 | 93 | 92 | 96 | 88 | 90 |
| 8 | 98 | 100 | 100 | 97 | 99 |
| 9 | 99 | 101 | 100 | 99 | 101 |
| 12 | 100 | 103 | 100 | 101 | 103 |

Figure 12:
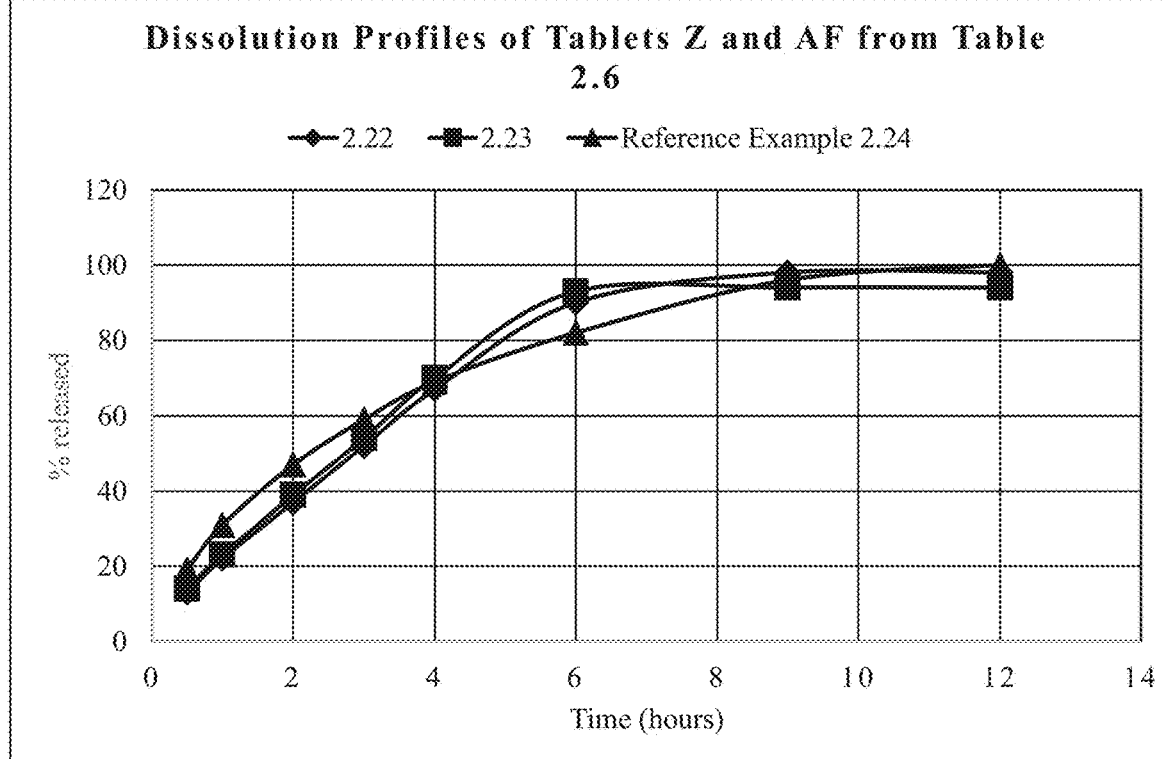
FIG. 12: Dissolution Profile of Tablets Z, AF and Reference Tablet MS Contin® 200 mg (Table 2.6) (% morphine sulfate released over time).

Tests were carried out to evaluate two different 200 mg tablet formulations, one being a monolithic tablet, the other being abi-layer tablet (tablets Z and AF, see Tables IV and V, respectively). 200 mg MS Contin® was used as reference. The results of the in vitro dissolution test are given in Table 2.6. These results are also displayed graphically in FIG. 12.

TABLE 2.6

| | Example | | Reference Example 2.24 |
|---|---|---|---|
| | 2.22 | 2.23 | |
| | | Morphine sulfate (mg) | |
| | 200 | 200 | 200 |
| | | Tablet | |
| Time (hours) | Z | AF | MS Contin® |
| 0.5 | 13 | 14 | 19 |
| 1 | 22 | 23 | 31 |
| 2 | 37 | 39 | 47 |
| 3 | 52 | 54 | 59 |
| 4 | 67 | 70 | 69 |
| 6 | 90 | 93 | 82 |

TABLE 2.6-continued

| | Example | | |
|---|---|---|---|
| | 2.22 | 2.23 | Reference Example 2.24 |
| | Morphine sulfate (mg) | | |
| | 200 | 200 | 200 |
| | Tablet | | |
| Time (hours) | Z | AF | MS Contin ® |
| 9 | 98 | 94 | 96 |
| 12 | 98 | 94 | 100 |

Figure 13:
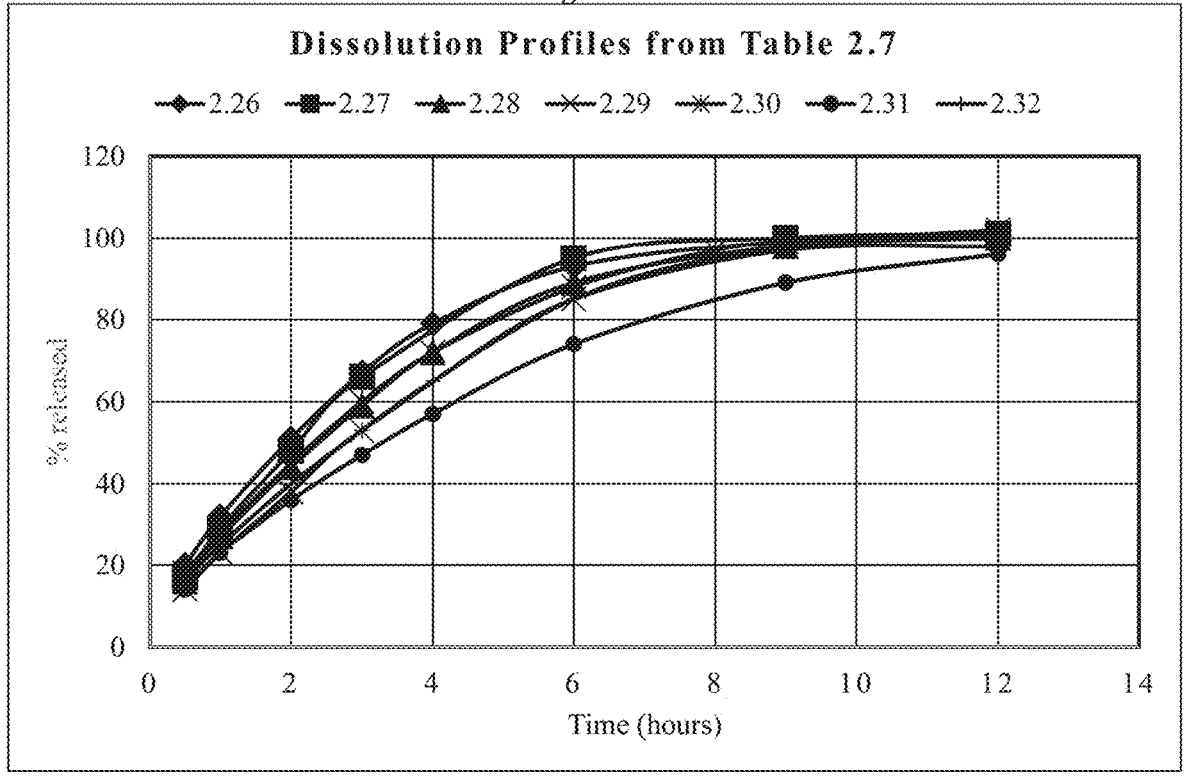
FIG. 13: Dissolution Profile of Tablets K to N, W, AA and AB (Table 2.7) (% morphine sulfate released over time).

The results of in vitro dissolution tests carried out on tablets K, L, M, N, W, AA, and AB which all contained POLYOX N12K (MW 1,000,000) or POLYOX N60K (MW 2,000,000) are given in Table 2.7. These results are also displayed graphically in FIG. 13.

TABLE 2.7

| | Example | | | | | | |
|---|---|---|---|---|---|---|---|
| | 2.26 | 2.27 | 2.28 | 2.29 | 2.30 | 2.31 | 2.32 |
| | | | | Tablet | | | |
| | K | L | M | N | W | AA | AB |
| | | | | Morphine sulfate (mg) | | | |
| Time (hours) | 15 | 30 | 30 | 60 | 100 | 200 | 200 |
| 0.5 | 20 | 17 | 16 | 14 | 18 | 14 | 16 |
| 1 | 32 | 29 | 27 | 23 | 28 | 23 | 25 |
| 2 | 51 | 48 | 44 | 38 | 45 | 36 | 40 |
| 3 | 67 | 66 | 59 | 53 | 60 | 47 | 53 |
| 4 | 79 | — | 72 | — | 72 | 57 | 65 |
| 6 | 93 | 95 | 89 | 85 | 88 | 74 | 85 |
| 8 | — | — | — | — | 97 | — | — |
| 9 | 99 | 100 | 98 | 98 | 99 | 89 | 97 |
| 12 | 100 | 101 | 100 | 102 | 101 | 96 | 98 |

Figure 14:
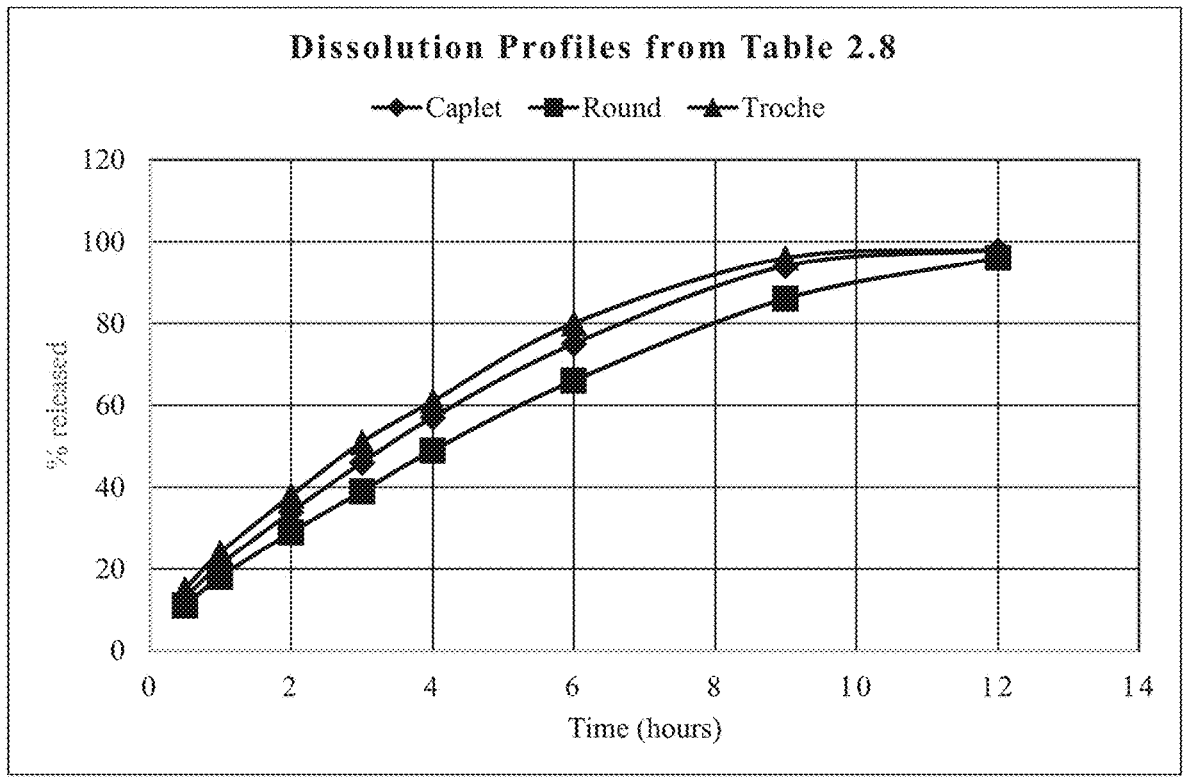
FIG. 14: Dissolution Profile of Various Tablet Shapes (Table 2.8) (% morphine sulfate released overtime).

In the following various tablet shapes and their in vitro dissolution profile are presented. In vitro dissolution tests were carried out in a USP Apparatus (Basket 1) according to the procedure described in Example 2.1 (above). The results of the in vitro dissolution tests carried out are shown in Table 2.8. These results are displayed graphically in FIG. 14.

TABLE 2.8

| | Average % Released Example | | |
|---|---|---|---|
| | 2.33 | 2.34 | 2.35 |
| | | Tablet | |
| | AC | AD | AE |
| | | Shape | |
| Time (h) | Caplet (0.680 × 0.320 inch) | Round (11.5 mm) | Troche (0.780 × 0.300 inch) |
| 0.5 | 13 | 11 | 15 |
| 1 | 21 | 18 | 24 |
| 2 | 34 | 29 | 38 |
| 3 | 46 | 39 | 51 |
| 4 | 57 | 49 | 61 |
| 6 | 75 | 66 | 80 |
| 9 | 94 | 86 | 96 |
| 12 | 98 | 96 | 98 |

The results in Table 2.8 demonstrate that the caplet shaped tablet formulation reduced the in vitro release rate of the tablets by approximately 10% compared to the troche shaped tablet. The round tablet shape provided an even slower in vitro release.

In Vivo Pharmacokinetic Studies

Example 3

Clinical studies in Example 3 were carried out as follows.

Clinical Study Procedures

This was a randomized, open-label, crossover, pilot study in healthy adult male and female subjects. The study was comprised of up to a maximum of 6 iterations, with up to 8 treatments studied across a maximum of 5 periods in each iteration. An iteration was the process of repeating the study design each time with a unique group of subjects who underwent a set of predefined treatments. Iterations could have been run in parallel or sequentially. A total of 6 iterations were completed.

Studies were performed on up to 24 subjects for each iteration.
Diagnosis and Main Criteria for Inclusion:
Healthy male and female subjects aged 18 to 50 years, inclusive, with no clinically significant medical history, who were deemed suitable to take part in this clinical study by the investigator.
Study Drug and Mode of Administration:
Tablets F to T, W, Z, AA, AB and AF were tested in this pilot study and compared to MS Contin® reference tablets.
A single dose (one tablet) was administered orally with 240 mL water. Treatments were administered in the fasted state, depending on the iteration methodology. The treatment schedule diagram for Example 3 is given in FIG. 96. The minimum wash-out period between study drug administration was 5 days.
Concomitant Medication:
A naloxone HCL challenge test (before first dose of naltrexone) was carried out before each trial. Naltrexone HCl tablets, 50 mg (Mallinckrodt, Inc; Lot Number 1170U82358) were administered q12h (i.e., every 12 hours) from 12 hours pre-dose through 36 hours post-dose for the tablets of this application or MS Contin® in order to minimize opioid related adverse events (AEs). Naloxone HCl and naltrexone HCl were protocol-specified drugs, distinct from study drug. The use of other concomitant medications during this trial was discouraged, unless necessary to treat AEs. The use of other concomitant medications was to be approved by the sponsor (or designee) in advance, when possible.
Duration of Treatment:
Subjects were screened no more than 28 days before check-in of period 1. There was a maximum of 5 treatment periods in each iteration. The study drug was administered in each period according to the study randomization schedule. There was a minimum 5-day washout period between study drug administrations. Subjects were confined to the study unit from check-in (day −1) to the end-of-study (EOS) visit or they could have left the clinical unit during the washout period.
The EOS procedures were conducted 3 days (72 hours) after the last dose of tablets in this application or MS Contin®; or upon early discontinuation from the study. A follow-up phone call was made to inquire about AEs and concomitant medications 7 to 10 days after last study drug administration.

Total study duration was up to 82 days for each iteration.

Study Procedures:

Pre-Randomization Phase:

Screening:

Subjects were screened within 28 days of check-in (day −1). Screening activities included demography, drug, alcohol, and cotinine screens, physical examination, 12-lead electrocardiogram (ECG), vital signs (systolic/diastolic blood pressure, pulse rate, respiratory rate, and oral temperature), pulse oximetry ($SpO_2$), medical and medication history, clinical laboratory testing, serum pregnancy test (females only), serum follicle-stimulating hormone test (postmenopausal women only), and inclusion/exclusion criteria were evaluated.

Check-in:

Subjects checked into the unit on day −1 and remained confined until the EOS visit or they checked in to the clinical unit on the day prior to dosing in each period. For period 1 only, subjects received a naloxone HCl challenge test. Serum chemistry, hematology, and urinalysis tests were performed. Urine pregnancy test (for all female subjects), vital signs, $SpO_2$, 12-lead ECG, alcohol, cotinine, and urine drug screens were performed and inclusion/exclusion criteria were verified.

Treatment Phase:

For all periods in each iteration, subjects were administered study drug and naltrexone HCl tablets (50 mg). The 12-lead ECG, vital sign (including $SpO_2$) measurements, and blood samples for drug concentration measurements were obtained at pre-specified times. Adverse events and concomitant medications were recorded throughout the study.

End-of-Study Visit:

EOS procedures included a physical examination, 12-lead ECG, vital sign measurements, $SpO_2$, serum pregnancy test for female subjects, and clinical laboratory tests.

Post-Treatment Phase:

There was a follow-up phone call 7 to 10 days after last study drug administration.

Pharmacokinetics:

Blood samples for determining morphine plasma concentrations were obtained from each subject during each treatment period at the following time points:

Test tables according to the present invention: pre-dose and at 0.5, 1, 1.5, 2, 2.5, 3, 3.5, 4, 5, 6, 8, 10, 12, 18, 24, 36, 48, and 72 hours post study drug administration.

Plasma concentrations of morphine were quantified by a validated liquid chromatography tandem mass spectrometry method.

Safety Variables:

Safety was assessed using recorded AEs, clinical laboratory test results, vital signs, $SpO_2$, physical examinations, and 12-lead ECGs.

Statistical Methods:

Analysis Populations

The enrolled population consisted of subjects who signed the informed consent form. The randomized safety population was the group of subjects who were randomized, received at least 1 dose of the study drug, and had at least 1 post-dose safety assessment.

The full analysis for pharmacokinetics population (FAP) was the group of subjects who were randomized, received at least 1 dose of study drug, and had at least 1 valid pharmacokinetic (PK) metric. Subjects who experienced emesis within 12 hours of dosing with MS Contin® or the tablets in this application could have been excluded from PK analysis. Subjects who experienced emesis at or before 2 times the median time to maximum observed plasma concentration ($T_{max}$) of the morphine sulfate oral IR solution could have been excluded from PK analysis.

No subjects or profiles/metrics were excluded from the analysis set and there were no events of emesis that affected the PK metrics.

Pharmacokinetics:

The plasma concentrations for morphine were summarized by treatment at each time point for each iteration for the randomized safety population. Listings and figures of individual plasma concentrations for morphine were based on the randomized safety population. Mean plasma concentrations versus time profiles were presented by iteration for morphine in figures on both linear and semi-logarithmic scales for the randomized safety population.

Plasma concentrations of morphine were analyzed to determine the following PK metrics by non-compartmental PK analysis: area under the plasma concentration-time curve from hour 0 to the last measurable plasma concentration ($AUC_t$), area under the plasma concentration-time curve extrapolated to infinity (AUCinf), maximum observed plasma concentration ($C_{max}$), $T_{max}$, and apparent terminal phase half-life ($t_{1/2}$).

Pharmacokinetic analyses and summaries were based on the FAP (full analysis for pharmacokinetics population).

Results 15 mg Reference Formulations:

The results of a reference PK study (in the fasted state) with tablets F, G, H, which were POLYOX 301 (MW 4,000,000) based formulations containing 15 mg morphine sulfate compared to 15 mg MS Contin® are shown in Table 3.1.

TABLE 3.1

| Reference examples | | $C_{max}$ | $AUC_t$ | $T_{max}$ | $C_{max}$ ratio | $C_{max}$ Lower | $C_{max}$ Upper | $AUC_t$ ratio |
|---|---|---|---|---|---|---|---|---|
| 3.1 | F | 5.35 | 66 | 2.5 | 76.9 | 68.5 | 86.4 | 100.8 |
| 3.2 | G | 5.64 | 65 | 2.5 | 79.5 | 70.8 | 89.3 | 98.0 |
| 3.3 | H | 3.93 | 67 | 2 | 55.2 | 49.2 | 62 | 102.1 |
| 3.4 | MS Contin ® 15 mg | 7.14 | 65 | 1.5 | | | | |

The in vivo results demonstrate that the POLYOX 301 (MW 4,000,000) based 15 mg formulations F, G and H were not bioequivalent to 15 mg MS Contin®, as is evident from the $C_{max}$ ratio.

100 mg Reference Formulations:

The results of another reference PK study (in the fasted state) for the 100 mg tablet formulations O and P (also containing POLYOX 301; MW 4,000,000) are presented in Table 3.2.

TABLE 3.2

| Reference examples | | $C_{max}$ | $AUC_t$ | $AUC_{inf}$ | $T_{max}$ | $C_{max}$ ratio | $C_{max}$ Lower | $C_{max}$ Upper | $AUC_t$ ratio |
|---|---|---|---|---|---|---|---|---|---|
| 3.5 | O | 34.8 | 434 | 456 | 3.5 | 87.1 | 78 | 97.3 | 92.5 |
| 3.6 | P | 35.3 | 456 | 473 | 3.75 | 88.4 | 79.3 | 98.7 | 97.5 |
| 3.7 | MS Contin® 100 mg | 39.8 | 471 | 491 | 2.5 | | | | |

This in-vivo data indicates that the $C_{max}$ and the $AUC_t$ of the 100 mg formulations were lower than the respective values of the MS Contin® reference.

Evaluating Different Viscosity Grades of PEO

The results of a PK study for the 100 mg tablet formulations R, S and T along with 100 mg MS Contin® as a reference (in the fasted state) are given in Table 3.3. This study demonstrates the effect of using three different grades of polyethylene oxide having different approximate molecular weights (MW 900,000; MW 1,000,000 and MW 2,000,000) while keeping the tablet weight constant.

TABLE 3.3

| Example | | $C_{max}$ | $AUC_t$ | $T_{max}$ | $C_{max}$ ratio | $C_{max}$ Lower | $C_{max}$ Upper | $AUC_t$ ratio |
|---|---|---|---|---|---|---|---|---|
| 3.8 | R | 45.7 | 420 | 3 | 128.1 | 117.5 | 139.8 | 106.3 |
| 3.9 | S | 44.1 | 402 | 3 | 124.0 | 113.7 | 135.3 | 102.6 |
| 3.10 | T | 39.6 | 408 | 3 | 109.5 | 100.5 | 119.5 | 103.7 |
| Reference example 3.11 | MS Contin® 100 mg | 35.9 | 396 | 2.5 | | | | |

Evaluating 100 mg Tablets with a Tablet Weight of 330 mg and 15 mg Tablet Formulations The results of the comparison between tablet W, which contained 100 mg morphine sulfate and had a total weight of 330 mg, with 100 mg MS Contin® as a reference is shown in Table 3.4. Tablets containing 15 mg morphine sulfate (tablets I and J) with different total weights compared to 15 mg MS Contin® as a reference are also detailed in Table 3.4.

TABLE 3.4

| Example | | $C_{max}$ | $AUC_t$ | $AUC_{inf}$ | $T_{max}$ | $C_{max}$ ratio | $C_{max}$ Lower | $C_{max}$ Upper | $AUC_t$ ratio |
|---|---|---|---|---|---|---|---|---|---|
| 3.12 | I | 5.4 | 57 | 59 | 2.5 | 81.6 | 74.5 | 89.3 | 100.3 |
| 3.14 | J | 4.8 | 57 | 59 | 2.5 | 74.5 | 68.0 | 81.6 | 98.8 |
| Reference Example 3.14 | MS Contin® 15 mg | 6.5 | 57 | 59 | 1.5 | | | | |
| 3.15 | W | 39.2 | 488 | 495 | 3.5 | 98.7 | 90.6 | 107.6 | 100.7 |
| Reference Example 3.16 | MS Contin® 100 mg | 39.9 | 484 | 490 | 2.5 | | | | |

These results demonstrate that the 100 mg formulation (W) at a tablet weight of 330 mg achieved a mean $C_{max}$ ratio of 98.7% and is thus bioequivalent to MS Contin® 100 mg.

Monolithic and Bilayer 200 mg Tablets:

Pharmacokinetic studies (in the fasted state) were carried out on two different 200 mg tablet formulations, namely a monolithic tablet (Z), and a bi-layer tablet (AF) compared to 200 mg MS Contin® as reference.

TABLE 3.5

| Ex. | Tablet | | $C_{max}$ | $AUC_t$ | $AUC_{inf}$ | $T_{max}$ | $C_{max}$ ratio | $C_{max}$ Lower | $C_{max}$ Upper | $AUC_t$ ratio |
|---|---|---|---|---|---|---|---|---|---|---|
| 3.17 | Monolayer | Z | 105.1 | 1128 | 1173 | 3 | 130.4 | 119.8 | 141.9 | 100.1 |
| 3.18 | Bilayer | AF | 116.6 | 1101 | 1128 | 3.25 | 146.8 | 134.9 | 159.8 | 98.2 |

TABLE 3.5-continued

| Ex. | Tablet | $C_{max}$ | $AUC_t$ | $AUC_{inf}$ | $T_{max}$ | $C_{max}$ ratio | $C_{max}$ Lower | $C_{max}$ Upper | $AUC_t$ ratio |
|---|---|---|---|---|---|---|---|---|---|
| 3.19 | MS Contin® 200 mg | 79.1 | 1117 | 1141 | 2.25 | | | | |

In vivo study with tablets containing POLYOX N12K (MW 1,000,000) and POLYOX N60K (MW 2,000,000):

The results of a PK study to evaluate the in vivo performance of tablets AB and AA which contain 200 mg morphine sulfate and POLYOX N12K (MW 1,000,000) and POLYOX N60K (MW 2,000,000) (see Table IV, above), respectively, are given in Table 3.6. Furthermore, Table 3.6 contains in vivo PK data of tablets L, N, M and K, all containing POLYOX N60K (MW 2,000,000).

TABLE 3.6

| Ex. | | $C_{max}$ | $AUC_t$ | $AUC_{inf}$ | $T_{max}$ | $C_{max}$ ratio | $C_{max}$ Lower | $C_{max}$ Upper | $AUC_t$ ratio |
|---|---|---|---|---|---|---|---|---|---|
| 3.21 | MS Contin® 200 mg | 85.4 | 1007 | 1036 | 3 | | | | |
| 3.22 | AA | 73.8 | 1073 | 1100 | 3.29 | 88.2 | 79.2 | 98.2 | 103.0 |
| 3.23 | AB | 90 | 1043 | 1064 | 3 | 109.6 | 98.3 | 122.3 | 111.1 |
| 3.24 | L | 16.3 | 134 | | 3 | | | | |
| 3.25 | N | 23.5 | 243 | 260 | 3.5 | | | | |
| 3.26 | M | 13.3 | 133 | 165 | 2.5 | | | | |
| 3.27 | K | 5.75 | 45.1 | 49 | 2 | | | | |

The $C_{max}$ and AUC results in Table 3.6 for the 15 (K), 30 (M) and 60 (N) mg tablets according to the present invention increased linearly, thus demonstrating dose proportionality across these strengths, and also dose proportionality with respect to the 100 mg tablet (W) (see Table 3.4 above with PK data for tablet W).

Example 4

Example 4.1: In Vivo PK Studies with Tablets a, B, C and D in the Fasted State to Demonstrate Dose Proportionality Study Design (Methodology):

This was a single-center, randomized, open-label, single-dose, 4-treatment, 4-period crossover study in healthy adult male and female subjects. Treatments were separated by a minimum 7-day washout.

Number of Subjects (Planned and Analyzed):

A sample size of 55 to complete 48 subjects in a 4-way complete block design would have at least 95% statistical power to test for dose proportionality, given an estimate of the intra-subject coefficient of variation (CV) equal to 20% and that the true value of the slope was between 1.012 and 1.248.

Fifty-seven subjects (36 male subjects and 21 female subjects) were randomized to a treatment sequence in this study. Fifty-one subjects completed the study. Fifty-seven subjects were included in the randomized safety population and the full analysis population (FAP) for pharmacokinetics. Two subjects (3.5%) discontinued from the study due to adverse events (AEs), 1 subject (1.8%) discontinued due to administrative reasons, 2 subjects (3.5%) discontinued due to subject's choice (withdrawal by subject), and 1 subject (1.8%) was lost to follow-up.

Diagnosis and Main Criteria for Inclusion:

Healthy male and female subjects aged 18 to 55 years with no clinically significant medical history and who were deemed suitable to take part in this clinical study by the investigator.

Study Drug, Dose and Mode of Administration, Batch Number:

Tablets A, B, C and D were administered orally each as a single dose with 240 mL of water according to the randomization schedule in the fasted state. There was a minimum 7-day washout period between study drug administrations.

Concomitant Medication:

A naloxone hydrochloride (HCl) challenge test was performed before the first dose of naltrexone HCl. Naltrexone HCl was administered as described in example 3.

Duration of Treatment:

Subjects were screened no more than 28 days before check-in of period 1. Study drug was administered in each period according to the study randomization schedule. Subjects were confined to the unit the day before study drug administration and for 72 hours following study drug administration during each period. Subjects had end-of-study (EOS) procedures performed 3 days (72 hours) after last dose of study drug or upon early discontinuation from the study. A follow-up phone call was made to inquire about AEs (adverse effects) and concomitant medications 7 to 10 days after last study drug administration.

The total duration of the study was up to approximately 61 days.

The study procedure was carried out in a similar manner to Example 3.

Statistical Methods:

Analysis Populations

The enrolled population consisted of all subjects who signed the informed consent form. The randomized safety population consisted of all subjects who were randomized and received at least 1 dose of the study drug.

The full analysis population (FAP) for pharmacokinetics consisted of all subjects who were randomized, received study drug, and had at least 1 valid pharmacokinetic (PK) metric. Subjects who experienced emesis within 12 hours after morphine dosing could have been excluded from PK analysis.

Pharmacokinetics:

Blood samples to determine morphine plasma concentrations were taken and analyzed as detailed in Example 3.

Plasma concentrations of morphine were analyzed to determine the following PK metrics for each treatment: area under the plasma concentration versus time curve (AUC) from hour 0 to the last measurable plasma concentration ($AUC_t$), AUC extrapolated to infinity (AUCinf), maximum observed plasma concentration ($C_{max}$), time to maximum plasma concentration ($T_{max}$), and apparent terminal phase half-life ($t_{1/2}$).

Plasma concentrations of morphine were summarized at each time point for each tablet dose level using the FAP. Listings and figures of individual plasma concentrations were based on the randomized safety population. Pharmacokinetic metric analyses, summaries, and figures of mean plasma concentrations were based on the FAP.

Descriptive statistics (including mean, standard deviation, CV, median, minimum, maximum, and geometric mean values) were tabulated by tablet dose level, as applicable, for all plasma concentrations and PK metrics. Graphical displays of $C_{max}$ and AUC versus dose were presented.

A power model approach was used to assess the dose proportionality of morphine only.

For morphine $C_{max}$, $AUC_t$, and AUCinf, a mixed-model approach was used to estimate the magnitude of the slope ($\beta$) and to derive confidence intervals (CIs) around the slope. Dose proportionality was concluded when the 90% CI of the slope for each PK metric fell entirely within (0.88, 1.12) using the equation (1+ln(0.8)/ln(r), 1+ln(1.25)/ln(r)), where r is defined as the ratio of (highest dose/lowest dose).

Figure 95A:
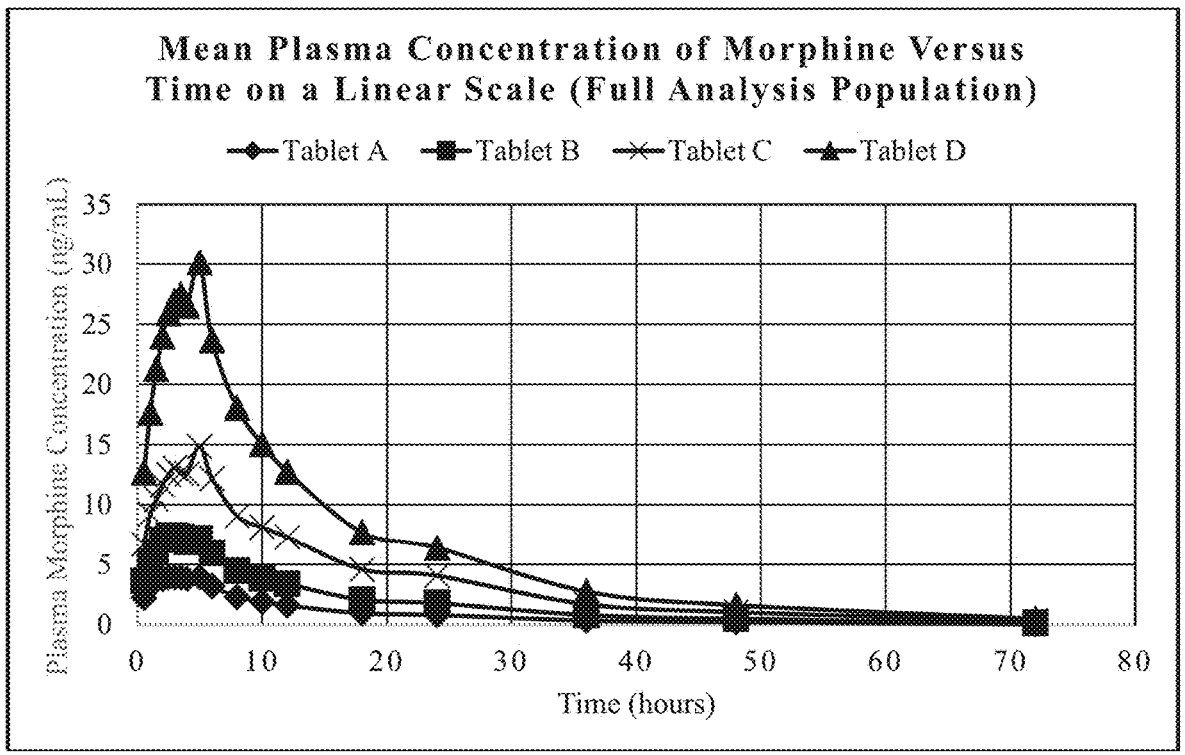
Figure 95B:
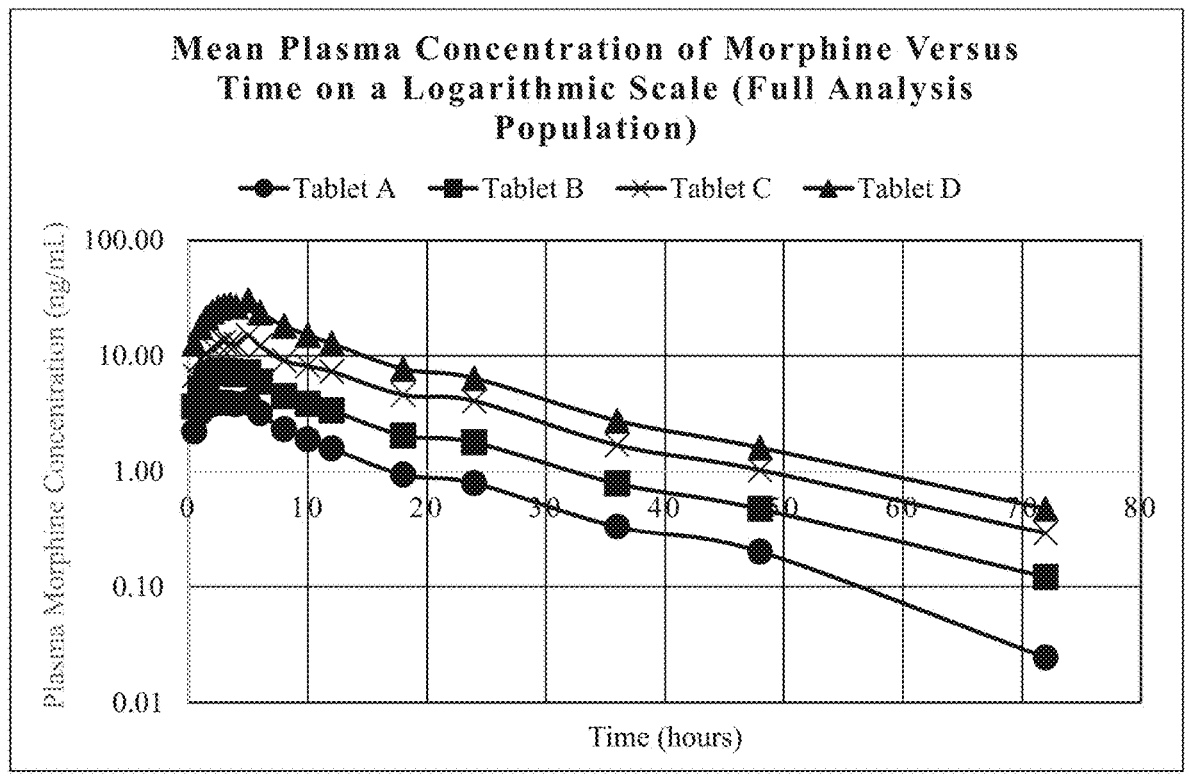

The in vivo PK data obtained for tablets A, B, C and D (15 mg, 30 mg, 60 mg and 100 mg) in the fasted state are presented in Table 4.1 (see FIGS. 95a and 95b for a graphical representation of this data).

TABLE 4.1

|  |  | Tablet | | | |
| --- | --- | --- | --- | --- | --- |
|  |  | A | B | C | D |
| Number of subjects |  | 51 | 53 | 52 | 54 |
| $AUC_t$ (h · ng/mL) | Mean | 57.53 | 119.57 | 249.85 | 450.85 |
|  | SD | 18.09 | 36.04 | 79.62 | 132.86 |
| $AUC_{inf}$ (h · ng/mL) | Mean | 61.88[a] | 124.35 | 256.84 | 462.01 |
|  | SD | 17.89[a] | 36.55 | 81.3 | 136.82 |
| $C_{max}$ (ng/mL) | Mean | 5.21 | 9.28 | 17.34 | 35.67 |
|  | SD | 1.73 | 3.18 | 5.82 | 11.63 |
| $T_{max}$ (h) | Median | 3 | 3 | 4 | 4 |
|  | Minimum, maximum | 1.00, 8 | 1.00, 6 | 0.50, 24 | 0.50, 6.22 |
| $t_{1/2}$ (h) | Mean | 13.67 | 13.43 | 12.78 | 12.69 |
|  | SD | 5.32 | 3.52 | 3.3 | 3.44 |

[a] N = 49

Abbreviations: N = number of subjects in the population; SD standard deviation.

After a single-dose, oral administration of the tablets A, B, C and D, mean morphine total exposure ($AUC_t$ and AUCinf) increased with increasing dose over the 15- to 100-mg dose range ($AUC_t$ range: 57.5 to 450.9 h·ng/mL; AUCinf range: 61.9 to 462.0 h·ng/mL). The mean $C_{max}$ of morphine also increased with increasing dose over the 15 to 100 mg dose range ($C_{max}$ range: 5.2 to 35.7 ng/mL). The median $T_{max}$ of morphine ranged from 3.0 to 4.0 hours and the elimination $t_{1/2}$ of morphine ranged from 12.7 to 13.7 hours over the 15- to 100-mg dose range.

A statistical analysis of the dose proportionality of morphine is given in Table 4.2 below:

TABLE 4.2

| Parameter | Estimated slope | Standard error | Lower 90% Confidence Interval | Upper 90% Confidence Interval |
| --- | --- | --- | --- | --- |
| $AUC_t$ (h · ng/mL) | 1.088 | 0.012 | 1.068 | 1.108 |
| $AUC_{inf}$ (h · ng/mL) | 1.066 | 0.012 | 1.047 | 1.086 |
| $C_{max}$ (ng/mL) | 0.994 | 0.021 | 0.959 | 1.028 |

A statistical power model was utilized as a sensitivity tool. The 90% CI for the slope for $AUC_t$, $AUC_{inf}$ and $C_{max}$ were contained within the range of 0.88 to 1.12, indicating that following oral administration of tablets in the dose range 15 to 100 mg, both peak and total exposure increased dose proportionally.

Example 4.2: In Vivo Bioequivalence Studies with Tablet D and 100 mg MS Contin® as a Reference in the Fasted State Study Design (Methodology):

This was a randomized, open-label, single-center, single-dose, 2-treatment, 2-period, 2-way, crossover study in healthy subjects. Treatments were separated by a minimum 7-day washout.

Number of Subjects (Planned and Analyzed):

Up to approximately 80 healthy subjects were planned to be randomized to ensure that approximately 72 subjects completed the study.

Seventy-eight subjects (44 male subjects and 34 female subjects) were randomly assigned to a treatment sequence in this study. Seventy-five subjects completed the study. Seventy-eight subjects were included in the randomized safety population and 76 subjects were included in the full analysis population (FAP) for pharmacokinetics. One subject discontinued due to an adverse event (AE) and 2 subjects discontinued due to subject's choice (withdrawal by subject).

Diagnosis and Main Criteria for Inclusion:

Healthy male and female subjects aged 18 to 55 years with no clinically significant medical history, who were deemed suitable to take part in this clinical study by the investigator.

Study Drug, Dose and Mode of Administration:

Tablet D (1×100 mg) and MS Contin® (1×100 mg) were each administered as a single dose orally with 240 mL water according to the randomization schedule in the fasted state.

Concomitant Medication:

A naloxone hydrochloride (HCl) challenge test was performed before the first dose of naltrexone HCl, which was administered as described in Example 3.

Duration of Treatment:

Subjects were screened no more than 28 days before check-in of period 1. There were 2 treatment periods. Study drug was administered in each period according to the study randomization schedule. There was a minimum 7-day washout period between study drug administrations. Subjects were confined to the study unit from the day before study drug administration (check-in) and for 72 hours after study drug administration during each period. Subjects had end-of-study (EOS) procedures performed 3 days (72 hours) after the last dose of study drug, or upon early discontinuation from the study. A follow-up phone call was made to inquire about AEs and concomitant medications 7 to 10 days after the last study drug administration.

The total study duration was up to approximately 50 days.

Study Procedures:
Pre-Randomization Phase:
Screening:

Subjects were screened within 28 days of check-in, period 1 (day −1). Screening activities included the following: demography, drug, alcohol, and cotinine screens, physical examination, 12-lead electrocardiogram (ECG), vital signs (systolic/diastolic blood pressure, pulse rate, respiratory rate, and oral temperature), pulse oximetry ($SpO_2$), medical and medication history, clinical laboratory testing, urine pregnancy test (female subjects only), follicle-stimulating hormone test (self-reported postmenopausal women only), and inclusion/exclusion criteria evaluation.

Treatment Phase:

Check-in: Subjects checked into the study unit the day before dosing in each period (day −1, period 1, day 7, period 2). In period 1 check-in only, subjects received a naloxone HCl challenge test and had chemistry, hematology, and urinalysis tests performed. Pregnancy tests for women of childbearing potential included a serum pregnancy test (period 1) and a urine pregnancy test (period 2). Vital signs, $SpO_2$, 12-lead ECG, and alcohol, cotinine, and urine drug screens were performed at check-in for both periods.

Period 1 and Period 2:

Study drug was administered on day 1. Naltrexone HCl tablets (50 mg) were administered with 240 mL of water every 12 hours from approximately 12 hours before study drug administration through 36 hours after study drug administration.

Vital sign measurements (including $SpO_2$) and blood samples for drug concentration measurements were obtained at pre-specified times. Adverse events and concomitant medications were recorded throughout the study.

Optional Pharmacogenomics:

Subjects participating in the optional exploratory PG portion of the study had samples collected pre-dose (or at check-in) and 72 hours post-dose in period 1 only.

End-of-Study Visit:

EOS procedures included a physical examination, 12-lead ECG, vital signs, $SpO_2$, serum pregnancy test for female subjects, and clinical laboratory tests.

Posttreatment Phase:

There was a follow-up phone call 7 to 10 days after last study drug administration.

Statistical Methods:

Analysis Populations

The enrolled population consisted of subjects who signed the informed consent form. The randomized safety population was the group of subjects who were randomized and received at least 1 dose of the study drug. The full analysis population (FAP) for PK metrics was the group of subjects who were randomized, received study drug, and had at least 1 valid PK metric. Subjects who experienced emesis within 12 hours after morphine dosing were excluded from the PK analysis for the affected period only.

Pharmacokinetics:

Blood samples for determining the morphine plasma concentrations were taken and analyzed as detailed in Example 3. The plasma concentrations for morphine were summarized at each time point by treatment for the FAP. Individual plasma concentration profiles were based on the randomized safety population. Mean plasma concentration profiles were based on the FAP.

Plasma concentrations of morphine were analyzed by noncompartmental PK analysis to determine the following PK metrics: area under the plasma concentration versus time curve from hour 0 to the last measurable plasma concentration ($AUC_t$), area under the plasma concentration versus time curve extrapolated to infinity (AUCinf), maximum observed plasma concentration ($C_{max}$), time to maximum plasma concentration ($T_{max}$), and apparent plasma terminal phase half-life ($t_{1/2}$).

Descriptive statistics (n, mean, standard deviation, CV, median, minimum, maximum, and geometric mean values) were tabulated by treatment and analyte for all plasma concentrations and PK metrics.

For morphine $AUC_t$, AUCinf, and $C_{max}$, a mixed-model analysis of variance (SAS PROC MIXED) was used to compare logarithmic-transformed (base e) values from the test and reference treatments with fixed effects for sequence, treatment, and period, and subject nested within sequence as a random effect. The 90% confidence intervals (CIs) were estimated for the ratio of population geometric means (test/reference) of exponentiated least squares (LS) means. Bioequivalence was established if the 90% CIs fell within the range of 80% to 125%. Inter-subject variability, intra-subject variability, and intra-subject variability CVs were also calculated. The comparison of interest was tablet D (100 mg) in the fasted state (test) versus MS Contin® 100 mg in the fasted state (reference).

The in vivo data is presented in Table 4.3.

TABLE 4.3

| | | Tablet D | MS Contin® 100 mg |
|---|---|---|---|
| Number of subjects | | 75 | 75 |
| $AUC_t$ | Mean | 466.38 | 466.2 |
| | SD | 136.68 | 130.22 |
| $AUC_{inf}$ | Mean | 475.49 | 476.35 |
| | SD | 139 | 132.8 |
| $C_{max}$ | Mean | 39.51 | 40.08 |
| | SD | 14.59 | 15.89 |
| $T_{max}$ | Median | 4 | 2.5 |
| | Minimum, maximum | 0.5, 8.0 | 0.5, 5.68 |
| $t_{1/2}$ | Mean | 12.53 | 12.6 |
| | SD | 3.21 | 3.02 |

Mean morphine total exposure ($AUC_t$) was 466.4 ng*hr/mL for tablet D and 466.2 for MS Contin®, and $AUC_{inf}$ was 475.5 and 476.4 ng*hr/mL for tablet D and MS Contin®, respectively. The mean $C_{max}$ of morphine was 39.5 and 40.1 ng/mL with a median $T_{max}$ of approximately 4.0 and 2.5 hours for tablet D and MS Contin®, respectively. The mean elimination $t_{1/2}$ of morphine was 12.5 and 12.6 hours for tablet D and MS Contin®, respectively. The statistical analysis of bioequivalence for morphine is presented in Table 4.4.

TABLE 4.4

|  | N | Tablet D (100-mg) | N | MS Contin® 100 mg | LS Mean Ratio (Tablet D 100 mg/MS Contin® 100 mg tablet) | 90% CI for LS N Mean Ratio |
|---|---|---|---|---|---|---|
| $AUC_t$ (h · ng/mL) | 75 | 421.06 | 75 | 419.22 | 100.44 | (97.93, 103.01) |
| $AUC_{inf}$ (h · ng/mL) | 75 | 430.73 | 75 | 429.96 | 100.18 | (97.67, 102.75) |
| $C_{max}$ (ng/mL) | 75 | 32.87 | 75 | 32.561 | 100.94 | (96.23, 105.88) |

The 90% CIs for the geometric LS (=least squares) mean ratios of $AUC_t$, $AUC_{inf}$, and $C_{max}$ were within the predefined bioequivalence acceptance limits of 80% to 125%, indicating bioequivalence between tablet D (100 mg) and MS Contin® 100 mg in the fasted state.

Example 4.3: In Vivo Bioequivalence Studies with Tablet D and 100 mg MS Contin® in the Fed State Study Design (Methodology):

This was a randomized, open-label, single-center, single-dose, 2-treatment, 2-period, 2-way crossover study in healthy subjects. Treatments were separated by a minimum 7-day washout. There was an optional exploratory pharmacogenomic (PG) sampling portion of this study.

Number of Subjects (Planned and Analyzed):

Up to approximately 80 healthy subjects were planned to be randomized in order to ensure that approximately 72 subjects completed the study.

The results from this pilot study, suggest that the pharmacokinetic (PK) intra-subject coefficient of variation should not exceed 20%. With this estimate of variability and the assumption that treatment differences between fed tablet D (100 mg) and MS Contin® 100 mg would not exceed 12%, it was projected that 72 subjects in a 2-way crossover study would generate a statistical power value of at least 90%.

Eighty-three subjects (41 male subjects and 42 female subjects) were randomly assigned to a treatment sequence in this study. Seventy-one subjects completed the study. Eighty-three subjects were included in the randomized safety population and 81 subjects were included in the full analysis population (FAP) for pharmacokinetics. Two subjects discontinued due to adverse events (AEs), 4 subjects discontinued due to subject's choice (withdrawal by subject), and 6 subjects discontinued due to administrative reasons.

Diagnosis and Main Criteria for Inclusion:

Healthy male and female subjects aged 18 to 55 years with no clinically significant medical history, who were deemed suitable to take part in this clinical study by the investigator.

Study Drug, Dose and Mode of Administration:

Tablet D (1×100 mg) and MS Contin® (1×100 mg) were each administered as a single dose orally with 240 mL water according to the randomization schedule in the fed state.

Concomitant Medication:

A naloxone hydrochloride (HCl) challenge test was performed before the first dose of naltrexone HCl. This test was performed as described in Example 3.

Duration of Treatment:

Subjects were screened no more than 28 days before check-in of period 1. There were 2 treatment periods. Study drug was administered in each period according to the study randomization schedule. There was a minimum 7-day washout period between study drug administrations. Subjects were confined to the study unit from the day before study drug administration (check-in) and for 72 hours after study drug administration during each period. Subjects had end-of-study (EOS) procedures performed 3 days (72 hours) after the last dose of study drug, or upon early discontinuation from the study. A follow-up phone call was made to inquire about AEs and concomitant medications 7 to 10 days after the last study drug administration.

The total study duration was up to approximately 47 days.

Study Procedures:

Prerandomization Phase:

Screening:

Subjects were screened within 28 days of check-in, period 1 (day −1). Screening activities included demography, drug, alcohol, and cotinine screens, physical examination, 12-lead electrocardiogram (ECG), vital signs (systolic/diastolic blood pressure, pulse rate, respiratory rate, and oral temperature), pulse oximetry (SpO2), medical and medication history, clinical laboratory testing, urine pregnancy test (female subjects only), follicle-stimulating hormone test (self-reported postmenopausal female subjects only), and inclusion/exclusion criteria evaluation.

Treatment Phase:

Check-In:

Subjects checked into the study unit the day before start of dosing in each period. In period 1 check-in only, subjects received a naloxone HCl challenge test, and had chemistry, hematology, and urinalysis tests performed. Pregnancy tests for women of childbearing potential included a serum pregnancy test (period 1) and a urine pregnancy test (period 2). Vital sign and SpO2 measurements, 12-lead ECG, and alcohol, cotinine, and urine drug screens were performed at check-in for both periods.

Study drug was administered on day 1.

Naltrexone HCl tablets (50 mg) were administered with 240 mL of water every 12 hours from approximately 12 hours before study drug administration through 36 hours after study drug administration.

Vital sign measurements (including $SpO_2$) and blood samples for drug concentration measurements were obtained at pre-specified times. Adverse events and concomitant medications were recorded throughout the study.

For fed dosing, subjects fasted from food (not including water) overnight for at least 10 hours (with water fasting beginning 3 hours prior to dosing). Subjects started the standardized high-fat breakfast 30 minutes prior to the administration of the dose. Each dose was administered 5 minutes after completing breakfast, where the breakfast was consumed over a 25-minute time interval. No food was allowed for 4 hours post-dose, and no water was allowed for 2 hours post-dose.

Pharmacokinetics:

Blood samples for determining plasma concentrations of morphine were taken and analyzed as detailed in Example 3.

Safety:

Safety was assessed using recorded AEs, clinical laboratory test results, vital sign and $SpO_2$ measurements, physical examinations, and 12-lead ECGs.

Statistical Methods:

Analysis Populations

The enrolled population consisted of all subjects who signed the informed consent form. The randomized safety population consisted of the group of subjects who were randomized and received at least 1 dose of the study drug.

No subjects were excluded from the randomized safety population.

The full analysis population for PK metrics consisted of the group of subjects who were randomized, received at least 1 dose of study drug, and had at least 1 valid PK metric. Subjects who experienced emesis within 12 hours after morphine dosing could have been excluded from the PK analysis.

Pharmacokinetics:

Plasma concentrations of morphine were analyzed by non-compartmental PK analysis to determine the following PK metrics: area under the plasma concentration versus time curve from hour 0 to the last measurable plasma concentration ($AUC_t$), area under the plasma concentration versus time curve extrapolated to infinity (AUCinf), maximum observed plasma concentration ($C_{max}$), time to maximum plasma concentration ($T_{max}$), and apparent terminal phase half-life ($t_{1/2}$).

The plasma concentrations for morphine were summarized at each time point by treatment for the FAP. Listings and figures of individual plasma concentrations were based on the randomized safety population. Pharmacokinetic metric analyses and summaries were based on the FAP.

Descriptive statistics (n, mean, standard deviation, coefficient of variation, median, minimum, maximum values, and geometric mean) were tabulated by treatment, as applicable, for all plasma concentrations and PK metrics.

For morphine, $AUC_t$, AUCinf, and $C_{max}$, a mixed-model analysis of variance (SAS PROC MIXED) was used to compare (test versus reference) logarithmic-transformed (base e) values from the test and reference treatments with fixed effects for sequence, treatment, and period, and subject nested within sequence as a random effect. The 90% confidence intervals (CIs) were estimated for the ratio of population geometric means (test/reference) of exponentiated least squares (LS) means. Bioequivalence (test versus reference) was established if the 90% CIs fell within the range of 80% to 125%. Inter-subject variability, intra-subject variability, and intra-subject variability coefficient of variation were also calculated. The comparison of interest was tablet D, 100 mg tablet, (in the fed state, test) versus MS Contin® 100 mg (in the fed state, reference).

The in vivo data is presented in Table 4.5.

TABLE 4.5

| | | Tablet | |
|---|---|---|---|
| | | D | MS Contin® 100 mg |
| Number of subjects | | 73 | 76 |
| $AUC_t$ | Mean | 491.14 | 510.5 |
| | SD | 130.51 | 131.87 |
| $AUC_{inf}$ | Mean | 501.83 | 520.27 |
| | SD | 133.79 | 135.08 |
| $C_{max}$ | Mean | 43.11 | 56.49 |
| | SD | 14.67 | 19.1 |
| $T_{max}$ | Median | 6 | 3 |
| | Minimum, maximum | 1.5, 10.42 | 1.0, 10.0 |
| $t_{1/2}$ | Mean | 12.52 | 12.63 |
| | SD | 3.96 | 4.06 |

Mean morphine total exposure was 491.1 and 510.5 ng*hr/mL for AU and 501.8 and 520.3 ng*hr/mL for $AUC_{inf}$ for tablet D (100 mg) and the 100 mg MS Contin® tablets, respectively. The mean $C_{max}$ of morphine was 43.1 and 56.5 ng/mL with a median $T_{max}$ of approximately 6.0 and 3.0 hours for the tablet D (100 mg) and the MS Contin® 100 mg tablets, respectively. The mean elimination $t_{1/2}$ of morphine was 12.5 and 12.6 hours for tablet D (100 mg) and 100 mg MS Contin® tablets, respectively.

The statistical analysis of plasma pharmacokinetic metrics of morphine are given in Table 4.6.

TABLE 4.6

| Parameter | N | Tablet D | N | MS Contin® 100 mg | LS Mean Ratio (Tablet D 100-mg/MS Contin® 100-mg tablet) | 90% CI for LS Mean Ratio |
|---|---|---|---|---|---|---|
| $AUC_t$ (h · ng/mL) | 73 | 467.648 | 76 | 484.243 | 96.573 | (94.377, 98.820) |
| $AUC_{inf}$ (h · ng/mL) | 73 | 478.397 | 76 | 493.855 | 96.87 | (94.575, 99.220) |
| $C_{max}$ (ng/mL) | 73 | 39.75 | 76 | 52.027 | 76.402 | (71.479, 81.664) |

The geometric LS mean ratios (90% CIs) for $AUC_t$ and $AUC_{inf}$ were 96.573 (94.377, 98.820) and 96.870 (94.575, 99.220), respectively. The geometric LS mean ratio (90% CIs) for $C_{max}$ was 76.402 (71.479, 81.664).

After oral administration in the fed state, bioequivalence between tablet D and the 100 mg MS Contin® tablets was established for $AUC_t$ and $AUC_{inf}$.

Example 4.4: In Vivo Bioequivalence Studies with Tablets E and 200 mg MS Contin® in the Fasted State Study Design (Methodology):

This was a single-center, randomized, open-label, 2-period, 2-sequence, single-dose, 2-way crossover study in healthy adult male and female subjects. Treatments were separated by a minimum 7-day washout.

Number of Subjects (Planned and Analyzed):

Up to approximately 80 healthy subjects were planned to be randomized in order to ensure that approximately 72 subjects completed the study.

The results from this pilot study suggested that the pharmacokinetic (PK) intra-subject coefficient of variation should not exceed 200. With this estimate of variability and the assumption that treatment differences between fasted tablet E (200 mg) and MS Contin® 200 mg would not exceed 12%, it was projected that 72 subjects in a 2-way crossover study would generate a statistical power value of at least 90%.

Eighty-two subjects (39 male subjects and 43 female subjects) were randomized to a treatment sequence in this study. Seventy-five subjects (91.5%) completed the study. Eighty-two subjects were included in the randomized safety population and 82 subjects were included the full analysis population (FAP) for PK metrics. One subject (1.2%) discontinued from the study due to a treatment-emergent adverse event (TEAE), 5 subjects (6.1%) discontinued due to administrative reasons, and 1 subject (1.2%) discontinued due to subject's choice (withdrawal by subject).

Diagnosis and Main Criteria for Inclusion:

Healthy male and female subjects aged 18 to 55 years with no clinically significant medical history, who were deemed suitable to take part in this clinical study by the investigator.

Study Drug, Dose and Mode of Administration:

Tablet E (1×200 mg) and MS Contin® (1×200 mg) were each administered as single dose orally with 240 mL water according to the randomization schedule in the fasted state.

Concomitant Medication:

A naloxone hydrochloride (HCl) challenge test was performed before the first dose of naltrexone HCl. Naltrexone HCl administration was performed as described in example 3.

Duration of Treatment:

Subjects were screened no more than 28 days before check-in of period 1. There were 2 treatment periods. Study drug was administered in each period according to the study randomization schedule. There was a minimum 7-day washout period between study drug administrations. Subjects were confined to the study unit from the day before study drug administration (check-in) and for 72 hours after study drug administration during each period. Subjects had end-of-study (EOS) procedures performed 3 days (72 hours) after the last dose of study drug, or upon early discontinuation from the study. A follow-up phone call was made to inquire about AEs and concomitant medications 7 to 10 days after the last study drug administration.

The total study duration was up to approximately 46 days.

Pre-Randomization Phase:

Screening:

Subjects were screened within 28 days of check-in, period 1 (day −1). Screening activities included demography, drug, alcohol, and cotinine screens, physical examination, 12-lead electrocardiogram (ECG), vital signs (systolic/diastolic blood pressure, pulse rate, respiratory rate, and oral temperature), pulse oximetry ($SpO_2$), medical and medication history, clinical laboratory testing, urine pregnancy test (female subjects only), follicle-stimulating hormone test (self-reported postmenopausal women only), and inclusion/exclusion criteria evaluation.

Treatment Phase:

Check-In:

Subjects checked into the study unit the day before the start of dosing in each period. In period 1 check-in only, subjects received a naloxone HCl challenge test, and had chemistry, hematology, and urinalysis tests performed. Pregnancy tests for women of childbearing potential included a serum pregnancy test (period 1) and a urine pregnancy test (period 2). Vital sign and $SpO_2$ measurements, 12-lead ECG, and alcohol, cotinine, and urine drug screens were performed at check-in for both periods.

Period 1 and Period 2: Study drug was administered on day 1. Naltrexone HCl tablets (50 mg) were administered with 240 mL of water every 12 hours from approximately 12 hours before study drug administration through 36 hours after study drug administration.

Vital sign measurements (including $SpO_2$) and blood samples for drug concentration measurements were obtained at pre-specified times. Adverse events and concomitant medications were recorded throughout the study.

End-of-Study Visit

EOS procedures included a physical exam, 12-lead ECG, vital sign and $SpO_2$ measurements, serum pregnancy test for female subjects, and clinical laboratory tests.

Post Treatment Phase

There was a follow-up phone call made 7 to 10 days after last study drug administration.

Pharmacokinetics:

Blood samples for determining plasma concentrations of morphine were taken and analyzed as detailed in Example 3.

Statistical Methods:

Analysis Populations

The enrolled population consisted of subjects who signed the informed consent form.

The randomized safety population consisted of the group of subjects who were randomized and received at least dose of the study drug. After review of the data, no subjects were excluded from the randomized safety population.

The full analysis population for PK metrics consisted of the group of subjects who were randomized, received study drug, and had at least 1 valid PK metric. Subjects who experienced emesis within 12 hours after morphine dosing were excluded from the PK analysis.

The in vivo data for tablet E (200 mg morphine sulfate, test) and MS Contin® (200 mg, reference) in the fasted state is presented in Table 4.7.

TABLE 4.7

|  |  | Tablet | |
| --- | --- | --- | --- |
|  |  | E | MS Contin® 200 mg |
| Number of subjects |  | 79 | 76 |
| $AUC_t$ (h · ng/mL) | Mean | 1011.84 | 1002.92 |
|  | SD | 268.83 | 281.07 |
| $AUC_{inf}$ (h · ng/mL) | Mean | 1031.06 | 1027.35[a] |
|  | SD | 273.13 | 291.98[a] |
| $C_{max}$ (ng/mL) | Mean | 76.07 | 73.56 |
|  | SD | 26.97 | 24.62 |

TABLE 4.7-continued

|  |  | Tablet | |
|---|---|---|---|
|  |  | E | MS Contin® 200 mg |
| $T_{max}$ (h) | Median | 4 | 3 |
|  | Minimum, maximum | 0.5, 10.0 | 0.5, 8.0 |
| $t_{1/2}$ (h) | Mean | 12.01 | 12.38[a] |
|  | SD | 2.85 | 3.22[a] |

[a] N = 75

Following single-dose, oral administration of tablet E (200 mg) or MS Contin® 200 mg in the fasted state, mean morphine total exposure ($AUC_t$) was 1011.8 and 1002.9 h·ng/mL for tablet E (200 mg) and MS Contin®, respectively. Mean AUCinf for morphine was 1031.1 and 1027.4 h·ng/mL for tablet E and MS Contin® respectively. The mean $C_{max}$ of morphine was 76.1 and 73.6 ng/mL with a median $T_{max}$ of 4.0 and 3.0 hours for tablet E (200 mg) and MS Contin®, respectively. The mean elimination $t_{1/2}$ of morphine was approximately 12 hours for both treatments.

The statistical analysis of plasma pharmacokinetic metrics of morphine is given in Table 4.8.

TABLE 4.8

| Parameter | N | Tablet E | N | MS Contin® 200 mg | LS Mean Ratio (Tablet E, 200-mg/MS Contin® 200-mg tablet) | 90% CI for LS Mean Ratio |
|---|---|---|---|---|---|---|
| $AUC_t$ (h · ng/mL) | 79 | 1004.719 | 76 | 992.456 | 101.236 | (98.558, 103.986) |
| $AUC_{inf}$ (h · ng/mL) | 79 | 1027.848 | 75 | 1021.23 | 100.648 | (97.996, 103.372) |
| $C_{max}$ (ng/mL) | 79 | 73.119 | 76 | 71.767 | 101.883 | (97.421, 106.551) |

The 90% CIs for the geometric LS means ratios of $AUC_t$, $AUC_{inf}$, and $C_{max}$ were within the predefined range of 80% to 125%, indicating bioequivalence between tablet E and MS Contin® 200 mg in the fasted state.

Example 4.5: In Vivo Bioequivalence Studies with Tablets E and 200 mg MS Contin® in the Fed State Study Design (Methodology):
This was a randomized, open-label, single-center, single-dose, 2-treatment, 2-period, 2-way crossover study in healthy adult male and female subjects. Treatments were separated by a minimum 7-day washout. There was an optional exploratory pharmacogenomic (PG) sampling portion of this study.

Number of Subjects (Planned and Analyzed):
Up to approximately 80 subjects were randomized in order to ensure that approximately 72 subjects completed the study. The results from the pilot study suggested that the pharmacokinetic (PK) intra-subject coefficient of variation (CV) did not exceed 20%. With this estimate of variability and the assumption that treatment differences between fed tablet E (200 mg) and MS Contin® 200 mg would not exceed ±12%, it was projected that 72 subjects in a 2-way crossover study would generate a statistical power value of at least 90%.

Eighty subjects (44 male subjects and 36 female subjects) were randomized to a treatment sequence in this study. Seventy-three subjects completed the study. Eighty subjects were included in the randomized safety population and the full analysis population (FAP) for pharmacokinetics. Six subjects (7.5%) discontinued due to administrative reasons, and 1 subject (1.25%) discontinued due to subject's choice (withdrawal by subject).

Study Drug, Dose and Mode of Administration:
Tablet E (1×200 mg) and MS Contin® (1×200 mg) were each administered as a single dose orally with 240 mL water according to the randomization schedule in the fed state.

Concomitant Medication:
A naloxone hydrochloride (HCl) challenge test was performed as in example 3 before the first dose of naltrexone HCl. Naltrexone HCl administration was also performed as described in example 3.

Duration of Treatment:
Subjects were screened no more than 28 days before check-in of period 1. Study drug was administered in each period according to the study randomization schedule. There was a minimum 7-day washout period between study drug administrations. Subjects were confined to the unit the day before study drug administration and for 72 hours following study drug administration during each period. Subjects had end-of-study (EOS) procedures performed 3 days (72 hours) after last dose of study drug or upon early discontinuation from the study. A follow-up phone call was made to inquire about AEs and concomitant medications 7 to 10 days after last study drug administration.

The total duration of the study was up to approximately 46 days.

Study Procedures:
Prerandomization Phase:
Screening:
Screening occurred within 28 days of check-in, period 1. Screening activities included demography, drug, alcohol, and cotinine screens, physical examination, 12-lead electrocardiogram (ECG), vital signs (systolic/diastolic blood pressure, pulse rate, respiratory rate, and oral temperature), pulse oximetry ($SpO_2$), medical and medication history, clinical laboratory testing, urine pregnancy test (female subjects only), follicle-stimulating hormone test (self-reported postmenopausal women only), and inclusion/exclusion criteria evaluation.

Treatment Phase:
Check-In:
Subjects checked into the unit the day before start of dosing. In period 1 check-in only, subjects received a naloxone HCl challenge test and had chemistry, hematology, and urinalysis tests performed.

For all periods: Pregnancy tests for women of childbearing potential included serum pregnancy test (period 1) and urine pregnancy test (period 2); vital sign, SpO$_2$, and 12-lead ECG measurements were collected; and alcohol, cotinine, and urine drug screens were performed at check-in.

For all periods, subjects were administered study drug and naltrexone HCl tablets (50 mg). Vital sign measurements (including SpO$_2$) and blood samples for drug concentration measurements were obtained at pre-specified times. Adverse events and concomitant medications were recorded throughout the study.

For fed dosing, subjects fasted from food (not including water) overnight for at least 10 hours (with water fasting beginning 3 hours prior to dosing). Subjects started the standardized high-fat breakfast 30 minutes prior to the administration of the dose. Each dose was administered 5 minutes after completing breakfast, where the breakfast was consumed over a 25-minute time interval. No food was allowed for 4 hours post-dose, and no water was allowed for 2 hours post-dose.

Pharmacokinetics:
Blood samples for determining plasma concentrations of morphine were taken and analyzed as detailed in Example 3.

Safety:
Safety was assessed using recorded AEs, clinical laboratory test results, vital signs, SpO$_2$, physical examinations, and 12-lead ECGs.

Statistical Methods:
Analysis Populations

The enrolled population consisted of all subjects who signed the informed consent form.

The randomized safety population consisted of all subjects who were randomized and received at least 1 dose of the study drug. The full analysis population (FAP) for pharmacokinetics consisted of all subjects who were randomized, received study drug, and had at least 1 valid PK metric. Subjects experiencing emesis within 12 hours after morphine dosing could have been excluded from the PK analysis.

As documented in the statistical analysis plan 2, after review of the data, no subjects were excluded from the FAP.

Pharmacokinetics:
Plasma concentrations of morphine were analyzed to determine the following PK metrics for each treatment: area under the plasma concentration versus time curve (AUC$_t$) from hour 0 to the last measurable plasma concentration (AUC$_t$), AUC extrapolated to infinity (AUCinf), maximum observed plasma concentration (C$_{max}$), time to maximum plasma concentration (T$_{max}$), and apparent terminal phase half-life (t$_{1/2}$).

Plasma concentrations of morphine were summarized at each time point for each treatment using the FAP. Listings and figures of individual plasma concentrations were based on the randomized safety population. Pharmacokinetic metric analyses, summaries, and figures of mean plasma concentrations were based on the FAP.

Descriptive statistics (including n, mean, standard deviation, CV, median, minimum, maximum, and geometric mean values) were tabulated by treatment, as applicable, for all plasma concentrations and PK metrics.

The bioequivalence of tablets E (200 mg) to the MS Contin® 200 mg tablets (reference) was assessed in the fed state. For morphine AUC$_t$, AUCinf, and C$_{max}$, a mixed-model analysis of variance (SAS PROC MIXED) was used to compare (test versus reference) logarithmic-transformed (base e) values from the test and reference treatments, with fixed effects for sequence, treatment, and period; and a random effect of subject nested within sequence. The 90% confidence intervals (CIs) were estimated for the ratios of population geometric means (test/reference) of exponentiated least squares (LS) means. Bioequivalence (test versus reference) would be established if the 90% CIs fell within the range of 80% to 125%.

The comparison of interest was the tablet E (200 mg), in the fed state, versus MS Contin® 200 mg tablet (in the fed state)

The PK values for tablet E (200 mg morphine sulfate, test) and MS Contin® (200 mg, reference) in the fed state are presented in Table 4.9.

TABLE 4.9

| Tablet | | E | MS Contin® 200 mg |
|---|---|---|---|
| Number of subjects | | 74 | 76 |
| AUC$_t$ | Mean | 1002.52 | 1060.52 |
| | SD | 218.66 | 225.11 |
| AUC$_{inf}$ | Mean | 1016.14 | 1076.29 |
| | SD | 221.64 | 229.43 |
| C$_{max}$ | Mean | 84.83 | 112.4 |
| | SD | 31.33 | 40.81 |
| T$_{max}$ | Median | 8 | 4 |
| | Minimum, maximum | 1.5, 12.0 | 1.0, 12.0 |
| t$_{1/2}$ | Mean | 11.65 | 12.39 |
| | SD | 2.87 | 3.81 |

Following single dose, oral administration of tablet E (200 mg) or MS Contin® 200 mg in the fed state, mean morphine total exposure (AUC$_t$) was 1002.5 and 1060.5 ng*hr/mL for tablets E and MS Contin®, respectively. Mean AUC$_{inf}$ for morphine was 1016.1 and 1076.3 ng*hr/mL for tablets E (200 mg) and MS Contin®, respectively. The mean C$_{max}$ of morphine was 84.8 and 112.4 ng/mL with a median T$_{max}$ of 8.0 and 4.0 hours for tablets E and MS Contin®, respectively. The mean elimination t$_{1/2}$ of morphine was 11.7 and 12.4 hours for tablets E (200 mg) and MS Contin®, respectively.

The statistical analysis of plasma pharmacokinetic metrics of morphine is given in Table 4.10.

TABLE 4.10

| Parameter | N | Tablet E in the fed state | N | MS Contin® 200 mg | LS Mean Ratio (Tablet E, 200 mg/MS Contin® 200-mg tablet) | 90% CI for LS Mean Ratio |
|---|---|---|---|---|---|---|
| AUCt (h · ng/mL) | 74 | 978.48 | 76 | 1014.63 | 96.44 | (94.15, 98.78) |
| AUC$_{inf}$ (h · ng/mL) | 74 | 994.14 | 76 | 1031.68 | 96.36 | (94.09, 98.69) |
| C$_{max}$ (ng/mL) | 74 | 81.41 | 76 | 104.99 | 77.55 | (73.30, 82.04) |

The geometric LS mean ratios (90% CIs) for $AUC_t$ and $AUC_{inf}$ were 96.44 (94.15, 98.78) and 96.36 (94.09, 98.69), respectively. The geometric LS mean ratio (900 CIs) for $C_{max}$ was 77.55 (73.30, 82.04).

After oral administration in the fed state, bioequivalence was thus established between tablet E and 200 mg MS Contin® with respect to $AUC_t$ and $AUC_{inf}$.

Breaking Strength Tests (Schleuniger)

Example 5

Two pilot scale batches were manufactured to demonstrate the effect of polyethylene oxide particle size (regular grade vs. fine particle grade) and of the curing variables (time and temperature) on finished tablet hardness (determined as breaking strength measured by means of a Schleuniger apparatus as described herein in the Definitions). The compositions of the tablets according to the invention and tested in this example are provided in Table VI. Certain manufacturing conditions (such as curing time and temperature) were varied as described in Table 5.1. For each batch, the bulk tablets were split into two portions for curing and coating; one portion was cured at 75° C. and the other at 78° C.

Table 5.1 also specifies that different particle size grades of the POLYOX resins were used for the two batches manufactured (identified as tablets AG and AH). In order to compare solely the effect of particle size, the same lots of morphine sulfate and the same processing steps were used for both batches. Specifically, regular POLYOX N60K grade was used compared to fine particle POLYOX N60K (FP). According to specification from the manufacturer, in POLYOX N60K FP, 96 to 100% of the particles pass through a 60 mesh (250 micron; 0.250 mm) screen.

The breaking strength test was carried out as described in the "Definitions", herein above.

The results of the breaking strength test are also provided in Table 5.1 below.

The tablet hardness results in Table 5.1 (below) demonstrate that POLYOX fine particle grade provides harder core tablets (16.0 Kp/156.8 N) compared to POLYOX regular grade (10.8 Kp/105.84 N). This indicates that a stronger physical bond of particles is achieved when the fine particle material is used. For both batches comparing the hardness data of the uncured tablets to the cured tablets demonstrates that curing increases the breaking strength and that POLYOX fine particle grade provides harder cured tablets compared to regular grade POLYOX. Within each batch, both curing temperatures (75° or 78° C.) provided rather similar cured tablet hardness values.

For the batch manufactured with POLYOX regular grade, cured tablets were readily reduced to smaller particles in about 20-30 seconds by grinding with a mortar and pestle.

For the batch manufactured with POLYOX FP grade cured tablets were flattened and remained intact after 1 minute of applying pressure and grinding motion using a mortar and pestle.

It is thus demonstrated that a combination of using FP grade polyethylene oxide, a curing temperature of 75° C. and a curing time of 45 minutes are preferred and provide sufficient breaking strength for the 100 mg morphine sulfate as well as the 200 mg morphine sulfate tablets according to the present invention. The curing time and temperature are however dependent on the concentration of morphine sulfate in the tablet formulation. Therefore, a curing temperature of 72° C. and a curing time of 30 minutes are preferred and provide sufficient breaking strength for the lower strength tablets according to the present invention, namely the 15 mg, 30 mg, and 60 mg tablets.

TABLE 5.1

Influence of particle size, curing time and temperature on tablet breaking strength

| Example | 5.1, Tablet AG | | | | | | 5.2, Tablet AH | | | | | |
| --- | --- | --- | --- | --- | --- | --- | --- | --- | --- | --- | --- | --- |
| POLYOX grade | Regular | | | | | | Fine Particle | | | | | |
| Compression Force (KN) | 12 | | | | | | 12 | | | | | |
| Uncured Tablet (Core): | | | | | | | | | | | | |
| Weight (mg) | 331 | | | | | | 331 | | | | | |
| Thickness (mm) | 3.76 | | | | | | 3.76 | | | | | |
| Breaking strength (Kp) | 10.8 | | | | | | 16 | | | | | |
| Breaking strength (N) | 105.84 | | | | | | 156.8 | | | | | |
| Curing Temperature | 75° C. | | | 78° C. | | | 75° C. | | | 78° C. | | |
| Curing Time (min) | Start | 45 | 60 | Start | 45 | 60 | Start | 45 | 60 | Start | 45 | |
| Tablet | | | | | | | | | | | | |
| Weight (mg) | 334 | 330 | 331 | 327 | 329 | 331 | 325 | 325 | 326 | 327 | 327 | |
| Thickness (mm) | 4.02 | 3.95 | 3.89 | 3.97 | 3.95 | 3.89 | 3.98 | 3.92 | 3.91 | 3.96 | 3.9 | |

TABLE 5.1-continued

Influence of particle size, curing time and temperature on tablet breaking strength

| Example | 5.1, Tablet AG | | | | | | | 5.2, Tablet AH | | | |
|---|---|---|---|---|---|---|---|---|---|---|---|
| Breaking strength (Kp) | 18.2 | 20.9 | 23.5 | 18.2 | 21 | 23 | 25 | 27.4 | 27.8 | 26.2 | 28.4 |
| Breaking strength (N)[1] | 178.4 | 205.0 | 230.5 | 178.5 | 205.4 | 225.6 | 245.2 | 268.7 | 272.6 | 256.9 | 278.5 |

[1]A conversion factor of 1 Kp = 9.807N was used.

Example 6

The results of the breaking strength tests carried out on tablets containing 15 mg and 60 mg morphine sulfate and having a total mass of 175 mg are shown in Table 6.1.

TABLE 6.1

| | Reference Tablet | | | | | | | | |
|---|---|---|---|---|---|---|---|---|---|
| Morphine Sulfate/mg | 15 | | | | 60 | | | | |
| POLYOX 301 FP[2] (Mw 4,000,000)/mg | 157.26 | | | | 112.26 | | | | |
| Magnesium stearate/mg | 0.87 | | | | 0.87 | | | | |
| Colloidal Silicon Dioxide/mg | 0.87 | | | | 0.87 | | | | |
| Total tablet mass/mg | 174 | | | | 174 | | | | |
| Weight ratio morphine sulfate/POLYOX | 0.086 | | | | 0.34 | | | | |
| Tablet shape | troche/caplet | | | | troche/caplet | | | | |
| Curing time/mins | 30 | | | | 30 | | | | |
| Temperature/° C. | 72 | | | | 72 | | | | |
| Breaking strength/kp | OL[1] | 25.2 | 22.8 | 25.3 | OL[1] | 14.7 | 16 | 16.4 | 16.9 | 17.3 |
| Breaking strength/N | OL[1] | 247.1 | 223.6 | 248.1 | OL[1] | 144.2 | 156.9 | 160.8 | 165.7 | 169.7 |

[1]OL = LOADCELL OVERLOAD (the machine reached its maximum level)
[2]POLYOX 301 was screened through a 60-mesh screen to obtain FP material for blending.

The results in Table 6.1 compare the effect of the content of polyethylene oxide (or the weight ratio of morphine sulfate to polyethylene oxide) on the breaking strength: Higher drug loading (and thus a lower content of polyethylene oxide) results in tablets having lower values of breaking strength.

Example 7

In Example 7 the breaking strength of tablets A, B, C and D (15 mg, 30 mg, 60 mg and 100 mg) was tested, both cured and uncured.

The breaking strength test was carried out as described in Example 5, and the effect of the compression force applied during dry compression to form the extended release matrix formulation on the breaking strength of the (uncured) tablet was determined. These results are presented in Table 7.1, below.

These results demonstrate that the breaking strength of the tablets increases following the curing step. A breaking strength of over 200 N was achieved for all of the cured tablets A-E.

As a comparison, Table 7.2 below shows exemplary values for the breaking strength of commercial MS Contin® tablets of various strengths.

It is evident that the breaking strength of all MS Contin® tablets is significantly lower than even the lowest value of breaking strength measured for the uncured tablets according to the present invention. This demonstrates the abuse-deterrent properties of the morphine sulfate dosage forms of the present invention.

TABLE 7.1

| | Example<br>Tablet<br>Strength | 7.1<br>A[1]<br>15 mg | | 7.2<br>B[1]<br>30 mg | | 7.3<br>C[1]<br>60 mg | | 7.4<br>D[1]<br>100 mg | | 7.5<br>E[1]<br>200 mg | |
|---|---|---|---|---|---|---|---|---|---|---|---|
| Uncured (core tablet) | Compression Force (KN) | 2 | 8.8 | 4 | 9.8 | 7 | 13.7 | 12 | 12.4 | n/a | 13.8 |
| | Tablet (core) Weight (mg) | 127 | 125.3 | 176 | 175.1 | 331 | 329.8 | 331 | 331.4 | 599 | 602.0 |
| | Breaking strength (Kp) | 9 | 12 | 11 | 13.2 | 14.2 | 14.4 | 16 | 10.7 | 14.8 | 14.9 |
| | Breaking strength (N) | 88.3 | 117.7 | 107.9 | 129.5 | 139.3 | 141.2 | 156.9 | 104.9 | 145.14 | 146.12 |
| | Thickness (mm) | 3.65 | 3.41 | 3.71 | 3.58 | 3.93 | 3.88 | 3.76 | 3.87 | 5.36 | 5.33 |
| Cured coated tablet | Weight (mg) | 130 | | 182 | | 343 | | 343 | | 624 | |
| | Breaking strength (Kp) | OL[2] | OL[2] | OL[2] | OL[2] | 33.8 | 35.2 | 27.2 | 28.5 | 41.4 | 43.9 |
| | Breaking strength (N) | OL[2] | OL[2] | OL[2] | OL[2] | 331.48 | 345.21 | 266.75 | 279.50 | 406.01 | 430.53 |

[1]Batches were prepared with the same compositions, but different compression forces were applied.
[2]OL = LOADCELL OVERLOAD (the machine reached its maximum level)

TABLE 7.2

MS Contin ® Tablets - Average Tablet Weight and Breaking Strength:

| Strength (three batches tested for each) | Weight (mg) | | Sample Size | Breaking Strength (Kp) | | Breaking strength (N) | Sample size |
|---|---|---|---|---|---|---|---|
| | Average | Range | | Average | Range | | |
| 15 mg | 149.8 | 146.7-153.2 | 260 | 4.7 | 1.8-5.6 | 46.09 | 130 |
| | 149.6 | 144.4-155.1 | 320 | 4 | 3.0-4.6 | 39.23 | 160 |
| | 150.6 | 146.8-154.5 | 240 | 5.6 | 3.9-6.6 | 54.92 | 120 |
| 30 mg | 150.3 | 147.1-153.2 | 260 | 5.2 | 1.9-6.1 | 51.00 | 130 |
| | 150.5 | 145.4-154.8 | 280 | 4.6 | 1.8-5.4 | 45.11 | 140 |
| | 149.8 | 146.1-152.8 | 260 | 5.2 | 3.9-6.9 | 51.00 | 130 |
| 60 mg | 149.9 | 145.6-154.0 | 260 | 5.5 | 3.3-6.4 | 53.94 | 130 |
| | 149.9 | 146.6-152.9 | 240 | 5.4 | 3.0-6.2 | 52.96 | 120 |
| | 149.5 | 145.9-152.9 | 280 | 5.9 | 4.9-7.2 | 57.86 | 140 |
| 100 mg | 150.4 | 146.7-155.0 | 360 | 6.8 | 4.5-7.7 | 66.69 | 180 |
| | 151 | 147.3-156.4 | 360 | 6.3 | 3.7-7.6 | 61.78 | 180 |
| | 149.8 | 146.8-152.1 | 240 | 7.4 | 5.4-8.9 | 72.57 | 120 |
| 200 mg | 300.5 | 290.9-305.6 | 140 | 6.8 | 5.8-7.3 | 66.69 | 70 |
| | 299.3 | 293.4-305.2 | 120 | 6.4 | 6.0-6.8 | 62.76 | 60 |
| | 300.6 | 293.8-305.5 | 120 | 7 | 6.1-7.4 | 68.65 | 60 |

Instron (Crush Resistance)

Example 8

In Example 8 the crush resistance of tablets A-E was tested. This was carried out using an Instron single column benchtop tester (model number 4443) with a maximum load of 1 KN, equipped with upper compression platen T512-21-2 and lower compression platen T489-73. The measurement method was performed as described in the "Definitions", above, with the specific settings as specified in the "Instron Test Method", below.

Instron Test Method
1. The tablet was placed on the lower platen and, using tweezers, held on the lower platen so that the tablet length was perpendicular to the lower platen and the load was perpendicular to the thickness and in line with the diameter of the tablet.
2. The upper platen was lowered so that it was just above the tablet end, and it was ensured that the upper platen was not touching the tablet end. (The height of the upper platen position was adjusted for each tablet strength as each tablet strength had a different length).
3. It was ensured that the test method had the following settings:

| | |
|---|---|
| Pre-test speed: | 5 mm/min at maximum force of 1N |
| Upper platen test speed: | 60 mm/min |
| Upper force limit: | 500N |

4. The test was started (the upper platen then began to lower).
5. Once the tablet was held in place between the two platens, the tweezers were removed.
6. At the end of the test (after the upper platen had raised), the tablet was removed.
7. For each strength the test was performed on 10 tablets.

The tablets deemed to be resistant to crushing/breaking under a specific load include not only those which have not broken but also those which may have suffered plastic deformation under the action of the force. The crush resistance results from the Instron test are presented in Tables 8.1 to 8.5.

TABLE 8.1

Crush Resistance Test Results of Tablets A (15 mg), Cured/Coated Tablets

| Tablet | Weight (mg) | Thickness (mm) | Length (mm) | Maximum Compressive Load (N) | Compressive extension at Maximum Compressive Load (mm) |
|---|---|---|---|---|---|
| 1 | 129.3 | 3.68 | 10 | 500 | 6.837 |
| 2 | 129.8 | 3.7 | 10.01 | 504 | 7.736 |
| 3 | 130.2 | 3.72 | 9.99 | 508 | 6.918 |
| 4 | 129.1 | 3.68 | 9.97 | 502 | 7.681 |
| 5 | 127.7 | 3.65 | 9.99 | 503 | 6.966 |
| 6 | 128.2 | 3.67 | 9.99 | 514 | 7.706 |
| 7 | 130.5 | 3.7 | 9.99 | 505 | 6.925 |
| 8 | 127.8 | 3.67 | 10.01 | 503 | 7.057 |
| 9 | 130.2 | 3.68 | 10.02 | 514 | 7.659 |
| 10 | 128.9 | 3.7 | 9.97 | 508 | 7.762 |
| Avg | 129.1 | 3.68 | 10 | 504 | 6.941 |
| St dev | 1.3 | 0 | 0 | 2.9 | 0.1 |
| Min | 127.7 | 3.65 | 9.99 | 500 | 6.837 |
| Max | 130.5 | 3.72 | 10.01 | 508 | 7.057 |

Note:
tablets 2, 4, 6, 9, and 10 are not included in the final calculations because these tablets were compromised during the test.

TABLE 8.2

Crush Resistance Test Results of Tablets B (30 mg), Cured/Coated Tablets

| Tablet | Weight (mg) | Thickness (mm) | Length (mm) | Maximum Compressive Load (N) | Compressive extension at Maximum Compressive Load (mm) |
|---|---|---|---|---|---|
| 1 | 181.3 | 3.8 | 11.1 | 516 | 8.485 |
| 2 | 178.5 | 3.77 | 11.12 | 522 | 8.566 |
| 3 | 182.7 | 3.83 | 11.11 | 519 | 8.526 |
| 4 | 181.2 | 3.8 | 11.11 | 512 | 8.491 |
| 5 | 182.1 | 3.82 | 11.1 | 506 | 7.107 |
| 6 | 181.1 | 3.82 | 11.13 | 504 | 7.159 |
| 7 | 181.3 | 3.8 | 11.1 | 505 | 7.281 |
| 8 | 180 | 3.79 | 11.1 | 500 | 7.272 |
| 9 | 182.1 | 3.81 | 11.12 | 504 | 6.999 |
| 10 | 178.5 | 3.79 | 11.1 | 163 | 1.354 |
| Avg | 181.3 | 3.81 | 11.11 | 504 | 7.164 |
| St dev | 0.9 | 0 | 0 | 2.3 | 0.1 |
| Min | 180 | 3.79 | 11.1 | 500 | 6.999 |
| Max | 182.1 | 3.82 | 11.13 | 506 | 7.281 |

Note:
tablets 1, 2, 3, 4, and 10 are not included in the final calculations because these tablets were compromised during the test.

TABLE 8.3

Crush Resistance Test Results of Tablets C (60 mg), Cured/Coated Tablets

| Tablet | Weight (mg) | Thickness (mm) | Length (mm) | Maximum Compressive Load (N) | Compressive extension at Maximum Compressive Load (mm) |
|---|---|---|---|---|---|
| 1 | 343.9 | 4.06 | 15.82 | 507 | 11.151 |
| 2 | 345.2 | 4.05 | 15.84 | 502 | 12.109 |
| 3 | 345.3 | 4.06 | 15.84 | 506 | 10.813 |
| 4 | 344.3 | 4.09 | 15.82 | 513 | 12.724 |
| 5 | 345.6 | 4.07 | 15.87 | 505 | 12.092 |
| 6 | 336 | 4.01 | 15.83 | 500 | 11.668 |
| 7 | 339.4 | 4.04 | 15.81 | 506 | 10.781 |
| 8 | 346.6 | 4.09 | 15.82 | 503 | 10.879 |
| 9 | 340 | 4.05 | 15.84 | 501 | 11.989 |
| 10 | 341.7 | 4.03 | 15.84 | 508 | 12.168 |
| 11 | 342.5 | 4.04 | 15.83 | 508 | 12.049 |
| 12 | 339.3 | 4.03 | 15.84 | 502 | 12.025 |
| Avg | 342.3 | 4.05 | 15.83 | 504 | 11.611 |
| St dev | 3.3 | 0 | 0 | 2.9 | 0.6 |
| Min | 336 | 4.01 | 15.81 | 500 | 10.781 |
| Max | 346.6 | 4.09 | 15.87 | 508 | 12.168 |

Note:
tablet 4 is not included in the final calculations because the tablet was compromised during the test.

TABLE 8.4

Crush Resistance Test Results of Tablets E (100 mg), Cured/Coated Tablets

| Tablet | Weight (mg) | Thickness (mm) | Length (mm) | Maximum Compressive Load (N) | Compressive extension at Maximum Compressive Load (mm) |
|---|---|---|---|---|---|
| 1 | 344.5 | 3.92 | 15.99 | 501 | 12.858 |
| 2 | 342.8 | 3.91 | 16 | 506 | 13.042 |
| 3 | 341 | 3.9 | 16 | 505 | 12.207 |
| 4 | 347.4 | 3.93 | 16.02 | 503 | 12.833 |
| 5 | 345 | 3.92 | 16.01 | 502 | 12.493 |
| 6 | 341.2 | 3.89 | 16.01 | 510 | 13.009 |
| 7 | 343.7 | 3.89 | 16.03 | 507 | 12.243 |
| 8 | 338.5 | 3.88 | 16 | 503 | 12.262 |
| 9 | 340.4 | 3.9 | 16 | 517 | 12.974 |
| 10 | 341 | 3.91 | 15.99 | 507 | 13.096 |
| 11 | 343 | 3.91 | 16.01 | 504 | 10.891 |
| 12 | 345.1 | 3.94 | 16 | 503 | 11.162 |
| Avg | 342.1 | 3.9 | 16.01 | 504 | 12.301 |
| St dev | 2.9 | 0 | 0 | 2.2 | 0.1 |
| Min | 338.5 | 3.88 | 16 | 502 | 12.207 |
| Max | 345 | 3.92 | 16.03 | 507 | 12.493 |

Note:
tablets 1, 2, 4, 6, 9, 10, 11 and 12 are not included in the final calculations because these tablets were compromised during the test.

TABLE 8.5

Crush Resistance Test Results of Tablets E (200 mg), Cured/Coated Tablets

| Tablet | Weight (mg) | Thickness (mm) | Length (mm) | Maximum Compressive Load (N) | Compressive extension at Maximum Compressive Load (mm) |
|---|---|---|---|---|---|
| 1 | 622.8 | 5.32 | 17.17 | 503 | 13.218 |
| 2 | 624.9 | 5.34 | 17.18 | 508 | 13.983 |
| 3 | 618.9 | 5.28 | 17.19 | 503 | 13.544 |
| 4 | 634.3 | 5.4 | 17.21 | 501 | 9.924 |
| 5 | 634.3 | 5.4 | 17.21 | 518 | 13.53 |
| 6 | 622.1 | 5.31 | 17.18 | 507 | 12.927 |
| 7 | 621.6 | 5.32 | 17.2 | 502 | 12.983 |
| 8 | 633 | 5.38 | 17.2 | 506 | 12.652 |
| 9 | 622.6 | 5.33 | 17.18 | 500 | 10.722 |

TABLE 8.5-continued

Crush Resistance Test Results of Tablets
E (200 mg), Cured/Coated Tablets

| Tablet | Weight (mg) | Thickness (mm) | Length (mm) | Maximum Compressive Load (N) | Compressive extension at Maximum Compressive Load (mm) |
|---|---|---|---|---|---|
| 10 | 618.2 | 5.29 | 17.2 | 500 | 13.754 |
| 11 | 625 | 5.32 | 17.21 | 506 | 13.229 |
| 12 | 615.4 | 5.29 | 17.16 | 503 | 10.871 |
| Avg | 624.5 | 5.33 | 17.19 | 506 | 13.313 |
| St dev | 5.7 | 0 | 0 | 5.2 | 0.4 |
| Min | 618.2 | 5.28 | 17.17 | 500 | 12.652 |
| Max | 634.3 | 5.4 | 17.21 | 518 | 13.983 |

Note:
tablets 4, 9 and 12 are not included in the final calculations because these tablets were held for a longer period with the tweezers during the test.

Cracking Force Tests (Texture Analyser)

Example 9

In Example 9 the cracking force of tablets A-E was tested using an indentation test. This was carried out using a texture analyzer as described in the "Definitions", above, with the specific settings as described below.

Texture Analyser Method:
1. The Texture Analyser was set up with the ⅛-inch diameter stainless steel ball probe (TA-18A).
2. The probe height was calibrated to 6 mm above the tablet stand.
3. The test method was set up with the following settings:

| Pre-test speed: | 0.5 mm/sec | Automatic trigger force: | 10 g |
|---|---|---|---|
| Test speed: | 0.5 mm/sec | Post test speed: | 1.0 mm/sec |
| Test distance | 3.0 mm | | |

4. The tablet weight and thickness were recorded.
5. The tablet was placed on the stand (tablet face up) so that the tablet was in alignment with the shape of the stand tip (i.e., the tablet was not perpendicular to the length of the stand tip).
6. The stand was positioned with the tablet under the ball probe so that the ball probe was centered over the tablet face.
7. The probe height was calibrated with the following settings:
   Return distance: 2 mm/Return speed: 10 mm/sec/Contact force: 0.5 g
   The 'OK' button was clicked, and the probe was watched as it lowered onto the tablet surface. If the probe was centered over the tablet face, the next step was performed. If the probe was not centered over the tablet face, the stand position was adjusted, and the probe height was calibrated again to check if the probe was centered over the tablet face. The stand position was continued to be adjusted, and the probe height was continued to be calibrated until the probe was centered over the tablet face.
8. The 'Run a Test' button was clicked, then the 'Start Test' button was clicked. The probe was watched to lower onto the tablet face. If the probe was not centered on the tablet, a new tablet was tested.
9. The cracking force (CF) and the Cracking distance (CD) was recorded.

Penetration depth to crack (PC)=distance from the tablet surface to the first local maximum.

For this test, after compression, the tablets were cured and film coated in a coating pan. Prior to initiating the curing process, the tablets were film coated with Opadry II to a weight gain of 0.5-1.5% to eliminate tablet sticking during the curing process. After this initial film coat was achieved, the curing process was initiated. The rotating tablet bed was heated until the target exhaust temperature was achieved and curing continued at the target exhaust temperature for the time specified in the batch record. At the end of the curing process the tablet bed was cooled and film coating was continued until the target weight gain was achieved.

The curing conditions for tablets A, B and C were: 72° C. for 30 min.

The curing conditions for tablets D and E were: 75° C. for 45 min.

The indentation test results for tablets A (uncured and cured tablets) are given in Table 9.1.

TABLE 9.1

| A | Uncured | | | | Cured | | | |
|---|---|---|---|---|---|---|---|---|
| Example | 1 | 2 | 3 | Mean | 1 | 2 | 3 | Mean |
| Weight (mg) | 126.5 | 124.8 | 125.2 | | 129.1 | 127.8 | 129.3 | |
| Thickness (mm) | 3.57 | 3.54 | 3.55 | | 3.69 | 3.68 | 3.69 | |
| Cracking force (N) | 160.4 | 162.8 | 146 | 156.4 | 222.3 | 196.8 | 196.8 | 205.3 |
| Penetration depth to crack (mm) | 1.18 | 1.39 | 1.33 | 1.3 | 2.14 | 1.70 | 1.71 | 1.85 |

The indentation test results for tablets B (uncured and cured tablets) are given in Table 9.2.

TABLE 9.2

| B | Uncured | | | | Cured | | | |
|---|---|---|---|---|---|---|---|---|
| Example | 1 | 2 | 3 | Mean | 1 | 2 | 3 | Mean |
| Weight (mg) | 172.1 | 174.8 | 172.7 | | 181 | 184 | 182.2 | |
| Thickness (mm) | 3.67 | 3.7 | 3.69 | | 3.82 | 3.84 | 3.84 | |
| Cracking force (N) | 119.0 | 139.7 | 133.4 | 130.7 | 230.6 | 229.2 | 231.4 | 230.4 |
| Penetration depth to crack (mm) | 1.17 | 1.31 | 1.22 | 1.23 | 2.04 | 1.94 | 2.09 | 2.02 |

The indentation test results for tablets C (uncured and cured tablets) are given in Table 9.3.

TABLE 9.3

| C | Uncured | | | | Cured | | | |
|---|---|---|---|---|---|---|---|---|
| Example | 1 | 2 | 3 | Mean | 1 | 2 | 3 | Mean |
| Weight (mg) | 326.9 | 329.5 | 328 | | 344.3 | 343 | 341.7 | |
| Thickness (mm) | 3.88 | 3.91 | 3.89 | | 4.06 | 4.06 | 4.02 | |
| Cracking force (N) | 157.8 | 154.4 | 148.9 | 153.7 | 237.2 | 232.5 | 228.3 | 232.7 |
| Penetration depth to crack (mm) | 1.12 | 1.13 | 1.07 | 1.11 | 1.89 | 1.9 | 1.96 | 1.92 |

The indentation test results for tablets D (uncured and cured tablets) are given in Table 9.4.

TABLE 9.4

| D | Uncured | | | | Cured | | | |
|---|---|---|---|---|---|---|---|---|
| Example | 1 | 2 | 3 | Mean | 1 | 2 | 3 | Mean |
| Weight (mg) | 328.6 | 330.9 | 330.8 | | 345.2 | 343.2 | 342.7 | |
| Thickness (mm) | 3.82 | 3.84 | 3.84 | | 3.92 | 3.92 | 3.91 | |
| Cracking force (N) | 107.3 | 113.2 | 102.8 | 107.8 | 175.7 | 178.2 | 175.4 | 176.4 |
| Penetration depth to crack (mm) | 0.8 | 0.74 | 0.73 | 0.76 | 1.32 | 1.4 | 1.26 | 1.33 |

The indentation test results for tablets E (uncured and cured tablets) are given in Table 9.5.

TABLE 9.5

| E | Uncured | | | | Cured | | | |
|---|---|---|---|---|---|---|---|---|
| Example | 1 | 2 | 3 | Mean | 1 | 2 | 3 | Mean |
| Weight (mg) | 602.1 | 595.4 | 599.3 | | 617.6 | 621.4 | 624.5 | |
| Thickness (mm) | 5.46 | 5.46 | 5.47 | | 5.29 | 5.3 | 5.3 | |
| Cracking force (N) | 130.7 | 126.3 | 107.7 | 121.57 | 237.8 | 230.5 | 218.4 | 228.9 |
| Penetration depth to crack (mm) | 1.08 | 1.05 | 0.95 | 1.03 | 1.63 | 1.5 | 1.53 | 1.55 |

All of the cured tablets shown above could withstand a cracking force of at least 170 N, and tablets B, C and E could withstand a cracking force of greater than 200 N and some a cracking force of or even greater than about 230 N.

Dissolution after Physical Manipulation

Example 10

In Example 10 the dissolution of physically manipulated tablets was investigated. Testing was performed on intact, halved, quartered, sliced and milled tablets B, D and E as well as 100 mg MS Contin® as reference. Cutting and slicing of tablets B, D and E was performed using a tablet cutter (LGS Corp.)/razor blade. Milling was performed with an IKA mill. MS Contin® 100 mg tablets were crushed/ground using a glass mortar and pestle as described below in Example 13. Manipulation was performed following the procedures detailed below:
Priming of the Mill (One Dedicated Mill was Used for Each Dose Strength):
  1. 5 (n=5) tablets were weighed.
  2. The tablets were placed in the IKA mill. The jar on the mill was screwed tightly. The mill was activated by pressing down on the mill and holding the "on" button on the mill for 30 seconds, then it was paused for 5 seconds, and milling was continued for another 30 seconds.

The mill jar was held and tilted in both directions continuously while milling to get a homogenous blend of particles.
  3. The fine particles were allowed to settle for 1 minute.
  4. The mill jar was unscrewed, and all the milled material was collected, using a brush, from the jar and blade assembly into a tared weigh boat. The weight percent recovery was calculated. The priming sample was not used.
Milling Procedure for the Tablets:
  1. 20 tablets were weighed. The Average Tablet Weight (ATW) was determined.
  2. The tablets were placed in the primed IKA mill. The jar was screwed tightly on the mill: The mill was activated by pressing down on the mill and holding the "on" button on the mill for 30 second, then it was paused for 5 seconds, and milling was continued for another 30 seconds. The mill jar was held and tilted in both directions continuously while milling to get a homogenous blend of particles.
  3. The fine particles were allowed to settle for 1 minute.
  4. The mill jar was unscrewed and all the milled material was collected, using a brush, from the jar and blade assembly into a tared weigh boat. The weight percent recovery was calculated. If a weight percent recovery of 97.0% had not been achieved, the milling procedure was repeated.
  5. For the dissolution test, milled material was weighed into weigh boats, or appropriate receptacles, to the equivalent to one dosage unit (ATW±3%). The weigh boat was labelled 1. The same procedure was repeated for the other 5 samples, and the weigh boats were labelled 2 to 6; respectively.

When this milling procedure was performed to prepare samples for the syringeability tests in Examples 13.2 and 13.3 below, step 5 of the milling procedure was as follows: An aliquot of milled material (equivalent to the ATW 3.0%) was transferred into a tared 20 mL vial and the weight was recorded on the experimental worksheet for the corresponding sample ID. A total of 15 aliquots of milled material could be used from each milled condition.

Halved, Quartered and Sliced Tablet Preparation:
Halved:
1. One tablet was weighed and cut in half on a cutting board using a razor blade.
2. The two pieces of cut tablet were collected into a weighing boat labeled 1.
3. The same procedure was repeated for the other 5 tablets, and the weigh boats were labelled 2 to 6; respectively.
Quartered:
1. One tablet was weighed and cut in half on a cutting board using a razor blade.
2. Each half was cut in two pieces. The four pieces of cut tablet were collected into a weighing boat labeled 1.
3. The same procedure was repeated for the other 5 tablets, and the weigh boats were labelled 2 to 6; respectively.
Sliced:
1. One tablet was weighed and placed flat on the cutting board.
2. The tablet was cut in half using a razor blade while holding the tablet with tweezers.
3. Each half of the sliced tablet was placed flat-side down and sliced in half to create 4 tablet quarters. Each tablet quarter was sliced into 5 pieces. Each of these pieces were cut twice across the longest axis. This resulted in approximately 40 tablet pieces. Note: for 30 mg tablets, 20 tablet pieces resulted due to tablet size.
4. All the sliced tablet pieces (about 20 or 40 tablet pieces) were collected into a weighing boat and labelled 1.
5. The same procedure was repeated for the other 5 tablets, and the weigh boats were labelled 2 to 6; respectively.

Whole Tablet Preparation:
Into a weighing boat, one tablet was weighed and labelled 1. This was repeated 5 times, labelling 2-6.
Sample Transfer to Dissolution Baskets
Note: Sliced, milled and crushed materials could spill through 10 mesh baskets; for such cases 40 mesh baskets were used.
1. The dissolution apparatus was set up.
2. One sample was placed in each dry basket, and a stainless steel spring was inserted horizontally into the top of the basket (similarly to FIG. 92), and then the baskets were attached to the shafts.
3. For milled and crushed samples only, about 10 milliliters of the dissolution media was removed from each vessel and set aside.
4. The previously weighed samples were transferred into individual dissolution baskets. This step was performed over the corresponding dissolution vessel for the case some of the material fell through the basket mesh.
5. For milled and crushed samples only, each weigh boat was rinsed with the 10 milliliters of previously set aside dissolution media, into the corresponding vessels. All the rinsing media was collected to the vessel. This was performed to ensure complete transfer of the sample.
Note: It was attempted to perform steps 5 to 7 quickly, and the dissolution baths were started immediately following transfer of the material. Timing was critical for this experimentation.
6. The basket rotation speed was set at 100 rpm and the rotating baskets were slowly immersed in the preheated dissolution media.
7. Samples were taken as per the sampling time points specified in Table 1.
8. No more than 12 sample solutions were injected between standard solution injections.
9. The filtered sample solution was stable for 4 days.

The tablets were analyzed using the USP apparatus 1 (Basket) method described in Example 2. 40 mesh baskets were used for milled, sliced and crushed tablets to avoid spillage.

Figure 15:
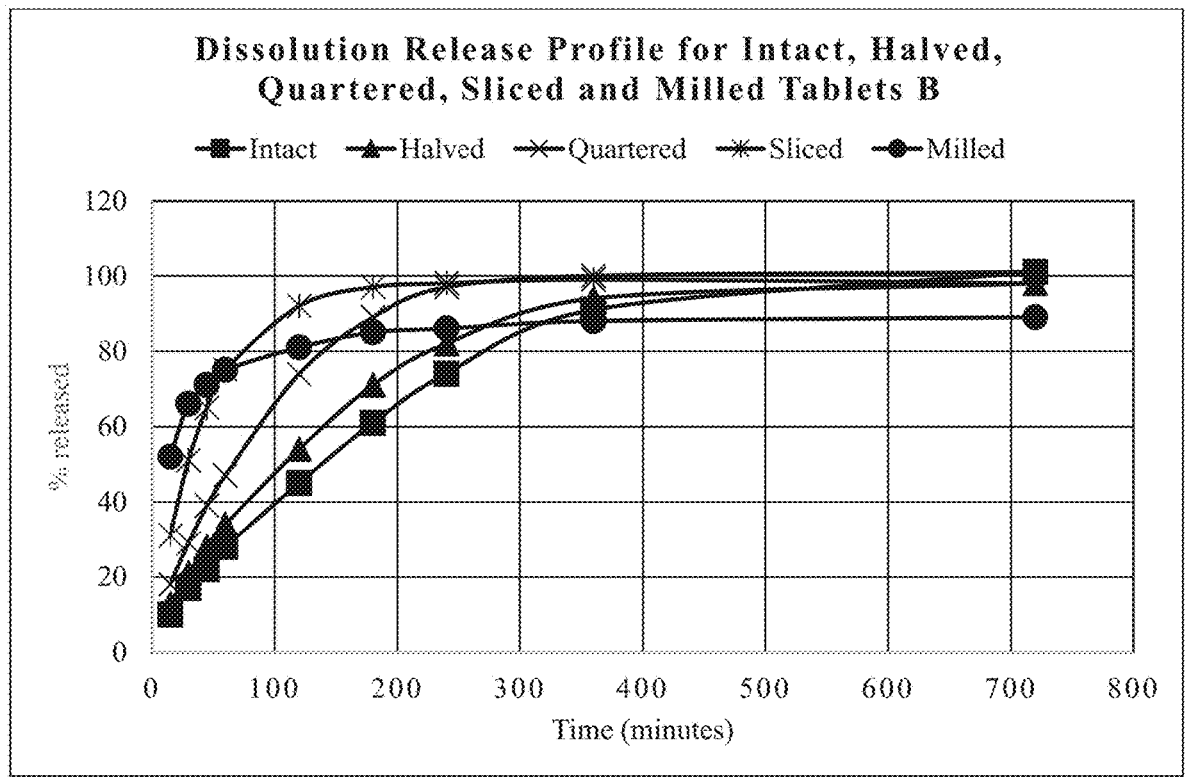
FIG. 15: Dissolution Profile for Intact, Halved, Quartered, Sliced and Milled Tablets B (30 mg) (% morphine sulfate released over time).

The results for these tests are given in Table 10.1 for the tablets B (30 mg morphine sulfate). These results are also displayed graphically in FIG. 15.

TABLE 10.1

| Physical Manipulation | % morphine sulfate released at time/mins | 15 | 30 | 45 | 60 | 120 | 180 | 240 | 360 | 720 |
|---|---|---|---|---|---|---|---|---|---|---|
| Intact | Mean (n = 6) | 10 | 17 | 22 | 28 | 45 | 61 | 74 | 91 | 101 |
| | Min | 10 | 16 | 21 | 26 | 43 | 59 | 71 | 89 | 98 |
| | Max | 11 | 18 | 23 | 29 | 47 | 63 | 75 | 93 | 103 |
| | % RSD | 3.2 | 3.88 | 4.18 | 4.11 | 3.27 | 2.49 | 2.16 | 2.01 | 2.12 |
| Halved | Mean (n = 6) | 13 | 21 | 28 | 34 | 54 | 71 | 82 | 94 | 98 |
| | Min | 12 | 20 | 26 | 32 | 52 | 68 | 79 | 91 | 95 |
| | Max | 14 | 22 | 29 | 35 | 56 | 72 | 85 | 96 | 100 |
| | % RSD | 4.54 | 3.52 | 3.54 | 3.65 | 2.93 | 2.54 | 2.45 | 2.1 | 1.96 |
| Quartered | Mean (n = 6) | 18 | 29 | 39 | 47 | 74 | 89 | 97 | 100 | 101 |
| | Min | 16 | 27 | 36 | 44 | 68 | 83 | 90 | 96 | 97 |
| | Max | 20 | 32 | 42 | 52 | 81 | 96 | 103 | 105 | 106 |
| | % RSD | 6.72 | 6.48 | 6.36 | 6.3 | 5.95 | 5.03 | 4.34 | 3.12 | 3.05 |
| Sliced | Mean (n = 6) | 31 | 51 | 65 | 75 | 92 | 97 | 98 | 99 | 98 |
| | Min | 30 | 48 | 62 | 72 | 90 | 95 | 96 | 96 | 95 |
| | Max | 33 | 54 | 69 | 80 | 96 | 100 | 101 | 102 | 101 |
| | % RSD | 4.08 | 4.04 | 3.84 | 3.71 | 2.58 | 2.24 | 2.14 | 2.4 | 2.3 |
| Milled | Mean (n = 6) | 52 | 66 | 71 | 75 | 81 | 85 | 86 | 88 | 89 |
| | Min | 21 | 54 | 64 | 68 | 75 | 80 | 83 | 86 | 87 |
| | Max | 70 | 81 | 85 | 86 | 87 | 89 | 89 | 91 | 92 |
| | % RSD | 31.86 | 14.03 | 11.06 | 9.52 | 5.92 | 3.68 | 2.55 | 2.03 | 2.16 |

Figure 16:
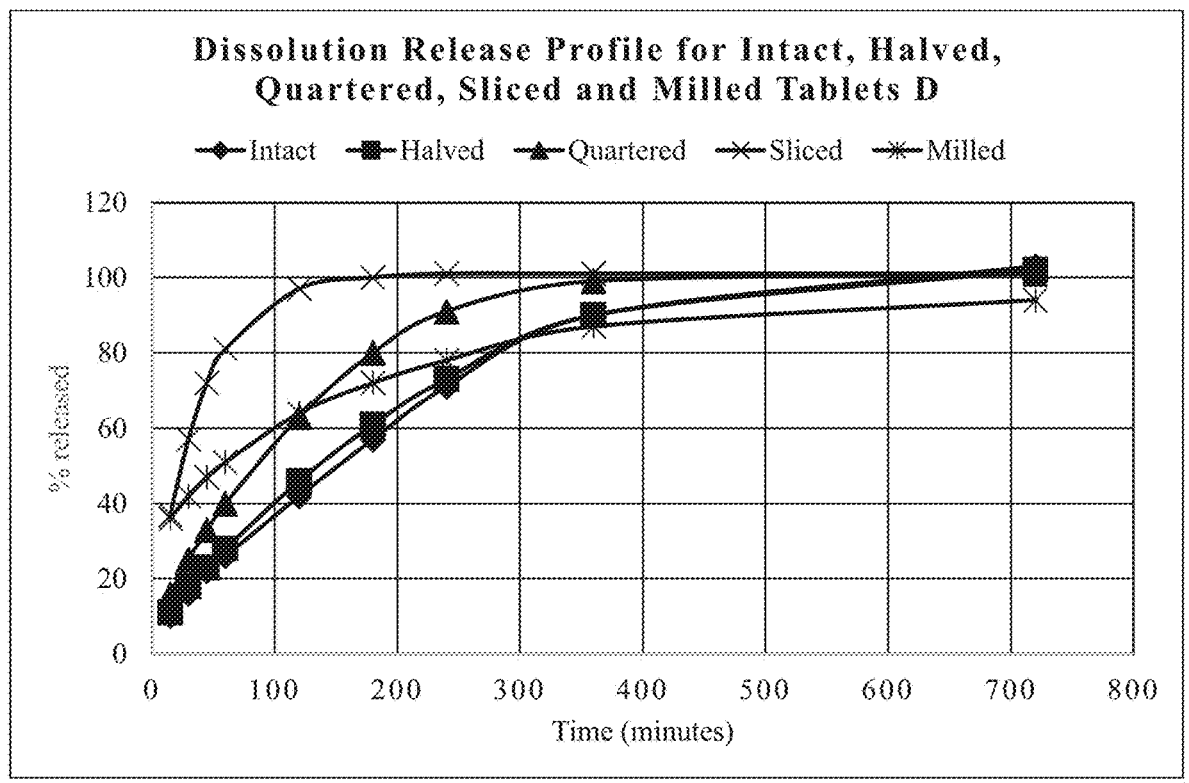
FIG. 16: Dissolution Profile for Intact, Halved, Quartered, Sliced and Milled Tablets D (100 mg) (% morphine sulfate released over time).

The results for the dissolution tests are given in Table 10.2 for the tablets D (100 mg morphine sulfate). These results are displayed graphically in FIG. 16.

TABLE 10.2

| Physical Manipulation | % morphine sulfate released at time/mins | 15 | 30 | 45 | 60 | 120 | 180 | 240 | 360 | 720 |
|---|---|---|---|---|---|---|---|---|---|---|
| Intact | Mean (n = 6) | 10 | 16 | 22 | 26 | 42 | 57 | 71 | 90 | 103 |
|  | Min | 10 | 15 | 20 | 24 | 39 | 54 | 67 | 88 | 102 |
|  | Max | 11 | 17 | 22 | 27 | 44 | 59 | 73 | 92 | 104 |
|  | % RSD | 3.1 | 4.56 | 4.91 | 4.81 | 4.57 | 3.7 | 3.03 | 1.71 | 0.91 |
| Halved | Mean (n = 6) | 11 | 18 | 23 | 28 | 46 | 61 | 73 | 90 | 102 |
|  | Min | 11 | 17 | 23 | 27 | 43 | 57 | 68 | 84 | 101 |
|  | Max | 12 | 19 | 25 | 30 | 49 | 65 | 78 | 95 | 104 |
|  | % RSD | 3.09 | 3.06 | 3.61 | 3.96 | 4.26 | 4.41 | 4.74 | 4.4 | 1.1 |
| Quartered | Mean (n = 6) | 16 | 25 | 33 | 40 | 63 | 80 | 91 | 99 | 101 |
|  | Min | 14 | 23 | 30 | 36 | 58 | 73 | 82 | 90 | 92 |
|  | Max | 17 | 27 | 35 | 43 | 68 | 86 | 96 | 103 | 104 |
|  | % RSD | 5.25 | 6.36 | 6.79 | 7.05 | 6.48 | 5.98 | 5.4 | 4.73 | 4.58 |
| Sliced | Mean (n = 6) | 37 | 57 | 72 | 81 | 97 | 100 | 101 | 101 | 101 |
|  | Min | 35 | 56 | 70 | 80 | 95 | 98 | 99 | 99 | 99 |
|  | Max | 38 | 60 | 74 | 83 | 99 | 102 | 103 | 103 | 103 |
|  | % RSD | 2.7 | 2.35 | 2.07 | 1.64 | 1.54 | 1.47 | 1.5 | 1.45 | 1.37 |
| Milled | Mean (n = 6) | 36 | 42 | 47 | 51 | 64 | 72 | 78 | 87 | 94 |
|  | Min | 29 | 34 | 38 | 42 | 54 | 63 | 70 | 81 | 93 |
|  | Max | 48 | 60 | 67 | 73 | 86 | 91 | 93 | 94 | 96 |
|  | % RSD | 19.28 | 21.19 | 21.67 | 21.44 | 18.51 | 14.21 | 10.48 | 5.62 | 1.32 |

Figure 17:
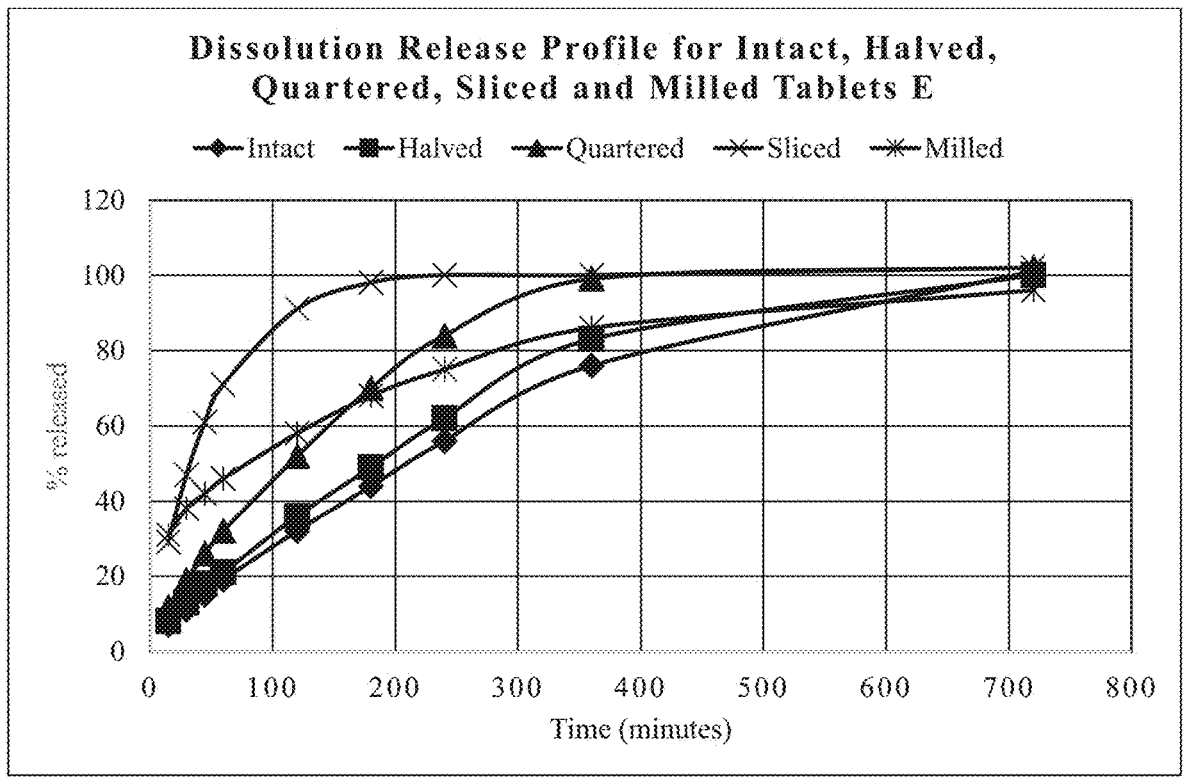
FIG. 17: Dissolution Profile for Intact, Halved, Quartered, Sliced and Milled Tablets E (200 mg) (% morphine sulfate released over time).

The results for the dissolution tests are given in Table 10.3 for the tablets E (200 mg morphine sulfate). These results are also displayed graphically in FIG. 17.

TABLE 10.3

| Physical Manipulation | % morphine sulfate released at time/mins | 15 | 30 | 45 | 60 | 120 | 180 | 240 | 360 | 720 |
|---|---|---|---|---|---|---|---|---|---|---|
| Intact | Mean (n = 6) | 7 | 11 | 15 | 19 | 32 | 44 | 56 | 76 | 101 |
|  | Min | 7 | 11 | 14 | 18 | 30 | 41 | 53 | 74 | 100 |
|  | Max | 7 | 12 | 16 | 20 | 33 | 45 | 57 | 77 | 103 |
|  | % RSD | 2.86 | 3.64 | 3.8 | 3.95 | 3.81 | 3.48 | 2.64 | 1.82 | 1.01 |
| Halved | Mean (n = 6) | 8 | 13 | 18 | 21 | 36 | 49 | 62 | 83 | 100 |
|  | Min | 7 | 12 | 16 | 19 | 32 | 44 | 56 | 77 | 98 |
|  | Max | 8 | 14 | 19 | 23 | 38 | 51 | 65 | 87 | 102 |
|  | % RSD | 6.25 | 6.85 | 6.44 | 6.9 | 6.11 | 5.69 | 5.5 | 4.04 | 1.56 |
| Quartered | Mean (n = 6) | 12 | 19 | 26 | 32 | 52 | 70 | 84 | 99 | 102 |
|  | Min | 11 | 18 | 24 | 29 | 48 | 65 | 78 | 95 | 100 |
|  | Max | 12 | 20 | 27 | 33 | 54 | 73 | 86 | 103 | 105 |
|  | % RSD | 3.81 | 4.21 | 4.18 | 4.23 | 4.31 | 4.07 | 3.55 | 2.62 | 1.93 |
| Sliced | Mean (n = 6) | 29 | 47 | 61 | 71 | 91 | 98 | 100 | 100 | 102 |
|  | Min | 27 | 45 | 59 | 68 | 88 | 95 | 97 | 97 | 99 |
|  | Max | 30 | 48 | 63 | 74 | 95 | 102 | 104 | 104 | 106 |
|  | % RSD | 3.03 | 3.13 | 3.05 | 3.13 | 2.78 | 2.33 | 2.4 | 2.71 | 2.41 |
| Milled | Mean (n = 6) | 31 | 38 | 42 | 46 | 58 | 68 | 75 | 86 | 96 |
|  | Min | 25 | 32 | 37 | 40 | 50 | 60 | 67 | 81 | 93 |
|  | Max | 40 | 45 | 49 | 52 | 63 | 72 | 80 | 89 | 100 |
|  | % RSD | 16.72 | 13.39 | 11.67 | 10.34 | 8.04 | 6.68 | 5.7 | 3.64 | 2.16 |

The results for these tests are given in Table 10.4 commercial MS Contin® (100 mg morphine sulfate) as a reference. These results are also displayed graphically in FIG. 18.

TABLE 10.4

| Physical Manipulation | % morphine sulfate released at time/mins | 15 | 30 | 45 | 60 | 120 | 180 | 240 | 360 | 720 |
|---|---|---|---|---|---|---|---|---|---|---|
| Intact | Mean | 15 | 24 | 31 | 37 | 55 | 67 | 77 | 91 | 103 |
|  | Min | 14 | 23 | 30 | 35 | 53 | 67 | 76 | 90 | 101 |

TABLE 10.4-continued

| Physical Manipulation | % morphine sulfate released at time/mins | 15 | 30 | 45 | 60 | 120 | 180 | 240 | 360 | 720 |
|---|---|---|---|---|---|---|---|---|---|---|
| | Max | 15 | 24 | 31 | 38 | 56 | 68 | 78 | 92 | 104 |
| | % RSD | 2.33 | 2.08 | 1.77 | 2.19 | 1.33 | 0.93 | 0.88 | 0.8 | 0.85 |
| Crushed | Mean | 96 | 99 | 100 | 100 | 100 | 100 | 100 | 100 | 100 |
| | Min | 92 | 97 | 98 | 98 | 98 | 99 | 99 | 98 | 99 |
| | Max | 98 | 101 | 101 | 102 | 101 | 102 | 102 | 102 | 101 |
| | % RSD | 1.95 | 1.47 | 1.11 | 1.38 | 1.07 | 1.15 | 1.1 | 1.64 | 0.96 |

Tablets B, D and E according to the present invention were hard and required considerable time and effort to manipulate. The release rate of morphine sulfate was directly related to the particle size of morphine sulfate. When the tablets were halved, quartered, sliced and milled the particle size of the tablet was reduced accordingly. This reduction increased the surface area of the tablet; therefore, the rate of dissolution increased, see FIGS. 15 to 18. The results obtained showed the lowest dissolution rate for intact tablets for all of tablets B, D and E according to the present invention. The dissolution rate increased as the particle size decreased, following the order intact, halved, quartered and sliced. The milled tablet particles are smaller than sliced particles; however, the rate of dissolution for milled tablets is slower than sliced tablets. This is due to the hydrogelling properties of the polyethylene oxide in the tablets of the invention. As the particle size is reduced further, the gelling property of the tablet increases and this gelling effect decreases the rate of dissolution.

The increase in dissolution rate observed for all tablets of the invention upon reduction of the particle size by means of manipulation, however, did not affect the controlled released properties. All manipulated samples of the invention maintain some degree of controlled released properties.

Figure 18:
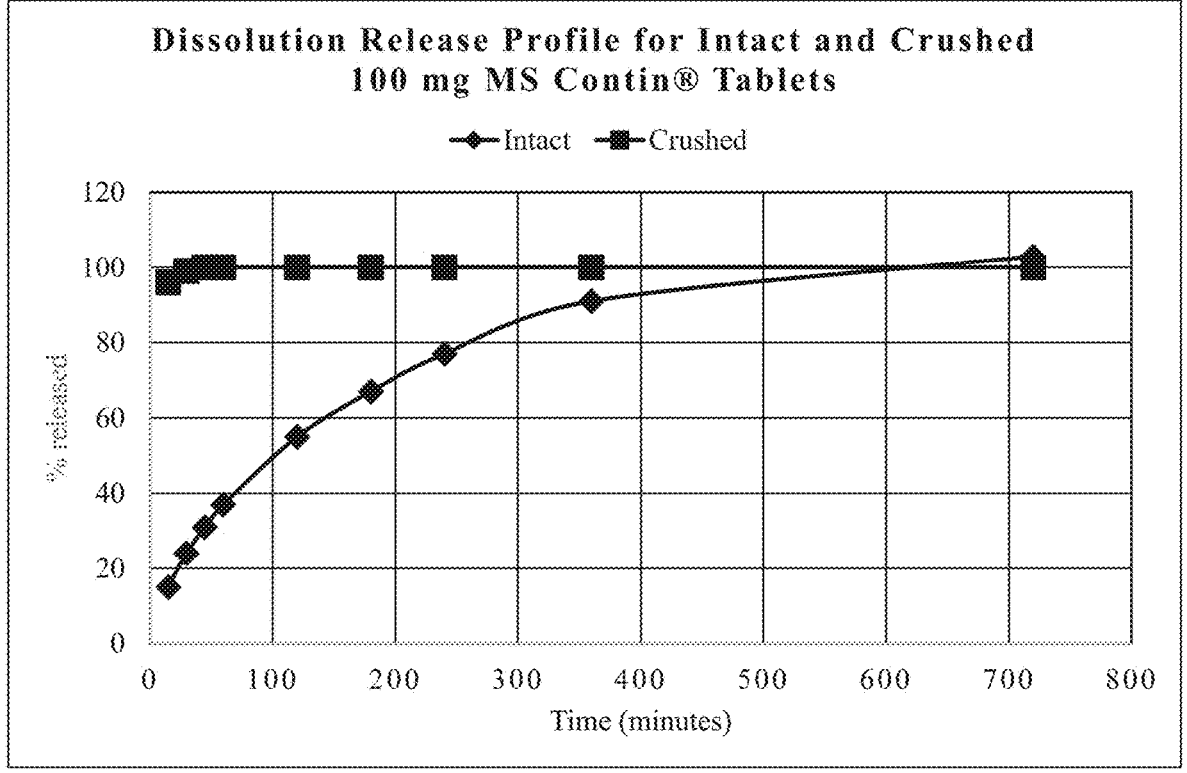
FIG. 18: Dissolution Profile for Intact and Crushed 100 mg MS Contin® Tablets (% morphine sulfate released over time).
Figure 19:
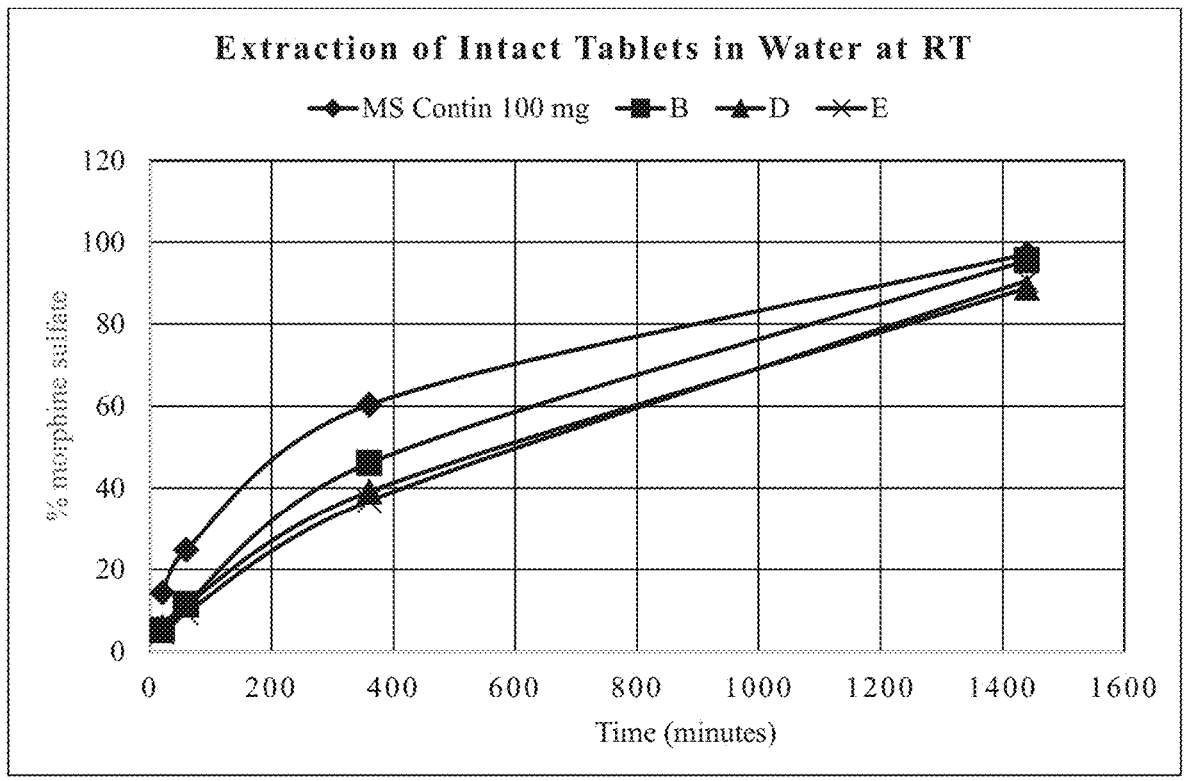
FIG. 19: Extraction of Intact Tablets in Water at RT
Figure 20:
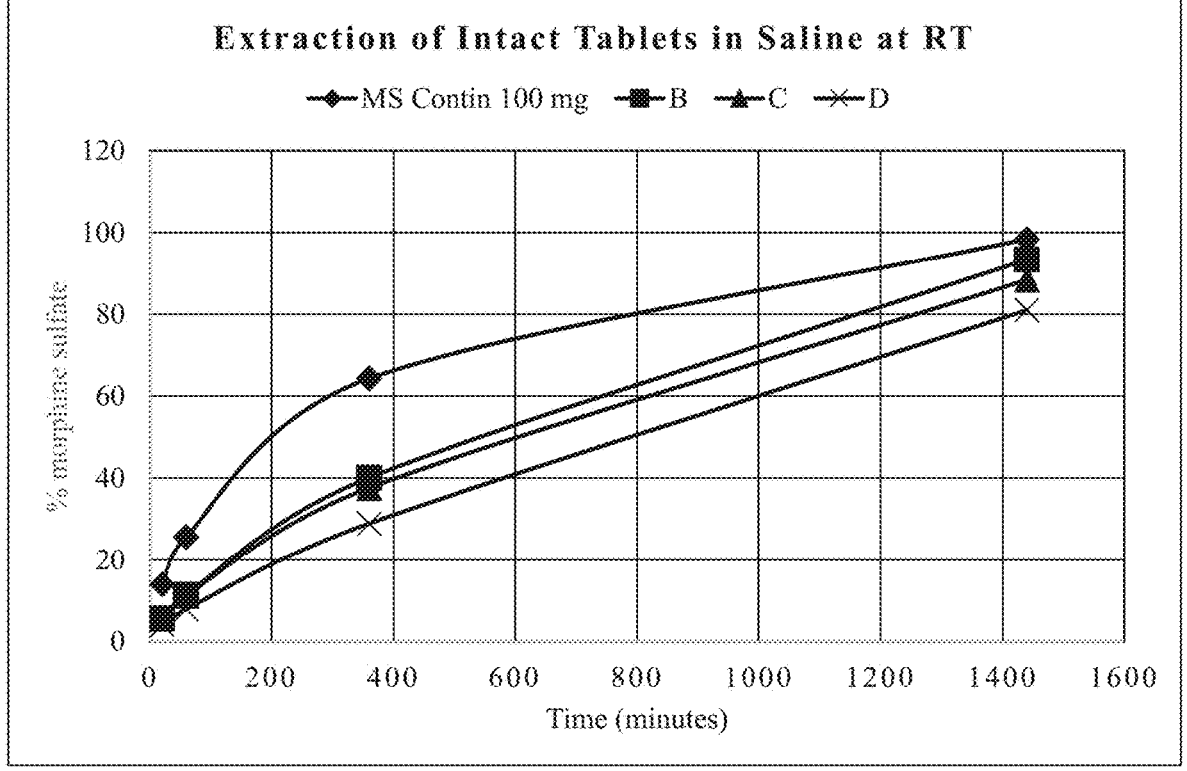
FIG. 20: Extraction of Intact Tablets in Saline at RT
Figure 21:
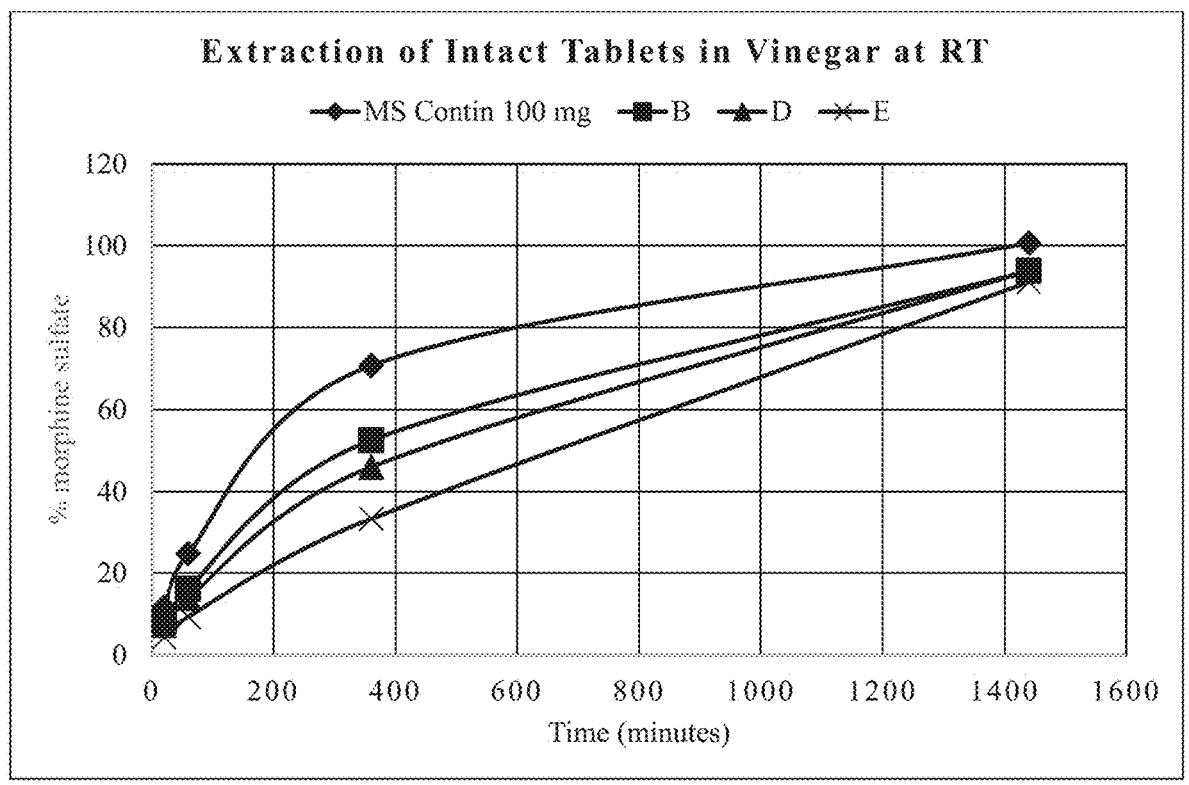
FIG. 21: Extraction of Intact Tablets in Vinegar at RT
Figure 22:
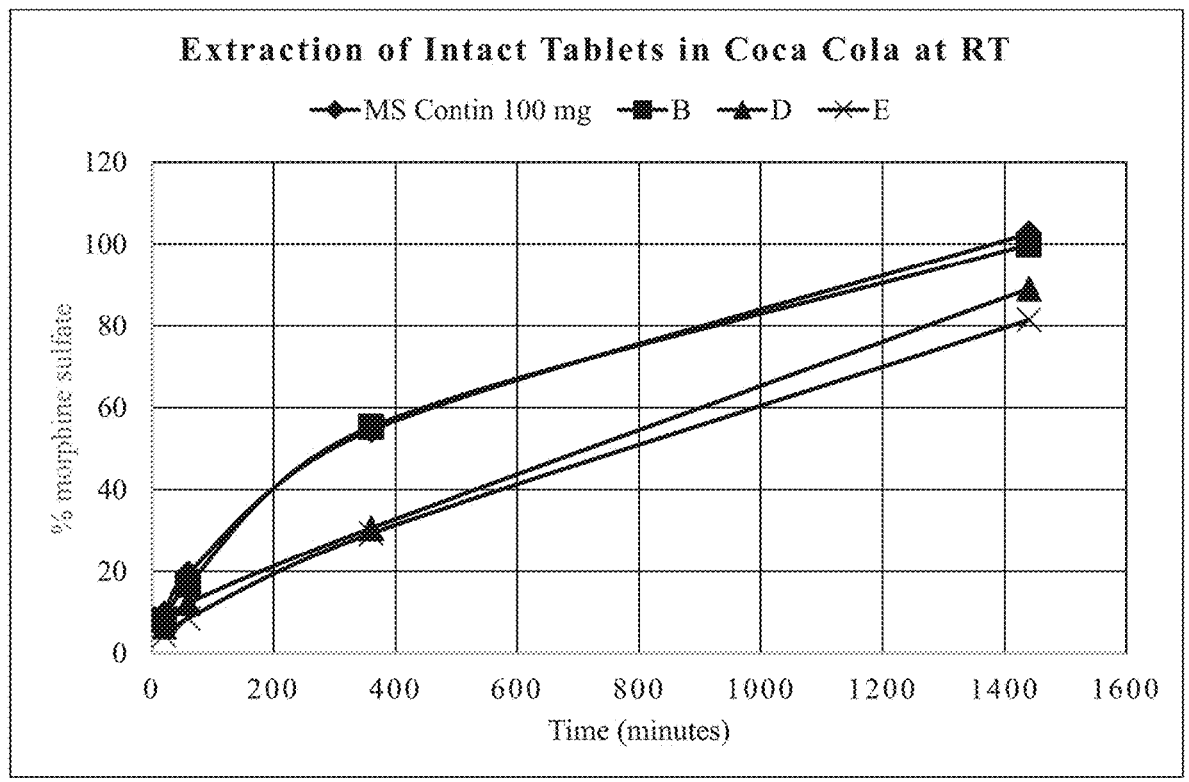
FIG. 22: Extraction of Intact Tablets in Coca Cola at RT
Figure 23:
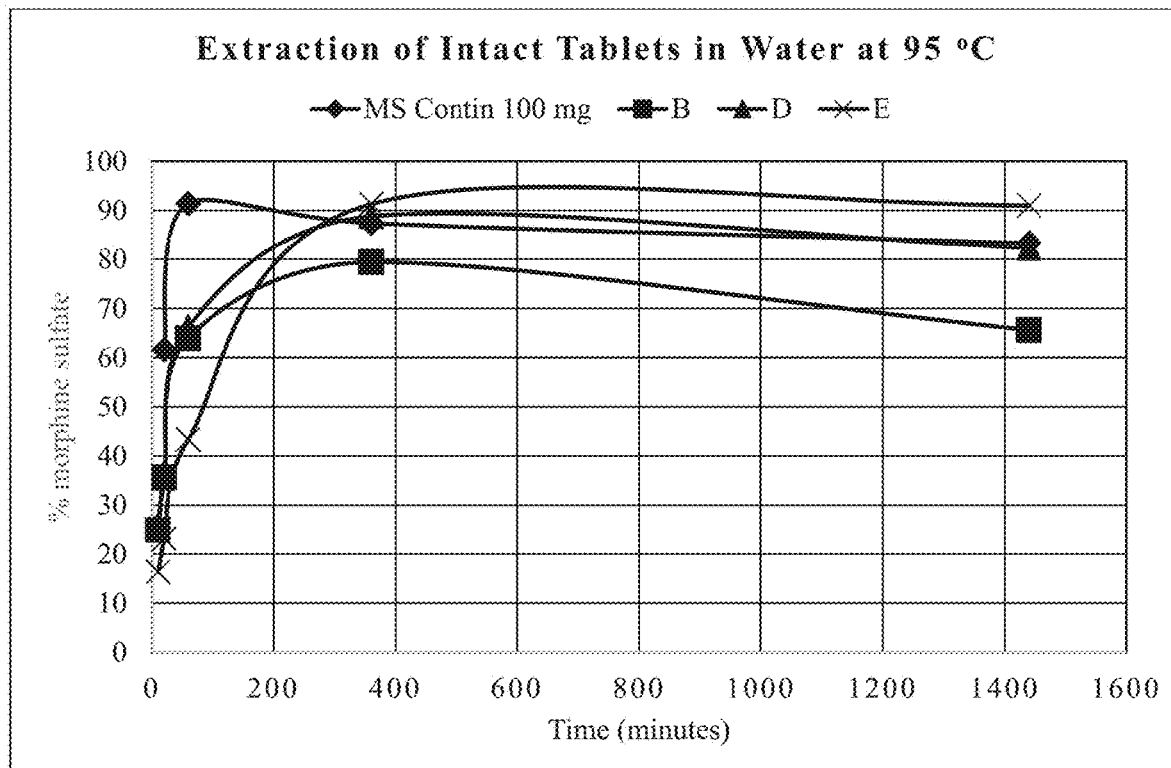
FIG. 23: Extraction of Intact Tablets in Water at 95° C.
Figure 24:
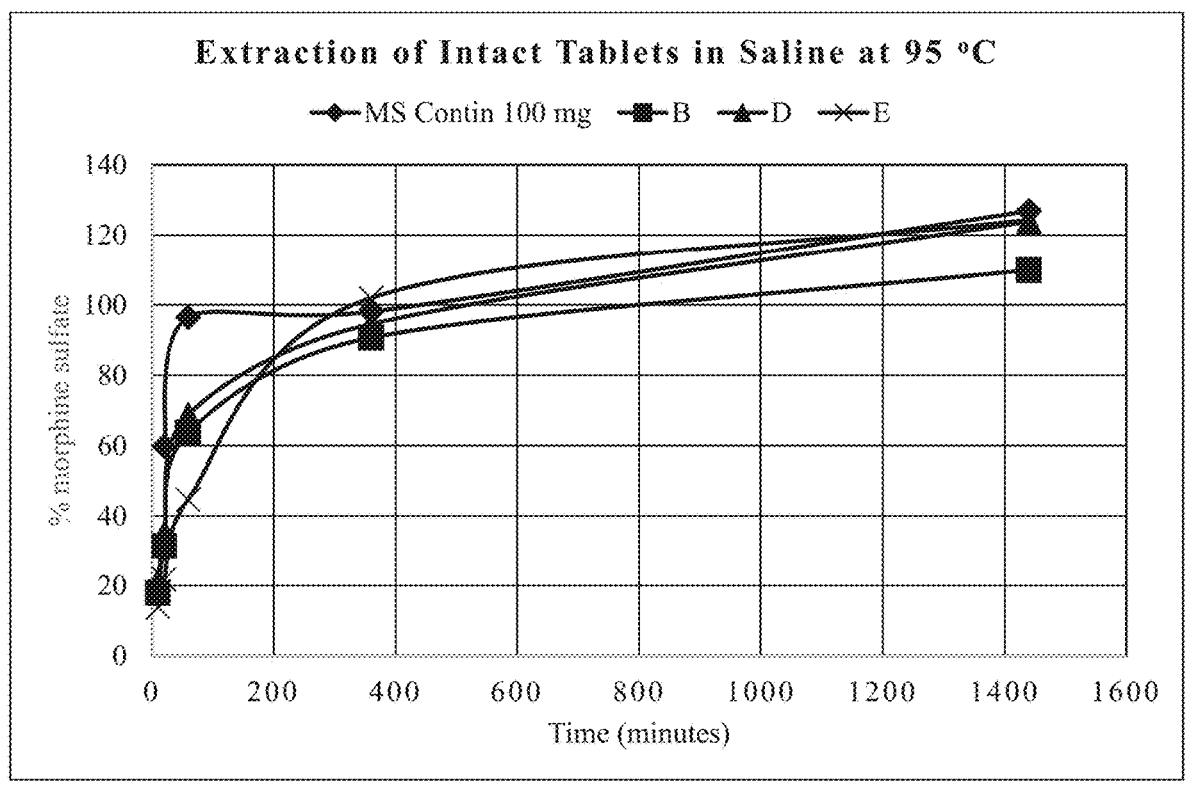
FIG. 24: Extraction of Intact Tablets in Saline at 95° C.
Figure 25:
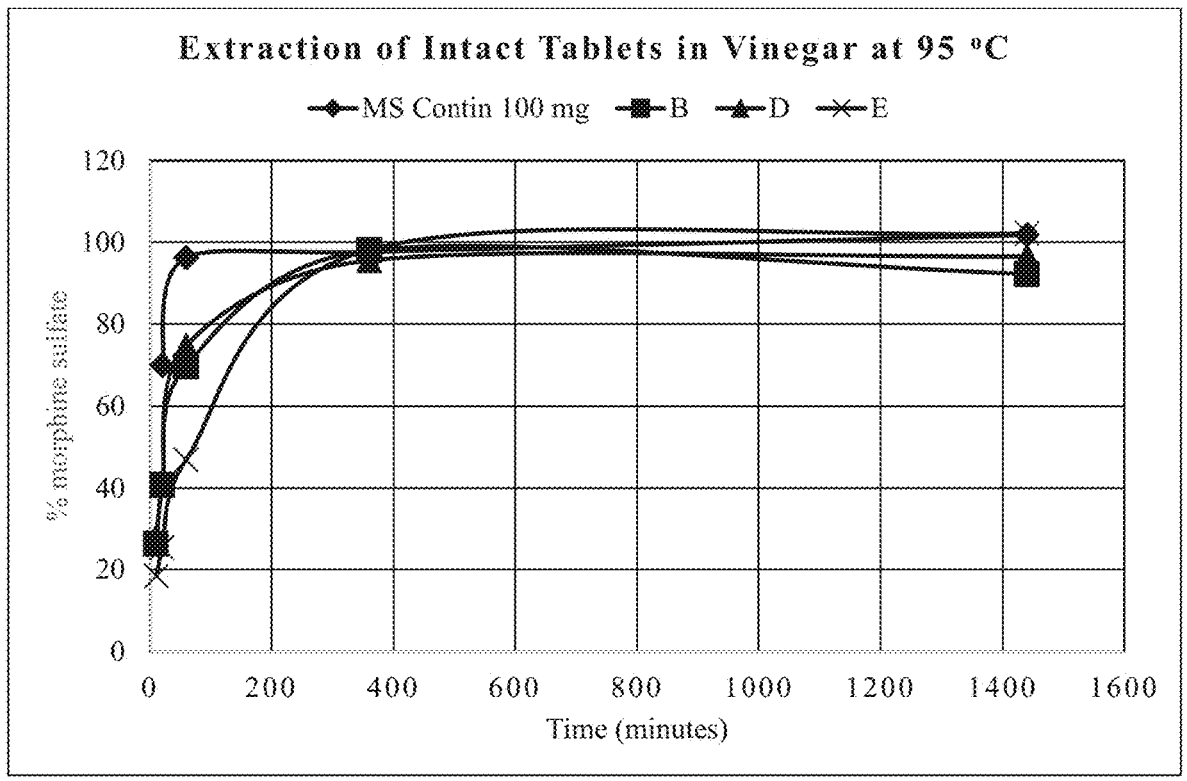
FIG. 25: Extraction of Intact Tablets in Vinegar at 95° C.
Figure 26:
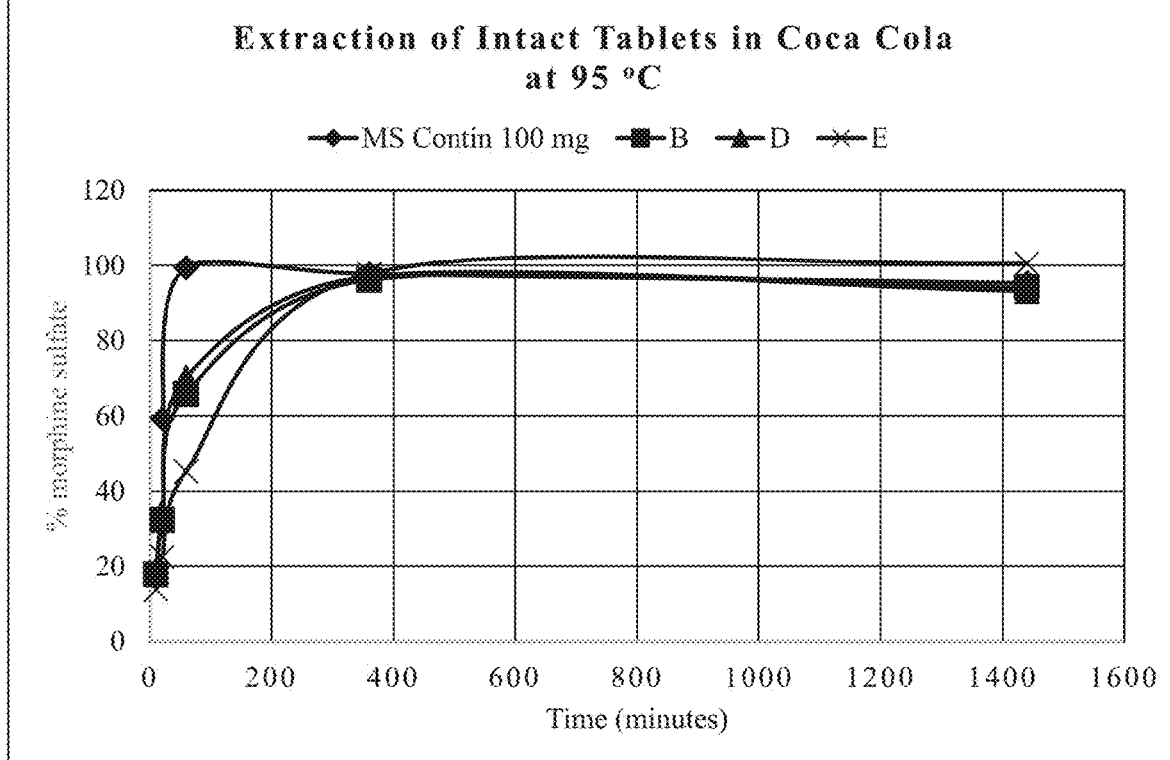
FIG. 26: Extraction of Intact Tablets in Coca Cola at 95° C.
Figure 27:
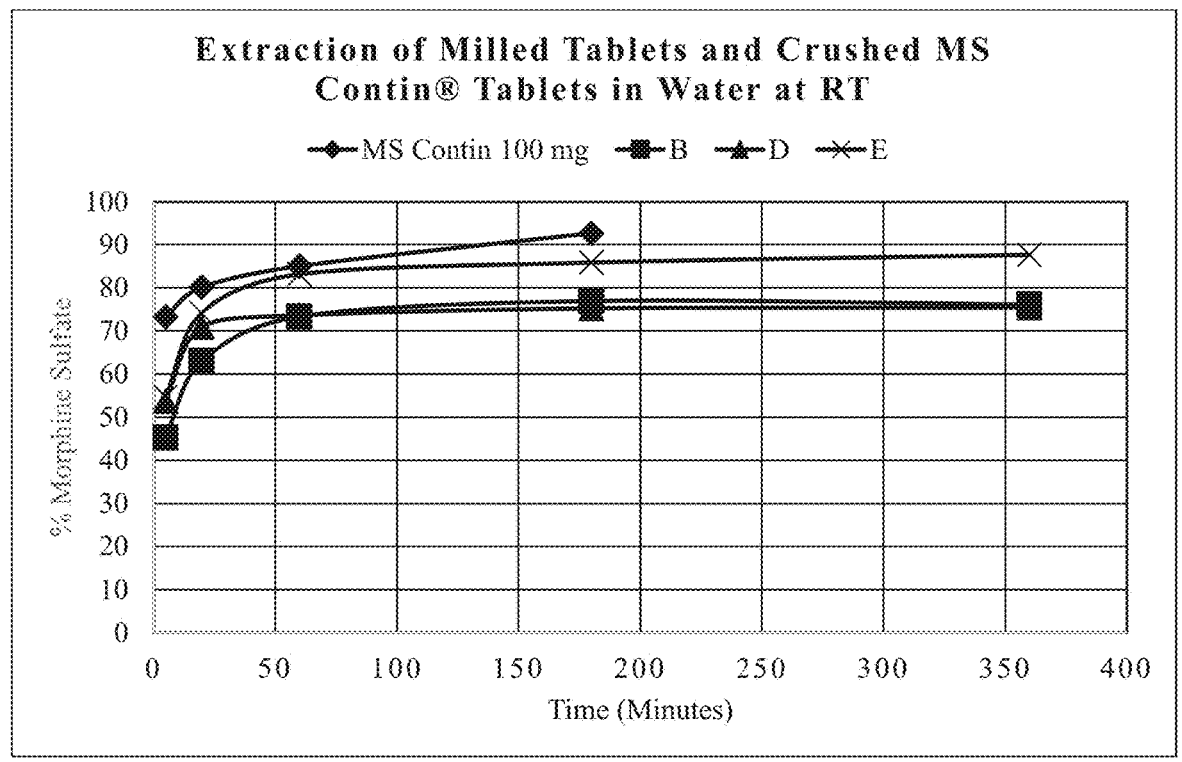
FIG. 27: Extraction of Milled Tablets and Crushed MS Contin® Tablets in Water at RT
Figure 28:
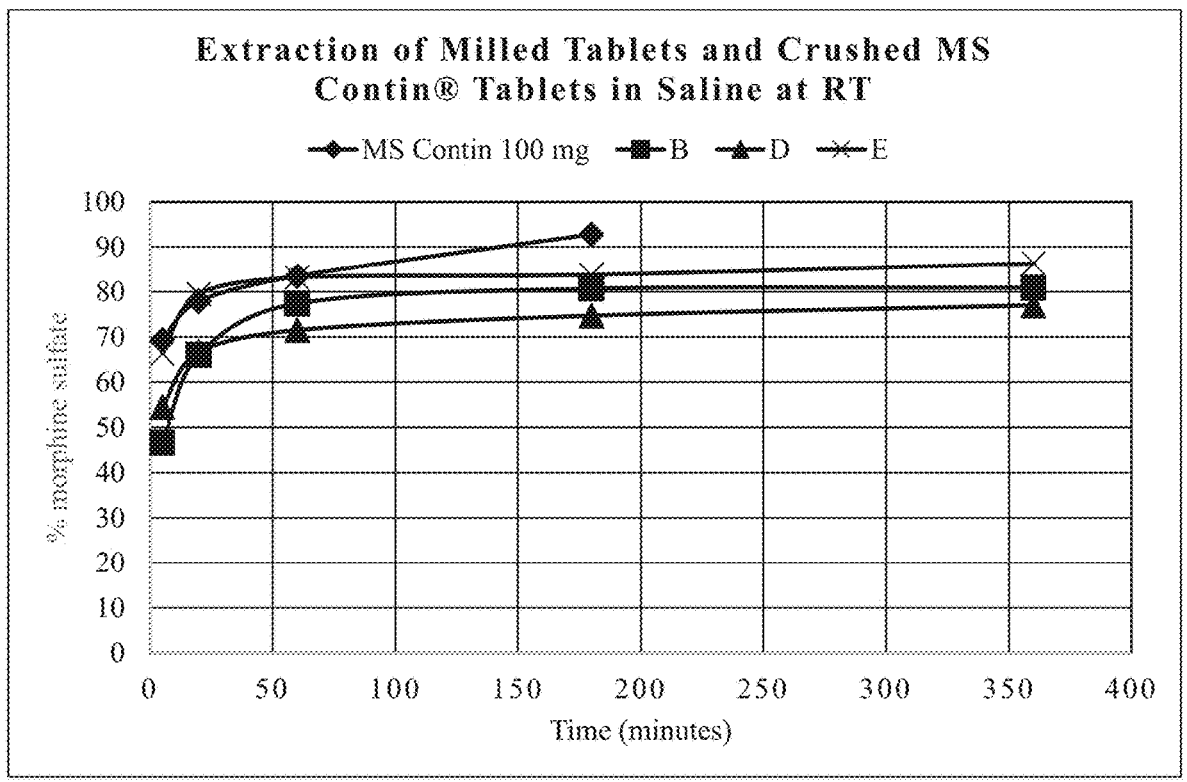
FIG. 28: Extraction of Milled Tablets and Crushed MS Contin® Tablets in Saline at RT
Figure 29:
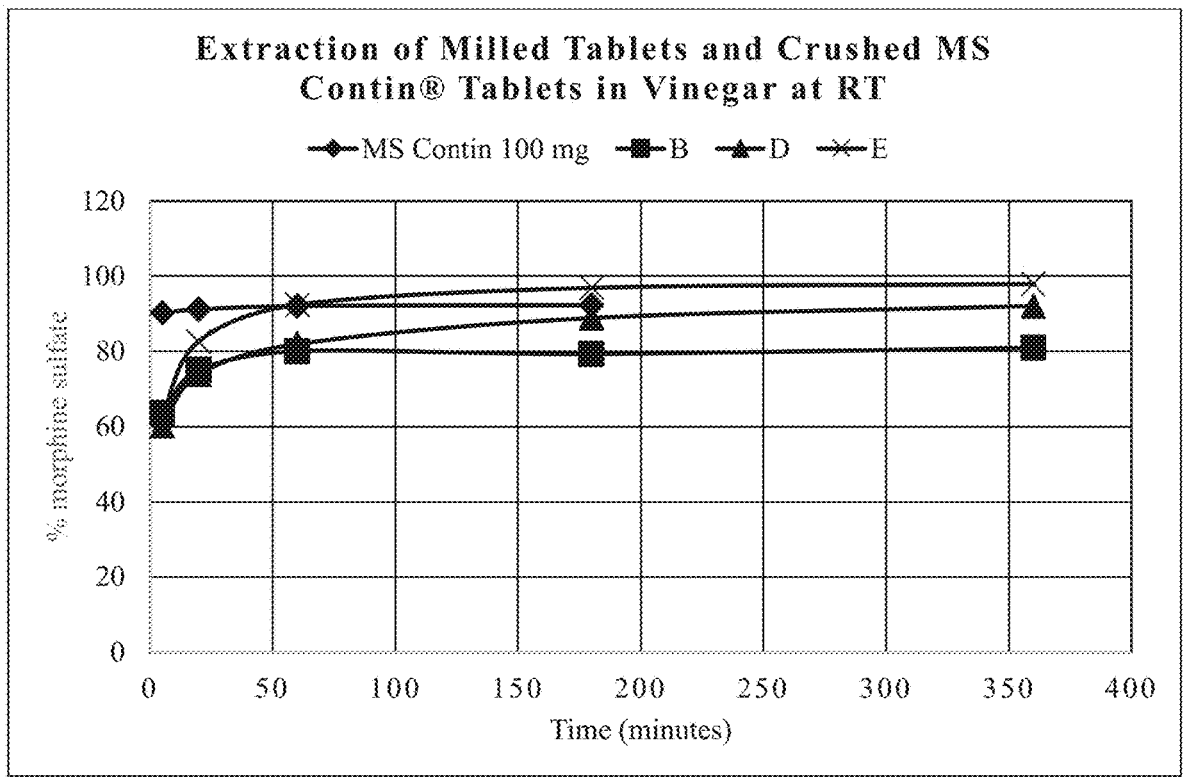
FIG. 29: Extraction of Milled Tablets and Crushed MS Contin® Tablets in Vinegar at RT
Figure 30:
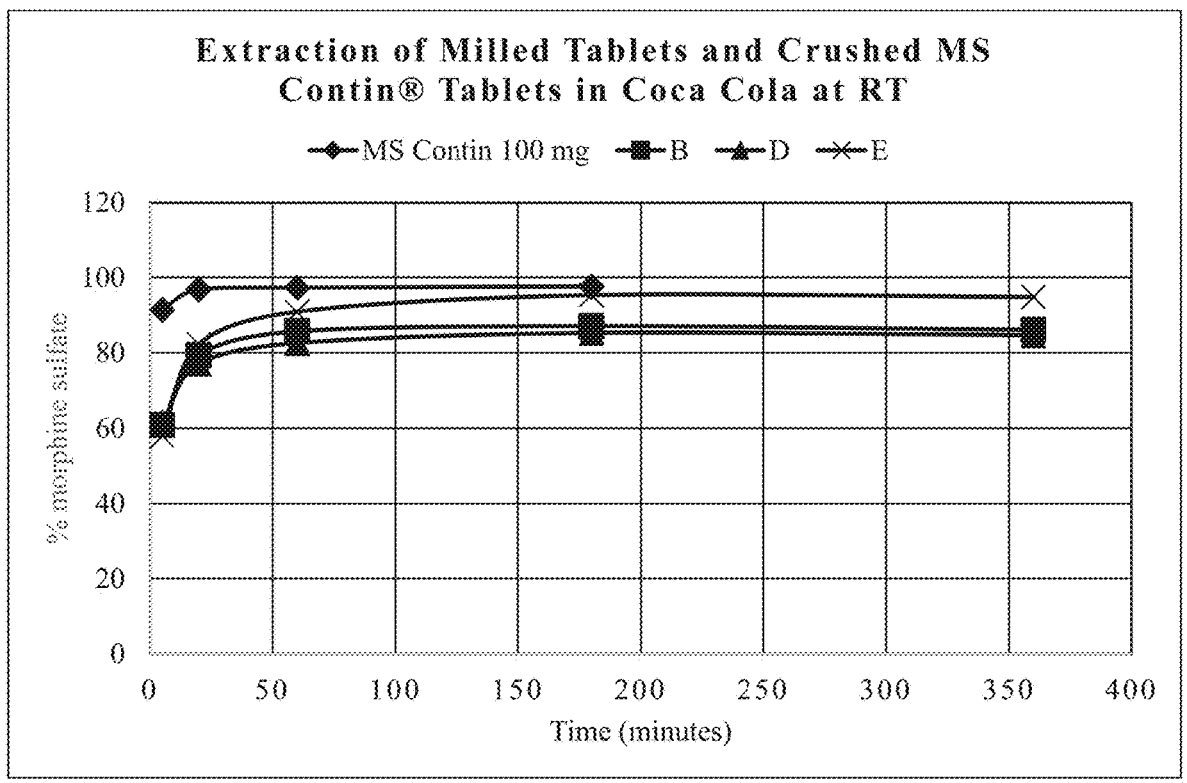
FIG. 30: Extraction of Milled Tablets and Crushed MS Contin® Tablets in Coca Cola at RT
Figure 31:
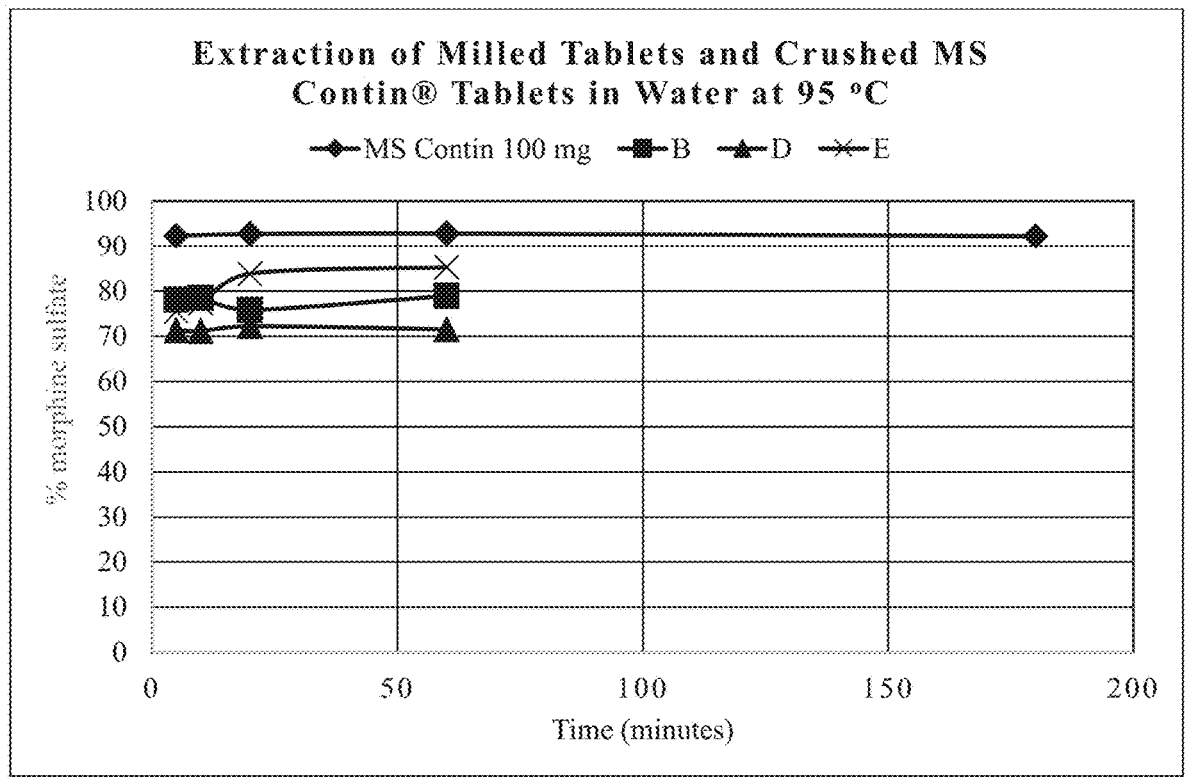
FIG. 31: Extraction of Milled Tablets and Crushed MS Contin® Tablets in Water at 95° C.
Figure 32:
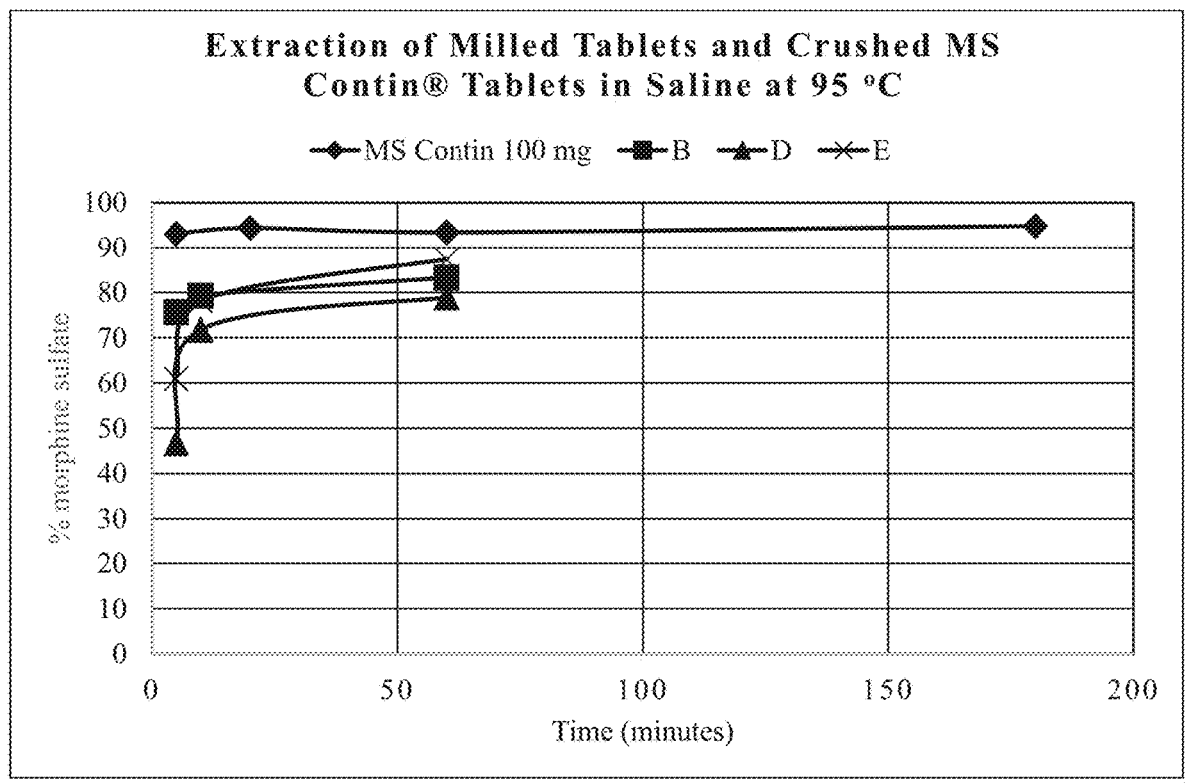
FIG. 32: Extraction of Milled Tablets and Crushed MS Contin® Tablets in Saline at 95° C.
Figure 33:
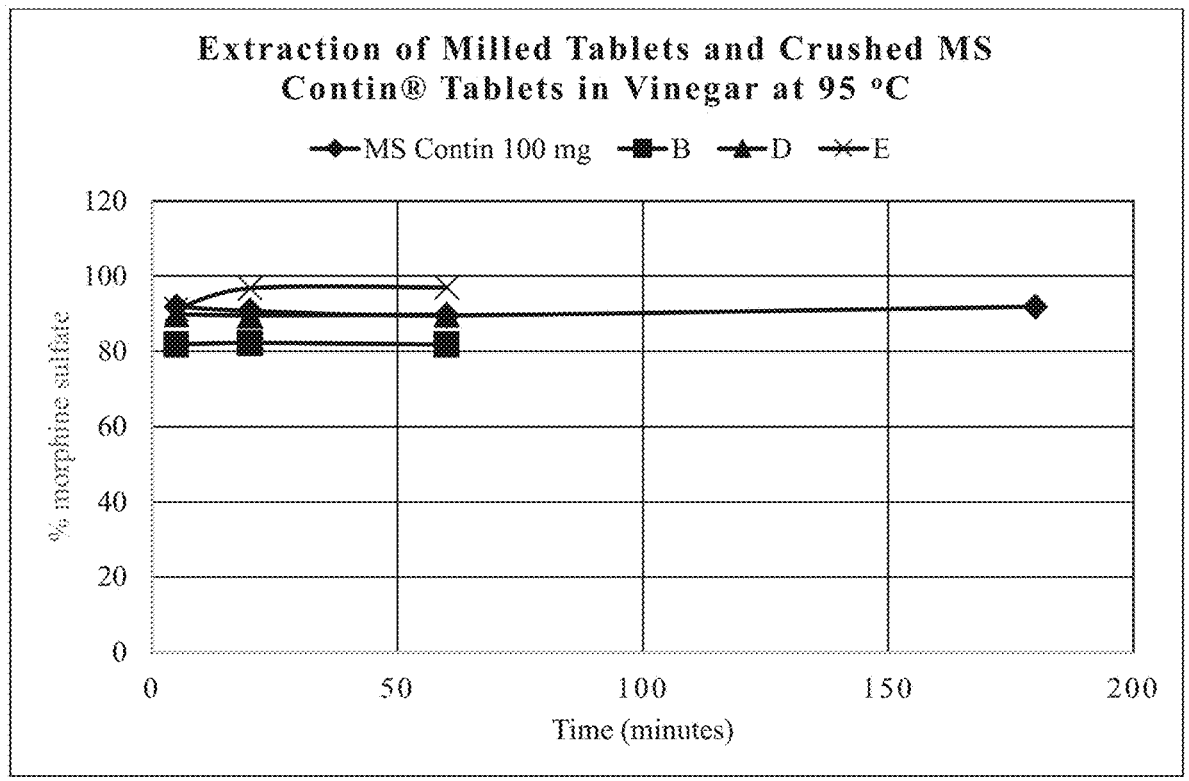
FIG. 33: Extraction of Milled Tablets and Crushed MS Contin® Tablets in Vinegar at 95° C.
Figure 34:
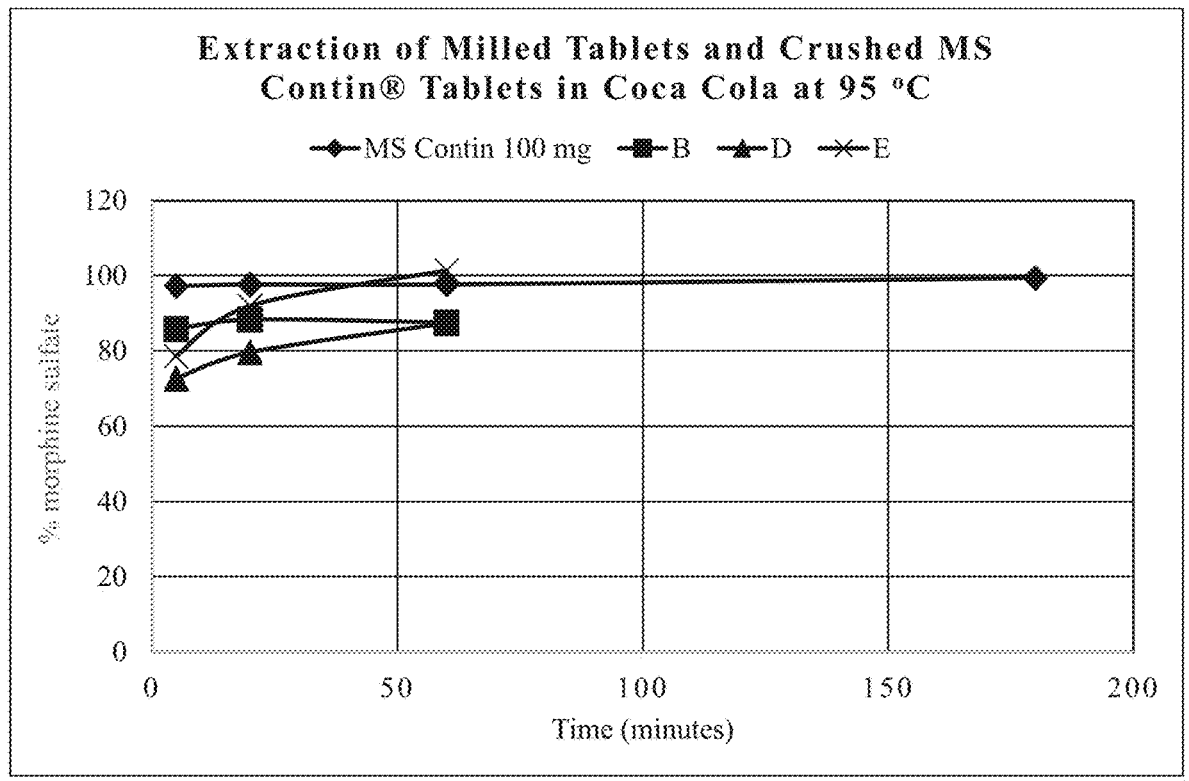
FIG. 34: Extraction of Milled Tablets and Crushed MS Contin® Tablets in Coca Cola at 95° C.

In contrast, dissolution of MS Contin® crushed tablets showed dose dumping with 96% of the morphine sulfate released within 15 minutes (see FIG. 18).

Finally, oven pre-treatment of the tablets according to the present invention produced increased rates in dissolution particularly at higher temperatures. There was little change in dissolution rates at 90° C., and the greatest changes occurred at 190° C., 210° C., and 230° C. Oven pre-treatment conditions (temperature/duration) that shortened dissolution time to release ≥80% morphine for Tablet D (100 mg morphine sulfate) have been summarized in Table 10.5 (conditions that did not alter time to release ≥80% morphine sulfate were not included).

TABLE 10.5

MSR - (100 mg) Mean Dissolution Times to Release ≥80% Morphine Sulfate for Tablet D

| Oven Pre-treatment | Dissolution Time to ≥80% Release of Morphine Sulfate, Percent Release |
|---|---|
| Untreated | 360 minutes, 90% |
| 130° C./240 minutes | 240 minutes, 81% |
| 130° C./360 minutes | 240 minutes, 82% |
| 130° C./480 minutes | 240 minutes, 87% |
| 140° C./240 minutes | 240 minutes, 87% |
| 140° C./360 minutes | 240 minutes, 93% |
| 150° C./120 minutes | 240 minutes, 84% |
| 150° C./240 minutes | 180 minutes, 82% |
| 170° C./30 minutes | 240 minutes, 81% |
| 170° C./60 minutes | 240 minutes, 93% |
| 170° C./120 minutes | 180 minutes, 89% |
| 190° C./30 minutes | 240 minutes, 94% |
| 190° C./60 minutes | 180 minutes, 85% |
| 210° C./10 minutes | 240 minutes, 91% |
| 210° C./30 minutes | 240 minutes, 90% |
| 230° C./10 minutes | 240 minutes, 91% |
| 230° C./30 minutes | 180 minutes, 83% |

Oven pre-treatment of Tablets D at elevated temperatures (≥130° C.) produced moderate increases in release rates compared to untreated tablets, although controlled release of morphine sulfate continued to be evident. The dissolution profiles of other dosage strengths (in particular, Tablets B and E) were affected similarly by oven pre-treatment. Microwave pre-treatment did not appear to alter the release rates of any of the dosage forms according to the present invention.

In Vitro Release Properties in Common Solvents

Large Volume Extraction

Example 11

Example 11 discloses the results of extraction studies carried out to demonstrate the release properties the dosage forms of the invention (as compared to MS Contin®) in a variety of extraction solvents.

The extraction studies were performed on tablets B (30 mg), D (100 mg), E (200 mg) and MS Contin® 100 mg as a reference. The extraction was carried out according to the extraction procedure described below on both intact and milled (ground in the case of MS Contin®) tablets in 100 mL of solvent at room temperature (RT, meaning 25° C.) and at elevated temperatures (50° C. and 95° C., depending on the solvent as specified below).

Milling Procedure:

Milling was performed in the same way as described in Example 10, above. MS Contin® was crushed (i.e., ground) with a glass mortar and pestle as described in Example 13 below.

Extraction Procedure:

1. The milled material was mixed well to ensure a homogeneous blend of particles, as the smaller particles tend to segregate from the larger particles.

2. For the elevated temperature conditions, the bath was set to the required temperature. Enough time was allowed for the water bath to equilibrate to reach the desired temperature. Also solvents were pre-warmed to 50° C. or 95° C. prior to starting.

3. A sample (milled or crushed material) was weighed equivalent to the ATW 3% and transferred into the glass (sample) jar. When analyzing a whole (intact) tablet, one tablet was selected, weighed and transferred into a sample jar. Triplicate samples were prepared (the values reported in the Tables below are the average of three samples).

4. To each sample jar, 100 mL of solvent were added, and the jars were capped.

5. The sample jars were placed in a shaker.

6. The shaker was started at the speed setting of 150. Using a calibrated timer, the extraction began immediately.

7. At each time point, shaking was first stopped, the sample jar was removed and 1.0 mL of the sample solution was pipetted into a 25 mL volumetric flask.

8. The sample jar was placed back into the shaker and shaking was resumed. Extraction was continued until the last time point.

9. The pipette (from step 7) was rinsed twice with SGF into the volumetric flask. All sample solutions were diluted to volume with SGF and mixed well.

10. A portion of the solution from Step 9 was filtered using a 25 mm glass fiber 1.0 μm filter into a HPLC vial for analysis.

The results of the extractions were analyzed using HPLC as described in Table 11.1.

TABLE 11.1

| Equipment | Conditions |
| --- | --- |
| Mobile phase | Ammonium acetate/Hexanesulfonic acid Buffer pH 4.36/Acetonitrile - 90:10 (v/v) |
| Flow rate | 1.0 ml/min |
| Column | Waters XBridge Shield RP18, 4.6 × 100 mm, 3.5 μm |
| Column temperature | 45° C. |
| Injection volume | 10 μL |
| Detector | UV set at 240 nm |
| Run time | Approximately 5 min |

The percent label claim of the amount of dissolved morphine sulfate was calculated for each time point.

Extraction tests were carried out at 25° C. for a variety of household solvents. The average percentage recovery results for extraction of morphine sulfate from intact tablets B, D and E and 100 mg MS Contin® in water, saline, vinegar and Coca-Cola are given in Table 11.2 (see FIG. 19, FIG. 20, FIG. 21 and FIG. 22 respectively).

TABLE 11.2

Extraction of morphine sulfate from intact tablets in household solvents at room temperature (25° C.)

| Tablet 25° C. | Solvent | 20 minutes | 60 minutes (1 hr) | 360 minutes (6 hrs) | 1440 minutes (24 hrs) |
| --- | --- | --- | --- | --- | --- |
| MS Contin® 100 mg | Water | 14.3 | 24.8 | 60.3 | 97.1 |
|  | Saline | 14 | 25.6 | 64.3 | 98.4 |
|  | Vinegar | 11.7 | 24.7 | 70.7 | 100.6 |
|  | Coca cola | 9.8 | 19.5 | 54.5 | 102.6 |
| B | Water | 5.2 | 11.6 | 46.1 | 95.5 |
|  | Saline | 5.6 | 11.4 | 40.1 | 93.4 |
|  | Vinegar | 8.2 | 16.1 | 52.5 | 93.8 |
|  | Coca Cola | 8.1 | 16.7 | 55.3 | 99.9 |
| D | Water | 6 | 11.4 | 39.1 | 88.8 |
|  | Saline | 5.8 | 11.2 | 37.6 | 88.4 |
|  | Vinegar | 7.3 | 13.8 | 46.0 | 93.8 |
|  | Coca Cola | 6.5 | 12.2 | 30.6 | 89 |
| E | Water | 4.7 | 9.4 | 36.8 | 90.6 |
|  | Saline | 4.1 | 7.9 | 28.9 | 81 |
|  | Vinegar | 4.4 | 9.3 | 33.3 | 91.1 |
|  | Coca Cola | 4.4 | 8.5 | 29.3 | 81.4 |

The average percentage recovery results for the extraction of morphine sulfate from intact tablets B, D and E and MS Contin® at elevated temperature (95° C.) in water, saline, vinegar and Coca Cola are given in Table 11.3 (see FIG. 23, FIG. 24, FIG. 25 and FIG. 26 respectively).

TABLE 11.3

Extraction of morphine sulfate from intact tablets in household solvents at 95° C.

| Tablet 95° C. | Solvent | 10 minutes | 20 minutes | 60 minutes (1 hr) | 360 minutes (6 hrs) | 1440 minutes (24 hrs) |
| --- | --- | --- | --- | --- | --- | --- |
| MS Contin® 100 mg | Water | NA | 61.6 | 91.4 | 87.4 | 83.3 |
|  | Saline | NA | 59.8 | 96.5 | 98.1 | 126.9 |
|  | Vinegar | NA | 70 | 96.2 | 97.6 | 101.7 |
|  | Coca cola | NA | 59.2 | 99.4 | 97.7 | 95.3 |
| B | Water | 24.9 | 35.6 | 63.9 | 79.4 | 65.6 |
|  | Saline | 18 | 31.4 | 63.6 | 90.7 | 110 |
|  | Vinegar | 26.2 | 40.7 | 69.7 | 98 | 92.2 |
|  | Coca Cola | 17.8 | 32.4 | 65.8 | 96.1 | 94.1 |
| D | Water | 26 | 36.7 | 66.2 | 88.8 | 82.3 |
|  | Saline | 21.4 | 35.1 | 68.7 | 94.6 | 123.9 |
|  | Vinegar | 28.0 | 40.7 | 74.7 | 95.5 | 96.5 |
|  | Coca Cola | 19.1 | 34.6 | 70.2 | 97 | 93.1 |
| E | Water | 16.3 | 23.1 | 43.3 | 91.3 | 91 |
|  | Saline | 13.9 | 21.9 | 44.7 | 102 | 124.4 |
|  | Vinegar | 18.4 | 25.3 | 46.9 | 98.1 | 102.1 |
|  | Coca Cola | 13.8 | 22.6 | 45.3 | 97.7 | 100.5 |

The average percentage recovery for extraction of morphine sulfate from milled tablets B, D and E and crushed 100 mg MS Contin® tablets at room temperature (25° C.) in water, saline, vinegar and Coca-Cola is given in Table 11.4 (see FIG. 27, FIG. 28, FIG. 29 and FIG. 30 respectively).

TABLE 11.4

Extraction of morphine sulfate from milled and crushed tablets in household solvents at room temperature

| Sample 25° C. | Solvent | 5 minutes | 20 minutes | 60 minutes (1 hr) | 180 minutes (3 hrs) | 360 minutes (6 hrs) |
|---|---|---|---|---|---|---|
| MS Contin ® 100 mg | Water | 73.2 | 80.1 | 85 | 92.6 | NA |
| | Saline | 69.4 | 77.9 | 83.5 | 92.8 | NA |
| | Vinegar | 90.2 | 91.1 | 92 | 92.2 | NA |
| | Coca Cola | 91.4 | 96.8 | 97.3 | 97.6 | NA |
| B | Water | 45.3 | 63 | 73.3 | 76.9 | 76.1 |
| | Saline | 46.6 | 66 | 77.4 | 80.7 | 80.9 |
| | Vinegar | 63.6 | 75 | 80 | 79.3 | 80.9 |
| | Coca Cola | 60.9 | 79.4 | 85.7 | 87.1 | 86.1 |
| D | Water | 53.8 | 70.9 | 73.6 | 75.2 | 75.4 |
| | Saline | 54.5 | 66.6 | 71.5 | 74.7 | 77 |
| | Vinegar | 60.3 | 73.9 | 81.9 | 88.8 | 92.0 |
| | Coca Cola | 61.5 | 77.1 | 82.6 | 85.3 | 84.7 |
| E | Water | 54.6 | 74.2 | 83.1 | 85.8 | 87.6 |
| | Saline | 66.4 | 79.5 | 83.2 | 83.8 | 86.3 |
| | Vinegar | 63.7 | 82.6 | 92.3 | 96.8 | 97.8 |
| | Coca Cola | 58 | 82.2 | 90.9 | 95.3 | 94.8 |

The average percentage recovery for extraction of morphine sulfate from milled tablets B, D and E and crushed 100 mg MS Contin® tablets at elevated temperature (95° C.) in water saline, vinegar and Coca-Cola is given in Table 11.5 (see FIG. 31, FIG. 32, FIG. 33 and FIG. 34).

TABLE 11.5

Extraction of morphine sulfate from milled and crushed tablets in household solvents at 95° C.

| Sample 95° C. | Solvent | 5 minutes | 10 minutes | 20 minutes | 60 minutes (1 hr) | 180 minutes (3 hrs) |
|---|---|---|---|---|---|---|
| MS Contin ® 100 mg | Water | 92.3 | NA | 92.7 | 92.8 | 92.2 |
| | Saline | 93.1 | NA | 94.4 | 93.4 | 94.8 |
| | Vinegar | 91.8 | NA | 90.7 | 89.5 | 91.8 |
| | Coca cola | 97.2 | NA | 97.6 | 97.6 | 99.3 |
| B | Water | 78.1 | 78.4 | 75.8 | 78.9 | NA |
| | Saline | 75.6 | 79.3 | NA | 83.3 | NA |
| | Vinegar | 81.8 | NA | 82.2 | 81.8 | NA |
| | Coca Cola | 85.7 | NA | 88.3 | 87.5 | NA |
| D | Water | 71.3 | 71.1 | 72.2 | 71.5 | NA |
| | Saline | 46.7 | 71.8 | NA | 78.9 | NA |
| | Vinegar | 89.8 | NA | 89.5 | 89.7 | NA |
| | Coca Cola | 72.6 | NA | 79.6 | 87.3 | NA |
| E | Water | 75.5 | 77.3 | 83.8 | 85.2 | NA |
| | Saline | 60.9 | 78.2 | NA | 87.4 | NA |
| | Vinegar | 91.1 | NA | 96.7 | 96.9 | NA |
| | Coca Cola | 78.6 | NA | 91.9 | 101.3 | NA |

Figure 35:
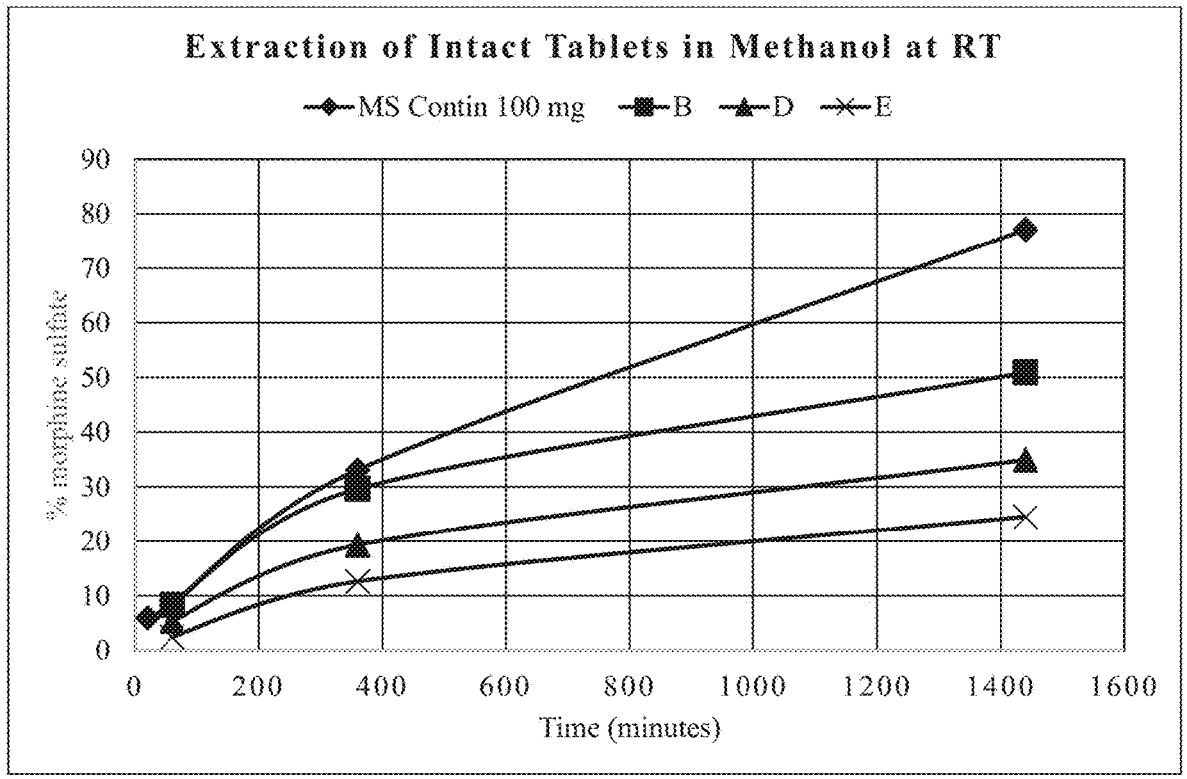
FIG. 35: Extraction of Intact Tablets in Methanol at RT
Figure 36:
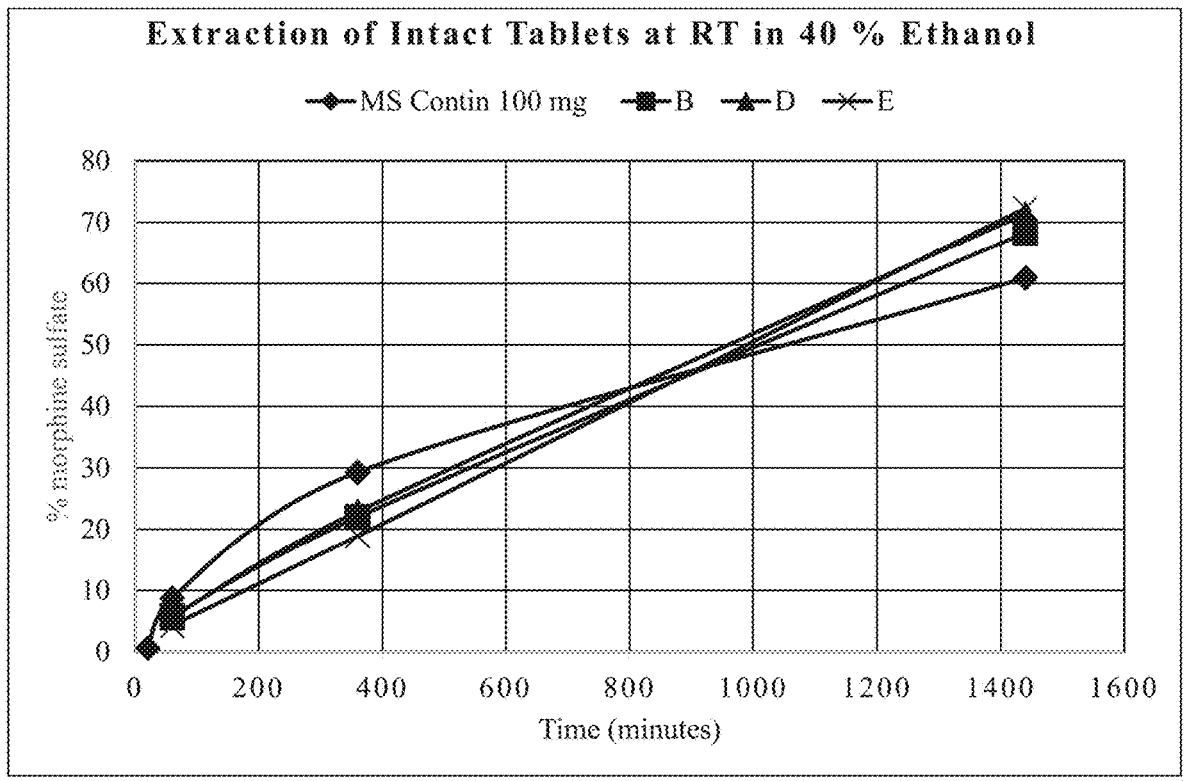
FIG. 36: Extraction of Intact Tablets at RT in 40% Ethanol
Figure 37:
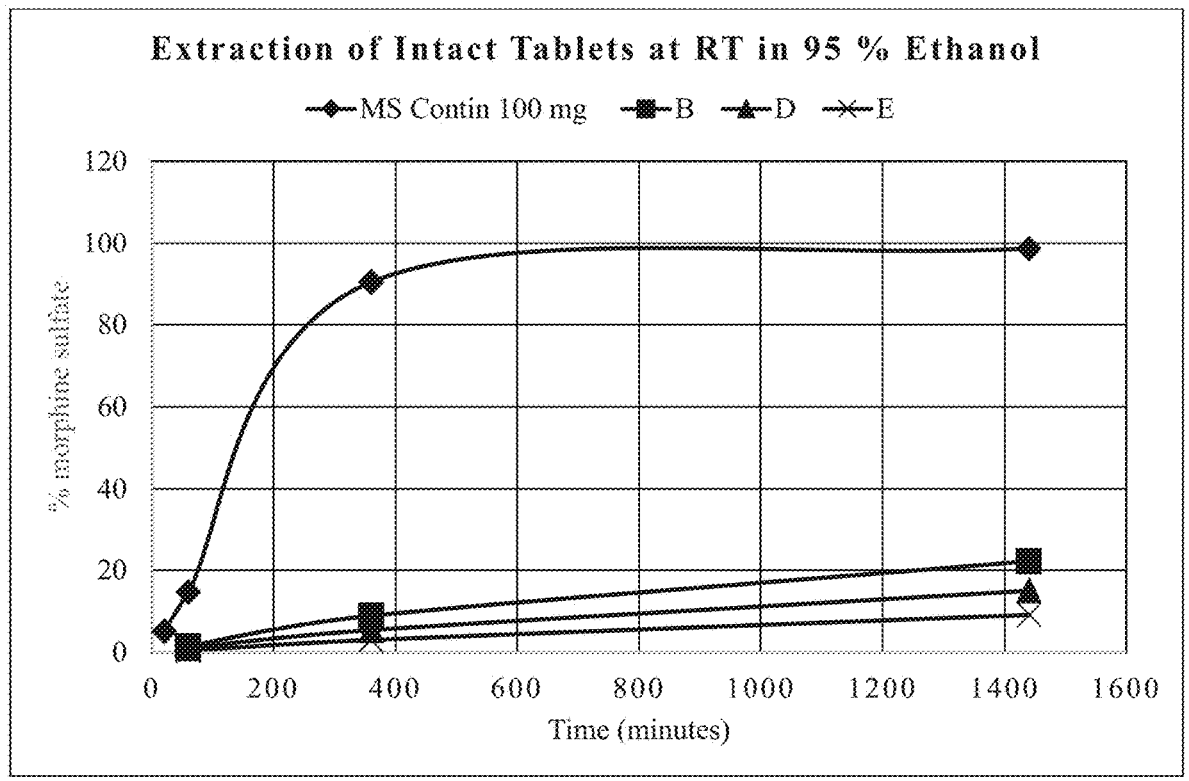
FIG. 37: Extraction of Intact Tablets at RT in 95% Ethanol

Extraction tests were carried out at 25° C. for a variety of organic solvents. The average percentage recovery results for extraction of morphine sulfate from B, D and E and 100 mg MS Contin® intact tablets in methanol, 40% ethanol and 95% ethanol are given in Table 11.6 (see FIG. 35, FIG. 36 and FIG. 37 respectively).

TABLE 11.6

Extraction of morphine sulfate from intact tablets in organic solvents at room temperature (25° C.)

| Tablet 25° C. | Solvent | 20 minutes | 60 minutes (1 hr) | 360 minutes (6 hrs) | 1440 minutes (24 hrs) |
|---|---|---|---|---|---|
| MS Contin ® 100 mg | Methanol | 5.9 | 8.4 | 33.1 | 77.1 |
| | 40% Ethanol | 0.6 | 8.7 | 29.3 | 60.9 |
| | 95% Ethanol | 5.1 | 14.7 | 90.4 | 98.6 |
| B | Methanol | NA | 8.3 | 29.6 | 50.9 |
| | 40% Ethanol | NA | 5.8 | 22 | 68.3 |
| | 95% Ethanol | NA | 1.4 | 8.9 | 22.2 |
| D | Methanol | NA | 5.3 | 19.3 | 34.9 |
| | 40% Ethanol | NA | 5.6 | 22.9 | 71.4 |
| | 95% Ethanol | NA | 1 | 5.4 | 15 |
| E | Methanol | NA | 2.4 | 12.6 | 24.5 |
| | 40% Ethanol | NA | 4.3 | 18.9 | 72.3 |
| | 95% Ethanol | NA | 0.4 | 3 | 9.1 |

Figure 38:
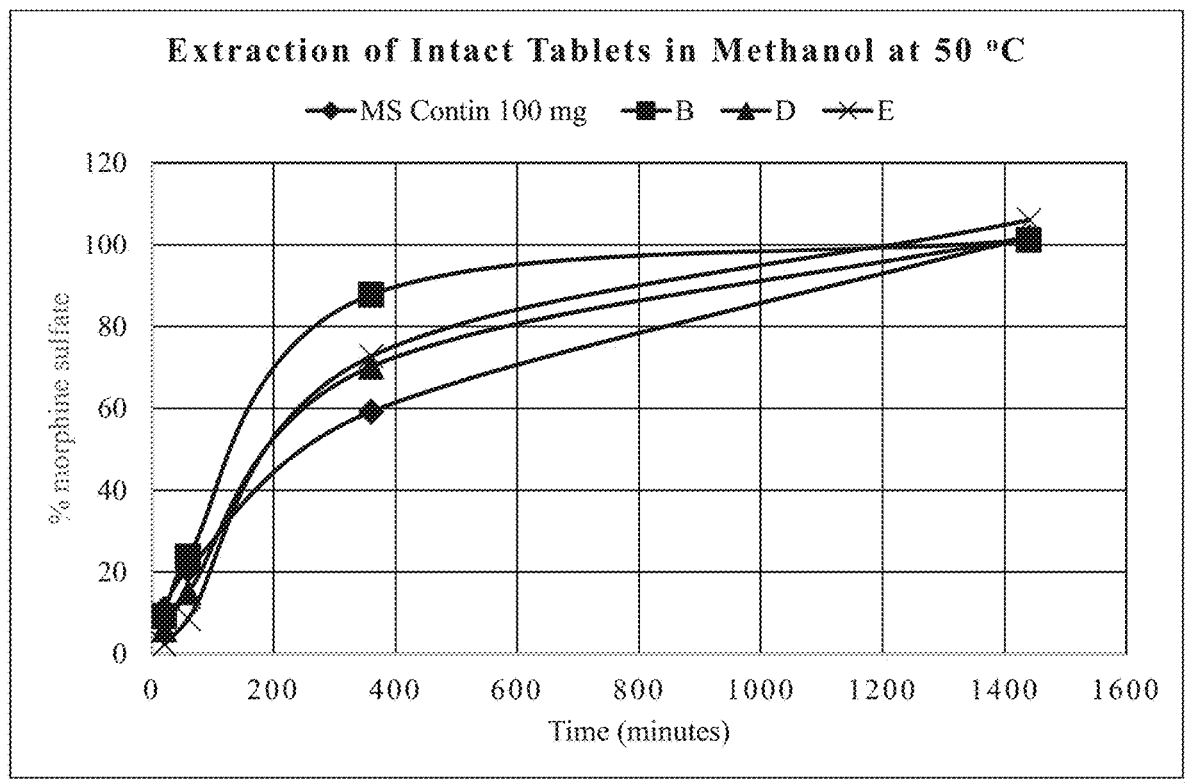
FIG. 38: Extraction of Intact Tablets in Methanol at 50° C.
Figure 39:
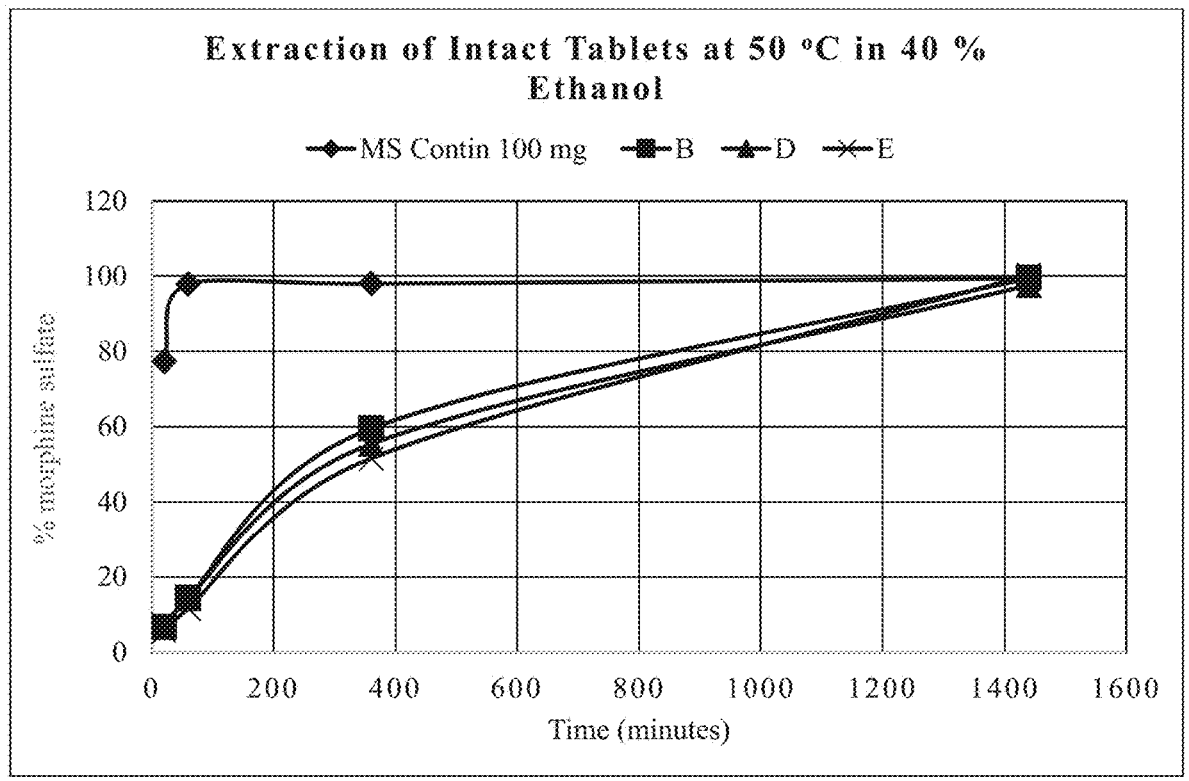
FIG. 39: Extraction of Intact Tablets at 50° C. in 40% Ethanol
Figure 40:
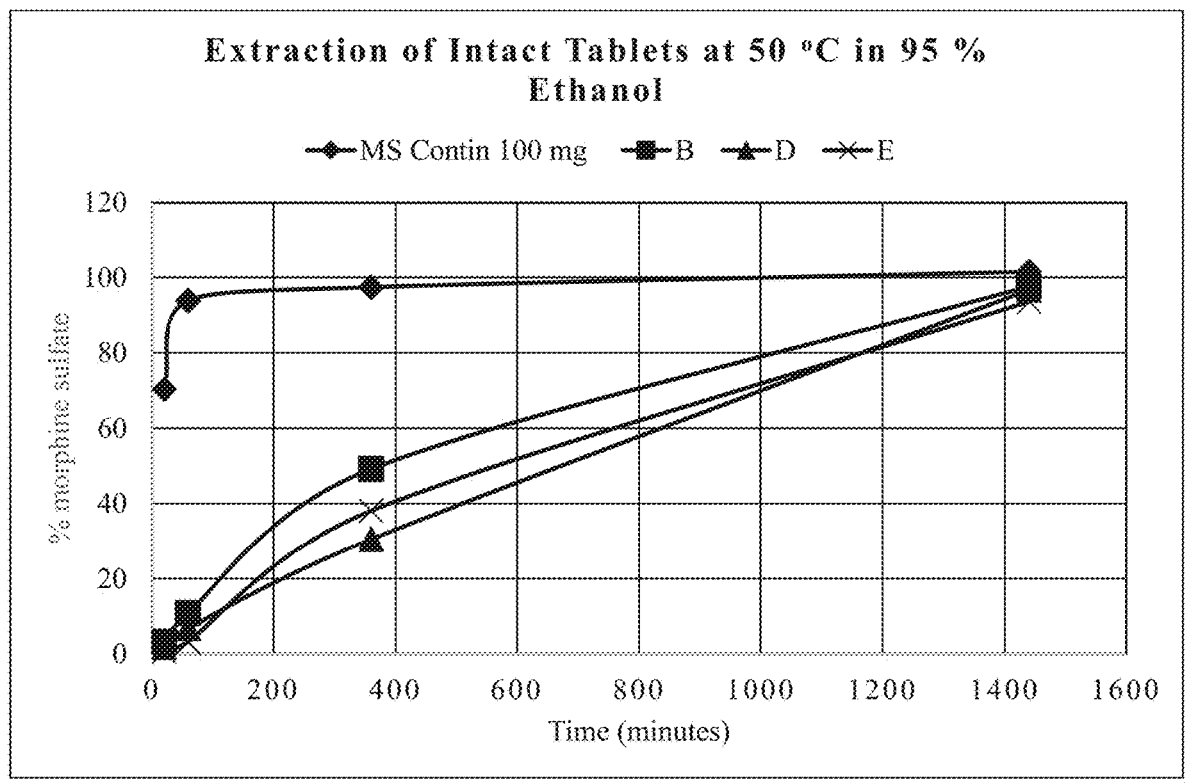
FIG. 40: Extraction of Intact Tablets at 50° C. in 95% Ethanol

The results for the tests carried out with B, D and E and 100 mg MS Contin® intact tablets in methanol, 40% ethanol and 95% ethanol at 50° C. are given in Table 11.7 (see FIG. 38, FIG. 39 and FIG. 40 respectively).

TABLE 11.7

Extraction of morphine sulfate from intact tablets in organic solvents at 50° C.

| Tablet 50° C. | Buffer | 20 minutes | 60 minutes (1 hr) | 360 minutes (6 hrs) | 1440 minutes (24 hrs) |
|---|---|---|---|---|---|
| MS Contin® 100 mg | Methanol | 11.1 | 20.5 | 59.2 | 101.9 |
|  | 40% Ethanol | 77.3 | 97.8 | 97.9 | 99.3 |
|  | 95% Ethanol | 70.4 | 93.8 | 97.4 | 101.5 |
| B | Methanol | 9.2 | 23.9 | 87.7 | 101.2 |
|  | 40% Ethanol | 6.7 | 14.4 | 59.5 | 99.4 |
|  | 95% Ethanol | 3.2 | 10.8 | 49.2 | 97.6 |
| D | Methanol | 6.0 | 15.0 | 70.2 | 102 |
|  | 40% Ethanol | 6.8 | 14.3 | 55.4 | 97.5 |
|  | 95% Ethanol | 1.9 | 6.8 | 30.5 | 96.7 |
| E | Methanol | 2.4 | 8.5 | 72.7 | 106.1 |
|  | 40% Ethanol | 5.5 | 11.6 | 51.6 | 100.2 |
|  | 95% Ethanol | 0.6 | 3.2 | 38.1 | 93.6 |

Figure 41:
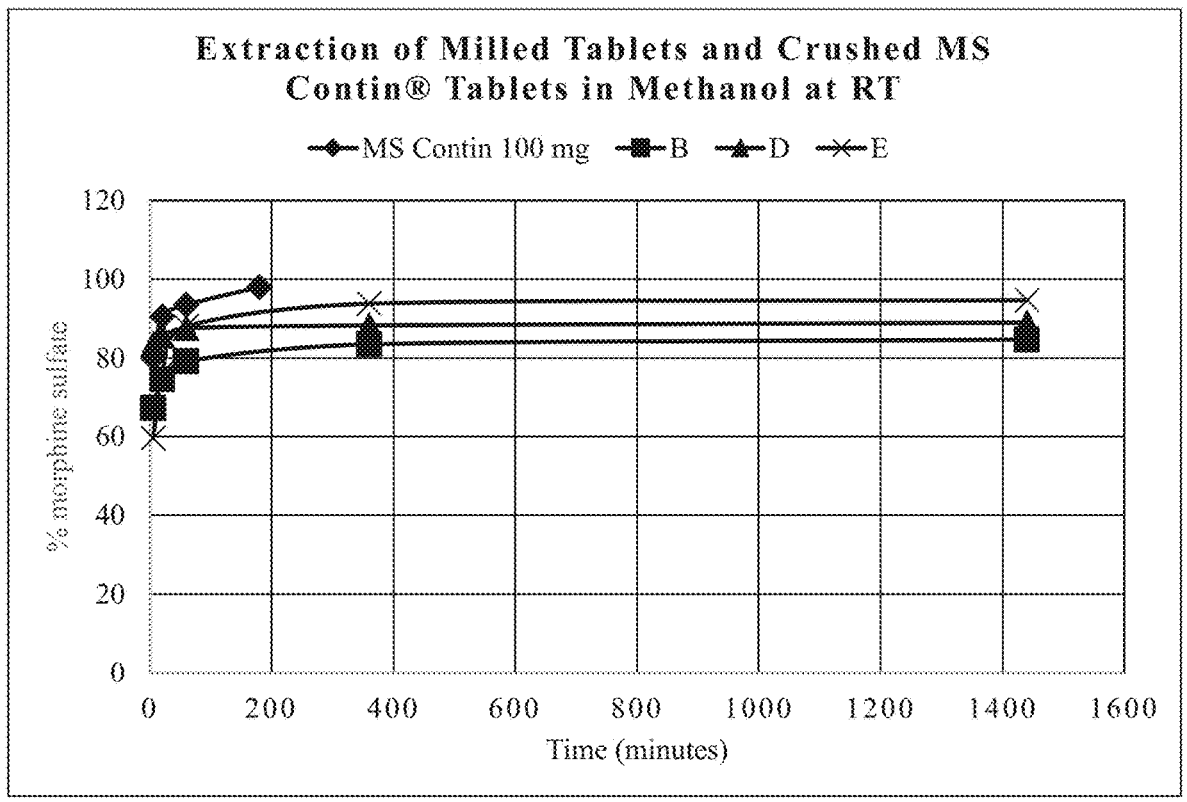
FIG. 41: Extraction of Milled Tablets and Crushed MS Contin® Tablets in Methanol at RT
Figure 42:
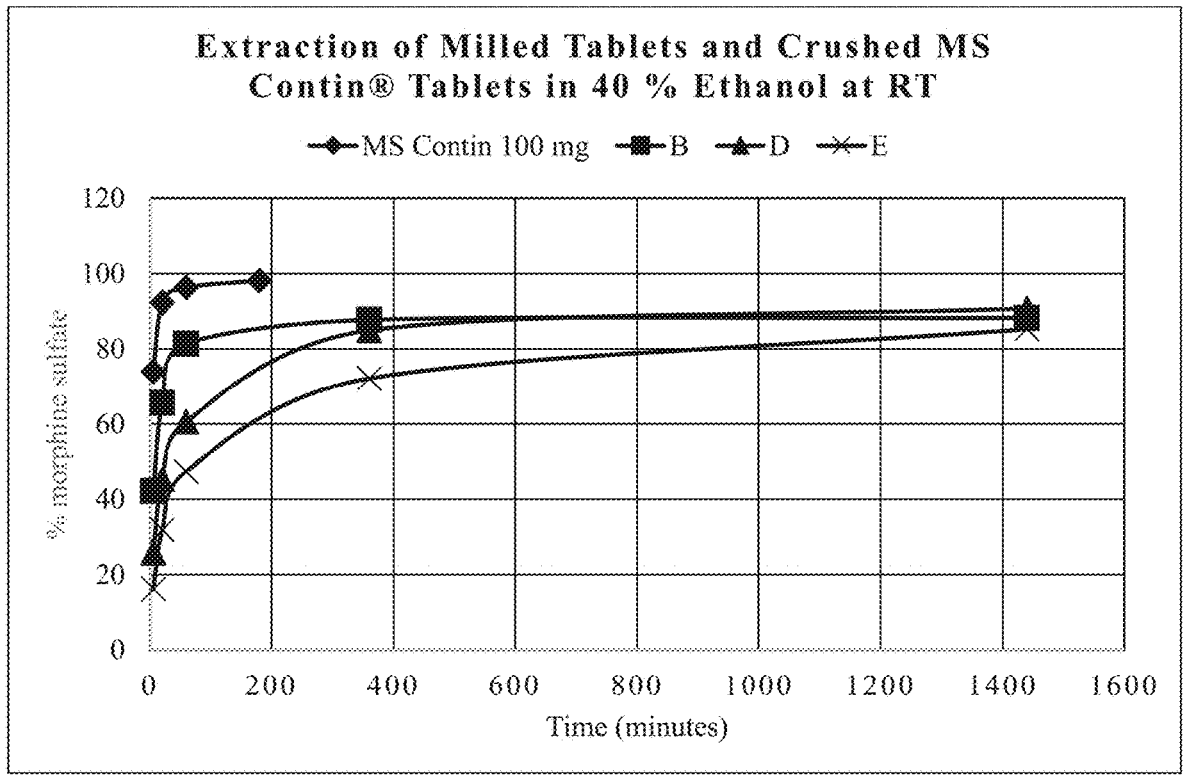
FIG. 42: Extraction of Milled Tablets and Crushed MS Contin® Tablets in 40% Ethanol at RT
Figure 43:
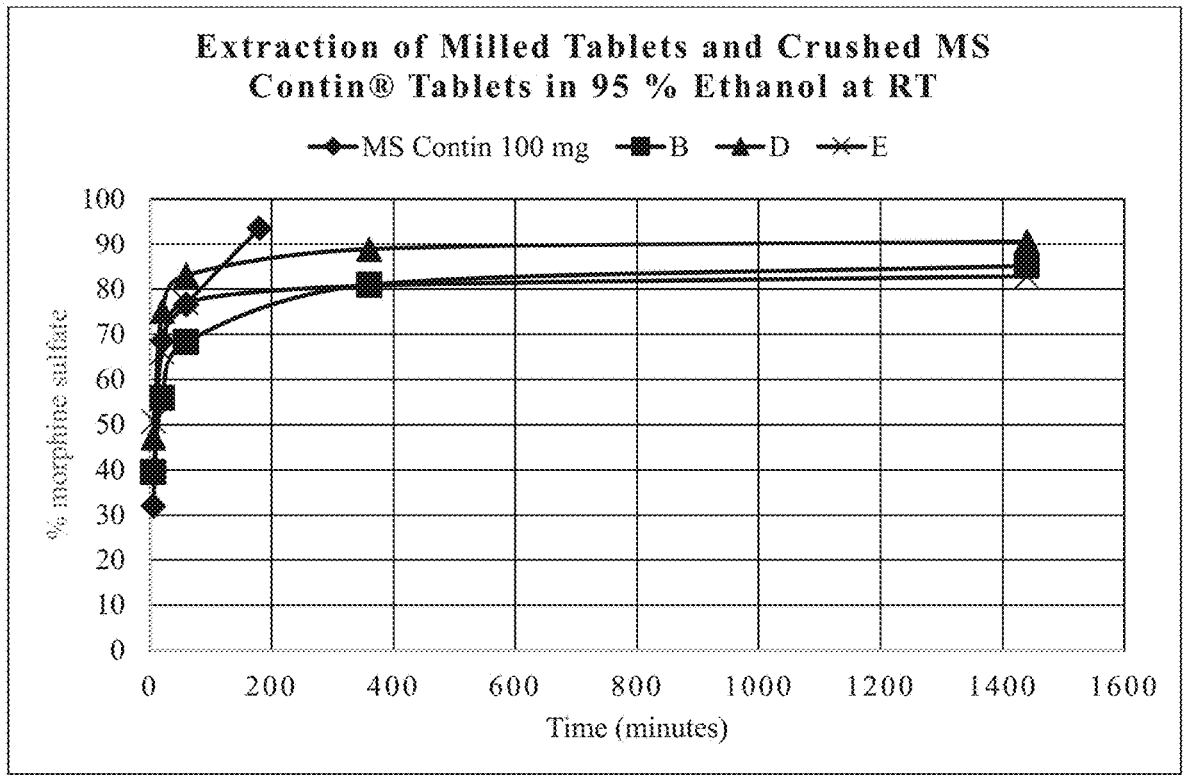
FIG. 43: Extraction of Milled Tablets and Crushed MS Contin® Tablets in 95% Ethanol at RT

The average percentage recovery for extraction of morphine sulfate from milled tablets B, D and E and crushed 100 mg MS Contin® tablets at room temperature (25° C.) in organic solvents are given in Table 11.8 (see FIG. 41, FIG. 42 and FIG. 43 respectively).

TABLE 11.8

Extraction of morphine sulfate from milled and crushed tablets at room temperature in organic solvents

| Sample 25° C. | Solvent | 5 minutes | 20 minutes | 60 minutes (1 hr) | 180 minutes (3 hrs) | 360 minutes (6 hrs) | 1440 minutes (24 hrs) |
|---|---|---|---|---|---|---|---|
| MS Contin® 100 mg | Methanol | 80 | 90.5 | 93.5 | 98.0 | NA | NA |
|  | 40% Ethanol | 73.9 | 92.3 | 96.3 | 98.1 | NA | NA |
|  | 95% Ethanol | 32 | 68.5 | 76.5 | 93.5 | NA | NA |
| B | Methanol | 67.2 | 74.5 | 79.2 | NA | 83.5 | 84.7 |
|  | 40% Ethanol | 42.2 | 65.5 | 81.3 | NA | 87.7 | 88.2 |
|  | 95% Ethanol | 39.5 | 55.9 | 68.2 | NA | 80.9 | 85.1 |
| D | Methanol | 83.5 | 85.6 | 87.6 | NA | 88.3 | 89 |
|  | 40% Ethanol | 25.8 | 45.2 | 60.5 | NA | 84.9 | 90.7 |
|  | 95% Ethanol | 47.1 | 75.1 | 83 | NA | 88.8 | 90.6 |
| E | Methanol | 59.5 | 76.2 | 88 | NA | 93.8 | 94.7 |
|  | 40% Ethanol | 16.1 | 31.9 | 47.3 | NA | 72.1 | 85.2 |
|  | 95% Ethanol | 50.7 | 65.9 | 77 | NA | 80.7 | 82.8 |

Figure 44:
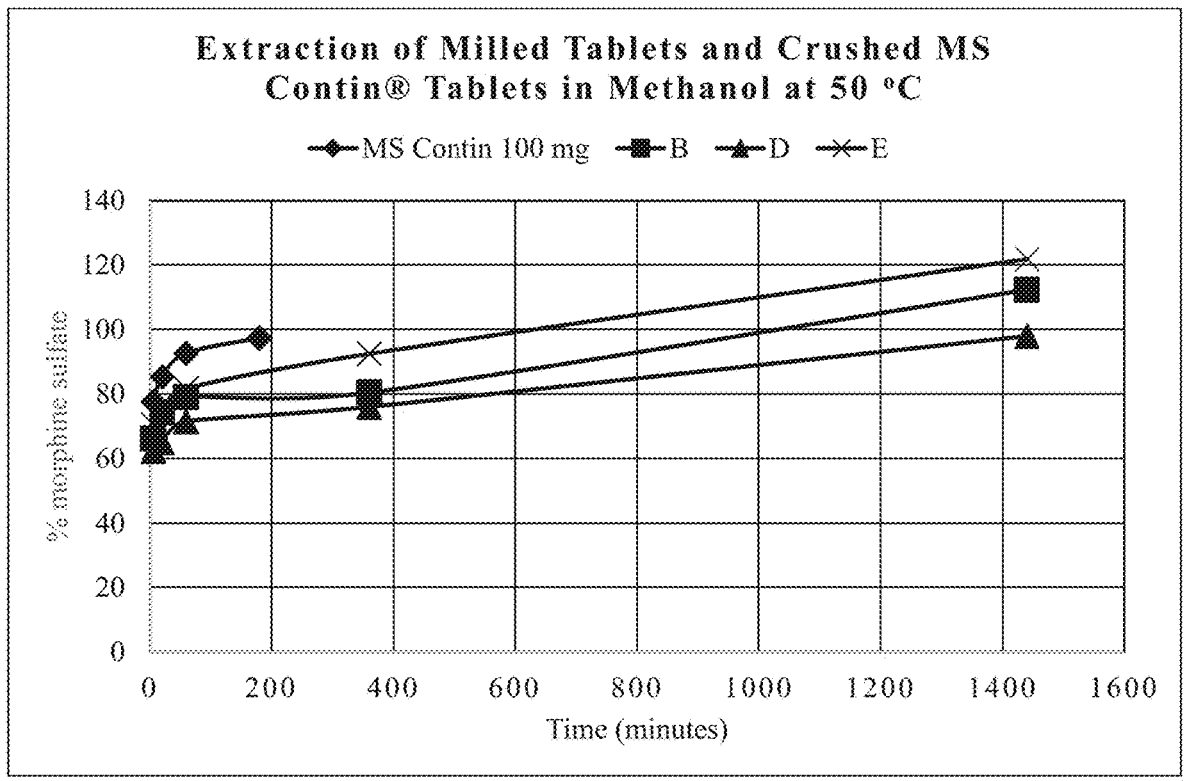
FIG. 44: Extraction of Milled Tablets and Crushed MS Contin® Tablets in Methanol at 50° C.
Figure 45:
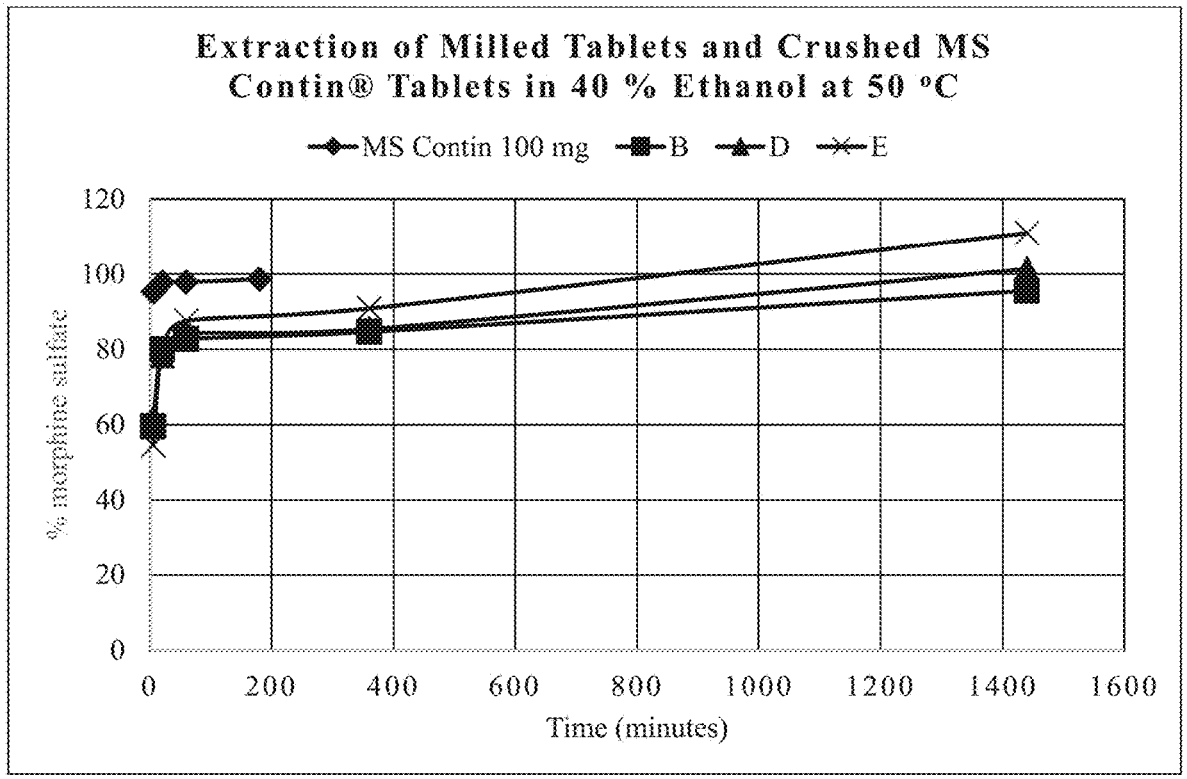
FIG. 45: Extraction of Milled Tablets and Crushed MS Contin® Tablets in 40% Ethanol at 50° C.
Figure 46:
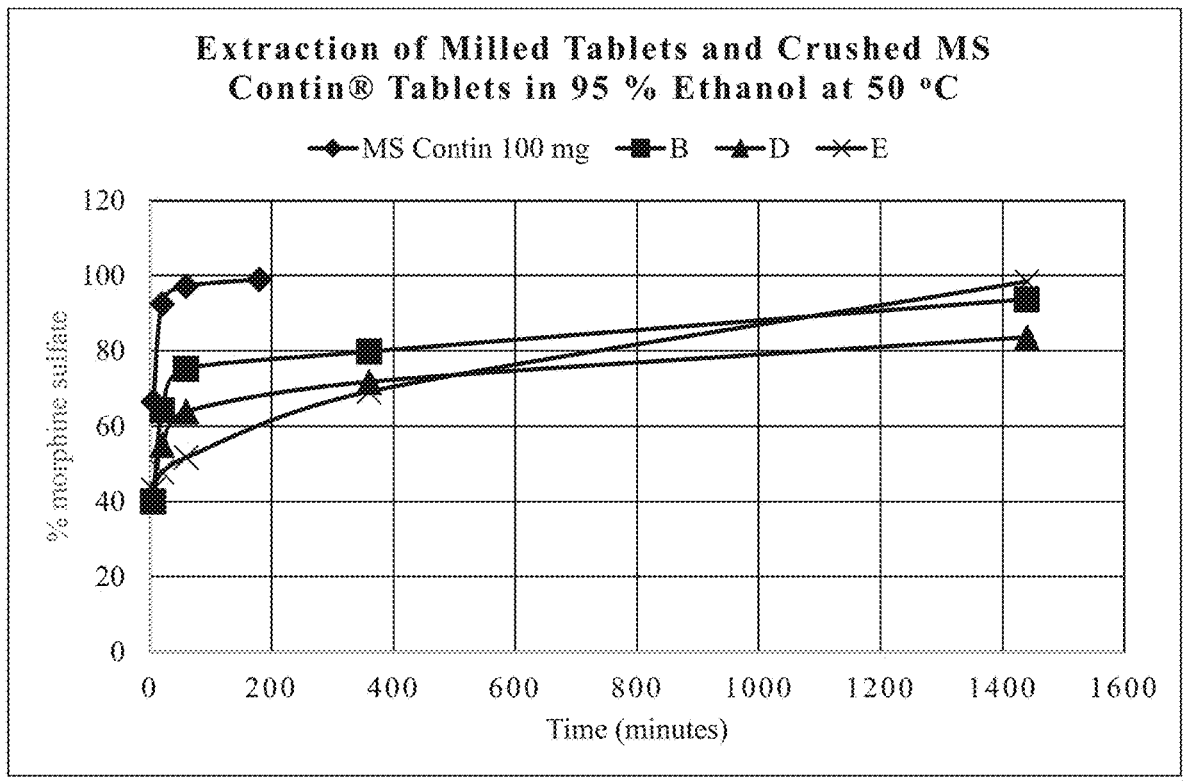
FIG. 46: Extraction of Milled Tablets and Crushed MS Contin® Tablets in 95% Ethanol at 50° C.
Figure 47:
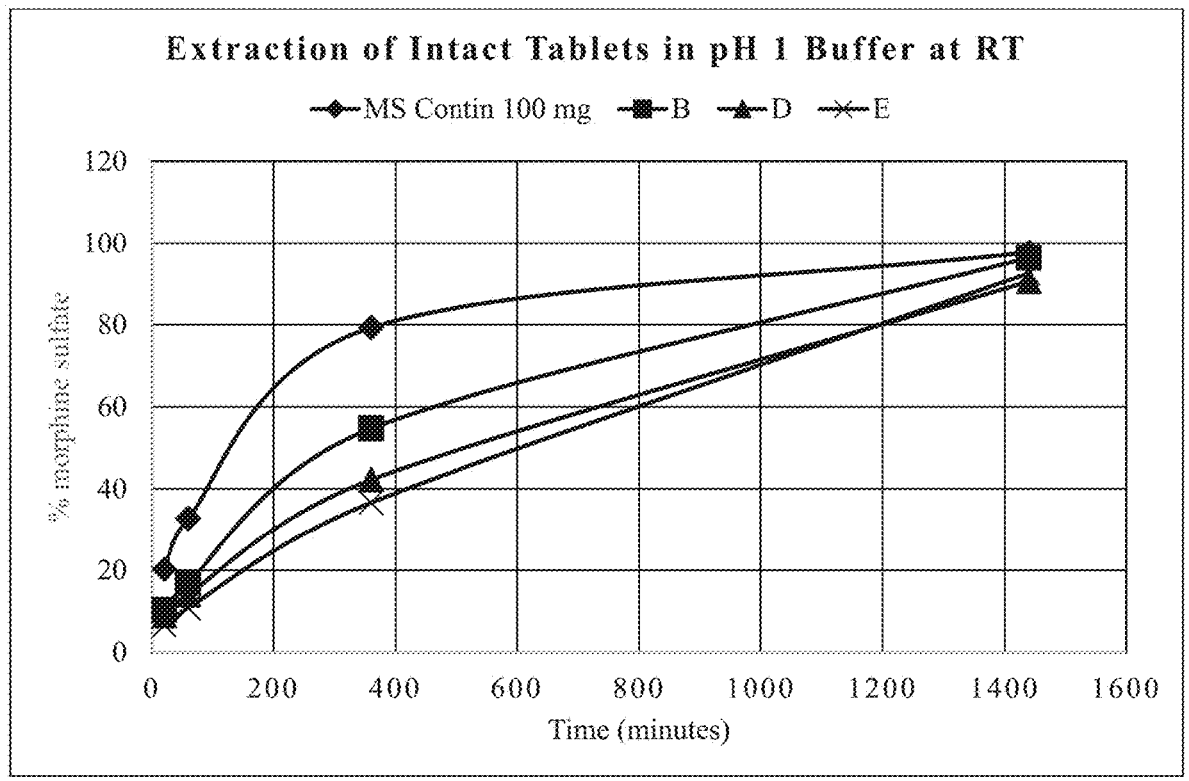
FIG. 47: Extraction of Intact Tablets in pH 1 Buffer at RT
Figure 48:
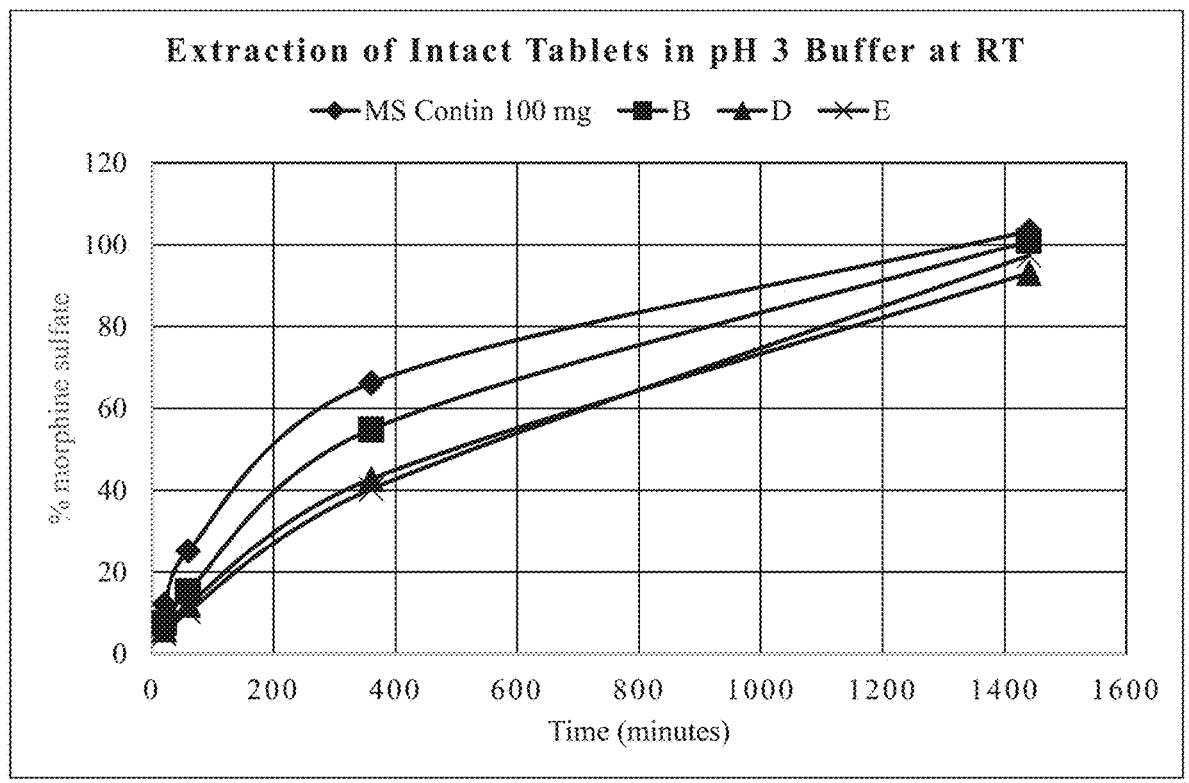
FIG. 48: Extraction of Intact Tablets in pH 3 Buffer at RT
Figure 49:
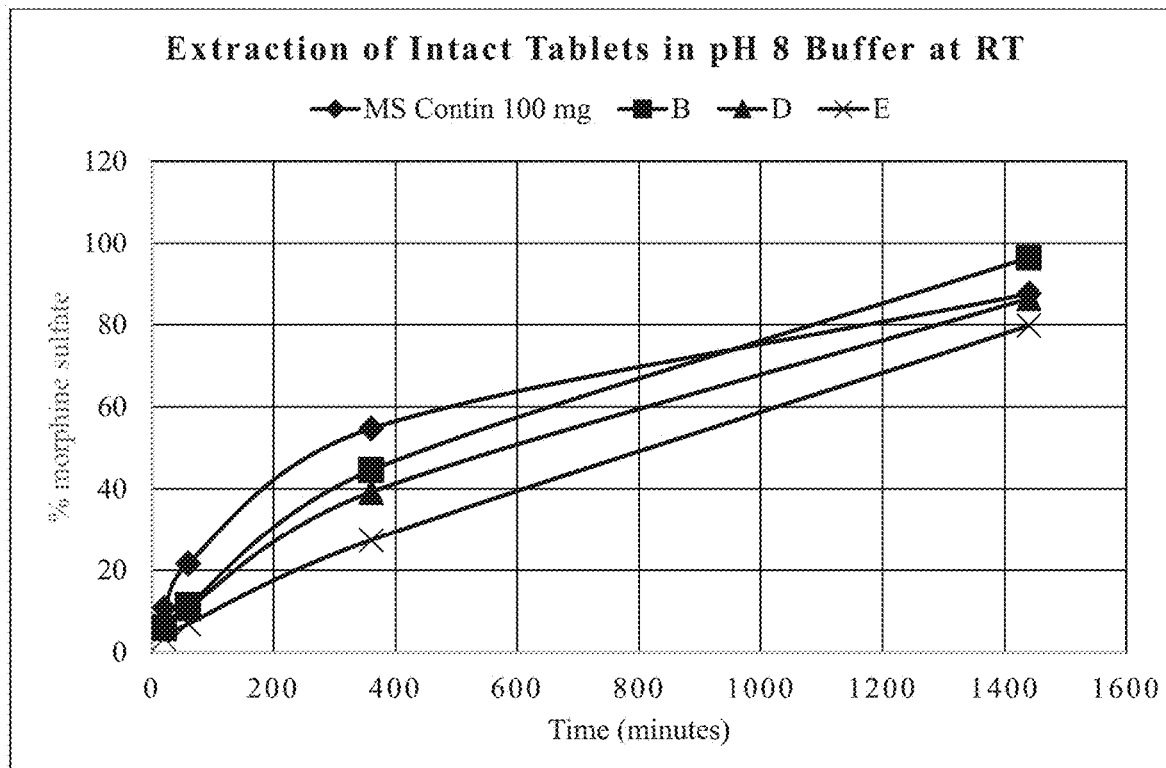
FIG. 49: Extraction of Intact Tablets in pH 8 Buffer at RT
Figure 50:
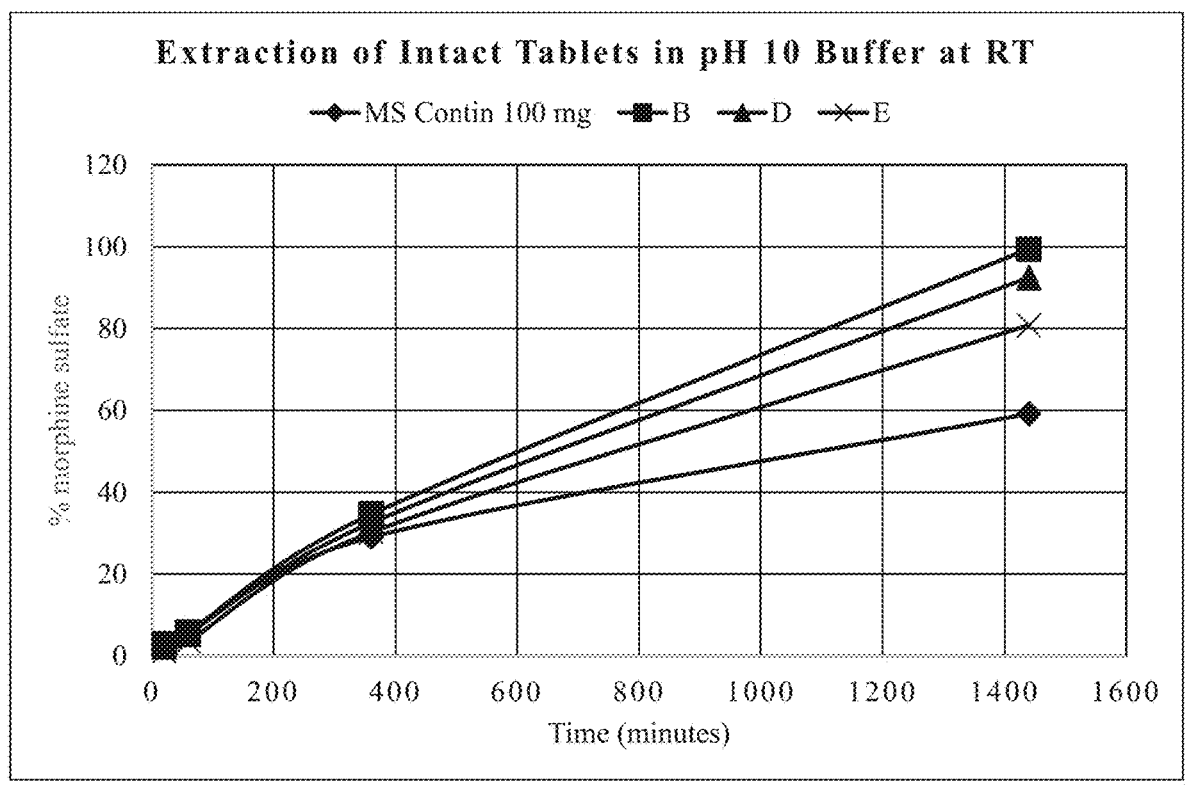
FIG. 50: Extraction of Intact Tablets in pH 10 Buffer at RT
Figure 51:
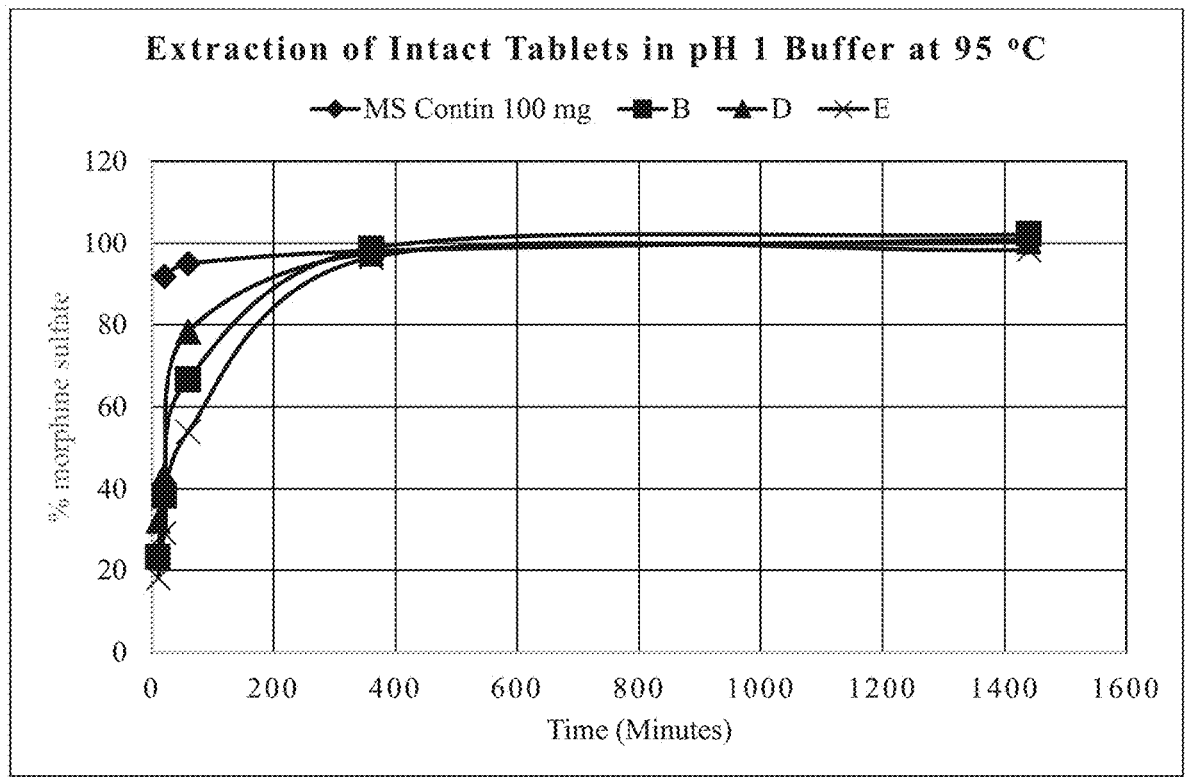
FIG. 51: Extraction of Intact Tablets in pH 1 Buffer at 95° C.
Figure 52:
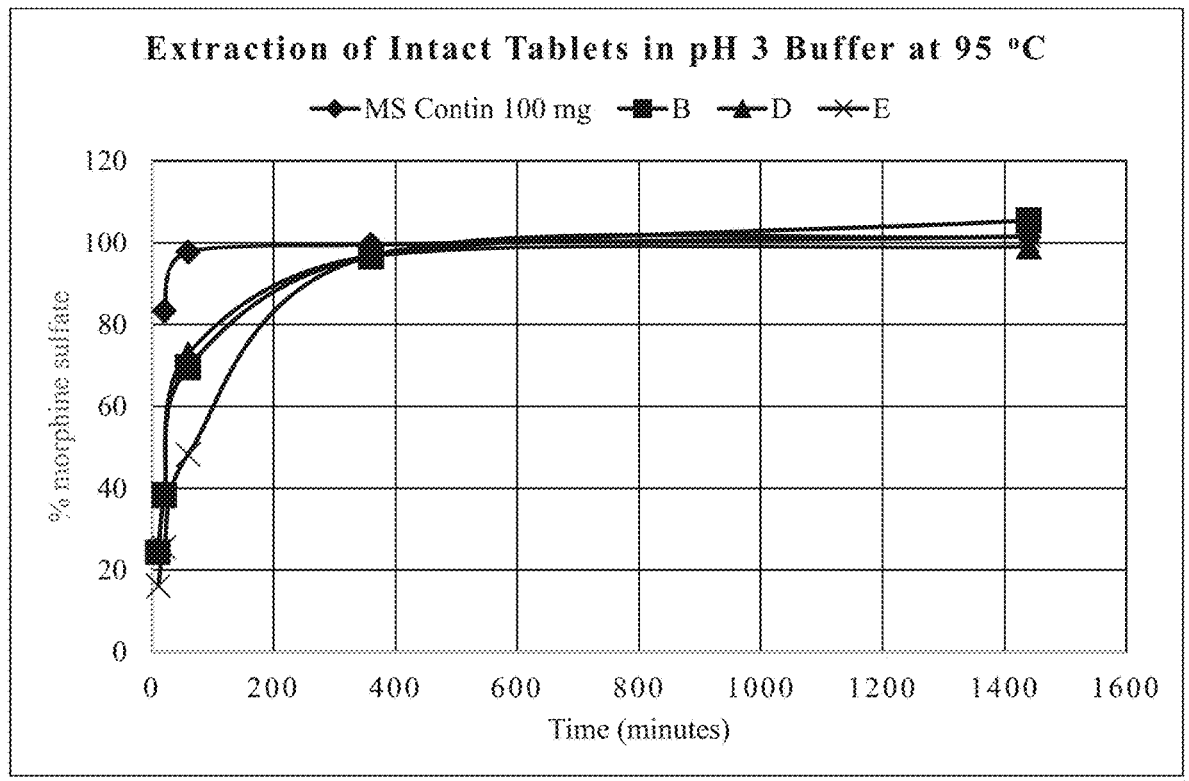
FIG. 52: Extraction of Intact Tablets in pH 3 Buffer at 95° C.
Figure 53:
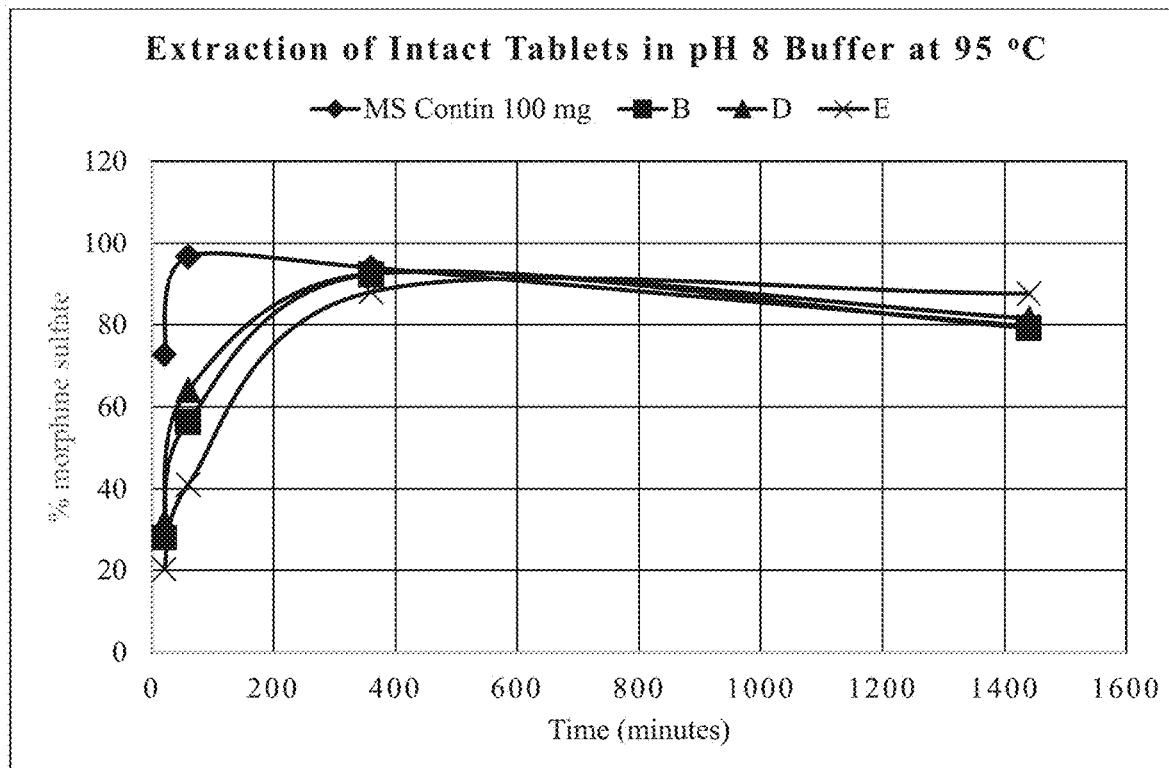
FIG. 53: Extraction of Intact Tablets in pH 8 Buffer at 95° C.
Figure 54:
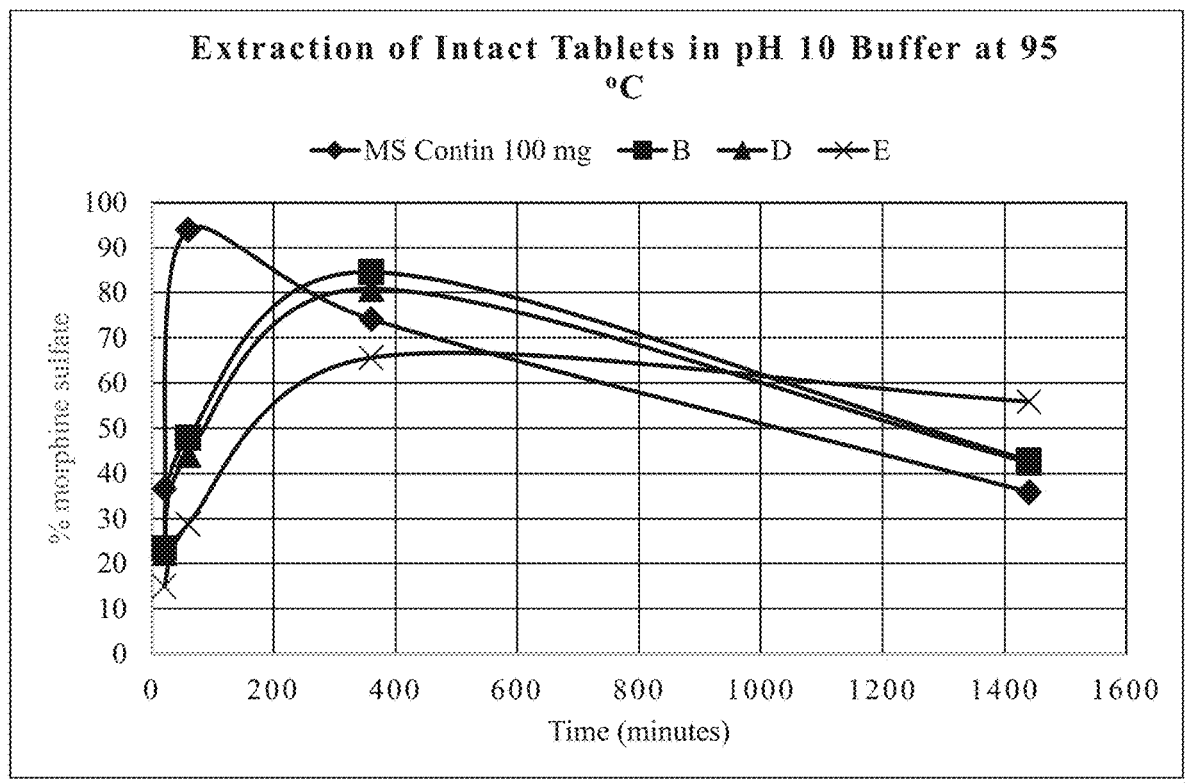
FIG. 54: Extraction of Intact Tablets in pH 10 Buffer at 95° C.
Figure 55:
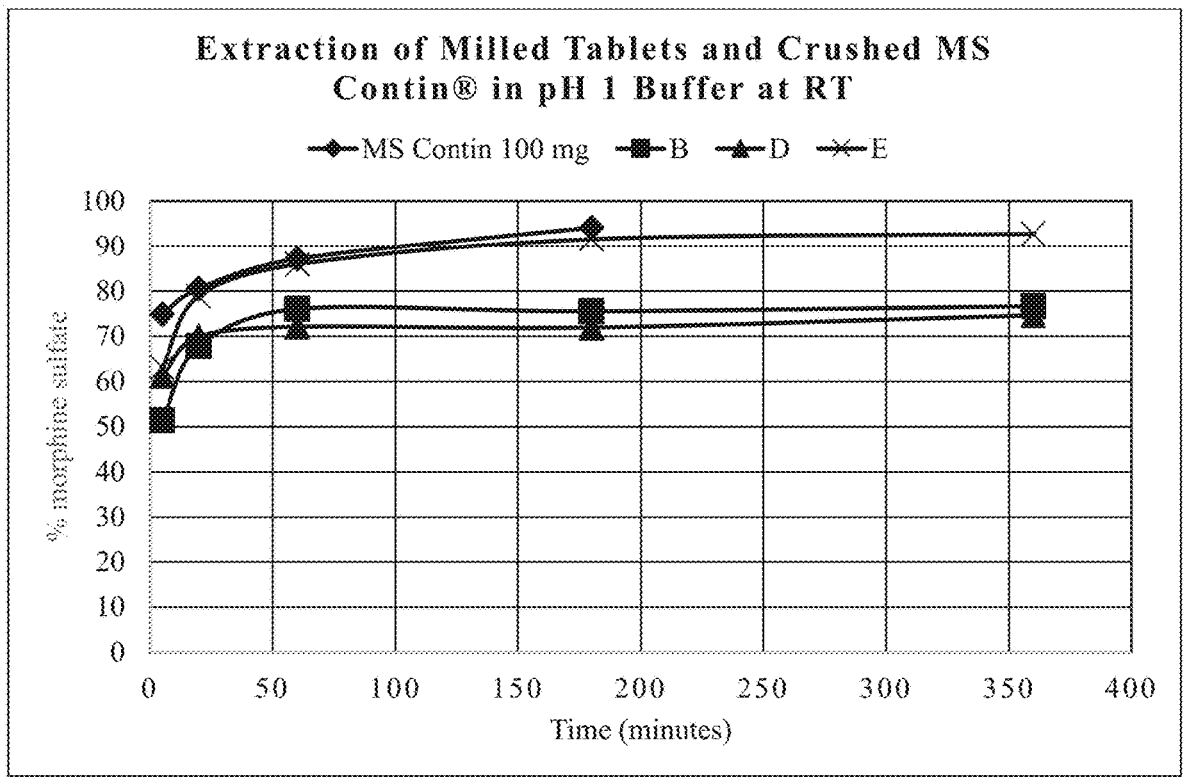
FIG. 55: Extraction of Milled Tablets and Crushed MS Contin® Tablets in pH 1 Buffer at RT
Figure 56:
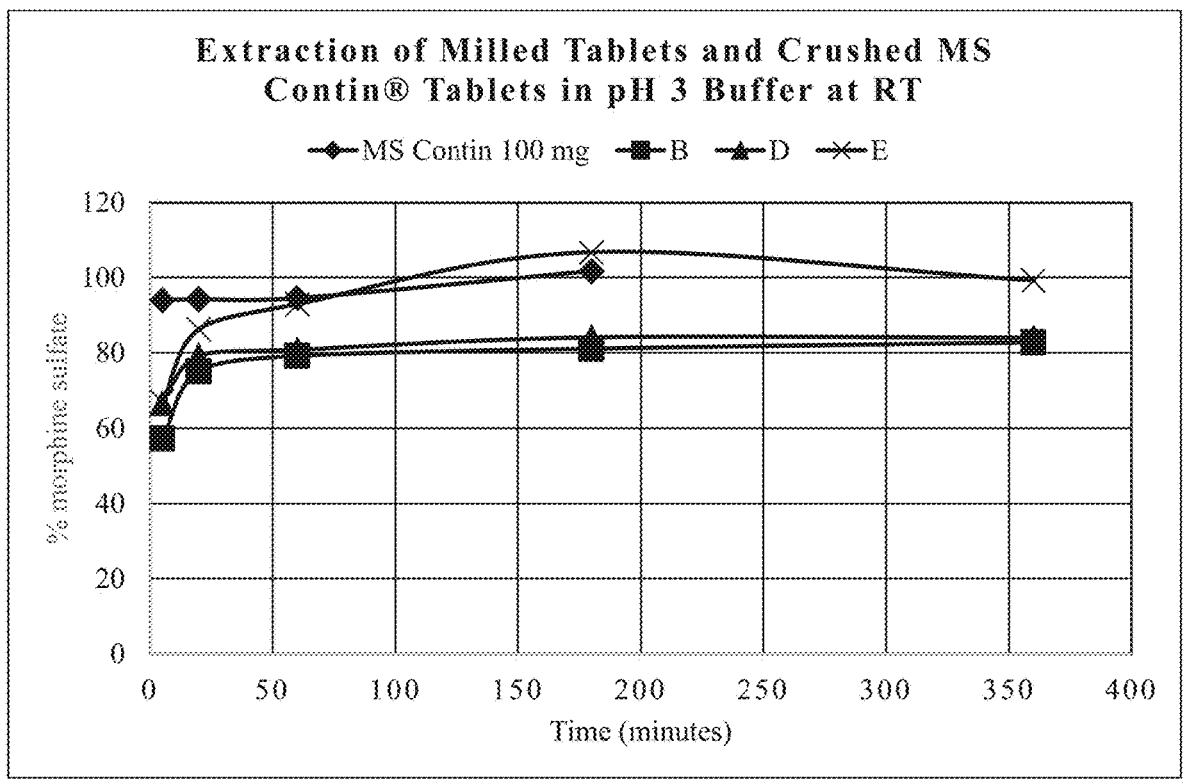
FIG. 56: Extraction of Milled Tablets and Crushed MS Contin® Tablets in pH 3 Buffer at RT
Figure 57:
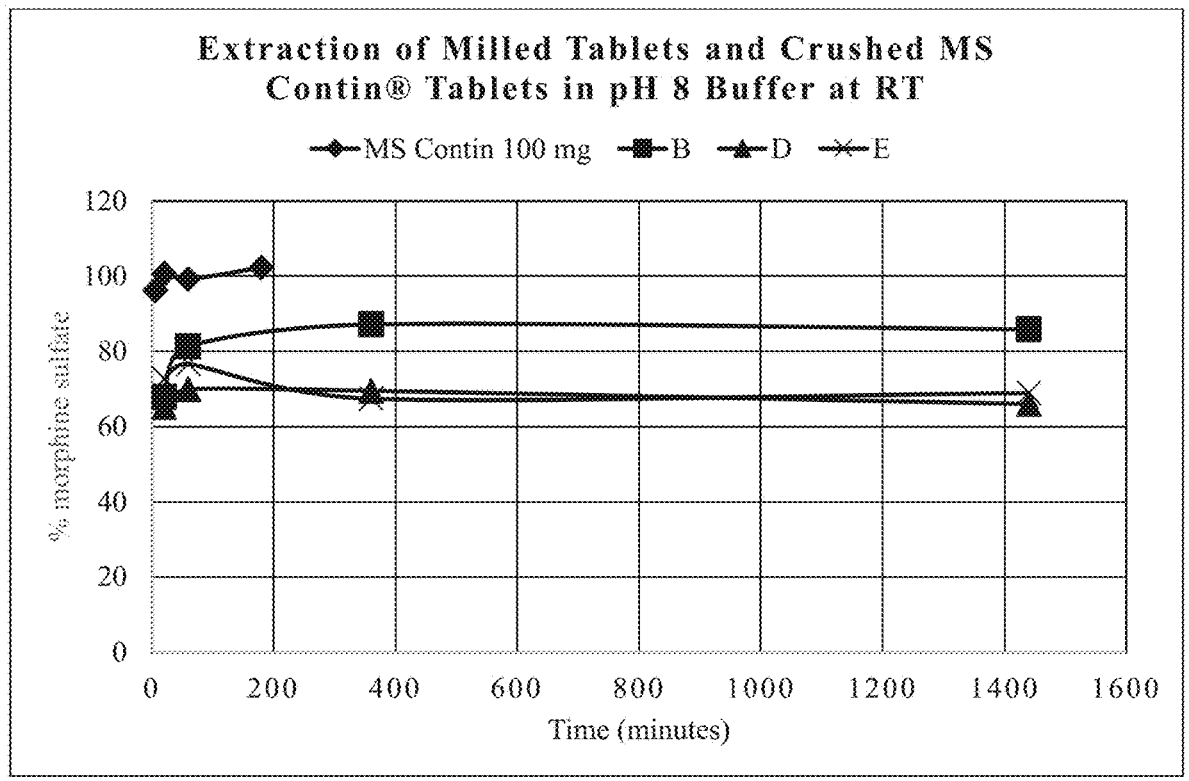
FIG. 57: Extraction of Milled Tablets and Crushed MS Contin® Tablets in pH 8 Buffer at RT
Figure 58:
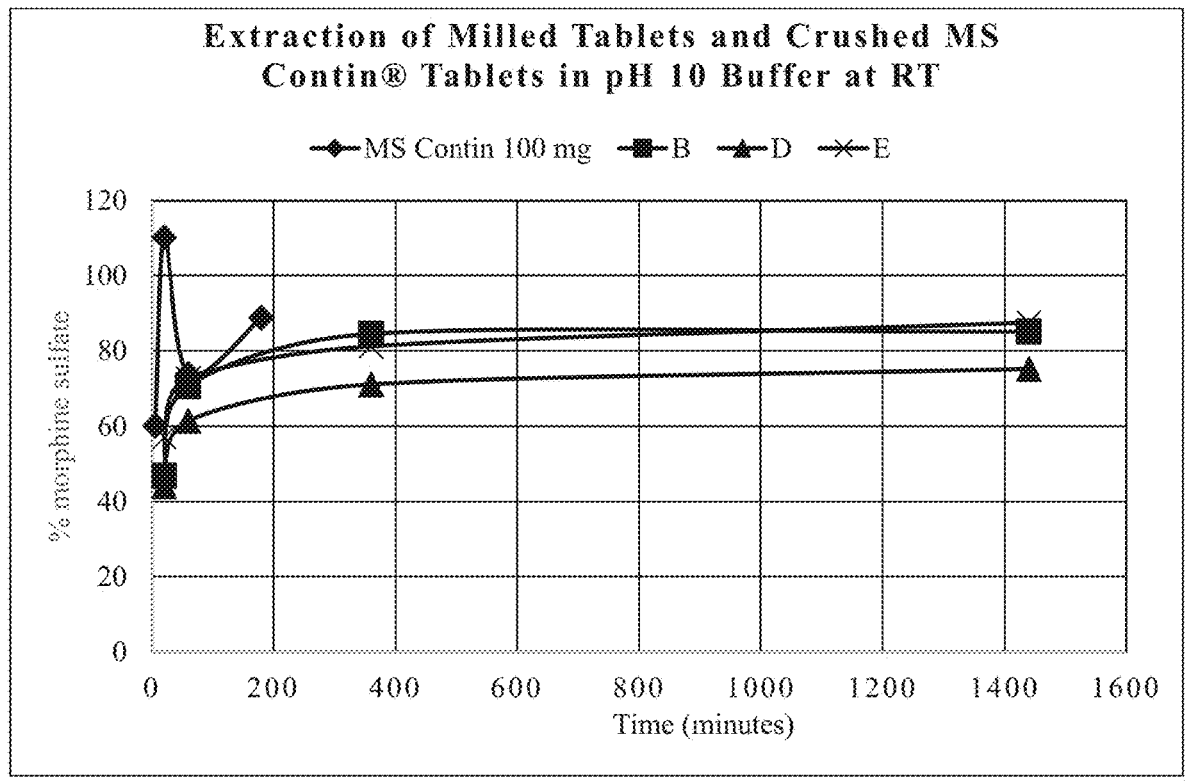
FIG. 58: Extraction of Milled Tablets and Crushed MS Contin® Tablets in pH 10 Buffer at RT
Figure 59:
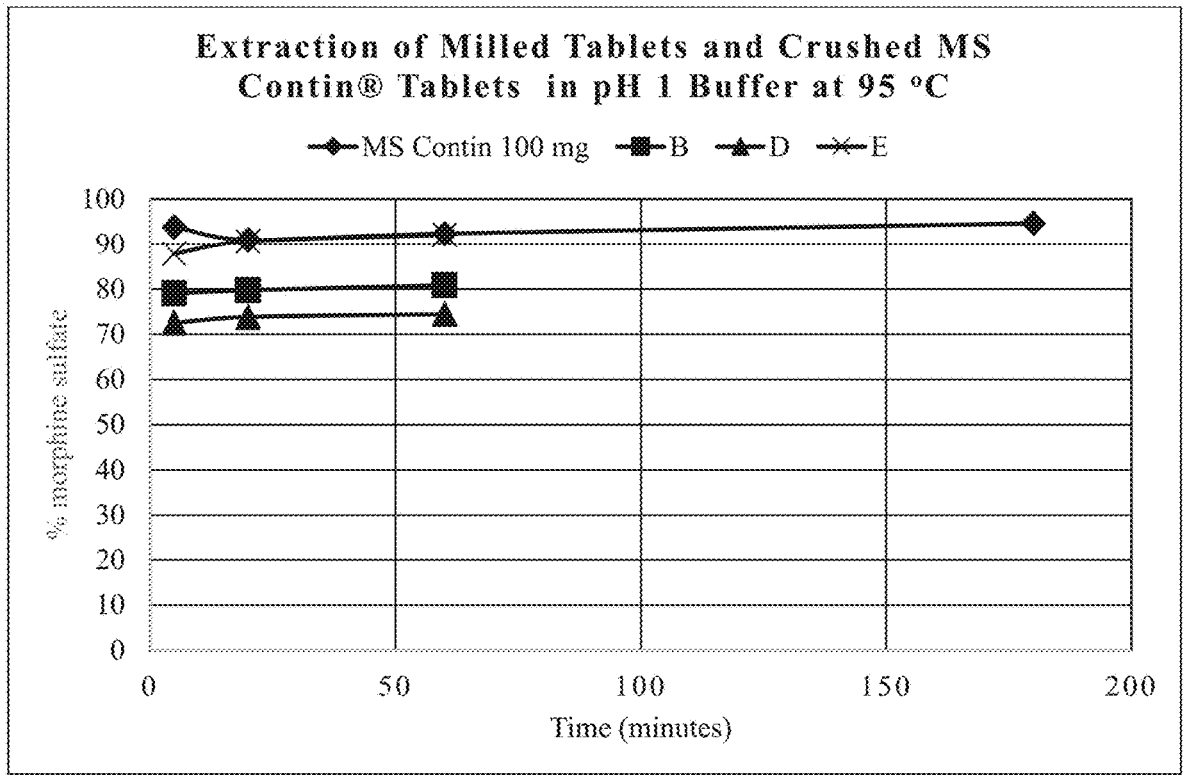
FIG. 59: Extraction of Milled Tablets and Crushed MS Contin® Tablets in pH 1 Buffer at 95° C.
Figure 60:
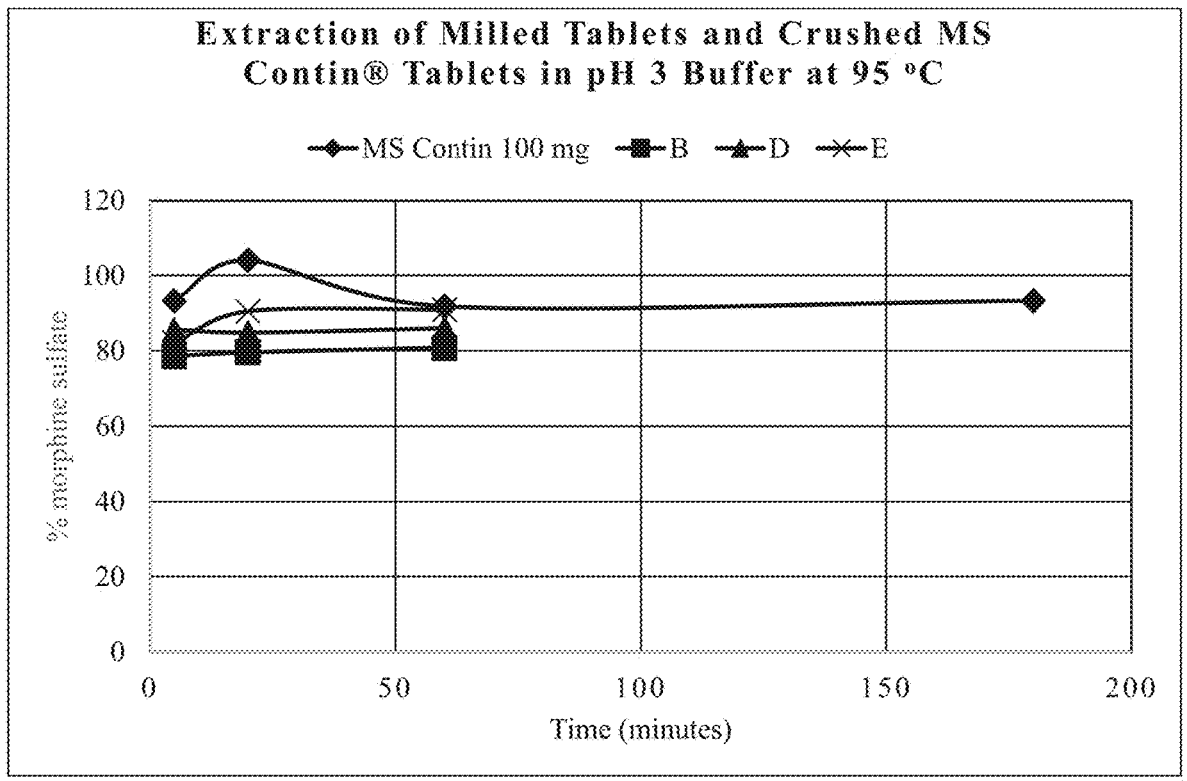
FIG. 60: Extraction of Milled Tablets and Crushed MS Contin® Tablets in pH 3 Buffer at 95° C.
Figure 61:
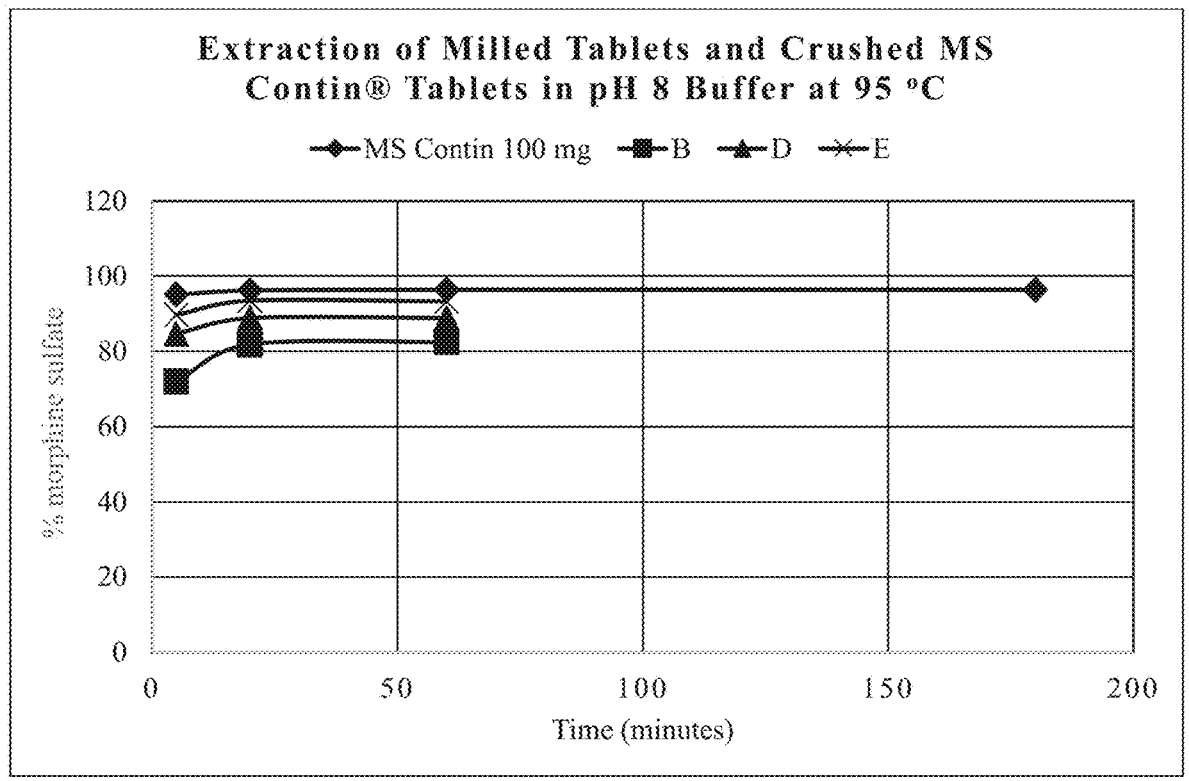
FIG. 61: Extraction of Milled Tablets and Crushed MS Contin® Tablets in pH 8 Buffer at 95° C.
Figure 62:
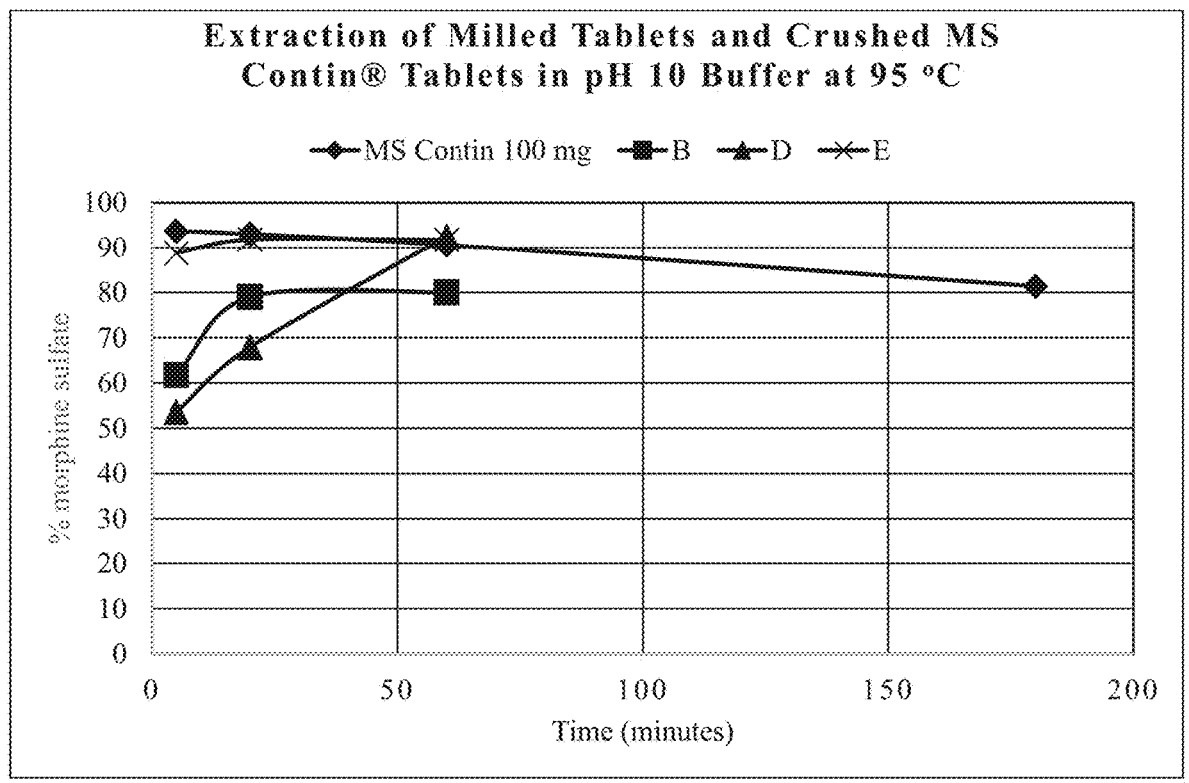
FIG. 62: Extraction of Milled Tablets and Crushed MS Contin® Tablets in pH 10 Buffer at 95° C.
Figure 63:
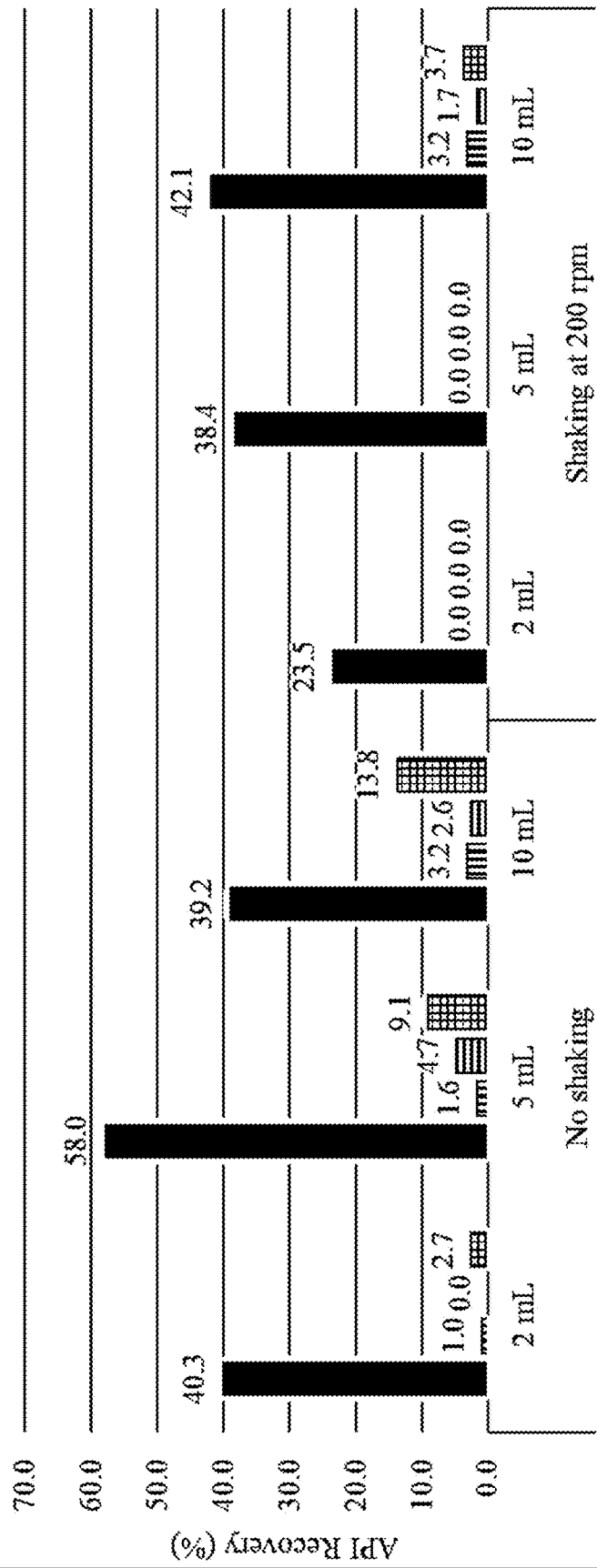
FIG. 63: Syringeability Test: Morphine Recovered from Intact Samples in RT Water after 24 Hours
Figure 64:
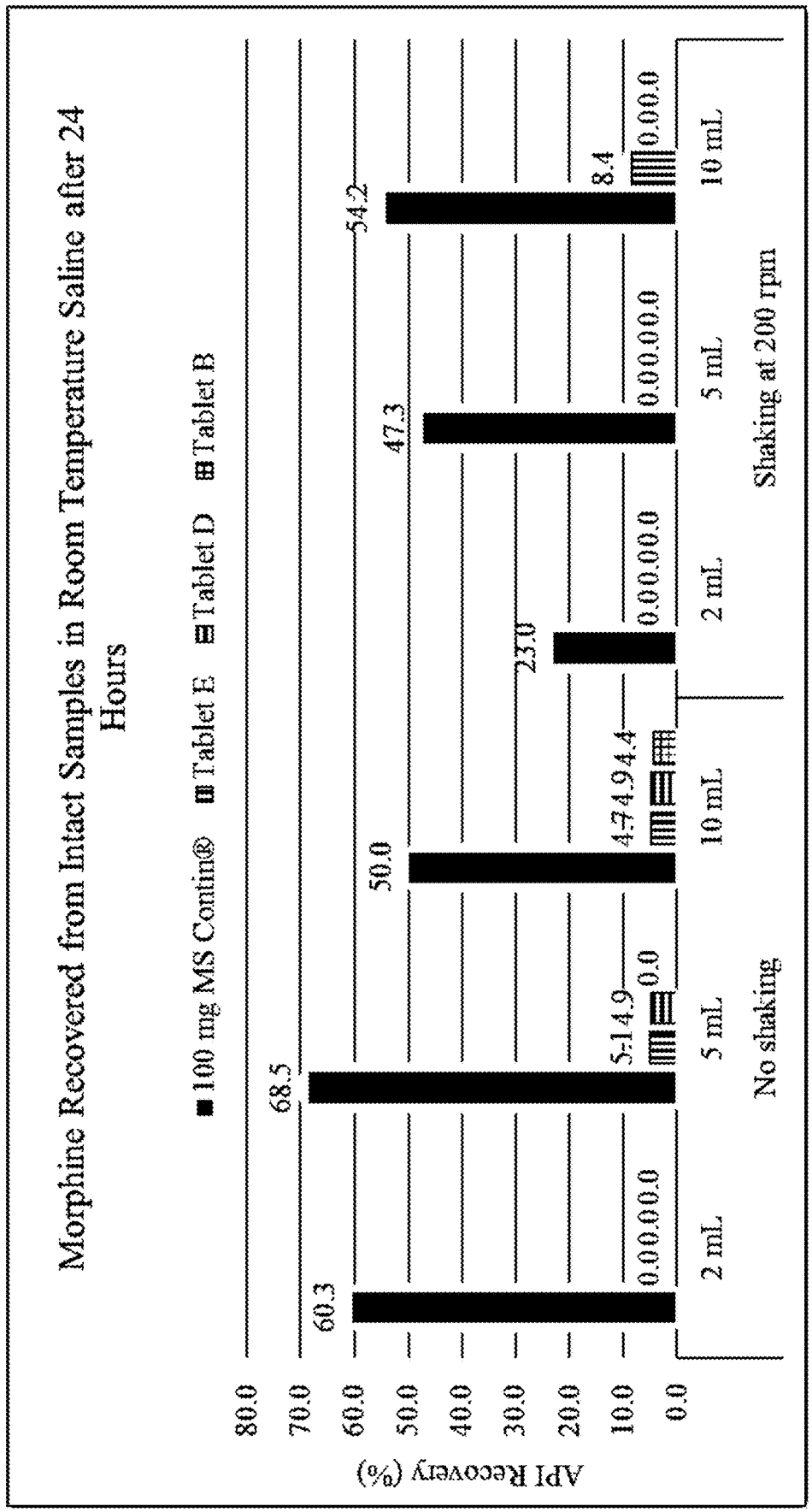
FIG. 64: Syringeability Test: Morphine Recovered from Intact Samples in RT Saline after 24 Hours
Figure 65:
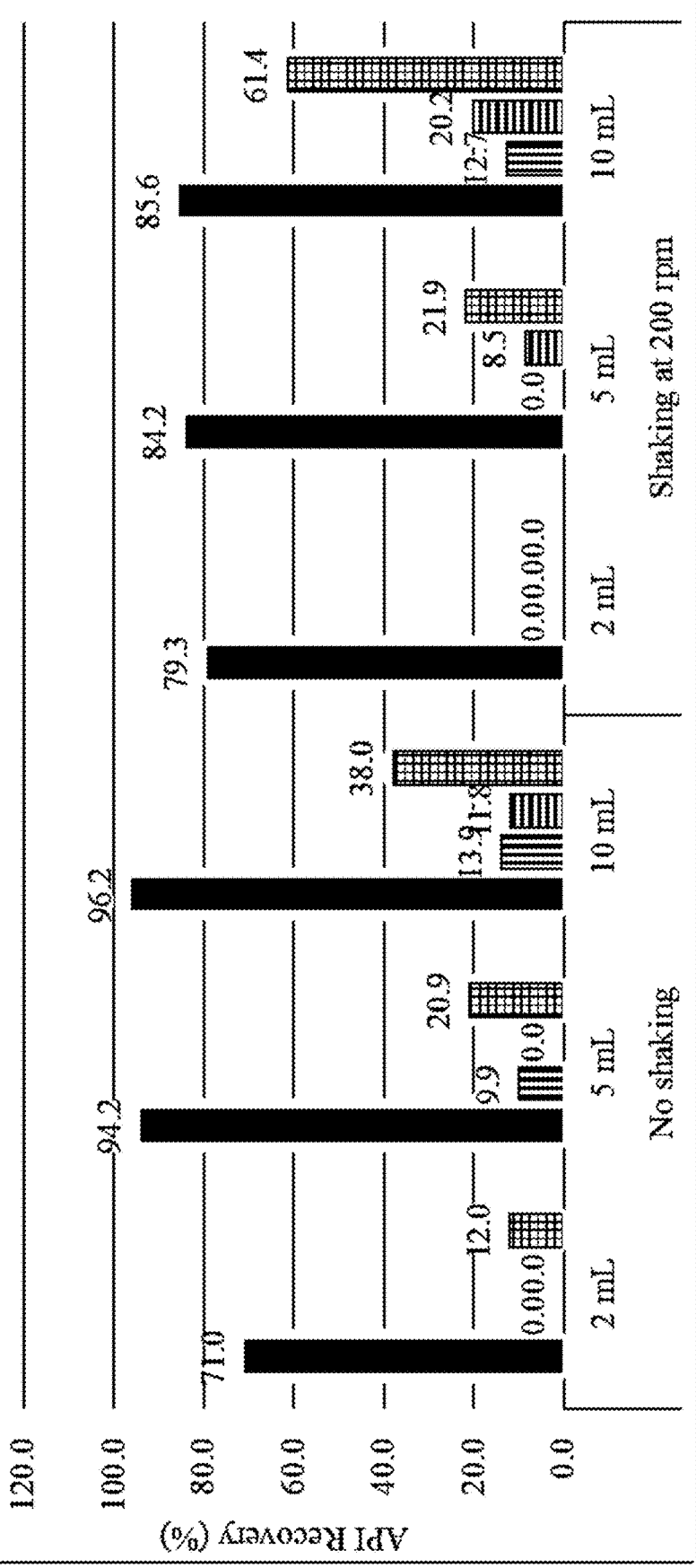
FIG. 65: Syringeability Test: Morphine Recovered from Intact Samples in 90° C. Water after 24 Hours
Figure 66:
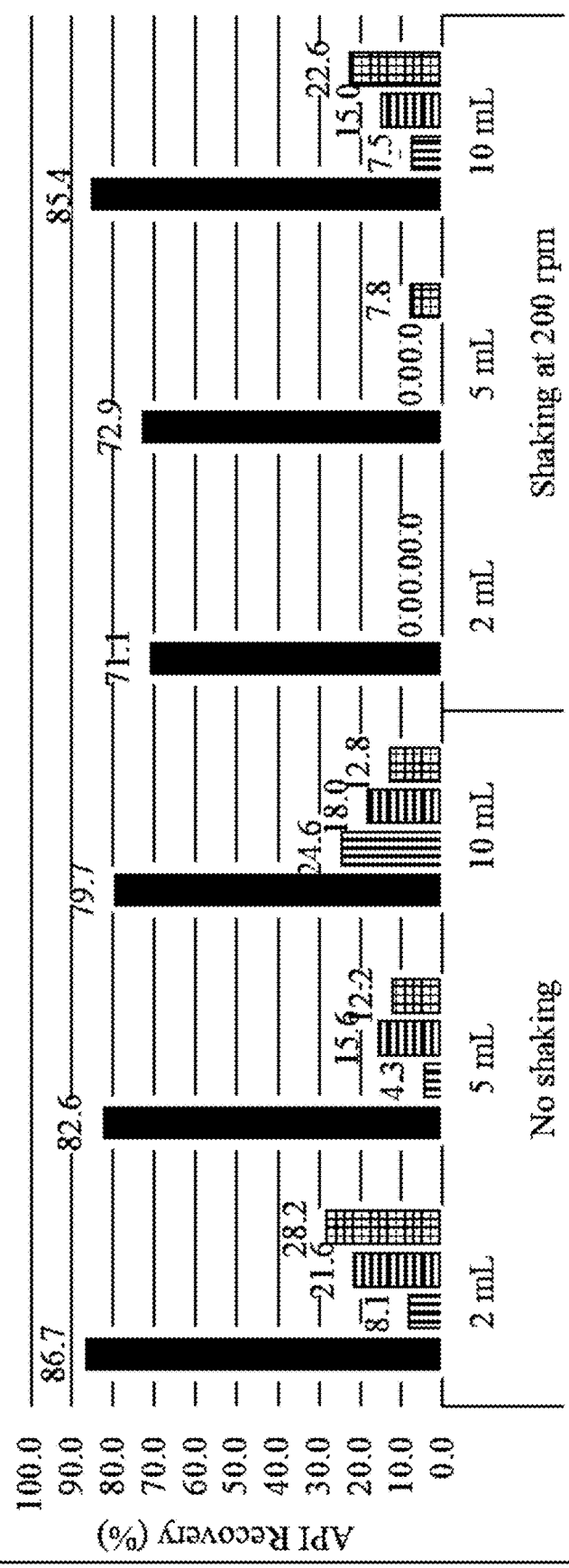
FIG. 66: Syringeability Test: Morphine Recovered from Intact Samples in 90° C. Saline after 24 Hours
Figure 67:
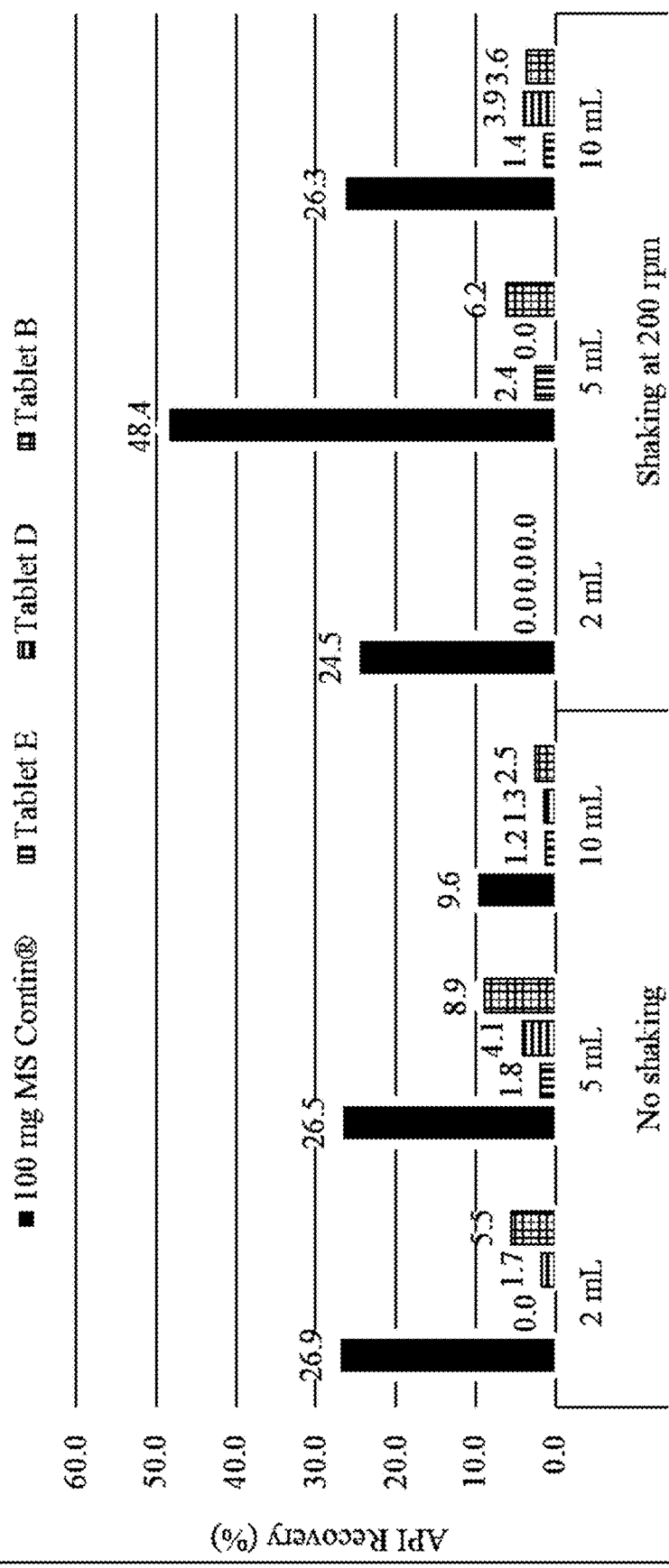
FIG. 67: Syringeability Test: Morphine Recovered from Sliced Samples in RT Water after 30 Minutes
Figure 68:
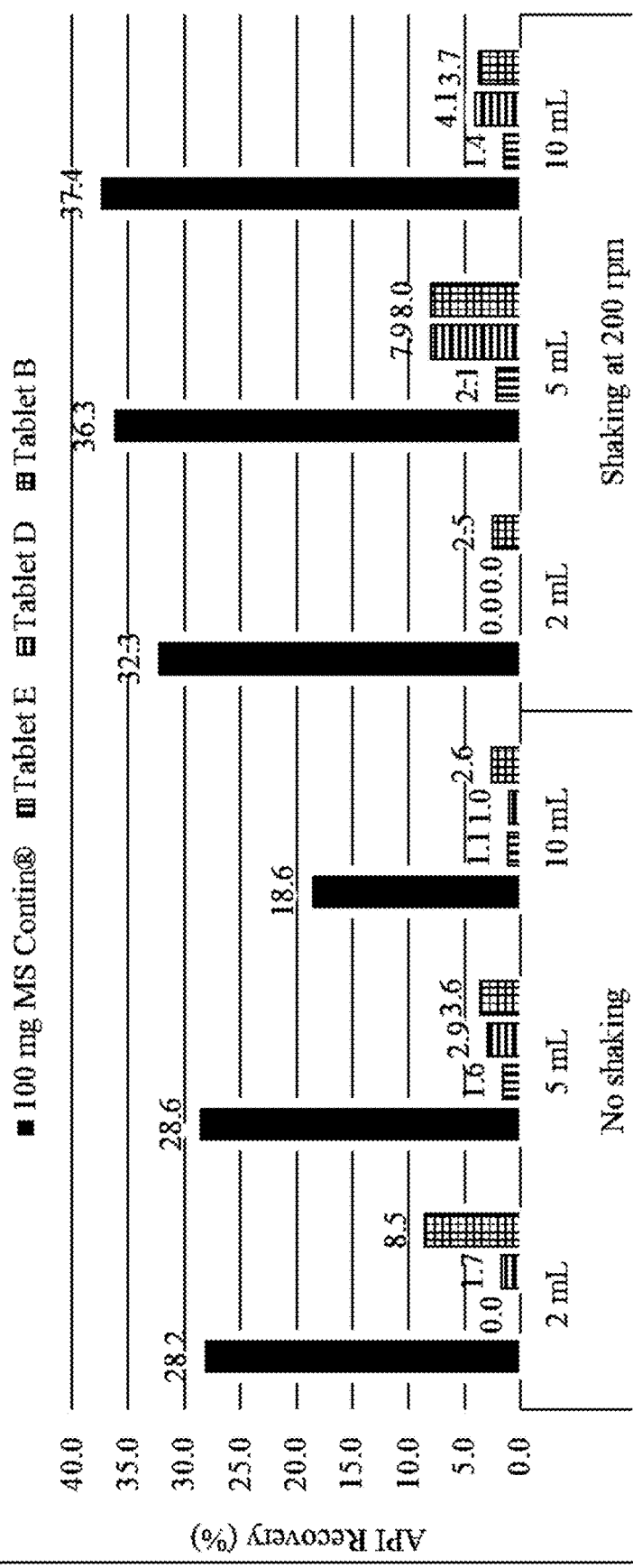
FIG. 68: Syringeability Test: Morphine Recovered from Sliced Samples in RT Saline after 30 Minutes
Figure 69:
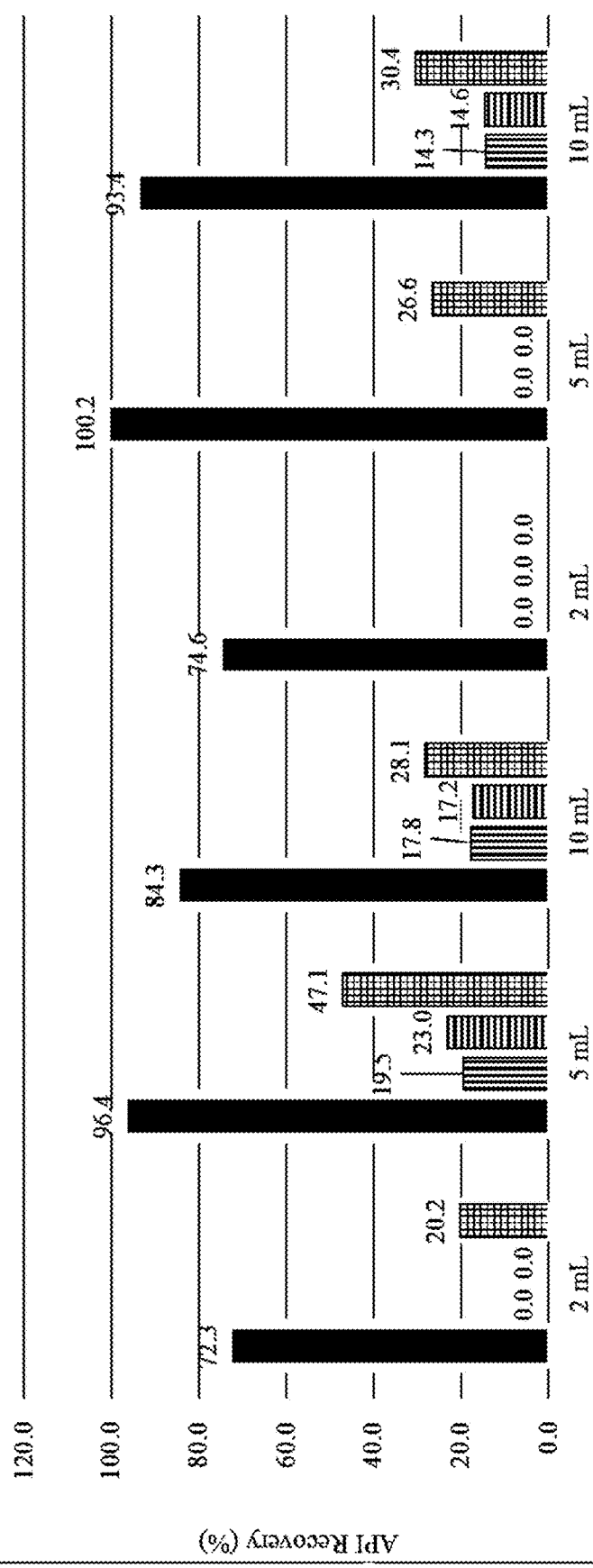
FIG. 69: Syringeability Test: Morphine Recovered from Sliced Samples in 90° C. Water after 30 Minutes
Figure 70:
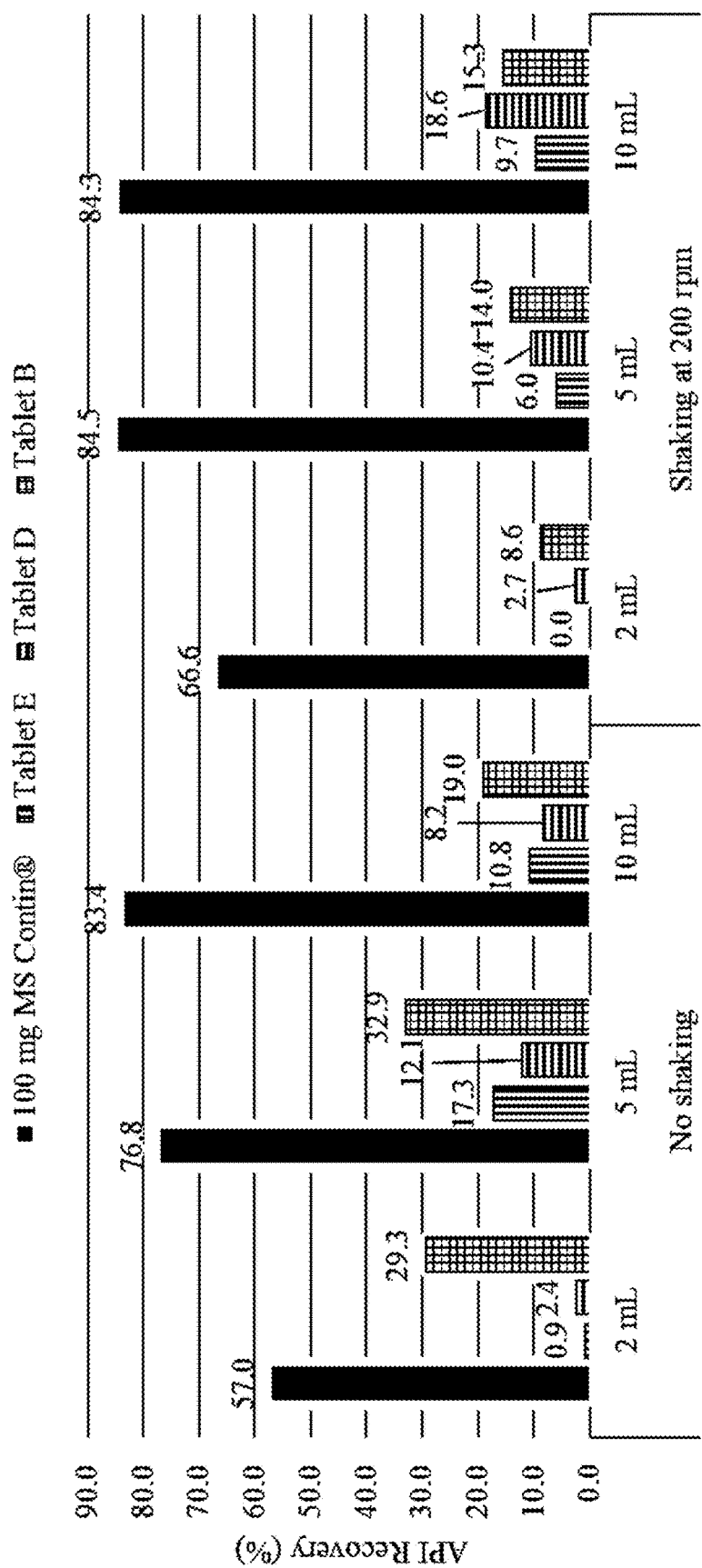
FIG. 70: Syringeability Test: Morphine Recovered from Sliced Samples in 90° C. Saline after 30 Minutes
Figure 71:
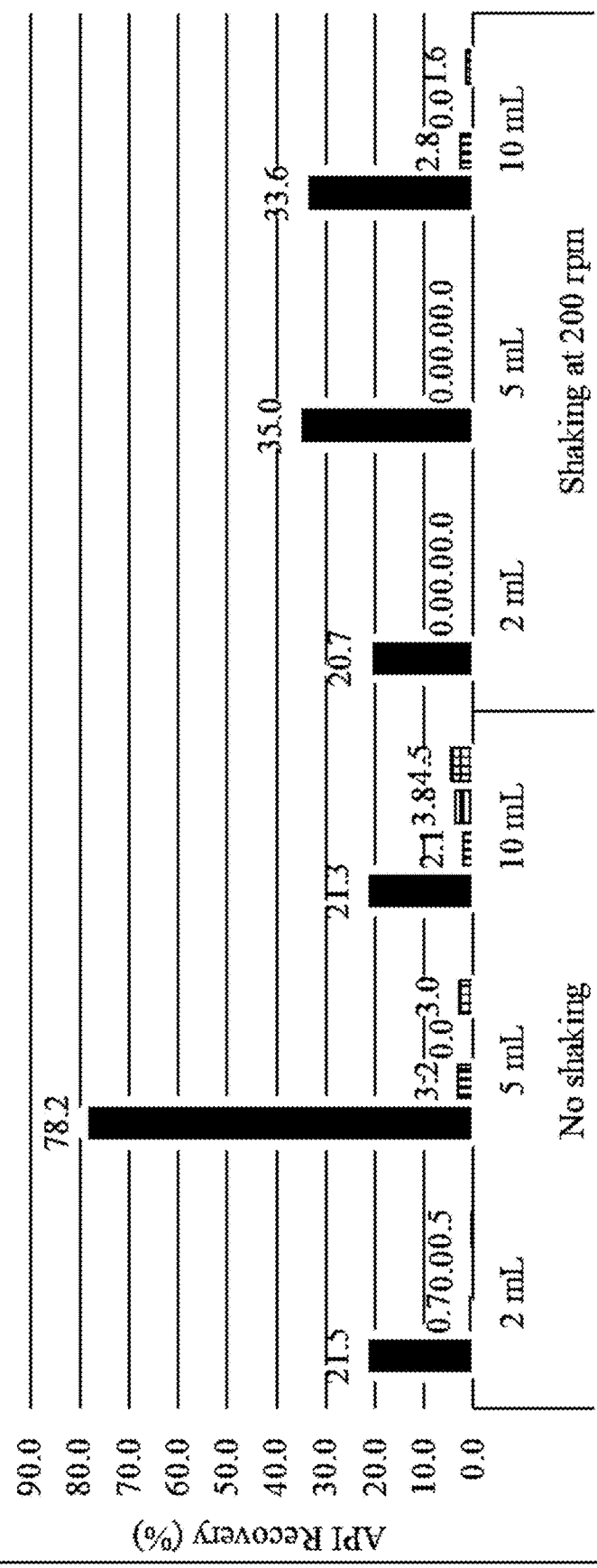
FIG. 71: Syringeability Test: Morphine Recovered from Milled Samples in RT Water at 30 Minutes
Figure 72:
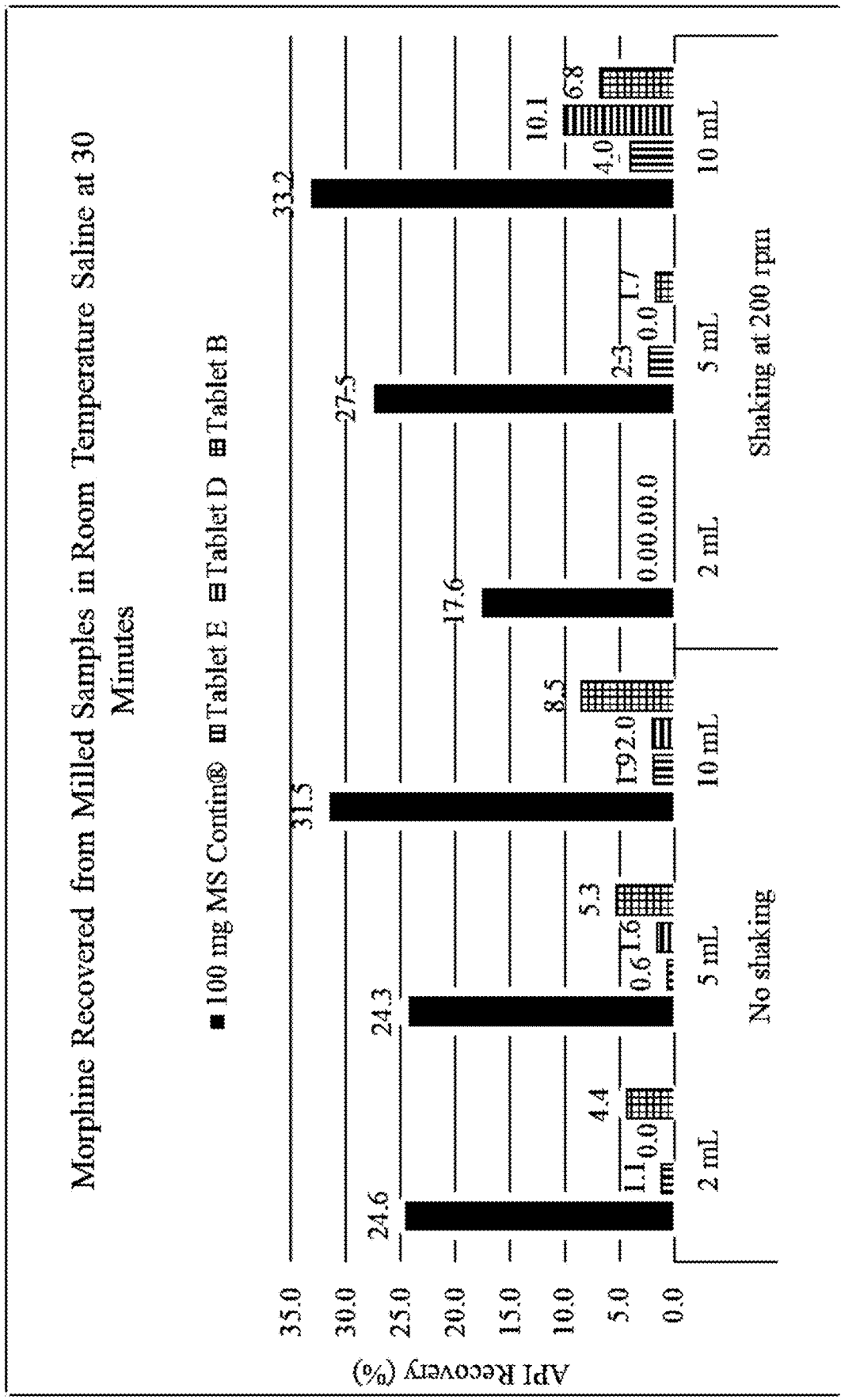
FIG. 72: Syringeability Test: Morphine Recovered from Milled Samples in RT Saline at 30 Minutes
Figure 73:
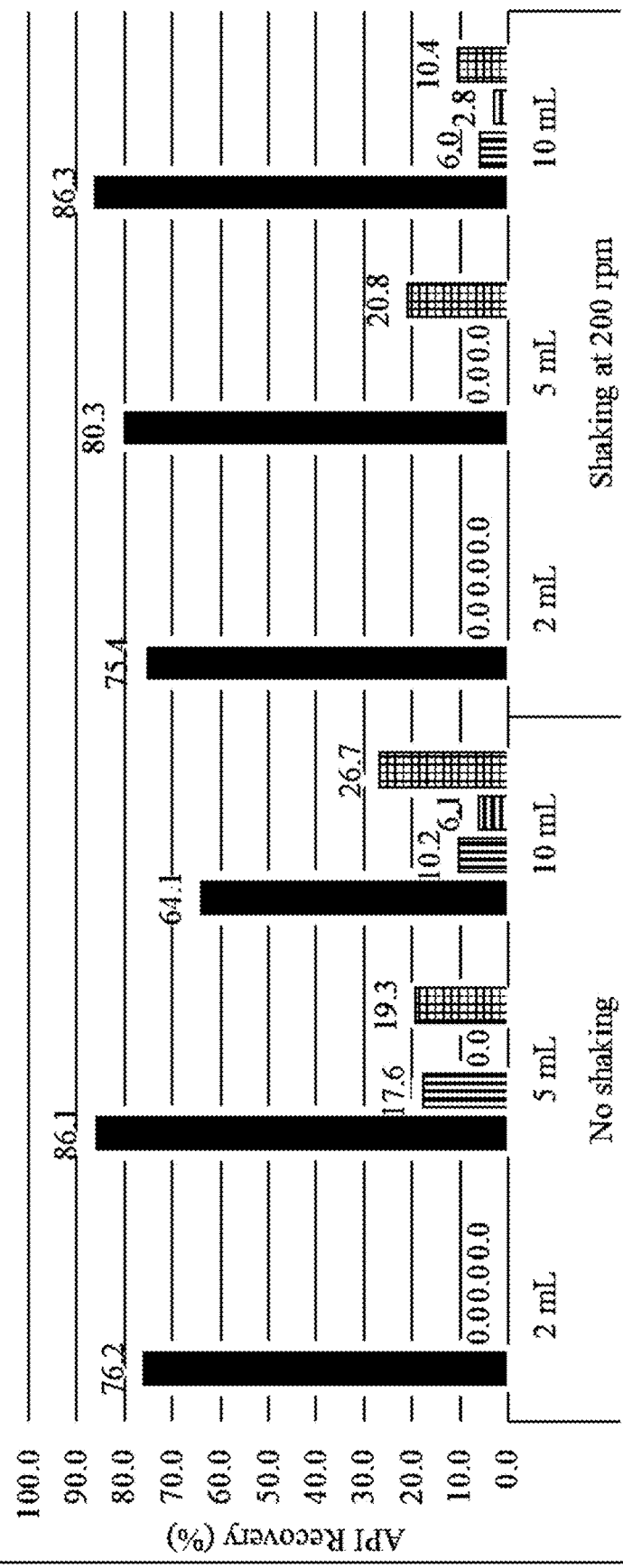
FIG. 73: Syringeability Test: Morphine Recovered from Milled Samples in 90° C. Water at 30 Minutes
Figure 74:
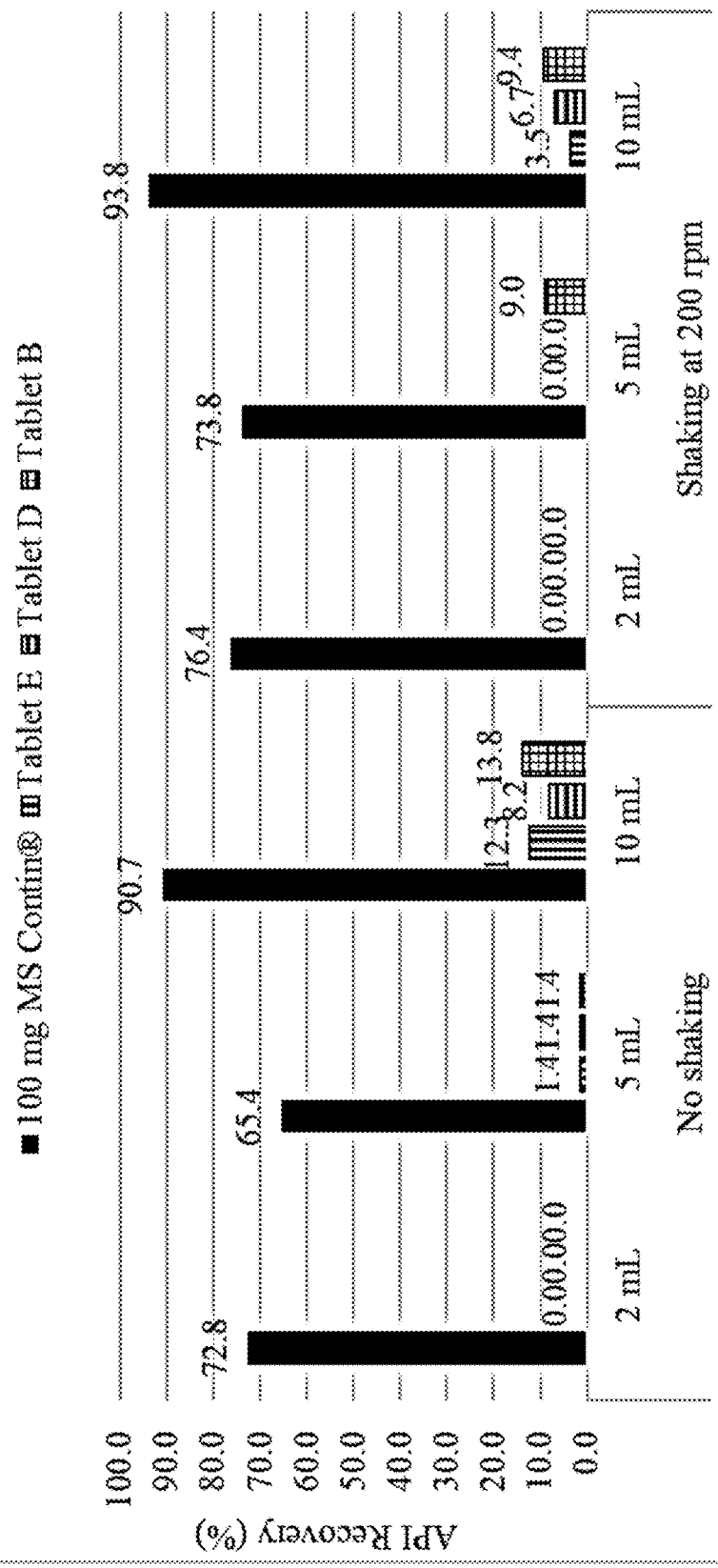
FIG. 74: Syringeability Test: Morphine Recovered from Milled Samples in 90° C. Saline at 30 Minutes

The average percentage recovery for extraction of morphine sulfate from milled tablets B, D and E and crushed 100 mg MS Contin® tablets at 50° C. in organic solvents are given in Table 11.9 (see FIG. 44, FIG. 45 and FIG. 46 respectively).

TABLE 11.9

Extraction of morphine sulfate from milled and crushed tablets in organic solvents at 50° C.

| Sample 50° C. | Solvent | 5 minutes | 20 minutes | 60 minutes (1 hr) | 180 minutes (3 hrs) | 360 minutes (6 hrs) | 1440 minutes (24 hrs) |
|---|---|---|---|---|---|---|---|
| MS Contin® 100 mg | Methanol | 77.7 | 85.3 | 92.6 | 97.3 | NA | NA |
|  | 40% Ethanol | 95.2 | 97.7 | 97.8 | 98.6 | NA | NA |
|  | 95% Ethanol | 66.6 | 92.5 | 97.1 | 98.9 | NA | NA |
| B | Methanol | 66.2 | 74.3 | 79.1 | NA | 80.4 | 112.2 |
|  | 40% Ethanol | 59.5 | 80 | 82.7 | NA | 84.6 | 95.5 |
|  | 95% Ethanol | 40.1 | 64.2 | 75.2 | NA | 79.8 | 93.7 |
| D | Methanol | 62.3 | 65.1 | 71.5 | NA | 76.0 | 97.9 |
|  | 40% Ethanol | 61.6 | 78.3 | 84.1 | NA | 85.3 | 101.3 |
|  | 95% Ethanol | 42.3 | 55.1 | 63.9 | NA | 71.8 | 83.6 |
| E | Methanol | 70.4 | 75.7 | 81.7 | NA | 92.4 | 121.7 |
|  | 40% Ethanol | 54.5 | 79.9 | 87.5 | NA | 90.8 | 110.9 |
|  | 95% Ethanol | 43.2 | 47.9 | 51.7 | NA | 69.2 | 98.4 |

Extraction tests were carried out at 25° C. with intact tablets in buffers of pH 1, 3, 8 and 10 using 0.1 N HCl (pH 1) and pH 3, 8, and 10 buffers (as per USP).

The average percentage recovery results from tablets B, D and E and 100 mg MS Contin® intact tablets in buffer solutions are given in Table 11.10 (see FIG. 47, FIG. 48, FIG. 49 and FIG. 50 respectively).

TABLE 11.10

Extraction of morphine sulfate from intact tablets in buffer solutions at room temperature

| Sample 25° C. | Buffer pH | 20 minutes | 60 minutes (1 hr) | 360 minutes (6 hrs) | 1440 minutes (24 hrs) |
|---|---|---|---|---|---|
| MS Contin® 100 mg | 1 | 20.2 | 32.7 | 79.3 | 97.7 |
|  | 3 | 12.2 | 25.2 | 66.2 | 103.4 |
|  | 8 | 10.8 | 21.6 | 54.7 | 87.6 |
|  | 10 | 3.1 | 5.8 | 29.1 | 59.2 |
| B | 1 | 10.3 | 16.9 | 54.7 | 96.4 |
|  | 3 | 7.5 | 15.2 | 54.9 | 100.9 |
|  | 8 | 6.1 | 11.4 | 44.5 | 96.4 |
|  | 10 | 2.9 | 5.7 | 34.7 | 99.4 |
| D | 1 | 8.9 | 14 | 42.2 | 90.6 |
|  | 3 | 6 | 12 | 42.8 | 93 |
|  | 8 | 5.8 | 10.7 | 39.2 | 86.4 |
|  | 10 | 2.2 | 5.3 | 32.6 | 92.4 |
| E | 1 | 6.6 | 10.8 | 36.6 | 92.6 |
|  | 3 | 5 | 10.4 | 40.3 | 97.3 |
|  | 8 | 3.4 | 6.9 | 27.4 | 79.8 |
|  | 10 | 1.3 | 3.5 | 30.3 | 80.8 |

Extraction tests were carried out at 95° C. with intact tablets in the same buffers of pH 1, 3, 8 and 10. The average percentage recovery results from tablets B, D and E and 100 mg MS Contin® intact tablets in these buffers are given in Table 11.11 (see FIG. 51, FIG. 52 FIG. 53 and FIG. 54 respectively).

TABLE 11.11

Extraction of morphine sulfate from intact tablets in buffer solutions at 95° C.

| Sample 95° C. | Buffer pH | 10 minutes | 20 minutes | 60 minutes (1 hr) | 360 minutes (6 hrs) | 1440 minutes (24 hrs) |
|---|---|---|---|---|---|---|
| MS Contin® 100 mg | 1 | NA | 91.8 | 94.9 | 98 | 101 |
|  | 3 | NA | 83.3 | 97.7 | 99.6 | 101.5 |
|  | 8 | NA | 72.7 | 96.6 | 93.9 | 79.6 |
|  | 10 | NA | 36.6 | 94 | 74.1 | 35.9 |
| B | 1 | 23.2 | 38.3 | 66.7 | 98.7 | 102.2 |
|  | 3 | 24.4 | 38.4 | 69.5 | 96.6 | 105.5 |
|  | 8 | NA | 28 | 56.3 | 92.3 | 79.2 |
|  | 10 | NA | 23.4 | 47.9 | 84.5 | 42.9 |
| D | 1 | 32 | 43.5 | 78.3 | 97.4 | 100.3 |
|  | 3 | 24.7 | 38.5 | 72.8 | 96.6 | 99 |
|  | 8 | NA | 31.9 | 64.1 | 92.5 | 81.5 |
|  | 10 | NA | 22.3 | 44.1 | 80.8 | 42.4 |
| E | 1 | 18.1 | 29.1 | 53.9 | 96.4 | 98.2 |
|  | 3 | 16.1 | 25.5 | 48.3 | 96.7 | 101.7 |
|  | 8 | NA | 20.2 | 41 | 88 | 87.6 |
|  | 10 | NA | 15 | 28.8 | 65.6 | 55.9 |

Extraction tests were carried out at 25° C. (room temperature) with milled tablets and crushed 100 mg MS Contin® tablets in the same buffers of pH 1, 3, 8 and 10. The average percentage recovery results from milled tablets B, D and E and crushed MS Contin® tablets are given in Table 11.12 (see FIG. 55, FIG. 56, FIG. 57 and FIG. 58 respectively).

TABLE 11.12

Extraction of morphine sulfate from milled and crushed tablets in buffer solutions at room temperature

| Sample 25° C. | Buffer pH | 5 minutes | 20 minutes | 60 minutes (1 hr) | 180 minutes (3 hrs) | 360 minutes (6 hrs) | 1440 minutes (24 hrs) |
|---|---|---|---|---|---|---|---|
| MS Contin® 100 mg | 1 | 74.8 | 80.5 | 87.1 | 94.1 | NA | NA |
|  | 3 | 94 | 94.2 | 94.5 | 101.7 | NA | NA |
|  | 8 | 96.1 | 100.5 | 99.1 | 102.2 | NA | NA |
|  | 10 | 60.2 | 110.3 | 74 | 88.8 | NA | NA |
| B | 1 | 51.4 | 67.8 | 76 | 75.5 | 76.6 | NA |
|  | 3 | 57.3 | 75.1 | 79.2 | 81.1 | 82.8 | NA |
|  | 8 | NA | 67.9 | 81.2 | NA | 87.1 | 85.8 |
|  | 10 | NA | 46.9 | 70.7 | NA | 84.5 | 85.1 |
| D | 1 | 61.2 | 69.9 | 72.1 | 71.9 | 74.6 | NA |
|  | 3 | 66.7 | 79.2 | 80.8 | 84.1 | 84 | NA |
|  | 8 | NA | 65.2 | 69.9 | NA | 69.5 | 66 |
|  | 10 | NA | 44.2 | 61.4 | NA | 71.1 | 75.2 |
| E | 1 | 63.1 | 78.9 | 85.9 | 91.5 | 92.7 | NA |
|  | 3 | 67 | 86.2 | 92.9 | 106.7 | 99.2 | NA |
|  | 8 | NA | 72.7 | 76.6 | NA | 67.4 | 68.9 |
|  | 10 | NA | 57.2 | 72.6 | NA | 81.2 | 87.5 |

Extraction tests were carried out at 95° C. with milled tablets and crushed 100 mg MS Contin® tablets in buffers of pH 1, 3, 8 and 10. The average percentage recovery results from milled tablets B, D and E and crushed 100 mg MS Contin® tablets are given in Table 11.13 (see FIG. 59, FIG. 60, FIG. 61 and FIG. 62 respectively).

TABLE 11.13

Extraction of morphine sulfate from milled and crushed tablets in buffer solutions at 95° C.

| Sample 95° C. | Buffer pH | 5 minutes | 20 minutes | 60 minutes (1 hr) | 180 minutes (3 hrs) |
|---|---|---|---|---|---|
| MS Contin ® | 1 | 93.8 | 90.9 | 92.3 | 94.6 |
| 100 mg | 3 | 93.3 | 104 | 91.8 | 93.3 |
|  | 8 | 95 | 96.1 | 96.3 | 96.3 |
|  | 10 | 93.7 | 93 | 90.6 | 81.4 |
| B | 1 | 79 | 79.7 | 80.8 | NA |
|  | 3 | 78.6 | 79.6 | 80.8 | NA |
|  | 8 | 72 | 81.8 | 82.4 | NA |
|  | 10 | 61.8 | 79 | 80 | NA |
| D | 1 | 72.5 | 73.8 | 74.4 | NA |
|  | 3 | 85.6 | 84.8 | 86 | NA |
|  | 8 | 84.6 | 88.8 | 88.8 | NA |
|  | 10 | 53.6 | 67.9 | 92.4 | NA |
| E | 1 | 87.8 | 90.6 | 92 | NA |
|  | 3 | 82.1 | 90.5 | 90.9 | NA |
|  | 8 | 89.6 | 93.4 | 93.2 | NA |
|  | 10 | 88.8 | 91.8 | 91.7 | NA |

This extraction study demonstrates that the rate of extraction of morphine sulfate in all solvents was related to particle size and temperature. The extraction results for intact tablets B, D and E using a wide range of solvents at both temperature conditions (25° C. and 95° C.) demonstrated the abuse deterrent properties of tablets according to the present invention. Intact MS Contin® generally showed faster extraction than intact tablets B, D and E at both temperature conditions. The effect is particularly pronounced e.g. in alcoholic solvents at elevated temperature, such as in 40% ethanol, see FIGS. 39 and 40. It can be seen that MS Contin® releases the active agent very fast and does not show controlled release any more. In contrast, the tablets according to the present invention still maintain controlled release properties, even under conditions of elevated temperature and after having been manipulated.

MS Contin® tablets can easily be crushed to a fine powder using a mortar and pestle. However, the tablets according to the present invention are hard to crush; therefore electric grinders (coffee grinder, spice grinder or mill) are required to reduce these tablets to powders. Crushing or milling the tablets into powder increased the extraction rates as expected. This is due to an increase in surface area of milled tablets, leading to greater exposure to solvent.

As expected, higher temperature showed further increase in the extraction rate of crushed/milled tablets. The extraction rate of milled tablets of this invention is slow compared to the crushed 100 mg MS Contin® reference tablets.

Physical Manipulation Tests

Example 12

Physical manipulation of morphine sulfate tablets B, D and E as compared to 100 mg MS Contin® tablets were evaluated using spoons, pill crusher, food grater, foot file, razor blade, mortar/pestle, hammer, spice grinder, coffee grinder and mill. The conditions used in each test are detailed in Table 12.1.

TABLE 12.1

| Device and Testing Condition | |
|---|---|
| Device and Brand | Condition |
| Spoons - Winco ®, 18/0 stainless steel teaspoons | The tablet was placed between two spoons and crushed for up to 5 minutes or until a reasonably fine powder was obtained, whichever came first. |
| Pill crusher - Life Brand | The crusher cup was opened and the tablet was placed inside. The crusher cup was replaced and the crusher cup was turned as far as possible without breaking the crusher. The crusher cup was opened, and the crushed tablet was collected. |
| Food grater - Microplane ®, stainless steel blade, 5100506, 18/8 gauge | The tablet was grated for up to 5 minutes or until a reasonably fine powder was obtained, whichever came first. |
| Foot file - Ultra Pedi Tool | The tablet was grated for up to 5 minutes or until a reasonably fine powder was obtained, whichever came first. |
| Razor blade - GEM ® stainless steel uncoated single edge industrial | The tablet was cut for up to 5 minutes or until a reasonably fine powder was obtained, whichever came first. |
| Mortar/pestle - CoorsTek ®, Porcelain Ceramic Mortar and Pestle # 60319 | The tablets was ground for up to 5 minutes or until a reasonably fine powder was obtained, whichever came first. |
| Hammer - Tekton ®, 16 oz wood claw hammer | The tablet was hammered for 1 minute (20 or more strokes) or until a reasonably fine powder was obtained, whichever came first. |
| Spice grinder - Waring ® Commercial, Model WSG30 | The tablet was ground for 1 minute or until a reasonably fine powder was obtained, whichever came first. The grinder was activated in 15 second intervals resting for 10 seconds. |
| Coffee grinder-Krups ® | The tablet was ground for 1 minute or until a reasonably fine powder was obtained, whichever came first. The grinder was activated in 15 second intervals resting for 10 seconds. |
| Mill- IKA ® All basic | The tablet was ground for 1 minute or until a reasonably fine powder was obtained, whichever came first. The grinder \vas activated in 15 second intervals resting for 10 seconds. |

The results for these tests are shown in FIG. 78 to FIG. 87.

The time and effort required to reduce the tablets to fragments or powders depends on the device used. Electrical grinders are the only devices which could efficiently reduce the particle size of tablets B, D and E. Pre-treatment of the tablets did not help the manipulation of the tablets. The tablets in this application are difficult to manipulate, and therefore more effort and time is required to manipulate. In contrast, MS Contin® is easy to convert to powder. A fine powder can be obtained readily by crushing the tablets using two spoons.

Physical manipulation of tablets B, D and E according to the invention was much harder than of MS Contin® tablets. All devices mentioned in Table 12.1 are effective in reducing the particle size of MS Contin® tablets. Simple household tools are very effective at making a fine powder of MS Contin®, for example a fine powder with a particle size distribution of 90%≤425 µm was prepared by pressing the tablets between two spoons for 5 minutes (see FIG. 78). Also, with MS Contin® a particle size distribution of 100%≤1000 µm was obtained by using mortar and pestle for 5 minutes. In contrast, the tablets of the present invention were difficult to crush or grind, and the resulting particles are generally not as small as the MS Contin® particles.

In conclusion, the tablets B, D and E of this application were more resistant to crushing than MS Contin® tablets. However, if it was possible to reduce tablets B, D and E into fine powders using the grinders and mills presented in Table 12.1 above, the hydrogelling properties of the polyethylene oxide contained in these powders made extraction of the morphine sulfate from powdered formulations of tablets B, D and E more difficult than from crushed MS Contin®.

Thermal treatment (e.g. at 90° C. or 230° C. for 240 minutes in an oven) or microwave treatment (e.g. for 300 seconds) prior to manipulation did not significantly change the abuse-deterrent properties of the tablets according to the present invention. Pre-treatment of the tablets by heating, freezing or microwave did not facilitate the particle size reduction of the tablets in this application. Rather, heating, while it may also produce discoloration and darkening of the tablets, generally made the tablets harder. Freezing had no effect on particle size reduction.

In conclusion, physical manipulation of tablets B, D and E according to the present invention using readily available household tools such as spoons, pill crusher, food grater, foot file and hammer was not easily possible. Razor blade, mortar and pestle, spice grinder, coffee grinder and mill were effective in reducing the particle size of these tablets, but a significant reduction in particle size was only achieved using electric grinders (spice grinder, coffee grinder and mill). In contrast, MS Contin® can be more easily crushed into a fine powder using two spoons.

Syringeability Tests

Tablets E, D, and B were subjected to a comprehensive series of in vitro tests to evaluate the potential for abuse via injection. In these tests, the intact or manipulated tablets were first subjected to extraction under various conditions, and then it was attempted to aspirate the resulting solutions into a needle. From the aspirated volumes the amount of morphine recovered from the original dosage form in the various test runs was determined. This testing included altogether three volumes (2 mL, 5 mL, 10 mL), four injectable solvents (water, saline solution, 40% ethanol and 95% ethanol), at room temperature (i.e., 25° C.) and elevated temperatures (60° C. and 90° C.), with and without agitation at 200 RPM, for intact, sliced, and milled tablets for various incubation times. In certain tests, the tablets were additionally thermally pre-treated or by means of microwave prior to the extraction. The reference drug MS Contin® 100 mg was evaluated as the non-abuse-deterrent comparator in certain conditions as specified below.

In some cases, as described below, syringeability testing was performed using an iterative process (see FIG. 98) whereby attempts were first made to draw the extraction media into a small diameter needle (27-gauge). If ≤10% of the initial extraction media could be drawn into the syringe, then larger needles (25-gauge, 22-gauge, and 18-gauge) were iteratively attempted. When ≥10% was syringe-able, the volume was recorded and syringeable liquid was analyzed for morphine sulfate content via analytical testing. Either the tablets were tested intact, or sliced or milled (in the case of MS Contin® they were crushed/ground). The manipulation procedure for preparing the manipulated tablets to be subjected to the syringeability experiments was as follows:

Milling Procedure—Tablets B, D and E:

Milling of the tablets B, D and E was performed according to the "Milling procedure for the tablets" as described in Example 10, above, with a slight change in step 5 as also indicated there.

Grinding Procedure—MS Contin® 100 mg Tablets:
The Grinding Procedure Used is Outlined Below:

a) 20 intact tablets were weighed and the weight was recorded on the milling and grinding worksheet.

b) The Average Tablet Weight (ATW) was calculated and recorded on the milling and grinding work sheet.

c) All 20 tablets were ground in a glass mortar and pestle for 4 minutes.

d) The ground tablet material was transferred to a clean, tared 200 mL glass beaker, using a brush dedicated and labeled for MS Contin® 100 mg tablets.

e) The total weight of crushed tablets and the calculated % recovery was recorded on the milling and grinding work sheet.

f) The crushed tablet was mixed thoroughly with a clean spatula to ensure a homogeneous mixture and the weight of a sample equivalent to the ATW 3% was transferred to a labeled 20 mL scintillation vial. The weight of the transferred material was recorded daily worksheet.

g) Step f) was repeated for a maximum of 15 samples (5 sets of triplicates).

h) The remaining unused portion of ground material was disposed of.

Slicing Procedure for Tablets B, D, E and MS Contin®:

The slicing procedure was carried out using a 7.25-inch chef's knife and a cutting board.

The slicing procedure used is outlined below:

a) The weight of a single tablet was recorded on the experimental worksheet.

b) The tablet was placed on the center of the cutting board and cut in half (longitudinally if applicable). The two halves were cut in half longitudinally/parallel with the first cut.

c) Each quarter was cut in half longitudinally/parallel with the first and second cuts.

d) All 8 slices were aligned together and cut 4 times perpendicular to the previous cuts so that each slice was cut into 5 separate pieces for a total of 40 pieces.

e) The sliced tablet material was transferred to a tared 20 mL scintillation vial labeled with the sample ID, using a brush dedicated and labeled for the specific tablet and dose and the weight was recorded daily worksheet.

Syringeability—Sample Preparation (all Samples)

The preparation of the samples for performing the syringeability tests (further details are provided below) was conducted as follows:

a. All triplicate sets were performed by 1 scientist.

b. All sample IDs on the labeled 20 mL scintillation vial containing sliced, milled or ground material were verified with the sample ID on the experimental worksheet. For intact tablets, a 20 mL scintillation vial was labeled with the appropriate sample ID at the time of experimentation c. A capped 20 mL scintillation vial with the same sample ID number was weighed and recorded on the experimental worksheet (expelling vial).

d. Each tablet was prepared as described above and used (optionally after thermal or microwave treatment as indicated for the respective individual tests) as:
　i. Intact tablet
　ii. Sliced tablet
　iii. Milled or ground tablet e. The appropriate volume of extraction solvent was added to the extraction vial at its experimental temperature (for 60° C. and 90° C., pre-heated solvent was used).

f. The vial was capped.

g. To ensure proper wetting of ground, milled or sliced material for agitated samples only, the extraction vial was vigorously swirled for 3 seconds after solvent addition.

h. For non-agitated room temperature samples, solutions were incubated on the bench top with no further agitation.

i. For non-agitated heated samples, samples were incubated at the proper temperature (60° C. and 90° C.) in the water bath shaker with no further agitation. For all agitated samples, samples were incubated at the proper temperature (RT (i.e., 25° C.), 60° C. or 90° C.) in the water bath shaker (set to 200 RPM).

Syringeability Assessment (for Example 13.1, Below)

a. At the end of the extraction duration, attempts were made to draw/syringe the solution for injection (expelling into a collection vessel) as follows:

b. Syringe barrels (3 cc, 5 cc, or 10 cc) were fitted with the 27-gauge needle (the first needle gauge size of the needle testing order 27>25>22>18).
　i. In the case of Example 13.1, refer to the syringeability decision tree (FIG. 98) for details on sequential needle gauge assessments and the criteria for Pass or Fail for each needle gauge. For Examples 13.2 and 13.3, further details on the needle gauge used are provided below in the respective Examples.
　ii. The following barrels were used: 3 cc syringe for 2 mL extractions, 5 cc syringe for 5 mL extractions, and 10 cc syringe for 10 mL extractions.

c. Needle tips were carefully inserted into one end of the cotton heads of a Q-tip.
　i. While holding the Q-Tip by the shaft positioned vertically in one hand, the needle tip was positioned at the base of the upper cotton head and pushed up along the shaft and into the cotton head.
　ii. The needle was kept parallel with the Q-Tip shaft as to not clog with material.
　iii. The needle tip was not protruding out of the top of the cotton head. It was kept just below the surface of the cotton.

d. The needle tip with Q-Tip attached was introduced into the extract and allowed to soak in the extract for 5 seconds.

e. Attempts were made to load the syringe with the solution, for a maximum of 2 minutes (a timer was used)

f. If the 27-gauge needle was unsuccessful at drawing ≥10% of the extraction volume (volume of liquid used), the volume drawn was recorded then expelled back into the extraction vial from where it was drawn and repeated with the 25-gauge needle. Again, refer to the syringeability decision tree in FIG. 98 for further details regarding the iterative process of aspirating the extraction volume using different needle gauges in Example 13.1. Further details on the needle gauges employed in Examples 13.2 and 13.3 are provided in the respective Examples.

i. Cycles were completed as needed, stopping at the final 18-gauge needle.

g. After successful syringing (100% of the extraction volume drawn), all air from the syringe was expelled, without expelling any liquid and the volume of the solution in the syringe (using syringe graduations) was recorded.
　i. If the successful volume to be drawn was a volume that resides between syringe gradations, the next highest gradation was used to make the determination. For instance, if the successful volume was 0.5 mL but the gradations are in 200 UL/0.2 mL increments, 600 μL/0.6 mL was used as the pass criteria.

h. For heated extractions, the syringe contents were allowed to cool to ambient temperature as judged by touch before expelling. Cooling times took up to 30 minutes.
　i. The plunger was compressed until all material was expelled through the needle (for maximum of 2 minutes) collecting the expelled material in each sample's respective labeled, pre-weighed expelling vial.

j. Gross weights of each capped, 20 mL expelling vial with expelled material were measured.

k. The expelled solution was assayed by liquid chromatography/ultraviolet detection for morphine concentration, total drug expelled, and percent morphine recovery. All samples were diluted with SGF in a suitable labeled, glass tube/vial. Dilutions were performed assuming a 100% recovery of the tablet dose strength so that the final concentration would be below the assay's ULOQ (upper limit of quantification) of 280 μg/mL.

l. For samples where the LC-UV result was above the assay's ULOQ, an additional dilution was performed to bring the dilution below the ULOQ. All dilutions were recorded for each sample.

m. One of each set of triplicate samples was measured for viscosity using a viscometer.
　i. The remaining volume after removal of the aliquot for dilution for LC-UV analysis (20 μL, 25 μL or 50 μL aliquot) must have been ≥0.8 mL (minimum volume for viscosity is 1 mL) to measure the viscosity using viscometer.

Calculations

Since both the tablets according to the invention and the comparator MS Contin® tablets contain morphine sulfate pentahydrate and samples were analyzed against the morphine free base-calibration curve, a correction factor was applied to the assayed value to calculate morphine sulfate pentahydrate equivalent to the amount of free base assayed. The following equation was applied to calculate the amount of recovered morphine base as morphine sulfate pentahydrate in milligrams:

$$\text{Morphine Sulfate Pentahydrate Recovery} = \frac{\text{observed concentration}\left(\frac{\mu g}{ml}\right) * \text{volume of solvent used (ml)} * \text{dilution factor}}{1{,}000{,}000\left(\frac{\mu g}{mg}\right)} \times \frac{\text{MW(Salt)}}{\text{MW(free base)}}$$

The molecular weights of morphine sulfate pentahydrate and morphine base used for this particular calculation are 379.43 and 285.34, respectively.

The percent recovery of API (active pharmaceutical ingredient, i.e., morphine sulfate pentahydrate) from sliced, milled and ground tablet material was calculated from the amount recovered and the dosage nominal content as shown by the following equation:

$$\% \text{ Recovery } API = \frac{\text{Observed weight of } API \text{ (mg)}}{\text{Mass of ground material (mg)}} \times \frac{\text{Average tablet mass (mg)}}{\text{Tablet Dosage (mg)}} \times 100$$

The expected API recovery in the expelled fraction in mg assuming 100% release of API into the solution was calculated using the following equation:

$$\text{Expected } API \text{ in Expelled Fraction} = \frac{\left( \frac{\text{Mass of ground material (mg)}}{\text{Average Tablet mass (mg)}} \times \text{Tablet Dosage (mg)} \right)}{\text{Extraction volume (mL)}} \times \text{Volume Expelled (g)}$$

Example 13.1 Syringeability Following Extraction in Water and Saline

The ability to syringe morphine sulfate from intact tablets was evaluated at 1 hour and/or at 24 hours under each condition. All syringeability experiments, regardless of time, temperature, or volume for intact 100 mg MS Contin® reference tablets were easily drawn through small 27-gauge needles. In contrast, at 24-hour time points and in syringeability experiments that were shaken, intact tablets E, D, and B generally swelled or formed a highly viscous material that often required the use of larger needles to obtain any syringeable liquid.

Intact MS Contin® 100 mg tablets released substantially higher amounts of morphine sulfate relative to tablets B, D and E of the present invention under all testing conditions. At room temperature, the maximum amount of morphine sulfate released from intact tablet B, D and E was 4% at 1-hour and 14% at 24-hour time points at room temperature. The comparator, MS Contin®, released up to 29% within 1-hour and almost 60% within 24 hours at room temperature. As expected for all tablets, room temperature extractions yielded lower quantities of syringeable morphine sulfate relative to extractions at near boiling temperatures (90° C.).

The ability to syringe manipulated tablets was evaluated at 30 seconds, 5 minutes, and 30 minutes, also using 2, 5 or 10 mL of water or saline at room temperature (25° C.) or at 90° C., with or without agitation. Sliced and ground MS Contin® tablets were compared to each strength of tablets B, D and E that were sliced or milled. Consistent with intact tablets, sliced and ground MS Contin® tablets were easily drawn into a syringe through the smallest gauge needles.

When manipulated and dissolved in small volumes of injectable solvent, the tablets according to the present invention form a gelatinous material making passage through a needle difficult or impossible in many circumstances; large 18-gauge needles were often required to syringe the extraction media in order to aspirate any material into the barrel. When syringeable liquid was analyzed for morphine sulfate content, the tablets B, D and E according to the present invention released substantially less morphine sulfate than the comparator MS Contin®. Furthermore, even when these small volume extractions were heated to near boiling temperatures for extended periods of time, which is not likely to be repeatable by abusers in non-laboratory settings, tablets B, D and E showed substantial resistance to extraction for injection relative to MS Contin®.

Figure 99:
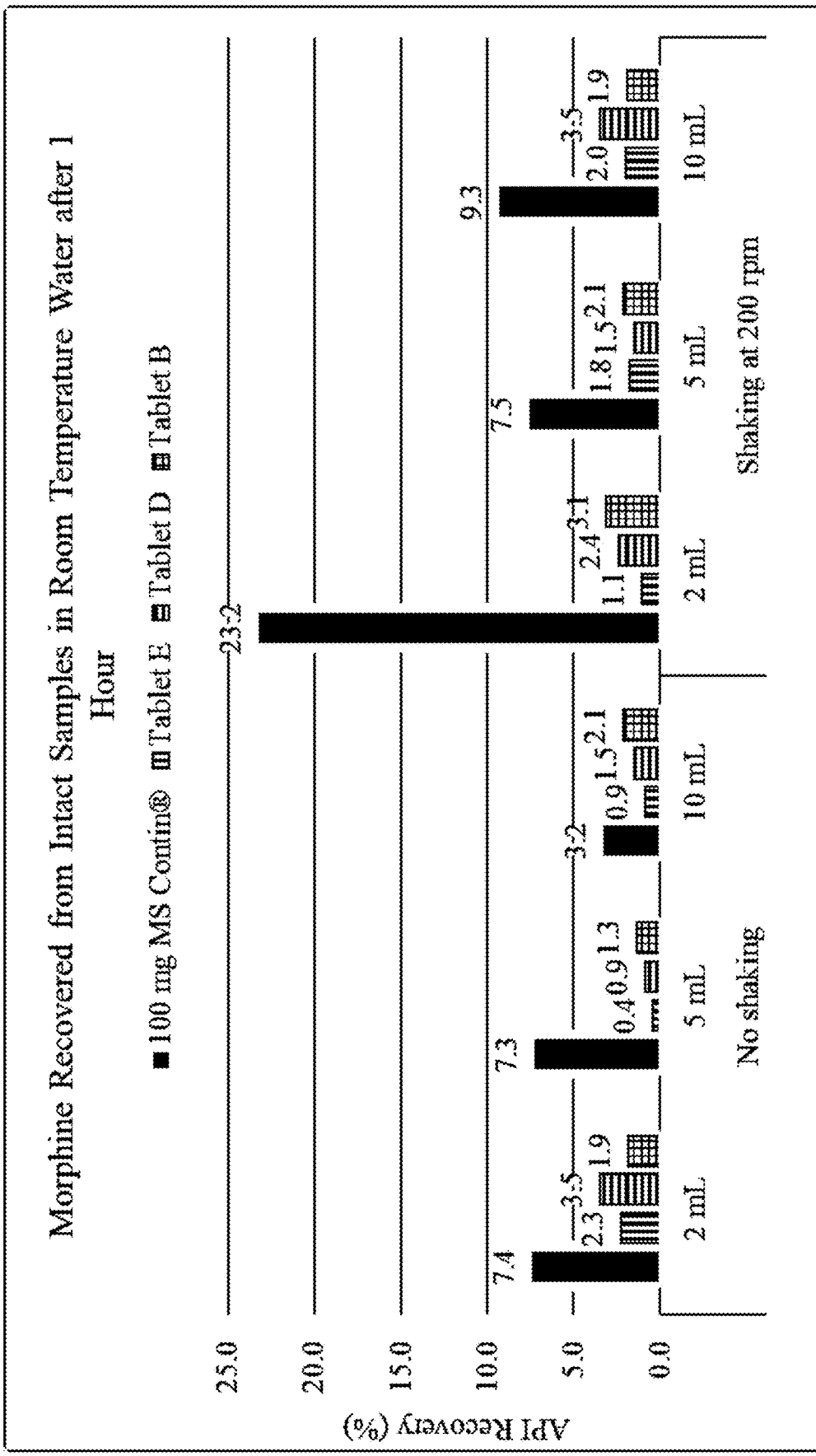
FIG. 99: Morphine Recovered from Intact Samples in Room Temperature Water after 1 Hour
Figure 100:
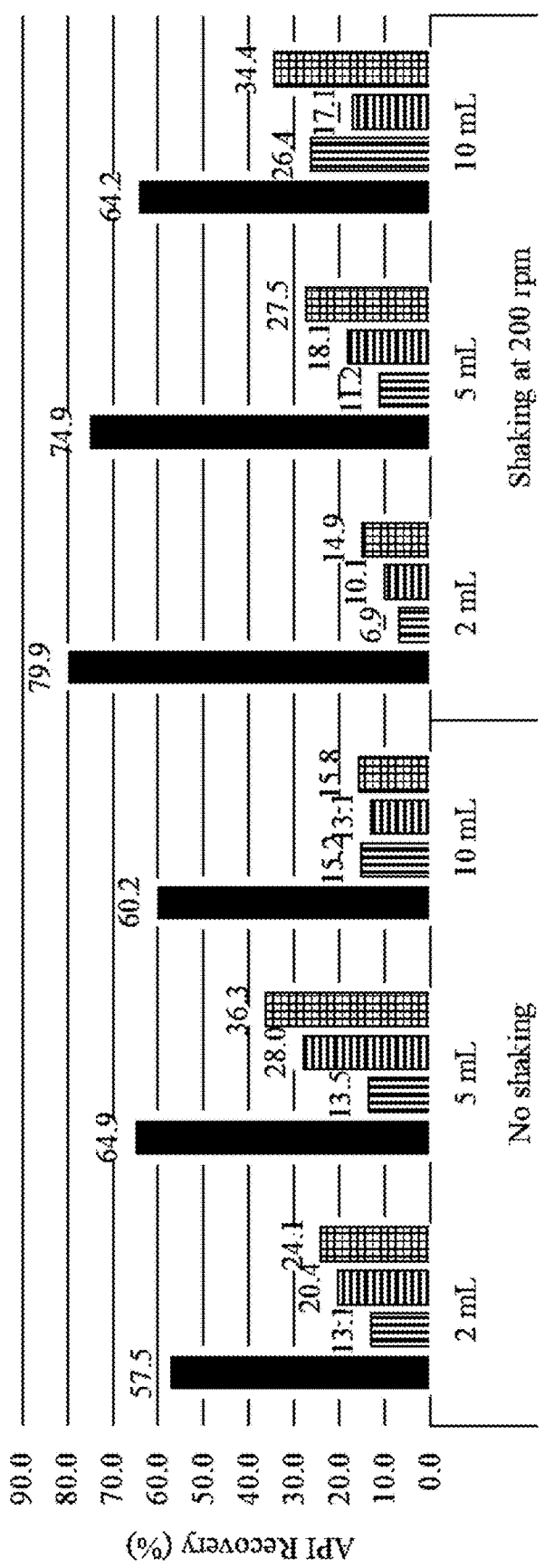
FIG. 100: Morphine Recovered from Intact Samples in 90° C. Tap Water after 1 Hour

Final data corresponding to the results of the syringeability tests of Example 13.1 are given in FIG. 63 to FIG. 74 as well as in FIGS. 99 and 100.

Example 13.2 Syringeability Following Extraction in Ethanol

Figure 103:
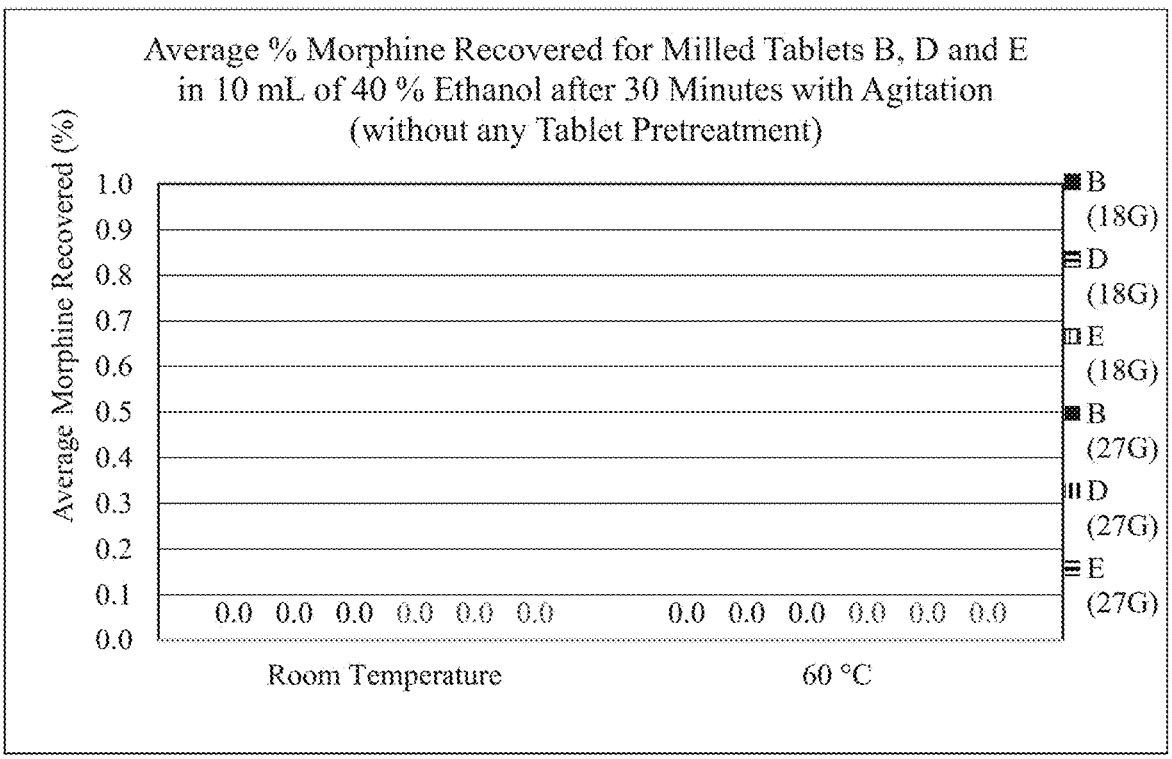
FIG. 103: The Average Percentage of Morphine Recovered for Milled Tablets in 10 mL of 40% Ethanol after 30 Minutes with Agitation
Figure 104:
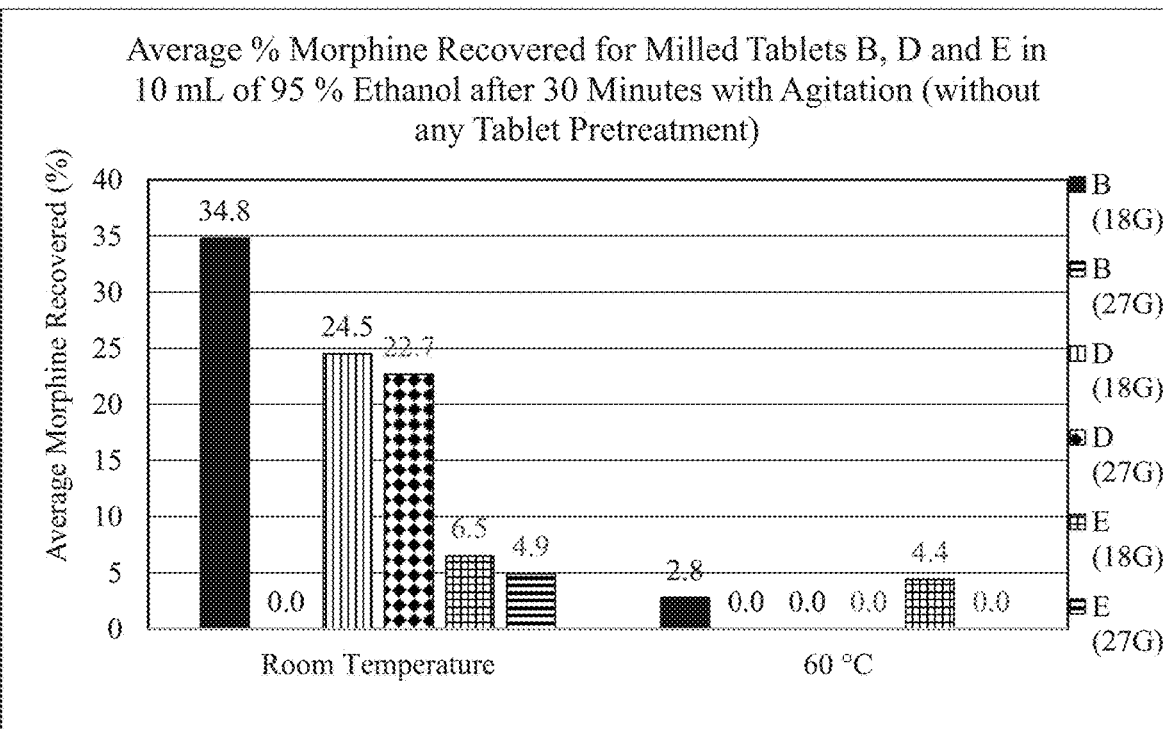
FIG. 104: The Average Percentage of Morphine Recovered for Milled Tablets in 10 mL of 95% Ethanol after 30 Minutes with Agitation

This series of tests related to the syringeability of tablets B, D and E following extraction in ethanol. Extraction from intact and milled tablets was conducted in 40% and 95% ethanol at room temperature (i.e., 25° C.) and at 60° C. (without any thermal or microwave pre-treatment of the tablets). In the tests represented in FIGS. 101 to 104, extractions from intact tablets (using 10 mL of extraction solvent) were conducted for one hour with agitation (200 rpm), and extractions from milled tablets (also using 10 mL of extraction solvent) were conducted for 30 minutes, also with agitation (200 rpm). An 18-gauge needle was generally used in order to aspirate the extraction solution in these tests. For the milled tablets only, if ≥10% of the extraction volume was drawn through 2 out of 3 of these large gauge needles, attempts were also made to aspirate the extraction volume through 27 gauge needles (as shown in FIGS. 103 and 104). In any other respect, the syringeability testing was conducted in the same way as described above for Example 13.1.

The summary results of the syringeability tests with intact tablets in 10 mL of 40% ethanol after one hour (with agitation) at room temperature and at 60° C. are displayed in FIG. 101. Even with 10 mL of 40% ethanol and an 18-gauge needle, the percent morphine extracted and available for injection was relatively low compared to similar tests with water (see FIG. 99 for comparison at room temperature and FIG. 100 at 90° C.).

The summary results of the syringeability tests with intact tablets in 10 mL of 95% ethanol after one hour (with agitation) at room temperature and at 60° C. are displayed in FIG. 102. Even with a 10 mL volume and an 18 gauge needle, the percent morphine recovered was very low.

The summary results of the syringeability tests with milled tablets in 10 mL 40% ethanol after 30 minutes (with agitation) at room temperature and at 60° C. are displayed in FIG. 103. As is evident from FIG. 103, extraction of morphine in these studies with 40% ethanol was not as effective as similar studies with water. No morphine at all could be recovered from 10 mL of 40% ethanol after 30 minutes and with agitation at room temperature or even at 60° C.

The summary results of the syringeability tests with milled tablets in 10 mL of 95% ethanol after 30 minutes (with agitation) at room temperature and at 60° C. are displayed in FIG. 104. Both the results obtained with an 18 gauge needle as well as with a 27 gauge needle are displayed. 95% ethanol is not a highly effective solvent for extracting morphine. Even with the use of large needles, and a relatively high extraction volume of 10 mL, however, the data showed that under these conditions at room temperature more morphine could be recovered in the syringeability test than at 60° C.

Example 13.3 Syringeability Following Extraction with Prior Thermal Treatment In these tests intact, sliced or milled dosage forms according to the present invention were additionally subjected to so-called "crisping", i.e., thermal pretreatment or microwave pretreatment prior to being subjected to extraction. Recovery of morphine after syringeability testing from these pre-treated tablets was compared to recovery of morphine after syringeability testing from the corresponding untreated tablets according to the present invention.

The pre-treatment times at 170° C. and at 230° C. in the oven used for pretreating certain tablets B, D and E prior to syringeability testing in this Example are summarized in Tables 13.3a and 13.3b below. The microwave pre-treatment was conducted at 30 second intervals until the tablets turned golden brown. Where thermal or microwave pre-treatments were conducted, such pre-treatment was performed following any physical manipulation (i.e., slicing or milling).

TABLE 13.3a

Oven Pre-treatment Times at 170° C.
Oven (170° C.) Pre-treatment times (minutes)

| Tablet | B | D | E |
|---|---|---|---|
| Intact | 40 | 40 | 40 |
| Sliced | 30 | 30 | 30 |
| Milled | 30 | 40 | 40 |

TABLE 13.3b

Oven Pre-treatment Times at 230° C.
Oven (230° C.) Pre-treatment times (minutes)

| Tablet | B | D | E |
|---|---|---|---|
| Intact | 5 | 7 | 8 |
| Sliced | 4 | 4 | 5 |
| Milled | 4 | 4 | 5 |

Oven Pretreatment Procedure:
  A. The oven was preheated to the desired temperature (170° C. or 230° C.).
  B. For intact and sliced experiments, an intact tablet or sliced tablet was placed in the center of a 20 mL glass vial. For milled experiments, one tablet equivalent of the average tablet weight (ATW) 3.0% of milled material was transferred into a 20 mL glass vial, ensuring that the material was evenly distributed along the bottom.
  C. The material was incubated in the oven for the appropriate time/temperature, as indicated in the above Tables 13.3a and 13.3b.
  D. After incubation, the material was allowed to cool to room temperature before proceeding with the syringeability procedure and any physical changes to the material were documented.
Microwave Pretreatment Procedure:
  A. For intact and sliced experiments, an intact tablet or sliced tablet was placed in the center of a 20 mL glass vial. For milled experiments, one tablet equivalent of the ATW±3.0% of milled material was transferred into a 20 mL glass vial, ensuring that the material was evenly distributed along the bottom.
  B. The 20 mL glass vial containing the sample was placed in the center of the microwave and heated for a minimum of two minutes.
  C. Samples were then microwaved in 30 second increments until tablet/manipulated material appeared golden brown.
  D. The material was allowed to cool to room temperature before proceeding with the syringeability procedure.

FIGS. 105 to 110 summarize the syringeability tests that were conducted to determine the effect of thermal (at 170° C. or 230° C. in the oven) or microwave pre-treatment on the amount of morphine recovered from extraction of intact, sliced and milled tablets in 2 mL or 10 mL of room temperature tap water (after 1 hour without agitation for intact tablets, and after 5 minutes with agitation for sliced and milled tablets). The average percent of morphine recovered shown in FIGS. 105 to 110 is the amount obtained when using an 18-gauge needle only to aspirate the extraction volume. In any other respect, the syringeability test was performed in the same way as detailed above for Example 13.1.

There was only a minimal increase in the recovered amount of morphine from thermally or microwave-pretreated intact tablets and only a minor increase in the case of sliced tablets (see FIGS. 105 and 108 for intact tablets and FIGS. 107 and 110 for sliced tablets) as compared to non-pretreated tablets. There was also almost no difference in morphine recovery in the case of 10 mL of extraction volume versus 2 mL of extraction volume (water).

For milled tablets, the amount of recovered morphine increased after thermal or microwave pretreatment as shown in FIG. 106 for extraction with 10 mL room temperature water after 5 minutes with agitation as compared to no thermal or microwave pretreatment. For extraction with 2 mL room temperature water after 5 minutes with agitation from milled tablets (see FIG. 109), only for Tablet B (30 mg) was an increase in the amount of recovered morphine observed after thermal or microwave pre-treatment as compared to no pre-treatment, while morphine recovery from tablets D and E (100 and 200 mg, respectively) was generally low or even zero under all conditions tested.

Generally, it can be derived from these tests that thermal pre-treatment somewhat increased the amount of morphine recovered, with little discernable difference between the individual pre-treatment methods. In this context, it must however be borne in mind that potential abusers who intend to inject the extracted solutions intravenously tend to prefer low extraction volumes (2 mL or even 1 mL). For these volumes, extractability of morphine from the dosage forms of the present invention is low, even when thermal or microwave pre-treatment is applied.

Simulated Smoking Tests

Example 14

Figure 93:
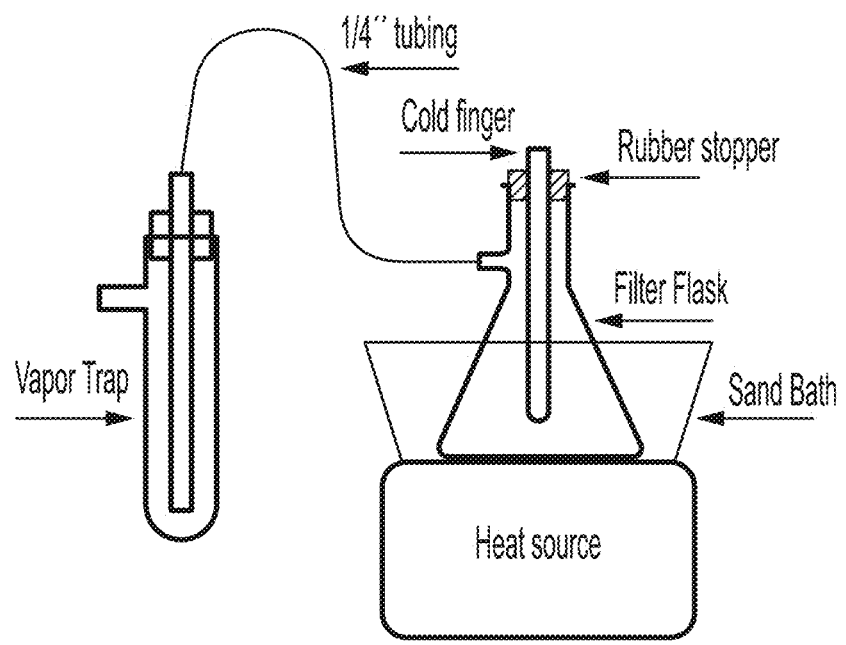
FIG. 93: Apparatus Used for Simulated Smoking Tests
Figure 94:
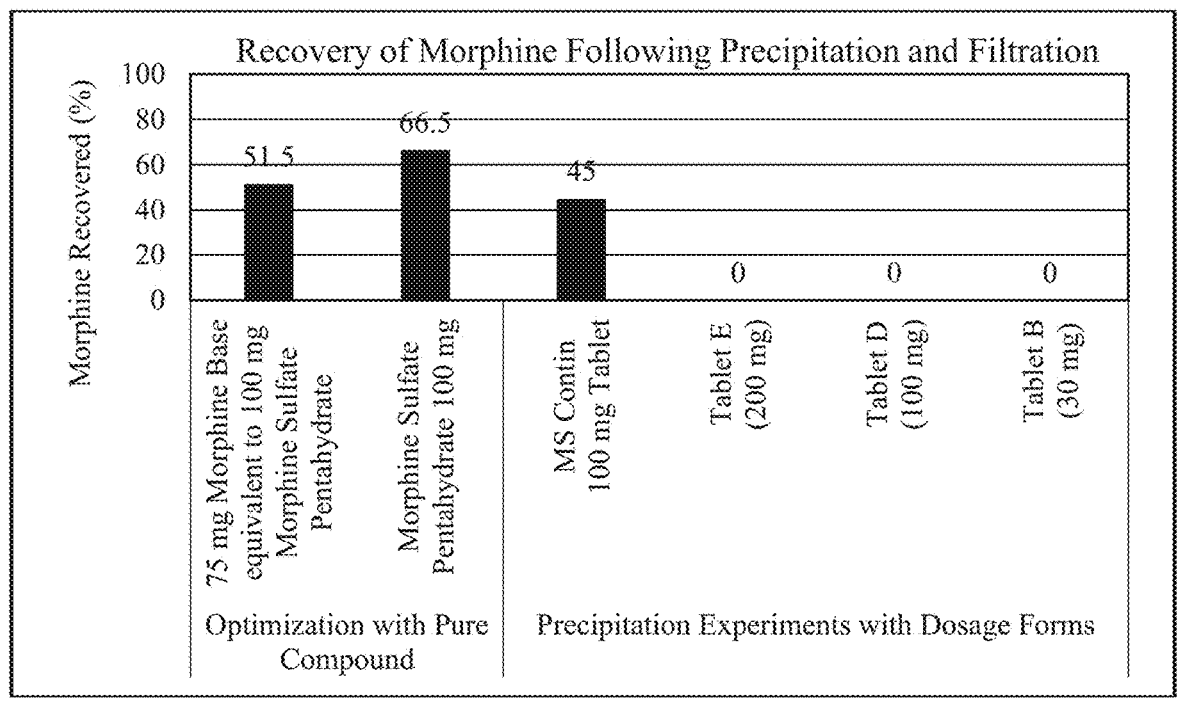
FIG. 94: Recovery of Morphine Base Following Precipitation
FIG. 95a,b: Mean Plasma Concentrations of Morphine Versus Time for Tablets A, B, C and D (linear and logarithmic scale)

The purpose of these experiments was to evaluate the feasibility of smoking tablets B, D and E compared to the 100 mg MS Contin® reference tablet through simulation of inhalation of volatilized morphine after heating the dosage forms in an apparatus with modified cold fingers as shown in FIG. 93.

A series of experiments was therefore conducted to identify the optimal time and temperature for volatilizing morphine base. A simulated smoking time of 15 minutes at 300° C. was determined to be optimal for volatilizing morphine while minimizing degradation. Purified morphine hemi (sulfate pentahydrate) (the active pharmaceutical ingredient; API) was very difficult to volatilize and required an additional step, namely alkalization by the addition of NaOH to obtain measurable amounts of volatilized API at the optimized time and temperature. A Sterno™ burner was also used to heat samples as a real-world comparison.

Sample Preparation for one step (in-situ alkalization) was carried out as follows:
  a. For each preparation, an empty piece of weigh paper was tared.
  b. Each tablet was milled or ground in the same manner as described above for the syringeability experiments (see Example 13).
  c. The manipulated material was transferred to the weigh paper and the weight was recorded on the experimental worksheet.
  d. The material was transferred into the reaction flask (125 mL vacuum flask), ensuring the material was deposited at the bottom of the flask and minimal powder was deposited on the side walls.
  e. 1 mL of 0.1N NaOH in Ethanol was added to the ground material in the reaction flask and stirred for 20 seconds.
  f. The pH was measured with a small piece of Whatman™ pH paper and small additions (0.5 mL) of 0.1N NaOH were added until a pH of 9 was obtained according to the color chart for the pH paper.
  g. The pH adjusted solution was stirred for 20 seconds and then dried to completeness under a stream of nitrogen.
  h. The rubber stopper with cold finger (20×150 mm test tube) was attached to the flask and sealed with Parafilm®.
  i. The simulated smoking procedure, extraction and analysis steps described below were then continued.

The simulated smoking procedure was carried out as follows, using the apparatus as shown in FIG. 93:
  a. A sand bath was heated by setting the hot plate to the designated temperature and inserting a temperature probe, centered into the sand where the filter flask will be placed.
  b. The heat source was verified with a temperature probe and the temperature documented on the worksheet (excluding torch assessment using Sterno burner).
  c. The rubber stopper and cold finger (20×150 mm test tube) assembly (see FIG. 93) was attached and sealed with Parafilm®.
  d. A 20-30 mL aliquot of DI Water was added to the vapor trap.
  e. Once the sand bath had maintained a stable desired temperature, the temperature probe was removed and dry ice was added to the cold finger.
  f. Once the filter flask was placed in the sand bath, sand was carefully pressed back around the flask.
  g. The vapor trap hose was attached to the side port of the filter flask.
  h. Each sample was heated at the designated temperature using a traceable thermometer.
  i. At the end of the experiment, the vacuum tubing was removed from the filter flask while being careful to avoid back flushing of vapor trap solvent into the reaction chamber.
  j. The filter flask assembly was removed from the sand bath avoiding agitation so as not to disturb any deposition on the cold finger.

The extraction and analysis procedure was carried out as follows:
  a. The cold finger was removed from the reaction chamber of the heating apparatus so as not to disturb any deposited material.
  b. The cold finger was placed into a clean 200 mL Erlenmeyer flask, filled with 200 mL of 0.1 N HCl and sealed with Parafilm. The flask was vortexed to dissolve any material sublimed to the cold finger (cold finger wash).
  c. The residue from the side walls of the filter flask was collected by means of a side-wall wash by sealing the side port of the filter flask with Parafilm and then inverting the filter flask into a beaker filled with 300 mL of 0.1N HCl. The air was vacuumed from within the filter flask to draw up the 0.1 N HCl along the side walls of the filter flask being careful not to allow the wash to disturb the leftover residue on the bottom of the filter flask (side wall wash).
  d. After washing the side walls of the filter flask, 50 mL of 0.1 N HCl was added to the filter flask and shaken at 100 RPM for 1 hour at room temperature to dissolve the remaining residue on the bottom of the filter flask (residue wash).
  e. 1 mL aliquots of the cold finger wash, sidewall wash, and residue wash were taken and diluted in a labeled test tube 1:50 in DI water (20 µL of aliquot to 980 µL of SGF) for LC-UV analysis.
  f. Samples where the LC-UV result was above the assay's ULOQ, had an additional dilution performed to bring the result below the ULOQ. All dilutions will be recorded for each sample.

Calculations

Since both the tablets according to the invention and the comparator MS Contin® tablets contain morphine sulfate pentahydrate and samples were analyzed against the morphine free base-calibration curve, a correction factor was applied to the assayed value to calculate morphine sulfate pentahydrate equivalent to the amount of free base assayed. The following equation was applied to calculate the amount of recovered morphine base as morphine sulfate pentahydrate in milligrams:

$$\text{Morphine Sulfate Pentahydrate Recovered} = \frac{\text{observed concentration}\left(\frac{\mu g}{ml}\right) * \text{volume of solvent used (ml)} * \text{dilution factor}}{1{,}000 \left(\mu \frac{g}{mg}\right)} \times \frac{\text{MW(Salt)}}{\text{MW(free base)}}$$

The molecular weights of morphine sulfate pentahydrate and morphine base used for this particular calculation are 379.43 and 285.34, respectively.

The percent recovery of morphine sulfate pentahydrate from milled and ground tablet material was calculated from the amount recovered and the dosage nominal content as shown by the following equation:

$$\% \text{ Recovery } API = \frac{\text{Observed weight of } API \text{ (mg)}}{\text{Mass of ground material (mg)}} \times \frac{\text{Average tablet mass (mg)}}{\text{Tablet Dosage (mg)}} \times 100$$

The smoking-simulation technique was verified on pure morphine base, and heating at 300° C. and 320° C. for 15 minutes produced the highest volatilization recovery (not shown in Tables 14.2 and 14.3). Morphine sulfate pentahydrate, the API, was not readily volatilizable with maximum volatilization recovery of less than 1%. When the API was alkalinized with simple addition of excess molar concentration of NaOH, about 21% of API was volatilized when heated with a Sterno burner for 15 minutes. This was considered as an optimized technique to apply to the dosage forms, especially since isolation of pure morphine from API via precipitation was not feasible.

TABLE 14.2

Figure 76:
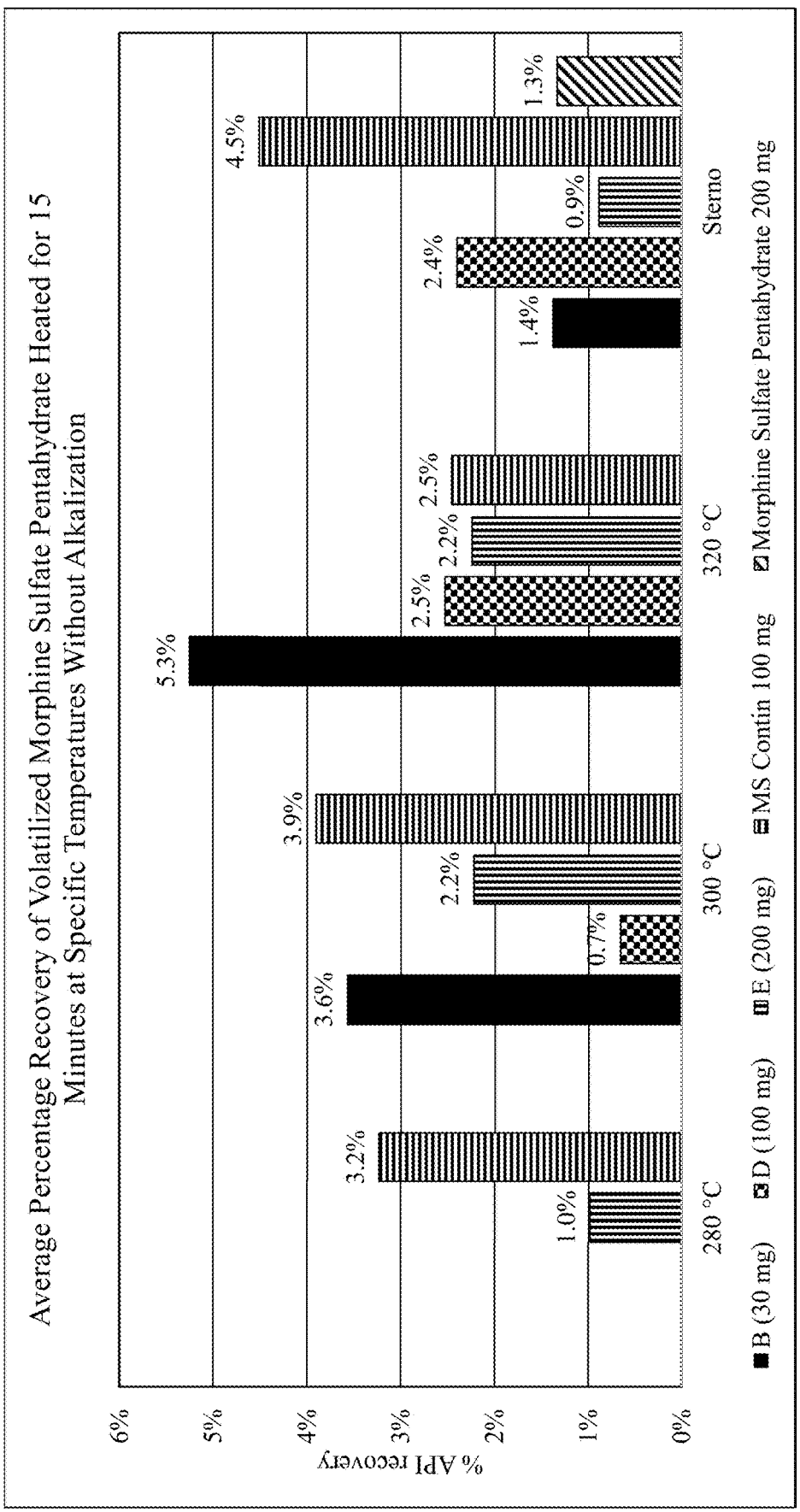
FIG. 76: Results from Simulated Smoking Experiments without Alkalization

Average % Recovery of Volatilized and Residual
from Smoking Simulations without Alkalization (see FIG. 76).
Average % Recovery of Volatilized and Residual Morphine Sulfate
Pentahydrate from Smoking Simulation without Alkalization.

| | Heated 15 Minutes | | | | | | |
|---|---|---|---|---|---|---|---|
| | B | | | D | | | E |
| Temp | Vol. | Resid. | Total | Vol. | Resid. | Total | Vol. |
| 280 | n/a | 31.70% | 31.70% | n/a | 64.00% | 64.00% | 0.98% |
| 300 | 3.57% | 27.40% | 31.00% | 0.66% | 56.70% | 57.30% | 2.22% |
| 320 | 5.25% | 19.80% | 25.00% | 2.53% | 8.63% | 11.20% | 2.24% |
| Sterno | 1.38% | 1.56% | 2.42% | 2.40% | 6.89% | 9.29% | 0.89% |

| | Heated 15 Minutes | | | | | | |
|---|---|---|---|---|---|---|---|
| | E | | MS Contin® 100 mg | | | Morphine Sulfate Pentahydrate 200 mg | | |
| Temp | Resid. | Total | Vol. | Resid. | Total | Vol. | Resid. | Total |
| 280 | 65.30% | 66.30% | 3.23% | 70.40% | 73.70% | n/a | n/a | n/a |
| 300 | 32.90% | 35.20% | 3.90% | 31.70% | 25.00% | n/a | n/a | n/a |
| 320 | 9.66% | 11.90% | 2.45% | 16.10% | 18.60% | n/a | n/a | n/a |
| Sterno | 39.70% | 40.60% | 4.51% | 10.40% | 7.98% | 1.33% | 19.80% | 21.20% |

TABLE 14.3

Figure 77:
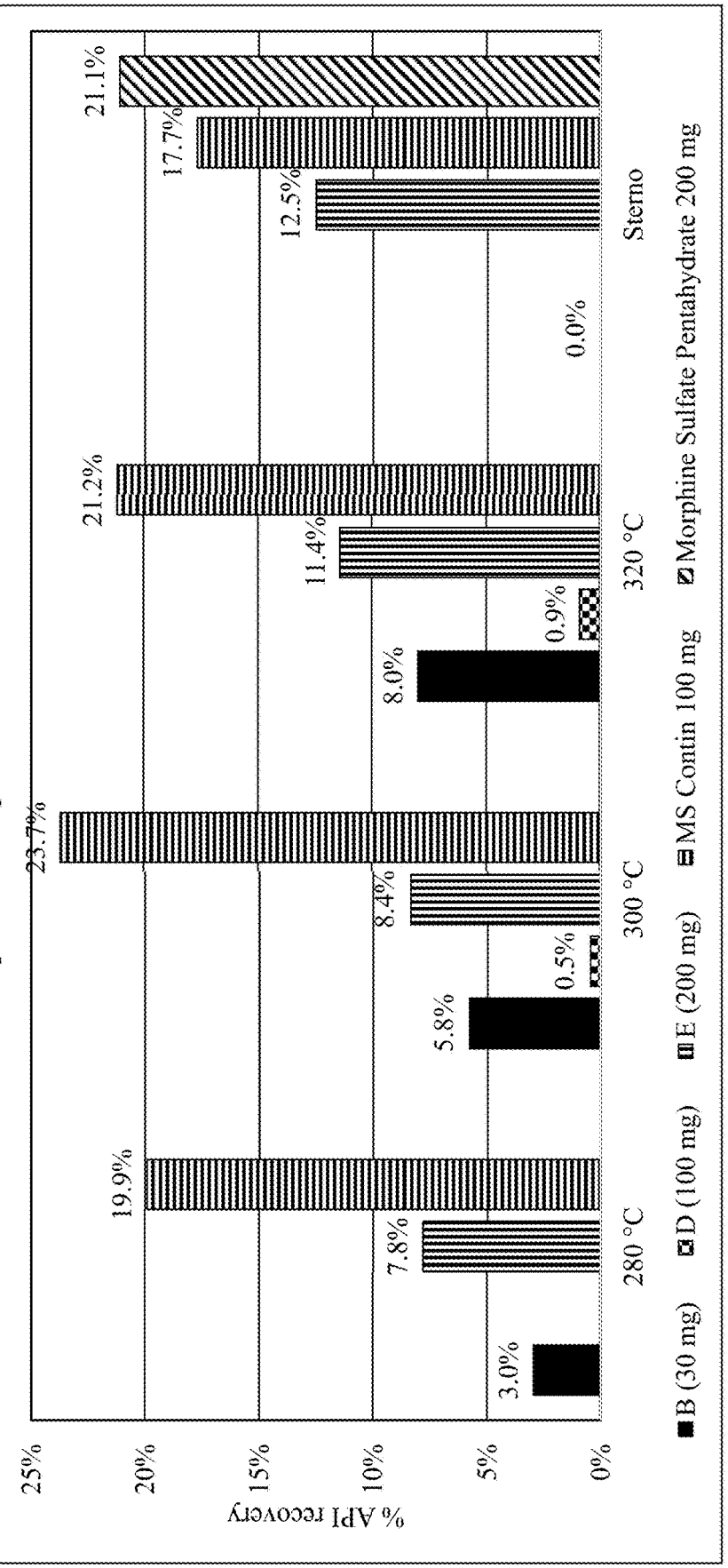
FIG. 77: Results from Simulated Smoking Experiments with Alkalization
Figure 78:
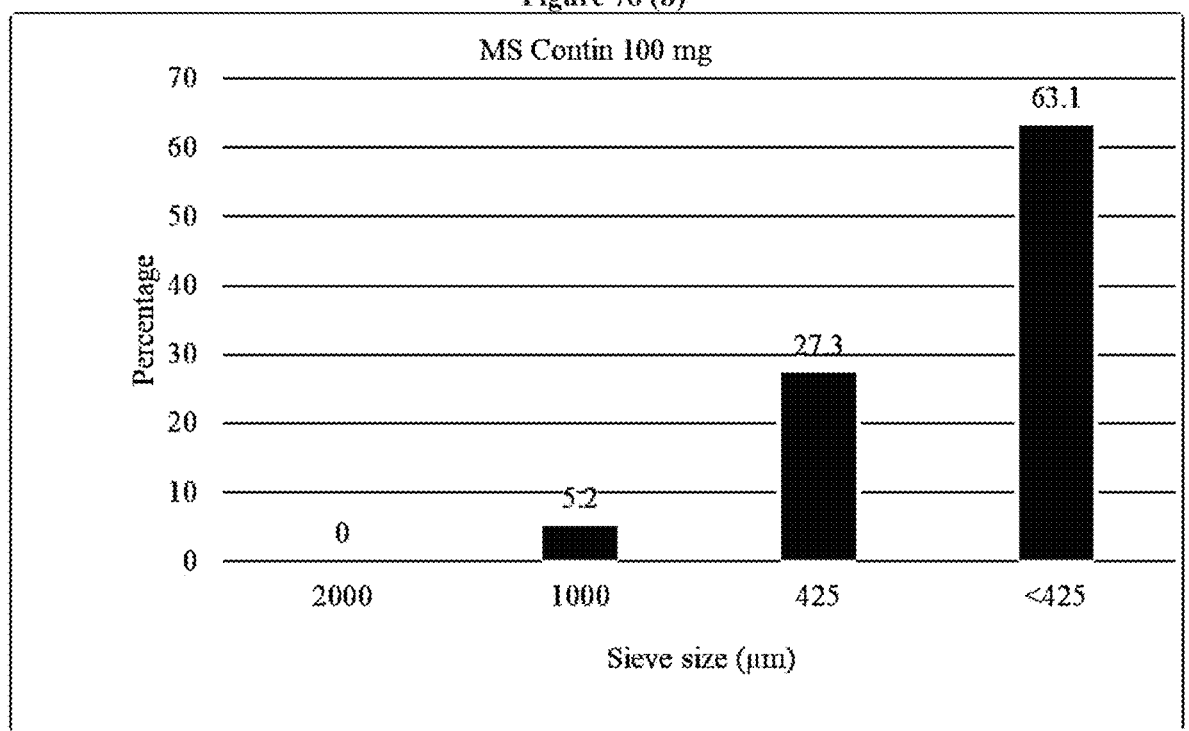
FIGS. 78a,b: Manipulation with Spoons—Winco®, 18/0 Stainless Steel Teaspoons
Figure 79:
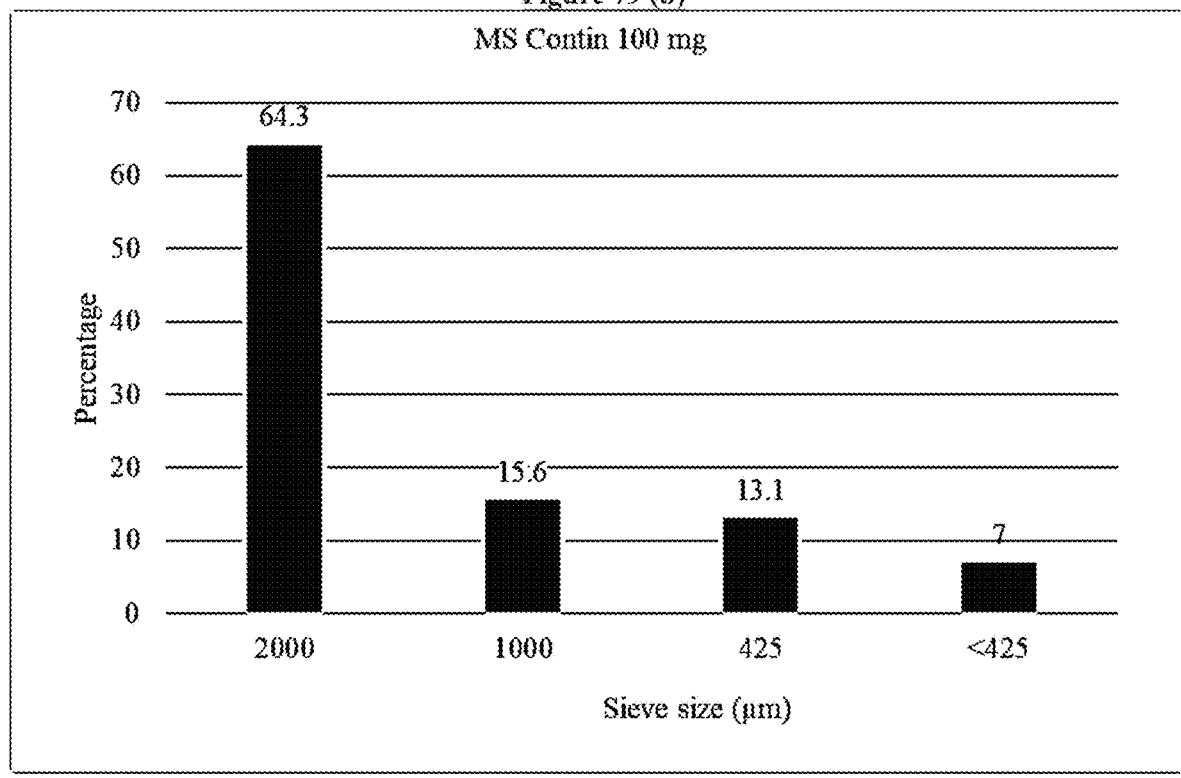
FIGS. 79a,b: Manipulation with Pill Crusher—Life Brand
Figure 80:
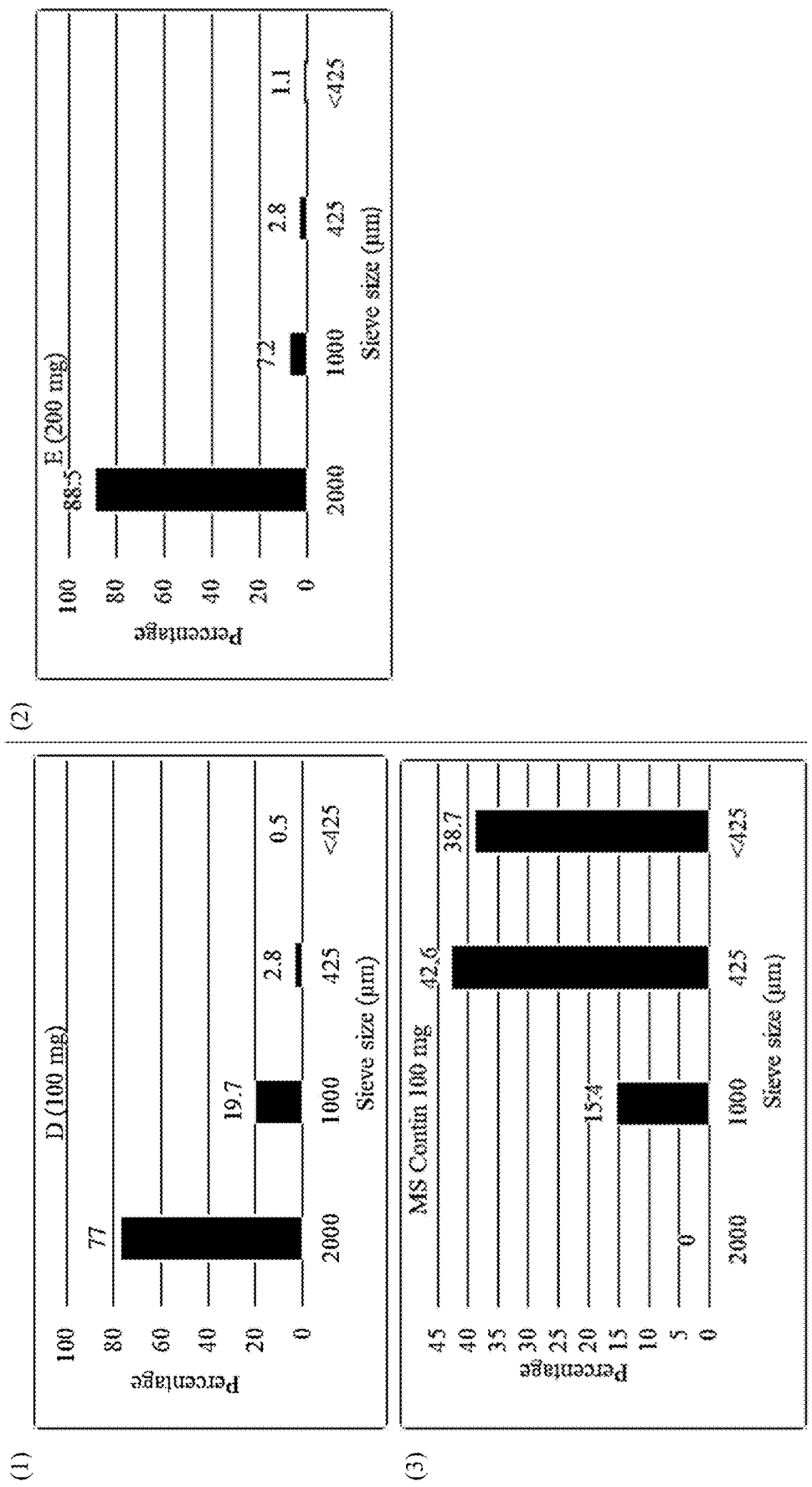
FIGS. 80a,b: Manipulation with Mortar/Pestle—CoorsTek®, Porcelain Ceramic Mortar and Pestle #60319
Figure 81:
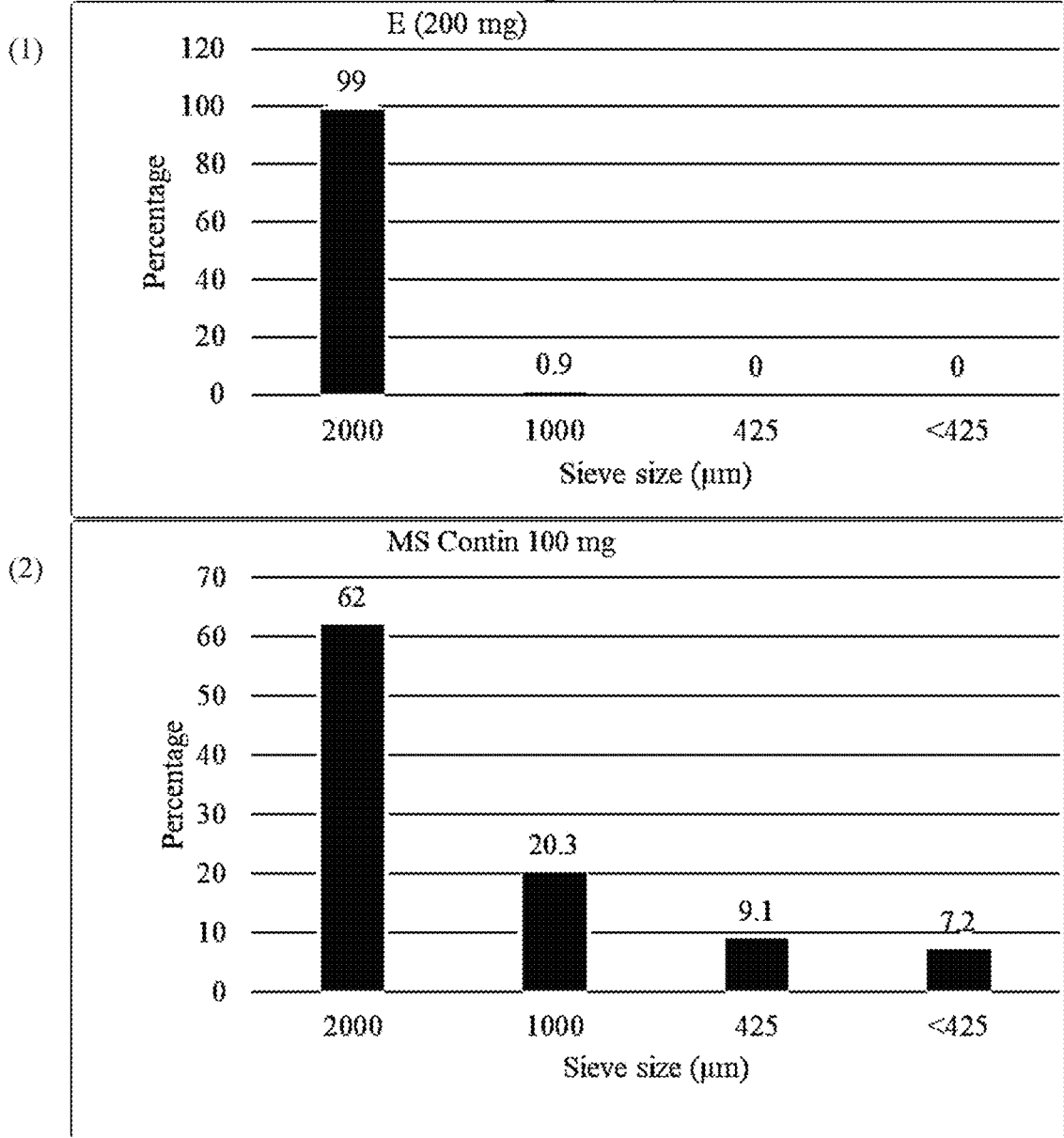
FIGS. 81a,b: Manipulation with Hammer—Tekton®, 16 oz Wood Claw hammer
Figure 82:
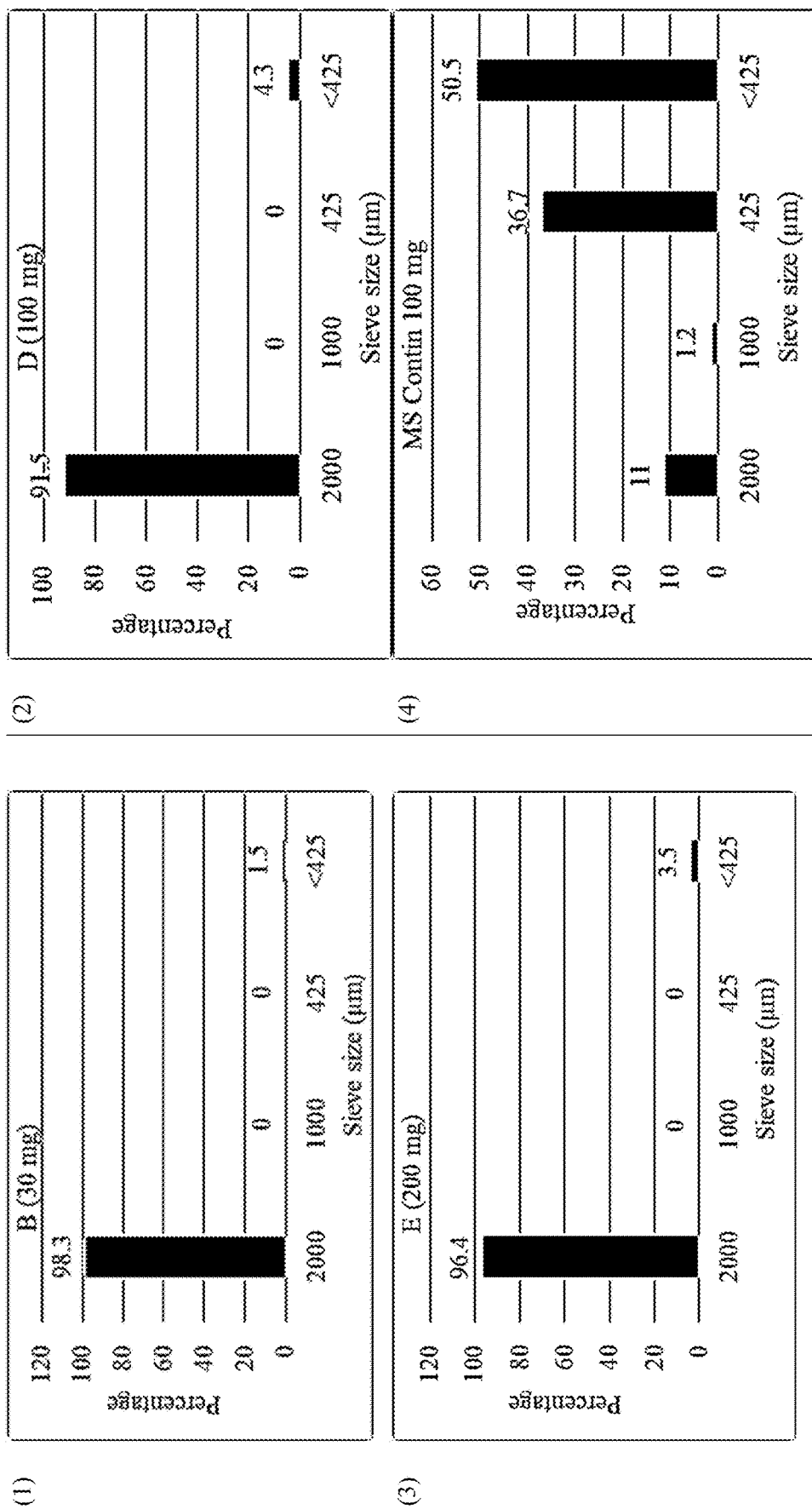
FIGS. 82a,b: Manipulation with Foot File—Ultra Pedi Tool
Figure 83:
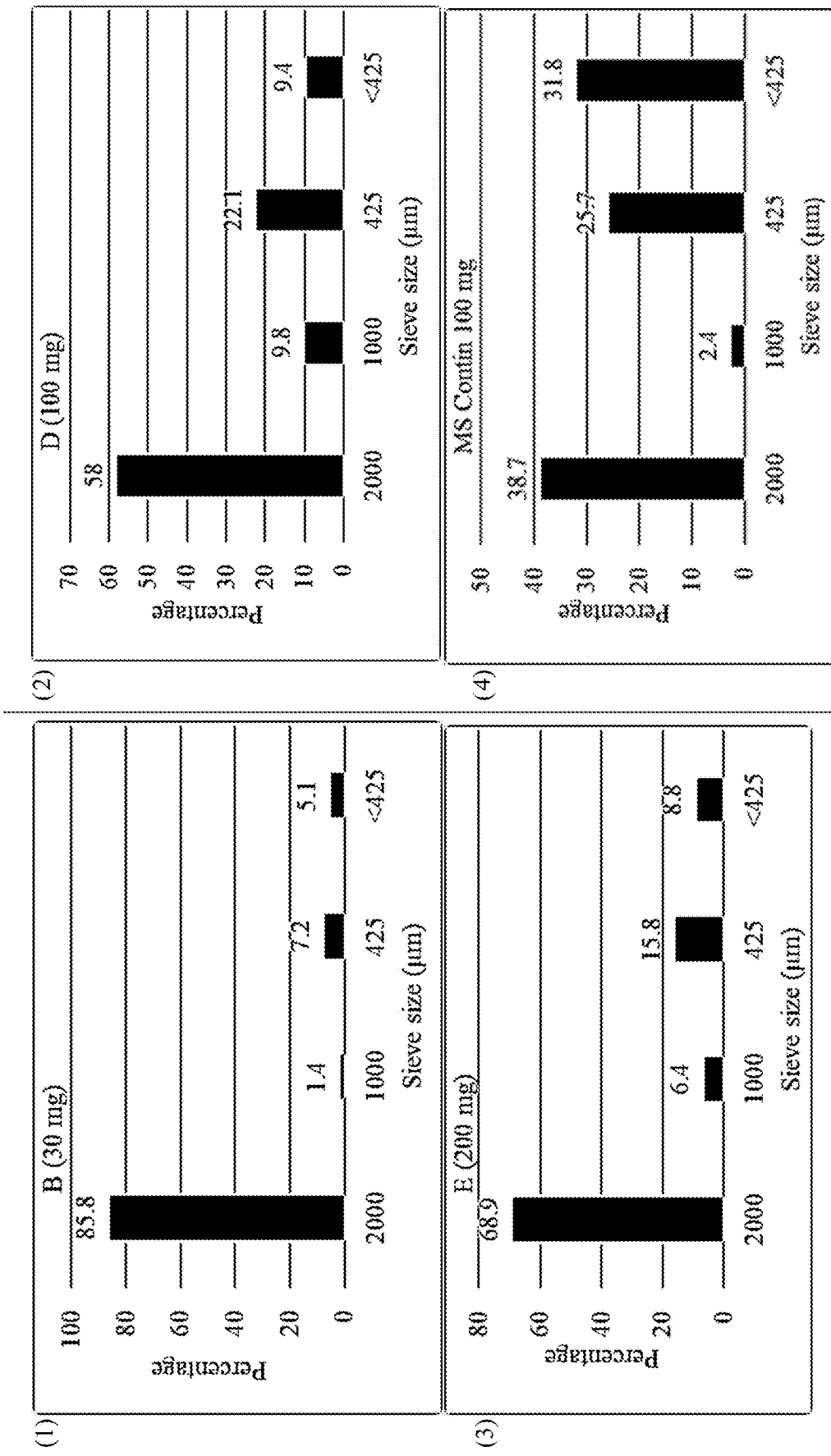
FIGS. 83a,b: Manipulation with Food Grater—Microplane®, 5100506, 18/8 Gauge Stainless Steel Blade FIGS. 84a,b: Manipulation with Razor Blade—GEM® Stainless Steel Uncoated Single Edge Industrial FIGS. 85a,b: Manipulation with Spice Grinder—Waring® Commercial, Model WSG30
Figure 84:
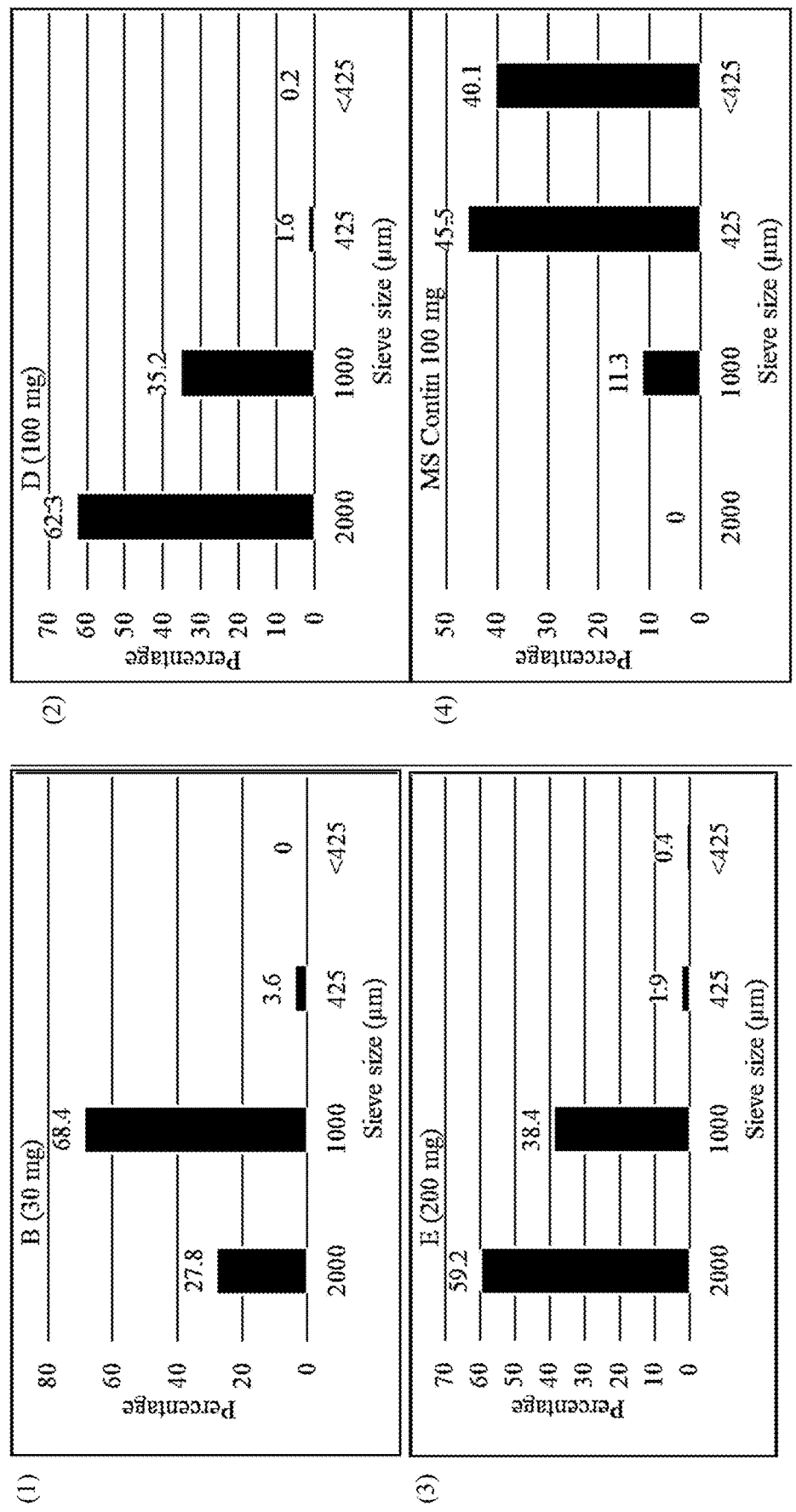
Figure 85:
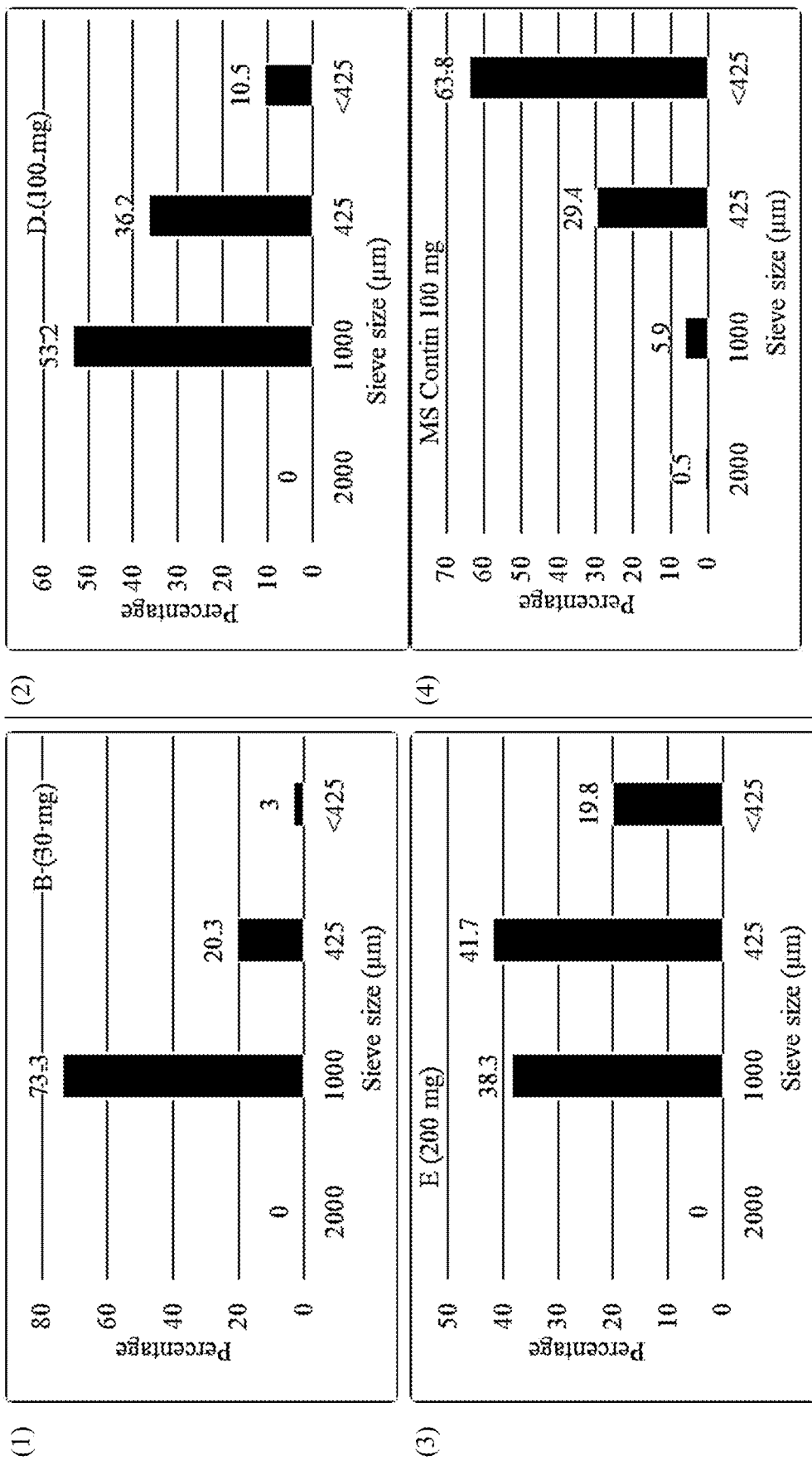
Figure 86:
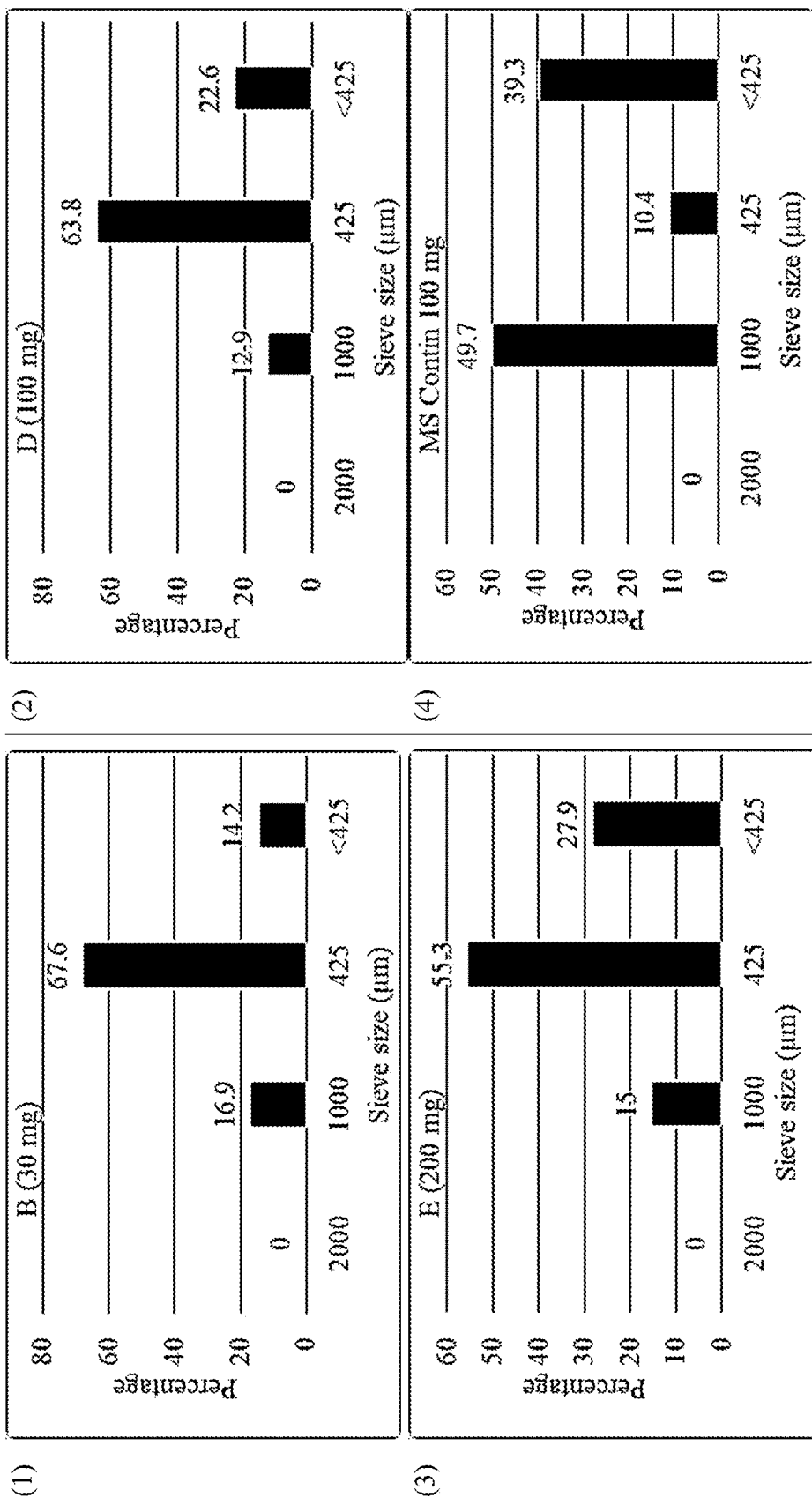
FIGS. 86a,b: Manipulation with Coffee Grinder Krups®
Figure 87:
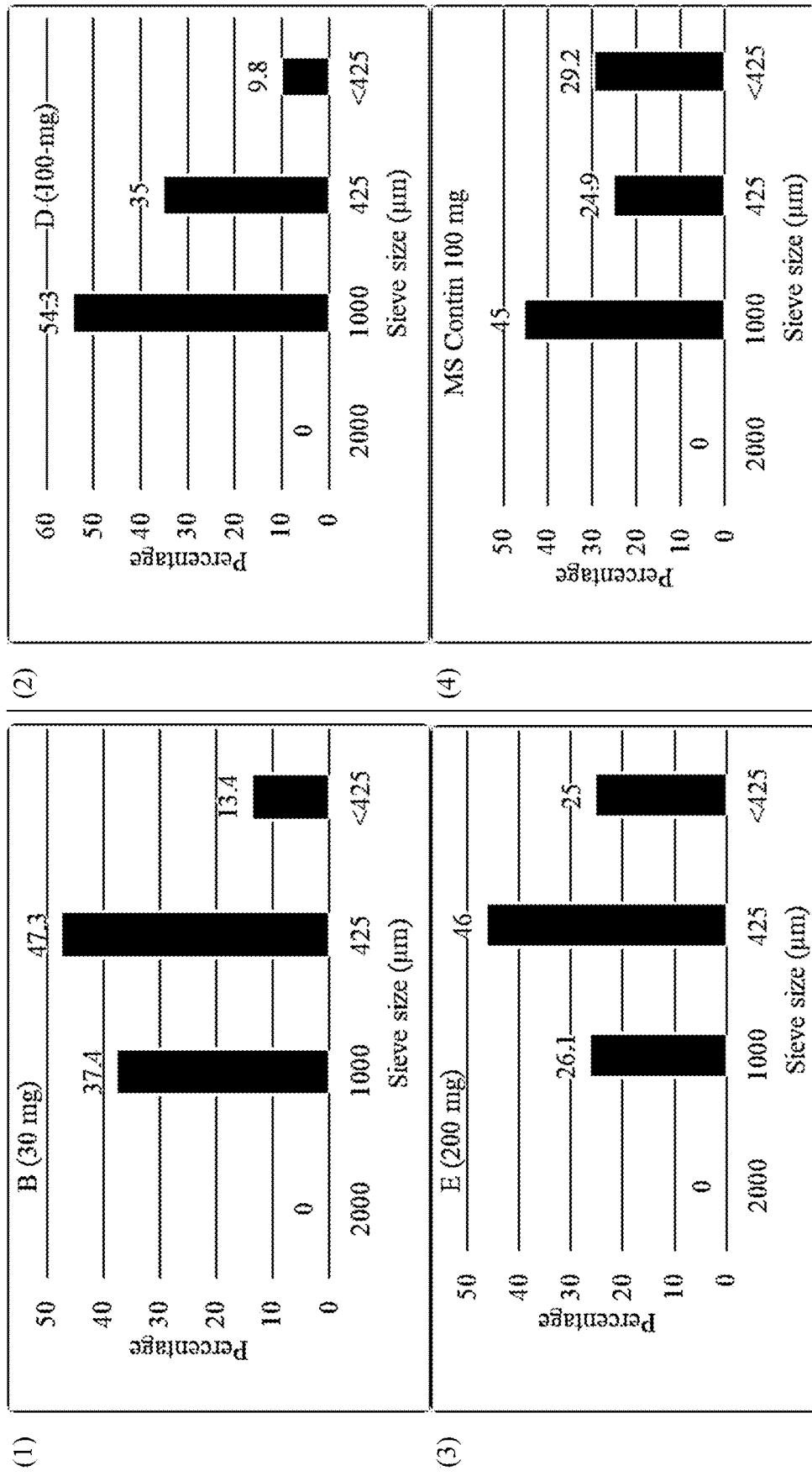
FIGS. 87a,b: Manipulation with Mill—IKA® A11 Basic

Average % Recovery of Volatilized and Residual
from Smoking Simulations with Alkalization (see FIG. 77).
Average % Recovery of Volatilized and Residual Morphine Sulfate
Pentahydrate from Smoking Simulation with Alkalization.

| | Heated 15 Minutes | | | | | | |
|---|---|---|---|---|---|---|---|
| | B | | | D | | | E |
| Temp | Vol. | Resid. | Total | Vol. | Resid. | Total | Vol. |
| 280 | 2.95% | 18.1% | 21.0% | n/a | 15.3% | 15.3% | 7.81% |
| 300 | 5.79% | 13.1% | 18.9% | 0.473% | 10.4% | 10.9% | 8.37% |
| 320 | 7.99% | 14.1% | 22.1% | 0.893% | 6.33% | 7.22% | 11.4% |
| Sterno | n/a | 5.60% | 3.73% | n/a | 2.21% | 0.74% | 12.5% |

| | Heated 15 Minutes | | | | | | |
|---|---|---|---|---|---|---|---|
| | E | | MS Contin® 100 mg | | | Morphine Sulfate Pentahydrate 200 mg | | |
| Temp | Resid. | Total | Vol. | Resid. | Total | Vol. | Resid. | Total |
| 280 | 31.3% | 39.1% | 19.9% | 45.6% | 65.6% | n/a | n/a | n/a |
| 300 | 11.6% | 20.0% | 23.7% | 17.1% | 40.8% | n/a | n/a | n/a |
| 320 | 9.35% | 20.8% | 21.2% | 2.61% | 22.9% | n/a | n/a | n/a |
| Sterno | 23.94% | 36.5% | 17.7% | n/a | 17.7% | 21.1% | 1.05% | 21.5% |

When the manipulated tablets were subjected to the simulated smoking experiments as is (without alkalization), only about 5% or less of the morphine content was volatilized from any tablet (including MS Contin®), see Table 14.2 and FIG. 76. However, when the optimized technique (with alkalization) was applied to manipulated tablets, MS Contin® was more smokable, where about 18 to 24% of morphine was volatilized. Only about 8 to 13% of the morphine content of tablet E (200 mg) was volatilizable, and less than 10% was volatilizable from tablets D and B (100 and 30 mg respectively), see Table 14.3 and FIG. 77. The data demonstrate that each strength of tablets according to the present invention is more resistant to attempt to smoke than MS Contin®.

Liquid/Liquid Extraction

Example 15

To investigate the isolation of morphine free base from tablets B, D and E as well as the comparator, MS Contin® 100 mg tablets, via liquid/liquid extraction the following extraction experiments were performed:
  a. All experiments were performed in triplicate.
  b. For optimization experiments, a tablet dose equivalent to 100 mg of morphine sulfate pentahydrate was used.
  c. For each tablet preparation, the manipulation (milling/grinding) was performed as described in Example 13.
  d. The weight of the tared weigh paper and manipulated material was recorded on the experimental worksheet.

e. The manipulated material was transferred to a separatory funnel labeled with the sample identification.
f. 50 mL of extraction solvent (0.1N HCl) was added to the separatory funnel.
g. The glass stopper was inserted and the separatory funnel was shaken vigorously to dissolve all of the pharmaceutical product.
h. Following dissolution, the pH was adjusted to pH 10 with small, 20-50 µL aliquots of 12 N NaOH.
i. After pH adjustment, 50 mL of methylene chloride: isopropanol (80:20) was added to the separatory funnel (addition 1).
j. The funnel was shaken for 10 minutes followed by rest for 20 minutes to allow the organic and aqueous phased to separate.
k. The lower organic phase (addition 1) was collected into a 125 mL Erlenmeyer flask labeled with the sample identification and a 1 mL aliquot of the organic phase was transferred to a test tube labeled with the sample identification and evaporated to dryness under a stream of nitrogen.
l. A second addition (addition 2) of 50 mL of Methylene Chloride:isopropanol (80:20) was added to the aqueous phase remaining in the separatory funnel.
m. The funnel was shaken for 10 minutes followed by rest to allow the organic and aqueous phased to separate.
n. The lower organic phase (addition 2) was collected into a 125 mL Erlenmeyer flask labeled with the sample identification and a 1 mL aliquot of the organic phase was transferred to a test tube labeled with the sample identification and evaporated to dryness under a stream of nitrogen.
o. The dried organic phases (addition 1 and 2) were reconstituted with 1 mL of 0.1N HCl.
p. Aliquots of the reconstituted organic residues and the aqueous phases were diluted at a 1:10 ratio by diluting 100 µL of extract into 900 µL of Simulated Gastric Fluid.
q. The diluted samples were filtered with 1 µm glass fiber syringe filters into 2 mL LC vials and run on HPLC-UV for analysis.

Calculations

Since both the tablets according to the invention and the comparator MS Contin® tablets contain morphine sulfate pentahydrate and samples were analyzed against the morphine free base-calibration curve, a correction factor was applied to the assayed value to calculate morphine sulfate pentahydrate equivalent to the amount of free base assayed. The following equation was applied to calculate the amount of recovered morphine base as morphine sulfate pentahydrate in milligrams:

$$\text{Morphine Sulfate Pentahydrate Recovered} = \frac{\text{observed concentration}\left(\frac{\mu g}{ml}\right) * \text{volume of solvent used (ml)} * \text{dilution factor}}{1,000\left(\mu\frac{g}{mg}\right)} \times \frac{MW(\text{Salt})}{MW(\text{free base})}$$

The molecular weights of morphine sulfate pentahydrate and morphine base used for this particular calculation are 379.43 and 285.34, respectively.

The percent recovery of morphine sulfate pentahydrate from milled and ground tablet material was calculated from the amount recovered and the dosage nominal content as shown by the following equation:

$$\% \text{ Recovery } API = \frac{\text{Observed weight of } API \text{ (mg)}}{\text{Mass of ground material (mg)}} \times \frac{\text{Average tablet mass (mg)}}{\text{Tablet Dosage (mg)}} \times 100$$

Figure 75:
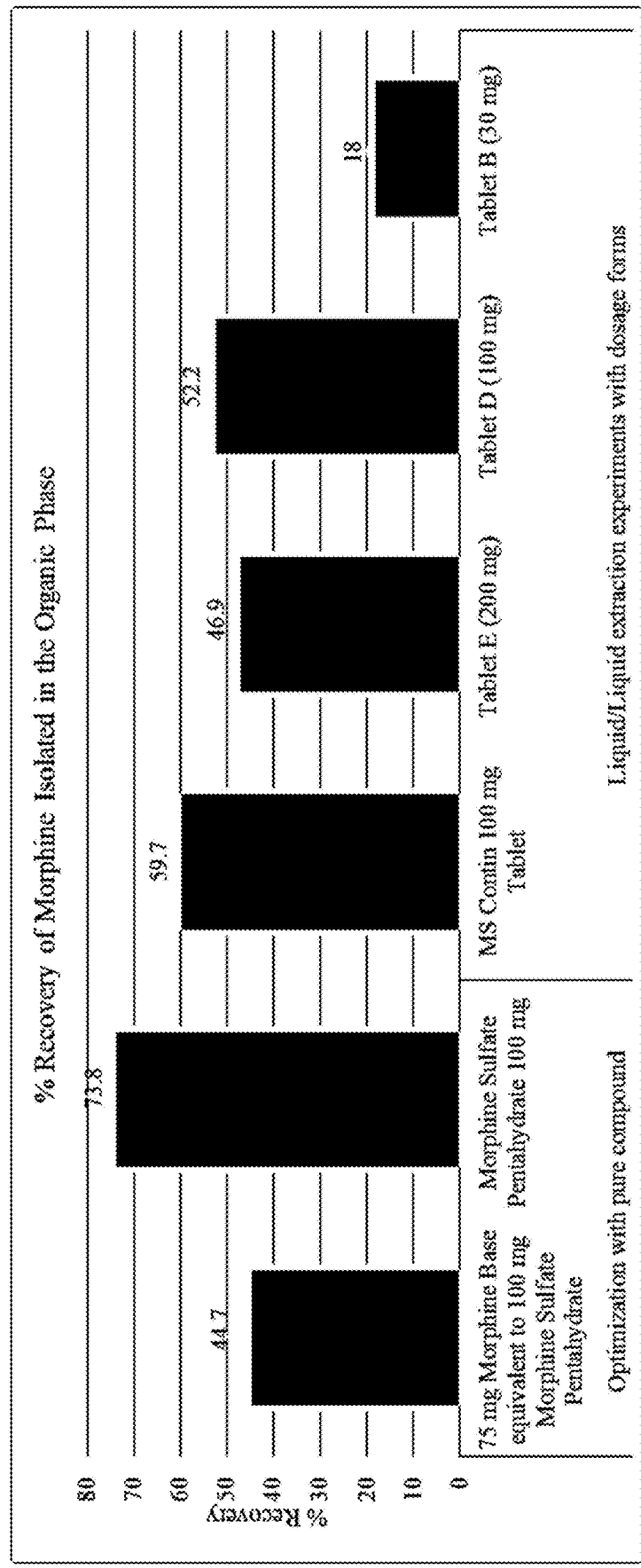
FIG. 75: Percentage Recovery of Morphine Isolated in the Organic Phase (Liquid-Liquid Extraction)

The results from the liquid-liquid extraction test are provided in Table 15.1 and are graphically displayed in FIG. 75.

TABLE 15.1

|  | Optimization with pure compound | | Liquid/Liquid extraction experiments with dosage forms | | | |
| --- | --- | --- | --- | --- | --- | --- |
|  | 75 mg morphine base equivalent to 100 mg morphine sulfate pentahydrate | morphine sulfate pentahydrate 100 mg | MS Contin® 100 mg Tablet | E Tablet | D Tablet | B Tablet |
| Average API % recovery from organic phase | 44.7 | 73.8 | 59.7 | 46.9 | 52.2 | 18 |

MS Contin® 100 mg tablets had the highest average % API from the combined organic phases at 59.7%. The tablets E, D and B (containing 200, 100 and 30 mg of morphine sulfate, respectively) had average API % recoveries of 46.9%, 52.2%, and 18.0% respectively in the combined organic phases. B tablets showed lower API recoveries than tablets D and E. These data show that each strength of the tablets in this application is more resistant to extraction relative to MS Contin® 100 mg.

Precipitation of Morphine Base

Example 16

To investigate the isolation of morphine free base from tablets B, D and E as well as the comparator, MS Contin® 100 mg tablets via precipitation the following experiments were performed:

a. All experiments were performed in triplicate.
b. For optimization experiments, a tablet dose equivalent to 100 mg of morphine sulfate pentahydrate was used.
c. For each tablet preparation, the manipulation was performed according to the procedure described above in example 13.

d. The weight of the tared weigh paper and manipulated material was recorded on the experimental worksheet.

e. The manipulated material was transferred to a 125 mL Erlenmeyer flask labeled with the sample identification.

f. 30 mL of extraction solvent (0.1N HCl) was added to the flask.

g. The glass stopper was inserted and the flask was shaken vigorously to dissolve all the pharmaceutical product.

h. Following dissolution, the pH was adjusted to pH 10 with small, 20-50 µL aliquots of 12 N NaOH.

i. The pH adjusted solution was shaken at 200 RPM for 10 minutes in a water bath shaker at room temperature.

j. After shaking at 200 RPM, the solution was placed in a freezer for 20 minutes.

k. After freezer incubation, 5 mL of acetone was added and the solution was mixed well.

l. The solution was then poured from the Erlenmeyer flask into the Buchner funnel that was fitted with a 0.45 um filter which was pre-wet with pH 10 buffer.

m. The Erlenmeyer flask was rinsed with 10 mL of pH 10 buffer and transfer to the Buchner funnel.

n. The solution was filtered under vacuum until all solution was filtered and the filter paper was dry.

o. The precipitate collected on the filter paper was transferred to a tared weigh paper and the mass of the collected precipitate was recorded.

p. The precipitate was then transferred to a clean 125 mL Erlenmeyer flask labeled with the sample identification and reconstituted with 50 mL of 0.1 N HCl.

q. The filter paper was transferred to a 50 mL plastic container and reconstituted with 30 mL of 0.1 N HCl.

r. Aliquots of the reconstituted precipitate solution, reconstituted filter solution, and the filtrate were diluted at a 1:10 ratio by diluting 100 µL of extract into 900 µL of Simulated Gastric Fluid.

s. The diluted samples were filtered with 1 µm glass fiber syringe filters into 2 mL LC vials and run on HPLC-UV for analysis.

Calculations

Since both the tablets according to the invention and the comparator MS Contin® tablets contain morphine sulfate pentahydrate and samples were analyzed against the morphine free base-calibration curve, a correction factor was applied to the assayed value to calculate morphine sulfate pentahydrate equivalent to the amount of free base assayed. The following equation was applied to calculate the amount of recovered morphine base as morphine sulfate pentahydrate in milligrams:

$$\text{Morphine Sulfate Pentahydrate Recovered} = \frac{\text{observed concentration}\left(\frac{\mu g}{ml}\right) * \text{volume of solvent used (ml)} * \text{dilution factor}}{1{,}000 \left(\mu \frac{g}{mg}\right)} \times \frac{\text{MW(Salt)}}{\text{MW(free base)}}$$

The molecular weights of morphine sulfate pentahydrate and morphine base used for this particular calculation are 379.43 and 285.34, respectively.

The percent recovery of morphine sulfate pentahydrate from milled and ground tablet material was calculated from the amount recovered and the dosage nominal content as shown by the following equation:

$$\% \text{ Recovery } API = \frac{\text{Observed weight of } API \text{ (mg)}}{\text{Mass of ground material (mg)}} \times \frac{\text{Average tablet mass (mg)}}{\text{Tablet Dosage (mg)}} \times 100$$

The results of the tests described above for 100 mg MS Contin® and tablets B, D and E are given in Table 16.1.

TABLE 16.1

| | Optimization with pure compound | | Precipitation | | | |
|---|---|---|---|---|---|---|
| | 75 mg morphine | | Experiments with dosage forms | | | |
| | base equivalent to 100 mg morphine sulfate pentahydrate | morphine sulfate pentahydrate 100 mg | MS Contin® 100 mg Tablet | Tablet E | Tablet D | Tablet B |
| Average API % recovery as precipitate | 51.5 | 66.5 | 45 | n/a | n/a | n/a |

All three dose strengths of the tablets according to the invention were unable to be filtered, even after 3 hours under vacuum. No purification of the API was possible with the tablets according to the invention. MS Contin® was filterable after about 1 hour under vacuum and recovered 45% of the labeled dose strength as precipitate.

Drug Liking/Intranasal Administration

Example 17

The objective of this in vivo study was to evaluate the abuse potential and pharmacodynamic (PD) effects of manipulated dosage forms of the present invention when intranasally-administered, as compared to manipulated MS Contin® reference tablets and placebo in recreational opioid users with a history of intranasal abuse.

Methodology

This was a single-center, randomized, double-blind, placebo- and positive-controlled crossover study in healthy male and female recreational opioid users with a history of intranasal abuse. This study evaluated the abuse potential, pharmacodynamic (PD), pharmacokinetic (PK) and safety profile of intranasally-administered manipulated tablets C (60 mg morphine sulfate) according to the present invention compared to manipulated (milled) 60 mg MS Contin® and placebo. The abuse potential, PK profile, and safety of the tablets administered orally as intact tablets were also evaluated.

The study was conducted in 2 parts. Part 1 essentially consisted of a dose finding study. Subjects who participated in Part 1 were to complete a Screening visit, Dose Selection Phase and a follow-up telephone call. Part 2 contained the actual Treatment Phase. Subjects who participated in Phase 2 were to complete a Screening visit, Qualification Phase, Treatment Phase (only if randomized to treatment after qualification) and a follow-up telephone call. Subjects who participated in Part 1 were not eligible to participate in Part 2 of the study. All subjects followed the same screening, end of study (EOS; performed only during the Dose Selection Phase and Treatment Phase), and follow-up procedures. All subjects received a naloxone challenge to ensure that subjects were not physically dependent on opioids (as also described in Example 3). In Part 1 of the study, 60 mg morphine sulfate (tablet C) was identified as the appropriate dose to be used in the Qualification and Treatment Phase of Part 2:

Qualification Phase

The Qualification Phase included a naloxone challenge to ensure that subjects were not dependent on opioids. Eligible subjects received the following treatments administered intranasally in a randomized, double-blind, 2-period crossover:

MS Contin® 60 mg tablet, manipulated

Lactose placebo powder

The washout period between treatments was at least 24 hours. Subjects were discharged approximately 24 hours after the last study drug administered. The total duration of the Qualification Phase was up to 3 days. Subjects in Part 2 had to demonstrate the ability to differentiate between active drug and placebo in the Qualification Phase before participation in the Treatment Phase.

Treatment Phase

The washout period between the Qualification Phase and the Treatment Phase was at least 72 hours. In the Treatment Phase, subjects received 1 oral and 1 intranasal treatment each period in a randomized, double-blind, double-dummy, 4-period crossover:

Placebo tablet, intact oral+tablet C, manipulated intranasal

Placebo tablet, intact oral+MS Contin® 60 mg tablet, manipulated intranasal

Placebo tablet, intact oral+placebo lactose powder intranasal

Tablet C, intact oral+placebo lactose powder intranasal

At each treatment period, subjects received treatments according to a randomization sequence in a double-blind, double-dummy, 4-period crossover manner. Subjects received the oral treatment first, followed immediately by the intranasal treatment.

For oral treatments: Subjects received intact tablet C or a matching placebo tablet with 240 mL water. Subjects were required to ingest the tablet within a period of approximately 1 minute.

For intranasal treatments: Subjects received manipulated tablets C, manipulated MS Contin® 60 mg tablets or placebo powder for intranasal administration. MS Contin® 60 mg tablets were crushed and ground by standardized methods using a mortar and pestle (as described in Example 13). The tablets C were milled with a Krups coffee mill. Prior to milling, the tablets were cut into eight pieces with a razor blade. The unit dose placebo powder samples for nasal administration consisted of 180±5 mg of lactose monohydrate. Subjects insufflated the prepared treatments as quickly as possible, up to a maximum of 5 minutes. Subjects were provided drug paraphernalia (i.e., a straw) to assist with the drug administration. A single nostril was to be used for administration within each dosing period; however, the nostril used may have changed between dosing periods. Subjects were not allowed to blow their nose for 1 hour postdose. Subjects were also instructed not to spit for at least 5 minutes after dosing.

The washout period between each of the above combined treatments was at least 4 days. Subjects were confined to the clinical research unit the day prior to study drug administration and for approximately 72 hours following the last study drug administration. End-of-study procedures were performed prior to discharge for all subjects, including those who discontinued early. A follow-up telephone call was conducted approximately 5 to 8 days after discharge or after early withdrawal from the study.

Subjects who met all the following inclusion criteria were entered into the study:

1. Provided written informed consent.
2. Male or female subjects 18 to 55 years of age, inclusive.
3. Body mass index (BMI) within the range of 18.0 to 34.0 kg/m2, inclusive, and a minimum weight of at least 50.0 kg at screening.
4. Moderately experienced opioid users who met the following criteria: 1) had used opioids for non-therapeutic purposes (i.e., for psychoactive effects) on at least 10 occasions in the past year and 2) had used opioids at least 3 times in the 12 weeks prior to Screening.
5. Must have experienced at least 3 occasions of intranasal opioid drug use for the purpose of recreational abuse/misuse in the last 12 months.
6. Must have reported taking a dose of opioid equivalent to 30 mg morphine sulfate (by any route of administration) or higher on at least one occasion in the past year.
7. Heterosexually active females of childbearing potential must have been using an adequate and reliable method of contraception during the study and through to at least 30 days after the last study drug administration. Heterosexually active females who were postmenopausal and not using approved contraception must have been post-menopausal ≥1 year and had an elevated serum follicle stimulating hormone (FSH) level (i.e., ≥50 mIU/mL).
8. Female subjects must have had a negative pregnancy test at screening and/or admission.
9. Able to speak, read, and understand English sufficiently to understand the nature of the study, to provide written informed consent, and to allow completion of all study assessments.
10. Must have been willing and able to abide by all study requirements and restrictions.

A subject was not eligible for inclusion in this study if any of the following criteria applied:

1. Clinically significant abnormality on physical examination, medical history, 12-lead electrocardiogram (ECG), vital signs, or laboratory values, as judged by the investigator or designee at screening.
2. Self-reported drug or alcohol dependence history (in the past 2 years) or subjects who had ever been in a drug rehabilitation program (other than treatment for smoking cessation or on a case-by-case basis; eg, as a requirement for reduced incarceration or in lieu of incarceration for the use of marijuana only) or current drug or alcohol dependence (within the last 12 months; except nicotine or caffeine), as defined by the Diagnostic and Statistical Manual of Mental Disorders (DSM-IV).
3. History or presence of any clinically significant illness (eg, cardiovascular, pulmonary, hepatic, renal, hematologic, gastrointestinal, endocrine, immunologic, dermatologic, neurologic, oncologic, musculoskeletal, or psychiatric) or any other condition, which in the opinion of the investigator would jeopardize the safety of the subject or the validity of the study results.
4. History or presence of hypotension, judged to be clinically significant based on investigator or designee judgment.
5. Use of prohibited medications (i.e., non-prescription, prescription medications, herbal or natural health products).
6. Female subjects who were pregnant or lactating or who were planning to become pregnant during the study or within 30 days after last study drug administration.
7. Evidence of clinically significant hepatic or renal impairment including alanine aminotransferase (ALT) or aspartate aminotransferase (AST)>1.5× the upper limit of normal (ULN) or serum total bilirubin >100% above ULN.
8. History of severe allergic reaction (including anaphylaxis) to any food, medication, or beesting or previous status asthmaticus.
9. History of allergy or hypersensitivity to morphine sulfate, naloxone or related drugs (eg, other opioids or opioid antagonists), or any of the drug excipients or other drug product components.
10. History of allergy to lactose.
11. Positive for Hepatitis B, Hepatitis C.
12. Whole blood donated within 56 days prior to entry into Dose Selection or Qualification Phase or through the EOS visit and for 30 days after completion of EOS visit, except as required by this protocol.
13. Plasma donated within 14 days prior to entry into Dose Selection or Qualification Phase or through the EOS visit, except as required by this protocol.
14. Difficulty with venous access or unsuitable for or unwilling to undergo catheter insertion.
15. Treatment with any investigational drug within 30 days prior to first drug administration of the Naloxone Challenge.
16. Consumption of greater than 20 cigarettes per day on average, in the month prior to screening, or inability to abstain from smoking (or use of any nicotine-containing substance) for at least 18 hours.
17. Positive urine drug screen at screening and/or admission. Positive results may have been repeated and/or subjects rescheduled at the investigator's discretion. On a case-by-case basis, at the discretion of the investigator, positive tetrahydrocannabinol (THC) may have been acceptable for subjects examined (full or brief physical examination) and interviewed by a licensed medical doctor to verify that they were not under the influence of cannabinoids.
18. Clinically significant abnormalities in the intranasal cavity (including presence of a deviated septum, perforated nasal septum, rhinorrhea, or excessive sneezing).
19. Any medical condition that in the opinion of the investigator would have interfered with the study procedures or data integrity or compromised the safety of the subject.
20. Subjects who participated in Part 1 Dose Selection Phase were not eligible for Part 2 Qualification/Treatment Phases.
21. A subject who, in the opinion of the investigator or designee, was considered unsuitable or unlikely to comply with the study protocol for any other reason.

The study analysis populations for Part 2 of the study were as follows:
Qualification Randomized Safety Population: Included all 98 subjects who were randomized to the Qualification Phase and received at least 1 dose of study drug.
Treatment Randomized Safety Population: Included all 40 subjects who were randomized to the Treatment Phase and received at least 1 dose of study drug.
Treatment Full Analysis for PD Population: Included 37 subjects who were randomized to the Treatment Phase and who completed all treatments in the Treatment Phase.
Treatment Full Analysis for PK Population: Included 39 subjects who were randomized to the Treatment Phase, received study drug, and had at least 1 valid PK metric for that treatment.

Pharmacodynamic Endpoints

The primary measures were the "at this moment" Drug Liking visual analog scale (VAS), Overall Drug Liking (ODL) VAS, and Take Drug Again (TDA) VAS after intranasal drug administration. Conclusions regarding relative abuse potential took into account responses on all primary and secondary measures, described below:

Balance of Effects:
Drug Liking VAS ("at this moment") (maximum effect [Emax], minimum effect [Emin], area under the effect curve from 0 to 12 hours postdose [AUE0-12], AUE from 0 to 24 hours postdose [AUE0-24], time-averaged area under the effect curve [TA_AUE]),
ODL VAS ($E_{max}$, $E_{min}$)
TDA VAS ($E_{max}$)
Subjective Drug Value (SDV; $E_{max}$)
Good and Bad Effects VAS ($E_{max}$, $AUE_{0-12}$, $AUE_{0-24}$, TA_AUE), The Drug Liking VAS and the ODL VAS assessed slightly different aspects of drug liking. Drug Liking VAS assessed the subject's liking of the drug "at the moment" the question was asked, was considered less likely to recall bias, and was useful for understanding the time-course of the effects. The ODL VAS was deemed to assess "global" drug effects (i.e., subjective effects over the whole course of the experience, including any carry-over effects) and had the additional advantage that the subject was generally sober at the time of the assessment (i.e., 12 hours or next day). Other VAS items measured positive, negative, and other subjective effects to assess the pharmacologic response to the study drugs. The TDA VAS indicated the subject's willingness to take the drug again. Pupillometry was used as an objective physiological PD measure as it is a sensitive measure of central opioid action and appears to be resistant to tolerance development with repeated administration.

Other effects of interest in this study were the following:
Positive effects:
High VAS,
Good Effects VAS ($E_{max}$, $AUE_{0-12}$, $AUE_{0-24}$, TA_AUE).
Negative subjective effects:
Bad Effects VAS ($E_{max}$, $AUE_{0-12}$, $AUE_{0-24}$, TA_AUE),
Feeling Sick VAS ($E_{max}$, $AUE_{0-12}$, $AUE_{0-24}$, TA_AUE)

Subject-rated assessment of intranasal irritation (SRAII) ($E_{max}$ for burning, need to blow nose, runny nose/nasal discharge, facial pain/pressure, nasal congestion, and nasal irritation)

Sedative Effects:
  Drowsiness/Alertness VAS ($E_{min}$, $AUE_{0-12}$, $AUE_{0-24}$, TA_AUE)

Other Effects:
  Any Effects VAS ($E_{max}$, $AUE_{0-12}$, $AUE_{0-24}$, TA_AUE)
  Ease of Snorting VAS (0.25-hour postdose),
  Open-ended feedback questions.

Objective Measures:
  Pupillometry (maximum pupil constriction [MPC], pupillometry area over the curve from 0 to 24 hours postdose ($PAOC_{0-24}$), time-averaged PAOC [TA_PAOC]),
  A nasal examination of both nostrils and observer-rated assessment of intranasal irritation measure (ORAII, $E_{max}$ for nasal congestion, irritation, and discharge) was conducted.

Each PD test cycle included objective and subjective measurements. Subjects rated their current perceptions of their subjective state and of the drug's effects. Subjective PD measures were administered and data were captured electronically using computerized proprietary software (PsychometRx™, formerly Scheduled Measurement System [SMS]; INC Research Toronto, Inc.). The observer-rated assessment of intranasal irritation, open-ended feedback questions and pupillometry measurements were documented on source documentation. Testing conditions for PD assessments were to remain as consistent as possible for each treatment period. Subjects were monitored carefully to ensure that they were completing the PD assessments appropriately.

For determining the subjective drug effects, each VAS was scored as an integer from 0 to 100, with anchors such as "Not at all" (score=0) to "Extremely" (score=100). Scales that referred specifically to drug effects (i.e., Good Drug Effects, Bad Drug Effects, Good and Bad Drug Effects, and Any Drug Effects) were not administered predose. When appropriate, VASs were administered as bipolar measures, meaning that the neutral point equaled 50 (eg, Drug Liking, ODL, and Alertness/Drowsiness). The neutral point was also labeled with an anchor, such as "neither like nor dislike". Other VASs were administered as unipolar measures (eg, Good, Bad, and Any Effects) where the neutral point equaled 0.

Pharmacokinetic Endpoints
  The PK endpoints included the following:
  $AUC_{last}$: Area under the plasma concentration-time curve from hour 0 to the last measurable plasma concentration. This parameter is also referred to as $AUC_{0-t}$ in the statistical analysis plan (SAP).
  $AUC_{inf}$: Area under the plasma concentration-time curve extrapolated to infinity.
  $C_{max}$: Maximum observed plasma concentration
  $T_{max}$: Time to maximum plasma concentration
  $t_{1/2}$: Apparent terminal phase half-life
  $C_{max}/T_{max}$ ratio: Average rate of increase in plasma concentration between dosing and $T_{max}$.

Serial PK blood samples were collected and analyzed to compare the exposure of morphine between manipulated tablets according to the present invention and MS Contin® tablets administered intranasally in opioid-experienced non-dependent recreational users.

Figure 97:
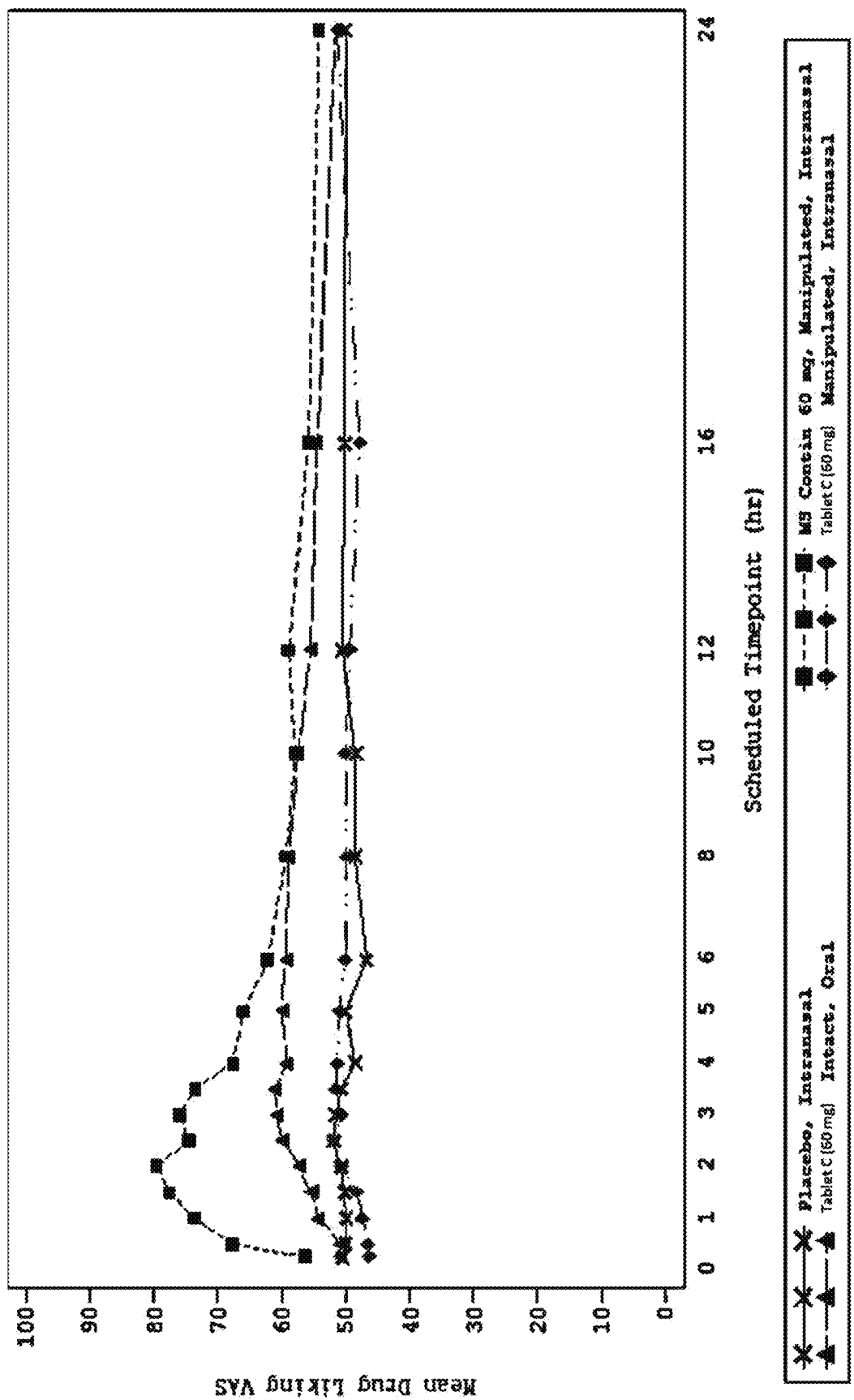
FIG. 97: Mean Curves of Drug Liking VAS for the Treatment Phase (Example 17)
FIGS. 98a,b: Syringeability Decision Tree (Example 13)

Safety Endpoints
  The safety endpoints included the following:
  Type, incidence, and severity of AEs
  Vital signs including pulse oximetry
  Clinical laboratory tests
  12-lead ECGs
  Physical examination Results for the Treatment Phase Mean scores of Drug Liking VAS are depicted graphically by time point and treatment in FIG. 97. Intranasal administration of manipulated MS Contin® produced the greatest mean Drug Liking VAS scores, followed by oral intact tablet C. Mean scores for intranasal manipulated tablet C were close to neutral (50 points) and similar to those for intranasal placebo.

Summary statistics for the PD parameters of "at the moment" Drug Liking VAS are presented for the Treatment Phase in Table 17.1, below. Intranasal administration of manipulated MS Contin® produced the greatest mean Drug Liking VAS scores, followed by oral intact tablet C. Mean scores for intranasal manipulated tablet C were close to neutral (50 points), and similar to those for intranasal placebo.

Mean and median Drug Liking VAS $E_{max}$ were greatest for intranasal manipulated MS Contin®, followed by oral intact tablet C, intranasal manipulated tablet C, and intranasal placebo. Median $E_{max}$ for intranasal manipulated MS Contin® was 37 points greater than that of placebo, 36 points greater than intranasal manipulated tablet C, and 21 points greater than oral intact tablet C. Intranasal manipulated tablet C had a similar median $E_{max}$ score compared with placebo (51 vs 50, respectively) and a lower score compared with oral intact tablet C (51 vs 66, respectively). The median time to peak effects ($TE_{max}$) was 1.5 hours for both intranasal manipulated MS Contin® and intranasal manipulated tablet C, and earlier compared with oral intact tablet C (median of 3 hours).

Consistent with $E_{max}$ scores, mean and median Drug Liking $AUE_{0-12}$, $AUE_{0-24}$, and TA_AUE were greater for intranasal manipulated MS Contin® compared with the other treatments, while the values were similar between intranasal manipulated tablet C and placebo.

Mean and median $E_{min}$ were neutral or slightly below neutral across all treatments.

TABLE 17.1

Pharmacodynamic Parameters of "at the moment" Drug Liking VAS for the Treatment Phase

| Parameter | Statistic | Placebo, Intranasal (N = 37) | MS Contin ® 60 mg Manipulated, Intranasal (N = 37) | Tablet C (60 mg) Intact, Oral (N = 37) | Tablet C (60 mg) Manipulated, Intranasal (N = 37) |
|---|---|---|---|---|---|
| $E_{max}$ | Mean (SD) | 53.4 (8.42) | 86.6 (14.68) | 66.9 (16.25) | 58.89 (13.82) |
| | Median | 50 | 87 | 66 | 51 |
| | Range | 50-84 | 51-100 | 50-100 | 50-100 |
| | 95% CI | 50.6, 56.2 | 81.7, 91.5 | 61.4, 72.3 | 54.3, 63.6 |

TABLE 17.1-continued

Pharmacodynamic Parameters of "at the moment" Drug Liking VAS for the Treatment Phase

| Parameter | Statistic | Placebo, Intranasal (N = 37) | MS Contin® 60 mg Manipulated, Intranasal (N = 37) | Tablet C (60 mg) Intact, Oral (N = 37) | Tablet C (60 mg) Manipulated, Intranasal (N = 37) |
|---|---|---|---|---|---|
| $TE_{max}$ (h) | Median | 0.25 | 1.5 | 3 | 1.5 |
|  | Range | 0.25-4.00 | 0.25-10.00 | 0.25-16.00 | 0.25-24.00 |
| Emin | Mean (SD) | 41.4 (18.3) | 44.1 (17.62) | 47.0 (10.17) | 36.8 (18.24) |
|  | Median | 50 | 50 | 50 | 46 |
|  | Range | 0-50 | 0-100 | 3-63 | 0-50 |
|  | 95% CI | 35.2, 47.5 | 38.2, 49.9 | 43.6, 50.4 | 30.7, 42.9 |
| $TE_{min}$ (h) | Median | 0.25 | 4 | 0.25 | 0.5 |
|  | Range | 0.25-16.00 | 0.25-24.00 | 0.23-24.00 | 0.25-16.00 |
| $AUE_{0-12}$ | Mean (SD) | 578.5 (74.34) | 762.9 (177.43) | 681.1 (138.29) | 587.3 (161.84) |
|  | Median | 588 | 750 | 630 | 588 |
|  | Range | 240-770 | 348-1175 | 535-1150 | 101-1168 |
|  | 95% CI | 553.7, 603.3 | 703.8, 822.1 | 635.0, 727.2 | 533.3, 641.3 |
| $AUE_{0-24}$ | Mean (SD) | 1180.1 (78.41) | 1432.2 (287.76) | 1324.8 (270.88) | 1178.4 (271.00) |
|  | Median | 1188 | 1356 | 1230 | 1188 |
|  | Range | 832-1404 | 957-2375 | 1000-2350 | 301-2368 |
|  | 95% CI | 1154.0, 1206.3 | 1336.2, 1528.1 | 1234.5, 1415.1 | 1088.0, 1268.8 |
| TA_AUE | Mean (SD) | 49.68 (3.304) | 60.30 (12.116) | 55.78 (11.412) | 49.61 (11.404) |
|  | Median | 50 | 57.1 | 51.8 | 50 |
|  | Range | 35.0-59.1 | 40.3-100.0 | 42.1-99.0 | 12.7-99.7 |
|  | 95% CI | 48.57, 50.78 | 56.26, 64.34 | 51.98, 59.59 | 45.81, 53.41 |

$AUE_{0-12}$ = area under the effect curve from time 0 to 12 hours postdose; $AUE_{0-24}$ = area under the effect curve from time 0 to 24 hours postdose; CI = confidence interval; $E_{max}$ = maximum effect; $E_{min}$ = minimum effect; N = number of subjects in the treatment group; PD = pharmacodynamic; SD = standard deviation; TA_AUE = time-averaged area under the effect curve; $TE_{max}$ = time of peak effect, $TE_{min}$ = time of minimum effect; VAS = visual analog scale Responses range from 0 (strong disliking) to 50 (neither like nor dislike) to 100 (strong liking).

Inferential statistical analysis results for Drug Liking VAS are presented in Table 17.2, below. The overall treatment effects were significant for $E_{max}$, $AUE_{0-12}$, $AUE_{0-24}$, and TA_AUE (P<0.001 for each parameter).

Drug Liking VAS $E_{max}$ results for MS Contin® were significantly higher (P<0.001) compared with placebo, thereby confirming study validity.

For Drug Liking VAS $E_{max}$, significant differences in median $E_{max}$ values were observed for all pairwise treatment comparisons (P≤0.041). The median $E_{max}$ value for intranasal manipulated tablet C was significantly lower vs. intranasal manipulated MS Contin® (P<0.001) and oral intact tablet C (P=0.006). The difference in median $E_{max}$ between intranasal manipulated tablet C vs. placebo was zero, but statistically significant (P=0.041). For oral intact tablet C, the median Drug Liking VAS $E_{max}$ value was significantly greater vs. placebo (P<0.001) and significantly lower vs intranasal manipulated MS Contin® (P<0.001).

For the Drug Liking VAS $AUE_{0-12}$, $AUE_{0-24}$, and TA_AUE parameters, significant differences were observed for all pairwise treatment comparisons (P<0.001), except for intranasal manipulated tablet C vs. placebo (P≥0.627 across all 3 parameters).

Overall treatment effects were statistically significant (P=0.001) for Drug Liking VAS $E_{min}$. A significantly (P=0.001) lower difference in $E_{min}$ was observed for intranasal manipulated tablet C vs. oral intact tablet C. The results from the comparison of oral intact tablet C vs placebo was also significant (P=0.024) although the median difference was zero. None of the other comparisons was significant (P≥0.078).

TABLE 17.2

Inferential Statistical Results for "at the moment" Drug Liking VAS $E_{max}$, AUE and TA_AUE for the Treatment Phase

| Drug Liking VAS | $E_{max}$ Median Difference (IQR) | P value | $AUE_{0-12}$ Median Difference (IQR) | P value | $AUE_{0-24}$ Median Difference (IQR) | P value | TA_AUE Median Difference (IQR) | P value |
|---|---|---|---|---|---|---|---|---|
| Overall Treatment Effect |  | <0.001 |  | <0.001 |  | <0.001 |  | <0.001 |
| MS Contin® vs Placebo | 35 (18.0, 50.0) | <0.001 | 168 (71.0, 284.0) | <0.001 | 178 (78.0, 360.0) | <0.001 | 7.5 (3.20, 15.10) | <0.001 |
| MS Contin® 60 mg, Manipulated, Intranasal vs Placebo, Intranasal |  |  |  |  |  |  |  |  |
| Tablet C vs Placebo | 14 (1.0, 20.0) | <0.001 | 48 (6.0, 120.0) | <0.001 | 48 (1.0, 121.0) | <0.001 | 2 (0.10, 5.10) | <0.001 |
| Tablet C (60 mg), Intact, Oral vs Placebo, Intranasal |  |  |  |  |  |  |  |  |
| Tablet C (60 mg), Manipulated, Intranasal vs Placebo, Intranasal | 0 (0.0, 9.0) | 0.041 | −1 (−26.0, 37.0) | 0.874 | −1 (−33.0, 36.0) | 0.627 | −0.1 (−1.30, 1.50) | 0.694 |
| Tablet C vs MS Contin® | −20 (−33.0, −8.0) | <0.001 | −79 (−162.0, 6.0) | <0.001 | −118 (−222.0, 10.0) | <0.001 | −4.9 (−9.40, 0.40) | <0.001 |
| Tablet C (60 mg), Intact, Oral vs MS Contin® 60 mg, Manipulated, Intranasal |  |  |  |  |  |  |  |  |
| Tablet C (60 mg), Manipulated, Intranasal vs MS Contin® 60 mg, Manipulated, Intranasal | −27 (−49.0, −12.0) | <0.001 | −151 (−235.0, −49.0) | <0.001 | −164 (−327.0, −64.0) | <0.001 | −6.9 (−13.70, −2.70) | <0.001 |

TABLE 17.2-continued

Inferential Statistical Results for "at the moment" Drug Liking VAS $E_{max}$, AUE and TA_AUE for the Treatment Phase

| Drug Liking VAS | $E_{max}$ Median Difference (IQR) | P value | $AUE_{0-12}$ Median Difference (IQR) | P value | $AUE_{0-24}$ Median Difference (IQR) | P value | TA_AUE Median Difference (IQR) | P value |
|---|---|---|---|---|---|---|---|---|
| Tablet C Manipulated vs Intact Tablet C (60 mg), Manipulated, Intranasal vs tablet C (60 mg), Intact, Oral | −7 (−17.0, 0.0) | 0.006 | −52 (−122.0, 0.0) | <0.001 | −52 (−151.0, 6.0) | <0.001 | −2.2 (−6.40, 0.30) | <0.001 |

$AUE_{0-12}$ = area under the effect curve from time 0 to 12 hours postdose; $AUE_{0-24}$ = area under the effect curve from time 0 to 24 hours postdose; $E_{max}$ = maximum effect; IQR = inter-quartile range; PD = pharmacodynamic; TA_AUE = time-averaged area under the effect curve; VAS = Visual analog scale. Overall Treatment Effect was assessed using Friedman's test. Pairwise treatment comparisons were assessed using the Wilcoxon sign-rank test on the within-subject differences.

Summary statistics for the PD parameters of Overall Drug Liking (ODL) VAS are presented in Table 17.3, below.

Median ODL VAS $E_{max}$ was greatest for intranasal manipulated MS Contin®, followed by oral intact Tablet C, and both intranasal manipulated Tablet C and placebo (the latter two treatments had equivalent median $E_{max}$ values of 50.0 or neutral). Median $E_{max}$ for intranasal manipulated MS Contin® was 38 points greater than intranasal manipulated Tablet C and placebo, and 24 points greater than oral intact Tablet C for ODL VAS.

Median ODL VAS $E_{min}$ was neutral or towards the higher end of the acceptable neutral range (i.e., 59.0) for all treatments, except intranasal manipulated MS Contin® (value of 74.0).

TABLE 17.3

Summary Pharmacodynamic Parameters of Overall Drug Liking (ODL) VAS for the Treatment Phase

| Parameter | Statistic | Placebo, Intranasal (N = 37) | MS Contin ® 60 mg, Manipulated, Intranasal (N = 37) | Tablet C (60 mg), Intact, Oral (N = 37) | Tablet C (60 mg), Manipulated, Intranasal (N = 37) |
|---|---|---|---|---|---|
| $E_{max}$ | Mean (SD) | 49.2 (17.68) | 80.4 (24.37) | 66.7 (17.25) | 50.9 (22.01) |
|  | Median | 50 | 88 | 64 | 50 |
|  | Range | 0-100 | 0-100 | 27-100 | 0-100 |
|  | 95% CI | 43.3, 55.1 | 72.3, 88.5 | 61.0, 72.5 | 43.5, 58.2 |
| $E_{min}$ | Mean (SD) | 48.3 (17.58) | 69.8 (27.19) | 59.2 (18.06) | 38.9 (24.30) |
|  | Median | 50 | 74 | 59 | 50 |
|  | Range | 0-100 | 0-100 | 3-100 | 0-99 |
|  | 95% CI | 42.4, 54.2 | 60.7, 78.8 | 53.2, 65.3 | 30.8, 47.0 |

CI = confidence interval; $E_{max}$ = maximum effect; $E_{min}$ = minimum effect; N = number of subjects in the treatment group; PD = pharmacodynamic; SD = standard deviation; VAS = visual analog scale Responses range from 0 (strong disliking) to 50 (neither like nor dislike) to 100 (strong liking).

Inferential statistical analysis results for ODL VAS are presented in Table 17.4, below. The overall treatment effects were significant for $E_{max}$ and $E_{min}$ (P<0.001 for each parameter).

Overall Drug Liking VAS $E_{max}$ results for MS Contin® were significantly higher (P<0.001) compared with placebo, thereby confirming study validity.

For ODL VAS $E_{max}$, significant differences in median $E_{max}$ values were observed for all pairwise treatment comparisons (P<0.001), except for intranasal manipulated Tablet C vs placebo (P=0.879). Median $E_{max}$ values were significantly lower for intranasal manipulated Tablet C vs. intranasal manipulated MS Contin® and oral intact Tablet C. For oral intact tablet C, the median ODL $E_{max}$ was significantly greater vs placebo and significantly lower vs intranasal manipulated MS Contin®.

For ODL VAS $E_{min}$, significant differences in median $E_{min}$ values were observed for all treatment comparisons (P≤0.037). Median $E_{min}$ values were significantly lower for intranasal manipulated tablet C vs. all other treatments. Oral intact tablet C showed a significantly greater difference in median $E_{min}$ vs placebo (P=0.002) and a significantly lower difference vs. intranasal manipulated MS Contin® (P=0.019).

TABLE 17.4

Inferential Statistical Results for Overall Drug Liking (ODL) VAS, $E_{max}$ and $E_{min}$ for the Treatment Phase

| Overall Drug Liking VAS | $E_{max}$ Median Difference (IQR) | P value | $E_{min}$ Median Difference (IQR) | P value |
|---|---|---|---|---|
| Overall Treatment Effect | | <0.001 | | <0.001 |
| MS Contin ® vs Placebo | 38 | | 24 | |
| MS Contin ® 60 mg, Manipulated, Intranasal vs Placebo, Intranasal | (15.0, 50.0) | <0.001 | (4.0, 41.0) | <0.001 |
| Tablet C vs Placebo | | | | |
| Tablet C (60 mg), Intact, Oral vs Placebo, Intranasal | 14 (0.0, 26.0) | <0.001 | 9 (0.0, 16.0) | 0.002 |
| Tablet C (60 mg), Manipulated, Intranasal vs Placebo, Intranasal | 0 | 0.879 | −2 | 0.037 |
| | (−4.0, 10.0) | | (−35.0, 0.0) | |
| Tablet C vs MS Contin ® | | | | |
| Tablet C (60 mg), Intact, Oral vs MS Contin ® 60 mg, Manipulated, Intranasal | −15 | <0.001 | −17 | 0.019 |
| | (−32.0, −1.0) | | (−30.0, 1.0) | |
| Tablet C (60 mg), Manipulated, Intranasal vs MS Contin ® 60 mg, Manipulated, Intranasal | −31 | <0.001 | −31 | <0.001 |
| | (−50.0, −7.0) | | (−50.0, −14.0) | |
| Tablet C Manipulated vs Intact | | | | |
| Tablet C (60 mg) Manipulated, Intranasal vs Tablet C (60 mg) Intact, Oral | −12 (−26.0, 0.0) | <0.001 | −15 (−37.0, 0.0) | <0.001 |

$E_{max}$ = maximum effect; $E_{min}$ = minimum effect; IQR = inter-quartile range; PD = pharmacodynamic; VAS = Visual analog scale. Overall Treatment Effect was assessed using Friedman's test. Pairwise treatment comparisons were assessed using the Wilcoxon sign-rank test on the within-subject differences.

Summary statistics for Take Drug Again (TDA) VAS $E_{max}$ are presented in Table 17.5, below. Similar to the results observed for ODL VAS, median $E_{max}$ was greatest for intranasal manipulated MS Contin®, followed by oral intact tablet C, and both intranasal manipulated tablet C and placebo (the latter two treatments had equivalent median $E_{max}$ values of 50.0 or neutral). Median $E_{max}$ for MS Contin® was 44 points greater than intranasal manipulated tablet C and placebo, and 28 points greater than oral intact tablet C.

Contin® were significantly higher (P<0.001) compared with placebo, thereby confirming study validity.

Significant differences in median TDA VAS $E_{max}$ values were observed for all pairwise treatment comparisons (P<0.001), except for intranasal manipulated tablet C vs placebo (P=0.552). Median $E_{max}$ values were significantly lower for intranasal manipulated tablet C vs intranasal

TABLE 17.5

Summary Pharmacodynamic Parameter $E_{max}$ of Take Drug Again (TDA) VAS for the Treatment Phase

| Parameter | Statistic | Placebo, Intranasal (N = 37) | MS Contin ® 60 mg, Manipulated, Intranasal (N = 37) | Tablet C (60 mg), Intact, Oral (N = 37) | Tablet C (60 mg), Manipulated, Intranasal (N = 37) |
|---|---|---|---|---|---|
| $E_{max}$ | Mean (SD) | 46.5 (21.02) | 81.8 (25.46) | 65.8 (22.22) | 42.7 (29.44) |
| | Median | 50 | 94 | 66 | 50 |
| | Range | 0-100 | 0-100 | 0-100 | 0-100 |
| | 95% CI | 39.5, 53.5 | 73.3, 90.3 | 58.3, 73.2 | 32.9, 52.5 |

CI = confidence interval; $E_{max}$ = maximum effect; N = number of subjects in the treatment group; PD = pharmacodynamic; SD = standard deviation; VAS = visual analog scale Responses range from 0 (definitely not) to 50 (neutral) to 100 (definitely so).

Inferential statistical analysis results for TDA VAS are presented in Table 17.6, below.

The overall treatment effects were significant for $E_{max}$ (P<0.001). Take Drug Again VAS $E_{max}$ results for MS manipulated MS Contin® and oral intact tablet C. For oral intact tablet C, the median TDA VAS $E_{max}$ was significantly greater vs placebo and significantly lower vs intranasal manipulated MS Contin®.

TABLE 17.6

Inferential Statistical Results for Take Drug Again (TDA) VAS, $E_{max}$ for the Treatment Phase

| Take Drug Again VAS | $E_{max}$ Median Difference (IQR) | P value |
|---|---|---|
| Overall Treatment Effect |  | <0.001 |
| MS Contin® vs Placebo |  |  |
| MS Contin® 60 mg. Manipulated, Intranasal vs Placebo, Intranasal | 47 (20.0, 50.0) | <0.001 |
| Tablet C (60 mg) vs Placebo |  |  |
| Tablet C (60 mg), Intact, Oral vs Placebo, Intranasal | 14 (1.0, 25.0) | <0.001 |
| Tablet C (60 mg), Manipulated, Intranasal vs Placebo, Intranasal | 0 (−40.0, 11.0) | 0.552 |
| Tablet C (60 mg) vs MS Contin® |  |  |
| Tablet C (60 mg), Intact, Oral vs MS Contin® 60 mg, Manipulated, Intranasal | −24 (−33.0, 0.0) | <0.001 |
| Tablet C (60 mg), Manipulated, Intranasal vs MS Contin® 60 mg, Manipulated, Intranasal | −39 (−50.0, −22.0) | <0.001 |
| Tablet C (60 mg) Manipulated vs Intact |  |  |
| Tablet C (60 mg), Manipulated, Intranasal vs Tablet C (60 mg), Intact, Oral | −19 (−47.0, 0.0) | <0.001 |

$E_{max}$ = maximum effect; IQR = inter-quartile range; PD = pharmacodynamic; VAS = visual analog scale. Overall Treatment Effect was assessed using Friedman's test. Pairwise treatment comparisons were assessed using the Wilcoxon sign-rank test on the within-subject differences.

Summary of the Results:

Drug Liking VAS $E_{max}$, ODL VAS $E_{max}$, and TDA VAS $E_{max}$ (primary measures) for intranasal manipulated MS Contin® 60 mg were significantly higher compared with intranasal placebo (P<0.001 for each parameter), thereby confirming study validity.

Intranasal administration of manipulated tablet C (60 mg) resulted in statistically significant differences in subjective and objective effects compared with manipulated MS Contin® 60 mg. Significantly lower peak ($E_{max}$) and TA_AUE values were observed for most measures of balance, including primary measures (i.e., Drug Liking VAS, ODL VAS, and TDA VAS), and positive and objective (pupillometry) effects following intranasal manipulated tablet C compared with manipulated MS Contin® 60 mg.

Intranasal administration of manipulated tablet C resulted in statistically significant differences in Drug Liking VAS, High VAS, and Good Effects VAS $E_{max}$ values compared with intranasal placebo; however, differences in ODL VAS $E_{max}$ and TDA VAS $E_{max}$ were not statistically significant. There were no statistically significant differences in sedative effects and negative effects for intranasal manipulated tablet C compared with intranasal placebo.

Compared with oral administration of intact tablet C, intranasal administration of manipulated tablet C, resulted in statistically significant differences (decrease) in most measures of balance, including Drug Liking VAS, ODL VAS, and TDA VAS, and positive effects and pupillometry (MPC only).

Twenty-nine of 37 subjects (78%) showed at least a 30% reduction and 73% at least a 50% reduction in Drug Liking VAS $E_{max}$ for intranasal manipulated tablet C (60 mg) compared with intranasal manipulated MS Contin® 60 mg, and the reductions were statistically significant (P<0.001 and P=0.003, respectively). In addition, 22 of 37 subjects (59%) showed at least a 30% reduction, and 57% at least a 50% reduction, in Drug Liking VAS Ex for intranasal manipulated tablet C compared with the oral intact tablet; however, the results were not statistically significant (P=0.125 and 0.206, respectively).

The median percent dose insufflated was similar between intranasal manipulated MS Contin® 60 mg and intranasal manipulated tablet C (60 mg), 98% and 99%, respectively; however, a greater number of subjects had lower percent insufflation values for manipulated tablet C compared with manipulated MS Contin® 60 mg, as shown by the mean values (84% vs 96%, respectively).

Significantly (P≤0.018) greater subject-rated nasal irritation peak effects were observed for intranasal manipulated tablet C compared with manipulated MS Contin® 60 mg for Need to Blow Nose, Nasal Congestion, and Nasal Irritation. Overall, subjects had greater difficulty insufflating the dose of manipulated tablet C and generally described a more negative experience compared with manipulated MS Contin® 60 mg (median Ease of Snorting VAS score for manipulated tablet C was 70 [closer to 100="very difficult"] vs manipulated MS Contin® 60 mg and placebo of 2 and 0, respectively [close or at 0="very easy"])

Oral administration of intact tablet C resulted in statistically significant differences (increase) for almost all subjective and objective (pupillometry) effects compared with placebo; differences in negative effects (Bad Effects VAS and Feeling Sick VAS) and peak Drowsiness/Alertness VAS scores were not statistically significant. For all measures of subjective and objective (pupillometry) effects, statistically significant decreases were observed for oral intact tablet C compared with intranasal administration of MS Contin® 60 mg.

Pharmacokinetics of Morphine

TABLE 17.7

Summary of Morphine Pharmacokinetic Parameters for the Treatment Phase

| Parameter | Statistic | MS Contin® 60 mg, Manipulated, Intranasal | Tablet C (60 mg), Intact, Oral | Tablet C (60 mg), Manipulated, Intranasal |
|---|---|---|---|---|
| N |  | 39 | 37 | 38 |
| $C_{max}$ (ng/mL) | n, missing | 0 | 0 | 0 |
|  | Mean (SD) | 50.08 (23.553) | 14.51 (4.097) | 12.27 (6.540) |
|  | Median | 43.9 | 14.5 | 11.35 |
|  | Range | 13.0-121.0 | 8.7-24.4 | 2.3-26.4 |

TABLE 17.7-continued

Summary of Morphine Pharmacokinetic Parameters for the Treatment Phase

| Parameter | Statistic | MS Contin ® 60 mg, Manipulated, Intranasal | Tablet C (60 mg), Intact, Oral | Tablet C (60 mg), Manipulated, Intranasal |
|---|---|---|---|---|
| | Geo Mean (Geo %CV) | 45.44 (47.03) | 13.95 (28.99) | 10.57 (62.55) |
| $T_{max}$ (h) | n, missling | 0 | 0 | 0 |
| | Median | 1.08 | 2.58 | 2.58 |
| | Range | 0.17-2.58 | 1.08-8.08 | 0.17-10.08 |
| $AUC_{last}$ (h · ng/mL) | n, missing | 0 | 0 | 0 |
| | Mean (SD) | 247.2 (71.46) | 200.9 (40.17) | 161.7 (114.70) |
| | Median | 229.9 | 197.3 | 112.6 |
| | Range | 60-449 | 133-320 | 8-438 |
| | Geo Mean (Geo % CV) | 235.8 (34.4) | 197.2 (19.5) | 120.8 (104.1) |
| $AUC_{inf}$ (h · ng/mL) | n, missing | 1 | 2 | 2 |
| | Mean (SD) | 257.9 (79.32) | 216.9 (45.22) | 170.7 (117.21) |
| | Median | 239.9 | 214 | 121 |
| | Range | 62-528 | 134-325 | 8-446 |
| | Geo Mean (Geo %CV) | 245.0 (35.6) | 212.5 (20.8) | 130.1 (99.0) |
| $t^{1/2}$ (h) | n, missing | 2 | 2 | 2 |
| | Median | 15.2 | 17.46 | 9.35 |
| | Range | 6.8-36.9 | 5.7-31.3 | 2.8-25.2 |
| Cmax/Tmax Ratio (ng/mL/h) | n, missing | 0 | 0 | 0 |
| | Mean (SD) | 76.37 (68.462) | 5.513 (2.6941) | 6.154 (4.1341) |
| | Median | 49.81 | 5.519 | 5.074 |
| | Range | 12.1-325.9 | 1.24-12.28 | 0.98-15.51 |
| | Geo Mean (Geo % CV) | 55.28 (94.72) | 4.835 (59.608) | 4.812 (85.975) |

$AUC_{inf}$ = area under the plasma concentration vs time curve extrapolated to infinity; $AUC_{last}$ = area under the plasma concentration vs time curve from time 0 to last quantifiable concentration; $C_{max}$ = maximum plasma concentration; CV = coefficient of variation, Geo = geometric; n = number of observations; N = number of subjects in the treatment group; PK = pharmacokinetic; SD = standard deviation; $t^{1/2}$ = terminal elimination half-life, $T_{max}$ = time to maximum plasma concentration Table 17.7 shows that the mean rate and extent of morphine absorption ($C_{max}$, $AUC_{last}$, and $AUC_{inf}$) was highest following intranasal administration of manipulated MS Contin® 60 mg (50.08 ng/mL, 247.2 h·ng/mL, and 257.9 h·ng/mL respectively); and lowest after intranasal administration of manipulated tablet C (60 mg), 12.27 ng/mL, 161.7 h·ng/mL, and 170.7 h·ng/mL respectively. The mean $C_{max}$, $AUC_{Last}$, and $AUC_{inf}$ of morphine following oral administration of intact tablets C were 14.51 ng/mL, 200.9 h·ng/mL, and 216.9 h·ng/mL respectively.

The peak morphine plasma levels were achieved very quickly, within 1.08 hours following intranasal administration of manipulated MS Contin® 60 mg as opposed to within 2.58 hours following oral and intranasal administration of intact and manipulated tablet C, respectively (median values).

The $C_{max}$, $AUC_{last}$ and $AUC_{inf}$ of morphine were slightly higher after oral administration of intact tablets C than intranasal administration of manipulated tablets C.

The terminal elimination half-life was highest following oral administration of intact tablets C (17.46 hours); following intranasal administration of manipulated MS Contin® 60 mg and tablets C, the terminal elimination half-lives were 15.20 hours and 9.35 hours, respectively (median values).

Both the mean and median values of the $C_{max}/T_{max}$ ratio were highest (76.37 ng/mL/h and 49.81 ng/mL/h, respectively) following intranasal manipulated MS Contin® 60 mg as compared with oral intact tablet C (5.513 ng/mL/h and 5.519 ng/mL/h, respectively) and intranasal manipulated tablet C (6.154 ng/mL/h and 5.074 ng/mL/h, respectively).

Conclusions

This study demonstrated that intranasal administration of manipulated tablet C produced temporary aversive nasal effects and statistically significant reductions in peak positive subjective measures of drug liking (eg, primary measures Drug Liking VAS $E_{max}$, ODL $E_{max}$, and TDA $E_{max}$) compared with intranasal administration of manipulated MS Contin® 60 mg. The rate and extent of morphine exposure ($C_{max}$, $AUC_{last}$, and $AUC_{inf}$) were lowest after intranasal administration of manipulated tablet C, possibly attributed, in part, to the greater difficulty some of the subjects experienced insufflating the dose of manipulated tablet C compared with manipulated MS Contin® and placebo powder. The incidence of TEAEs was consistent with the known effects of opioids and was higher following intranasal manipulated MS Contin® compared with intranasal manipulated tablet C and oral intact tablet C. Taken together, the results of the study indicate that the physicochemical properties of the tablets described in this application provide barriers that lower the intranasal abuse potential of the tablets of this application compared to MS Contin®.

Storage Stability

Example 18

Experimental stability studies were conducted on tablets AI and AJ. The experimental stability packaging configuration consisted of 100 tablets in a HDPE 120 cc thick wall bottle, with and without oxygen absorber packets; and induction sealed cap. The study duration and condition for each packaging configuration was 6 months at 25° C./60% RH and 40° C./75% RH ("RH" meaning "residual humidity"). The experimental stability results (in-vitro dissolution rates of morphine sulfate before/after storage under these conditions) are presented in Tables 18.1 to 18.4. In these Tables, "25/60" and "40/75" mean "25° C./60% RH" and "40° C./75% RH", respectively.

TABLE 18.1

Experimental Stability Tablet AI (15 mg, no oxygen absorber)

|  |  | Initial in-vitro dissolution | In-vitro dissolution after 6 Months | |
|---|---|---|---|---|
|  |  |  | 25/60 | 40/75 |
| Assay (% LC) |  | 93.5 | 94.6 | 94.9 |
| Average | 1 hr | 23 (23-24) | 24 (23-25) | 25 (24-26) |
| % Dissolved | 2 hr | 36 (35-37) | 37 (36-39) | 38 (37-39) |
| (min-max) | 6 hr | 70 (67-72) | 72 (70-74) | 75 (73-76) |
|  | 12 hr | 89 (87-92) | 92 (87-95) | 94 (92-95) |
| MNO (%) |  | <LOQ | <LOQ | <LOQ |
| PDM (%) |  | <LOQ | <LOQ | <LOQ |
| Total Deg. (%) |  | <LOQ | <LOQ | 0.1 |

LOQ = 0.05%

TABLE 18.2

Experimental Stability Tablet AI (15 mg, with one oxygen absorber)

|  |  | Initial in-vitro dissolution | In-vitro dissolution after 6 Months | |
|---|---|---|---|---|
|  |  |  | 25/60 | 40/75 |
| Assay (% LC) |  | 93.5 | 95.1 | 94.8 |
| Average | 1 hr | 23 (23-24) | 24 (22-25) | 24 (23-25) |
| % Dissolved | 2 hr | 36 (35-37) | 37 (35-39) | 38 (36-39) |
| (min-max) | 6 hr | 70 (67-72) | 71 (67-74) | 74 (70-76) |
|  | 12 hr | 89 (87-92) | 90 (85-94) | 92 (86-96) |
| MNO (%) |  | <LOQ | <LOQ | <LOQ |
| PDM (%) |  | <LOQ | <LOQ | <LOQ |
| Total Deg. (%) |  | <LOQ | <LOQ | <LOQ |

LOQ = 0.05%

TABLE 18.3

Experimental Stability Tablet AJ (100 mg, no oxygen absorber)

|  |  | Initial in-vitro dissolution | In-vitro dissolution after 6 Months | |
|---|---|---|---|---|
|  |  |  | 25/60 | 40/75 |
| Assay (% LC) |  | 95.2 | 94.1 | 94.7 |
| Average | 1 hr | 22 (20-23) | 22 (22-23) | 22 (22-23) |
| % Dissolved | 3 hr | 46 (45-48) | 47 (44-48) | 48 (47-49) |
| (min-max) | 9 hr | 86 (85-87) | 87 (86-87) | 88 (87-90) |
|  | 12 hr | 92 (91-92) | 92 (90-93) | 94 (93-96) |
| MNO (%) |  | ND | <LOQ | <LOQ |
| PDM (%) |  | <LOQ | <LOQ | <LOQ |
| MPN (%) |  | ND | <LOQ | <LOQ |
| Total Deg. (%) |  | <LOQ | <LOQ | 0.1 |

ND = not detected,
LOQ = 0.05%

TABLE 18.4

Experimental Stability Tablet AJ (100 mg, with one oxygen absorber)

|  |  | Initial in-vitro dissolution | In-vitro dissolution after 6 Months | |
|---|---|---|---|---|
|  |  |  | 25/60 | 40/75 |
| Assay (% LC) |  | 95.2 | 95 | 94.8 |
| Average | 1 hr | 22 (20-23) | 22 (21-23) | 23 (22-23) |
| % Dissolved | 3 hr | 46 (45-48) | 47 (46-48) | 49 (47-49) |
| (min-max) | 9 hr | 86 (85-87) | 87 (85-89) | 88 (85-90) |
|  | 12 hr | 92 (91-92) | 92 (91-95) | 94 (92-95) |

TABLE 18.4-continued

Experimental Stability Tablet AJ (100 mg, with one oxygen absorber)

|  | Initial in-vitro dissolution | In-vitro dissolution after 6 Months | |
|---|---|---|---|
|  |  | 25/60 | 40/75 |
| MNO (%) | ND | <LOQ | <LOQ |
| PDM (%) | <LOQ | <LOQ | ND |
| MPN (%) | ND | <LOQ | <LOQ |
| Total Deg. (%) | <LOQ | <LOQ | 0.1 |

ND = not detected,
LOQ = 0.05%

A comparison between the degradation data at both conditions for containers without an oxygen absorber and with one oxygen absorber indicated no significant increase in degradant formation. The 6-month dissolution data for each strength and each packaging configuration indicated a slight increase.

What is claimed is:

1. A solid oral extended release pharmaceutical dosage form comprising a cured extended release matrix formulation, the extended release matrix formulation comprising:
   morphine sulfate in an amount of 15 mg, 30 mg, 60 mg, 100 mg or 200 mg;
   about 60 wt % to about 96 wt % polyethylene oxide having an approximate molecular weight of from about 900,000 to about 2,000,000 based on rheological measurements, wherein the polyethylene oxide used for preparing the extended release matrix formulation is in the form of polyethylene oxide particles, wherein about 96% or more of the polyethylene oxide particles pass through a 25 mesh (0.707 mm; 707 microns) sieve and wherein about 90% or more of the polyethylene oxide particles pass through a 60 mesh (0.250 mm; 250 microns) sieve,
   wherein the dosage form is free of spray dried lactose; and
   a lubricant in an amount of about 0.75% to about 5% by weight of the extended release matrix formulation,
   wherein the dosage form is bioequivalent to a commercial extended-release morphine sulfate product containing an equimolar amount of morphine sulfate as tested in a comparative clinical study, wherein the commercial extended-release morphine sulfate product comprises:
   (i) 15 mg morphine sulfate, 85 mg lactose, 35 mg cetostearyl alcohol, 10 mg hydroxyethyl cellulose, 3 mg talc, 2 mg magnesium stearate and 5 mg of a film coating;
   (ii) 30 mg morphine sulfate, 70 mg lactose, 35 mg cetostearyl alcohol, 10 mg hydroxyethyl cellulose, 3 mg talc, 2 mg magnesium stearate and 5 mg of a film coating;
   (iii) 60 mg morphine sulfate, 42.2 mg lactose, 32.8 mg cetostearyl alcohol, 10 mg hydroxyethyl cellulose, 3 mg talc, 2 mg magnesium stearate and 5 mg of a film coating;
   (iv) 100 mg morphine sulfate, 35 mg cetostearyl alcohol, 10 mg hydroxyethyl cellulose, 3 mg talc, 2 mg magnesium stearate and 5 mg of a film coating; or
   (v) 200 mg morphine sulfate, 70 mg cetostearyl alcohol, 20 mg hydroxyethyl cellulose, 6 mg talc, 4 mg magnesium stearate and 10 mg of a film coating, and wherein less than about 13% of the morphine sulfate content in the dosage form is volatizable when subjected to a simulated smoking experiment with alkalization.

2. The solid oral extended release pharmaceutical dosage form of claim 1, wherein the polyethylene oxide has an approximate molecular weight of about 1,000,000 or of about 2,000,000 based on rheological measurements.

3. The solid oral extended release pharmaceutical dosage form of claim 1, wherein curing of the extended release matrix formulation is performed at a temperature of from about 72° C. to about 78° C. for a time period of from about 30 to about 60 min.

4. The solid oral extended release pharmaceutical dosage form of claim 1, wherein the extended release matrix formulation in the dosage form comprises:
   (i) the morphine sulfate in the form of morphine hemi (sulfate pentahydrate) (having a molecular weight of 758.8 g/mol) in an amount of about 4 to about 8% by weight of the extended release matrix formulation or in an equimolar amount of another solvate or hydrate of morphine sulfate, and the polyethylene oxide in an amount of about 92 to about 96% by weight thereof, or
   (ii) the morphine sulfate in the form of morphine hemi (sulfate pentahydrate) (having a molecular weight of 758.8 g/mol) in an amount of about 6 to about 10% by weight of the extended release matrix formulation or in an equimolar amount of another solvate or hydrate of morphine sulfate, and the polyethylene oxide in an amount of about 88 to about 93% by weight thereof, or
   (iii) the morphine sulfate in the form of morphine hemi (sulfate pentahydrate) (having a molecular weight of 758.8 g/mol) in an amount of about 10 to about 15% by weight of the extended release matrix formulation or in an equimolar amount of another solvate or hydrate of morphine sulfate, and the polyethylene oxide in an amount of about 84 to about 91% by weight thereof, or
   (iv) the morphine sulfate in the form of morphine hemi (sulfate pentahydrate) (having a molecular weight of 758.8 g/mol) in an amount of about 15 to about 20% by weight of the extended release matrix formulation or in an equimolar amount of another solvate or hydrate of morphine sulfate, and the polyethylene oxide in an amount of about 78 to about 86% by weight thereof, or
   (v) the morphine sulfate in the form of morphine hemi (sulfate pentahydrate) (having a molecular weight of 758.8 g/mol) in an amount of about 27 to about 36% by weight of the extended release matrix formulation or in an equimolar amount of another solvate or hydrate of morphine sulfate, and the polyethylene oxide in an amount of about 60 to about 70% by weight thereof.

5. The solid oral extended release pharmaceutical dosage form of claim 4, wherein the extended release matrix formulation in the dosage form comprises:
   the morphine sulfate in the form of morphine hemi (sulfate pentahydrate) (having a molecular weight of 758.8 g/mol) is in an amount of from about 15 to about 200 mg, or in an amount of about 5, about 10, about 15, about 30, about 60, about 100 or about 200 mg, or in an equimolar amount of another solvate or hydrate of morphine sulfate.

6. The solid oral extended release pharmaceutical dosage form of claim 5, wherein the extended release matrix formulation contains a glidant in an amount of about 0.1 to about 2.5% by weight of the extended release matrix formulation.

7. The solid oral extended release pharmaceutical dosage form of claim 6, wherein the lubricant comprises magnesium stearate and the glidant comprises colloidal silicon dioxide.

8. The solid oral extended release pharmaceutical dosage form of claim 1, the dosage form having a breaking strength of at least about 200 N, at least about 250 N, at least about 300 N, at least about 350 N, or at least about 400 N.

9. The solid oral extended release pharmaceutical dosage form of claim 1, the dosage form having a cracking force of at least about 150 N, at least about 170 N, at least about 200 N, or at least about 230 N.

10. The solid oral extended release pharmaceutical dosage form of claim 1, the dosage form having a penetration depth to crack of at least about 1.25 mm, at least about 1.5 mm, at least about 1.75 mm, or at least about 2 mm.

11. The solid oral extended release pharmaceutical dosage form of claim 1, the dosage form having a crush resistance of at least about 400 N or at least about 500 N.

12. The solid oral extended release pharmaceutical dosage form of claim 1, the dosage form after administration providing a dose adjusted $C_{max}$ of morphine of from about 3 ng/mL to about 9 ng/ml or from about 5 ng/ml to about 7 ng/ml, per 15 mg of morphine hemi (sulfate pentahydrate) (having a molecular weight of 758.8 g/mol) or an equimolar amount of another solvate or hydrate of morphine sulfate included in the dosage form.

13. The solid oral extended release pharmaceutical dosage form of claim 1, the dosage form after administration providing a dose adjusted $AUC_t$ of morphine of from about 30 ng*hr/mL to about 100 ng*hr/mL or from about 40 ng*hr/mL to about 80 ng*hr/mL, per 15 mg of morphine hemi (sulfate pentahydrate) (having a molecular weight of 758.8 g/mol) or an equimolar amount of another solvate or hydrate of morphine sulfate included in the dosage form.

14. The solid oral extended release pharmaceutical dosage form of claim 1, the dosage form after administration providing a dose adjusted $AUC_{inf}$ of morphine after administration of from about 30 ng*hr/mL to about 100 ng*hr/mL or from about 40 ng*hr/mL to about 80 ng*hr/mL, per 15 mg of morphine hemi (sulfate pentahydrate) (having a molecular weight of 758.8 g/mol) or an equimolar amount of another solvate or hydrate of morphine sulfate included in the dosage form.

15. The solid oral extended release pharmaceutical dosage form of claim 1, providing a $T_{max}$ of from about 2 to about 5 hours or from about 2 to about 4 hours, after administration in the fasted state.

16. The solid oral extended release pharmaceutical dosage form of claim 1, wherein the dosage form is a tablet comprising 15 mg of morphine hemi (sulfate pentahydrate) (having a molecular weight of 758.8 g/mol) or an equimolar amount of another solvate or hydrate of morphine sulfate included in an extended release matrix formulation, and wherein the dosage form has a breaking strength of at least about 230 N and/or a cracking force of at least about 180 N and/or a crush resistance of at least about 400 N; or
   wherein the dosage form is a tablet comprising 30 mg of morphine hemi (sulfate pentahydrate) (having a molecular weight of 758.8 g/mol) or an equimolar amount of another solvate or hydrate of morphine sulfate included in an extended release matrix formulation, and wherein the dosage form has a breaking strength of at least about 250 N and/or a cracking force of at least about 200 N and/or a crush resistance of at least about 400 N; or wherein the dosage form is a tablet comprising 60 mg of morphine hemi (sulfate pentahydrate) (having a molecular weight of 758.8 g/mol) or an equimolar amount of another solvate or hydrate of morphine sulfate included in an extended release matrix formulation, and wherein the dosage form has a breaking strength of at least about 280 N and/or a cracking force of at least about 200 N and/or a crush resistance of at least about 400 N; or wherein the dosage form is a tablet comprising 100 mg of morphine hemi (sulfate pentahydrate) (having a molecular weight of 758.8 g/mol) or an equimolar amount of another solvate or hydrate of morphine sulfate included in an extended release matrix formulation, and wherein the dosage form has a breaking strength of least about 200 N and/or a cracking force of at least about 170 N and/or a crush resistance of at least about 400 N; or wherein the dosage form is a tablet comprising 200 mg of morphine hemi (sulfate pentahydrate) (having a molecular weight of 758.8 g/mol) or an equimolar amount of another solvate or hydrate of morphine sulfate included in an extended release matrix formulation, and wherein the dosage form has a breaking strength of least about 350 N, and/or a cracking force of at least about 180 N and/or a crush resistance of at least about 400 N.

17. The solid oral extended release pharmaceutical dosage form of claim 1, wherein the dosage form provides an in-vitro dissolution rate of morphine sulfate, when measured in a USP Apparatus 1 (basket) at 100 rpm in 900 ml simulated gastric fluid without enzymes (SGF) at 37° C., characterized by the amount of morphine sulfate released from the dosage form, of
from about 5% to about 35% released after 0.5 hour;
from about 18% to about 50% released after 1 hour;
from about 29% to about 70% released after 2 hours;
from about 40% to about 85% released after 3 hours;
from about 49% to about 95% released after 4 hours;
greater than about 65% released after 6 hours;
greater than about 70% released after 8 hours;
greater than about 75% released after 9 hours; and/or
greater than about 85% released after 12 hours.

18. The solid oral extended release pharmaceutical dosage form of claim 1, wherein the dosage form provides an in-vitro dissolution rate of morphine sulfate, when measured in a USP Apparatus 1 (basket) at 100 rpm in 900 ml simulated gastric fluid without enzymes (SGF) comprising 4%, 10%, 20% or 40% ethanol at 37° C., characterized in that the amount of morphine sulfate released from the dosage form after 0.5 hours and after 1 hour deviates no more than 20%-points or no more than 10%-points from the amount of morphine sulfate released from the dosage form after 0.5 hours and after 1 hour when measured in a USP Apparatus 1 (basket) at 100 rpm in 900 ml simulated gastric fluid without enzymes (SGF) without ethanol at 37° C.

19. The solid oral extended release pharmaceutical dosage form of claim 1, wherein crushing the dosage form between two spoons or by means of a mortar and pestle results in less than about 10% or less than about 5% of the resulting particles having a particle size of less than 1000 um.

20. The solid oral extended release pharmaceutical dosage form of claim 1, wherein recovery of the morphine sulfate is:
less than about 20% or less than about 10%, based on a syringeability test whereby one intact dosage form is subjected to dissolution in 2, 5, or 10 ml of water or saline without or with agitation at room temperature for 1 hour or for 24 hours and the resultant solution is aspirated by an iterative process starting with a 27 gauge needle and subsequently using 25, 22 and 18 gauge needles in case less than 10% of the extraction volume could be loaded in the respective larger gauge (smaller diameter) needle; or is:
less than about 20% or less than about 15%, based on a syringeability test whereby one sliced or one milled dosage form is subjected to extraction in 2, 5, or 10 mL of water or saline without or with agitation at room temperature for 30 minutes and the resultant solution is aspirated by an iterative process starting with a 27 gauge needle and subsequently using 25, 22 and 18 gauge needles in case less than 10% of the extraction volume could be loaded in the respective larger gauge (smaller diameter) needle.

21. The solid oral extended release pharmaceutical dosage form of claim 1, wherein recovery of the morphine sulfate is:
less than about 5% or less than about 3%, based on a syringeability test whereby one intact dosage form is subjected to dissolution in 10 mL of 40% or 95% ethanol with agitation at room temperature for 1 hour and the resultant solution is aspirated with an 18-gauge needle; or is:
less than about 3% or less than about 2%, based on a syringeability test whereby one milled dosage form is subjected to dissolution in 10 mL of 40% ethanol with agitation at room temperature or 60° C. for 30 minutes and the resultant solution is aspirated with a 27-gauge needle or an 18-gauge needle.

22. A solid oral extended release pharmaceutical dosage form comprising a cured extended release matrix formulation, wherein the cured extended release matrix formulation comprises:
a therapeutically effective amount of morphine sulfate, and
polyethylene oxide,
wherein the dosage form is free of spray dried lactose,
wherein less than about 13% of the morphine sulfate content in the dosage form is volatizable when subjected to a simulated smoking experiment with alkalization,
and is obtainable by at least the following steps:
(a) combining at least morphine sulfate and polyethylene oxide in the form of polyethylene oxide particles having an approximate molecular weight of from about 900,000 to about 2,000,000, or of about 1,000,000, or of about 2,000,000, to form a composition based on rheological measurements, wherein about 96% or more of the polyethylene oxide particles pass through a 25 mesh (0.707 mm; 707 microns) sieve or wherein about 90% or more of the polyethylene oxide particles used in step (a) pass through a 60 mesh (0.250 mm; 250 microns) sieve,
(b) shaping the composition of step (a) to form the extended release matrix formulation, wherein the polyethylene oxide is in an amount of about 60 wt % to about 90 wt % based on the total weight of the extended release matrix formulation, and
(c) curing the extended release matrix formulation of step (b) by subjecting it to a temperature of from about 72° C. to about 78° C. for a period of from about 30 minutes to about 60 minutes.

23. A process of preparing a solid oral extended release pharmaceutical dosage form comprising a cured extended release matrix formulation, wherein the extended release matrix formulation comprises:

a therapeutically effective amount of morphine sulfate, and about 60 wt % to about 90 wt % polyethylene oxide, the process comprising at least the following steps:

(a) combining at least morphine sulfate and polyethylene oxide in the form of polyethylene oxide particles to form a composition, (b) shaping the composition of step (a) to form the extended release matrix formulation, and (c) curing the extended release matrix formulation of step (b), wherein the polyethylene oxide particles in step (a) have an approximate molecular weight of from about 900,000 to about 2,000,000 based on rheological measurements, wherein about 96% or more of the polyethylene oxide particles pass through a 25 mesh (0.707 mm; 707 microns) sieve, and wherein about 90% or more of the polyethylene oxide particles pass through a 60 mesh (0.250 mm; 250 microns) sieve, and wherein less than about 13% of the morphine sulfate content in the dosage form is volatizable when subjected to a simulated smoking experiment with alkalization.

24. The process of claim 23, wherein the polyethylene oxide particles in step (a) have an approximate molecular weight of about 1,000,000 or of about 2,000,000 based on rheological measurements.

25. The process of claim 24, wherein in step (c) the extended release matrix formulation is subjected to a temperature of from about 72° C. to about 78° C. for a period of from about 25 minutes to about 60 minutes.

26. The process of claim 25, wherein the polyethylene oxide particles are included in the extended release matrix formulation in an amount of about 55 to about 95% by weight thereof.

27. The process of claim 26, wherein the morphine sulfate is included in the extended release matrix formulation in the form of morphine hemi (sulfate pentahydrate) (having a molecular weight of 758.8 g/mol) in an amount of about 2.5 to about 40% by weight of the extended release matrix formulation or in an equimolar amount of another solvate or hydrate of morphine sulfate.

28. The process of claim 27, wherein in step (a) a lubricant, the lubricant comprising magnesium stearate, and/or a glidant, the glidant comprising colloidal silicon dioxide, is/are added.

29. A method of treating pain in a subject in need thereof, the method comprising administering to the subject the solid oral extended release pharmaceutical dosage form of claim 1.

30. The method of treating pain of claim 29, the method comprising administering the solid oral extended release pharmaceutical dosage form to the subject twice a day or every 12 hours.

31. The solid oral extended release pharmaceutical dosage form of claim 1, comprising 15 mg morphine sulfate, and wherein the commercial extended-release morphine sulfate product comprises 15 mg morphine sulfate, 85 mg lactose, 35 mg cetostearyl alcohol, 10 mg hydroxyethyl cellulose, 3 mg talc, 2 mg magnesium stearate and 5 mg of a film coating.

32. The solid oral extended release pharmaceutical dosage form of claim 1, comprising 30 mg morphine sulfate, and wherein the commercial extended-release morphine sulfate product comprises 30 mg morphine sulfate, 70 mg lactose, 35 mg cetostearyl alcohol, 10 mg hydroxyethyl cellulose, 3 mg talc, 2 mg magnesium stearate and 5 mg of a film coating.

33. The solid oral extended release pharmaceutical dosage form of claim 1, comprising 60 mg morphine sulfate, and wherein the commercial extended-release morphine sulfate product comprises 60 mg morphine sulfate, 42.2 mg lactose, 32.8 mg cetostearyl alcohol, 10 mg hydroxyethyl cellulose, 3 mg talc, 2 mg magnesium stearate and 5 mg of a film coating.

34. The solid oral extended release pharmaceutical dosage form of claim 1, comprising 100 mg morphine sulfate, and wherein the commercial extended-release morphine sulfate product comprises 100 mg morphine sulfate, 35 mg cetostearyl alcohol, 10 mg hydroxyethyl cellulose, 3 mg talc, 2 mg magnesium stearate and 5 mg of a film coating.

35. The solid oral extended release pharmaceutical dosage form of claim 1, comprising 200 mg morphine sulfate, and wherein the commercial extended-release morphine sulfate product comprises 200 mg morphine sulfate, 70 mg cetostearyl alcohol, 20 mg hydroxyethyl cellulose, 6 mg talc, 4 mg magnesium stearate and 10 mg of a film coating.

* * * * *